United States Patent
Hinklin et al.

(10) Patent No.: US 11,780,835 B2
(45) Date of Patent: Oct. 10, 2023

(54) PYRAZOLO[3,4-B]PYRIDINE COMPOUNDS AS INHIBITORS OF TAM AND MET KINASES

(71) Applicant: Array BioPharma Inc., Boulder, CO (US)

(72) Inventors: Ronald Jay Hinklin, Boulder, CO (US); Shelley Allen, Boulder, CO (US); Patrick Barbour, Boulder, CO (US); Adam Cook, Boulder, CO (US); Joshua Dahlke, Boulder, CO (US); John Gaudino, Boulder, CO (US); Ellen Laird, Boulder, CO (US); Oren T. McNulty, Boulder, CO (US); Qian Zhao, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 17/376,571

(22) Filed: Jul. 15, 2021

(65) Prior Publication Data
US 2023/0011441 A1     Jan. 12, 2023

Related U.S. Application Data

(62) Division of application No. 16/555,432, filed on Aug. 29, 2019, now Pat. No. 11,104,676.

(60) Provisional application No. 62/858,686, filed on Jun. 7, 2019, provisional application No. 62/724,829, filed on Aug. 30, 2018.

(51) Int. Cl.
C07D 471/04     (2006.01)
(52) U.S. Cl.
CPC ................................. C07D 471/04 (2013.01)
(58) Field of Classification Search
CPC .................................................. C07D 471/04
See application file for complete search history.

(56) References Cited

U.S. PATENT DOCUMENTS

| 3,773,919 | A | 11/1973 | Boswell et al. |
| 9,029,538 | B2 | 5/2015 | Dandu et al. |
| 10,195,208 | B2 | 2/2019 | Hao et al. |
| 2017/0275290 | A1 | 9/2017 | Li et al. |
| 2018/0305313 | A1 | 10/2018 | Park et al. |

FOREIGN PATENT DOCUMENTS

| WO | 2006/004833 A2 | 1/2006 |
| WO | 2006/014325 A2 | 2/2006 |
| WO | 2006/077319 | 7/2006 |
| WO | 2007/103308 A2 | 9/2007 |
| WO | 2012/167600 A1 | 12/2012 |
| WO | 2013/074633 A1 | 5/2013 |
| WO | 2015/017607 A2 | 2/2015 |
| WO | 2015/100117 A1 | 7/2015 |
| WO | 2016/004272 A1 | 1/2016 |
| WO | 2016/193680 A1 | 12/2016 |
| WO | 2018/022438 A1 | 2/2018 |
| WO | 2018/026663 A1 | 2/2018 |
| WO | 2018/039275 A1 | 3/2018 |
| WO | 2018/093654 A1 | 5/2018 |
| WO | 2018/121228 A1 | 7/2018 |
| WO | 2019/101178 A1 | 5/2019 |
| WO | 2019/113190 A1 | 6/2019 |

OTHER PUBLICATIONS

Sun "A systematic analysis of FDA-approved anticancer drugs" BMC Systems Biology 2017, 11 (Suppl 5):87, 27-43.*
Pfizer Inc., "Study of PF-07265807 in Participants With Metastatic Solid Tumors", Clinical Trial Record NCT04458259.
Linger et al., "TAM receptor tyrosine kinases: biologic functions, signaling, and potential therapeutic targeting in human cancer," Adv. in Cancer Res., 2008, 100:35-83.
Liu et al., "Novel mechanism of lapatinib resistance in HER2-positive breast humor cells: activation of AXL," Cancer Res., 2009, 69:6871-6878.
Liu et al., "Design, synthesis and structure-activity relationships of novel 4-phenoxyquinoline derivatives containing 1, 2, 4-triazolone moiety as c-Met kinase inhibitors," Eur. J. Med. Chem. 123, 431-46, 2016.
Ma et al., "c-MET mutational analysis in small cell lung cancer: novel juxtamembrane domain mutations regulating cytoskeletal functions," Cancer Res., 2003, 63:6272-81.
Macleod et al., "Altered ErbB receptor signaling and gene expression in cisplatin-resistant ovarian cancer," Cancer Res., 2005, 65:6789-6800.

(Continued)

*Primary Examiner* — David K O'Dell
(74) *Attorney, Agent, or Firm* — Fariba Shoarinejad

(57) ABSTRACT

Provided herein are compounds of the Formula (I): and stereoisomers, tautomers and pharmaceutically acceptable salts thereof, wherein $R^1$, $R^2$, $R^9$, $X^1$ and G are as defined herein, which are inhibitors of one or more TAM kinases and/or c-Met kinase, and are useful in the treatment and prevention of diseases which can be treated with a TAM kinase inhibitor and/or a c-Met kinase inhibitor.

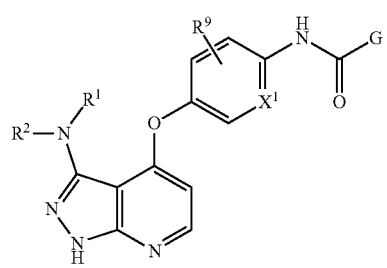

9 Claims, No Drawings
Specification includes a Sequence Listing.

(56) References Cited

OTHER PUBLICATIONS

Mahadevan et al., "A novel tyrosine kinase switch is a mechanism of imatinib resistance in gastrointestinal stromal tumors," Oncogene, 2007, 26:3909-3919.
Mendenhall et al., "MET-Mutated NSCLC with major response to crizotinib," J. Thorne. Oncol., 2015, 10:e33-e34.
Meyer et al., "The receptor AXL diversifies EGFR signaling and limits the response to EGFR-targeted inhibitors in triple-negative breast cancer cells," Sci. Signal, 2013, 6:ra66.
Myers, et al., "AXL Inhibitors in Cancer: A Medicinal Chemistry Perspective," J Med Chem., 2016, 59:3593-3608.
Miller et al., "Reduced proteolytic shedding of receptor tyrosine kinases is a post-translational mechanism of kinase inhibitor resistance," Cancer Discovery, 2016, 6:382-399.
Mizuno et al., "HGF-MET cascade, a key target for inhibiting cancer metastasis: the impact of NK4 discovery on cancer biology and therapeutics," Int. J. Mol. Sci., 2013, 14 :888-919.
Mo et al., "Targeting MET in cancer therapy," Chronic Dis. Transl. Med., 2017, 3(3):148-153.
Nakamura et al., "Molecular cloning and expression of human hepatocyte growth factor," Nature, 1989, 342:440-443.
Niederst et al., "Bypass mechanisms of resistance to receptor tyrosine kinase inhibition in lung cancer," Sci. Signaling, 2013, 6:re6.
Nishimura et al., "Autoimmune dilated cardiomyopathy in PD-1 receptor-deficient mice," Science, 2001, 291:319-322.
Nones et al., "Genome-wide DNA methylation patterns in pancreatic ductal adenocarcinoma reveal epigenetic deregulation of SLIT-ROBO, ITGA2 and MET signaling," Int. J. Cancer, 2014, 135:1 110-1118.
Norman et al., "Structure-Based Design of Novel Class II c-Met Inhibitors: 1. Identification of Pyrazolone-Based Derivatives," J. Med. Chem. 55, 1858-67, 2012.
O'Bryan et al., "Axl, a transforming gene isolated from primary human myeloid leukemia cells, encodes a novel receptor tyrosine kinase," Mol. Cell Biol., 1991, 11 :5016-5031.
Onozato et al., "Activation of MET by gene amplification or by splice mutations deleting the iuxtamembrane domain in primary resected lung cancers," J. Thorne. Oncol., 2009, 4:5-11.
Organ et al., "An overview of the c-MET signaling pathway," Ther. Adv. Med. Oncol., 2011, 3(1 Suppl):S7-S19.
Paolino et al., "The E3 ligase Cbl-b and TAM receptors regulate cancer metastasis via natural killer cells," Nature, 2014, 507:508-512.
Pardoll et al., "The blockade of immune checkpoints in cancer immunotherapy," Cancer, 2012, 12:252-264.
Patani, "Bioisosterism: A Rational Approach in Drug Design" Chem. Rev. 1996, 96, 3147-3176.
Peschard et al., "Mutation of the c-Cbl TKB domain binding site on the Met receptor tyrosine kinase converts it into a transforming protein," Mol. Cell, 2001, 8:995-1004.
Schlegel et al., "MERTK receptor tyrosine kinase is a therapeutic target in melanoma," J. Clin. Invest., 2013, 123(5):2257-2267.
Schmidt et al., "Germline and somatic mutations in the tyrosine kinase domain of the MET protooncogene in papillary renal carcinomas," Nat Genet., 1997, 16:68-73.
Schmidt et al., Two North American families with hereditary papillary renal carcinoma and identical novel mutations in the MET proto-oncogene, Cancer Res., 1998, 58:1719-1722.
Schoumacher et al., "Key roles of AXL and MER receptor tyrosine kinases in resistance to multiple anticancer therapies," Curr. Oncol. Rep., 2017, 19(3):19.
Seo et al., "The transcriptional landscape and mutational profile of lung adenocarcinoma," Genome Res., 2012, 22:2109-2 119.
Shaver et al., "Diverse, biologically relevant, and targetable gene rearrangements in triple-negative breast cancer and other malignancies," Cancer Res., 2016, 76(16):4850-4860.

Shiozawa et al., "GAS6/AXL axis regulates prostate cancer invasion, proliferation, and survival in the bone marrow niche," Neoplasia, 2010, 12 :116-127.
Song et al., "Overexpression of receptor tyrosine kinase Axl promotes tumor cell invasion and survival in pancreatic ductal adenocarcinoma," Cancer, 2011, 117 :734-743.
Tovar et al., "MET in human cancer: germline and somatic mutations," Ann. Transl. Med., 2017, 5(10):205.
Waizenegger et al., "Role of growth arrest-specific gene 6-Mer axis in multiple myeloma," Leukemia, 2014, 29:696-704.
Wang et al., "TIG 1 promotes the development and progression of inflammatory breast cancer through activation of Axl kinase," Cancer Res., 2013, 73:6516-6525.
Wang et al., "Mer receptor tyrosine kinase promotes invasion and survival in glioblastoma multiforme," Oncogene, 2013, 32:872-882.
Waqar et al., "MET mutation associated with responsiveness to crizotinib," J. Thorac. Oncol., 2015, 10:e29-31.
Ware et al., "A mechanism of resistance to gefitinib mediated by cellular reprogramming and the acquisition of an FGF2-FGFR1 autocrine growth 1000," Oncogenesis, 2013, 2:e39.
Weber et al., "Demethylation of a LINE-I antisense promoter in the cMet locus impairs Met signaling through induction of illegitimate transcription," Oncogene, 2010, 29:5775-5784.
Wilson et al., "AXL inhibition sensitizes mesenchymal cancer cells to antimitotic drugs," Cancer Res., 2014, 74(20):5878-5890.
Wislicenus, J., "Adolph Strecker's Short Textbook of Organic Chemistry" 1881, Spottiswoode: London, pp. 38-39.
Zenali et al., "Retrospective review of MET gene mutations," Oncoscience, 2015, 2(5):533-541.
Zeng et al., "c-Met gene amplification is associated with advanced stage colorectal cancer and liver metastases," Cancer Lett., 2008, 265:258-269.
Zhang et al., "Regulation of the MET oncogene: molecular mechanisms," Carcinogenesis, 2016, 4:345-355.
Zhang et al., "Activation of the AXL kinase causes resistance to EGFR-targeted therapy in lung cancer," Nat. Genet., 2012, 44(8):852-860.
Zhang et al., "Function of the c-Met receptor tyrosine kinase in carcinogenesis and associated therapeutic opportunities," Mol. Cancer, 2018, 17:45.
Zhao et al., "Differential expression of Axl and con-elation with invasion and multidrug resistance in cancer cells," Cancer Invest., 2012, 30:287-294.
Zhu et al., "A genomic screen identifies TYR03 as a MITF regulator in melanoma," Proc. Natl Acad. Sci. USA, 2009, 106:1 7025-17030.
Abella et al., "Met/Hepatocyte growth factor receptor ubiquitination suppresses transformation and is required for Hrs phosphorylation," Mol. Cell. Biol., 2005, 25:9632-45.
Akalu et al., "TAM receptor tyrosine kinases as emerging targets of innate immune checkpoint blockade for cancer therapy," Immunol. Rev., 2017, 276:165-177.
Allen et al., "Identification of small molecule inhibitors of proline-rich tyrosine kinase 2 (Pyk2) with osteogenic activity in osteoblast cells," Bioorganic & Medicinal Chemistry Letters 19, 4924-28, 2009.
Asaoka et al., "Gastric cancer cell line Hs746T harbors a splice site mutation of c-Met causing iuxtamembrane domain deletion," Biochem. Biophys. Res. Comm., 2010, 394:1042-46.
Bardelli et al., "Uncoupling signal transducers from oncogenic MET mutants abrogates cell transformation and inhibits invasive growth," Proc. Natl. Acad. Sci., 1998, 95: 14379-14383.
Ben-Batalla et al., "Axl, a prognostic and therapeutic target in acute myeloid leukemia mediates paracrine crosstalk of leukemia cells with bone marrow stroma," Blood, 2013, 122:2443-2452.
Birchmeier et al., "Met, metastasis, motility and more," Nat. Rev. Mol. Cell. Biol., 2003, 4:915-925.
Brand et al., "AXL mediates resistance to cetuximab therapy," Cancer Res., 2014, 74:5152-5164.
Brandao et al., "Inhibition of MerTK increases chemosensitivity and decreases oncogenic potential in T-cell acute lymphoblastic leukemia," Blood Cancer J., 2013, 3, e101.

(56) References Cited

OTHER PUBLICATIONS

Chambers et al., "Lymphoproliferation in CTLA-4-deficient mice is mediated by costimulation-dependent activation of CD4+ T cells," Immunity, 1997, 7:885-895.
Comoglio et al., "Drug development of MET inhibitors: targeting oncogene addiction and expedience," Nat. Rev. Dmg Discov., 2008, 7:504-516.
Cook et al., "MerTK inhibition in tumor leukocytes decreases tumor growth and metastasis," J. Clin. Invest., 2013, 123:3231-3242.
Demarest et al., "Evaluation of Tyro3 expression, Gas6-mediated akt phosphorylation, and the impact of anti-Tyro3 antibodies in melanoma cell lines," 2013, Biochemistry 52:3102-3118.
Diaz et al., "Pharmacokinetic drivers of toxicity for basic molecules: Strategy to lower pKa results in decreased tissue exposure and toxicity for a small molecule Met inhibitor," Toxicology and Applied Pharmacology, 2013, 266:86-94.
Dufies et al., "Mechanisms of AXL overexpression and function in Imatinib-resistant chronic myeloid leukemia cells," Oncotarget, 201 1, 2 :874-885.
Elkabets et al., "AXL Mediates Resistance to PI3Kalpha Inhibition by Activating the EGFR/PKC/mTOR Axis in Head and Neck and Esophageal Squamous Cell Carcinomas," Cancer Cell, 2015, 27:533-546.
Feneyrolles et al., "Axl kinase as a key target for oncology: focus on small molecule inhibitors," Mol. Cancer Ther., 2014, 13:2141-2148.
Frampton et al., "Activation of MET via diverse exon 14 splicing alterations occurs in multiple tumor types and confers clinical sensitivity to MET inhibitors," Cancer Discov., 2015, 5(8):850-859.
Giles et al., "Axl mediates acquired resistance of head and neck cancer cells to the epidermal growth factor receptor inhibitor erlotinib," Mol. Cancer Ther., 2013, 12:2541-2558.
Gioia et al., "Quantitative phosphoproteomics revealed interplay between Syk and Lyn in the resistance to nilotinib in chronic myeloid leukemia cells," Blood, 2011, 118:2211-2221.
Goyal et al., "Targeting the HGF/c-MET pathway in hepatocellular carcinoma," Clin. Cancer Res., 2013, 19:2310-2318.
Graham et al., "Cloning and developmental expression analysis of the murine c-mer tyrosine kinase," Oncogene, 1995, 10:2349-2359 [abstract].
Graham et al., "The TAM family: phosphatidylserine-sensing receptor tyrosine kinases gone awry in cancer," Nature Reviews Cancer, 2014, 14:769-785.
Han et al., "Gas6/ Axl mediates tumor cell apoptosis, migration and invasion and predicts the clinical outcome of osteosarcoma patients," Biochem. Biophys. Res. Commun., 2013, 435:493-500.
Heist et al., "MET Exon 14 skipping in non-small cell lung cancer," Oncologist, 2016, 21(4) :481-186.
Hong et al., "Receptor tyrosine kinase AXL is induced by chemotherapy drugs and overexpression of AXL confers chug resistance in acute myeloid leukemia," Cancer Lett., 2008, 268:314-324.
Huang et al., "Differential mechanisms of acquired resistance to insulin-like growth factor-l receptor antibody therapy or to a small-molecule inhibitor, BMS-754807, in a human rhabdomyosarcoma model," Cancer Res., 2010, 70:7221-7231.
Hutterer et al., "Axl and growth arrest-specific gene 6 are frequently overexpressed in human gliomas and predict poor prognosis in patients with glioblastoma multiforme," Clin. Cancer Res., 2008, 14:130-138.
Ichimura et al., "Expression of c-met/HGF receptor in human non-small cell lung carcinomas in vitro and in vivo and its prognostic significance," Jpn J. Cancer Res., 1996, 87:1063-1069.
International Search Report and Written Opinion for PCT/US2019/048701 dated Dec. 6, 2019, 17 pages.
Jeffers et al., "Activating mutations for the Met tyrosine kinase receptor in human cancer," Proc. Natl. Acad. Sci. U.S.A., 1997, 94(21):11445-11450.

Jenkins et al., "Response to crizotinib in a patient with lung adenocarcinoma harboring a MET splice site mutation," Clin. Lung Cancer, 2015, 16:e101-e104.
Keating et al., "Inhibition of Mer and Axl receptor tyrosine kinases in astrocytoma cells leads to increased apoptosis and improved chemosensitivity," Mol. Cancer Ther., 2010, 9: 1298-1307.
Keating et al., "Lymphoblastic leukemia/lymphoma in mice overexpressing the Mer (MerTK) receptor tyrosine kinase," Oncogene, 2006, 25:6092-6100.
Kim et al., "Epithelial-mesenchymal transition leads to crizotinib resistance in H2228 lung cancer cells with EML4-ALK translocation," Mol. Oncol., 2013, 7:1093-1102.
Kong-Beltran et al., "Somatic mutations lead to an oncogenic deletion of met in lung cancer," Cancer Res., 2006, 66(1):283-289.
Koorstra et al., "The Axl receptor tyrosine kinase confers an adverse prognostic influence in pancreatic cancer and represents a new therapeutic target," Cancer Biology & Therapy, 2009, 8:618-326.
Lai et al., "An extended family of protein-tyrosine kinase genes differentially expressed in the vertebrate nervous system," Neuron, 1991, 6:691-704.
Lay et al., "Sulfasalazine suppresses drug resistance and invasiveness of lung adenocarcinoma cells expressing AXL," Cancer Res., 2007, 67:3878-3887.
Lee et al., "An alternatively spliced form of Met receptor is tumorigenic," Exp. Mol. Med., 2006, 38:565-73.
Lee et al., "Cbl-independent degradation of Met: ways to avoid agonism of bivalent Met-targeting antibody," Oncogene, 2014, 33:34-43.
Lee et al., "Identification of a novel type of alternative splicing of a tyrosine kinase receptor. Juxtamembrane deletion of the c-met protein kinase C serine phosphorylation regulatory site," J. Biol. Chem., 1994, 269:19457-61.
Lee-Sherick et al., "Aberrant Mer receptor tyrosine kinase expression contributes to leukemogenesis in acute myeloid leukemia," Oncogene, 2013, 32:5359-5368.
Lew et al., "Differential TAM receptor-ligand-phospholipid interactions delimit differential TAM bioactivities," eLife, 2014, 3:e03385.
Li et al., "Axl as a potential therapeutic target in cancer: role of Axl in tumor growth, metastasis and angiogenesis," Oncogene, 2009, 28:3442-3455.
Liao et al., "Design and biological evaluation of novel 4-(2-fluorophenoxy) quinoline derivatives bearing an imidazoline moiety as c-Met kinase inhibitors," Bioorganic & Medicinal Chemistry 23, 4410-22, 2015.
Liederer et al., "Preclinical absorption, distribution, metabolism, excretion, and pharmacokinetic-pharmacodynamic modelling of N-( 4-(3-( (3 S, 4 R)-1-ethyl-3-fluoropiperidine-4-ylamino )-1H-pyrazolo[3, 4-b ]pyridin-4-yloxy )-3-fluorophenyl)-2-( 4-fluorophenyl)-3-oxo-2,3-dihydropyridazine-4-carboxamide, a novel MET kinase inhibitor," Xenobiotica, 2011; 4 1(4): 327-339.
Liederer et al., "Preclinical stereoselective disposition and toxicokinetics of two novel MET inhibitors," Xenobiotica, 2012; 42(5): 456-465.
Linger et al., "Mer or Axl receptor tyrosine kinase inhibition promotes apoptosis, blocks growth, and enhances chemosensitivity of human non-small cell lung cancer," Oncogene, 2013, 32:3420-3431.
Linger et al., "Mer receptor tyrosine kinase is a therapeutic target in pre-B-cell acute lymphoblastic leukemia," Blood, 2013, 122:1599-1609.
Lu et al., "Homeostatic regulation of the immtme system by receptor tyrosine kinases of the Tyro 3 family," Science, 2001, 293:306-311.
Schmidt et al., "Novel mutations of the MET proto-oncogene in papillary renal carcinomas," Oncogene, 1999, 18:2343-2350.
Tai et al., "Axl promotes cell invasion by inducing MMP-9 activity through activation of NF-[kappa]B and Brg-1," Oncogene, 2008, 27:4044-4055.

\* cited by examiner

PYRAZOLO[3,4-B]PYRIDINE COMPOUNDS AS INHIBITORS OF TAM AND MET KINASES

CROSS-REFERENCE TO RELATED APPLICATIONS

This application is a divisional application from United States Application No. 16/555,432, filed Aug. 29, 2019, which claims the benefit of priority to U.S. Provisional Application No. 62/858,686, filed Jun. 7, 2019 and U.S. Provisional Application No. 62/724,829, filed Aug. 30, 2018, the entire contents of each of which are incorporated herein by reference.

REFERENCE TO SEQUENCE LISTING

This application was filed electronically via EFS-Web and included an electronically submitted sequence listing in .txt format. The .txt file contains a sequence listing entitled "PC040219B_SEQ_LISTING_ST25.txt". The text file is 1.44 KB, and was created and submitted electronically via EFS-Web on Jul. 15, 2021. The sequence listing contained in this .txt file is part of the specification and is herein incorporated by reference in its entirety.

BACKGROUND

Provided herein are novel inhibitors of TAM and MET kinases, pharmaceutical compositions comprising the compounds, processes for making the compounds, and the use of the compounds in therapy. More particularly, provided herein are pyrazolo[3,4-b]pyridine compounds useful in the treatment and prevention of diseases which can be treated with a TAM kinase inhibitor or MET kinase inhibitor.

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including TYRO3, AXL and Mer (Graham et ah, 2014, Nature Reviews Cancer 14, 769-785; Linger et ah, 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and TYRO3 (Graham et ah, 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et ah, 1991, Mol Cell Biol 11, 5016-5031; Graham et ah, 2014, Nature Reviews Cancer 14, 769-785; Linger et ah, 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et ah, 2014, Molecular Cancer Therapeutics 13, 2141-2148; Linger et al., 2008, Advances in Cancer Research 100, 35-83).

MER (also known as MERTK, EYK, RYK, RP38, NYK and TYRO 12) was originally identified as a phosphoprotein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

The MET family includes mesenchymal-epithelial transition factor (c-Met), a single pass tyrosine kinase receptor that is expressed on the surface of various epithelial cells; its ligand is hepatocyte growth factor/scatter factor (HGF/SF) (Nakamura et al., *Nature* 342:440-443, 1989). The binding of HFG to c-Met initiates a series of intracellular signals that mediate embrogenesis and would healing in normal cells (Organ, Ther. Adv. Med. Oncol. 3(1 Supply):S7-S19, 2011). However, in cancer cells, aberrant HGF/c-Met axis activation, which is closely related to c-Met gene mutations, overexpression, and amplification, promotes tumor development and progression—e.g., by stimulating the PI3K/AKT, Ras/MAPK, JAK/STAT, SRC, and Wnt/β-catenin signal pathways (Zhang et al., *Mol. Cancer* 17:45, 2018; Mizuno et al., *Int. J. Mol. Sci.* 14:888-919, 2013). The constitutive activation of the aforementioned c-Met-dependent signaling pathways confers cancer cells with competitive growth advantage relative to normal cells and increases the likelihood of metastasis—e.g., by enabling access to blood supply and conferring ability to dissociate from tissues (Comoglio et al., *Nat. Rev. Drug Discov.* 7:504-516, 2008; Birchmeier et al., *Nat. Rev. Mol. Cell. Biol.* 4:915-925, 2003).

Accordingly, there is a need in the art for compounds and methods of use thereof for the modulation of TAM and MET kinases in treatment of cancer.

SUMMARY OF THE INVENTION

Provided herein is a compound of the Formula I:

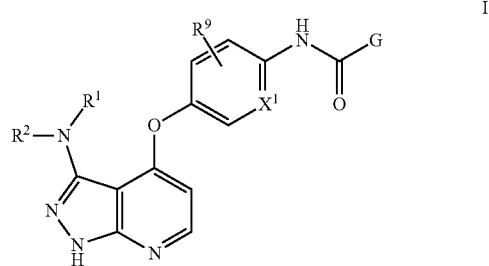

and stereoisomers, tautomers and pharmaceutically acceptable salts thereof, wherein $R^1$, $R^2$, $R^9$, $X^1$ and G are as defined herein.

Also provided herein is a pharmaceutical composition comprising a compound of Formula I or a pharmaceutically acceptable salt thereof, in admixture with a pharmaceutically acceptable diluent or carrier.

Also provided herein is a method of inhibiting cell proliferation, in vitro or in vivo, the method comprising contacting a cell with an effective amount of a compound of Formula I or a pharmaceutically acceptable salt thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of Formula I or a pharmaceutically acceptable salt thereof or a pharmaceutical composition thereof as defined herein.

Also provided herein is a compound of Formula I or a pharmaceutically acceptable salt thereof, or a pharmaceutical composition thereof as defined herein for use in therapy.

Also provided herein is a compound of Formula I or a pharmaceutically acceptable salt thereof or a pharmaceutical composition thereof as defined herein for use in the treatment of cancer and/or inhibiting metastasis associated with a particular cancer.

Also provided herein is a compound of Formula I or a pharmaceutically acceptable salt thereof for use in the inhibition of TAM kinase activity.

Also provided herein is a compound of Formula I or a pharmaceutically acceptable salt thereof or a pharmaceutical composition thereof as defined herein, for use in the treatment of a TAM-associated disease or disorder such as cancer. In some embodiments, the TAM-associated cancer is a cancer having a chromosomal translocation that results in the expression of a TMEM87B-MERTK fusion protein (e.g., amino acids 1-55 of TMEM87B and amino acids 433-1000 of MERTK) or a AXL-MBIP fusion protein.

Also provided herein is the use of a compound of Formula I or a pharmaceutically acceptable salt thereof, as defined herein in the manufacture of a medicament for the treatment of cancer and/or inhibiting metastasis associated with a particular cancer.

Also provided herein is a use of a compound of Formula I or a pharmaceutically acceptable salt thereof, as defined herein in the manufacture of a medicament for the inhibition of TAM kinase activity.

Also provided herein is the use of a compound of Formula I or a pharmaceutically acceptable salt thereof, as defined herein, in the manufacture of a medicament for the treatment of a TAM-associated disease or disorder such as cancer.

Also provided herein is a pharmaceutical combination which comprises (a) a compound of Formula I or a pharmaceutically acceptable salt thereof, and (b) an additional therapeutic agent. Also provided herein is a pharmaceutical combination which comprises (a) a compound of Formula I or a pharmaceutically acceptable salt thereof, and (b) an additional therapeutic agent, for use in therapy. In one embodiment, the compound of Formula I or the pharmaceutically acceptable salt thereof and the additional therapeutic agent are formulated as separate compositions or dosages for simultaneous, separate or sequential use for use in therapy, wherein the amounts of the compound of Formula I or a pharmaceutically acceptable salt thereof and of the additional therapeutic agent are together therapeutically effective. Also provided herein is a pharmaceutical composition comprising such a combination. Also provided herein is a commercial package or product comprising such a combination as a combined preparation for simultaneous, separate or sequential use.

In one embodiment, the additional therapeutic agent is an anticancer agent (e.g., any of the additional anticancer agents described herein). Accordingly, provided herein is a pharmaceutical combination for treating cancer (e.g., a TAM-associated cancer) in a patient in need thereof, which comprises (a) a compound of Formula I or a pharmaceutically acceptable salt thereof, and (b) an additional anticancer agent (e.g., any of the additional anticancer agents described herein), wherein the compound of Formula I or the pharmaceutically acceptable salt thereof and the additional therapeutic are formulated as separate compositions or dosages for simultaneous, separate or sequential use for the treatment of cancer, wherein the amounts of the compound of Formula I or a pharmaceutically acceptable salt thereof and of the additional anti cancer agent are together effective in treating the cancer.

Also provided herein is a pharmaceutical combination for treating cancer (e.g., a TAM-associated cancer) in a patient in need thereof, which comprises (a) a compound of Formula I or a pharmaceutically acceptable salt thereof, and (b) an additional anticancer agent (e.g., any of the additional anticancer agents described herein), wherein the compound of Formula I or the pharmaceutically acceptable salt thereof and the additional therapeutic are formulated as separate compositions or dosages for simultaneous, separate or sequential use for the treatment of cancer, wherein the amounts of the compound of Formula I or a pharmaceutically acceptable salt thereof and of the additional anti cancer agent are together effective in treating the cancer. Also provided herein is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided are methods of treating an individual with cancer that include administering a compound of Formula I or a pharmaceutically acceptable salt thereof, before, during, or after administration of another anticancer agent (e.g., another anticancer agent to which the subject has previously developed resistance, e.g., any of the additional anticancer agents described herein).

Also provided herein are methods of treating a patient identified or diagnosed as having a TAM-associated cancer that include administering to a patient identified or diagnosed as having a TAM-associated cancer a therapeutically effective amount of a compound of Formula I or a pharmaceutically acceptable salt thereof, or pharmaceutical composition including a therapeutically effective amount of a compound of Formula I or a pharmaceutically acceptable salt thereof.

Also provided herein are methods of treating a patient having a cancer that include (a) identifying the patient as having a TAM-associated cancer, and (b) administering to the patient identified as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of decreasing the risk of developing a metastasis or an additional metastasis in a patient identified or diagnosed as having a TAM-associated cancer that include administering to a patient identified or diagnosed as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of decreasing the risk of developing a metastasis or an additional metastasis in a patient having a cancer that include: (a) identifying a patient having a TAM-associated cancer, and (b) administering to the identified as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of decreasing migration and/or invasion of a cancer cell in a patient identified or diagnosed as having a TAM-associated cancer that include administering to a patient identified or diagnosed as having a TAM-associated cancer a therapeutically effective amount of a compound of Formula T or a pharmaceutically acceptable salt thereof, or a pharmaceutical composition including a therapeutically effective amount of a compound of Formula I or a pharmaceutically acceptable salt thereof.

Also provided herein are methods of decreasing migration and/or invasion of a cancer cell in a patient having a cancer that include (a) identifying the patient as having a TAM-associated cancer; and (b) administering to the patient identified as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of selecting a treatment for a patient identified or diagnosed as having a TAM-associated cancer that include selecting a compound of Formula I or a pharmaceutically acceptable salt thereof, or a pharmaceutical composition including a therapeutically effective amount of a compound of Formula I or a pharmaceutically acceptable salt thereof, for a patient identified or diagnosed as having a TAM-associated cancer.

Also provided herein are methods of selecting a treatment for a patient that include (a) identifying the patient as having a TAM-associated cancer, and (b) selecting a compound of Formula I or a pharmaceutically acceptable salt thereof, or a pharmaceutical composition including a therapeutically effective amount of a compound of Formula I or a pharmaceutically acceptable salt thereof, for the patient identified as having a TAM-associated cancer.

Also provided herein are methods of selecting a treatment for a patient identified or diagnosed as having a cancer that include (a) administering an additional anticancer agent to the patient, (b) after (a), detecting increased expression and/or activity of a TAM kinase in a cancer cell from the patient, and (c) after (b), selecting a compound of Formula I or a pharmaceutically acceptable salt thereof, or a pharmaceutical composition including a therapeutically effective amount of a compound of Formula I or a pharmaceutically acceptable salt thereof, for the patient.

Also provided herein are methods of treating a patient identified or diagnosed as having a cancer that include: (a) administering to the patient identified or diagnosed as having a cancer one or more doses of at least one additional anticancer agent; (b) after (a), detecting an increase in the expression and/or activity of a TAM kinase in a cancer cell or an immune cell from the subject; and (c) after (b), administering to the patient a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (c) further includes administering to the patent the at least one additional anticancer agent.

Also provided are methods of treating a patient identified or diagnosed as having a cancer that include: (a) detecting an increase in the expression and/or activity of a TAM kinase in a cancer cell or an immune cell from a patient identified or diagnosed as having a cancer and previously administered one or more doses of at least one additional anticancer agent; and (b) after (a), administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient the at least one additional anticancer agent.

Also provided herein are methods of treating a patient identified or diagnosed as having a cancer that has been previously administered one or more doses of at least one additional anticancer agent and has been identified as having a cancer cell or an immune cell that has increased expression and/or activity of a TAM kinase that include administering a therapeutically effective amount of a compound of Formula I or a pharmaceutically acceptable salt thereof, or a pharmaceutical composition including a therapeutically effective amount of a compound of Formula I or a pharmaceutically acceptable salt thereof, to the patient. In some embodiments of these methods, step (b) further includes administering to the patient the at least one additional anti cancer agent.

Also provided herein are methods of treating a patient identified or diagnosed as having a cancer that include: (a) selecting a patient identified or diagnosed as having increased expression and/or activity of a TAM kinase in a cancer cell or an immune cell; and (b) after (a) administering to the selected patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient at least one additional anticancer agent.

Also provided herein are methods of treating a patient identified or diagnosed as having a cancer that include: (a) selecting a patient identified or diagnosed as having a cancer that has been previously administered one or more doses of an additional anticancer agent and identified as having a cancer cell or an immune cell having increased expression and/or activity of a TAM kinase; and (b) after (a), administering to the selected patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient at least one additional anticancer agent.

Also provided herein are methods of treating a patient identified or diagnosed as having a TAM-associated cancer that include: (a) administering to the patient identified or diagnosed as having a TAM-associated cancer one or more doses of a TAM kinase inhibitor; (b) after (a), detecting resistance of the TAM-associated cancer in the patient to the TAM kinase inhibitor; and (c) after (b), administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof, in some embodiments of these methods, step (c) further includes administering to the patient at least one additional anti cancer agent.

Also provided herein are methods of treating a patient identified or diagnosed as having a TAM-associated cancer that include: (a) detecting resistance of the TAM-associated cancer in the patient to a TAM kinase inhibitor that was previously administered to the patient; and (b) after (a), administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient at least one additional anticancer agent.

Also provided herein are methods of treating a patient identified or diagnosed as having a TAM-associated cancer and determined to have previously developed resistance to a TAM kinase inhibitor that include administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. Some embodiments of these methods further include administering to the patient at least one additional anticancer agent.

Also provided herein are methods of decreasing immune tolerance in a subject in need thereof that include administering to the subject a therapeutically effective amount of a compound of Formula I or a pharmaceutically acceptable salt thereof, or a pharmaceutical composition thereof as defined herein.

Also provided herein are methods of inhibiting angiogenesis in a subject in need thereof, the method comprising administering to the subject a therapeutically effective amount of a compound of Formula I or a pharmaceutically acceptable salt thereof, or a pharmaceutical composition thereof as defined herein.

Also provided herein are methods of suppressing resistance to a therapeutic agent in a subject in need thereof that include administering to the subject a therapeutically effective amount of (i) a compound of Formula I or a pharmaceutically acceptable salt thereof, or any of the pharmaceutical compositions thereof described herein, and (ii) the therapeutic agent, where the therapeutic agent is selected from the group consisting of a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor (e.g., a Type 1 c-Met inhibitor), a RAF inhibitor, an Akt inhibitor, a FTL-3 inhibitor, and a MAP kinase pathway inhibitor.

Also provided herein are methods of treating a patient identified or diagnosed as having a TAM-associated cancer that include administering radiation therapy before or after administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of treating a patient identified or diagnosed as having a TAM-associated cancer that include administering surgery before or after administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods for inhibiting a TAM kinase activity in a mammalian cell in need thereof that include contacting the mammalian cell with a compound of Formula I or a pharmaceutically acceptable salt thereof, or a pharmaceutical composition including a therapeutically effective amount of a compound of Formula I or a pharmaceutically acceptable salt thereof.

Also provided herein is a process for preparing a compound of Formula I or a pharmaceutically acceptable salt thereof.

Also provided herein is a compound of Formula I or a pharmaceutically acceptable salt thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

DETAILED DESCRIPTION OF THE INVENTION

Provided herein is a compound of the Formula I:

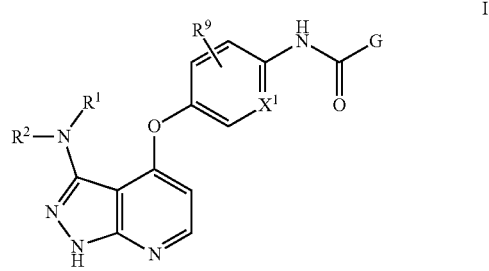

and stereoisomers, tautomers and pharmaceutically acceptable salts thereof, wherein:
$X^1$ is CH or N,
$R^1$ is hydrogen or C1-C6 alkyl, R² is
(a) hydrogen,
(b) C1-C6 alkyl,
(c) hydroxyC1-C6 alkyl,
(d) dihydroxyC2-C6 alkyl,
(e) C1-C6 fluoroalkyl optionally substituted with OH,
(f) (di-C1-C6 alkoxy)C2-C6 alkyl-,
(g) (C1-C6 alkoxy)C1-C6 alkyl- wherein said alkyl portion is optionally substituted with OH,
(h) Cyc¹,
(i) Cyc²,
(j) (hetCyc¹)C1-C6 alkyl- wherein said alkyl portion is optionally substituted with OH,
(k) (Ar¹)C1-C6 alkyl- wherein said alkyl portion is optionally substituted with OH,
(l) (hetAr¹)C1-C6 alkyl- wherein said alkyl portion is optionally substituted with OH, or
(m) (HOSO₃)C1-C6 alkyl-;
Cyc¹ is a 3-4 membered cycloalkyl ring optionally substituted with 1-2 substituents independently selected from halogen, hydroxy, C1-C3 alkyl, hydroxyC1-C3 alkyl, C1-C3 alkoxy, (C1-C3 alkoxy)C1-C3 alkyl- and R'R"NC(═O)—;
R' and R" are independently hydrogen or C1-C6 alkyl;
Cyc² is a 5-membered cycloalkyl ring substituted with 1-2 substituents independently selected from C1-C3 alkyl, (C1-C3 alkoxy)C1-C3 alkyl- and hydroxyC1-C3 alkyl-;
hetCyc¹ is a 5-6 membered saturated heterocyclic ring having 1-2 ring heteroatoms independently selected from O, N and SO₂, wherein said ring is optionally substituted with oxo;
Ar¹ is phenyl;
hetAr¹ is pyridyl;
G is

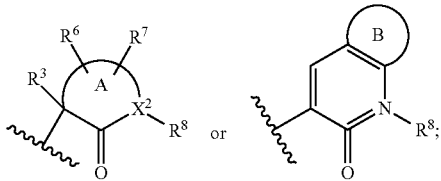

X² is C or N;
Ring A, including the atoms at the points of attachment, is a 5-6 membered heterocyclic ring optionally having an additional 1-2 ring nitrogen atoms when X² is N and having one ring nitrogen atom when X² is C;
R³ is hydrogen, methyl or absent;
Ring B, including the atoms at the points of attachment, is a 6-membered saturated carbocyclic optionally substituted with oxo or a 6-membered aromatic carbocyclic ring optionally substituted with OH;
R⁶ is hydrogen, halogen, C1-C6 alkyl, C1-C6 alkoxy, hydroxyC1-C6 alkyl, C3-C6 cycloalkyl, (C3-C6 cycloalkyl)C1-C6 alkyl- or hetCyc², provided that when R⁶ is on the ring carbon atom adjacent to the carbon linked to the —NHC(═O)— moiety of Formula I, then R⁶ is not halogen, and
R⁷ is hydrogen, C1-C6 alkyl, oxo or thioxo,
or optionally when R⁶ and R⁷ are on the same carbon atom, R⁶ and R⁷ together with the carbon atom to which they are attached form a cyclopropyl ring;
hetCyc² is a 4-6 membered saturated heterocyclic ring having a ring nitrogen atom and optionally substituted with C1-C6 alkyl;

R⁸ is Ar², hetAr², C3-C6 cycloalkyl, hetCyc³ or C1-C6 alkyl;
Ar² is phenyl optionally substituted with one or more substituents independently selected from halogen, C1-C2 alkyl and C1-C2 alkoxy;
hetAr² is a 5-6 membered heteroaryl having 1-2 ring nitrogen atoms and optionally substituted with one or more substituents independently selected from halogen, C1-C2 alkyl and C1-C2 alkoxy;
hetCyc³ is a 5-6 membered heterocyclic ring having a ring oxygen atom; and
R⁹ is hydrogen or halogen.

For complex chemical names employed herein, the substituent group is named before the group to which it attaches. For example, methoxyethyl comprises an ethyl backbone with a methoxy substituent.

The term "heterocyclic ring" when specifically referring to Ring A means that Ring A is a saturated, partially unsaturated or aromatic 5-6 membered heterocyclic ring.

The term "halogen" means —F (sometimes referred to herein as "fluoro" or "fluoros"), —Cl, —Br and —I.

The terms "C1-C2 alkyl", "C1-C3 alkyl", "C1-C6 alkyl" and "C2-C6 alkyl" as used herein refer to saturated linear or branched-chain monovalent hydrocarbon radicals of one to two, one to three, one to six or two to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The terms "C1-C2 alkoxy", "C1-C3 alkoxy" and "C1-C6 alkoxy" as used herein refers to a saturated linear or branched-chain monovalent alkoxy radical of one to two, one to three, or one to six carbon atoms, respectively, wherein the radical is on the oxygen atom. Examples include methoxy, ethoxy, propoxy, isopropoxy, butoxy and tert-butoxy.

The term "C1-C6 fluoroalkyl" as used herein include C1-C6 alkyl and C1-C6 alkoxy groups, respectively, that are substituted with one or more fluorines, such as, but not limited to, fluoromethyl, difluoromethyl, trifluoromethyl, 2,2,2-trifluoroethyl, and the like.

The term "(C1-C6 alkoxy)C1-C6 alkyl-" as used herein refers to saturated linear or branched-chain monovalent radicals of one to six carbon atoms, wherein one of the carbon atoms is substituted with a C1-C6 alkoxy group as defined herein. Examples include methoxymethyl (CH₃OCH₂—) and methoxyethyl (CH₃OCH₂CH₂—).

The term "(C1-C3 alkoxy)C1-C3 alkyl-" as used herein refers to saturated linear or branched-chain monovalent radicals of one to three carbon atoms, wherein one of the carbon atoms is substituted with a C1-C3 alkoxy group as defined herein.

The term "(di-C1-C6 alkoxy)C2-C6 alkyl-" as used herein refers to saturated linear or branched-chain monovalent radicals of two to six carbon atoms, wherein two of the carbon atoms are substituted with a C1-C6 alkoxy group as defined herein.

The terms "hydroxyC1-C3 alkyl-" and "hydroxyC1-C6 alkyl-" as used herein refers to a saturated linear or branched-chain monovalent alkyl radicals of one to six carbon atoms, respectively, wherein one of the carbon atoms is substituted with a hydroxyl group.

The term "dihydroxyC2-C6 alkyl-" as used herein refers to a saturated linear or branched-chain monovalent alkyl radical of two to six carbon atoms, wherein two of the carbon atoms are substituted with a hydroxyl group, provided two hydroxyl groups are not on the same carbon atom.

The term "(hetCyc$^1$)C1-C6 alkyl-" as used herein refers to a saturated linear or branched-chain monovalent alkyl radicals of one to six carbon atoms, respectively, wherein one of the carbon atoms is substituted with a hetCyc$^1$ group as defined herein.

The term "(Ar$^1$)C1-C6 alkyl-" as used herein refers to a saturated linear or branched-chain monovalent alkyl radicals of one to six carbon atoms, respectively, wherein one of the carbon atoms is substituted with a Ar$^1$ group as defined herein.

The term "(hetAr$^1$)C1-C6 alkyl-" as used herein refers to a saturated linear or branched-chain monovalent alkyl radicals of one to six carbon atoms, respectively, wherein one of the carbon atoms is substituted with a hetAr$^1$ group as defined herein.

The term "(HOSO$_3$)C1-C6 alkyl-" as used herein refers to a saturated linear or branched-chain monovalent alkyl radicals of one to six carbon atoms, respectively, wherein one of the carbon atoms is substituted with a HOSO$_3$— group.

The term "(C3-C6 cycloalkyl)C1-C6 alkyl-" as used herein refers to a saturated linear or branched-chain monovalent alkyl radicals of one to six carbon atoms, respectively, wherein one of the carbon atoms is substituted with a C3-C6 cycloalkyl group.

The term "C3-C6 cycloalkyl" as used herein refers to a saturated carbocyclic ring having three to six ring carbon atoms, that is, cyclopropyl, cyclobutyl, cyclopentyl or cyclohexyl.

The term "oxo" or "oxo group" as used herein means an oxygen atom that is double bonded to a carbon atom, i.e., =O.

The term "thioxo" as used herein means a sulfur atom that is double bonded to a carbon atom, i.e., =S.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer. Exemplary tautomerizations include, but are not limited to, amide-to-imide; enamine-to-imine; enamine-to-(a different) enamine tautomerizations; and keto-to-enol.

It will be appreciated that certain compounds provided herein may contain one or more centers of asymmetry and may therefore be prepared and isolated in a mixture of isomers such as a racemic mixture, or in an enantiomerically pure form. For compounds of the invention wherein stereochemistry is designated by straight thick bars or straight dashed bars, the straight thick bars or straight dashed bars indicate relative stereochemistry. For compounds of the invention wherein stereochemistry is designated by solid wedges or dashed wedges, the solid wedges or dashed wedges indicate absolute stereochemistry.

In one embodiment of Formula I, $X^1$ is CH.
In one embodiment of Formula I, $X^1$ is N.
In one embodiment of Formula I, $R^9$ is hydrogen.
In one embodiment of Formula I, $R^9$ is halogen.

In one embodiment of Formula I, $X^1$ is CH and $R^9$ is halogen. In one embodiment of Formula I, $X^1$ is CH and $R^9$ is fluoro.

In one embodiment of Formula I, $X^1$ is N and $R^9$ is hydrogen.

In one embodiment of Formula I, $R^1$ is hydrogen.
In one embodiment of Formula I, $R^1$ is C1-C6 alkyl. In one embodiment of Formula I, $R^1$ is methyl.

In one embodiment of Formula I, $R^2$ is hydrogen. In one embodiment of Formula I, $R^2$ is hydrogen and $R^1$ is hydrogen.

In one embodiment of Formula I, $R^2$ is C1-C6 alkyl. In one embodiment of Formula I, $R^2$ is C1-C6 alkyl and $R^1$ is hydrogen. In one embodiment of Formula I, $R^2$ is methyl or ethyl. In one embodiment of Formula I, $R^2$ is methyl or ethyl and $R^1$ is hydrogen.

In one embodiment of Formula I, $R^2$ is hydroxyC1-C6 alkyl. In one embodiment of Formula I, $R^2$ is hydroxyC1-C6 alkyl and $R^1$ is hydrogen. In one embodiment of Formula I, $R^2$ is hydroxyC1-C6 alkyl and $R^1$ is C1-C6 alkyl. In one embodiment of Formula I, $R^2$ is hydroxyC1-C6 alkyl and $R^1$ is methyl. In one embodiment of Formula I, $R^2$ is selected from the structures:

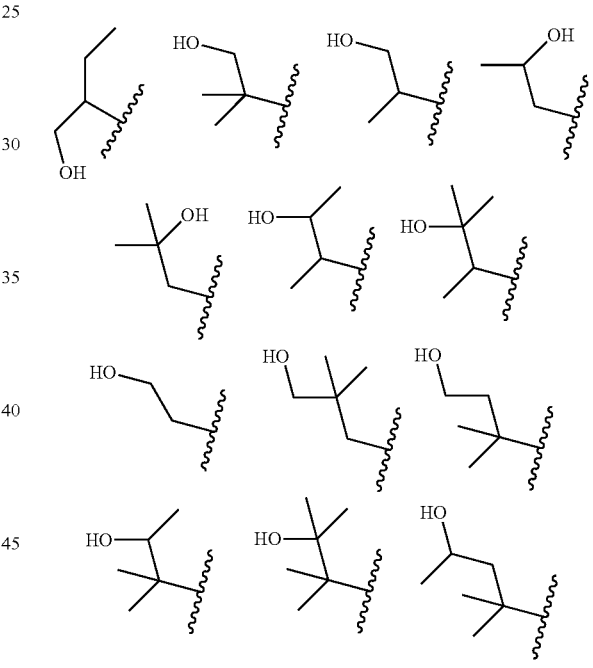

and $R^1$ is hydrogen or C1-C6 alkyl. In one of said embodiments, $R^1$ is hydrogen. In one of said embodiments, $R^1$ is C1-C6 alkyl. In one of said embodiments, $R^1$ is methyl.

In one embodiment of Formula I, $R^2$ is dihydroxyC2-C6 alkyl. In one embodiment of Formula I, $R^2$ is dihydroxyC2-C6 alkyl and $R^1$ is hydrogen. In one embodiment of Formula I, $R^2$ is selected from the structures:

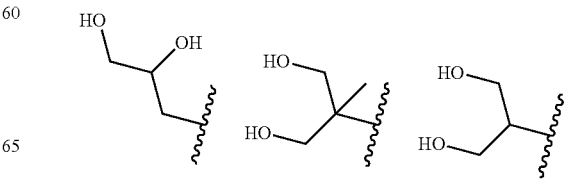

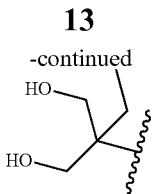

and R¹ is hydrogen or C1-C6 alkyl. In one of said embodiments, R¹ is hydrogen.

In one embodiment of Formula I, R² is C1-C6 fluoroalkyl optionally substituted with OH. In one embodiment of Formula I, R² is C1-C6 fluoroalkyl optionally substituted with OH and R¹ is hydrogen. In one embodiment of Formula I, R² is C1-C6 fluoroalkyl optionally substituted with OH and R¹ is C1-C6 alkyl. In one embodiment of Formula I, R² is selected from the structures:

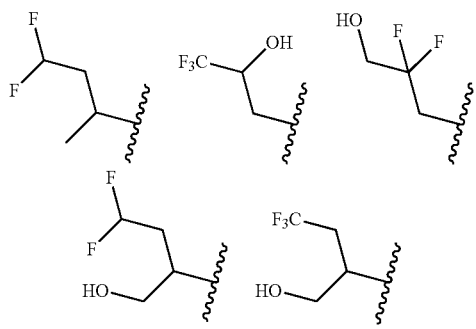

and R¹ is hydrogen or C1-C6 alkyl. In one of said embodiments, R¹ is hydrogen.

In one embodiment of Formula I, R² is (di-C1-C6 alkoxy)C2-C6 alkyl-. In one embodiment of Formula I, R² is (di-C1-C6 alkoxy)C2-C6 alkyl- and R¹ is hydrogen. In one embodiment of Formula I, R² is (di-C1-C6 alkoxy)C2-C6 alkyl- and R¹ is C1-C6 alkyl. In one embodiment, R² is

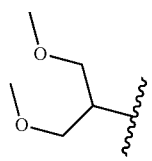 [SMILES: *C(COC)COC]

and R¹ is hydrogen or C1-C6 alkyl. In one of said embodiments, R¹ is hydrogen.

In one embodiment of Formula I, R² is (C1-C6 alkoxy)C1-C6 alkyl- wherein said alkyl portion is optionally substituted with OH. In one embodiment of Formula I, R² is (C1-C6 alkoxy)C1-C6 alkyl- wherein said alkyl portion is optionally substituted with OH and R¹ is hydrogen. In one embodiment of Formula I, R² is (C1-C6 alkoxy)C1-C6 alkyl- wherein said alkyl portion is optionally substituted with OH and R² is C1-C6 alkyl. In one embodiment, R² is selected from the structures:

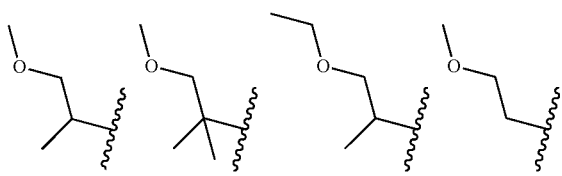

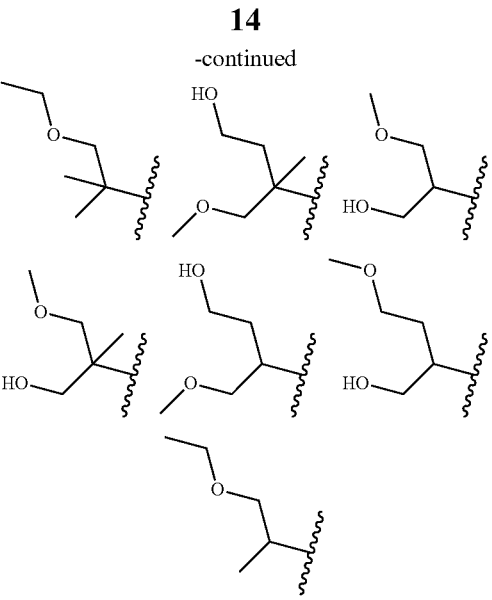

and R¹ is hydrogen or C1-C6 alkyl. In one of said embodiments, R¹ is hydrogen. In one of said embodiments, R¹ is C1-C6 alkyl. In one of said embodiments, R¹ is methyl.

In one embodiment of Formula I, R² is Cyc¹. In one embodiment of Formula I, R² is Cyc¹ and R¹ is hydrogen. In one embodiment of Formula I, R² is Cyc¹ and R¹ is C1-C6 alkyl. In one embodiment of Formula I, R² is selected from the structures:

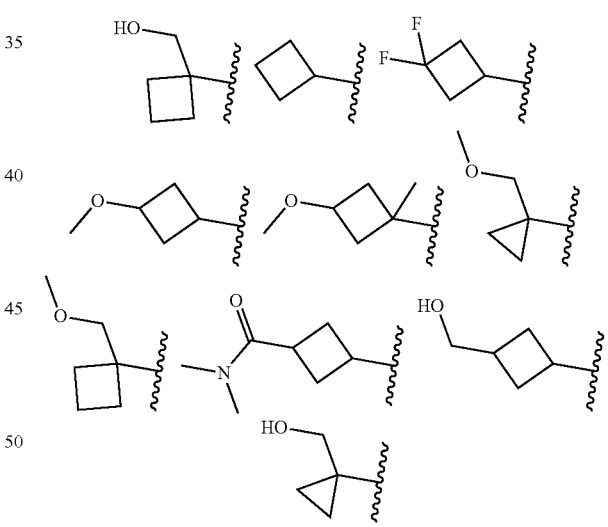

and R¹ is hydrogen or C1-C6 alkyl. In one of said embodiments, R¹ is hydrogen.

In one embodiment of Formula I, R² is Cyc². In one embodiment of Formula I, R² is Cyc² and R¹ is hydrogen. In one embodiment of Formula I, R² is Cyc² and R¹ is C1-C6 alkyl. In one embodiment of Formula I, R² is selected from the structures:

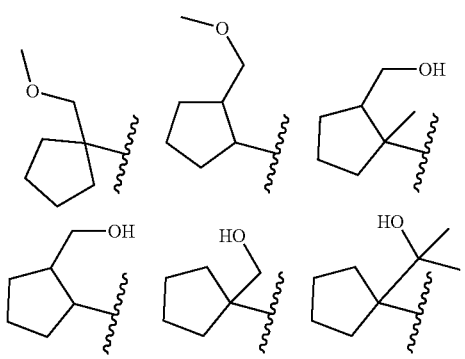

and R¹ is hydrogen or C1-C6 alkyl. In one of said embodiments, R¹ is hydrogen.

In one embodiment of Formula I, R² is (hetCyc¹)C1-C6 alkyl- wherein said alkyl portion is optionally substituted with OH. In one embodiment of Formula I, R² is (hetCyc¹)C1-C6 alkyl- wherein said alkyl portion is optionally substituted with OH and R¹ is hydrogen. In one embodiment of Formula I, R² is (hetCyc¹)C1-C6 alkyl- wherein said alkyl portion is optionally substituted with OH and R¹ is C1-C6 alkyl. In one embedment, R² is selected from the structures

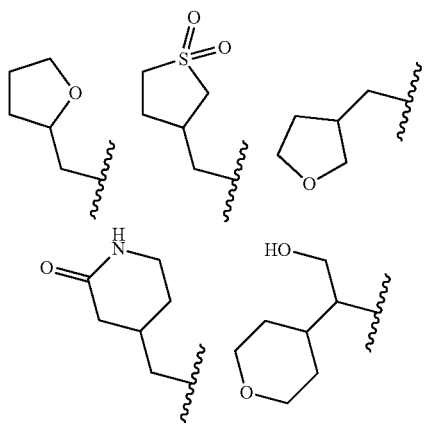

and R¹ is hydrogen or C1-C6 alkyl. In one of said embodiments, R¹ is hydrogen.

In one embodiment of Formula I, R² is (Ar¹)C1-C6 alkyl- wherein said alkyl portion is optionally substituted with OH. In one embodiment of Formula I, R² is (Ar¹)C1-C6 alkyl- wherein said alkyl portion is optionally substituted with OH and R¹ is hydrogen. In one embodiment of Formula I, R² is (Ar¹)C1-C6 alkyl- wherein said alkyl portion is optionally substituted with OH and R² is C1-C6 alkyl. In one of said embodiments, R² is (Ar¹)C1-C6 alkyl- wherein said alkyl portion is substituted with OH. In one embodiment, R² is

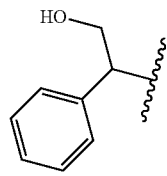 [SMILES: *C(CO)c1ccccc1]

and R¹ is hydrogen or C1-C6 alkyl. In one of said embodiments, R¹ is hydrogen.

In one embodiment of Formula I, R² is (hetAr¹)C1-C6 alkyl- wherein said alkyl portion is optionally substituted with OH. In one embodiment of Formula I, R² is (hetAr¹)C1-C6 alkyl- wherein said alkyl portion is optionally substituted with OH and R¹ is hydrogen. In one embodiment of Formula I, R² is (hetAr¹)C1-C6 alkyl- wherein said alkyl portion is optionally substituted with OH and R¹ is C1-C6 alkyl. In one of said embodiments, R² is (hetAr¹)C1-C6 alkyl- wherein said alkyl portion is substituted with OH. In one embodiment, R² is selected from the structures:

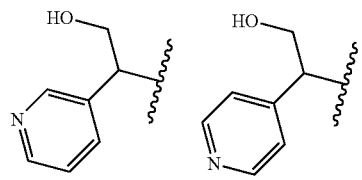

and R¹ is hydrogen or C1-C6 alkyl. In one of said embodiments, R¹ is hydrogen.

In one embodiment of Formula I, R² is (HOSO₃)C1-C6 alkyl-. In one embodiment of Formula I, R² is (HOSO₃)C1-C6 alkyl- and R¹ is hydrogen. In one embodiment of Formula I, R² is (HOSO₃)C1-C6 alkyl- and R¹ is C1-C6 alkyl. In one embodiment, R² is

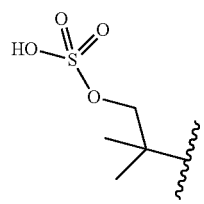 [SMILES: *C(C)(C)COS(=O)(=O)O]

and R¹ is hydrogen or C1-C6 alkyl. In one of said embodiments, R¹ is hydrogen.

In one embodiment of Formula I, G is

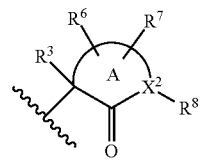

wherein X² is C or N, and Ring A is a 5-6 membered heterocyclic ring optionally having an additional 1-2 ring nitrogen atoms when X² is N and having one ring nitrogen atom when X² is C, and R³, R⁶, R⁷ and R⁸ are as defined for Formula I.

In one embodiment of Formula I, G is

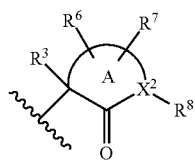

wherein X² is C or N, Ring A is a 5-6 membered heterocyclic ring having one ring nitrogen atom, and R³, R⁶, R⁷ and R⁸ are as defined for Formula I.

In one embodiment of Formula I, G is

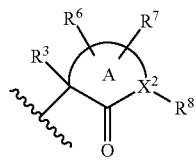

wherein X² is N, R³ is absent, Ring A is a 6-membered heterocyclic ring having one additional ring nitrogen atom, and R⁷ is oxo, wherein G has the formula A-1

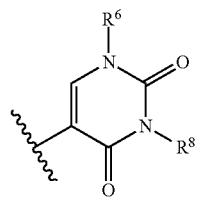

A-1 wherein R⁵ is C1-C6 alkyl, hydroxyC1-C6 alkyl, C3-C6 cycloalkyl, (C3-C6 cycloalkyl)C1-C6 alkyl- or hetCyc², and hetCyc² and R⁸ are as defined for Formula I. In one embodiment of formula A-1, R⁸ is Ar², wherein Ar² is phenyl optionally substituted with one or more substituents independently selected from halogen, C1-C2 alkyl and C1-C2 alkoxy. In one embodiment, Ar² is phenyl optionally substituted with one or more halogens. In one embodiment G is formula A-1 wherein formula A-1 is selected from the structures:

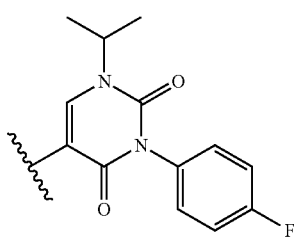

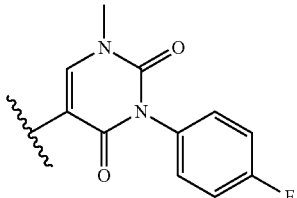

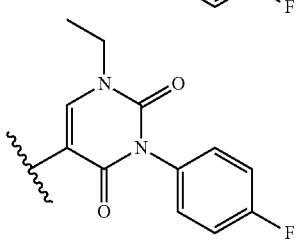

-continued

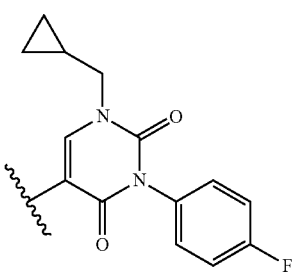

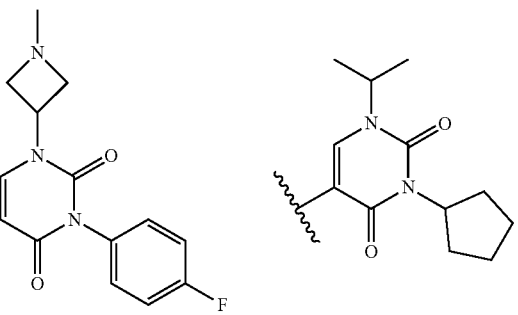

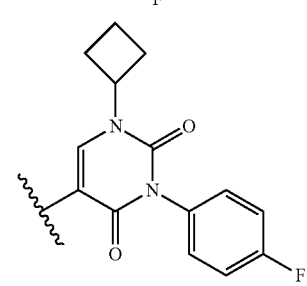

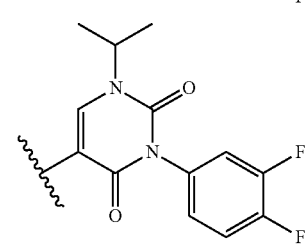

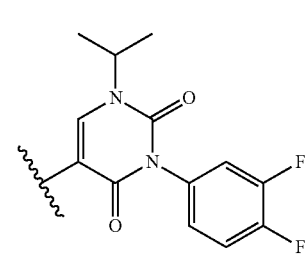

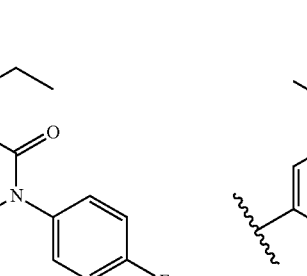

-continued

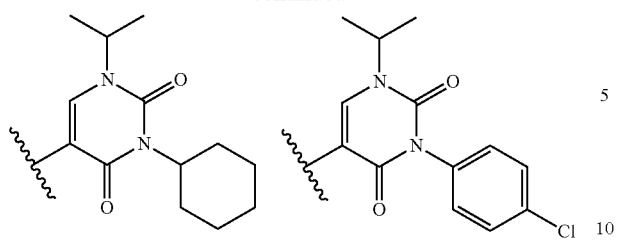
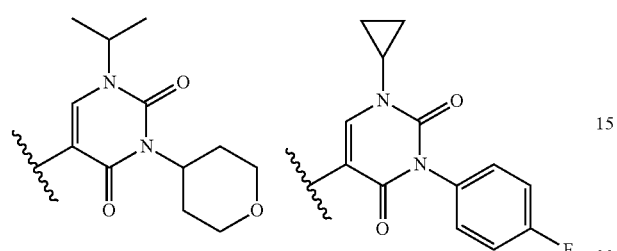
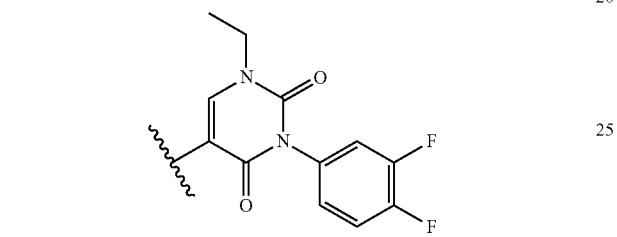
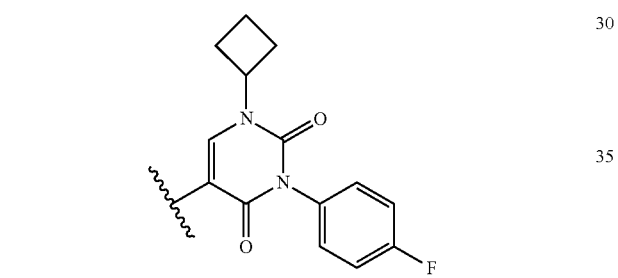
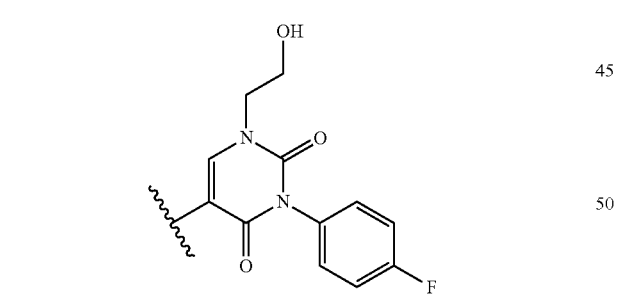
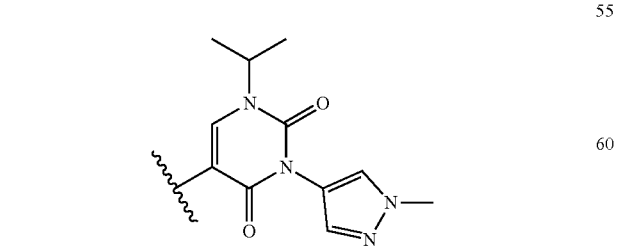

In one embodiment of Formula I, G is

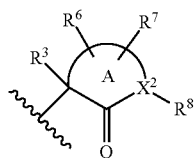

wherein $X^2$ is N, $R^3$ is absent, Ring A is a 6-membered heterocyclic ring having an additional ring nitrogen atom, and $R^7$ is hydrogen, wherein G has the formula A-2

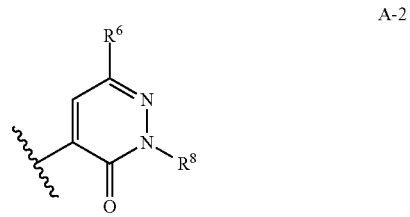

A-2 wherein $R^6$ is hydrogen, C1-C6 alkyl, or C3-C6 cycloalkyl, $R^7$ is hydrogen, and $R^8$ is as defined for Formula F In one embodiment of formula A-2, $R^8$ is $Ar^2$, wherein $Ar^2$ is phenyl optionally substituted with one or more substituents independently selected from halogen, C1-C2 alkyl and C1-C2 alkoxy. In one embodiment, $Ar^2$ is phenyl optionally substituted with one or more halogens. In one embodiment, Ring A is formula A-2 and is selected from the structures:

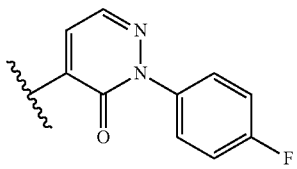
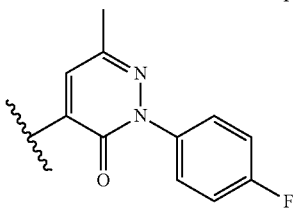
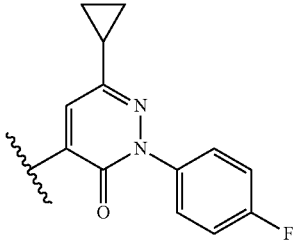
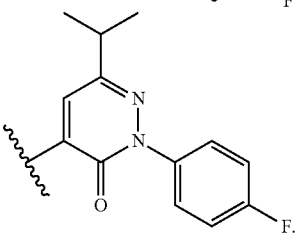

In one embodiment of Formula I, G is

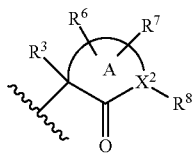

wherein $X^2$ is N, $R^3$ is absent, Ring A is a 6-membered heterocyclic ring, wherein G has the formula A-3

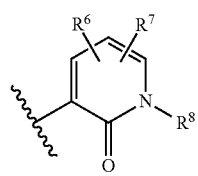

A-3 wherein $R^6$ is halogen, C1-C6 alkyl, C1-C6 alkoxy, or C3-C6 cycloalkyl, $R^7$ is hydrogen, provided that when $R^6$ is on the ring carbon atom adjacent to the carbon linked to the —NHC(═O)— moiety of Formula I, then $R^6$ is not halogen, and $R^8$ is as defined for Formula I. As used herein, "the ring carbon atom adjacent to the carbon linked to the —NHC(═O)— moiety of Formula I" refers to the carbon identified by the asterisk in the following structure:

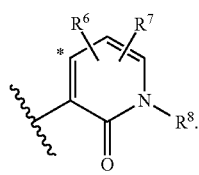

In one embodiment of formula A-3, $R^8$ is $Ar^2$, wherein $Ar^2$ is phenyl optionally substituted with one or more substituents independently selected from halogen, C1-C2 alkyl and C1-C2 alkoxy. In one embodiment, $Ar^2$ is phenyl optionally substituted with one or more halogens. In one embodiment, G is formula A-3 and is selected from the structures:

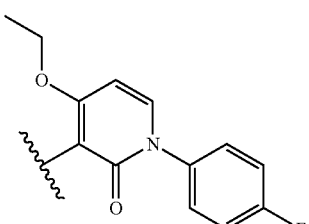

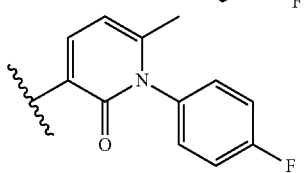

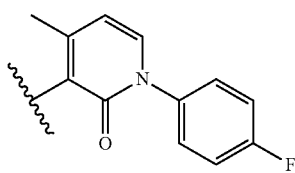

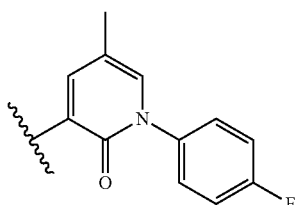

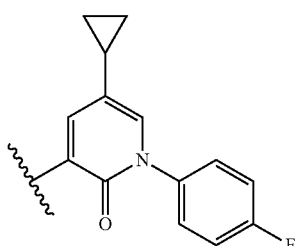

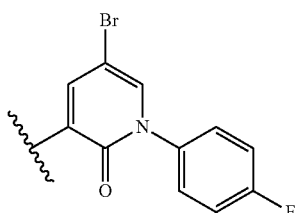

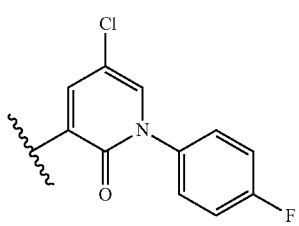

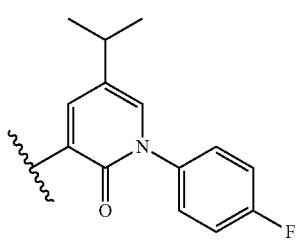

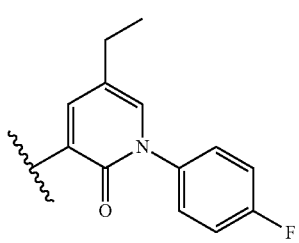

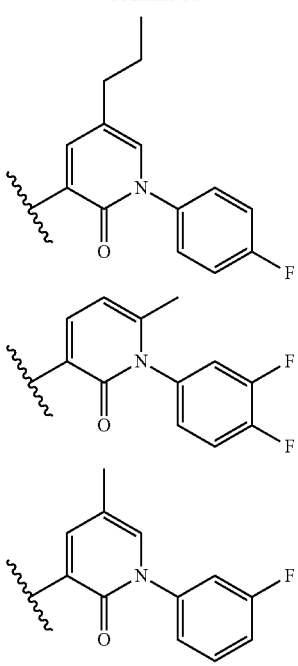

In one embodiment of Formula I, G is

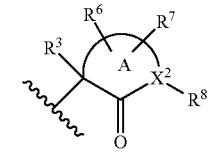

wherein $X^2$ is N, $R^3$ is absent, Ring A is a 6-membered heterocyclic ring having two additional ring nitrogen atoms, and $R^7$ is oxo or thiooxo, wherein G has the formula A-4

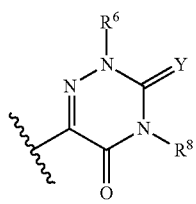

A-4 wherein Y is O or S, $R^6$ is C1-C6 alkyl, and $R^8$ is as defined for Formula I. In one embodiment of formula A-4, $R^8$ is $Ar^2$, wherein $Ar^2$ is phenyl optionally substituted with one or more substituents independently selected from halogen, C1-C2 alkyl and C1-C2 alkoxy. In one embodiment, $Ar^2$ is phenyl optionally substituted with one or more halogens. In one embodiment, G is formula A-4 and is selected from the structures:

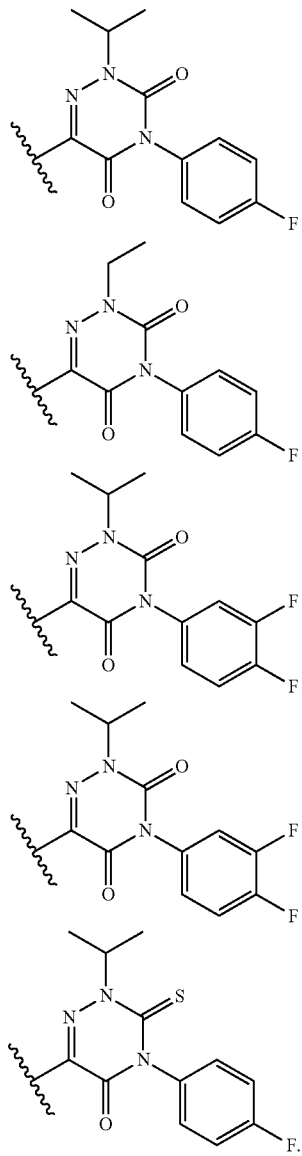

In one embodiment of Formula I, G is

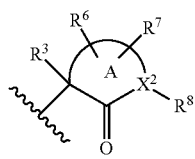

wherein $X^2$ is C, $R^3$ is absent, Ring A is a 6-membered heterocyclic ring having a ring nitrogen atom, wherein G has the formula A-5

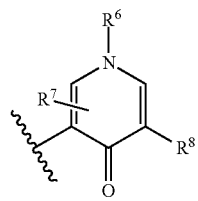
A-5 wherein R⁶ is C1-C6 alkyl, R⁷ is hydrogen, and R⁸ is as defined for Formula I. In one embodiment of formula A-5, R⁸ is Ar², wherein Ar² is phenyl optionally substituted with substituents independently selected from halogen, C1-C2 alkyl and C1-C2 alkoxy. In one embodiment, Ar² is phenyl optionally substituted with one or more halogens. In one embodiment, G is formula A-5 and is selected from the structures:

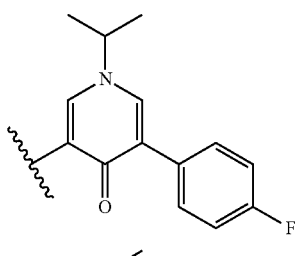

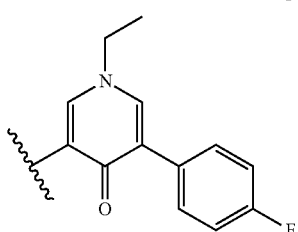

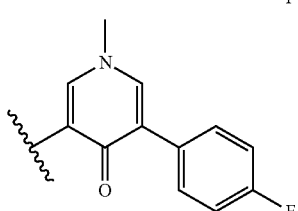

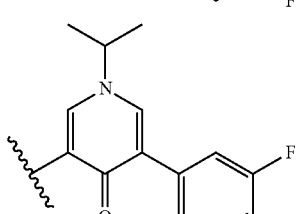

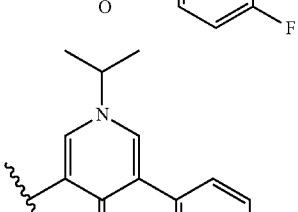

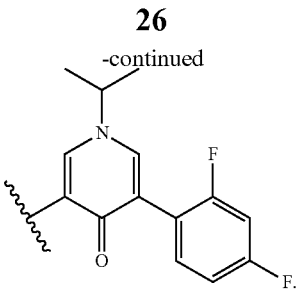

In one embodiment of Formula I, G is

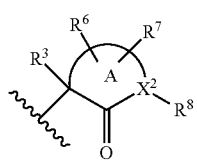

wherein X² is N, R³ is absent, Ring A is a 6-membered heterocyclic ring having two additional ring nitrogen atoms, wherein G has the formula A-6

A-6

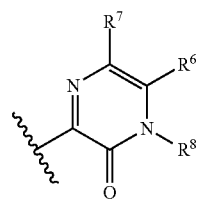

wherein R⁵ and R⁷ are hydrogen and R⁸ is as defined for Formula I. In one embodiment of formula A-6, R⁸ is Ar², wherein Ar² is phenyl optionally substituted with substituents independently selected from halogen, C1-C2 alkyl and C1-C2 alkoxy. In one embodiment, Ar² is phenyl optionally substituted with one or more halogens. In one embodiment, G is formula A-6 and has the structure:

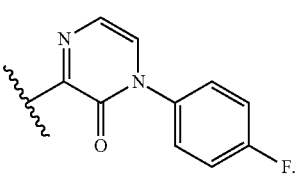 [SMILES: *c1nccn(-c2ccc(F)cc2)c1=O]

In one embodiment of Formula I, G is

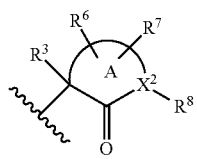

wherein X² is N, R³ is hydrogen or methyl, and Ring A is a 6-membered heterocyclic ring having a ring nitrogen atom, wherein G has the formula A-7

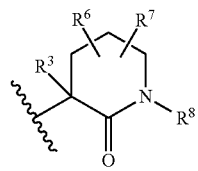

A-7 wherein $R^6$ and $R^7$ are hydrogen, or $R^6$ and $R^7$ are on the same carbon atom and $R^6$ and $R^7$ together with the carbon atom to which they are attached form a cyclopropyl ring, and $R^8$ is as defined for Formula I. In one embodiment of formula A-7, $R^8$ is $Ar^2$, wherein $Ar^2$ is phenyl optionally substituted with substituents independently selected from halogen, C1-C2 alkyl and C1-C2 alkoxy. In one embodiment, $Ar^2$ is phenyl optionally substituted with one or more halogens. In one embodiment, G is formula A-7 and is selected from the structures:

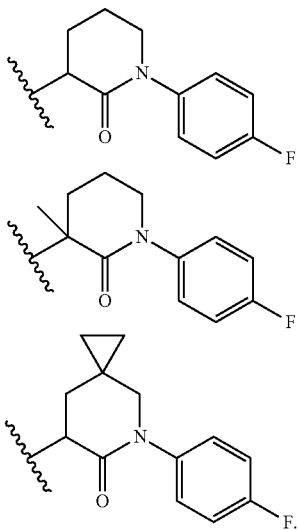

In one embodiment of Formula I, G is

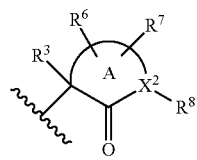

wherein $X^2$ is N, $R^3$ is absent, Ring A is a 5-membered heterocyclic ring having an additional ring nitrogen atom, wherein G has the formula A-8

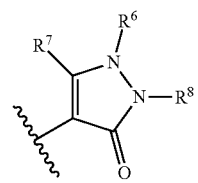

A-8 wherein $R^6$ is C1-C6 alkyl, $R^7$ is hydrogen or C1-C6 alkyl, and $R^x$ is as defined for Formula I. In one embodiment of formula A-8, $R^8$ is $Ar^2$, wherein $Ar^2$ is phenyl optionally substituted with substituents independently selected from halogen, C1-C2 alkyl and C1-C2 alkoxy. In one embodiment, $Ar^2$ is phenyl optionally substituted with one or more halogens. In one embodiment, G is formula A-8 and is selected from the structures:

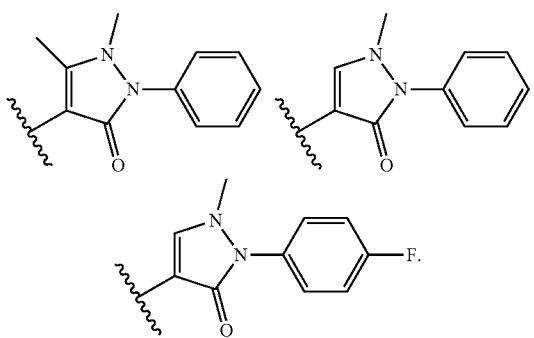

In one embodiment of Formula I, G is

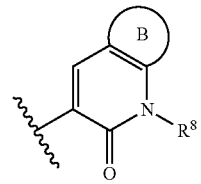

wherein Ring B and $R^8$ are as defined for Formula I.
In one embodiment of Formula I, G is

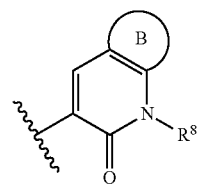

wherein Ring B is a 6-membered saturated carbocyclic optionally substituted with oxo. In one embodiment, G has the formula B-1

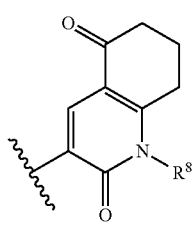

B-1 wherein $R^8$ is as defined for Formula I. In one embodiment of formula B-1, $R^8$ is $Ar^2$, wherein $Ar^2$ is phenyl optionally substituted with substituents independently selected from halogen, C1-C2 alkyl and C1-C2 alkoxy. In one embodiment, Ar² is phenyl optionally substituted with one or more halogens. In one embodiment, G is formula B-1 and is has the structure:

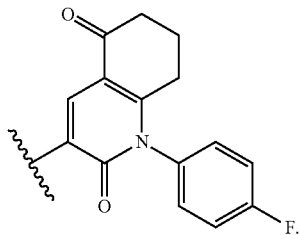 [SMILES: *c1cc2c(n(-c3ccc(F)cc3)c1=O)CCCC2=O]

In one embodiment of Formula I, G is

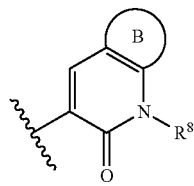

wherein Ring B is a 6-membered aromatic carbocyclic ring optionally substituted with OH. In one embodiment, G has the formula B-2

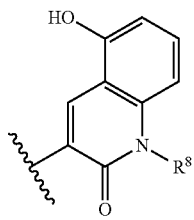

B-2 wherein R⁸ is as defined for Formula I. In one embodiment of formula B-2, R⁸ is Ar², wherein Ar² is phenyl optionally substituted with substituents independently selected from halogen, C1-C2 alkyl and C1-C2 alkoxy. In one embodiment, Ar² is phenyl optionally substituted with one or more halogens. In one embodiment of formula B-2, R⁸ is Ar², wherein Ar² is phenyl which is unsubstituted. In one embodiment, G is formula B-2 and is has the structure:

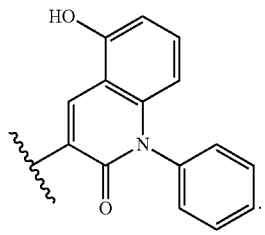 [SMILES: *c1cc2c(O)cccc2n(-c2ccccc2)c1=O]

In one embodiment, compounds of Formula I include Formula I-A, wherein:

X¹ is CH or N;
R¹ is hydrogen or C1-C6 alkyl;
R² is
(a) hydrogen,
(b) C1-C6 alkyl,
(c) hydroxyC1-C6 alkyl,
(g) (C1-C6 alkoxy)C1-C6 alkyl- wherein said alkyl portion is optionally substituted with OH, or
(h) Cyc¹;
Cyc¹ is a 3-4 membered cycloalkyl ring optionally substituted with 1-2 substituents independently selected from halogen, hydroxy, C1-C3 alkyl, hydroxyC1-C3 alkyl, C1-C3 alkoxy, (C1-C3 alkoxy)C1-C3 alkyl- and R'R"NC(=O)—;
X² is N, R³ is absent, Ring A is a 6-membered heterocyclic ring having one additional ring nitrogen atom, and R⁷ is oxo, wherein G has the formula I-AA

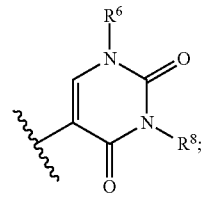

I-A

R⁶ is C1-C6 alkyl, hydroxyC1-C6 alkyl, C3-C6 cycloalkyl, (C3-C6 cycloalkyl)C1-C6 alkyl- or hetCyc²;
hetCyc² is a 4-6 membered saturated heterocyclic ring having a ring nitrogen atom and optionally substituted with C1-C6 alkyl;
R⁸ is Ar², hetAr², C3-C6 cycloalkyl, hetCyc³ or C1-C6 alkyl;
Ar² is phenyl optionally substituted with one or more substituents independently selected from halogen, C1-C2 alkyl and C1-C2 alkoxy;
hetAr² is a 5-6 membered heteroaryl having 1-2 ring nitrogen atoms and optionally substituted with one or more substituents independently selected from halogen, C1-C2 alkyl and C1-C2 alkoxy;
hetCyc³ is a 5-6 membered heterocyclic ring having a ring oxygen atom; and
R⁹ is hydrogen or halogen.

In one embodiment of Formula I-A, R¹ is hydrogen,
In one embodiment of Formula I-A, R⁹ is hydrogen.
In one embodiment of Formula I-A, R⁹ is halogen. In one embodiment of Formula I-A, R⁹ is fluoro.
In one embodiment of Formula I-A, X¹ is CH.
In one embodiment of Formula I-A, X¹ is CH and R⁹ is halogen. In one embodiment of Formula I-A, X¹ is CH and R⁹ is fluoro.
In one embodiment of Formula I-A, R¹ is H, X¹ is CH and R⁹ is fluoro.
In one embodiment of Formula I-A, R¹ is H, X¹ is CH, R⁸ is Ar² and R⁹ is fluoro.
In one embodiment of Formula I-A, X¹ is N.
In one embodiment of Formula I-A, X¹ is N and R⁹ is hydrogen.
In one embodiment of Formula I-A, R¹ is hydrogen, X¹ is N and R⁹ is hydrogen.
In one embodiment of Formula I-A, R¹ is hydrogen, X¹ is N, R⁸ is Ar² and R⁹ is hydrogen.
In one embodiment of Formula I-A, R² is H.
In one embodiment of Formula I-A, R² is C1-C6 alkyl.
In one embodiment of Formula I-A, R² is hydroxyC1-C6 alkyl.

In one embodiment of Formula I-A, $R^2$ is (C1-C6 alkoxy) C1-C6 alkyl- wherein said alkyl portion is optionally substituted with OH.

In one embodiment of Formula I-A, $R^2$ is $Cyc^1$.

In one embodiment of Formula I-A, $R^8$ is $Ar^2$. In one embodiment, $Ar^2$ is phenyl optionally substituted with one or more halogens.

In one embodiment of Formula I-A, $R^8$ is $hetAr^2$. In one embodiment of Formula I-A, $R^8$ is pyrazolyl optionally substituted with C1-C6 alkyl.

In one embodiment of Formula I-A, $R^8$ is C3-C6 cycloalkyl.

In one embodiment of Formula I-A, $R^8$ is $hetCyc^3$.

In one embodiment of Formula I-A, $R^8$ is C1-C6 alkyl.

In one embodiment, compounds of Formula I include Formula I-B, wherein:

$X^1$ is CH or N;
$R^1$ is hydrogen or C1-C6 alkyl;
$R^2$ is
(c) hydroxyC1-C6 alkyl,
(d) dihydroxyC2-C6 alkyl,
(e) C1-C6 fluoroalkyl optionally substituted with OH,
(f) (di-C1-C6 alkoxy)C2-C6 alkyl-,
(g) (C1-C6 alkoxy)C1-C6 alkyl- wherein said alkyl portion is optionally substituted with OH,
(h) $Cyc^1$,
(i) $Cyc^2$,
(j) ($hetCyc^1$)C1-C6 alkyl- wherein said alkyl portion is optionally substituted with OH,
(k) ($Ar^1$)C1-C6 alkyl- wherein said alkyl portion is optionally substituted with OH,
(l) ($hetAr^1$)C1-C6 alkyl- wherein said alkyl portion is optionally substituted with OH, or
(m)($HOSO_3$)C1-C6 alkyl-;

$Cyc^1$ is a 3-4 membered cycloalkyl ring optionally substituted with 1-2 substituents independently selected from halogen, hydroxy, C1-C3 alkyl, hydroxyC1-C3 alkyl, C1-C3 alkoxy, (C1-C3 alkoxy)C1-C3 alkyl- and R'R"NC(=O)—;

R' and R" are independently hydrogen or C1-C6 alkyl;

$Cyc^2$ is a 5-membered cycloalkyl ring substituted with 1-2 substituents independently selected from C1-C3 alkyl, (C1-C3 alkoxy)C1-C3 alkyl- and hydroxyC1-C3 alkyl-;

$hetCyc^1$ is a 5-6 membered saturated heterocyclic ring having 1-2 ring heteroatoms independently selected from O, N, and $SO_2$, wherein said ring is optionally substituted with oxo;

$Ar^1$ is phenyl;
$hetAr^1$ is pyridyl;
$X^2$ is N, $R^3$ is absent, Ring A is a 6-membered heterocyclic ring having an additional ring nitrogen atom, and $R^7$ is hydrogen, wherein G has the formula A-2

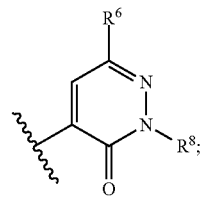

A-2

$R^6$ is hydrogen, C1-C6 alkyl, or C3-C6 cycloalkyl;
$R^8$ is $Ar^2$, $hetAr^2$, C3-C6 cycloalkyl, $hetCyc^3$ or C1-C6 alkyl;

$Ar^2$ is phenyl optionally substituted with one or more substituents independently selected from halogen, C1-C2 alkyl and C1-C2 alkoxy;

$hetAr^2$ is a 5-6 membered heteroaryl having 1-2 ring nitrogen atoms and optionally substituted with one or more substituents independently selected from halogen, C1-C2 alkyl and C1-C2 alkoxy;

$hetCyc^3$ is a 5-6 membered heterocyclic ring having a ring oxygen atom; and $R^9$ is hydrogen or halogen.

In one embodiment of Formula I-B, $X^1$ is CH.
In one embodiment of Formula I-B, $X^1$ is N.
In one embodiment of Formula I-B, $R^8$ is $Ar^2$. In one embodiment, $Ar^2$ is phenyl optionally substituted with one or more halogens.

In one embodiment of Formula I-B, $R^1$ is hydrogen.
In one embodiment of Formula I-B, $R^9$ is hydrogen.
In one embodiment of Formula I-B, $R^9$ is halogen. In one embodiment of Formula I-B, $R^9$ is fluoro.

In one embodiment of Formula I-B, $R^1$ is hydrogen, $X^1$ is CH, $R^8$ is $Ar^2$ wherein $Ar^2$ is as defined for Formula I-B, and $R^9$ is fluoro.

In one embodiment of Formula I-B, $R^1$ is hydrogen, $X^1$ is CH, $R^8$ is $Ar^2$ wherein $Ar^2$ is phenyl optionally substituted with one or more halogens, and $R^9$ is fluoro.

In one embodiment of Formula I-B, $R^1$ is hydrogen, $X^1$ is N, $R^8$ is $Ar^2$ wherein $Ar^2$ is as defined for Formula I-B, and $R^9$ is hydrogen.

In one embodiment of Formula I-B, $R^1$ is hydrogen, $X^1$ is N, $R^8$ is $Ar^2$ wherein $Ar^2$ is phenyl optionally substituted with one or more halogens, and $R^9$ is hydrogen.

In one embodiment, compounds of Formula I include Formula I-C, wherein:

$X^1$ is CH or N;
$R^1$ is hydrogen;
$R^2$ is
(c) hydroxyC1-C6 alkyl,
(e) C1-C6 fluoroalkyl optionally substituted with OH, or
(g) (C1-C6 alkoxy)C1-C6 alkyl- wherein said alkyl portion is optionally substituted with OH;

$X^2$ is N, $R^3$ is absent, Ring A is a 6-membered heterocyclic ring, wherein G has the formula A-3

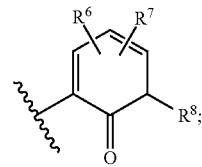

A-3

$R^6$ is halogen, C1-C6 alkyl, C1-C6 alkoxy, or C3-C6 cycloalkyl;
$R^7$ is hydrogen;
$R^8$ is $Ar^2$, $hetAr^2$, C3-C6 cycloalkyl, $hetCyc^3$ or C1-C6 alkyl, $Ar^2$ is phenyl optionally substituted with one or more substituents independently selected from halogen, C1-C2 alkyl and C1-C2 alkoxy;

$hetAr^2$ is a 5-6 membered heteroaryl having 1-2 ring nitrogen atoms and optionally substituted with one or more substituents independently selected from halogen, C1-C2 alkyl and C1-C2 alkoxy;

$hetCyc^3$ is a 5-6 membered heterocyclic ring having a ring oxygen atom; and $R^9$ is hydrogen or halogen.

In one embodiment of Formula I-C, $R^9$ is hydrogen.

In one embodiment of Formula I-C, $R^9$ is halogen. In one embodiment of Formula I-C, $R^9$ is fluoro.

In one embodiment of Formula I-C, $X^1$ is CH.

In one embodiment of Formula I-C, $X^1$ is CH and $R^9$ is halogen. In one embodiment of Formula I-C, $X^1$ is CH and $R^9$ is fluoro.

In one embodiment of Formula I-C, $X^1$ is N.

In one embodiment of Formula I-C, $X^1$ is N and $R^9$ is hydrogen.

In one embodiment of Formula I-C, $R^8$ is $Ar^2$. In one embodiment, $Ar^2$ is phenyl optionally substituted with one or more halogens.

In one embodiment of Formula I-C, $X^1$ is CH, $R^9$ is fluoro, and $R^8$ is $Ar^2$ wherein $Ar^2$ is phenyl optionally substituted with one or more halogens.

In one embodiment of Formula I-C, $X^1$ is N, $R^9$ is hydrogen, and $R^8$ is $Ar^2$ wherein $Ar^2$ is phenyl optionally substituted with one or more halogens.

In one embodiment, compounds of Formula I include Formula I-D, wherein:
$X^1$ is CH;
$R^1$ is hydrogen;
$R^2$ is
(c) hydroxyC1-C6 alkyl,
(e) C1-C6 fluoroalkyl optionally substituted with OH, or
(g) (C1-C6 alkoxy)C1-C6 alkyl- wherein said alkyl portion is optionally substituted with OH;
$R^3$ is absent;
$X^2$ is N;
$X^2$ is N, $R^3$ is absent, Ring A is a 6-membered heterocyclic ring having two additional ring nitrogen atoms, and R is oxo or thiooxo, wherein G has the formula

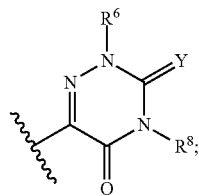

A-4

$R^6$ is C1-C6 alkyl,
Y is O or S;
$R^8$ is $Ar^2$, $hetAr^2$, C3-C6 cycloalkyl, $hetCyc^3$ or C1-C6 alkyl;
$Ar^2$ is phenyl optionally substituted with one or more substituents independently selected from halogen, C1-C2 alkyl and C1-C2 alkoxy;
$hetAr^2$ is a 5-6 membered heteroaryl having 1-2 ring nitrogen atoms and optionally substituted with one or more substituents independently selected from halogen, C1-C2 alkyl and C1-C2 alkoxy;
$hetCyc^3$ is a 5-6 membered heterocyclic ring having a ring oxygen atom; and
$R^9$ is hydrogen or halogen.

In one embodiment of Formula I-D, $R^x$ is $Ar^2$. In one embodiment, $Ar^2$ is phenyl optionally substituted with one or more halogens.

In one embodiment of Formula I-D, $R^9$ is halogen. In one embodiment of Formula I-D, $R^9$ is fluoro.

In one embodiment of Formula I-D, $Ar^2$ is phenyl optionally substituted with one or more halogens and $R^9$ is fluoro.

In one embodiment, compounds of Formula I include Formula I-E, wherein:
$X^1$ is CH or N;
$R^2$ is
(c) hydroxyC1-C6 alkyl,
(e) C1-C6 fluoroalkyl optionally substituted with OH, or
(g) (C1-C6 alkoxy)C1-C6 alkyl- wherein said alkyl portion is optionally substituted with OH;
$X^2$ is C, $R^3$ is absent, Ring A is a 6-membered heterocyclic ring having a ring nitrogen atom, wherein G has the formula A-5

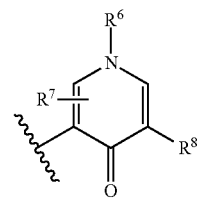

A-5

$R^6$ is C1-C6 alkyl;
$R^7$ is hydrogen;
$R^8$ is $Ar^2$, $hetAr^2$, C3-C6 cycloalkyl, $hetCyc^3$ or C1-C6 alkyl,
$Ar^2$ is phenyl optionally substituted with one or more substituents independently selected from halogen, C1-C2 alkyl and C1-C2 alkoxy;
$hetAr^2$ is a 5-6 membered heteroaryl having 1-2 ring nitrogen atoms and optionally substituted with one or more substituents independently selected from halogen, C1-C2 alkyl and C1-C2 alkoxy;
$hetCyc^3$ is a 5-6 membered heterocyclic ring having a ring oxygen atom; and
$R^9$ is hydrogen or halogen.

In one embodiment of Formula I-E, $R^1$ is hydrogen.

In one embodiment of Formula I-E, $X^1$ is CH.

In one embodiment of Formula I-E, $X^1$ is N.

In one embodiment of Formula I-E, $R^8$ is $Ar^2$. In one embodiment, $Ar^2$ is phenyl optionally substituted with one or more halogens.

In one embodiment of Formula I-E, $R^9$ is hydrogen.

In one embodiment of Formula I-E, $R^9$ is fluoro.

In one embodiment of Formula I-E, $R^1$ is hydrogen, $X^1$ is CH, $Ar^2$ is phenyl optionally substituted with one or more halogens, and $R^9$ is fluoro.

In one embodiment of Formula I-E, $R^1$ is hydrogen, $X^1$ is N, $Ar^2$ is phenyl optionally substituted with one or more halogens, and $R^9$ is hydrogen.

In one embodiment, compounds of Formula I include Formula I-F, wherein:
$X^1$ is CH;
$R^1$ is hydrogen;
$R^2$ is (c) hydroxyC1-C6 alkyl;
$X^2$ is N, $R^3$ is absent, Ring A is a 6-membered heterocyclic ring having two additional ring nitrogen atoms, wherein G has the formula A-6

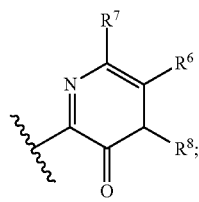

A-6

R$^6$ is hydrogen;
R$^7$ is hydrogen;
R$^8$ is Ar$^2$, hetAr$^2$, C3-C6 cycloalkyl, hetCyc$^3$ or C1-C6 alkyl;
Ar$^2$ is phenyl optionally substituted with one or more substituents independently selected from halogen, C1-C2 alkyl and C1-C2 alkoxy;
hetAr$^2$ is a 5-6 membered heteroaryl having 1-2 ring nitrogen atoms and optionally substituted with one or more substituents independently selected from halogen, C1-C2 alkyl and C1-C2 alkoxy;
hetCyc$^3$ is a 5-6 membered heterocyclic ring having a ring oxygen atom; and
R$^9$ is hydrogen or halogen.

In one embodiment of Formula I-F, R$^8$ is Ar$^2$. In one embodiment, Ar$^2$ is phenyl optionally substituted with one or more halogens.

In one embodiment of Formula I-F, R$^9$ is halogen. In one embodiment of Formula I-F, R$^9$ is fluoro.

In one embodiment of Formula I-F, Ar$^2$ is phenyl optionally substituted with one or more halogens, and R$^9$ is fluoro.

In one embodiment, compounds of Formula I include Formula I-G, wherein:
X$^1$ is CH;
R$^1$ is hydrogen;
R$^2$ is (c) hydroxyC1-C6 alkyl;
X$^2$ is N, R$^3$ is hydrogen or methyl, and Ring A is a 6-membered heterocyclic ring having a ring nitrogen atom, wherein G has the formula A-7

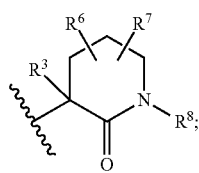

A-7

R$^6$ is hydrogen and R$^7$ is hydrogen,
or R$^6$ and R$^7$ are on the same carbon atom and R$^5$ and R$^7$ together with the carbon atom to which they are attached form a cyclopropyl ring;
R$^8$ is Ar$^2$, hetAr$^2$, C3-C6 cycloalkyl, hetCyc$^3$ or C1-C6 alkyl;
Ar$^2$ is phenyl optionally substituted with one or more substituents independently selected from halogen, C1-C2 alkyl and C1-C2 alkoxy;
hetAr$^2$ is a 5-6 membered heteroaryl having 1-2 ring nitrogen atoms and optionally substituted with one or more substituents independently selected from halogen, C1-C2 alkyl and C1-C2 alkoxy;
hetCyc$^3$ is a 5-6 membered heterocyclic ring having a ring oxygen atom; and
R$^9$ is hydrogen or halogen.

In one embodiment of Formula I-G, R$^8$ is Ar$^2$. In one embodiment, Ar$^2$ is phenyl optionally substituted with one or more halogens.

In one embodiment of Formula I-G, R$^9$ is halogen. In one embodiment of Formula I-G, R$^9$ is fluoro.

In one embodiment of Formula I-G, Ar$^2$ is phenyl optionally substituted with one or more halogens, and R$^9$ is fluoro.

In one embodiment, compounds of Formula I include Formula I-H, wherein:
X$^1$ is CH;
R$^1$ is hydrogen;
R$^2$ is (c) hydroxyC1-C6 alkyl;
X$^2$ is N, R$^3$ is absent, Ring A is a 5-membered heterocyclic ring having an additional ring nitrogen atom, wherein G has the formula A-8

A-8

R$^6$ is C1-C6 alkyl;
R$^7$ is hydrogen or C1-C6 alkyl;
R$^8$ is Ar$^2$, hetAr$^2$, C3-C6 cycloalkyl, hetCyc$^3$ or C1-C6 alkyl;
Ar$^2$ is phenyl optionally substituted with one or more substituents independently selected from halogen, C1-C2 alkyl and C1-C2 alkoxy;
hetAr$^2$ is a 5-6 membered heteroaryl having 1-2 ring nitrogen atoms and optionally substituted with one or more substituents independently selected from halogen, C1-C2 alkyl and C1-C2 alkoxy;
hetCyc$^3$ is a 5-6 membered heterocyclic ring having a ring oxygen atom; and
R$^9$ is hydrogen or halogen.

In one embodiment of Formula I-H, R$^8$ is Ar$^2$. In one embodiment of Formula I-H, R$^8$ is Ar$^2$ wherein Ar$^2$ is phenyl optionally substituted with one or more halogens.

In one embodiment of Formula I-H, R$^9$ is halogen. In one embodiment of Formula I-H, R$^9$ is fluoro.

In one embodiment of Formula I-H, R$^x$ is Ar$^2$ wherein Ar$^2$ is phenyl optionally substituted with one or more halogens, and R$^9$ is fluoro.

In one embodiment, compounds of Formula I include Formula I-I, wherein:
X$^1$ is CH;
R$^1$ is hydrogen;
R$^2$ is (c) hydroxyC1-C6 alkyl;
G is formula B-1

B-1

R⁸ is Ar², hetAr², C3-C6 cycloalkyl, hetCyc³ or C1-C6 alkyl;

Ar² is phenyl optionally substituted with one or more substituents independently selected from halogen, C1-C2 alkyl and C1-C2 alkoxy;

hetAr² is a 5-6 membered heteroaryl having 1-2 ring nitrogen atoms and optionally substituted with one or more substituents independently selected from halogen, C1-C2 alkyl and C1-C2 alkoxy;

hetCyc³ is a 5-6 membered heterocyclic ring having a ring oxygen atom; and

R⁹ is hydrogen or halogen.

In one embodiment of Formula I-I, R⁸ is Ar². In one embodiment, Ar² is phenyl optionally substituted with one or more halogens.

In one embodiment of Formula I-I, R⁹ is halogen. In one embodiment of Formula I-I, R⁹ is fluoro.

In one embodiment of Formula I-I, Ar² is phenyl optionally substituted with one or more halogens, and R⁹ is fluoro.

In one embodiment, compounds of Formula I include Formula I-J, wherein:

X¹ is CH;
R¹ is hydrogen;
R² is (c) hydroxyC1-C6 alkyl;
G is formula B-2

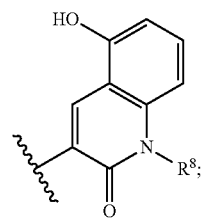

R⁸ is Ar², hetAr², C3-C6 cycloalkyl, hetCyc³ or C1-C6 alkyl,

Ar² is phenyl optionally substituted with one or more substituents independently selected from halogen, C1-C2 alkyl and C1-C2 alkoxy;

hetAr² is a 5-6 membered heteroaryl having 1-2 ring nitrogen atoms and optionally substituted with one or more substituents independently selected from halogen, C1-C2 alkyl and C1-C2 alkoxy;

hetCyc³ is a 5-6 membered heterocyclic ring having a ring oxygen atom; and

R⁹ is hydrogen or halogen.

In one embodiment of Formula I-J, R⁸ is Ar². In one embodiment, Ar² is phenyl optionally substituted with one or more halogens.

In one embodiment of Formula I-J, R⁹ is halogen. In one embodiment of Formula I-J, R⁹ is fluoro.

In one embodiment of Formula I-J, Ar² is phenyl optionally substituted with one or more halogens, and R⁹ is fluoro.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include hydrochloride salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

In one embodiment, the compounds of Formula I include the compounds of Examples 1-201 and stereoisomers and pharmaceutically acceptable salts and solvates thereof. In one embodiment, the compounds of Examples 1-201 are in the free base form. In one embodiment, one or more compounds of Examples 1-201 are hydrochloride acid salts.

In one embodiment, the compound of formula I is a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof.

In one embodiment, the compound of formula I is a compound of Example No. 25, or a pharmaceutically acceptable salt or solvate thereof.

In one embodiment, the compound of formula I is a compound of Example No. 37, or a pharmaceutically acceptable salt or solvate thereof.

In one embodiment, the compound of formula I is a compound of Example No. 46, or a pharmaceutically acceptable salt or solvate thereof.

In one embodiment, the compound of formula I is a compound of Example No. 48, or a pharmaceutically acceptable salt or solvate thereof.

In one embodiment, the compound of formula I is a compound of Example No. 55, or a pharmaceutically acceptable salt or solvate thereof.

In one embodiment, the compound of formula I is a compound of Example No. 58, or a pharmaceutically acceptable salt or solvate thereof.

In one embodiment, the compound of formula I is a compound of Example No. 72, or a pharmaceutically acceptable salt or solvate thereof.

In one embodiment, the compound of formula I is a compound of Example No. 76, or a pharmaceutically acceptable salt or solvate thereof.

In one embodiment, the compound of formula I is a compound of Example No. 77, or a pharmaceutically acceptable salt or solvate thereof.

In one embodiment, the compound of formula I is a compound of Example No. 78, or a pharmaceutically acceptable salt or solvate thereof.

In one embodiment, the compound of formula I is a compound of Example No. 83, or a pharmaceutically acceptable salt or solvate thereof.

In one embodiment, the compound of formula I is a compound of Example No. 84, or a pharmaceutically acceptable salt or solvate thereof.

In one embodiment, the compound of formula I is a compound of Example No. 85, or a pharmaceutically acceptable salt or solvate thereof.

In one embodiment, the compound of formula I is a compound of Example No. 91, or a pharmaceutically acceptable salt or solvate thereof.

In one embodiment, the compound of formula I is a compound of Example No. 97, or a pharmaceutically acceptable salt or solvate thereof.

In one embodiment, the compound of formula I is a compound of Example No. 100, or a pharmaceutically acceptable salt or solvate thereof.

In one embodiment, the compound of formula I is a compound of Example No. 103, or a pharmaceutically acceptable salt or solvate thereof.

In one embodiment, the compound of formula I is a compound of Example No. 105, or a pharmaceutically acceptable salt or solvate thereof.

In one embodiment, the compound of formula I is a compound of Example No. 107, or a pharmaceutically acceptable salt or solvate thereof.

In one embodiment, the compound of formula I is a compound of Example No. 108, or a pharmaceutically acceptable salt or solvate thereof.

In one embodiment, the compound of formula I is a compound of Example No. 114, or a pharmaceutically acceptable salt or solvate thereof.

In one embodiment, the compound of formula I is a compound of Example No. 115, or a pharmaceutically acceptable salt or solvate thereof.

In one embodiment, the compound of formula I is a compound of Example No. 119, or a pharmaceutically acceptable salt or solvate thereof.

In one embodiment, the compound of formula I is a compound of Example No. 121, or a pharmaceutically acceptable salt or solvate thereof.

In one embodiment, the compound of formula I is a compound of Example No. 124, or a pharmaceutically acceptable salt or solvate thereof.

In one embodiment, the compound of formula I is a compound of Example No. 125, or a pharmaceutically acceptable salt or solvate thereof.

In one embodiment, the compound of formula I is a compound of Example No. 126, or a pharmaceutically acceptable salt or solvate thereof.

In one embodiment, the compound of formula I is a compound of Example No. 127, or a pharmaceutically acceptable salt or solvate thereof.

In one embodiment, the compound of formula I is a compound of Example No. 129, or a pharmaceutically acceptable salt or solvate thereof.

In one embodiment, the compound of formula I is a compound of Example No. 151, or a pharmaceutically acceptable salt or solvate thereof.

In one embodiment, the compound of formula I is a compound of Example No. 152, or a pharmaceutically acceptable salt or solvate thereof.

In one embodiment, the compound of formula I is a compound of Example No. 163, or a pharmaceutically acceptable salt or solvate thereof.

In one embodiment, the compound of formula I is a compound of Example No. 169, or a pharmaceutically acceptable salt or solvate thereof.

In one embodiment, the compound of formula I is a compound of Example No. 188, or a pharmaceutically acceptable salt or solvate thereof.

In one embodiment, the compound of formula I is a compound of Example No. 190, or a pharmaceutically acceptable salt or solvate thereof.

In one embodiment, the compound of formula I is a compound of Example No. 199, or a pharmaceutically acceptable salt or solvate thereof.

In one embodiment, the compound of formula I is a compound of Example No. 200, or a pharmaceutically acceptable salt or solvate thereof.

In one embodiment, the compound of formula I is a compound of Example No. 201, or a pharmaceutically acceptable salt or solvate thereof.

In one embodiment, compounds of Formula I include compounds of Formula II and stereoisomers, tautomers and pharmaceutically acceptable salts thereof, wherein:

$X^1$ is CH or N;
$R^1$ is hydrogen or C1-C6 alkyl;
$R^2$ is
(a) hydrogen,
(b) C1-C6 alkyl,
(c) hydroxyC1-C6 alkyl,
(d) dihydroxyC2-C6 alkyl,
(e) C1-C6 fluoroalkyl optionally substituted with OH,
(g) (C1-C6 alkoxy)C1-C6 alkyl- wherein said alkyl portion is optionally substituted with OH,
(h) $Cyc^1$,
(i) $Cyc^2$,
(j) (hetCyc$^1$)C1-C6 alkyl- wherein said alkyl portion is optionally substituted with OH,
(k) (Ar$^1$)C1-C6 alkyl- wherein said alkyl portion is optionally substituted with OH,
(l) (hetAr$^1$)C1-C6 alkyl- wherein said alkyl portion is optionally substituted with OH, or
(m) (HOSO$_3$)C1-C6 alkyl-;

$Cyc^1$ is a 3-4 membered cycloalkyl ring optionally substituted with 1-2 substituents independently selected from halogen, hydroxy, hydroxyC1-C3 alkyl, C1-C3 alkoxy, (C1-C3 alkoxy)C1-C3 alkyl-, and R'R"NC(=O)—;

R' and R" are independently selected from C1-C6 alkyl;
$Cyc^2$ is a 5-membered cycloalkyl ring substituted with 1-2 substituents independently selected from C1-C3 alkyl, (C1-C3 alkoxy)C1-C3 alkyl- and hydroxyC1-C3 alkyl-;

hetCyc$^1$ is a 5-6 membered saturated heterocyclic ring having 1-2 ring heteroatoms independently selected from O, N and SO$_2$, wherein said ring is optionally substituted with oxo;

Ar$^1$ is phenyl;
hetAr$^1$ is pyridyl;
G is

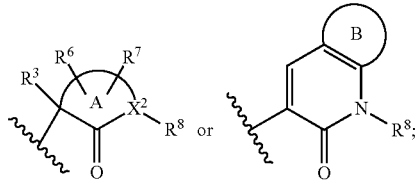

$X^2$ is C or N;
Ring A, including the atoms at the points of attachment, is a 5-6 membered heterocyclic ring optionally having an additional 1-2 ring nitrogen atoms when $X^2$ is N and having one ring nitrogen atom when $X^2$ is C;

$R^3$ is hydrogen or absent;
$R^6$ is hydrogen, halogen, C1-C6 alkyl, C1-C6 alkoxy, hydroxyC1-C6 alkyl, C3-C6 cycloalkyl, (C3-C6 cycloalkyl)C1-C6 alkyl- or hetCyc$^2$, provided that when $R^6$ is on the ring carbon atom adjacent to the carbon linked to the —NHC(=O)— moiety of Formula I, then $R^6$ is not halogen;

$R^7$ is hydrogen, C1-C6 alkyl, oxo or thioxo;
hetCyc$^2$ is a 4 membered saturated heterocyclic ring having a ring nitrogen atom substituted with C1-C6 alkyl;

Ring B, including the atoms at the points of attachment, is a 6-membered saturated carbocyclic optionally substituted with oxo or a 6-membered aromatic carbocyclic ring optionally substituted with OH;

R⁸ is Ar², hetAr², C3-C6 cycloalkyl, hetCyc³ or C1-C6 alkyl;

Ar² is phenyl optionally substituted with one or more substituents independently selected from halogen;

hetAr² is a 5-6 membered heteroaryl having 1-2 ring nitrogen atoms and optionally substituted with one or more substituents independently selected from C1-C2 alkyl; and R⁹ is hydrogen or halogen.

In one embodiment of Formula II, G is

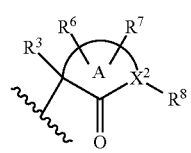

wherein X² is N, R³ is absent, Ring A is a 6-membered heterocyclic ring having one additional ring nitrogen atom, and R⁷ is oxo, such that G has the formula A-1

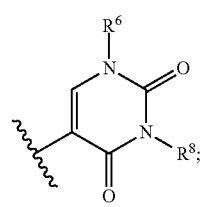

wherein R⁶ is C1-C6 alkyl, hydroxyC1-C6 alkyl, C3-C6 cycloalkyl, (C3-C6 cycloalkyl)C1-C6 alkyl- or hetCyc², and hetCyc² and R⁸ are as defined for Formula II.

In one embodiment of Formula II, G is

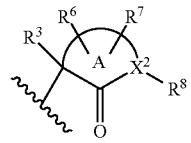

wherein X² is N, R³ is absent, Ring A is a 6-membered heterocyclic ring having an additional ring nitrogen atom, and R⁷ is hydrogen, such that G has the formula A-2

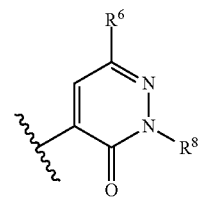

wherein R⁶ is hydrogen, C1-C6 alkyl, or C3-C6 cycloalkyl, R⁷ is hydrogen, and R⁸ is as defined for Formula II.

In one embodiment of Formula II, G is

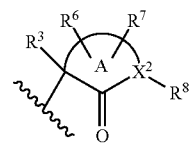

wherein X² is N, R³ is absent, Ring A is a 6-membered heterocyclic ring, such that G has the formula A-3

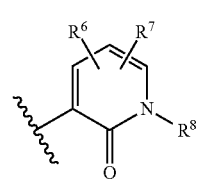

wherein R⁶ is halogen, C1-C6 alkyl, C1-C6 alkoxy, or C3-C6 cycloalkyl, R⁷ is hydrogen, provided that when R⁶ is on the ring carbon atom adjacent to the carbon linked to the —NHC(=O)— moiety of Formula II, then R⁶ is not halogen, and R⁸ is as defined for Formula II. As used herein, "the ring carbon atom adjacent to the carbon linked to the —NHC(=O)— moiety of Formula II" refers to the carbon identified by the asterisk in the following structure:

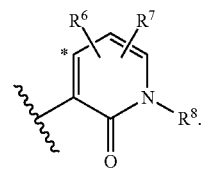

In one embodiment of Formula II, G is

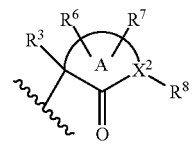

wherein X² is N, R³ is absent, Ring A is a 6-membered heterocyclic ring having two additional ring nitrogen atoms, and R⁷ is oxo or thiooxo, such that G has the formula A-4

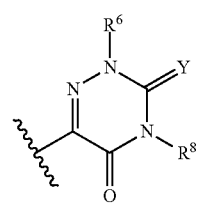

wherein Y is O or S, R⁶ is C1-C6 alkyl, and R⁸ is as defined for Formula II.

In one embodiment of Formula II, G is

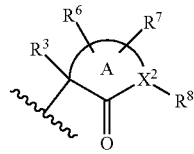

wherein $X^2$ is C, $R^3$ is absent, Ring A is a 6-membered heterocyclic ring having a ring nitrogen atom, such that G has the formula A-5

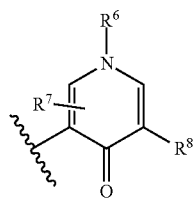

A-5 wherein $R^6$ is C1-C6 alkyl, $R^7$ is hydrogen, and $R^8$ is as defined for Formula II.

In one embodiment of Formula II, G is

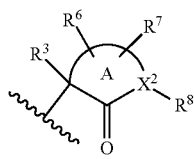

wherein $X^2$ is N, $R^3$ is absent, Ring A is a 6-membered heterocyclic ring having two additional ring nitrogen atoms, such that G has the formula A-6

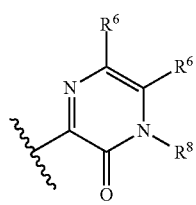

A-6 wherein $R^5$ and $R^7$ are hydrogen and $R^8$ is as defined for Formula II.

In one embodiment of Formula II, G is

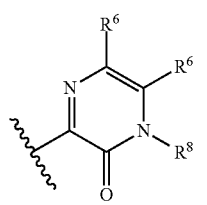

wherein $X^2$ is N, $R^3$ is hydrogen or methyl, and Ring A is a 6-membered heterocyclic ring having a ring nitrogen atom, such that G has the formula A-7

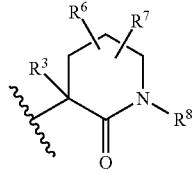

A-7 wherein $R^6$ and $R^7$ are hydrogen, and $R^8$ is as defined for Formula II.

In one embodiment of Formula II, G is

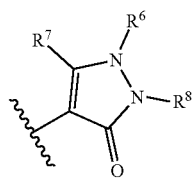

wherein $X^2$ is N, $R^3$ is absent, Ring A is a 5-membered heterocyclic ring having an additional ring nitrogen atom, such that G has the formula A-8

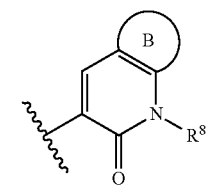

A-8 wherein $R^6$ is C1-C6 alkyl, $R^7$ is hydrogen or C1-C6 alkyl, and $R^8$ is as defined for Formula II.

In one embodiment of Formula II, G is

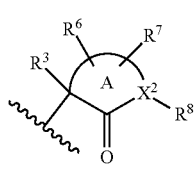

wherein Ring B and $R^8$ are as defined for Formula II.

In one embodiment of Formula II, G is

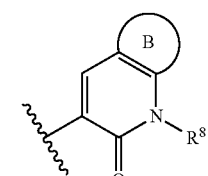

wherein Ring B is a 6-membered saturated carbocyclic optionally substituted with oxo.

In one embodiment of Formula II, G has the formula B-1

B-1 wherein $R^8$ is as defined for Formula II.

In one embodiment, the compound of Formula II is a compound of Example No. 2, 3, 4, 5, 6, 7, 8, 12, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 50, 51, 52, 53, 54, 55, 56, 57, 58, 59, 60, 61, 62, 63, 64, 65, 67, 68, 69, 70, 71, 72, 73, 75, 76, 77, 79, 80, 81, 84, 86, 87, 88, 89, 90, 91, 92, 93, 94, 95, 96, 97, 98, 99, 100, 101, 102, 103, 104, 105, 106, 107, 108, 109, 110, 113, 114, 115, 116, 117, 118, 119, 120, 121, 122, 128, 142, 144, 145, 146, 147, 148, 150, 151, 152, 153, 154, 155, 156, 157, 158, 159, 160, 161, 162, 163, 164, 166, 167, 168, 169, 170, 171, 172, 173, 179, 181, 182, 183, 184, 185, 186, 187, 189, 191, 192, 193, 194, 195, 196, or 197, or a pharmaceutically acceptable salt or solvate thereof.

In one embodiment, the compound of Formula II is a compound of Example No. 2, or a pharmaceutically acceptable salt or solvate thereof.

In one embodiment, the compound of Formula II is a compound of Example No. 3, or a pharmaceutically acceptable salt or solvate thereof.

In one embodiment, the compound of Formula II is a compound of Example No. 4, or a pharmaceutically acceptable salt or solvate thereof.

In one embodiment, the compound of Formula II is a compound of Example No. 5, or a pharmaceutically acceptable salt or solvate thereof.

In one embodiment, the compound of Formula II is a compound of Example No. 6, or a pharmaceutically acceptable salt or solvate thereof.

In one embodiment, the compound of Formula II is a compound of Example No. 7, or a pharmaceutically acceptable salt or solvate thereof.

In one embodiment, the compound of Formula II is a compound of Example No. 8, or a pharmaceutically acceptable salt or solvate thereof.

In one embodiment, the compound of Formula IT is a compound of Example No. 12, or a pharmaceutically acceptable salt or solvate thereof.

In one embodiment, the compound of Formula II is a compound of Example No. 13, or a pharmaceutically acceptable salt or solvate thereof.

In one embodiment, the compound of Formula II is a compound of Example No. 14, or a pharmaceutically acceptable salt or solvate thereof.

In one embodiment, the compound of Formula II is a compound of Example No. 16, or a pharmaceutically acceptable salt or solvate thereof.

In one embodiment, the compound of Formula II is a compound of Example No. 17, or a pharmaceutically acceptable salt or solvate thereof.

In one embodiment, the compound of Formula II is a compound of Example No. 18, or a pharmaceutically acceptable salt or solvate thereof.

In one embodiment, the compound of Formula II is a compound of Example No. 19, or a pharmaceutically acceptable salt or solvate thereof.

In one embodiment, the compound of Formula IT is a compound of Example No. 20, or a pharmaceutically acceptable salt or solvate thereof.

In one embodiment, the compound of Formula II is a compound of Example No. 21, or a pharmaceutically acceptable salt or solvate thereof.

In one embodiment, the compound of Formula II is a compound of Example No. 22, or a pharmaceutically acceptable salt or solvate thereof.

In one embodiment, the compound of Formula II is a compound of Example No. 23, or a pharmaceutically acceptable salt or solvate thereof.

In one embodiment, the compound of Formula II is a compound of Example No. 24, or a pharmaceutically acceptable salt or solvate thereof.

In one embodiment, the compound of Formula II is a compound of Example No. 25, or a pharmaceutically acceptable salt or solvate thereof.

In one embodiment, the compound of Formula II is a compound of Example No. 26, or a pharmaceutically acceptable salt or solvate thereof.

In one embodiment, the compound of Formula II is a compound of Example No. 27, or a pharmaceutically acceptable salt or solvate thereof.

In one embodiment, the compound of Formula IT is a compound of Example No. 28, or a pharmaceutically acceptable salt or solvate thereof.

In one embodiment, the compound of Formula II is a compound of Example No. 29, or a pharmaceutically acceptable salt or solvate thereof.

In one embodiment, the compound of Formula II is a compound of Example No. 30, or a pharmaceutically acceptable salt or solvate thereof.

In one embodiment, the compound of Formula II is a compound of Example No. 31, or a pharmaceutically acceptable salt or solvate thereof.

In one embodiment, the compound of Formula II is a compound of Example No. 32, or a pharmaceutically acceptable salt or solvate thereof.

In one embodiment, the compound of Formula II is a compound of Example No. 33, or a pharmaceutically acceptable salt or solvate thereof.

In one embodiment, the compound of Formula II is a compound of Example No. 34, or a pharmaceutically acceptable salt or solvate thereof.

In one embodiment, the compound of Formula IT is a compound of Example No. 35, or a pharmaceutically acceptable salt or solvate thereof.

In one embodiment, the compound of Formula II is a compound of Example No. 36, or a pharmaceutically acceptable salt or solvate thereof.

In one embodiment, the compound of Formula II is a compound of Example No. 37, or a pharmaceutically acceptable salt or solvate thereof.

In one embodiment, the compound of Formula II is a compound of Example No. 38, or a pharmaceutically acceptable salt or solvate thereof.

In one embodiment, the compound of Formula II is a compound of Example No. 39, or a pharmaceutically acceptable salt or solvate thereof.

In one embodiment, the compound of Formula II is a compound of Example No. 40, or a pharmaceutically acceptable salt or solvate thereof.

In one embodiment, the compound of Formula II is a compound of Example No. 41, or a pharmaceutically acceptable salt or solvate thereof.

In one embodiment, the compound of Formula II is a compound of Example No. 42, or a pharmaceutically acceptable salt or solvate thereof.

In one embodiment, the compound of Formula II is a compound of Example No. 43, or a pharmaceutically acceptable salt or solvate thereof.

In one embodiment, the compound of Formula II is a compound of Example No. 44, or a pharmaceutically acceptable salt or solvate thereof.

In one embodiment, the compound of Formula II is a compound of Example No. 45, or a pharmaceutically acceptable salt or solvate thereof.

In one embodiment, the compound of Formula II is a compound of Example No. 46, or a pharmaceutically acceptable salt or solvate thereof.

In one embodiment, the compound of Formula II is a compound of Example No. 47, or a pharmaceutically acceptable salt or solvate thereof.

In one embodiment, the compound of Formula II is a compound of Example No. 50, or a pharmaceutically acceptable salt or solvate thereof.

In one embodiment, the compound of Formula II is a compound of Example No. 51, or a pharmaceutically acceptable salt or solvate thereof.

In one embodiment, the compound of Formula II is a compound of Example No. 52, or a pharmaceutically acceptable salt or solvate thereof.

In one embodiment, the compound of Formula II is a compound of Example No. 53, or a pharmaceutically acceptable salt or solvate thereof.

In one embodiment, the compound of Formula II is a compound of Example No. 54, or a pharmaceutically acceptable salt or solvate thereof.

In one embodiment, the compound of Formula II is a compound of Example No. 55, or a pharmaceutically acceptable salt or solvate thereof.

In one embodiment, the compound of Formula II is a compound of Example No. 56, or a pharmaceutically acceptable salt or solvate thereof.

In one embodiment, the compound of Formula II is a compound of Example No. 57, or a pharmaceutically acceptable salt or solvate thereof.

In one embodiment, the compound of Formula II is a compound of Example No. 58, or a pharmaceutically acceptable salt or solvate thereof.

In one embodiment, the compound of Formula II is a compound of Example No. 59, or a pharmaceutically acceptable salt or solvate thereof.

In one embodiment, the compound of Formula II is a compound of Example No. 60, or a pharmaceutically acceptable salt or solvate thereof.

In one embodiment, the compound of Formula II is a compound of Example No. 61, or a pharmaceutically acceptable salt or solvate thereof.

In one embodiment, the compound of Formula II is a compound of Example No. 62, or a pharmaceutically acceptable salt or solvate thereof.

In one embodiment, the compound of Formula II is a compound of Example No. 63, or a pharmaceutically acceptable salt or solvate thereof.

In one embodiment, the compound of Formula II is a compound of Example No. 64, or a pharmaceutically acceptable salt or solvate thereof.

In one embodiment, the compound of Formula II is a compound of Example No. 65, or a pharmaceutically acceptable salt or solvate thereof.

In one embodiment, the compound of Formula II is a compound of Example No. 66, or a pharmaceutically acceptable salt or solvate thereof.

In one embodiment, the compound of Formula II is a compound of Example No. 67, or a pharmaceutically acceptable salt or solvate thereof.

In one embodiment, the compound of Formula II is a compound of Example No. 68, or a pharmaceutically acceptable salt or solvate thereof.

In one embodiment, the compound of Formula II is a compound of Example No. 69, or a pharmaceutically acceptable salt or solvate thereof.

In one embodiment, the compound of Formula II is a compound of Example No. 70, or a pharmaceutically acceptable salt or solvate thereof.

In one embodiment, the compound of Formula II is a compound of Example No. 71, or a pharmaceutically acceptable salt or solvate thereof.

In one embodiment, the compound of Formula II is a compound of Example No. 72, or a pharmaceutically acceptable salt or solvate thereof.

In one embodiment, the compound of Formula II is a compound of Example No. 73, or a pharmaceutically acceptable salt or solvate thereof.

In one embodiment, the compound of Formula II is a compound of Example No. 74, or a pharmaceutically acceptable salt or solvate thereof.

In one embodiment, the compound of Formula II is a compound of Example No. 75, or a pharmaceutically acceptable salt or solvate thereof.

In one embodiment, the compound of Formula II is a compound of Example No. 76, or a pharmaceutically acceptable salt or solvate thereof.

In one embodiment, the compound of Formula II is a compound of Example No. 77, or a pharmaceutically acceptable salt or solvate thereof.

In one embodiment, the compound of Formula II is a compound of Example No. 79, or a pharmaceutically acceptable salt or solvate thereof.

In one embodiment, the compound of Formula II is a compound of Example No. 80, or a pharmaceutically acceptable salt or solvate thereof.

In one embodiment, the compound of Formula II is a compound of Example No. 81, or a pharmaceutically acceptable salt or solvate thereof.

In one embodiment, the compound of Formula II is a compound of Example No. 84, or a pharmaceutically acceptable salt or solvate thereof.

In one embodiment, the compound of Formula II is a compound of Example No. 86, or a pharmaceutically acceptable salt or solvate thereof.

In one embodiment, the compound of Formula II is a compound of Example No. 87, or a pharmaceutically acceptable salt or solvate thereof.

In one embodiment, the compound of Formula II is a compound of Example No. 88, or a pharmaceutically acceptable salt or solvate thereof.

In one embodiment, the compound of Formula II is a compound of Example No. 89, or a pharmaceutically acceptable salt or solvate thereof.

In one embodiment, the compound of Formula II is a compound of Example No. 90, or a pharmaceutically acceptable salt or solvate thereof.

In one embodiment, the compound of Formula II is a compound of Example No. 91, or a pharmaceutically acceptable salt or solvate thereof.

In one embodiment, the compound of Formula II is a compound of Example No. 92, or a pharmaceutically acceptable salt or solvate thereof.

In one embodiment, the compound of Formula II is a compound of Example No. 93, or a pharmaceutically acceptable salt or solvate thereof.

In one embodiment, the compound of Formula II is a compound of Example No. 94, or a pharmaceutically acceptable salt or solvate thereof.

In one embodiment, the compound of Formula II is a compound of Example No. 95, or a pharmaceutically acceptable salt or solvate thereof.

In one embodiment, the compound of Formula II is a compound of Example No. 96, or a pharmaceutically acceptable salt or solvate thereof.

In one embodiment, the compound of Formula II is a compound of Example No. 97, or a pharmaceutically acceptable salt or solvate thereof.

In one embodiment, the compound of Formula II is a compound of Example No. 98, or a pharmaceutically acceptable salt or solvate thereof.

In one embodiment, the compound of Formula II is a compound of Example No. 99, or a pharmaceutically acceptable salt or solvate thereof.

In one embodiment, the compound of Formula II is a compound of Example No. 100, or a pharmaceutically acceptable salt or solvate thereof.

In one embodiment, the compound of Formula II is a compound of Example No. 101, or a pharmaceutically acceptable salt or solvate thereof.

In one embodiment, the compound of Formula II is a compound of Example No. 102, or a pharmaceutically acceptable salt or solvate thereof.

In one embodiment, the compound of Formula II is a compound of Example No. 103, or a pharmaceutically acceptable salt or solvate thereof.

In one embodiment, the compound of Formula II is a compound of Example No. 104, or a pharmaceutically acceptable salt or solvate thereof.

In one embodiment, the compound of Formula II is a compound of Example No. 105, or a pharmaceutically acceptable salt or solvate thereof.

In one embodiment, the compound of Formula II is a compound of Example No. 106, or a pharmaceutically acceptable salt or solvate thereof.

In one embodiment, the compound of Formula II is a compound of Example No. 107, or a pharmaceutically acceptable salt or solvate thereof.

In one embodiment, the compound of Formula II is a compound of Example No. 108, or a pharmaceutically acceptable salt or solvate thereof.

In one embodiment, the compound of Formula II is a compound of Example No. 109, or a pharmaceutically acceptable salt or solvate thereof.

In one embodiment, the compound of Formula II is a compound of Example No. 110, or a pharmaceutically acceptable salt or solvate thereof.

In one embodiment, the compound of Formula II is a compound of Example No. 113, or a pharmaceutically acceptable salt or solvate thereof.

In one embodiment, the compound of Formula II is a compound of Example No. 114, or a pharmaceutically acceptable salt or solvate thereof.

In one embodiment, the compound of Formula II is a compound of Example No. 115, or a pharmaceutically acceptable salt or solvate thereof.

In one embodiment, the compound of Formula II is a compound of Example No. 116, or a pharmaceutically acceptable salt or solvate thereof.

In one embodiment, the compound of Formula II is a compound of Example No. 117, or a pharmaceutically acceptable salt or solvate thereof.

In one embodiment, the compound of Formula II is a compound of Example No. 118, or a pharmaceutically acceptable salt or solvate thereof.

In one embodiment, the compound of Formula II is a compound of Example No. 119, or a pharmaceutically acceptable salt or solvate thereof.

In one embodiment, the compound of Formula II is a compound of Example No. 120, or a pharmaceutically acceptable salt or solvate thereof.

In one embodiment, the compound of Formula II is a compound of Example No. 121, or a pharmaceutically acceptable salt or solvate thereof.

In one embodiment, the compound of Formula II is a compound of Example No. 122, or a pharmaceutically acceptable salt or solvate thereof.

In one embodiment, the compound of Formula II is a compound of Example No. 128, or a pharmaceutically acceptable salt or solvate thereof.

In one embodiment, the compound of Formula II is a compound of Example No. 142, or a pharmaceutically acceptable salt or solvate thereof.

In one embodiment, the compound of Formula II is a compound of Example No. 144, or a pharmaceutically acceptable salt or solvate thereof.

In one embodiment, the compound of Formula II is a compound of Example No. 145, or a pharmaceutically acceptable salt or solvate thereof.

In one embodiment, the compound of Formula II is a compound of Example No. 146, or a pharmaceutically acceptable salt or solvate thereof.

In one embodiment, the compound of Formula II is a compound of Example No. 147, or a pharmaceutically acceptable salt or solvate thereof.

In one embodiment, the compound of Formula II is a compound of Example No. 148, or a pharmaceutically acceptable salt or solvate thereof.

In one embodiment, the compound of Formula II is a compound of Example No. 150, or a pharmaceutically acceptable salt or solvate thereof.

In one embodiment, the compound of Formula II is a compound of Example No. 151, or a pharmaceutically acceptable salt or solvate thereof.

In one embodiment, the compound of Formula II is a compound of Example No. 152, or a pharmaceutically acceptable salt or solvate thereof.

In one embodiment, the compound of Formula II is a compound of Example No. 153, or a pharmaceutically acceptable salt or solvate thereof.

In one embodiment, the compound of Formula II is a compound of Example No. 154, or a pharmaceutically acceptable salt or solvate thereof.

In one embodiment, the compound of Formula II is a compound of Example No. 155, or a pharmaceutically acceptable salt or solvate thereof.

In one embodiment, the compound of Formula II is a compound of Example No. 156, or a pharmaceutically acceptable salt or solvate thereof.

In one embodiment, the compound of Formula II is a compound of Example No. 157, or a pharmaceutically acceptable salt or solvate thereof.

In one embodiment, the compound of Formula II is a compound of Example No. 158, or a pharmaceutically acceptable salt or solvate thereof.

In one embodiment, the compound of Formula II is a compound of Example No. 159, or a pharmaceutically acceptable salt or solvate thereof.

In one embodiment, the compound of Formula II is a compound of Example No. 160, or a pharmaceutically acceptable salt or solvate thereof.

In one embodiment, the compound of Formula IT is a compound of Example No. 161, or a pharmaceutically acceptable salt or solvate thereof.

In one embodiment, the compound of Formula II is a compound of Example No. 162, or a pharmaceutically acceptable salt or solvate thereof.

In one embodiment, the compound of Formula II is a compound of Example No. 163, or a pharmaceutically acceptable salt or solvate thereof.

In one embodiment, the compound of Formula II is a compound of Example No. 164, or a pharmaceutically acceptable salt or solvate thereof.

In one embodiment, the compound of Formula II is a compound of Example No. 166, or a pharmaceutically acceptable salt or solvate thereof.

In one embodiment, the compound of Formula II is a compound of Example No. 167, or a pharmaceutically acceptable salt or solvate thereof.

In one embodiment, the compound of Formula II is a compound of Example No. 168, or a pharmaceutically acceptable salt or solvate thereof.

In one embodiment, the compound of Formula IT is a compound of Example No. 169, or a pharmaceutically acceptable salt or solvate thereof.

In one embodiment, the compound of Formula II is a compound of Example No. 170, or a pharmaceutically acceptable salt or solvate thereof.

In one embodiment, the compound of Formula II is a compound of Example No. 171, or a pharmaceutically acceptable salt or solvate thereof.

In one embodiment, the compound of Formula II is a compound of Example No. 172, or a pharmaceutically acceptable salt or solvate thereof.

In one embodiment, the compound of Formula II is a compound of Example No. 173, or a pharmaceutically acceptable salt or solvate thereof.

In one embodiment, the compound of Formula II is a compound of Example No. 179, or a pharmaceutically acceptable salt or solvate thereof.

In one embodiment, the compound of Formula II is a compound of Example No. 181, or a pharmaceutically acceptable salt or solvate thereof.

In one embodiment, the compound of Formula II is a compound of Example No. 182, or a pharmaceutically acceptable salt or solvate thereof.

In one embodiment, the compound of Formula IT is a compound of Example No. 183, or a pharmaceutically acceptable salt or solvate thereof.

In one embodiment, the compound of Formula II is a compound of Example No. 184, or a pharmaceutically acceptable salt or solvate thereof.

In one embodiment, the compound of Formula II is a compound of Example No. 185, or a pharmaceutically acceptable salt or solvate thereof.

In one embodiment, the compound of Formula II is a compound of Example No. 186, or a pharmaceutically acceptable salt or solvate thereof.

In one embodiment, the compound of Formula II is a compound of Example No. 187, or a pharmaceutically acceptable salt or solvate thereof.

In one embodiment, the compound of Formula II is a compound of Example No. 189, or a pharmaceutically acceptable salt or solvate thereof.

In one embodiment, the compound of Formula II is a compound of Example No. 191, or a pharmaceutically acceptable salt or solvate thereof.

In one embodiment, the compound of Formula IT is a compound of Example No. 192, or a pharmaceutically acceptable salt or solvate thereof.

In one embodiment, the compound of Formula II is a compound of Example No. 193, or a pharmaceutically acceptable salt or solvate thereof.

In one embodiment, the compound of Formula II is a compound of Example No. 194, or a pharmaceutically acceptable salt or solvate thereof.

In one embodiment, the compound of Formula II is a compound of Example No. 195, or a pharmaceutically acceptable salt or solvate thereof.

In one embodiment, the compound of Formula II is a compound of Example No. 196, or a pharmaceutically acceptable salt or solvate thereof.

In one embodiment, the compound of Formula II is a compound of Example No. 197, or a pharmaceutically acceptable salt or solvate thereof.

The term "pharmaceutically acceptable" indicates that the compound, or salt or composition thereof is compatible chemically and/or toxicologically with the other ingredients comprising a formulation and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as additional anticancer agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1-24 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

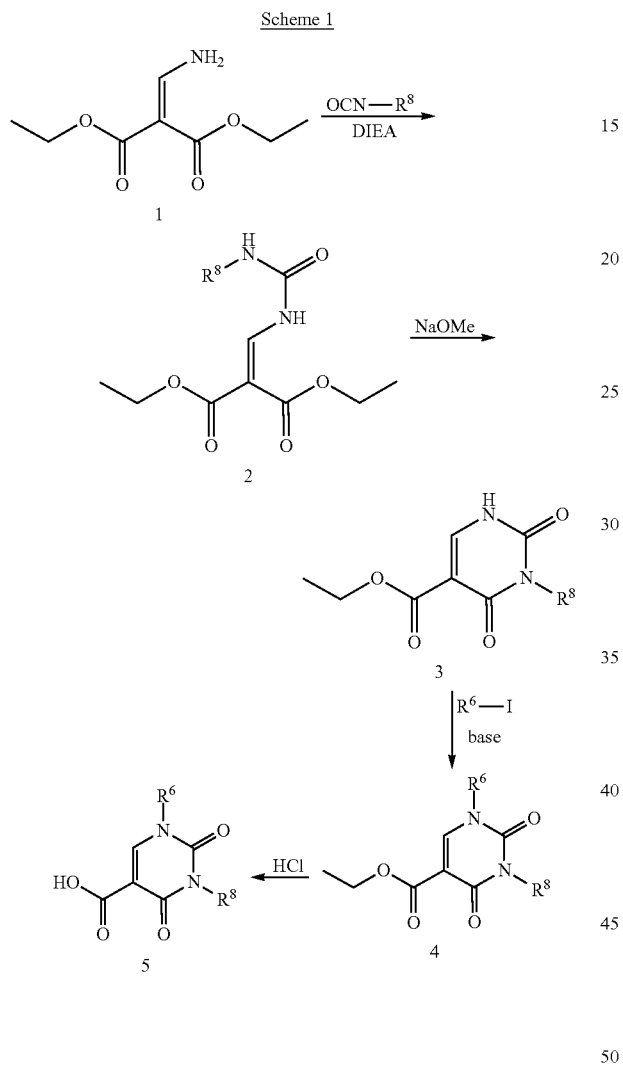

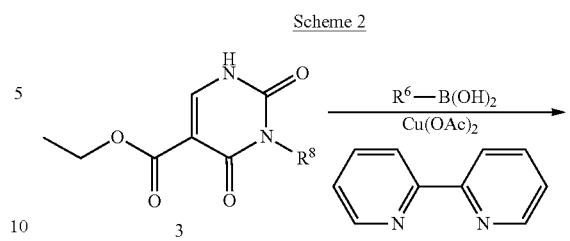

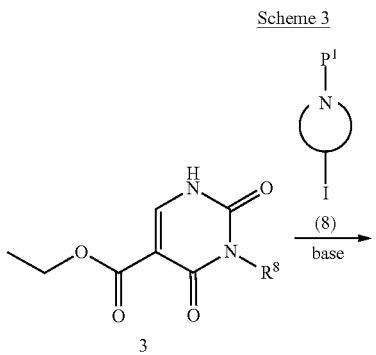

Scheme 1 shows a general process for the preparation of compound 5 wherein $R^6$ and $R^8$ are as defined for Formula I, which is an intermediate useful for the preparation of compounds of Formula I wherein G is Ring A and Ring A is A-1, $R^7$ is hydrogen and $R^3$ is absent.

Diethyl 2-(aminomethylene)malonate may be reacted with a reagent having the formula OCN—$R^8$ wherein $R^8$ is as defined for Formula I, to provide compound 2. Compound 2 may be treated with a strong base (e.g., sodium methoxide) to provide compound 3. Compound 3 may be reacted with a reagent having the formula $R^6$—I and a base, such as $K_2CO_3$, wherein $R^6$ is as defined for Formula I to provide compound 4. Treatment of compound 4 with aqueous acid provides compound 5.

Scheme 2 shows a general process for the preparation of compound 7 wherein $R^6$ is cyclopropyl, and $R^8$ is as defined for Formula I, which is an intermediate useful for the preparation of compounds of Formula I wherein G is Ring A and Ring A is A-1, $R^6$ is cyclopropyl, $R^7$ is hydrogen and $R^3$ is absent.

Compound 3, wherein $R^8$ is as defined for Formula I (prepared as in Scheme 1), may be treated with a reagent having the formula $R^6$—B(OH)$_2$, wherein $R^6$ is cyclopropyl, in the presence of Cu(OAc)$_2$ and 2,2'-bipyridine to provide compound 6. Treatment of compound 6 with aqueous acid provides compound 7.

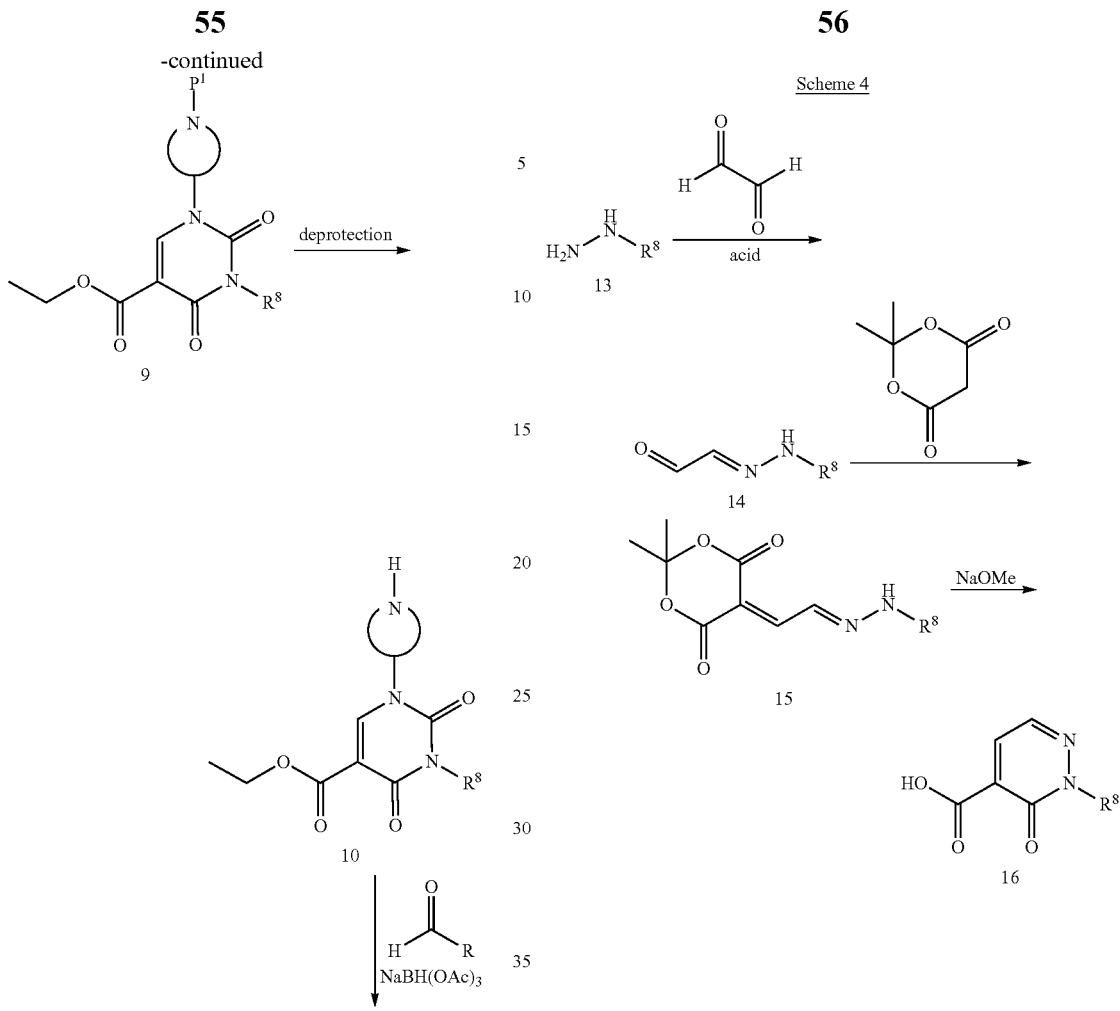

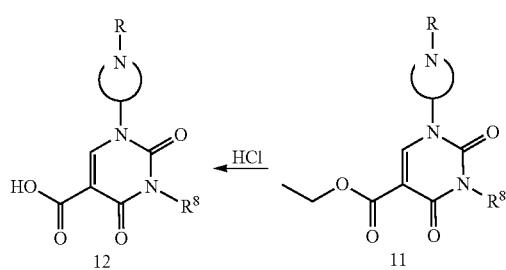

Scheme 3 shows a general process for the preparation of compound 12 wherein $R^6$ is hetCyc$^2$ and $R^8$ is as defined for Formula I, which is an intermediate useful for the preparation of compounds of Formula I wherein G is Ring A and Ring A is A-1, $R^7$ is hydrogen and $R^3$ is absent.

Compound 3, wherein $R^8$ is as defined for Formula I (prepared as in Scheme 1), may be treated with reagent (8), wherein $P^1$ is an amino protecting group (e.g., Boc) in the presence of a base (e.g., $K_2CO_3$) to provide compound 9. The protecting group $P^1$ of compound 9 may be removed to provide compound 10. Compound 10 may be reacted with a reagent having the formula RC(=O)H wherein R is C1-C6 alkyl, in the presence of a reducing agent (e.g., NaBH(OAc)$_3$) to provide compound 11. Compound 11 may be treated with aqueous acid to provide compound 12.

Scheme 4 shows a general process for the preparation of compound 16, wherein $R^8$ is as defined for Formula I, which is an intermediate useful for the preparation of compounds of Formula I wherein G is Ring A and Ring A is A-2, $R^6$ and $R^7$ are hydrogen and $R^3$ is absent.

Compound 13, wherein $R^8$ is as defined for Formula I, may be treated with oxalaldehyde in the presence of an acid to provide compound 14. Compound 14 may be treated with 2,2-dimethyl-1,3-dioxane-4,6-dione, in the presence of a carboxylic acid (e.g., acetic acid) and an amine base (e.g., piperidine) to provide compound 15. Compound 15 may be treated with a base (e.g., sodium methoxide) to provide compound 16.

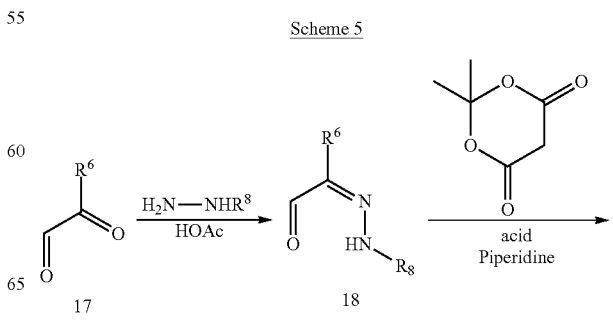

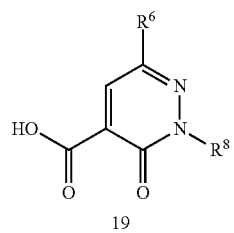

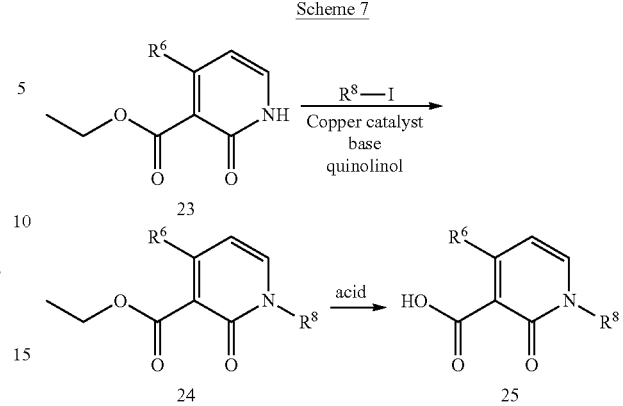

Scheme 5 shows a general process for the preparation of compound 19, wherein $R^6$ is hydrogen, C1-C6 alkyl, C1-C6 alkoxy, HOC1-C6 alkyl, C3-C6 cycloalkyl, (C3-C6 cycloalkyl)C1-C6 alkyl- or hetCyc², and $R^8$ is as defined for Formula I, which is an intermediate useful for the preparation of compounds of Formula I wherein G is Ring A and Ring A is A-2, $R^7$ is hydrogen and $R^3$ is absent.

Compound 17, wherein $R^6$ is hydrogen, C1-C6 alkyl, C1-C6 alkoxy, $P^2$OC1-C6 alkyl, C3-C6 cycloalkyl, (C3-C6 cycloalkyl)C1-C6 alkyl- or hetCyc², and wherein $P^2$ is a hydroxy protecting group, may be reacted with a reagent having the formula $H_2N$—$NHR^8$ wherein $R^8$ is as defined for Formula I, to provide compound 18, as the minor product. Compound 18 may be reacted with 2,2-dimethyl-1,3-dioxane-4,6-dione in the presence of an acid (e.g., HOAc) and piperidine to provide compound 19, after which, if $R^6$ is $P^2$OC1-C6 alkyl, the hydroxyl protecting group is removed.

Scheme 7 shows a general process for the preparation of compound 25, wherein $R^6$ is C1-C6 alkoxy and $R^8$ is as defined for Formula I, which is an intermediate useful for the preparation of compounds of Formula I wherein G is Ring A and Ring A is A-3, R is hydrogen and $R^3$ is absent.

Compound 23, wherein $R^6$ is C1-C6 alkoxy, may be reacted with a reagent having the formula $R^8$—I, wherein $R^8$ is as defined for Formula I, in the presence of a copper catalyst, a base, and quinolinol, to provide compound 24. Treatment of compound 24 with aqueous acid provides compound 25.

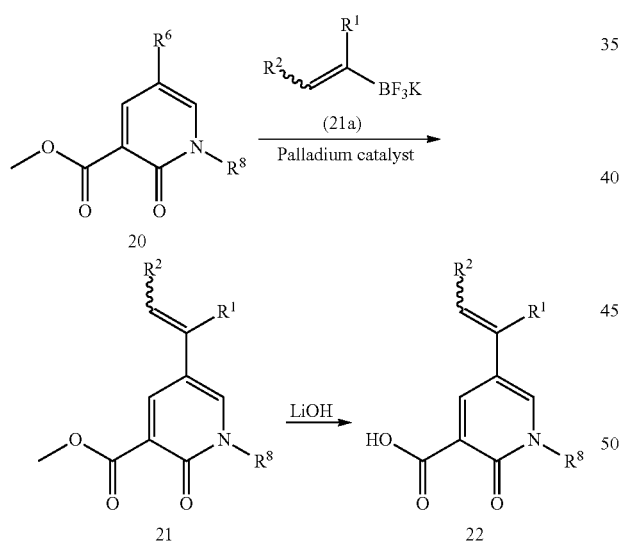

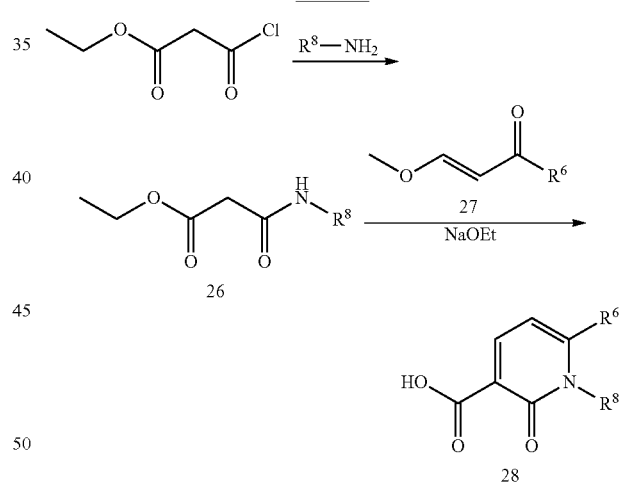

Scheme 6 shows a general process for the preparation of compound 22, wherein $R^8$ is as defined for Formula I, and $R^1$ and $R^2$ are independently H or C1-C3 alkyl, which is an intermediate useful for the preparation of compounds of Formula I wherein G is Ring A and Ring A is A-3, $R^6$ is C1-C6 alkyl, $R^7$ is hydrogen and $R^3$ is absent.

Compound 20, wherein $R^8$ is as defined for Formula I, may be reacted with compound 21a, wherein $R^1$ and $R^2$ are independently H or C1-C3 alkyl, in the presence of a palladium catalyst to provide compound 21. Compound 21 may be treated with lithium hydroxide to provide compound 22.

Scheme 8 show s a general process for the preparation of compound 28, wherein $R^6$ is C1-C6 alkyl and $R^8$ is as defined for Formula I, which is an intermediate useful for the preparation of compounds of Formula I wherein G is Ring A and Ring A is A-3, $R^7$ is hydrogen, and $R^3$ is absent.

Ethyl 3-chloro-3-oxopropanoate may be reacted with reagent $R^8$—$NH_2$, wherein $R^8$ is as defined for Formula I, to provide compound 26. Compound 26 may be reacted with reagent 27, wherein $R^5$ is C1-C6 alkyl, in the presence of a base (e.g., sodium ethoxide), to provide compound 28.

Scheme 9

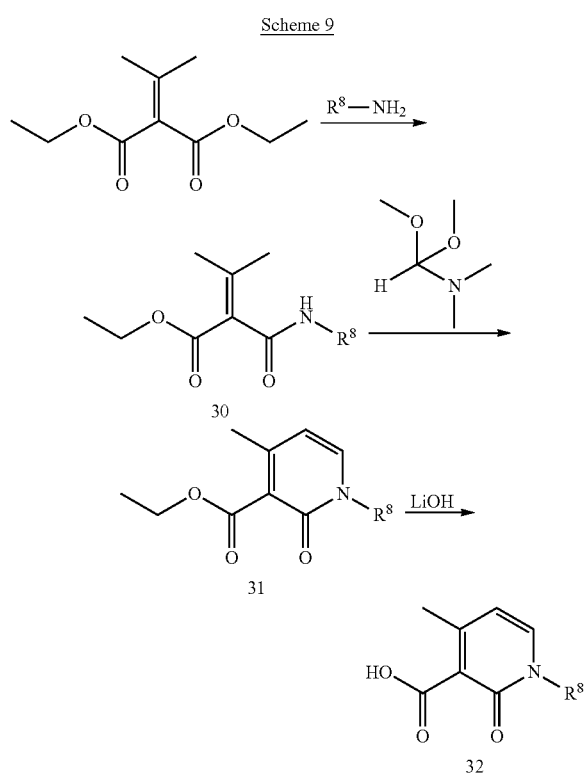

Scheme 9 shows a general process for the preparation of compound 32, wherein $R^8$ is as defined for Formula I, which is an intermediate useful for the preparation of compounds of Formula I wherein G is Ring A and Ring A is A-3, $R^6$ is methyl, $R^7$ is hydrogen and $R^3$ is absent.

Diethyl 2-(propan-2-ylidene)malonate may be reacted with a reagent having the formula $R^8$—$NH_2$ wherein $R^8$ is as defined for Formula I, in the presence of imidazole at elevated temperatures (e.g., at about 200° C.), to provide compound 30. Compound 30 may be reacted with 1,1-dimethoxy-N,N-dimethylmethanamine to provide compound 31. Treatment of compound 32 with lithium hydroxide provides compound 32.

Scheme 10

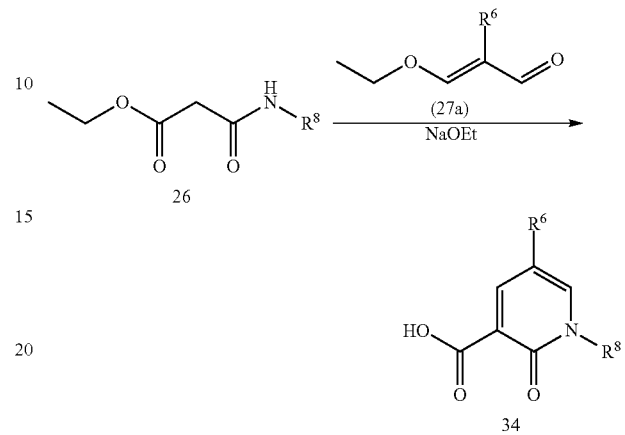

Scheme 10 shows a general process for the preparation of compound 34, wherein $R^8$ is as defined for Formula I, which is an intermediate useful for the preparation of compounds of Formula I wherein G is Ring A and Ring A is A-3, $R^6$ is C1-C6 alkyl, $R^7$ is hydrogen, and $R^3$ is absent.

Compound 34 may be prepared by treating compound 26 (prepared as in Scheme 8), wherein $R^8$ is as defined for Formula I, with reagent 27a wherein $R^6$ is C1-C6 alkyl, in the presence of sodium ethoxide.

Scheme 11

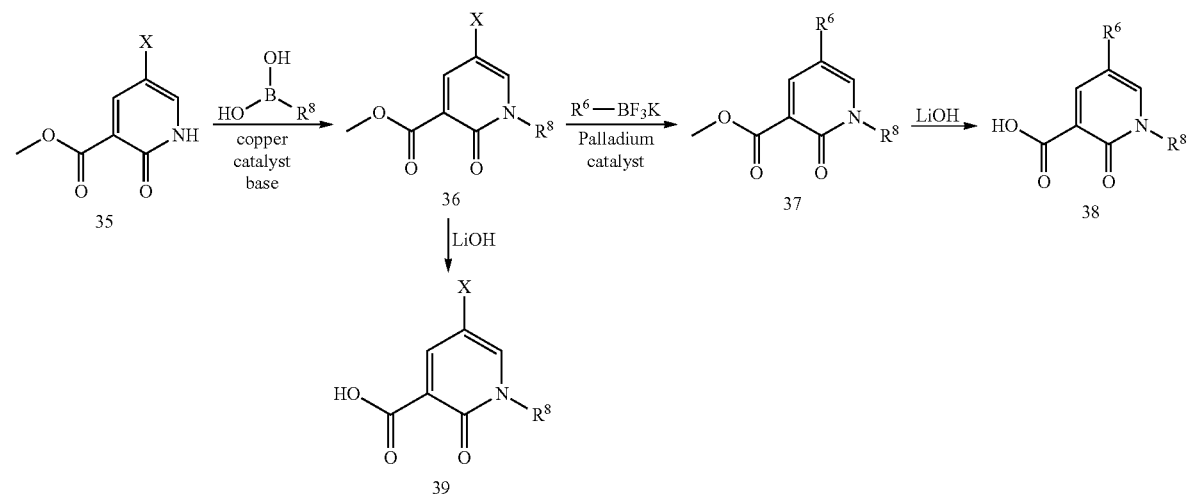

Scheme 11 shows a general process for the preparation of compound 38, wherein $R^8$ is $Ar^2$, $hetAr^2$, or C3-C6 cycloalkyl, and $R^5$ is C3-C6 cycloalkyl, and compound 39, wherein $R^8$ is as defined for Formula I and X is Cl or Br, which are intermediates useful for the preparation of compounds of Formula I wherein G is Ring A and Ring A is A-3, $R^7$ is hydrogen and $R^3$ is absent.

Compound 35, wherein X is Cl or Br, may be reacted with a boronic acid having the formula $(HO)_2B$—$R^8$, wherein $R^8$ is Ar², hetAr², or C3-C6 cycloalkyl, in the presence of a copper catalyst (e.g., copper(II) acetate) and a base (e.g., pyridine) to provide compound 36. Compound 36 may be treated with a compound having the formula $R^6$—$BF_3K$ wherein $R^6$ is C3-C6 cycloalkyl to provide compound 37. Treatment of compound 37 with lithium hydroxide provides compound 38. Compound 39 may be obtained by treating compound 36 with lithium hydroxide.

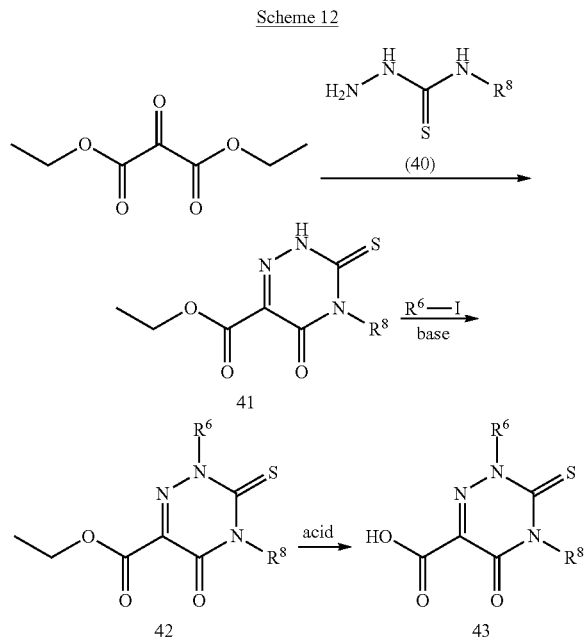

Scheme 12 shows a general process for the preparation of compound 43, wherein $R^6$ is C1-C6 alkyl, C1-C6 alkoxy, hydroxyC1-C6 alkyl, C3-C6 cycloalkyl, (C3-C6 cycloalkyl) C1-C6 alkyl- or hetCyc², and $R^8$ is as defined for Formula I, which is an intermediate useful for the preparation of compounds of Formula I wherein G is Ring A and Ring A is A-4, $R^7$ is thioxo, and $R^3$ is absent.

Diethyl 2-oxomalonate may be reacted with a compound having formula 40, wherein $R^8$ is as defined for Formula I, to provide compound 41. Compound 41 may be treated with a reagent having the formula $R^6$—I, wherein $R^6$ is C1-C6 alkyl, C1-C6 alkoxy, P²O-C1-C6 alkyl, C3-C6 cycloalkyl, (C3-C6 cycloalkyl)C1-C6 alkyl- or hetCyc² and P² is a hydroxyl protecting group, in the presence of a base (e.g., $K_2CO_3$), to provide compound 42. Treatment of compound 42 with aqueous acid provides compound 43, after which, if $R^6$ is P²OC1-C6 alkyl, the hydroxyl protecting group is removed.

Scheme 13 shows a general process for the preparation of compound 46, wherein $R^6$ is C1-C6 alkyl, C1-C6 alkoxy, hydroxyC1-C6 alkyl, C3-C6 cycloalkyl, (C3-C6 cycloalkyl) C1-C6 alkyl- or hetCyc² and $R^8$ is as defined for Formula I, which is an intermediate useful for the preparation of compounds of Formula I wherein G is Ring A and Ring A is A-4, $R^7$ is oxo, and $R^3$ is absent.

Compound 42, prepared according to Scheme 12, may be treated with hydrogen peroxide in the presence of an acid to provide compound 44. Compound 44 may be treated with a compound having the formula $R^6$—I wherein $R^6$ is C1-C6 alkyl, C1-C6 alkoxy, P²O-C1-C6 alkyl, C3-C6 cycloalkyl, (C3-C6 cycloalkyl)C1-C6 alkyl- or hetCyc² and P² is a hydroxy protecting group, in the presence of a base (e.g., $K_2CO_3$) to provide compound 45. Treatment of compound 45 with aqueous acid provides compound 46, after which, if $R^6$ is P²OC1-C6 alkyl, the hydroxyl protecting group is removed.

-continued

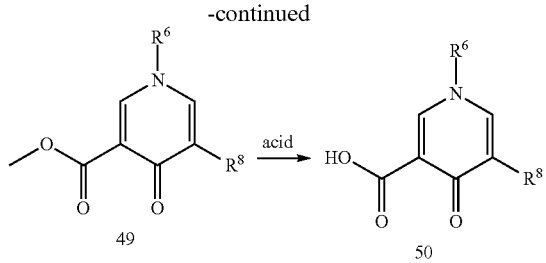

Scheme 14 shows a general process for the preparation of compound 50, wherein $R^6$ is C1-C6 alkyl, C1-C6 alkoxy, hydroxyC1-C6 alkyl, C3-C6 cycloalkyl, (C3-C6 cycloalkyl) C1-C6 alkyl- or hetCyc$^2$ and $R^8$ is Ar$^2$, hetAr$^2$ or cyclopropyl which is an intermediate useful for the preparation of compounds of Formula I wherein G is Ring A and Ring A is A-5, R is hydrogen and $R^3$ is absent.

Methyl 5-bromo-4-hydroxynicotinate may be treated with a compound having the formula $R^6$—I wherein $R^6$ is C1-C6 alkyl, C1-C6 alkoxy, P$^2$O-C1-C6 alkyl, C3-C6 cycloalkyl, (C3-C6 cycloalkyl)C1-C6 alkyl- or hetCyc$^2$ and P$^2$ is a hydroxy protecting group, in the presence of a base (e.g., Cs$_2$CO$_3$) to provide compound 47. Compound 47 may be treated with boronic acid 48, wherein $R^8$ is Ar$^2$, hetAr$^2$ or cyclopropyl, to provide compound 49. Treatment of compound 49 with aqueous acid provides compound 50, after which, if $R^6$ is P$^2$OC1-C6 alkyl, the hydroxyl protecting group is removed.

Scheme 15

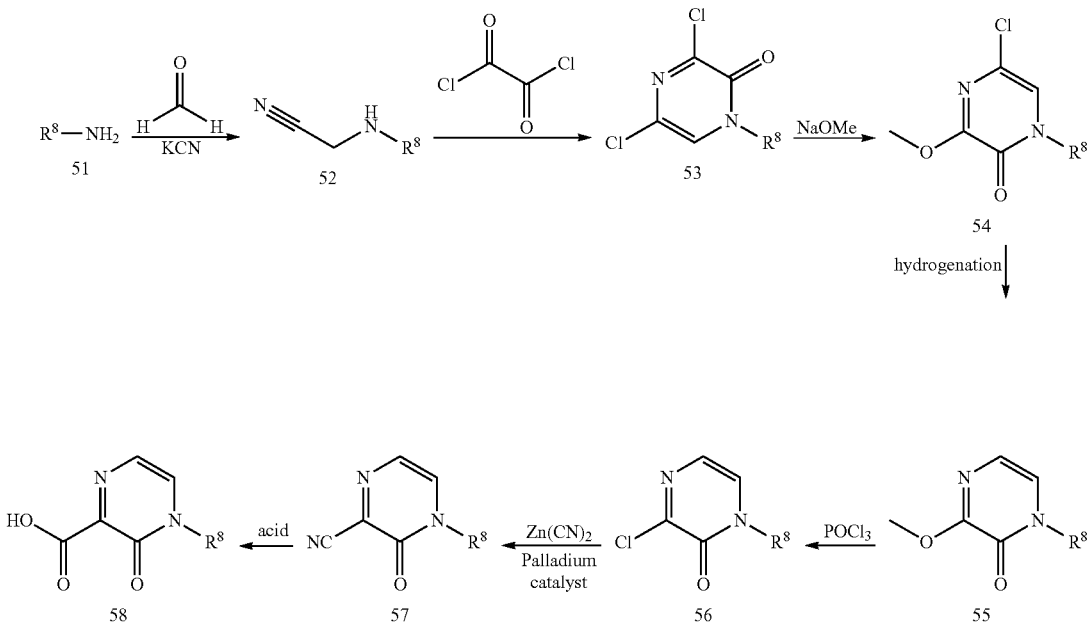

Scheme 15 shows a general process for the preparation of compound 58, wherein $R^8$ is as defined for Formula I, which is an intermediate useful for the preparation of compounds of Formula I wherein G is Ring A and Ring A is A-6, $R^6$ and $R^7$ are hydrogen, and $R^3$ is absent.

Compound 51, wherein $R^8$ is as defined for Formula I, may be treated with formaldehyde and potassium cyanide to provide compound 52. Compound 52 may be treated with oxalyl dichloride to provide compound 53. Compound 53 may be treated with sodium methoxide to provide compound 54. Compound 54 may be reduced under standard hydrogenation conditions (e.g., under a hydrogen atmosphere in the presence of a palladium catalyst such as palladium on carbon) to provide compound 55. Compound 55 may be converted to compound 56 upon treatment with phosphoryl chloride. Compound 56 may be treated with zinc cyanide in the presence of a palladium catalyst and a ligand (e.g. Pd$_2$dba$_3$ and dppf) to provide compound 57. The nitrile group of compound 57 may be hydrolyzed upon treatment with aqueous acid to provide compound 58.

Scheme 16

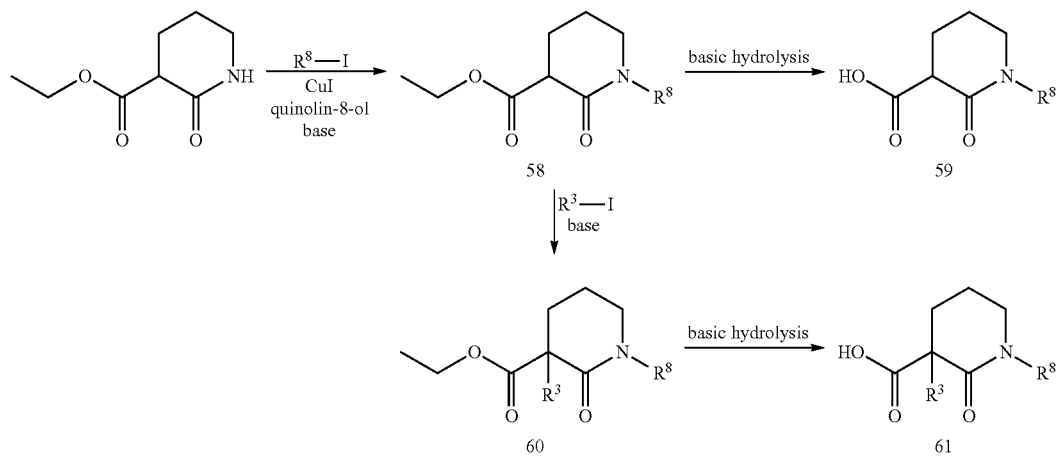

Scheme 16 shows a general process for the preparation of compound 59, wherein $R^8$ is $Ar^2$, $hetAr^2$, C3-C6 cycloalkyl or $hetCyc^3$, and compound 61, wherein $R^3$ is C1-C6 alkyl, and $R^8$ is $Ar^2$, $hetAr^2$, C3-C6 cycloalkyl or $hetCyc^3$, which are intermediates useful for the preparation of compounds of Formula I wherein G is Ring A and Ring A is A-7, $R^7$ is hydrogen, and $R^3$ is methyl.

Ethyl 2-oxopiperidine-3-carboxylate may be treated with reagent $R^8$—I, wherein $R^8$ is $Ar^2$, $hetAr^2$, C3-C6 cycloalkyl or $hetCyc^3$, in the presence of copper (I) iodide, quinlin-8-ol and a base (e.g., $CsCO_3$) to provide compound 58. Compound 58 may be hydrolyzed under basic conditions (e.g., LiOH) to provide compound 59.

Alternatively, compound 58 may be treated with a compound having the formula $R^3$—I wherein $R^3$ is C1-C6 alkyl to provide compound 60. Compound 60 may be hydrolyzed under basic conditions (e.g., LiOH) to provide compound 61.

Scheme 17 shows a general process for the preparation of compound 65, wherein $R^8$ is $Ar^2$, $hetAr^2$, C3-C6 cycloalkyl or $hetCyc^3$, which is an intermediate useful for the preparation of compounds of Formula I wherein G is Ring A and Ring A is A-7, $R^6$ and $R^7$ together form a cyclopropyl ring, and $R^3$ is hydrogen.

(1-Cyanocyclopropyl)methyl methanesulfonate may be treated with diethyl malonate in the presence of sodium hydride to provide compound 62. Compound 62 may undergo an intramolecular cyclization in the presence of hydrogen and a catalytic amount of platinum(IV) oxide to provide compound 63. Compound 63 may be treated with a compound having the formula $R^8$—I, wherein $R^8$ is $Ar^2$, $hetAr^2$, C3-C6 cycloalkyl or $hetCyc^3$, in the presence of copper (I) iodide, quinlin-8-ol and a base (e.g., $Cs_2CO_3$) to provide compound 64. Compound 64 may be hydrolyzed under basic conditions (e.g., LiOH) to provide compound 65.

Scheme 17

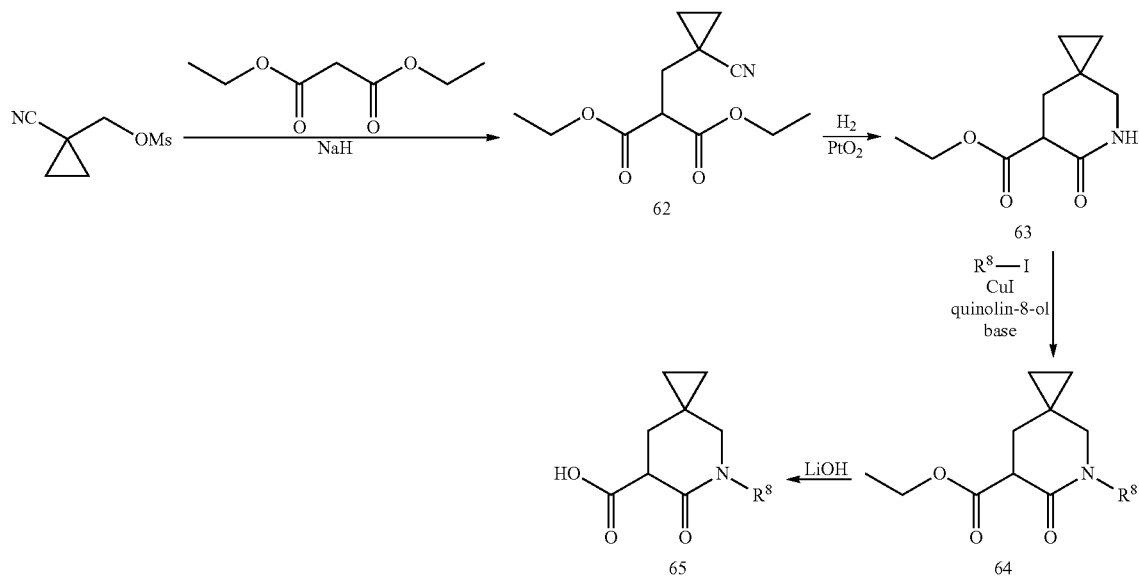

Scheme 18

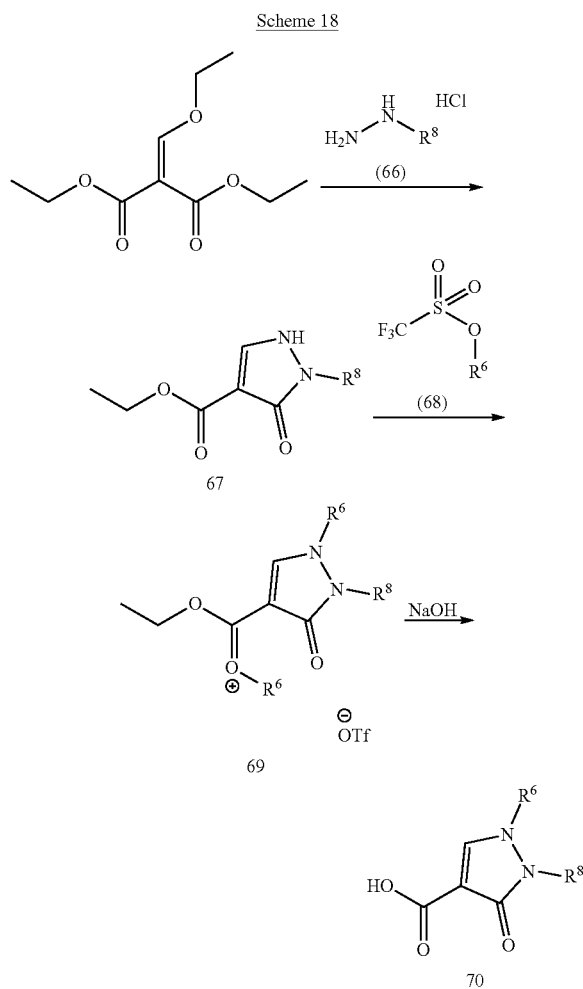

Scheme 18 shows a general process for the preparation of compound 70, wherein $R^8$ is as defined for Formula I, which is an intermediate useful for the preparation of compounds of Formula I wherein G is Ring A and Ring A is A-8, $R^7$ is hydrogen, and $R^3$ is absent.

Diethyl 2-(ethoxymethylene)malonate may be reacted with a compound 66, wherein $R^8$ is as defined for Formula I, to provide compound 67. Compound 67 may be reacted with compound 68, wherein $R^6$ is C1-C6 alkyl, to provide compound 69. Treatment of compound 69 with sodium hydroxide provides compound 70.

Scheme 19

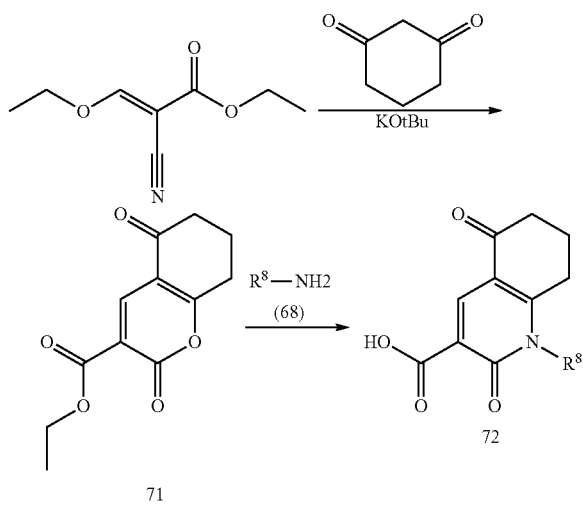

Scheme 19 shows a general process for the preparation of compound 72, wherein $R^8$ is as defined for Formula I, which is an intermediate useful for the preparation of compounds of Formula I wherein G is Ring B and Ring B is B-1.

Ethyl (E)-2-cyano-3-ethoxyacrylate may be reacted with cyclohexane-1,3-dione in the presence of potassium tert-butoxide to provide compound 71. Compound 71 may be reacted with the reagent $R^8$—I, wherein $R^8$ is as defined for Formula I, to provide compound 72.

Scheme 20

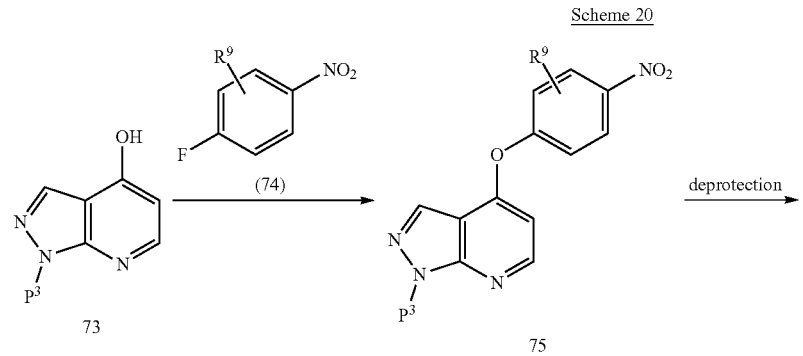

-continued

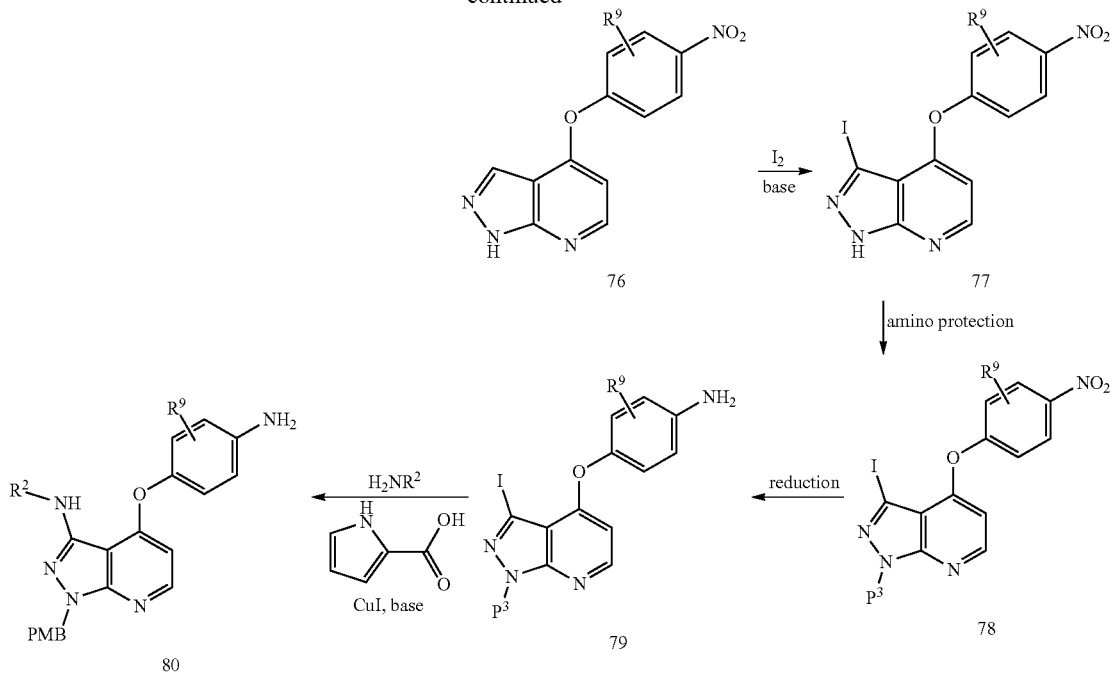

Scheme 20 shows a general process for the preparation of compound 79, wherein $R^9$ is as defined for Formula I, and compound 80, wherein $R^9$ and $R^2$ are as defined for Formula I, which are intermediates useful for the preparation of compounds of Formula T wherein $X^1$ is CH.

Compound 73, wherein $P^3$ is an amino protecting group (e.g., para-methoxybenzyl; PMB), may be reacted with compound 74, wherein $R^9$ is as defined for Formula I, in the presence of a base to provide compound 75. The amino protecting group of compound 75 may be removed under standard conditions (e.g., TFA) to provide compound 76. Compound 76 may be treated with $I_2$ in the presence of a base (e.g., KOH) to provide compound 77. The amino group of compound 77 may be protected under standard conditions to provide compound 78, wherein $P^3$ is an amino protecting group (e.g., para-methoxybenzyl; PMB). The nitro group of compound 78 may be reduced under standard conditions (e.g., tin(II) chloride) to provide compound 79. Compound 79 may be treated with a compound having the formula $H_2NR^2$, wherein $R^2$ is as defined for Formula I, in the presence of CuI, a ligand (e.g., 1H-pyrrole-2-carboxylic acid), and a base (e.g., potassium carbonate) to provide compound 80.

Scheme 21

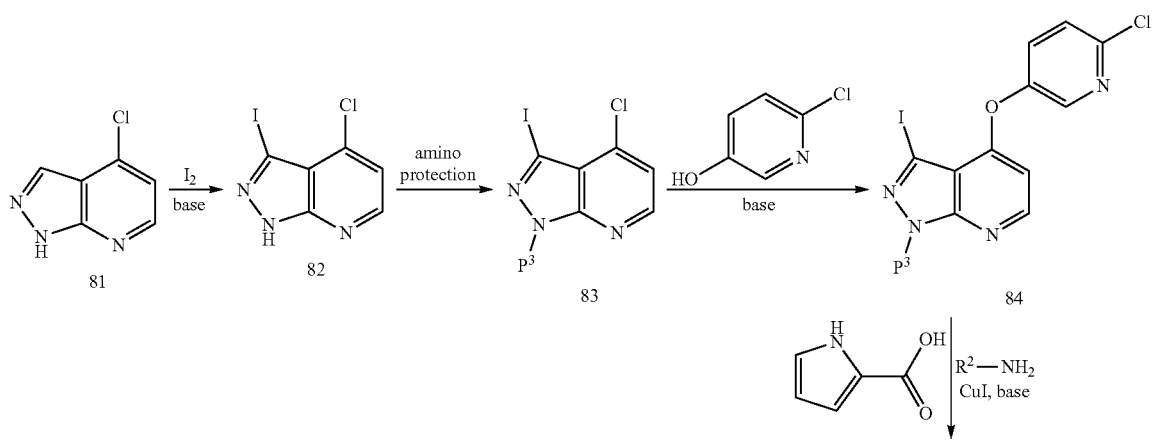

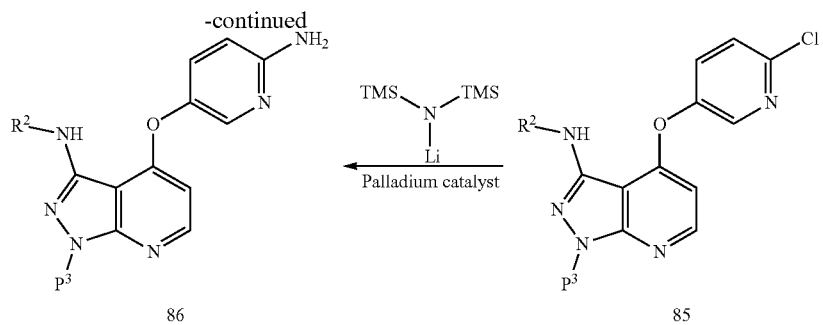

Scheme 21 shows a general process for the preparation of compound 86, wherein $R^2$ is hydrogen, C1-C6 alkyl, C1-C6 fluoroalkyl, (di-C1-C6 alkoxy)C2-C6 alkyl-, (C1-C6 alkoxy)C1-C6 alkyl-, $Cyc^1$, $Cyc^2$, $(hetCyc^1)$C1-C6 alkyl-, $(Ar^1)$C1-C6 alkyl-, $(hetAr^1)$C1-C6 alkyl-, or $(HOSO_3)$C1-C6 alkyl-, which is an intermediate useful for preparing compounds of Formula I wherein $X^1$ is N, $R^9$ is hydrogen, and $R^2$ is hydrogen, C1-C6 alkyl, C1-C6 fluoroalkyl, (di-C1-C6 alkoxy)C2-C6 alkyl-, (C1-C6 alkoxy)C1-C6 alkyl-, $Cyc^1$, $Cyc^2$, $(hetCyc^1)$C1-C6 alkyl-, $(Ar^1)$C1-C6 alkyl-, $(hetAr^1)$C1-C6 alkyl-, or $(HOSO_3)$C1-C6 alkyl-.

Compound 81 may be treated with $I_2$ in the presence of a base (e.g., KOH) to provide compound 82. The amino group of compound 82 may be protected under standard conditions (e.g., by treatment with 1-(chloromethyl)-4-methoxybenzene in the presence of base, e.g., $K_2CO_3$) to provide compound 83 wherein $P^3$ is an amino protecting group (e.g., PMB). Compound 83 may be treated with 2-chloro-5-hydroxypyridine in the presence of a base (e.g., $Cs_2CO_3$) to provide compound 84. Compound 84 may be treated with reagent $H_2NR^2$, wherein $R^2$ is hydrogen, C1-C6 alkyl, C1-C6 fluoroalkyl, (di-C1-C6 alkoxy)C2-C6 alkyl-, (C1-C6 alkoxy)C1-C6 alkyl-, $Cyc^1$, $Cyc^2$, $(hetCyc^1)$C1-C6 alkyl-, $(Ar^3)$C1-C6 alkyl-, $(hetAr^1)$C1-C6 alkyl-, or $(HOSO_3)$C1-C6 alkyl-, in the presence of CuI, ligand (e.g., 1H-pyrrole-2-carboxylic acid), and a base (e.g., potassium carbonate) to provide compound 85. Compound 85 may be treated with lithium bis(trimethylsilyl)amide in the presence of a palladium catalyst (e.g., $Pd_2dba_3$) and a ligand (e.g., X-Phos) to provide compound 86.

Scheme 22

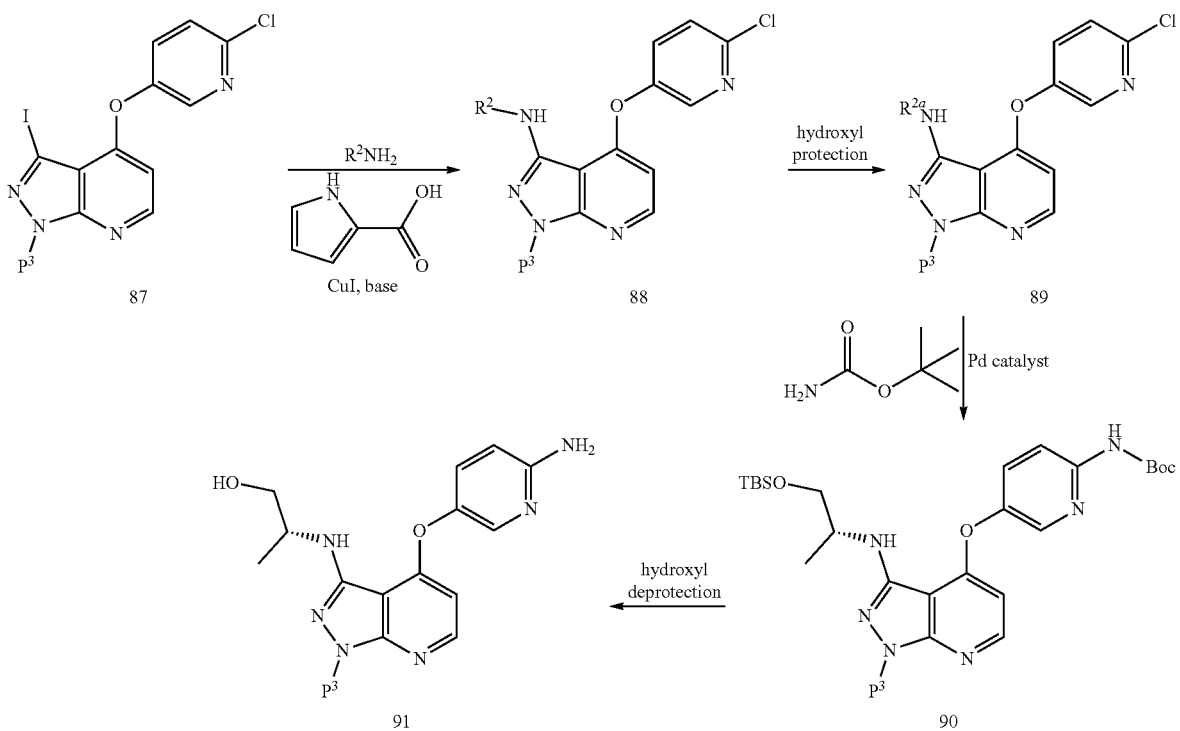

Scheme 22 shows a general process for the preparation of compound 91, wherein $R^2$ is hydroxyC1-C6 alkyl and $P^3$ is an amino protecting group, which is an intermediate useful for preparing compounds of Formula I wherein $X^1$ is N and $R^9$ is hydrogen.

Compound 87 (prepared as in Scheme 21), wherein $P^3$ is an amino protecting group, may be treated with a compound having the formula $H_2NR^2$, wherein $R^2$ is hydroxyC1-C6 alkyl, in the presence of CuI, ligand (e.g., 1H-pyrrole-2-carboxylic acid), and a base (e.g., potassium carbonate) to provide compound 88. The hydroxyl moiety of the $R^2$ group of compound 88 may be protected under standard conditions (e.g., by treatment with tert-butyldimethylsilyl chloride) to provide compound 89 wherein $R^{2a}$ is hydroxyC1-C6 alkyl wherein the hydroxyl moiety is protected. Compound 89 may be treated with tert-butyl carbamate in the presence of a palladium catalyst (e.g., $Pd_2dba_3$) and a ligand (e.g., X-Phos) to provide compound 90. Removal of the hydroxyl protecting group under standard conditions provides compound 91.

Compound 92, wherein $R^9$ and $X^1$ are as defined for Formula I and $P^3$ is an amino protecting group, may be treated with compound 93, wherein G is as defined for Formula I, in the presence of coupling reagents (e.g., in the presence of HATU or EDCI/HOBt and diisoproylethyl amine) to provide compound 94. Compound 94 may be treated with reagent $R^1R^2NH$, wherein $R^1$ and $R^2$ are as defined for Formula I and wherein if the $R^2$ moiety contains a hydroxyl group then the hydroxyl group is optionally protected with a hydroxyl protecting group, in the presence of copper(I) iodide and either in the presence of a base (e.g., $K_2CO_3$) and 1H-pyrrole-2-carboxylic acid, or in the presence of a ligand (e.g., N1,N2-dimethylethane-1,2-diamine) and a base (e.g., $K_3PO_4$) to provide compound 95. Removal of the amino protecting group and the hydroxyl group, if present, under standard conditions (e.g., trifluoroacetic acid) provides compound 96. In embodiments wherein G is B-1 (e.g., as in Scheme 19), a compound 95 wherein G is B-2 is formed as an oxidative by-product during the reaction step converting compound 94 to compound 95.

Scheme 23

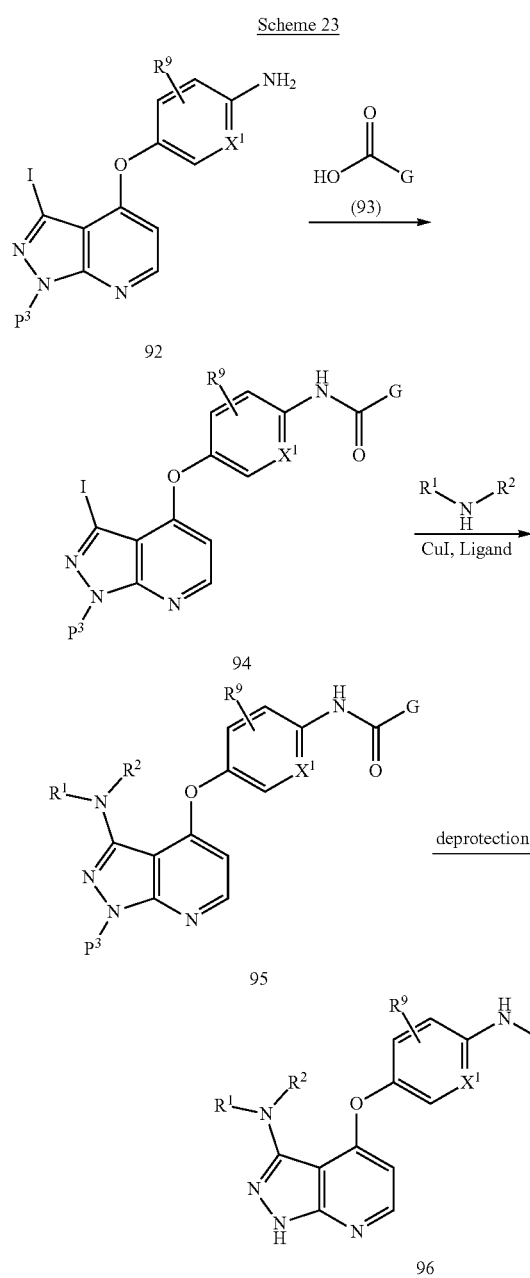

Scheme 24

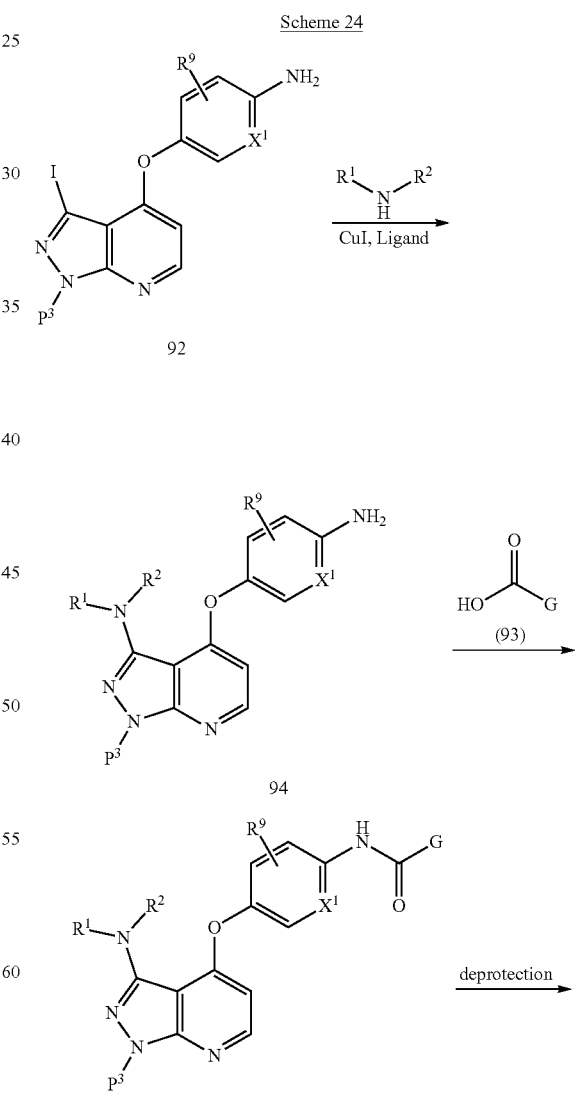

Scheme 23 shows a general process for the preparation of compound 96, which is a compound of Formula I wherein $R^1$, $R^2$, $X^1$, $R^9$ and G are as defined for Formula I.

-continued

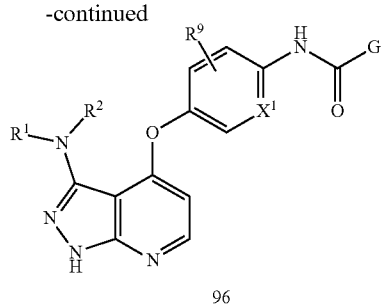

96

Scheme 24 shows an alternative general process for the preparation of compound 96, which is a compound of Formula I wherein $R^1$, $R^2$, $X^1$, $R^9$ and G are as defined for Formula I.

Compound 92, wherein $R^9$ and $X^1$ are as defined for Formula I and $P^3$ is an amino protecting group, may be treated with a reagent having the formula $R^1R^2NH$, wherein $R^1$ and $R^2$ are as defined for Formula I and wherein if the $R^2$ moiety contains a hydroxyl group then the hydroxyl group is optionally protected with a hydroxyl protecting group, in the presence of copper(I) iodide and either in the presence of a base (e.g., $K_2CO_3$) and 1H-pyrrole-2-carboxylic acid, or in the presence of a ligand (e.g., N1,N2-dimethylethane-1,2-diamine) and a base (e.g., $K_3PO_4$) to provide compound 97. Compound 97 may be treated with compound 93, wherein G is as defined for Formula I, in the presence of coupling reagents (e.g., in the presence of HATU or EDCI/HOBt and diisopropyl ethyl amine) to provide compound 95. Removal of the amino protecting group and the hydroxyl group, if present, under standard conditions (e.g., trifluoroacetic acid) provides compound 96.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amino protecting groups are para-methoxybenzyl (PMB), t-butyloxycarbonyl ("Boc"), benzyloxycarbonyl ("CBz") and 9-fluorenylmethyleneoxycarbonyl ("Fmoc"). Further examples of these groups, and other protecting groups, are found in T. W. Greene, et al., Greene's Protective Groups in Organic Synthesis. New York: Wiley Interscience, 2006.

Hydroxyl groups may be protected with any convenient hydroxyl protecting group, for example as described in T. W. Greene, et ah, Greene's Protective Groups in Organic Synthesis. New York: Wiley Interscience, 2006. Examples include benzyl, trityl, silyl ethers, and the like.

In one embodiment, provided herein is a process for preparing a compound of Formula I, comprising:

(a) reacting a compound having the formula

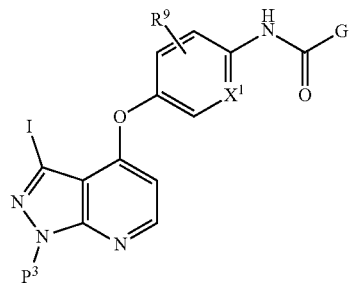

wherein $X^1$, G, and $R^9$ are as defined for Formula I and $P^3$ is an amino protecting group, with a reagent having the formula $R^1R^2NH$, wherein $R^1$ and $R^2$ are as defined for Formula I and wherein if the $R^2$ moiety contains a hydroxyl group then the hydroxyl group is optionally protected with a hydroxyl protecting group, in the presence of copper(I) iodide and either in the presence of a base and 1H-pyrrole-2-carboxylic acid, or in the presence of a ligand and a base, followed by removal of the amino protecting group and removal of the hydroxyl group, if present; or (b) reacting a compound having the formula:

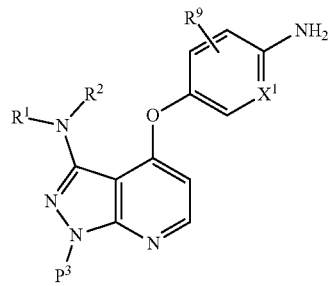

wherein $R^9$ and $X^1$ are as defined for Formula I, $P^3$ is an amino protecting group, and $R^1$ and $R^2$ are as defined for Formula I, wherein if the $R^2$ moiety contains a hydroxyl group then the hydroxyl group is optionally protected with a hydroxyl protecting group, with a reagent having the formula

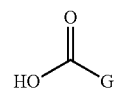

wherein G is as defined for Formula I, in the presence of coupling reagents, followed by removal of the amino protecting group and removal of the hydroxyl group, if present; and optionally forming a pharmaceutically acceptable salt thereof.

Compounds of Formula I or pharmaceutically acceptable salts thereof can modulate or inhibit the activity of one or more TAM kinases. The ability of compounds of Formula I to act as inhibitors of one or more TAM kinases may be demonstrated by the assays described in Examples A, B and C. $IC_{50}$ values are shown in the tables in the Examples.

Compounds of Formula I or pharmaceutically acceptable salts thereof can modulate or inhibit the activity of c-Met kinase. The ability of compounds of Formula I to act as inhibitors of wild type and certain mutant c-Met kinases may be demonstrated by the assay described in Example D. $IC_{50}$ values are shown in Table 9.

As used herein, the term "a TAM kinase" refers to one, two or all three of the TAM receptor tyrosine kinases, i.e., TYRO3, AXL and MER.

As used herein, the term "a TAM kinase inhibitor" refers to any compound exhibiting inhibition activity against one, two or all three of the TAM receptor kinases, i.e., the compounds exhibit inhibitory activity against AXL and/or MER and/or TYRO3.

As used herein, the term "a c-Met kinase inhibitor" refers to any compound exhibiting inhibitory activity against wild type or certain mutant c-Met kinases. In one embodiment, the term "a c-met kinase inhibitor" refers to any compound exhibiting inhibitory activity against wild type c-Met kinase or a mutant c-Met kinase selected from Del14, D1228H, D1228N, F1200I, L1195V, Y1230C, Y1230H and Y1230S.

In some embodiments, compounds of Formula I or pharmaceutically acceptable salts thereof have inhibitory activity against AXL. In some embodiments, compounds of Formula I or pharmaceutically acceptable salts thereof have inhibitory activity against MER. In some embodiments, a compound of Formula I has inhibitory activity against AXL and MER. In some embodiments, compounds of Formula I or pharmaceutically acceptable salts thereof have inhibitory activity against AXL, MER and TYRO3. In some embodiments, a compound of Formula I or pharmaceutically acceptable salts thereof has inhibitory activity against c-Met kinase. In some embodiments, a compound of Formula I or pharmaceutically acceptable salts thereof has inhibitory activity against one or more receptor tyrosine kinases selected from AXL, MER, TYRO3, and c-Met. In some embodiments, a compound of Formula I or pharmaceutically acceptable salts thereof has inhibitory activity against a c-Met kinase that does not include amino acids encoded by exon 14. In some embodiments, a compound of Formula I or pharmaceutically acceptable salts thereof has inhibitory activity against a mutated c-Met (e.g., any of the examples of mutated c-Met proteins described herein or known in the art) (e.g., a mutation in c-Met that causes resistance to a Type I c-Met inhibitor).

In one embodiment, compounds of Formula I or pharmaceutically acceptable salts thereof exhibit inhibition activity ($IC_{50}$) against a TAM kinase and/or c-Met of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, compounds of Formula I or pharmaceutically acceptable salts thereof exhibit inhibition activity ($IC_{50}$) against a TAM kinase and/or c-Met of less than about 25 nM, less than about 10 nM, less than about 5 nM, or less than about 1 nM as measured in an assay as provided herein.

In one embodiment, exemplary compounds of Formula I or pharmaceutically acceptable salts thereof exhibit inhibition activity ($IC_{50}$) against AXL of less than about 50 nM, less than about 25 nM, less than about 10 nM, or less than about 1 nM as measured in an assay as described herein.

In one embodiment, compounds of Formula I or pharmaceutically acceptable salts thereof exhibit inhibition activity ($IC_{50}$) against MER of less than about less than about 200 nM, less than about 100 nM, less than about 50 nM, less than about 25 nM, less than about 10 nM, or less than about 1 nM as measured in an assay as described herein. In some embodiments, compounds of Formula I or pharmaceutically acceptable salts thereof exhibit inhibition activity ($IC_{50}$) against MER of less than about 25 nM, less than about 10 nM, less than about 5 nM, or less than about 1 nM as measured in an assay as provided herein.

In one embodiment, compounds of Formula I or pharmaceutically acceptable salts thereof exhibit inhibition activity ($IC_{50}$) against TYRO3 of less than about 1000 nM, less than about 750 nM, less than about 500 nM, less than about 250 nM, less than about 200 nM, less than about 100 nM, less than about 50 nM, less than about 25 nM, less than about 10 nM, or less than about 1 nM as measured in an assay as described herein.

In one embodiment, compounds of Formula I or pharmaceutically acceptable salts thereof exhibit inhibition activity ($IC_{50}$) against c-Met of less than about 1000 nM, less than about 750 nM, less than about 500 nM, less than about 250 nM, less than about 200 nM, less than about 100 nM, less than about 50 nM, less than about 25 nM, less than about 10 nM, or less than about 1 nM as measured in an assay as described herein.

In some embodiments, compounds of Formula I or pharmaceutically acceptable salts thereof inhibit all of three of the TAM kinases (i.e., AXL, MER and TYRO3) within about a 5-fold difference.

In some embodiments, compounds of Formula I or pharmaceutically acceptable salts thereof are selective for AXL over MER. In some embodiments, a compound of Formula I or a pharmaceutically acceptable salt thereof, exhibits at least a 2-fold selectivity; at least a 3-fold selectivity; at least a 4-fold selectivity; at least a 5-fold selectivity; at least a 6-fold selectivity; at least a 7-fold selectivity; at least a 8-fold selectivity; at least a 9-fold selectivity; at least a 10-fold selectivity; at least a 11-fold selectivity; at least a 12-fold selectivity; at least a 13-fold selectivity; at least a 14-fold selectivity; at least a 15-fold selectivity; at least a 20-fold selectivity; at least a 25-fold selectivity; at least a 30-fold selectivity; at least a 35-fold selectivity; at least a 40-fold selectivity; at least a 45-fold selectivity; at least a 50-fold selectivity; or at least a 55-fold selectivity, for AXL over MER. In some embodiments, selectivity for AXL and MER is measured in an enzyme assay (e.g., an enzyme assay as provided herein.

In some embodiments, a compound of Formula I or a pharmaceutically acceptable salt thereof, exhibits at least a 5-fold selectivity; at least a 10-fold selectivity; at least a 15-fold selectivity; at least a 20-fold selectivity; at least a 25-fold selectivity; at least a 30-fold selectivity; at least a 35-fold selectivity; at least a 40-fold selectivity; at least a 50-fold selectivity, at least a 60-fold selectivity; at least a 70-fold selectivity; at least a 80-fold selectivity; at least a 90-fold selectivity; at least a 100-fold selectivity; at least a 125-fold selectivity, at least a 150-fold selectivity; or at least a 200-fold selectivity, for AXL over TYRO3. In some embodiments, selectivity for AXL and TYRO3 is measured in an enzyme assay (e.g., an enzyme assay as provided herein).

In some embodiments, compounds of Formula I or a pharmaceutically acceptable salt thereof exhibit at least a 5-fold selectivity; at least a 10-fold selectivity; at least a 15-fold selectivity; at least a 20-fold selectivity; at least a 25-fold selectivity; at least a 30-fold selectivity; at least a 35-fold selectivity; or at least a 40-fold selectivity; for MER over TYRO3. In some embodiments, selectivity for MER and TYRO3 is measured in an enzyme assay (e.g., an enzyme assay as provided herein.

In some embodiments, provided herein is a method for inhibiting AXL kinase, which comprises contacting the AXL kinase with compound of Formula I, or a pharmaceutically acceptable salt thereof.

In some embodiments, provided herein is a method for inhibiting MER kinase, which comprises contacting the MER kinase with compound of Formula I, or a pharmaceutically acceptable salt thereof.

In some embodiments, provided herein is a method for inhibiting TYRO3 kinase, which comprises contacting the TYRO3 kinase with compound of Formula I, or a pharmaceutically acceptable salt thereof.

In some embodiments, provided herein is a method for inhibiting c-Met kinase (e.g., any of the exemplary c-Met kinases described herein), which comprises contacting the c-Met kinase with compound of Formula I, or a pharmaceutically acceptable salt thereof.

Compounds of Formula I or pharmaceutically acceptable salts thereof are useful in the treatment of various diseases associated with increased (e.g., at least 1%, at least 2%, at least 4%, at least 6%, at least 8%, at least 10%, at least 12%, at least 14%, at least 16%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, or at least 300%) expression, level, and/or activity of one or more of the TAM kinases and/or c-Met kinase (e.g., in a cancer cell or in an immune cell) (e.g., as compared to a control, e.g., a non-cancerous tissue or cell, or a corresponding tissue or cell from a control subject that does not have cancer). In one embodiment, compounds of Formula I or pharmaceutically acceptable salts thereof are useful in treating or preventing proliferative disorders such as cancers. In one embodiment, tumors with an activating mutation (e.g., a point mutation or a chromosomal translocation) in a gene encoding a receptor tyrosine kinase and/or upregulation of the expression of a receptor tyrosine kinase (e.g., any of the TAM kinases or c-Met kinase described herein) may be particularly sensitive to compounds of Formula I. In one embodiment, tumors with a mutation in a MET gene that results in exon 14 skipping during mRNA splicing are sensitive to compounds of Formula I. In one embodiment, tumors having a mutation in a MET gene that results in expression of a c-Met protein having resistance to a Type I c-Met inhibitor are sensitive to compounds of Formula I.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a TAM-associated disease or disorder (e.g., a TAM-associated cancer) and/or has been identified or diagnosed as having a c-Met-associated disease or disorder (e.g., a c-Met-associated cancer) (e.g., as determined using a regulatory agency-approved, e.g., FDA-approved, assay or kit). In some embodiments, the subject has been identified or diagnosed as having a cancer associated with one or more TAM kinases and/or c-Met kinase (e.g., a TAK-associated cancer) (e.g., as determined using a regulatory agency-approved, e.g., FDA-approved, assay or kit). In some embodiments, the subject has a tumor that is associated with one or more TAM kinases and/or c-Met kinase (e.g., an increase in the expression, level, and/or activity of one or more TAM kinases and/or c-Met kinase in a cell (e.g., a cancer cell or an immune cell) as compared to a control, e.g., a non-cancerous tissue or a corresponding tissue from a control subject that does not have cancer) (e.g., as determined using a regulatory agency-approved assay or kit). In some embodiments, the subject is suspected of having a TAM-associated cancer and/or a c-Met-associated cancer. In some embodiments, the subject has a clinical record indicating that the subject has a tumor is associated with one or more TAM kinases (e.g., a TAM-associated cancer) and/or c-Met kinase (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics*, 15th Ed. Philadelphia: W.B. Saunders Company, 1996; Rudolph A M, et al. *Rudolph's Pediatrics*, 21st Ed. New York: McGraw-Hill, 2002; and Avery M D, First L R. *Pediatric Medicine*, 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

The phrase "therapeutically effective amount" means an amount of compound that, when administered to a patient in need of such treatment, is sufficient to (i) treat a TAM kinase-associated disease or disorder (e.g., a TAM-associated cancer) and/or a c-Met kinase-associated disease or disorder (e.g., a MET-associated cancer), (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the patient in need of treatment, but can nevertheless be routinely determined by one skilled in the art.

The term "regulatory agency" refers to a country's agency for the approval of the medical use of pharmaceutical agents with the country. For example, a non-limiting example of a regulatory agency is the U.S. Food and Drug Administration (FDA).

The term "TAM-associated disease or disorder" as used herein refers to diseases or disorders associated with or having increased expression and/or activity of one or more of the TAM kinases in a cell (e.g., a cancer cell or an immune cell) (e.g., as compared to a control, e.g., a non-cancerous tissue or cell, or a corresponding tissue or cell from a control subject that does not have cancer) and/or where activation of a TAM kinase expressed on non-cancer cells contributes to disease. Non-limiting examples of a TAM-associated disease or disorder include, for example, cancer (a TAM-associated cancer), e.g., any of the cancers described herein. In one embodiment, the disease is a cancer that overexpresses one or more TAM kinases after treatment with at least one additional anticancer agent (e.g., one or more of any of the additional anticancer agents described herein), e.g., a kinase-targeted therapeutic agent and/or a chemotherapeutic agent as described herein). In one embodiment, the disease is associated with signaling through one or more TAM kinases expressed in cells of the immune system (e.g., immune cells selected from the group of tumor-associated macrophages, natural killer (NK) cells, and subsets of tumor associated dendritic cells), wherein the expression of one or more TAM kinases in the immune cells may limit the ability of the patient's immune system to make an effective antitumor response.

The term "TAM-associated cancer" as used herein refers to cancers associated with or having increased expression and/or activity of one or more of the TAM kinases in a cancer cell or an immune cell (e.g., as compared to a control, e.g., a non-cancerous tissue or cell, or a corresponding tissue or cell from a control subject that does not have cancer). Non-limiting examples of a TAM-associated cancer are described herein. In some embodiments, the TAM-associated cancer is a cancer having a chromosomal translocation that results in the expression of a TMEM87B-MERTK fusion protein (e.g., amino acids 1-55 of TMEM87B and amino acids 433-1000 of MERTK) or a AXL-MBIP fusion protein. A description of an exemplary chromosomal translocation that results in the expression of a TMEM87B-MERTK fusion protein is provided in Shaver et al. (*Cancer Res.* 76(16):4850-4860, 2016). A description of an exemplary chromosomal translocation that results in the expression of an AXL-MBIP fusion protein is provided in Seo et al. (*Genome Res.* 22:2109-2119, 2012). Chromosomal translocations or the resulting expression of TMEM87B-MERTK or AXL-MBIP fusion proteins can be detected using. In Situ Hybridization (e.g., Fluorescent In Situ Hybridization (FISH)). Chromosomal translocations that result in the expression of TMEM87B-MERTK or AXL-MBIP can be detected by sequencing DNA from a sample obtained from the subject (e.g., blood, plasma, urine, cerebrospinal fluid, saliva, sputum, bronchoalveolar lavage, bile, lymphatic fluid, cyst fluid, stool ascites, or a tumor biopsy obtained from the subject). Exemplary methods that can be used to sequence DNA are known in the art and include, e.g., next-generation sequencing (NGS), traditional PCR, digital PCR, and microarray analysis. Additional methods that can be used to detect chromosomal translocations that result in the expression of TMEM87B-MERTK or AXL-MBIP fusion proteins, or the expression of TMEM87B-MERTK or AXL-MBIP fusion proteins, are known in the art.

The term "c-Met-associated disease or disorder" as used herein refers to diseases or disorders associated with or having increased expression, level, and/or activity of c-Met kinase in a cell (e.g., a cancer cell or an immune cell) (e.g., as compared to a control, e.g., a non-cancerous tissue or cell, or a corresponding tissue or cell from a control subject that does not have cancer) and/or where activation of c-Met kinase expressed in non-cancer cells contributes to disease. Non-limiting examples of a c-MET-associated disease or disorder include, for example, cancer (a c-Met-associated cancer), e.g., any of the cancers described herein. In one embodiment, the disease is a cancer that overexpresses c-Met kinase after treatment with at least one additional anticancer agent (e.g., one or more of any of the additional anti cancer agents described herein), e.g., a kinase-targeted therapeutic agent and/or a chemotherapeutic agent as described herein). In some embodiments, the disease is a cancer that has a higher protein level of c-Met kinase (e.g., due to mutation in a MET gene that results in decreased proteasome degradation of c-MET kinase in a mammalian cell). In some embodiments, the disease is a cancer that has a higher level of c-Met kinase activity due to an activating mutation in a c-Met gene (e.g., any of the activating mutations in a c-Met gene described herein) or an increase in the expression of a c-Met kinase in a mammalian cell. In some embodiments, the disease is a cancer that expresses a c-Met kinase that is resistant (e.g., to at least some extent as compared to a wildtype c-Met kinase) to a Type I c-Met inhibitor.

Receptor tyrosine kinases (RTKs) are cell surface proteins that transmit signals from the extracellular environment to the cell cytoplasm and nucleus to regulate cellular events such as survival, growth, proliferation, differentiation, adhesion, and migration. All RTKs contain an extracellular ligand binding domain and a cytoplasmic protein tyrosine kinase domain. Ligand binding leads to the dimerization of RTKs, which triggers the activation of the cytoplasmic kinase and initiates downstream signal transduction pathways. RTKs can be classified into distinct subfamilies based on their sequence similarity.

The TAM receptor tyrosine kinases (TYRO3, AXL (also known as UFO) and MER) is an emerging class of innate immune checkpoints that participate in key steps of antitumoral immunity (Akalu, T, et al., *Immunological Reviews* 2017; 276:165-177). TAM kinases are characterized by an extracellular ligand binding domain consisting of two immunoglobulin-like domains and two fibronectin type III domains. Two ligands, growth arrest specific 6 (GAS6) and protein S (ProS), have been identified for TAM kinases. GAS6 can bind to and activate all three TAM kinases, while ProS is a ligand for MER and TYRO3 (Graham et al., 2014, Nature reviews Cancer 14, 769-785).

TAM kinases are ectopically expressed or over-expressed in a wide variety of cancers, including breast, colon, renal, skin, lung, liver, brain, ovarian, prostate, and thyroid malignancies (Graham et al., 2014, Nature Reviews Cancer 14, 769-785; and Linger et al., 2008, Oncogene 32, 3420-3431) and play important roles in tumor initiation and maintenance. When activated, AXL and MER can regulate tumor cell survival, proliferation, migration and invasion, angiogenesis, and tumor-host interactions (Schoumacher, M. et al., Curr. Oncol. Rep. 2017; 19(3); 19). Accordingly, blocking TAM signaling may promote engagement of adaptive immunity and complement T-cell checkpoint blockade (Akalu, T, et al., Immunological Reviews 2017; 276:165-177). Therefore, TAM inhibition represents an attractive approach for targeting another class of oncogenic RTKs (Graham et al., 2014, Nature Reviews Cancer 14, 769-785; and Linger et al., 2008, Oncogene 32, 3420-3431).

AXL was originally identified as a transforming gene from DNA of patients with chronic myelogenous leukemia (O'Bryan et al., 1991, Molecular and Cellular Biology 11, 5016-5031). GAS6 binds to AXL and induces subsequent auto-phosphorylation and activation of AXL tyrosine kinase. AXL activates several downstream signaling pathways including PI3K-AKT, RAF-MAPK, PLC-PKC (Feneyrolles et al., 2014, Molecular Cancer Therapeutics 13, 2141-2148; Linger et al., 2008, Oncogene 32, 3420-3431). Over-expression or overactivation of the AXL protein has been correlated with the promotion of multiple tumorigenic processes. High levels of AXL expression have been associates with poor prognosis in different cancers such as glioblastoma multiforme (Hutterer, M., et al., Clin. Caner Res. 2008, 14, 130-138), breast cancer (Wang, X., Cancer Res. 2013, 73, 6516-6525), lung cancer (Niederst, M. et al, Sci. Signaling, 2013, 6, re6), osteosarcoma (Han, L, Biochem. Biophys. Res. Commun. 2013, 435, 493-500), and acute myeloid leukemia (Ben-Batalla, L., et al., Blood 2013, 122, 2443-2452). AXL is over-expressed or amplified in a variety of malignancies including lung cancer, prostate cancer, colon cancer, breast cancer, melanoma, and renal cell carcinoma (Linger et al., 2008, Oncogene 32, 3420-3431), and overexpression of AXL is correlated with poor prognosis (Linger et al., 2008, Oncogene 32, 3420-3431). AXL activation promotes cancer cell survival, proliferation, angiogenesis, metastasis, and resistance to chemotherapy and targeted therapies. AXL knockdown or AXL antibody can inhibit the migration of breast cancer and NSCLC cancer in vitro, and blocked tumor growth in xenograft tumor models (Li et al., 2009, Oncogene 28, 3442-3455). In pancreatic cancer cells, inhibition of AXL decreased cell proliferation and survival (Koorstra et al., 2009, Cancer Biology & Therapy 8, 618-626). In prostate cancer, AXL inhibition decreased cell migration, invasion, and proliferation (Tai et al., 2008, Oncogene 27, 4044-4055). In triple-negative breast cancer, patients typically present a significant clinical challenge, as they do not respond to the various targeted cancer therapies due to an apparent lack of RTK activation. However, patients with triple-negative breast cancer do show some response to taxane-based chemotherapy and studies have suggested that combining anti-mitotic drugs (e.g., docetaxel) with an AXL inhibitor sensitized cancer cells to the anti-mitotic drug, and AXL in combination with an anti-mitotic drug may be an appropriate combination therapy in this disease setting (Wilson, et al., Cancer Res. 2014, 74(20), 5878-5890).

TAM kinases can contribute to therapeutic resistance by at least three mechanisms: intrinsic survival signaling in tumor cells, induction of TAM kinases as an escape mechanism for tumors that have been treated with oncogene-targeted agents, and immunosuppression in the tumor microenvironment (Graham, et al, Nature Reviews Cancer, 2014, 14, 769-785).

TAM kinases were found to promote resistance to cytotoxic chemotherapies (chemoresistance) in leukemia cells and solid tumor cells (Graham, et al, Nature Reviews Cancer, 2014, 14, 769-785). Transgenic lymphocytes ectopically expressing MER were found to be more resistant to dexamethasone than wild-type lymphocytes (Keating, A. K., et al., Oncogene, 2006, 25, 6092-6100), and stimulation of B-ALL cells with GAS6 increased resistance to cytarabine (Shiozawa, Y., et al., Neoplasia, 2010, 12, 116-127). AXL is induced in acute myeloid leukemia (AML) cells that have been treated with cytotoxic chemotherapies, and it mediates increased chemoresistance (Hong, C. C., et al., Cancer Lett., 2008, 268, 314-324). Chemotherapy-resistant chronic myeloid leukemia (CML) cell lines have upregulated levels of AXL, and shRNA-mediated knockdown of AXL increases chemosensitivity in CML cells and xenograft models (Zhao, Y., et al., Cancer Invest. 2012, 30, 287-294). Similarly, shRNA-mediated MER knock-down sensitizes B-cell acute lymphoblastic leukemia (B-ALL) and T-lineage acute lymphoblastic leukemia (T-ALL) cells to a range of chemotherapies (Linger, R. M., et al., Blood, 2013, 122, 1599-1609; Brandao, L. N., et al., Blood Cancer J., 2013, 3, e101). In solid tumors such as non-small cell lung cancer, pancreatic ductal adenocarcinoma, astrocytoma, lung adenocarcinoma, ovarian cancer, melanoma, and glioblastoma multiforme, overexpression of AXL or MER promotes chemoresi stance, and shRNA-mediated inhibition sensitizes cells to treatment with cytotoxic chemotherapies (Linger, R. N., et al., Oncogene, 2013, 32, 3420-3431; Song, X., et al., Cancer, 2011, 117, 734-743; Keating, A. K., et al., Mol. Cancer Ther. 2010, 9, 1298-1307; Lay, J. D., et al., Cancer Res. 2007, 67, 3878-3887; Zhao, Y., et al., Cancer Invest, 2012, 30, 287-294; Macleod, K., Cancer Res. 2005, 65, 6789-6800; Zhu, S., et al., Proc. Natl Acad. Sci. USA, 2009, 106, 17025-17030; Wang, Y., et al., Oncogene 2013, 32, 872-882).

In contrast to chemoresistance, examples of acquired resistance for TAM kinases are currently limited to AXL. AXL is upregulated in imatinib-resistant CML and gastro-intestinal stromal tumor (GIST) cell lines and tumor samples (Mahadevan, D., et al., Oncogene, 2007, 26, 3909-3919; Dufies, M., et al., Oncotarget 2011, 2, 874-885; Gioia, R., et al., Blood, 2011, 118, 2211-2221), and siRNA-mediated knockdown of AXL restored imatinib sensitivity to resistant cell lines (Dufies, M., et al.). Similarly, AXL is induced in lapatinib-resistant HER2 (also known as ERBB2)-positive breast cancer cell lines, and AXL inhibition restored lapatinib sensitivity (Liu, L., et al., Cancer Res. 2009, 69, 6871-6878). AXL has been associated with acquired resistance to epidermal growth factor receptor (EGFR) tyrosine kinase inhibitors (e.g., lapatinib and erlotinib) and therapeutic antibodies (e.g., cetuximab) in triple-negative breast cancer (Meyer, A. S. et al., Sci. Signal 2013, 6, ra66), colorectal cancer (Brand, et al., Cancer Res. 2014, 74:5152-5164), head and neck cancer (Kiles, K. M, et al., Mol. Cancer Ther. 2013, 12, 2541-2558) cell lines, and non-small cell lung cancer (Zhang, Nat. Genet. 2013, 44(8), 852-860). AXL has also been associated with acquired resistance to inhibitors targeting other kinases, including PI3Kα inhibitors such as apelisib (BYL719) in head and neck and esophageal squamous cell carcinomas (Elkabets, et al., Cancer Cell 2015, 27:533-546), MEK inhibitors (e.g., U0126 (1,4-Diamino-2,3-dicyano-1,4-bis(o-aminophenylmercapto)butadiene) and PD325901 (1,4-Diamino-2,3-dicyano-1,4-bis(o-aminophenylmercapto)butadiene) in triple-negative breast cancer cell lines and melanoma cell lines (Miller, et al., Cancer Discovery 2016, 6:382-39), fibroblast growth factor (FGFR) (Ware, K. E., Oncogenesis 2013, 2, e39), anaplastic lymphoma kinase (ALK) (Kim, H R, et al., Mol.

Oncol. 2013, 7, 1093-1102) and insulin-like growth factor 1 receptor (IGF1R) (Huang, R., Cancer Res 2010, 70, 7221-7231), and AXL inhibition has been demonstrated to overcome or delay resistance to these inhibitors. AXL is upregulated in NSCLC cell lines and xenografts that are resistant to EGFR tyrosine kinase inhibitors (erlotinib) and antibody drugs (cetuximab) (Brad, T. M., et al., Cancer Res. 2014, 74, 5152-5164; Zhang, Z., et al., Nature Genet. 2012, 44, 852-860), and it is induced in 20% of matched tumor samples taken from patients with NSCLC after development of resistance to the EGFR inhibitor erlotinib.

Regarding MER and AXL dual inhibitors, the normal roles of MER and AXL in preventing or terminating innate immune-mediated inflammation and natural killer (NK) cell responses are subverted in the tumor microenvironment. MER and AXL decrease NK cell antitumor activity, which allows increased metastases.

MER was originally identified as a phospho-protein from a lymphoblastoid expression library (Graham et al., 1995, Oncogene 10, 2349-2359). Both GAS6 and ProS can bind to MER and induce the phosphorylation and activation of MER kinase (Lew et al., 2014. eLife, 3:e03385). Like AXL, MER activation also conveys downstream signaling pathways including PI3K-Akt and Raf-MAPK (Linger et al., 2008, Oncogene 32, 3420-3431). MER is over-expressed in many cancers including multiple myeloma, gastric, prostate, breast, melanoma and rhabdomyosarcoma (Linger et al., 2008, Oncogene 32, 3420-3431). MER knockdown inhibits multiple myeloma cell growth in vitro and in xenograft models (Waizenegger et al., 2014, Leukemia, 1-9). In acute myeloid leukemia, MER knockdown induced apoptosis, decreased colony formation, and increased survival in a mouse model (Lee-Sherick et al., 2013, Oncogene 32, 5359-5368). MER inhibition increased apoptosis, decreased colony formation, increased chemo-sensitivity, and decreased tumor growth in NSCLC (Linger et al., 2013, Oncogene 32, 3420-3431). Similar effects are observed for MER knockdown in melanoma (Schlegel et al., 2013) and glioblastoma (Wang et al., 2013, Oncogene 32, 872-882).

TYRO3 was originally identified through a PCR-based cloning study (Lai and Lemke, 1991, Neuron 6, 691-704). Both ligands, GAS6 and ProS, can bind to and activate Tyro3. TYRO3 also plays a role in cancer growth and proliferation. TYRO3 is over-expressed in melanoma cells, and knockdown of TYRO3 induces apoptosis in these cells (Demarest et al., 2013, Biochemistry 52, 3102-3118).

TAM kinases have emerged as potential immune-oncology targets. The durable clinical responses to immune checkpoint blockade observed in cancer patients clearly indicate that the immune system plays a critical role in tumor initiation and maintenance. Genetic mutations from cancer cells can provide a diverse set of antigens that the immune cells can use to distinguish tumor cells from their normal counterpart. However, cancer cells have evolved multiple mechanisms to evade host immune surveillance. In fact, one hallmark of human cancer is its ability to avoid immune destruction. Cancer cells can induce an immune-suppressive microenvironment by promoting the formation of M2 tumor associated macrophages, myeloid derived suppressor cells (MDSC), and regulatory T cells. Cancer cells can also produce high levels of immune checkpoint proteins such as PD-L1 to induce T cell anergy or exhaustion. It is now clear that tumors co-opt certain immune-checkpoint pathways as a major mechanism of immune resistance (Pardoll, 2012, Cancer 12, 252-264). Antagonizing these negative regulators of T-cell function with antibodies has shown striking efficacy in clinical trials of a number of malignancies including advanced melanoma, non-small cell lung and bladder cancer. While these therapies have shown encouraging results, not all patients mount an anti-tumor response suggesting that other immune-suppressive pathways may also be important.

5J TAM kinases have been shown to function as checkpoints for immune activation in the tumor milieu. All TAM kinases are expressed in NK cells, and TAM kinases inhibit the antitumor activity of NK cells. LDC1267, a small molecule TAM kinase inhibitor, activates NK cells, and blocks metastasis in tumor models with different histologies (Paolino et al., 2014, Nature 507, 508-512). In addition, MER kinase decreases the activity of tumor associated macrophages through the increased secretion of immune suppressive cytokines such as ILIO and IL4, and decreased production of immune activating cytokines such as IL12 (Cook et al., 2013, The Journal of Clinical Investigation 123, 3231-3242). MER inhibition has been shown to reverse this effect. As a result, MER knockout mice are resistant to PyVmT tumor formation (Cook et al., 2013, Journal of Clinical Investigation 123, 3231-3242). The role of TAM kinases in the immune response is also supported by knockout mouse studies. TAM triple knockout mice (TKO) are viable. However, these mice displayed signs of autoimmune disease including enlarged spleen and lymph nodes, autoantibody production, swollen footpad and joints, skin lesions, and systemic lupus erythematosus (Lu and Lemke, 2001, Science 293, 306-311). This is consistent with the knockout phenotype for approved immune-oncology targets such as CTLA4 and PD-1. Both CTLA-4 and PD-1 knockout mice showed signs of autoimmune disease, and these mice die within a few weeks afterbirth (Chambers et al., 1997, Immunity 7, 885-895; and Nishimura et al., 2001, Science 291, 319-322). Therefore, inhibition of TAM kinases alone or in combination with other immune therapies may increase the ability of the immune system to make a therapeutically beneficial immune response against the cancer.

The MET receptor tyrosine kinases (e.g., c-Met) controls growth, invasion and metastasis in cancer cells. The c-Met is activated in human cancer by a variety of different molecular mechanisms (see, e.g., Zhang et al., *Carcinogenesis* 4:345-355, 2016). For example, a c-Met-associated disease or condition (e.g., a c-Met-associated cancer) include: (i) mutations that alter the sequence and increase the activity of c-Met kinase; (ii) mutations in regulatory sequences controlling c-Met expression or regulators of c-Met expression that confer increased expression of c-Met; (iii) mutations that alter the c-Met polypeptide sequence to confer increased c-Met kinase half-life (e.g., a mutation in a MET gene that results in exon 14 skipping during mRNA splicing that results in an increased level of c-Met in a mammalian cell); (iv) methylation of a MET gene (see, e.g., Nones et al., *Int. J. Cancer* 135:1110-8, 2014); (v) methylation of long interspersed nuclear element (L1) present in the MET intron between exon 2 and exon 3 (Weber et al., *Oncogene* 29:5775-5784, 2010); (vi) MET gene amplification; or (vii) by simultaneous expression of receptor and ligand, which results in autocrine stimulation of cancer cells (Birchmeier et al., *Nat. Rev. Mol. Cell Biol.* 4:915-925, 2003).

Exemplary mutations in a MET gene that alter the sequence of a c-Met kinase and increase the activity of c-Met kinase (e.g., as compared to wildtype c-Met kinase) include, but are not limited to those listed in Table 1.

TABLE 1

Exemplary list of mutations in a MET gene that alter the sequence of a c-Met kinase and increase the activity of the c-Met kinase

| MET Isoform 1 mutation | MET Isoform 2 mutation | Reference |
|---|---|---|
| V1092I | V1110I | Schmidt et al., *Oncogene* 18: 2343-2350, 1999 |
| H1094L | H1112L | Schmidt et al., *Oncogene* 18: 2343-2350, 1999 |
| H1094R | H1112R | Schmidt et al., *Cancer Research* 58: 1719-1722, 1998 |
| H1094Y | H1112Y | Schmidt et al., *Oncogene* 18: 2343-2350, 1999 |
| H1106D | H1124D | Schmidt et al., *Oncogene* 18: 2343-2350, 1999 |
| D1228H | D1246H | Bardelli et al., *Proc. Natl. Acad. Sci.* 95: 14379-14383, 2002 |
| D1228N | D1246N | Bardelli et al., *Proc. Natl. Acad. Sci.* 95: 14379-14383, 2002 |
| Y1230C | Y1248C | Bardelli et al., *Proc. Natl. Acad. Sci.* 95: 14379-14383, 2002 |
| Y1230D | Y1248D | Schmidt et al., *Oncogene* 18: 2343-2350, 1999 |
| Y1230H | Y1248H | Bardelli et al., *Proc. Natl. Acad. Sci.* 95: 14379-14383, 2002 |
| M1250T | M1268T | Bardelli et al., *Proc. Natl. Acad. Sci.* 95: 14379-14383, 2002 |

Exemplary mutations that alter the c-Met polypeptide sequence to confer increased c-Met kinase half-life (as compared to a wildtype c-Met kinase) include, but are not limited to, the mutations listed in Table 2 that promote skipping of MET exon 14 during mRNA splicing. Other exemplary mutations that are predicted to promote skipping of MET exon 14 during mRNA splicing include, but are not limited to, those disclosed in Frampton et al., *Cancer Discovery* 5(8):850-9, 2015; and Heist et al., *Oncologist* 21(4):481-6, 2016. The portion of the c-Met protein encoded by exon 14, most prominently Y1003 in a DpYR motif, is required for efficient recruitment of the E3 ubiquitin-protein ligase CBL, which targets MET for ubiquitin-mediated degradation (Lee et al., *J. Biol. Chem.* 269:19457-61, 1994; Lee et al., *Exp. Mol Med.* 38:565-73, 2006; Lee et al., *Oncogene* 33:34-43, 2014). Skipping of MET exon 14 in mRNA splicing results in a c-Met kinase that maintains the reading frame and that demonstrates increased c-Met protein stability and prolonged signaling upon HGF stimulation, leading to increased oncogenic potential (Peschard et al., *Mol. Cell* 8:995-1004, 2001; Abella et al., *Mol. Cell. Biol.* 25:9632-45, 2005). Other exemplary mutations that alter the c-Met polypeptide sequence to confer increased c-Met kinase half-life include, but are not limited to an amino acid substitution at Y1003 (e.g., a Y1003F amino acid substitution) (Peschard et al., *Mol. Cell* 8:995-1004, 2001).

TABLE 2

Exemplary list of mutations that confer skipping of MET exon 14

| Chromosomal location | Reference sequence | Altered sequence (' — ' denotes deletion) | Reference |
|---|---|---|---|
| chr7:116411875-116411897 | AAGCTCTTTCTTTCTCTCTGTT | — | Kong-Beltran et al., *Cancer Res.* 66(1):283-289, 2006 |
| chr7:116412022-116412050 | ACCGAGCTACTTTTCCAGAAGGTATATT | — | Kong-Beltran et al., *Cancer Res.* 66(1):283-289, 2006 |
| chr7:116412043-116412044 | G | T | Kong-Beltran et al., *Cancer Res.* 66(1):283-289, 2006 |
| chr7:116411854-116411874 | CCCATGATAGCCGTCTTTAA | — | Onozato et al., *J. Thorac. Oncol.* 4:5-11, 2009. |
| chr7:116411884-116411895 | CTTTCTCTCTG | — | Onozato et al., *J. Thorac. Oncol.* 4:5-11, 2009. |
| chr7:116411886-116411905 | TTCTCTCTGTTTTAAGATC | — | Onozato et al., *J. Thorac. Oncol.* 4:5-11, 2009. |
| chr7:116412043-116412044 | G | A | Onozato et al., *J. Thorac. Oncol.* 4:5-11, 2009. |
| chr7:116412043-116412044 | G | T | Asaoka et al., *Biochem. Biophys. Res. Comm.* 394:1042-6, 2010. |
| chr7:116411884-116411896 | CTTTCTCTCTGT | — | Jenkins et al., *Clin. Lung Cancer* 16:e101-e104, 2015. |
| chr7:116412042-116412043 | G | C | Waqar et al., *J. Thorac. Oncol.* 10:e29-31, 2015. |
| chr7:116412042-116412043 | G | C | Mendenhall et al., *J. Thorac. Oncol.* 10:e23-34, 2015. |

Exemplary c-Met-associated cancers include, but are not limited to those listed in Table 3.

TABLE 3

Exemplary c-Met-associated cancers exhibiting increased expression and/or activity of c-Met

| Cancer type | Type of genetic alterations | Reference |
|---|---|---|
| Gastrointestinal cancer (GI); Gastric cancer | MET gene amplification; Amino acid substitution in kinase domain (e.g., an amino acid substitution at position 1108, e.g., an A1108S amino acid substitution); point mutation conferring skipping of MET exon 14 during mRNA splicing (e.g., chr7: 116412043-116412044, G to T mutation) | Mo et al., *Chronic Dis. Transl. Med.* 3(3): 148-153, 2017; Tovar et al., *Ann. Transl. Med.* 5(10): 205, 2017; Asaoka et al., *Biochem. Biophys. Res. Comm.* 394: 1042-6, 2010. |
| Colorectal Adenocarcinoma | Amino acid substitution at position 375 (e.g., a N375S amino acid substitution); an amino acid substitution at position 1010 (e.g., a T1010I amino acid substitution); an amino acid substitution at position 988 (e.g., a R988C amino acid substitution); an amino acid substitution at position 1253 (e.g., a Y1253D amino acid substitution); and an amino acid substitution at position 1248 (e.g., a Y1248H amino acid substitution) | Zenali et al., *Oncoscience* 2(5): 533-541, 2015. |
| Colorectal carcinoma (CRC) | MET gene amplification; MET overexpression; amino acid substitutions in JM domain of c-Met kinase (e.g., an amino acid substitution at position 970 (e.g., an R970C amino acid substitution) and an amino acid substitution at position 992 (e.g., a T992I amino acid substitution) | Zeng et al., *Cancer Lett.* 265: 258-269, 2008; Kong-Beltran et al., *Cancer Res.* 66: 283-9, 2006; Tovar et al., *Ann. Transl. Med.* 5(10): 205, 2017. |
| Non-small cell lung cancer (NSCLC) | Point mutation conferring skipping of MET exon 14 during mRNA splicing; MET gene amplification; amino acid substitutions in c-Met kinase domain (e.g., an amino acid substitution at position 970 (e.g., a R970C amino acid substitution), an amino acid substitution at position 988 (e.g., a R988C amino acid substitution); an amino acid substitution at position 1010 (e.g., a T1010I amino acid substitution); an amino acid substitution at position 1058 (e.g., a S1058P amino acid substitution)); amino acid substitution in the JM domain of c-Met kinase (e.g., an amino acid substitution at position 988 (e.g., a R988C amino acid substitution), an amino acid substitution at position 1010 (e.g., a T1010I amino acid substitution), an amino acid substitution at position 1058 (e.g., a S1058P amino acid substitution), an amino acid substitution at position 970 (e.g., a R970C amino acid substitution), and an amino acid substitution at position 992 (e.g., a T992I amino acid substitution)). | Ichimura et al., *Jpn J. Cancer Res.* 87: 1063-1069, 1996; Ma et al., *Cancer Res.* 63: 6272-81, 2003; Kong-Beltran et al., *Cancer Res.* 66: 283-9, 2006; Tovar et al., 2017, *Ann. Transl. Med.* 5(10): 205, 2017 |
| Heptacellular carcinoma (HCC) | MET overexpression; Amino acid substitutions in kinase domain of c-Met (e.g., an amino acid substitution at position 1191 (e.g., a T1191I amino acid substitution), an amino acid substitution at position 1262 (e.g., a J1262R amino acid substitution), or an amino acid substitution at position 1268 (e.g., a M1268T or an M1268I amino acid substitution)); an amino acid substitution at position 375 (e.g., an N375S amino acid substitution); an amino acid substitution at position 988 (e.g., a R988C amino acid substitution) | Goyal et al., *Clin. Cancer Res.* 19: 2310-2318, 2013; Tovar et al., *Ann. Transl. Med.* 5(10): 205, 2017; Zenali et al., *Oncoscience* 2(5): 533-541, 2015 |
| Hereditary papillary renal carcinoma (HPRC) | Amino acid substitutions in the kinase domain of c-Met (e.g., an amino acid substitution at position 112 (e.g., a H112R, a H112L, or a H112I amino acid substitution), an amino acid position as position 1230 (e.g., a Y1230C, a Y1230H, or a Y1230D amino acid substitution), an amino acid substitution at position 1246 (e.g., a D1246N amino acid substitution), an amino acid substitution at position 1248 (e.g., a Y1248C amino acid substitution), an amino acid substitution at position 1268 (e.g., a M1268T amino acid substitution or a M1268I amino acid substitution). | Tovar et al., *Ann. Transl. Med.* 5(10): 205, 2017 |
| Papillary renal carcinoma | Amino acid substitutions in the kinase domain of c-Met (e.g., those listed in Table 1) | Jeffers et al., *Proc. Natl. Acad. Sci. U.S.A.* 94(21): 11445-11450, 1997; Schmidt et al., *Nat. Genet.* 16: 68-73, 1997; Schmidt et al., *Oncogene* 18: 2343-50, 1991. |
| Melanoma | An amino acid substitution at position 375 (e.g., a N375S amino acid substitution); an amino acid substitution at position 988 (e.g., a R988C amino acid substitution); an amino acid substitution at position 1010 (e.g., a T1010I amino acid substitution). | Zenali et al., *Oncoscience* 2(5): 533-541, 2015. |
| Gastric adenocarcinoma | An amino acid substitution at position 375 (e.g., an N3755 amino acid substitution). | Zenali et al., *Oncoscience* 2(5): 533-541, 2015. |
| Appendiceal adenocarcinoma | An amino acid substitution at position 375 (e.g., an N375S amino acid substitution); an amino acid substitution at position 988 (e.g., a R988C amino acid substitution) | Zenali et al., *Oncoscience* 2(5): 533-541, 2015. |
| Duodenal adenocarcinoma | An amino acid substitution at position 375 (e.g., an N3755 amino acid substitution) | Zenali et al., *Oncoscience* 2(5): 533-541, 2015. |
| Pancreatic adenocarcinoma | An amino acid substitution at position 375 (e.g., an N3755 amino acid substitution) | Zenali et al., *Oncoscience* 2(5): 533-541, 2015. |
| Lung adenocarcinoma | An amino acid substitution at position 375 (e.g., an N375S amino acid substitution); an | Zenali et al., *Oncoscience* 2(5): 533-541, 2015. |

TABLE 3-continued

Exemplary c-Met-associated cancers exhibiting increased expression and/or activity of c-Met

| Cancer type | Type of genetic alterations | Reference |
|---|---|---|
| | amino acid substitution at position 988 (e.g., a R988C amino acid substitution); an amino acid substitution at position 1010 (e.g., a T1010I amino acid substitution) | |
| Thyroid papillary carcinoma | An amino acid substitution at position 375 (e.g., an N375S amino acid substitution) | Zenali et al., *Oncoscience* 2(5): 533-541, 2015. |
| Thyroid medullary carcinoma | An amino acid substitution at position 1010 (e.g., a T1010I amino acid substitution) | Zenali et al., *Oncoscience* 2(5): 533-541, 2015. |
| Ewing sarcoma | An amino acid substitution at position 1010 (e.g., a T1010I amino acid substitution) | Zenali et al., *Oncoscience* 2(5): 533-541, 2015. |
| Prostate adenocarcinoma | An amino acid substitution at position 375 (e.g., an N375S amino acid substitution) | Zenali et al., *Oncoscience* 2(5): 533-541, 2015. |
| Squamous cell carcinoma of the head and neck and cervix | An amino acid substitution at position 375 (e.g., an N375S amino acid substitution); an amino acid substitution at position 988 (e.g., a R988C amino acid substitution); an amino acid substitution at position 1010 (e.g., an T1010I amino acid substitution) | Zenali et al., *Oncoscience* 2(5): 533-541, 2015. |
| Renal cell carcinoma | An amino acid substitution at position 375 (e.g., an N375S amino acid substitution); an amino acid substitution at position 1092 (e.g., a V1092I amino acid substitution); an amino acid substitution at position 1094 (e.g., a H1094L, a H1094R, or a H1094Y amino acid substitution); an amino acid substitution at position 1106 (e.g., a H1106D amino acid substitution); an amino acid substitution at position 1228 (e.g., a D1228H or a D1228N amino acid substitution); an amino acid substitution at position 1230 (e.g., a Y1230C, a Y1230D, or a Y1230H amino acid substitution); an amino acid substitution at position 1250 (e.g., a M1250T amino acid substitution) | Zenali et al., *Oncoscience* 2(5): 533-541, 2015; Schmidt et al., *Oncogene* 18: 2343-2350, 1999; Scmidt et al., *Cancer Research* 58: 1719-1722, 1998; Bardelli et al., *Proc. Natl. Acad. Sci.* 95: 14379-14383, 2002. |
| Pheochromo-cytoma and composite pheochromo-cytoma | An amino acid substitution at position 375 (e.g., an N375S amino acid substitution); an amino acid substitution at position 988 (e.g., an R988C amino acid substitution) | Zenali et al., *Oncoscience* 2(5): 533-541, 2015. |
| Ovarian serous carcinoma | An amino acid substitution at position 375 (e.g., an N375S amino acid substitution); an amino acid substitution at position 1010 (e.g., a 1010I amino acid substitution) | Zenali et al., *Oncoscience* 2(5): 533-541, 2015. |
| Ovarian clear cell carcinoma | An amino acid substitution at position 375 (e.g., an N375S amino acid substitution) | Zenali et al., *Oncoscience* 2(5): 533-541, 2015. |
| Ovarian mixed carcinoma | An amino acid substitution at position 1010 (e.g., a T1010I amino acid substitution) | Zenali et al., *Oncoscience* 2(5): 533-541, 2015. |
| Peritoneal serous carcinoma | An amino acid substitution at position 1010 (e.g., a T1010I amino acid substitution) | Zenali et al., *Oncoscience* 2(5): 533-541, 2015. |
| Breast ductal adenocarcinoma | An amino acid substitution at position 375 (e.g., an N375S amino acid substitution); an amino acid substitution at position 1010 (e.g., a T1010I amino acid substitution). | Zenali et al., *Oncoscience* 2(5): 533-541, 2015. |
| Uterine leiomyosarcoma | An amino acid substitution at position 375 (e.g., an N375S amino acid substitution); amino acid substitution at position 1010 (e.g., a T1010I amino acid substitution) | Zenali et al., *Oncoscience* 2(5): 533-541, 2015. |
| Uterine endometrioid adenocarcinoma | An amino acid substitution at position 375 (e.g., an N375S amino acid substitution); an amino acid substitution at position 1010 (e.g., an T1010I amino acid substitution). | Zenali et al., *Oncoscience* 2(5): 533-541, 2015. |
| Uterine malignant mixed mullerian tumor | An amino acid substitution at position 375 (e.g., an N375S amino acid substitution) | Zenali et al., *Oncoscience* 2(5): 533-541, 2015. |
| Glioblastoma | An amino acid substitution at position 375 (e.g., an N375S amino acid substitution) | Zenali et al., *Oncoscience* 2(5): 533-541, 2015. |
| Anaplastic glioma | An amino acid substitution at position 375 (e.g., an N375S amino acid substitution) | Zenali et al., *Oncoscience* 2(5): 533-541, 2015. |
| Oligodendro-glioma | An amino acid substitution at position 1010 (e.g., an T1010I amino acid substitution) | Zenali et al., Oncoscience 2(5): 533-541, 2015. |
| Desmoplastic small round cell tumor | An amino acid substitution at position 375 (e.g., an N375S amino acid substitution) | Zenali et al., *Oncoscience* 2(5): 533-541, 2015. |
| Squamous cell carcinoma of rectum | An amino acid substitution at position 375 (e.g., N375S amino acid substitution) | Zenali et al., *Oncoscience* 2(5): 533-541, 2015. |
| Salivary gland carcinoma | An amino acid substitution at position 375 (e.g., an N375S amino acid substitution) | Zenali et al., *Oncoscience* 2(5): 533-541, 2015. |
| Heart angiosarcoma | An amino acid substitution at position 375 (e.g., a N375S amino acid substitution); an amino acid substitution at position 1010 (e.g., a T1010I amino acid substitution) | Zenali et al., *Oncoscience* 2(5): 533-541, 2015. |
| Gastrointestinal stromal tumor (GIST) | An amino acid substitution at position 1010 (e.g., a T1010I amino acid substitution); an amino acid substitution at position 988 (e.g., an R988C amino acid substitution) | Zenali et al., *Oncoscience* 2(5): 533-541, 2015. |
| Invasive thymoma | An amino acid substitution at position 375 (e.g., an N375S amino acid substitution) | Zenali et al., *Oncoscience* 2(5): 533-541, 2015. |
| Spindle sarcoma | An amino acid substitution at position 375 (e.g., an N375S amino acid substitution) | Zenali et al., *Oncoscience* 2(5): 533-541, 2015. |

In some embodiments, compounds of Formula I can be used to treat a c-Met associated cancer expressing a c-Met kinase that is resistant (e.g., to at least some extent as compared to a wildtype c-Met kinase) to a c-Met inhibitor (e.g., a Type I c-Met inhibitor). Non-limiting examples of amino acid substitutions that result in resistance of c-Met to a c-Met inhibitor (e.g., a Type I c-Met inhibitor) include: an amino acid substitution at position 1092 (e.g., a V1092I amino acid substitution in isoform 1 of c-Met or a V1110I amino acid substitution in isoform 2 of c-Met); an amino acid substitution at position 1094 (e.g., a H1094L amino acid substitution in isoform 1 of c-Met or a H1112L amino acid substitution in isoform 2 of c-Met; an H1094Y amino acid substitution in isoform 1 of c-Met or an H1112Y amino acid substitution in isoform 2 of c-Met); an amino acid substitution at position 1155 (e.g., a V1155L amino acid substitution in isoform 1 or a V1173L amino acid substitution in isoform 2 of c-Met); an amino acid substitution at position 1163 (e.g., a G1163R amino acid substitution in isoform 1 of c-Met or a G1181R amino acid substitution in isoform 2 of c-Met); an amino acid substitution at position 1195 (e.g., an L1195F amino acid substitution in isoform 1 of c-Met or a L1213F amino acid substitution in isoform 2 of c-Met; an L1195V amino acid substitution in isoform 1 of c-Met or an L1213V amino acid substitution in isoform 2 of c-Met); an amino acid substitution at position 1200 (e.g., an F1200I amino acid substitution in isoform 1 of c-Met or an F1218I amino acid substitution in isoform 2 of c-Met); an amino acid substitution at position 1211 (e.g., an M1211L amino acid substitution in isoform 1 of c-Met or an M1229L amino acid substitution in isoform 2 of c-Met); an amino acid substitution at position 1228 (e.g., a D1228A amino acid substitution in isoform 1 of c-Met or a D1246A amino acid substitution in isoform 2 of c-Met; a D1228G amino acid substitution in isoform 1 of c-Met or a D1246G amino acid substitution in isoform 2 of c-Met; a D1228H amino acid substitution in isoform 1 of c-Met or a D1246H amino acid substitution in isoform 2 of c-Met; a D1228N amino acid substitution in isoform 1 of c-Met or a D1246N amino acid substitution in isoform 2 of c-Met; a D1228V amino acid substitution in isoform 1 of c-Met or a D1246V amino acid substitutions in isoform 2 of c-Met; or a D1228Y amino acid substitution in isoform 1 of c-Met or a D1246Y amino acid substitution in isoform 2 of c-Met); an amino acid substitution at position 1230 (e.g., a Y1230C amino acid substitution in isoform 1 of c-Met or a Y1248C amino acid substitution in isoform 2 of c-Met; a Y1230H amino acid substitution in isoform 1 of c-Met or a Y1248H amino acid substitution in isoform 2 of c-Met; or a Y1230S amino acid substitution in isoform 1 of c-Met or a Y1248S amino acid substitution in isoform 2 of c-Met); or an amino acid substitution at position 1250 (e.g., a M1250T amino acid substitution in isoform 1 of c-Met or a M1268T amino acid substitution in isoform 2 of c-Met). Non-limiting examples of Type I inhibitors include crizotinib (PF-02341066), capmatinib, NVP-BVU972, AMG 337, bozitinib, glumetinib, savolitinib, and tepotinib. In some embodiments, amino acid substitutions that result in resistance of c-Met to a Type 1 c-Met inhibitor include L1195V, F1200I, D1228H, D1228N, Y1230C, Y1230H, and Y1230S.

In some embodiments, compounds of Formula I can be used to treat a c-Met associated cancer having a chromosomal translocation that result in a fusion protein including the c-Met kinase domain, where the fusion protein has increased c-Met activity as compared to a wildtype c-Met kinase (e.g., a Met-TPR fusion protein (Rodrigues et ah, *Mol. Cell. Biol.* 13:6711-6722, 1993) and the fusion protein/chromosomal translocation described in Cooper et ah, *Nature* 311(5981):29-33, 1984.

Accordingly, in one embodiment, provided herein is a method for treating a TAM-associated disease or disorder (e.g., a TAM-associated cancer), a c-Met-associated disease or disorder (e.g., a c-Met-associated cancer), or both, in a patient in need thereof, the method comprising administering to the patient a therapeutically effective amount of a compound of Formula I or a pharmaceutically acceptable salt thereof or a pharmaceutical composition thereof.

Also provided herein are methods of treating a patient identified or diagnosed as having a TAM-associated cancer, a c-Met-associated cancer, or both, that include administering to a patient identified or diagnosed as having a TAM-associated cancer, a c-Met-associated cancer, or both, a therapeutically effective amount of a compound of Formula I or a pharmaceutically acceptable salt thereof or a pharmaceutical composition thereof.

Also provided herein are methods of treating a patient having a cancer that include: (a) identifying the patient as having a TAM-associated cancer, a c-Met-associated cancer, or both, and (b) administering to the patient identified as having a TAM-associated cancer, a c-Met-associated cancer, or both, a therapeutically effective amount of a compound of Formula I or a pharmaceutically acceptable salt thereof or a pharmaceutical composition thereof.

Also provided herein are methods of decreasing the risk of developing a metastasis or an additional metastasis in a patient identified or diagnosed as having a TAM-associated cancer, a c-Met-associated cancer, or both, that include administering to the patient identified or diagnosed as having a TAM-associated cancer, a c-Met-associated cancer, or both, a therapeutically effective amount of a compound of Formula I or a pharmaceutically acceptable salt thereof or a pharmaceutical composition thereof. In some embodiments, the methods result in at least a 1% reduction (e.g., at least a 2% reduction, at least a 3% reduction, at least a 4% reduction, at least a 5% reduction, at least a 6% reduction, at least a 8% reduction, at least a 10% reduction, at least a 12% reduction, at least a 14% reduction, at least a 16% reduction at least a 18% reduction, at least a 20% reduction, at least a 25% reduction, at least a 30% reduction, at least a 35% reduction, at least a 40% reduction, at least a 45% reduction, at least a 50% reduction, at least a 55% reduction, at least a 60% reduction, at least a 65% reduction, at least a 70% reduction, at least a 75% reduction, at least a 80% reduction, at least a 85% reduction, at least a 90% reduction, at least a 95% reduction, or at least a 99% reduction) in the patient's risk of developing a metastasis or an additional metastasis, e.g., as compared to a population of subjects having a similar TAM-associated cancer and/or c-Met-associated cancer but receiving a different treatment or no treatment.

Also provided are methods of decreasing the risk of developing a metastasis or an additional metastasis in a patient having a cancer that include: (a) identifying the patient as having a TAM-associated cancer, a c-Met-associated cancer, or both; and (b) administering to the patient identified as having a TAM-associated cancer, a c-Met-associated cancer, or both, a therapeutically effective amount of a compound of Formula I or a pharmaceutically acceptable salt thereof or a pharmaceutical composition thereof. In some embodiments, the methods result in at least a 1% reduction (e.g., at least a 2% reduction, at least a 3% reduction, at least a 4% reduction, at least a 5% reduction, at least a 6% reduction, at least a 8% reduction, at least a 10% reduction, at least a 12% reduction, at least a 14% reduction, at least a 16% reduction, at least a 18% reduction, at least a 20% reduction, at least a 25% reduction, at least a 30% reduction, at least a 35% reduction, at least a 40% reduction, at least a 45% reduction, at least a 50% reduction, at least a 55% reduction, at least a 60% reduction, at least a 65% reduction, at least a 70% reduction, at least a 75% reduction, at least a 80% reduction, at least a 85% reduction, at least a 90% reduction, at least a 95% reduction, or at least a 99% reduction) in the patient's risk of developing a metastasis or an additional metastasis, e.g., as compared to a population of subjects having a similar TAM-associated cancer and/or c-Met-associated cancer, but receiving a different treatment or no treatment.

Also provided are methods of decreasing migration and/or invasion of a cancer cell in a patient identified as having a TAM-associated cancer, a c-Met-associated cancer, or both, that include administering to a patient identified or diagnosed as having a TAM-associated cancer, a c-Met-associated cancer, or both, a therapeutically effective amount of a compound of Formula T or a pharmaceutically acceptable salt thereof or a pharmaceutical composition thereof. In some embodiments, the methods result in at least a 1% decrease (e.g., at least a 2% decrease, at least a 3% decrease, at least a 4% decrease, at least a 5% decrease, at least a 6% decrease, at least a 8% decrease, at least a 10% decrease, at least a 12% decrease, at least a 14% decrease, at least a 16% decrease, at least a 18% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease) in the migration and/or invasion of a cancer cell in the patient, e.g., as compared to the migration and/or invasion of a cancer cell or a population of cancer cells in a subject having a similar TAM-associated cancer and/or c-Met-associated cancer but receiving a different treatment or no treatment.

Also provided herein are methods of decreasing migration and/or invasion of a cancer cell in a patient having a cancer that include: (a) identifying the patient as having a TAM-associated cancer, a c-Met-associated cancer, or both; and (b) administering to the patient identified as having a TAM-associated cancer, a c-Met-associated cancer, or both, a therapeutically effective amount of a compound of Formula I or a pharmaceutically acceptable salt thereof or a pharmaceutical composition thereof. In some embodiments, the methods result in at least a 1% decrease (e.g., at least a 2% decrease, at least a 3% decrease, at least a 4% decrease, at least a 5% decrease, at least a 6% decrease, at least a 8% decrease, at least a 10% decrease, at least a 12% decrease, at least a 14% decrease, at least a 16% decrease, at least a 18% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease) in the migration and/or invasion of a cancer cell in the patient, e.g., as compared to the migration and/or invasion of a cancer cell or a population of cancer cells in a subject having a similar TAM-associated cancer and/or a c-Met-associated cancer, but receiving a different treatment or no treatment.

Some embodiments of these methods further include administering to the patient at least one additional anticancer agent (e.g., any of the exemplary additional anticancer agents described herein or known in the art). For example, in some examples, the at least one anticancer agent or therapy can be selected from the group of: an immune checkpoint inhibitor, a kinase inhibitor, a chemotherapy, radiation, and surgery.

In some embodiments of any of the methods described herein, the patient was previously treated with at least one additional anticancer agent (e.g., any of the additional anticancer agents described herein) and the previous treatment with the at least one additional anti cancer agent was unsuccessful (e.g., the patient previously developed resistance to one or more of the at least one additional anti cancer agent).

In some embodiments of any of the methods described herein, the at least one additional anticancer agent is selected from the group of: a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor (e.g., a type I c-Met kinase inhibitor), a RAF inhibitor, an Akt inhibitor, a FTL-3 inhibitor, a MAP kinase pathway inhibitor.

In some embodiments of any of the methods described herein, the at least one additional anti cancer agent can include a kinase inhibitor, and the patient previously developed resistance to the kinase inhibitor. In some embodiments of any of the methods described herein, the at least one anti cancer agent includes a kinase inhibitor selected from the group of: bozitinib, 1-(6,7-Dihydro-5H-benzo[6,7]cyclohepta[1,2-c]pyridazin-3-yl)-N3-[7(S)-(1-pyrrolidinyl)-6,7,8,9-tetrahydro-5H-benzocycloheptene-2-yl]-1H-1,2,4-triazole-3,5-diamine (BGB324), crizotinib, foretinib, (N-[4-(2-Amino-3-chloropyridin-4-yloxy)-3-fluorophenyl]-4-ethoxy-1-(4-fluorophenyl)-2-oxo-1,2-dihydropyridine-3-carboxamide (BMS-777607), amuvatinib, BMS-796302, cabozantinib, glesatinib (MGCD265), 2-(4-Fluorophenyl)-N-[3-fluoro-4-(3-phenyl-1H-pyrrolo[2,3-b]pyridin-4-yloxy)phenyl]-1,5-dimethyl-3-oxo-2,3-dihydro-1H-pyrazole-4-carboxamide (NPS-1034), N-[4-[(6,7-Dimethoxyquinolin-4-yl)oxy]-3-fluorophenyl]-4-ethoxy-1-(4-fluoro-2-methylphenyl)-1H-pyrazole-3-carboxamide hydrochloride (LDC1267), gilteritinib, [3-(2-[[3-Fluoro-4-(4-methylpiperazin-1-yl)phenyl]amino]-5-methyl-7H-pyrrolo[2,3-d]pyrimidin-4-yl)phenyl]acetonitrile (SGI-7079), dubermatinib (TP-0903), trans-4-[2-(Butylamino)-5-[4-[(4-methylpiperazin-1-yl)methyl]phenyl]-7H-pyrrolo[2,3-d]pyrimidin-7-yl]cyclohexanol (UNC2025), 3-[3-[4-(Morpholin-4-ylmethyl)-1H-pyrrol-2-ylmethylene]-2-oxo-2,3-dihydro-1H-indol-5-ylmethyl]thiazolidine-2,4-dione hydrochloride (S49076), sunitinib, 12A11, Mab173, YW327.6S2, D9, E8, merestinib, [3-(2-[[3-Fluoro-4-(4-methylpiperazin-1-yl)phenyl]amino]-5-methyl-7H-pyrrolo[2,3-d]pyrimidin-4-yl)phenyl]acetonitrile (SGI-7079), N-[4-[(6,7-Dimethoxyquinolin-4-yl)oxy]-3-fluorophenyl]-4-ethoxy-1-(4-fluoro-2-methylphenyl)-1H-pyrazole-3-carboxamide hydrochloride, capmatinib, NVP-BVU972, AMG 337, bozitinib, glumetinib, savolitinib, and tepotinib.

In some embodiments of any of the methods described herein, the at least one additional anticancer agent includes dexamethasone, and the patient previously developed resistance to dexamethasone. In some embodiments of any of the methods described herein, the at least one additional anticancer agent includes cytarabine, and the patient previously developed resistance to cytarabine. In some embodiments of any of the methods described herein, the at least one additional anticancer agent includes imatinib, and the patient previously developed resistance to imatinib. In some embodiments of any of the methods described herein, the at least one additional anticancer agent includes lapatinib, and the patient previously developed resistance to lapatinib. In some embodiments of any of the methods described herein, the at least one additional anti cancer agent includes cetuximab, and the patient previously developed resistance to cetuximab. In some embodiments of any of the methods described herein, the at least one additional anticancer agent includes erlotinib, and the patient previously developed resistance to erlotinib. In some embodiments of any of the methods described herein, the at least one additional anticancer agent includes alpelisib, and the patient previously developed resistance to alpelisib. In some embodiments of any of the methods described herein, the at least one additional anticancer agent includes cisplatin, and the patient previously developed resistance to cisplatin. In some embodiments of any of the methods described herein, the at least one additional anticancer agent includes sunitinib, and the patient previously developed resistance to sunitinib. In some embodiments of any of the methods described herein, the at least one additional anticancer agent includes metformin, and the patient previously developed resistance to metformin.

In some embodiments of any of the methods described herein, the at least one additional anticancer agent includes an anti-PD-1 antibody, and the patient previously developed resistance to the anti-PD-1 antibody.

In some embodiments of any of the methods described herein, the at least one additional anticancer agent includes docetaxel, and the patient previously developed resistance to docetaxel. In some embodiments of any of the methods described herein, the at least one additional anticancer agent includes an EGFR inhibitor, and the patient previously developed resistance to the EGFR inhibitor.

In some embodiments of any of the methods described herein, the at least one additional anticancer agent is a Type 1 c-Met inhibitor, and the patient previously developed resistance to the c-Met inhibitor. In some embodiments of any of the methods described herein, the at least one additional Type 1 c-Met inhibitor includes crizotinib, and the patient previously developed resistance to crizotinib. In some embodiments of any of the methods described herein, the at least one additional Type 1 c-Met inhibitor includes capmatinib, and the patient previously developed resistance to capmatinib. In some embodiments of any of the methods described herein, the at least one additional Type 1 c-Met inhibitor includes NVP-BVU972, and the patient previously developed resistance to NVP-BVU972. In some embodiments of any of the methods described herein, the at least one additional Type I c-Met inhibitor includes AMG 337, and the patient previously developed resistance to AMG 337. In some embodiments of any of the methods described herein, the at least one additional Type 1 c-Met inhibitor includes bozitinib, and the patient previously developed resistance to bozitinib. In some embodiments of any of the methods described herein, the at least one additional Type 1 c-Met inhibitor includes glumetinib, and the patient previously developed resistance to glumetinib. In some embodiments of any of the methods described herein, the at least one additional Type 1 c-Met inhibitor includes savolitinib, and the patient previously developed resistance to savolitinib. In some embodiments of any of the methods described herein, the at least one additional Type 1 c-Met inhibitor includes tepotinib, and the patient previously developed resistance to tepotinib.

In some embodiments, the tumor developed a resistance mutation after treatment with the Type 1 c-Met inhibitor. In some embodiments, the resistance mutation in c-Met results in the expression of a c-Met protein including one or more of the following amino acid substitutions: L1195V, F1200I, D1228H, D1228N, D1230C, Y1230H, and Y1230S.

Also provided herein are methods of selecting a treatment for a patient identified or diagnosed as having a TAM-associated cancer, a c-Met-associated cancer, or both, that include selecting a compound of Formula I or a pharmaceutically acceptable salt thereof or a pharmaceutical composition thereof for the patient identified or diagnosed as having a TAM-associated cancer, a c-Met-associated cancer, or both. Some embodiments further comprise administering the selected compound of Formula I or the pharmaceutically acceptable salt thereof or the pharmaceutical composition thereof to the patient.

Also provided herein are methods of selecting a treatment for a patient that include: (a) identifying the patient as having a TAM-associated cancer, a c-Met-associated cancer, or both; and (b) selecting a compound of Formula I or a pharmaceutically acceptable salt thereof or a pharmaceutical composition thereof for the patient identified as having a TAM-associated cancer, a c-Met-associated cancer, or both. Some embodiments further comprise administering the selected compound of Formula I or the pharmaceutically acceptable salt thereof or the pharmaceutical composition thereof to the patient identified as having a TAM-associated cancer, a c-Met-associated cancer, or both.

In some embodiments of any of the methods described herein, the subject is identified or diagnosed as having a TAM-associated cancer (e.g., any of the TAM-associated cancers described herein, e.g., having any of the exemplary TAM mutations described herein). In some embodiments of any of the methods described herein, the subject is identified or diagnosed as having both a TAM-associated cancer (e.g., any of the TAM-associated cancers described herein, e.g., having any of the exemplary TAM mutations described herein) and a c-Met-associated cancer (e.g., any of the exemplary c-Met-associated cancers described herein, e.g., having any of the exemplary c-Met mutations described herein). In some embodiments of any of the methods described herein, the subject is identified or diagnosed as having a c-Met-associated cancer (e.g., any of the exemplary c-Met-associated cancers described herein, e.g., having any of the exemplary c-Met-associated mutations described herein).

In some embodiments of any of the methods described herein, the c-Met-associated cancer is a cancer having a mutation that increases the activity of a c-Met kinase. In some embodiments of any of the methods described herein, the mutation that increases the activity of a c-Met kinase results in one or more amino acid substitutions in the c-Met kinase. In some embodiments of any of the methods described herein, the c-Met-associated cancer is a cancer having a mutation that increases the expression of c-Met in a mammalian cell. In some embodiments of any of the methods described herein, the c-Met-associated cancer is a cancer having a mutation that confers increased half-life of c-Met kinase in a mammalian cell. In some embodiments of any of the methods described herein, the mutation that confers increased half-life of c-Met kinase in a mammalian cell is a mutation that results in c-Met exon 14 skipping during mRNA splicing. In some embodiments of any of the methods described herein, the c-Met-associated cancer is a cancer having a MET gene amplification. In some embodiments of any of the methods described herein, the c-Met-associated cancer is a c-Met-associated cancer that has resistance to a type I c-Met inhibitor.

In some embodiments of any of the methods described herein, the c-Met-associated cancer is selected from the group of: gastrointestinal cancer (GI), gastric cancer, colorectal adenocarcinoma, colorectal carcinoma (CRC), non-small cell lung cancer (NSCLC), hepatocellular carcinoma (HCC), hereditary papillary renal carcinoma (HPRC), papillary renal carcinoma, melanoma, gastric adenocarcinoma, appendiceal adenocarcinoma, duodenal adenocarcinoma, pancreatic adenocarcinoma, lung adenocarcinoma, thyroid papillary carcinoma, thyroid medullary carcinoma, Ewing sarcoma, prostate adenocarcinoma, squamous cell carcinoma of the head and neck and cervix, renal cell carcinoma, pheochromocytoma and composite pheochromocytoma, ovarian serous carcinoma, ovarian clear cell carcinoma, ovarian mixed carcinoma, peritoneal serous carcinoma, breast ductal adenocarcinoma, uterine leiomyosarcoma, uterine endometrioid adenocarcinoma, uterine malignant mixed mullerian tumor, glioblastoma, anaplastic glioma, oligodendroglioma, desmoplastic small round cell tumor, squamous cell carcinoma of rectum, salivary gland carcinoma, heart angiosarcoma, gastrointestinal stromal tumor, invasive thymoma, and spindle sarcoma.

Also provided herein are methods of selecting a treatment for a patient identified or diagnosed as having a cancer that include: (a) administering at least one additional anticancer agent to the patient (e.g., any of the additional anticancer agents described herein); (b) after (a), detecting increased expression, level, and/or activity of a TAM kinase and/or c-Met kinase in a cancer cell or an immune cell from the patient; and (c) after (b), selecting a compound of Formula I or a pharmaceutically acceptable salt thereof or a pharmaceutical composition thereof for the patient.

Also provided herein are methods of treating a patient identified or diagnosed as having a cancer that include: (a) administering to the patient identified or diagnosed as having a cancer one or more doses of at least one additional anticancer agent (e.g., at least one of any of the additional anticancer agents described herein); (b) after (a), detecting an increase in the expression, level, and/or activity of a TAM kinase and/or c-Met kinase in a cancer cell or an immune cell from the patient; and (c) after (b), administering to the patient a therapeutically effective amount of a compound of Formula T or a pharmaceutically acceptable salt thereof or a pharmaceutical composition thereof. In some embodiments, step (c) further includes administering to the patient the at least one additional anticancer agent.

Also provided herein are methods of treating a patient identified or diagnosed as having a cancer that include: (a) detecting an increase in the expression, level, and/or activity of a TAM kinase and/or c-Met kinase in a cancer cell or an immune cell from a patient identified or diagnosed as having a cancer and previously administered one or more doses of the at least on additional anticancer agent (e.g., any of the additional anticancer agents described herein); and (b) after (a), administering to the patient a therapeutically effective amount of a compound of Formula I or a pharmaceutically acceptable salt thereof or a pharmaceutical composition thereof. In some embodiments, step (b) further includes administering to the patient the at least one additional anti cancer agent.

Also provided herein are methods of treating a patient identified or diagnosed as having a cancer that has been previously administered one or more doses of at least one additional anticancer agent and has been identified as having a cancer cell or an immune cell that has increased expression, level, and/or activity of a TAM kinase and/or c-Met kinase that include a therapeutically effective amount of a compound of Formula I or a pharmaceutically acceptable salt thereof or a pharmaceutical composition thereof to the patient. In some embodiments, the method further includes administering to the patient that at least one additional anticancer agent.

Also provided herein are methods of treating a patient identified or diagnosed as having a cancer that include: (a) selecting a patient identified or diagnosed as having increased expression, level, and/or activity of a TAM kinase and/or c-Met kinase in a cancer cell or an immune cell; and (b) after (a) administering to the selected patient a therapeutically effective amount of a compound of Formula I or a pharmaceutically acceptable salt thereof or a pharmaceutical composition thereof. In some embodiments, step (b) further includes administering to the patient at least one additional anticancer agent (e.g., any of the additional anti cancer agents described herein).

Also provided are methods of treating a patient identified or diagnosed as having a cancer that include: (a) selecting a patient identified or diagnosed as having a cancer that has been previously administered one or more doses of an additional anticancer agent (e.g., any of the additional anti-cancer agents described herein) and identified as having a cancer cell or an immune cell having increased expression, level, and/or activity of a TAM kinase and/or c-Met kinase; and (b) after (a), administering to the selected patient a therapeutically effective amount of a compound of Formula I or a pharmaceutically acceptable salt thereof or a pharmaceutical composition thereof. In some embodiments, step (b) further includes administering to the patient the at least one additional anticancer agent.

In some embodiments of any of the methods described herein, increased expression, level, and/or activity of a TAM kinase is detected in a cancer cell or an immune cell. In some embodiments of any of the methods described herein, the patient is identified or diagnosed as having a cancer cell or an immune cell having increased expression, level, and/or activity of a TAM kinase.

In some embodiments of any of the methods described herein, an increased expression, level, and/or activity of a TAM kinase and a c-Met kinase are detected in a cancer cell or an immune cell. In some embodiments of any of the methods described herein, the patient is identified or diagnosed as having a cancer cell or an immune cell having increased expression, level, and/or activity of a TAM kinase and a c-Met kinase.

In some embodiments of any of the methods described herein, the increased expression, level, and/or activity of a TAM kinase in a cancer cell or an immune cell results from a chromosomal translocation that results in the expression of a TREM87B-MERTK fusion protein or an AXL-MBIP fusion protein.

In some embodiments of any of the methods described herein, increased expression, level, and/or activity of a c-Met kinase is detected in a cancer cell or an immune cell. In some embodiments of any of the methods described herein, the patient is identified or diagnosed as having a cancer cell or an immune cell having increased expression, level, and/or activity of a c-Met kinase.

Also provided are methods of treating a patient identified or diagnosed as having a TAM-associated cancer that include: (a) administering to the patient identified or diagnosed as having a TAM-associated cancer one or more doses of a TAM kinase inhibitor; (b) after (a), detecting resistance of the TAM-associated cancer in the patient to the TAM kinase inhibitor; and (c) after (b), administering to the patient a therapeutically effective amount of a compound of Formula I or a pharmaceutically acceptable salt thereof or a pharmaceutical composition thereof. In some embodiments, step (c) further includes administering to the patient at least one additional anti cancer agent (e.g., any of the additional anticancer agents described herein).

Also provided are methods of treating a patient identified or diagnosed as having a TAM-associated cancer that include: (a) detecting resistance of the TAM-associated cancer in the patient to a TAM kinase inhibitor that was previously administered to the patient; and (b) after (a), administering to the patient a therapeutically effective amount of a compound of Formula I or a pharmaceutically acceptable salt thereof or a pharmaceutical composition thereof. In some embodiments, step (b) further includes administering to the patient at least one additional anti cancer agent.

Also provided herein are methods of treating a patient identified or diagnosed as having a TAM-associated cancer and determined to have a previously developed resistance to a TAM kinase inhibitor that include administering to the patient a therapeutically effective amount of a compound of Formula I or a pharmaceutically acceptable salt thereof or a pharmaceutical composition thereof. Some embodiments of these methods further include administering to the patient at least one additional anticancer agent (e.g., any of the additional anticancer agents described herein or known in the art).

Also provided herein are methods of treating a patient identified or diagnosed as having a c-Met-associated cancer that include: (a) administering to the patient identified or diagnosed as having a c-Met-associated cancer one or more doses of a c-Met kinase inhibitor; (b) after (a), detecting resistance of the c-Met-associated cancer in the patient to the c-Met kinase inhibitor; and (c), after (b), administering to the patient a therapeutically effective amount of a compound of Formula I or a pharmaceutically acceptable salt thereof or a pharmaceutical composition thereof. Some embodiments of these methods further include administering to the patient at least one additional anticancer agent (e.g., any of the additional anticancer agents described herein or known in the art). In one embodiment, the c-Met inhibitor administered in step (a) is a Type I c-Met inhibitor. In one embodiment, the Type 1 c-Met inhibitor is crizotinib, capmatinib, NVP-BVU972, AMG 337, bozitinib, glumetinib, savolitinib, or tepotinib.

Also provided herein are methods of treating a patient identified or diagnosed as having a c-Met-associated cancer that include: (a) detecting resistance of the c-Met-associated cancer in the patient to a c-Met kinase inhibitor that was previously administered to the patient; and (b) after (a), administering to the patient a therapeutically effective amount of a compound of Formula I or a pharmaceutically acceptable salt thereof or a pharmaceutical composition thereof. Some embodiments of these methods, step (b) further includes administering to the patient at least one additional anticancer agent. In one embodiment, the c-Met inhibitor administered in step (a) is a Type I c-Met inhibitor. In one embodiment, the Type 1 c-Met inhibitor is crizotinib, capmatinib, NVP-BVU972, AMG 337, bozitinib, glumetinib, savolitinib, or tepotinib.

Also provided herein are methods of treating a patient identified or diagnosed as having a c-Met-associated cancer and determined to have previously developed resistance to a c-Met kinase inhibitor that include administering to the patient a therapeutically effective amount of a compound of Formula I or a pharmaceutically acceptable salt thereof or a pharmaceutical composition thereof. Some embodiments of these methods further include administering to the patient at least one additional anticancer agent. In one embodiment, the patient developed resistance to a Type I c-Met inhibitor. In one embodiment, the Type I c-Met inhibitor is crizotinib, capmatinib, NVP-BVU972, AMG 337, bozitinib, glumetinib, savolitinib, or tepotinib.

In some embodiments of any of the methods described herein, the step of identifying the patient as having a TAM-associated cancer and/or a c-Met-associated cancer includes performing an assay on a biopsy sample obtained from the patient. In some embodiments, the assay is selected from the group of sequencing, immunohistochemistry, enzyme-linked immunosorbent assay, and fluorescence in situ hybridization (FISH). In some embodiments, the assay is selected from the group of: denaturing gradient gel electrophoresis (DGGE), temperature gradient electrophoresis (TGGE), temperature gradient capillary electrophoresis, a single strand conformational polymorphism assay, a molecular beacon assay, a dynamic hybridization assay, a PCR-based assay and denaturing high performance liquid chromatography. Some embodiments of these methods can further include obtaining the biopsy sample from the patient.

In some embodiments of any of the methods described herein, a compound of Formula I is selected from the compounds described in Example Nos. 1-201, or pharmaceutically acceptable salts thereof. In some embodiments, a compound of Formula I is selected from i) Example Nos. 1-20; ii) Example Nos. 21-40; iii) Example Nos. 41-60; iv) Example Nos. 61-80; v) Example Nos. 81-100; vi) Example Nos. 101-120; vii) Example Nos. 121-140; viii) Example Nos. 141-160; ix) Example Nos. 161-180; x) Example Nos. 181-201 or pharmaceutically acceptable salts thereof.

The compounds and methods described herein are useful for the treatment of tumors and cancers (e.g., TAM-associated cancers and/or c-Met-associated cancers). The TAM-associated cancer and/or c-Met-associated cancer treated can be a primary tumor or a metastatic tumor. In one aspect, the methods described herein are used to treat a solid TAM-associated tumor, for example, melanoma, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; urinary tract cancer; ovarian cancer or carcinoma (ovarian epithelial carcinoma or surface epithelial-stromal tumor including serous tumor, endometrioid tumor and mucinous cystadenocarcinoma); liver and bile duct carcinoma (including hepatocellular carcinoma, cholangiocarcinoma, hemangioma); esophageal carcinoma or cancer (including esophageal adenocarcinoma and squamous cell carcinoma); oral and oropharyngeal squamous cell carcinoma; salivary gland adenoid cystic carcinoma: bladder cancer; bladder carcinoma; carcinoma of the uterus (including endometrial cancer or endometrial adenocarcinoma, ocular, uterine papillary serous carcinoma, uterine clear-cell carcinoma, uterine sarcomas and leiomyosarcomas, mixed mullerian tumors); glioma, glioblastoma, medulablastoma, and other tumors of the brain; kidney cancers (including renal cancer, renal cell carcinoma, clear cell carcinoma, Wilm's tumor); pituitary adenoma; cancer of the head and neck (including squamous cell carcinomas); cancer of the stomach (gastric cancers, stomach adenocarcinoma, gastrointestinal stromal tumor (GIST)); testicular cancer; germ cell tumor; neuroendocrine tumor; cervical cancer; carcinoids of the gastrointestinal tract, breast, and other organs; signet ring cell carcinoma; mesenchymal tumors including sarcomas (e.g., Kaposi's sarcoma), fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin (e.g., squamous cell skin cancer), including melanoma, cervical, retinoblastoma, head and neck cancer, pancreatic, brain, thyroid, testicular, renal, bladder, soft tissue, adrenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, eystosarcoma phylloide, salivary cancers, thymic carcinomas, and cancers of the vagina among others.

The compounds of Formula I or pharmaceutically acceptable salts thereof can also be used for treating lymphoma or lymphocytic or myelocytic proliferation disorder or abnormality (e.g., a TAM-associated lymphoma or lymphocytic or myelocytic proliferation disorder or abnormality). For example, the TAM-associated cancer can be a Hodgkin Lymphoma of a Non-Hodgkin Lymphoma. For example, the subject can be suffering from a TAM-associated Non-Hodgkin Lymphoma such as, but not limited to: an AIDS-Related Lymphoma; Anaplastic Large-Cell Lymphoma; Angioimmunoblastic Lymphoma; Blastic N-Cell Lymphoma; Burkitfs Lymphoma: Burkitt-like Lymphoma (Small Non-Cleaved Cell Lymphoma); Chronic Lymphocytic Leukemia/Small Lymphocytic Lymphoma: Cutaneous T-Cell Lymphoma; Diffuse Large B-Cell Lymphoma; Entcropathy-Type T-Cell Lymphoma; Follicular Lymphoma; Hepatosplenic Gamma-Delta T-Cell Lymphoma; Lymphoblastic Lymphoma: Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a TAM-associated Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In one embodiment, the methods as described herein may be useful to treat a patient suffering from a specific TAM-associated T-cell, a B-cell, or a NK-cell based lymphoma, proliferative disorder, or abnormality. For example, the patient can be suffering from a specific TAM-associated T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive. ALK negative anaplastic large cell lymphoma, mantle cell lymphoma, or primary cutaneous anaplastic large cell lymphoma; angioimmunoblastic lymphoma; cutaneous T-cell lymphoma, for example mycosis fungoides, Sezary syndrome, primary cutaneous anaplastic large cell lymphoma, primary cutaneous CD30+ T-cell lymphoproliferative disorder; primary cutaneous aggressive epidermolropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma: Enteropathy-type T-cell lymphoma; Hematosplenic gamma-delta T-cell Lymphoma: Lymphoblastic Lymphoma; Nasal NK/T-cell Lymphomas; Treatment-related T-cell lymphomas; for example lymphomas that appear after solid organ or bone marrow transplantation; T-cell prolymphocyte leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, the methods as described herein may be useful to treat a patient suffering from a specific TAM-associated B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mantle cell lymphoma (MCL); Burkitt lymphoma; Mediastinal large B cell lymphoma; Waldenstrom macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis; Chronic lymphocytic leukemia/small lymphocytic lymphoma; B-cell prolymphocyte leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; cell/histiocytic rich large B-cell lymphoma; DLBCL associated with chronic inflammation; Epstein-Barr vims (EBV)+ DLBCL of the elderly; Primary mediastinal (thymic) large B-cell lymphoma; Primary cutaneous DLBCL, leg type, ALK+ large B-cell lymphoma; Plasmablastic lymphoma; Large B-cell lymphoma arising in HHV8-associated multicentric, Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma.

In one embodiment, the methods as described herein may be useful to treat a patient suffering from a TAM-associated leukemia. For example, the subject may be suffering from an acute or chronic TAM-associated leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocyte leukemia (a subtype of AML); T-cell prolymphocyte leukemia (TPLL); large granular lymphocytic leukemia; or Adult T-cell chronic leukemia; large granular lymphocytic leukemia (LGL). In one embodiment, the patient suffers from an acute myelogenous leukemia, for example an undifferentiated AML (MO); myeloblasts leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In one embodiment, the compounds and methods described herein are useful for treating a TAM-associated cancer in a patient, wherein the cancer overexpresses AXL, MER, or TYRO3, or a combination thereof, e.g., as compared to a control non-cancerous tissue or a control cell (e.g., from the same or a different subject). In one embodiment, the cancer overexpresses AXL. In one embodiment, the cancer overexpresses MER. In an alternative embodiment, the cancer ectopically expresses MER. In one embodiment, the TAM-associated cancer is breast, colon, renal, skin, lung (including non-small cell lung cancer), liver, gastric, brain (including glioblastoma), ovarian, pancreatic, prostate, glioblastoma multiforme, osteosarcoma, thyroid malignancies, rhabdomyosarcoma, melanoma, acute myeloid leukemia, T-cell acute lymphoid leukemia, B-cell acute lymphoid leukemia, schwannoma, and mantle cell lymphoma.

In one embodiment, the TAM-associated cancer is selected from breast, colon, renal, skin, lung (including non-small cell lung cancer), liver, gastric, brain (including glioblastoma), ovarian, pancreatic, prostate, glioblastoma multiforme, osteosarcoma, thyroid malignancies, rhabdomyosarcoma, and melanoma.

In one embodiment, the TAM-associated cancer is selected from leukemias (including acute myeloid leukemia and chronic myeloid leukemia, B-cell myeloid leukemia (B-CLL), B-cell acute lymphoblastic leukemia, erythroid leukemia, and T-lineage acute lymphoblastic leukemia), non-small cell lung cancer, pancreatic ductal adenocarcinoma, astrocytoma, lung adenocarcinoma, ovarian cancer, melanoma, and glioblastoma multiforme.

In one embodiment, the TAM-associated cancer is selected from chronic myeloid leukemia, gastrointestinal stromal tumors (GIST), breast cancer (e.g., HER2 positive breast cancer and triple negative breast cancer), head and neck cancer, and non-small cell lung cancer.

In some embodiments of any of the methods described herein, the TAM-associated cancer is a cancer having overexpression of a TAM kinase, e.g., as compared to a non-cancerous tissue or cell in the same patient or a different subject. In some embodiments of any of the methods described herein, the TAM-associated cancer is a cancer having ectopic expression of a TAM kinase.

In some embodiments of any of the methods described herein, the TAM-associated cancer is a cancer having overexpression or ectopic expression of a TYRO3 protein. In some embodiments of any of the methods described herein, the TAM-associated cancer has one or more point mutations in a gene encoding TYRO3 that results in the expression of a TYRO3 that includes one or more amino acid substitutions. In some embodiments of any of the methods described herein, the TAM-associated cancer has a chromosomal translocation which results in the expression of a fusion protein including the kinase domain of TYRO3 and a fusion partner. Non-limiting examples of a TAM-associated cancer having overexpression or ectopic expression of TYRO3, or a mutation in a TYRO3 gene that results in the expression of TYRO3 having one or more point mutations or a TYRO3 fusion protein include: AML, multiple myeloma, lung cancer, melanoma, prostate cancer, endometrial cancer, thyroid cancer, schwannoma, pancreatic cancer, and brain cancer. Non-limiting aspects of TAM-associated cancers having increased expression and/or activity of TYRO3 are listed in Table 4.

TABLE 4

| TAM-Associated Cancers Having with Increased Expression and/or Activity of TYRO3 | |
|---|---|
| Melanoma | Amino acid substitutions at: Q67 and/or R462Q, and/or W708fs*5 |
| Lung Cancer | Amino acid substitution at E340 or N615K in TYRO3 |
| Pancreatic Cancer | Amino acid substitution R514Q in TYRO3 |
| Colon Cancer | Amino acid substitution G809D and/or M592I in TYRO3 |
| Brain Cancer | Amino acid substitution A709T in TYRO3 |
| AML, multiple myeloma lung cancer, melanoma, prostate cancer, endometrial cancer, thyroid cancer, and schwannoma | Overexpression or ectopic expression of TYRO3 |

Additional anticancer agents that are TYRO3 inhibitors include, e.g., 6 g, merestinib (LY2801653), ASLAN002 (BMS-777607; (N-[4-(2-Amino-3-chloropyridin-4-yloxy)-3-fluorophenyl]-4-ethoxy-1-(4-fluorophenyl)-2-oxo-1,2-dihydropyridine-3-carboxamide), LDC1267 (N-[4-[(6,7-Dimethoxyquinolin-4-yl)oxy]-3-fluorophenyl]-4-ethoxy-1-(4-fluoro-2-methylphenyl)-1H-pyrazole-3-carboxamide hydrochloride, and UNC2025 (trans-4-[2-(Butylamino)-5-[4-[(4-methylpiperazin-1-yl)methyl]phenyl]-7H-pyrrolo[2,3-d]pyrimidin-7-yl]cyclohexanol).

In some embodiments of any of the methods described herein, the TAM-associated cancer is a cancer having overexpression or ectopic expression of a AXL protein. In some embodiments of any of the methods described herein, the TAM-associated cancer has one or more point mutations in a gene encoding AXL that results in the expression of a AXL that includes one or more amino acid substitutions. In some embodiments of any of the methods described herein, the TAM-associated cancer has a chromosomal translocation which results in the expression of a fusion protein including the kinase domain of AXL and a fusion partner. Non-limiting examples of a TAM-associated cancer having overexpression or ectopic expression of AXL, or a mutation in a AXL gene that results in the expression of AXL having one or more point mutations or a AXL fusion protein include: AML, CML, B-CLL, lung cancer, glioblastoma, breast cancer, colorectal cancer, gastric cancer, pancreatic cancer, oesophageal cancer, melanoma, squamous cell skin cancer, prostate cancer, endometrial cancer, ovarian cancer, oral squamous cell carcinoma, thyroid cancer, bladder cancer, renal cancer, schwannoma, mesothelioma, Kaposi's sarcoma, osteosarcoma, erythroid leukemia, colon cancer, liver cancer, renal cell carcinoma, osteosarcoma, kidney cancer, PH+ CML, non-small cell lung cancer, triple-negative metastatic breast cancer, and HER2+ breast cancer. Non-limiting aspects of TAM-associated cancers having increased expression and/or activity of AXL are listed in Table 5.

TABLE 5

| TAM-Associated Cancers Having with Increased Expression and/or Activity of AXL | |
|---|---|
| Ovarian Cancer | Amino acid substitutions C24G and/or A358V in AXL |

TABLE 5-continued

TAM-Associated Cancers Having with Increased Expression and/or Activity of AXL

| | |
|---|---|
| Melanoma | One or more of the amino acid substitutions of P36L, R236C, G413W, E431K, A451T, E535K, G829E, I610V, A666T, S685F, and R784Q in AXL |
| Colon Cancer | One or more of the amino acid substitutions of N43T, M580K, and L684P in AXL |
| Skin Cancer | An amino acid substitution of P238L in AXL |
| Gastric Cancer | One or more of the amino acid substitutions of V289M, R492C, S842F, and P636H in AXL |
| Lung Cancer | One or more of the amino acid substitutions of R295W, L423Q, K526N, and S599F in AXL |
| Breast Cancer | One or more of the amino acid substitutions of T343M, E745K, and S747R in AXL |
| Prostate Cancer | An amino acid substitution of R368Q in AXL |
| Pancreatic Cancer | An amino acid substitution of E484D in AXL |
| Kidney Cancer | An amino acid substitution of P742T in AXL |
| AML, CML, B-CLL, lung cancer, glioblastoma, breast cancer, colorectal cancer, gastric cancer, pancreatic cancer, esophageal cancer, melanoma, squamous cell skin cancer, prostate cancer, endometrial cancer, ovarian cancer, oral squamous cell carcinoma, thyroid cancer, bladder cancer, renal cancer, schwannoma, mesothelioma, Kaposi's sarcoma, and osteosarcoma | Overexpression or ectopic expression of AXL |

Additional anticancer agents that are AXL inhibitors include, e.g., bozitinib (SKI-606, PF-5208765, Bosulif), Bemcentinib (BGB324; R428), crizotinib (PF-2341066, Xalkon), foretinib (GSK1363089, XL880), (N-[4-(2-Amino-3-chloropyridin-4-yloxy)-3-fluorophenyl]-4-ethoxy-1-(4-fluorophenyl)-2-oxo-1,2-dihydropyridine-3-carboxamide (BMS-777607; ASLAN002), LY2801653 (merestinib), amuvatinib (MP-470), cabozantinib (XL184, BMS-907351, Cometriq), glesatinib (MGCD265), NPS-1034 (2-(4-Fluorophenyl)-N-[3-fluoro-4-(3-phenyl-1H-pyrrolo[2,3-b]pyridin-4-yloxy)phenyl]-1,5-dimethyl-3-oxo-2,3-dihydro-1H-pyrazole-4-carboxamide), LDC1267 (N-[4-[(6,7-Dimethoxyquinolin-4-yl)oxy]-3-fluorophenyl]-4-ethoxy-1-(4-fluoro-2-methylphenyl)-1H-pyrazole-3-carboxamide hydrochloride), gilteritinib (ASP2215), SGI-7079 ([3-(2-[[3-Fluoro-4-(4-methylpiperazin-1-yl)phenyl]amino]-5-methyl-7H-pyrrolo[2,3-d]pyrimidin-4-yl)phenyl]acetonitrile), dubermatinib (TP-0903), trans-4-[2-(Butylamino)-5-[4-[(4-methylpiperazin-1-yl)methyl]phenyl]-7H-pyrrolo[2,3-d]pyrimidin-7-yl]cyclohexanol (UNC2025), 3-[3-[4-(Morpholin-4-ylmethyl)-1H-pyrrol-2-ylmethylene]-2-oxo-2,3-dihydro-1H-indol-5-ylmethyl]thiazolidine-2,4-dione hydrochloride (S49076), sunitinib (SU11248, Sutent), and the monoclonal antibodies of 12A11, Mab173, YW327.6S2, D9, and E8.

In some embodiments of any of the methods described herein, the TAM-associated cancer is a cancer having over expression or ectopic expression of a MER protein. In some embodiments of any of the methods described herein, the TAM-associated cancer has one or more point mutations in a gene encoding MER that results in the expression of a MER that includes one or more amino acid substitutions. In some embodiments of any of the methods described herein, the TAM-associated cancer has a chromosomal translocation which results in the expression of a fusion protein including the kinase domain of MER and a fusion partner. Non-limiting examples of a TAM-associated cancer having overexpression or ectopic expression of MER, or a mutation in a MER gene that results in the expression of MER having one or more point mutations or a MER fusion protein include: AML, ALL (B-ALL, T-ALL), lung cancer, glioma, melanoma, prostate cancer, schwannoma, mantle cell lymphoma, rhabdomyosarcoma, pancreatic cancer, breast cancer, gastric cancer, pituitary adenoma, urinary tract cancer, kidney cancer, liver cancer, colon cancer, and breast cancer. Non-limiting aspects of MER-associated cancers having increased expression and/or activity of MER are listed in Table 6.

TABLE 6

TAM-Associated Cancers Having with Increased Expression and/or Activity of MER

| | |
|---|---|
| Melanoma | One or more amino acid substitutions of P40S, V861I, K923R, and P802S in MER |
| Lung Cancer | One or more amino acid substitutions of S159F, I431F, S905F, P672S, N718Y, and M790V in MER |
| Urinary Tract Cancer | One or more amino acid substitutions of E204K, L586F, and S626C in MER |
| Gastric Cancer | An amino acid substitutions of S428G in MER |
| Kidney Cancer | Amino acid substitutions of A446G and/or P958L in MER |
| Liver Cancer | One or more amino acid substitutions of N454S, V873I, and D983N in MER |
| Lymphoma | An amino acid substitution of W485S/C in MER |
| Colon Cancer | One or more amino acid substitutions of D990N, L688M, and R722 in MER |
| Breast Cancer | An amino acid substitution of G594R in MER |
| Head and Neck Cancer | An amino acid substitution of A708S in MER |
| AML, ALL, lung cancer, glioma, melanoma, prostate cancer, schwannoma, mantle cell lymphoma, and rhabdomyosarcoma | Overexpression or ectopic expression of MER |

Additional anticancer agents that are MER inhibitors include, e.g., foretinib, merestinib (LY2801653), (N-[4-(2-Amino-3-chloropyridin-4-yloxy)-3-fluorophenyl]-4-ethoxy-1-(4-fluorophenyl)-2-oxo-1,2-dihydropyridine-3-carboxamide (ASLAN002; BMS-777607), [3-(2-[[3-Fluoro-4-(4-methylpiperazin-1-yl)phenyl]amino]-5-methyl-7H-pyrrolo[2,3-d]pyrimidin-4-yl)phenyl]acetonitrile (SGI-7079), dubermatinib (TP-0903), trans-4-[2-(Butylamino)-5-[4-[(4-methylpiperazin-1-yl)methyl]phenyl]-7H-pyrrolo[2,3-d]pyrimidin-7-yl]cyclohexanol (UNC2025), and 3-[3-[4-(Morpholin-4-ylmethyl)-1H-pyrrol-2-ylmethylene]-2-oxo-2,3-dihydro-1H-indol-5-ylmethyl]thiazolidine-2,4-dione hydrochloride (S49076).

Also provided are methods for treating a cancer (e.g., a TAM-associated cancer and/or c-Met-associated cancer) in a patient in need thereof, the method comprising: (a) determining if the cancer in the patient is a TAM-associated cancer, a c-Met-associated cancer, or both; and (b) if the cancer is determined to be a TAM-associated cancer, a c-Met-associated cancer, or both, administering to the patient a therapeutically effective amount of a compound of Formula I or a pharmaceutically acceptable salt thereof or a pharmaceutical composition thereof. Some embodiments of these methods further include administering to the subject at least one additional anticancer agent (e.g., an immunotherapy). In some embodiments, the subject was previously treated with at least one additional anticancer agent or therapy, e.g., a kinase inhibitor, an immunotherapy, chemotherapy, radiation therapy and/or surgery. In some embodiments the patient has a cancer that is resistant to the at least one additional anticancer agent. In one embodiment, the at least one additional anticancer agent does not include a compound of Formula I.

Also provided herein is a method for treating a patient diagnosed with or identified as having a TAM-associated cancer (e.g., any of the exemplary TAM-associated cancers disclosed herein), a c-Met-associated cancer (e.g., any of the exemplary c-Met-associated cancers disclosed herein), or both, comprising administering to the patient a therapeutically effective amount of a compound of Formula I or a pharmaceutically acceptable salt thereof, or a pharmaceutical composition thereof as defined herein. Some embodiments of these methods further include administering to the subject at least one additional anti cancer agent (e.g., an immunotherapy). In some embodiments, the subject was previously treated with at least one additional anticancer agent or therapy, e.g., a kinase inhibitor, an immunotherapy, chemotherapy, radiation therapy and or surgery. In one embodiment the patient has a cancer that is resistant to the previously administered at least one additional anticancer agent. In some embodiments, the at least one additional anticancer agent does not include a compound of Formula I.

In one embodiment, provided herein are methods for treating a patient diagnosed with (or identified as having) a cancer (e.g., a TAM-associated cancer, a c-Met-associated cancer, or both) that include administering to the patient a therapeutically effective amount of a compound of Formula I or a pharmaceutically acceptable salt thereof. Also provided herein are methods for treating a patient identified or diagnosed as having a TAM-associated cancer, a c-Met-associated cancer, or both, that include administering to the patient a therapeutically effective amount of a compound of Formula I or a pharmaceutically acceptable salt thereof or a pharmaceutical composition thereof. In some embodiments, the patient that has been identified or diagnosed as having a TAM-associated cancer, a c-Met-associated cancer, or both, through the use of a regulatory agency-approved, e.g., FDA-approved test or assay for identifying abnormal (e.g., increased) expression, level, and/or activity of one or more of the TAM kinases and/or c-Met kinase, in a patient or a biopsy sample from the patient or by performing any of the non-limiting examples of assays described herein. In some embodiments, the test or assay is provided as a kit. Some embodiments of these methods further include administering to the patient at least one additional anticancer agent (e.g., an immunotherapy). In some embodiments, the patient was previously treated with at least one additional anticancer agent or therapy, e.g., a kinase inhibitor, an immunotherapy (e.g., an immune checkpoint inhibitor), chemotherapy, radiation therapy and or surgery. In some embodiments, the patient has a cancer that is resistant to the at least one additional anticancer agent. In some embodiments, the at least one additional anticancer agent does not include a compound of Formula I.

Also provided is a compound of Formula I or a pharmaceutically acceptable salt thereof, for use in the treatment of a cancer in a patient in need thereof or a patient identified or diagnosed as having a TAM-associated cancer (e.g., any of the TAM-associated cancers described herein), a c-Met-associated cancer (e.g., any of the c-Met-associated cancers described herein), or both. Also provided is the use of a compound of Formula I or a pharmaceutically acceptable salt thereof for the manufacture of a medicament for treating a cancer in a patient identified or diagnosed as having a TAM-associated cancer, a c-Met-associated cancer, or both. In some embodiments, the cancer is a TAM-associated cancer. In some embodiments, the cancer is a c-Met-associated cancer. In some embodiments, the cancer is both a TAM-associated cancer and a c-Met-associated cancer. In some embodiments, a patient is identified or diagnosed as having a TAM-associated cancer, a c-Met-associated cancer, or both, through the use of a regulatory agency-approved, e.g., FDA-approved, kit for identifying abnormal (e.g., increased) expression, level, and/or activity of one or more of the TAM kinases and/or c-Met kinase, e.g., as compared to a non-cancerous tissue or cell from the same or a different subject. Some embodiments of these methods further include administering to the patient at least one additional anticancer agent (e.g., immunotherapy). In some embodiments, the subject was previously treated with at least one additional anticancer agent or therapy, e.g., an immune checkpoint inhibitor, a kinase inhibitor, an immunotherapy, chemotherapy, radiation therapy and/or surgery. In some embodiments, the patient has a cancer that is resistant to one or more of the at least one additional anticancer agents. In one embodiment, the at least one additional anticancer agent does not include a compound of Formula I.

In some embodiments of any of the methods or uses described herein, the patient has been identified or diagnosed as having a cancer associated with or having abnormal (e.g., increased) expression, level, and/or activity of one or more of the TAM kinases and/or c-Met kinase, e.g., as compared to a non-cancerous tissue or cell in the same or a different subject. In some embodiments, provided herein are methods for treating a TAM-associated cancer, a c-Met-associated cancer, or both, in a patient in need of such treatment, the method comprising a) detecting abnormal (e.g., increased) expression and/or activity of one or more of the TAM kinases and/or c-Met kinase, e.g., as compared to a non-cancerous tissue or cell in the same or a different subject; and b) after a), administering a therapeutically effective amount of a compound of Formula I or a pharmaceutically acceptable salt thereof. Some embodiments of these methods further include administering to the patient at least one additional anti cancer agent (e.g., immunotherapy). In some embodiments, the patient was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anti cancer agent does not include a compound of Formula I.

In some embodiments of any of the methods or uses described herein, the patient has a clinical record indicating that the patient has a tumor associated with or having abnormal (e.g., increased) expression, level, and/or activity of one or more of the TAM kinases and/or c-Met kinase, e.g., as compared to anon-cancerous tissue or cell in the same patient or a different subject). In some embodiments, the clinical record indicates that the patient should be treated with one or more of the compounds of Formula I or a pharmaceutically acceptable salts thereof or compositions provided herein. Some embodiments of these methods further include administering to the patient at least one additional anticancer agent (e.g., an immunotherapy). In some embodiments, the subject was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

Also provided are methods of treating a patient that include administering a therapeutically effective amount of a compound of Formula I or a pharmaceutically acceptable salt thereof to a patient having a clinical record that indicates that the patient has a cancer associated with or having abnormal (e.g., increased) expression, level, and/or activity of one or more of the TAM kinases and/or c-Met kinase, e.g., as compared to a non-cancerous tissue or cell from the patient or a different subject. Also provided is the use of a compound of Formula I or a pharmaceutically acceptable salt thereof for the manufacture of a medicament for treating a TAM-associated cancer, a c-Met-associated cancer, or both, in a patient having a clinical record that indicates that the patient has a cancer associated with or having abnormal (e.g., increased) expression, level, and/or activity of one or more of the TAM kinases and/or c-Met kinase, e.g., as compared to a non-cancerous tissue or cell from the patient or a different subject. Some embodiments of these methods and uses can further include: a step of performing an assay on a sample (e.g., a biopsy sample) obtained from the patient to determine whether the patient has abnormal (e.g., increased) expression, level, and/or activity of one or more of the TAM kinases and/or c-Met kinase (e.g., as compared to a non-cancerous tissue or cell from the patient or a different subject), and recording the information in a patient's clinical file (e.g., a computer readable medium) that the patient has been identified to have abnormal (e.g., increased) expression and/or activity of one or more of the TAM kinases and/or c-Met kinase. In some embodiments, the assay is an in vitro assay. Some embodiments of these methods further include administering to the patient at least one additional anticancer agent (e.g., an immunotherapy). In some embodiments, the subject was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

Also provided herein is a method of treating a patient in need thereof. The method includes performing an assay on a sample obtained from the patient to determine whether the subject has abnormal (e.g., increased) expression, level, and/or activity of one or more of the TAM kinases and/or c-Met kinase, e.g., as compared to a non-cancerous tissue or cell from the same patient or a different subject). The method also includes administering to a patient determined to have abnormal (e.g., increased) expression, level, and/or activity of one or more of the TAM kinases and/or c-Met kinase (e.g., as compared to a non-cancerous tissue or cell from the same patient or a different subject) a therapeutically effective amount of a compound of Formula I or a pharmaceutically acceptable salt thereof. Some embodiments of these methods further include administering to the patient at least one additional anticancer agent (e.g., an immunotherapy). In some embodiments, the patient was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

Also provided are methods (e.g., in vitro methods) of selecting a treatment for a patient identified or diagnosed as having a TAM-associated cancer, a c-Met-associated cancer, or both. Some embodiments can further include administering the selected treatment to the patient identified or diagnosed as having a TAM-associated cancer, a c-Met-associated cancer, or both. For example, the selected treatment can include administration of a therapeutically effective amount of a compound of Formula I or a pharmaceutically acceptable salt thereof. Some embodiments can further include a step of performing an assay on a sample (e.g., a biopsy sample) obtained from the patient to determine whether the patient has abnormal (e.g., increased) expression, level, and/or activity of one or more of the TAM kinases and/or c-Met kinase (e.g., as compared to a non-cancerous tissue or cell from the same patient or a different subject), and identifying and diagnosing a patient determined to have abnormal (e.g., increased) expression, level, and/or activity of one or more of the TAM kinases and/or c-Met kinase, as having a TAM-associated cancer and/or c-Met-associated cancer, respectively. In some embodiments, the patient has been identified or diagnosed as having a TAM-associated cancer, a c-Met-associated cancer, or both, through the use of a regulatory agency-approved, e.g., FDA-approved, kit for identifying abnormal (e.g., increased) expression, level, and/or activity of one or more of the TAM kinases and/or c-Met kinase in a patient or a biopsy sample from the patient. In some embodiments, the TAM-associated cancer is a cancer described herein or known in the art. In some embodiments, the c-Met-associated cancer is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. Some embodiments of these methods further include administering to the patient at least one additional anticancer agent (e.g., an immunotherapy). Some embodiments of these methods further include administering to the subject at least one additional anticancer agent (e.g., an immunotherapy). In some embodiments, the patient was previously treated with at least one additional anticancer agent or therapy, e.g., an immune checkpoint inhibitor, a kinase inhibitor, an immunotherapy, chemotherapy, radiation therapy, and/or surgery. In some embodiments, the patient has a cancer that is resistant to one or more of the at least one additional anti cancer agent. In one embodiment, the at least one additional anti cancer agent does not include a compound of Formula I.

Also provided herein are methods of selecting a treatment for a patient, wherein the methods include a step of performing an assay on a sample obtained from the patient to determine whether the patient has abnormal (e.g., increased) expression, level, and/or activity of one or more of the TAM kinases and/or c-Met kinase, e.g., as compared to a non-cancerous tissue or cell from the patient or a different subject. Some embodiments further include administering the selected treatment to the patient identified or diagnosed as having a TAM-associated cancer, a c-Met-associated cancer, or both. For example, the selected treatment can include administration of a therapeutically effective amount of a compound of Formula I or a pharmaceutically acceptable salt thereof to the patient identified or diagnosed as having a TAM-associated cancer, a c-Met-associated cancer, or both. In some embodiments, the assay is an in vitro assay. Some embodiments of these methods further include administering to the patient at least one additional anticancer agent (e.g., an immunotherapy). In some embodiments, the patient was previously treated with at least one additional anticancer agent or therapy, e.g., an immune checkpoint inhibitor, a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

Also provided are methods of selecting a patient for treatment, wherein the methods include selecting, identifying, or diagnosing a patient having a TAM-associated cancer, a c-Met-associated cancer, or both, and selecting the patient for treatment including administration of a therapeutically-effective amount of a compound of Formula I or a pharmaceutically acceptable salt thereof. In some embodiments, identifying or diagnosing a patient as having a TAM-associated cancer, a c-Met-associated cancer, or both, can include a step of performing an assay on a sample obtained from the patient to determine whether the patient has abnormal (e.g., increased) expression, level, and/or activity of one or more of the TAM kinases and/or c-Met kinase (e.g., as compared to a non-cancerous tissue or cell from the patient or a different subject), as having a TAM-associated cancer and/or c-Met-associated cancer, respectively. In some embodiments, the method of selecting a treatment can be used as a part of a clinical study that includes administration of various treatments of a TAM-associated cancer, a c-Met-associated cancer, or both. In some embodiments, the assay is an in vitro assay. Some embodiments of these methods further include administering to the subject at least one additional anticancer agent or therapy, e.g., an immune checkpoint inhibitor, a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

In some embodiments of any of the methods or uses described herein, an assay can be used to determine whether the patient has abnormal (e.g., increased) expression, level, and/or activity of one or more of the TAM kinases and/or c-Met kinase. In some embodiments, the sample is a biological sample or a biopsy sample (e.g., a paraffin-embedded biopsy sample) from the patient. In some embodiments, the patient is a patient suspected of having a TAM-associated cancer, a c-Met-associated cancer, or both, a patient having one or more symptoms of a TAM-associated cancer, a c-Met-associated cancer, or both, and/or a patient that has an increased risk of developing a TAM-associated cancer, a c-Met-associated cancer, or both).

In some embodiments of any the methods described herein, the compound of Formula I or a pharmaceutically acceptable salt thereof is administered in combination with a therapeutically effective amount of at least one additional anticancer agent selected from one or more additional therapies or therapeutic agents, for example an agent that works by the same or by a different mechanism of action. In one embodiment, the compound of Formula I is selected from the compounds described in Example Nos. 1-201, or pharmaceutically acceptable salts thereof. In some embodiments, a compound of Formula I is selected from i) Example Nos. 1-20; ii) Example Nos. 21-40; iii) Example Nos. 41-60; iv) Example Nos. 61-80; v) Example Nos. 81-100; vi) Example Nos. 101-120; vii) Example Nos. 121-140; viii) Example Nos. 141-160; ix) Example Nos. 161-180; x) Example Nos. 181-201 or pharmaceutically acceptable salts thereof.

Non-limiting examples of additional anticancer agents include immune-targeted agents including immunotherapy agents, anti-viral agents, kinase-targeted therapeutic agents, anti-viral vaccines, anti-hormonal agents, signal transduction pathway inhibitors, chemotherapeutics or other anticancer agents, angiogenesis inhibitors, and radiotherapy.

One or more of any of the additional anticancer agents described herein can be combined with the present compounds in a single dosage form, or the present compounds and the at least one additional anticancer agents can be administered simultaneously or sequentially as separate dosage forms.

In one embodiment, the compound of Formula I or a pharmaceutically acceptable salt thereof is administered daily for 28 consecutive days in a 28 days cycle.

In one embodiment, compounds of Formula I or pharmaceutically acceptable salts thereof may be combined with immune-targeted agents including immunotherapy drugs.

The term "immunotherapy agents" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy agent is an immune checkpoint inhibitor. As used herein, the term "immune checkpoint inhibitor" or "checkpoint inhibitor" refers to molecules that totally or partially reduce, inhibit, interfere with, or modulate the expression and/or activity of one or more checkpoint proteins. In some embodiments, the immunotherapy includes one or more immune checkpoint inhibitors. In some embodiments, the immune checkpoint inhibitor is a CTLA-4 inhibitor (e.g., an anti-CTLA-4 antibody), a PD-1 inhibitor (e.g., an anti-PD-1 monoclonal antibody) or a PD-L1 inhibitor (e.g., an anti-PD-L1 monoclonal antibody). In some embodiments, the CTLA-4 inhibitor is ipilimumab (Yervoy®) or tremelimumab (CP-675,206). In some embodiments, the PD-1 inhibitor is pembrolizumab (Keytruda®), nivolumab (Opdivo®), or pidilizumab. In some embodiments, the anti-PD-1 monoclonal antibody is nivolumab or pembrolizumab. In some embodiments, the anti-PD1 antibody is pembrolizumab. In some embodiments, the PD-L1 inhibitor is atezolizumab (Tecentriq®), avelumab (Bavencio®), durvalumab (Imfinzi™), MEDI4736, or MPDL3280A. In some embodiments, the PD-1 or PD-L1 inhibitor is a small molecule (e.g., those disclosed in US 2018/305313 and WO 2018/195321). In some embodiments, the PD-L1 inhibitor is atezolizumab (Tecentriq®), avelumab (Bavencio®), or durvalumab (Imfinzi™). In some embodiments, a checkpoint inhibitor can target 4-1BB (e.g., urelumab (BMS-663513) and PF-05082566 (PF-2566)), CD27 (e.g., varlilumab (CDX-1127), CD40 (e.g., CP-870,893), OX40, TIM-3, ICOS, BTLA, A2AR, B7-H3, B7-H4, BTLA, IDO, KIR, LAG3, TIM-3, and VISTA. Additional non-limiting examples of immune checkpoint inhibitors include ulocuplumab, urelumab, PF 05082566, TRX518, varlilumab, CP 870893, PDR001MEDI4736, avelumab, BMS 986016, MGA271, IPH2201, emactuzumab, INCB024360, MEDI6469, galunisertib, BKT140, bavituximab, lirilumab, bevacizumab, MNRP1685A, lambroizumab, CC 90002, BMS-936559, and MGA271.

In some embodiments, a compound of Formula I or pharmaceutically acceptable salt thereof is combined with an immune checkpoint inhibitor, wherein the immune checkpoint inhibitor is administered on one or more days in a 28 days cycle. In one embodiment the compound of Formula I or a pharmaceutically acceptable salt thereof is administered daily for 28 consecutive days in a 28 days cycle.

In some embodiments, a compound of Formula I or pharmaceutically acceptable salt thereof is combined with an immune checkpoint inhibitor, wherein the immune checkpoint inhibitor is administered one a week. In one embodiment, the immune checkpoint inhibitor is administered every two weeks. In one embodiment, the immune checkpoint inhibitor is administered every three weeks. In one embodiment, the immune checkpoint inhibitor is administered every 4 weeks. In one embodiment, the immune checkpoint inhibitor is administered on day 1 of a 28 day cycle. In one embodiment, the immune checkpoint inhibitor is administered on days 1 and 7 in a 28 day cycle. In one embodiment, the immune checkpoint inhibitor is administered in days 1, 7 and 14 in a 28 day cycle. In one embodiment, the immune checkpoint inhibitor is administered on days 1, 7, 14 and 21 in a 28 day cycle. In one embodiment, the immune checkpoint inhibitor is administered on days 1, 7, 14 and 28 in a 28 day cycle. In one embodiment the compound of Formula I or a pharmaceutically acceptable salt thereof is administered daily for 28 consecutive days in a 28 days cycle. In one embodiment, the immune checkpoint inhibitor is administered by intravenous infusion.

In some embodiments, a compound of Formula I or pharmaceutically acceptable salt thereof is combined with an immune checkpoint inhibitor, wherein the immune checkpoint inhibitor is administered on day 1 of cycles 1 through 13. In one embodiment the compound of Formula I or a pharmaceutically acceptable salt thereof is administered daily for 28 consecutive days in a 28 days cycle.

In some embodiments, the immunotherapy agent is a cellular immunotherapy (e.g., adoptive T-cell therapy, dendritic cell therapy, or a natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy agent is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Kcytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab, or amatuximab.

In some embodiments, the immunotherapy agent is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853), or anetumab ravtansine In some embodiments, the immunotherapy includes blinatumomab (AMG103; Blincyto®) or midostaurin (Rydapt).

In some embodiments, the immunotherapy agent includes a toxin. In some embodiments, the immunotherapy is denileukin diftitox (Ontak®).

In some embodiments, the immunotherapy agent is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®) In some embodiments, the IFNα therapy is IntronA® (Roferon-A®). In some embodiments, the G-CSF therapy is filgrastim (Neupogen®).

In some embodiments, the immunotherapy agent is an inhibitory nucleic acid-based immunotherapy agent (e.g., antisense oligonucleotides, small interfering RNAs (siRNAs), and short hairpin RNAs (shRNAs). In some embodiments, the inhibitory nucleic acid-based immunotherapy is CV9104 (see, e.g., Rausch et al. (2014) Human Vaccine Immunother. 10(11): 3146-52; and Kubler et al. (2015) J. Immunother. Cancer 3:26).

In some embodiments, the immunotherapy agent is bacillus Calmette-Guerin (BCG) therapy. In some embodiments, the immunotherapy agent is an oncolytic virus therapy. In some embodiments, the oncolytic virus therapy is talimogene alherparepvec (T-VEC; Imlygic®).

In some embodiments, the immunotherapy agent is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy agent is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) *Nature* 547: 217-221; Sahin et al. (2017) *Nature* 547: 222-226). In some embodiments, the cancer vaccine is RGSH4K or NEO-PV-01. In some embodiments, the cancer vaccine is a DNA-based vaccine. In some embodiments, the DNA-based vaccine is a mammaglobin-A DNA vaccine (see, e.g., Kim et al. (2016) Oncolmmunology 5(2): e1069940).

In some embodiments, immune-targeted agents are selected from aldesleukin, interferon alfa-2b, ipilimumab, lambrolizumab, nivolumab, prednisone, and sipuleucel-T.

Suitable antiviral agents contemplated for use in combination with a compound of Formula I or a pharmaceutically acceptable salt thereof can comprise nucleoside and nucleotide reverse transcriptase inhibitors (RTIs), non-nucleoside reverse transcriptase inhibitors (NRTIs), protease inhibitors, and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, 1L-2, IL-12, pentafuside, and Yissum Project No. 11607.

Compounds of Formula I and pharmaceutically acceptable salts thereof can be used in combination with one or more other kinase inhibitors for the treatment of diseases, such as cancer, that are impacted by one or more signaling pathways.

In certain embodiments, the patient to be treated with a combination therapy described herein has not been treated with an additional anticancer agent prior to the administration the combination therapy. In certain embodiments, the patient to be treated with a combination therapy described herein has been treated with at least one additional anticancer agent prior to administration of a compound of Formula I for use alone or in a combination therapy described herein. In certain embodiments, the patient to be treated with a compound of Formula I as monotherapy or in a combination therapy described herein has developed drug resistance to, or has a cancer that is refractory to, at least one additional anticancer agent.

In one embodiment, compounds of Formula I and pharmaceutically acceptable salts thereof can be combined with one or more inhibitors of the following kinases for the treatment of cancer: PIM (PIM 1, PIM 2, PIM 3), IDO, AKT 1, AKT2 and AKT3, TGFR, PKA, PKG, PKC, CaM-kinase, phosphorylase kinase, MEKK, ERK, MAPK, mTOR, EGFR, HER2, HER3, HER4, TNS-R, IGF-1R, IR-R, PDG-FaR, PDGF R, CSFTR, KIT, FLK-II, KDR/FLK-1, FLK-4, flt-1, FGFR, FGFR1, FGFR2, FGFR3, FGFR4, c-MET, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, FAK, SYK, FRK, JAK, ABL, ALK, and B-Raf.

Compounds of Formula I and pharmaceutically acceptable salts thereof can also be used in combination with one or more additional anticancer agents, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfdgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, signal transduction pathway inhibitors include kinase inhibitors of the Ras-Raf-MEK-ERK pathway (e.g., binimetinib, selumetinib, encorafenib, sorafenib, trametinib, cobimetinib, dabrafenib, and vemurafenib), kinase inhibitors of the PI3K-AKT-mTOR-S6K pathway (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, ((R)-amino-N-[5,6-dihydro-2-(1-methyl-1H-pyrazol-4-yl)-6-oxo-1H-pyrrolo[4,3,2-ef][2,3]benzodiazepin-8-yl]-cyclohexaneacetamide), and TG101209 (N-tert-butyl-3-(5-methyl-2-(4-(4-methylpiperazin-1-yl)phenylamino)pyrimidin-4-ylamino)benzenesulfonamide).

A combination of a compound of Formula I in combination with binimetinib, selumetinib, encorafenib, sorafenib, trametinib, or vemurafenib results in sensitization of tumors that are resistant to binimetinib, selumetinib, encorafenib, sorafenib, trametinib, or vemurafenib, respectively.

In one embodiment, there is provided a pharmaceutical combination which comprises (a) a compound of Formula I or a pharmaceutically acceptable salt or solvate thereof, and (b) an additional anticancer agent selected from the group consisting of (i) binimetinib, (ii) selumetinib, (iii) encorafenib, (iv) sorafenib, (v) trametinib, and (vi) vemurafenib, each optionally in the form of a pharmaceutically acceptable salt or solvate thereof, and combinations of any thereof.

In one embodiment, there is provided a pharmaceutical combination which comprises (a) a compound of Formula I or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Formula I or a pharmaceutically acceptable salt or solvate thereof, and (b) binimetinib or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) binimetinib or a pharmaceutically acceptable salt or solvate thereof.

In one embodiment, there is provided a pharmaceutical combination which comprises (a) a compound of Formula I or a pharmaceutically acceptable salt or solvate thereof, and (b) encorafenib or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) encorafenib or a pharmaceutically acceptable salt or solvate thereof.

In one embodiment, there is provided a pharmaceutical combination which comprises (a) a compound of Formula I or a pharmaceutically acceptable salt or solvate thereof, and (b) selumetinib or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) selumetinib or a pharmaceutically acceptable salt or solvate thereof.

In one embodiment, there is provided a pharmaceutical combination which comprises (a) a compound of Formula I or a pharmaceutically acceptable salt or solvate thereof, and (b) sorafenib or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) sorafenib or a pharmaceutically acceptable salt or solvate thereof.

In one embodiment, there is provided a pharmaceutical combination which comprises (a) a compound of Formula I or a pharmaceutically acceptable salt or solvate thereof, and (b) trametinib or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) trametinib or a pharmaceutically acceptable salt or solvate thereof.

In one embodiment, there is provided a pharmaceutical combination which comprises (a) a compound of Formula I or a pharmaceutically acceptable salt or solvate thereof, and (b) vemurafenib or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) vemurafenib or a pharmaceutically acceptable salt or solvate thereof.

In one embodiment, there is provided a pharmaceutical combination which comprises (a) a compound of Example No. 25, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 25, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 37, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 37, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 46, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 46, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 48, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 48, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 55, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 55, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 58, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 58, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 72, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 72, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 76, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 76, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 77, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 77, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 78, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 78, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 83, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 83, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 84, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 84, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 85, or a pharmaceutically acceptable salt or solvate thereof, and (b) an additional anticancer agent selected from the group consisting of (i) binimetinib, (ii) selumetinib, (iii)

encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 85, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 91, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 91, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 97, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 97, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 100, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 100, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 103, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 103, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 105, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 105, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 107, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 107, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 108, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 108, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 114, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 114, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 115, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 115, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 119, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 119, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 121, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 121, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 124, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 124, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 125, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 125, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 126, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 126, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 127, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 127, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 129, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 129, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 151, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 151, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 152, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 152, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 163, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 163, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 169, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 169, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 188, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 188, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 190, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 190, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 199, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 199, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 200, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 200, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In one embodiment, there is provided a pharmaceutical combination which comprises (a) a compound of Example No. 201, or a pharmaceutically acceptable salt or solvate thereof and (b) an additional anticancer agent selected from the group consisting of (i) binimetinib, (ii) selumetinib, (iii) encorafenib, (iv) sorafenib, (v) trametinib, (vi) vemurafenib, each optionally in the form of a pharmaceutically acceptable salt or solvate thereof, and combinations of any thereof.

In one embodiment, there is provided a pharmaceutical combination which comprises (a) a compound of Example No. 201, or a pharmaceutically acceptable salt or solvate thereof, and (b) an additional anticancer agent selected from the group consisting of (i) binimetinib and (ii) encorafenib, each optionally in the form of a pharmaceutically acceptable salt or solvate thereof, and a combination thereof.

In each of the above combinations, the compound of Formula I or the pharmaceutically acceptable salt thereof and the additional anticancer agent may be formulated as separate compositions or dosages for simultaneous, separate or sequential use for the treatment of cancer, wherein the amounts of the compound of Formula I or a pharmaceutically acceptable salt thereof and of the additional anticancer agent are together effective in treating the cancer. Also provided herein is a pharmaceutical composition comprising such a combination. Also provided herein is the use of such a combination for the preparation of a medicament for the treatment of cancer (e.g., a TAM-associated cancer or a c-Met-associated cancer). Also provided herein is a commercial package or product comprising such a combination as a combined preparation for simultaneous, separate or sequential use; and to a method of treatment of cancer a patient in need thereof.

Also provided are methods of treating an individual with cancer that include administering that include administering to a patient identified or diagnosed as having cancer (e.g., a TAM-associated cancer or a c-Met-associated cancer) a therapeutically effective amount of any of the combinations.

Also provided herein are methods of treating a patient identified or diagnosed as having a TAM-associated cancer or a c-Met-associated that include administering to a patient identified or diagnosed as having a TAM-associated cancer or a c-Met-associated a therapeutically effective amount of a therapeutically effective amount of any of the combinations.

A combination of a compound of Formula I in combination with an EGFR inhibitor (e.g., any of the EGFR inhibitors described herein) results in effective reduction in proliferation of cancer cells having resistance to EGFR inhibitors or cancer cells having resistance to c-Met inhibitors).

In one embodiment, there is provided a pharmaceutical combination which comprises (a) a compound of Formula I or a pharmaceutically acceptable salt or solvate thereof, and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib, each optionally in the form of a pharmaceutically acceptable salt or solvate thereof, and combinations of any thereof.

In one embodiment, there is provided a pharmaceutical combination which comprises (a) a compound of Formula I or a pharmaceutically acceptable salt or solvate thereof, and (b) cetuximab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) panitumumab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) erlotinib or a pharmaceutically acceptable salt or solvate thereof.

In one embodiment, there is provided a pharmaceutical combination which comprises (a) a compound of Formula I or a pharmaceutically acceptable salt or solvate thereof, and (b) lapatinib or a pharmaceutically acceptable salt or solvate thereof.

In one embodiment, there is provided a pharmaceutical combination which comprises (a) a compound of Formula I or a pharmaceutically acceptable salt or solvate thereof, and (b) gefitinib or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof and (b) an additional anti cancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof and (b) cetuximab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof and (b) panitumumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof and (b) erlotinib, each optionally in the form of a pharmaceutically acceptable salt or solvate thereof, and combinations of any thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof and (b) lapatinib, each optionally in the form of a pharmaceutically acceptable salt or solvate thereof, and combinations of any thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof and (b) gefitinib, each optionally in the form of a pharmaceutically acceptable salt or solvate thereof, and combinations of any thereof.

In one embodiment, there is provided a pharmaceutical combination which comprises (a) a compound of Example No. 25, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 37, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 46, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 48, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 55, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 58, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 72, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 76, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 77, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 78, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 83, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 84, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 85, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 91, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 97, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 100, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 103, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 105, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 107, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 108, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 114, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 115, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 119, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 121, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 124, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 125, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 126, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 127, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 129, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 151, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 152, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 163, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 169, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 188, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 190, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 199, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 200, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

In one embodiment, there is provided a pharmaceutical combination which comprises (a) a compound of Example No. 201, or a pharmaceutically acceptable salt or solvate thereof and (b) an additional anticancer agent selected from the group consisting of (i) cetuximab (or a biosimilar thereof), (ii) panitumumab (or a biosimilar thereof), (iii) erlotinib, (iv) lapatinib, and (v) gefitinib each optionally in the form of a pharmaceutically acceptable salt or solvate thereof, and combinations of any thereof.

A combination of a compound of Formula I in combination with an immune checkpoint inhibitor (e.g., any of the checkpoint inhibitors described herein, e.g., a PD-1 or a PD-L1 inhibitor) results in sensitization of tumors to immune checkpoint inhibitor therapy. For example, a compound of Formula I in combination with an immune checkpoint inhibitor can result in one or more (e.g., two, three, four, or five) of an increase in dendritic cell-dependent antigen presentation, an increase in NK cell response, an increase in T-cell trafficking, an increase in Type 1 macrophages which results in production of immune stimulating cytokines, and an enhancement of both innate and adaptive immune response.

In one embodiment, there is provided a pharmaceutical combination which comprises (a) a compound of Formula I or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Formula I or a pharmaceutically acceptable salt or solvate thereof, and (b) nivolumab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) pembrolizumab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) cemiplimab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) pidilizumab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) 1141PDCA-170 (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) atezolizumab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) avelumab (or a biosimilar thereof) or a pharmaceutically acceptable salt or solvate thereof.

In one embodiment, there is provided a pharmaceutical combination which comprises (a) a compound of Formula I or a pharmaceutically acceptable salt or solvate thereof, and (b) durvalumab (or a biosimilar thereof) or a pharmaceutically acceptable salt or solvate thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof and (b) an additional anti cancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) nivolumab (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) pembrolizumab (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) cemiplimab (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) pidilizumab (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) 1141PDCA-170 (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) atezolizumab (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) avelumab (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof, and (b) durvalumab (or a biosimilar thereof), each optionally in the form of a pharmaceutically acceptable salt or solvate thereof, and a combination thereof.

In one embodiment, there is provided a pharmaceutical combination which comprises (a) a compound of Example No. 25, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 37, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 46, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 48, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 55, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 58, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 72, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 76, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 77, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 78, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 83, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 84, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 85, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 91, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 97, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 100, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 103, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 105, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 107, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 108, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 114, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 115, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) f 141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 119, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 121, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 124, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 125, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 126, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 127, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 129, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 151, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 152, or a pharmaceutically acceptable salt or solvate thereof, and ((b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 163, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 169, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 188, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 190, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 199, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 200, or a pharmaceutically acceptable salt or solvate thereof, and (b) an additional anticancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

In one embodiment, there is provided a pharmaceutical combination which comprises (a) a compound of Example No. 201, or a pharmaceutically acceptable salt or solvate thereof, and (b) an additional anti cancer agent selected from the group consisting of (i) nivolumab (or a biosimilar thereof), (ii) pembrolizumab (or a biosimilar thereof), (iii) cemiplimab (or a biosimilar thereof), (iv) pidilizumab (or a biosimilar thereof), (v) 1141PDCA-170 (or a biosimilar thereof), (vi) atezolizumab (or a biosimilar thereof), (vii) avelumab (or a biosimilar thereof), and (viii) durvalumab (or a biosimilar thereof), each optionally in the form of a pharmaceutically acceptable salt or solvate thereof, and combinations of any thereof.

Angiogenesis inhibitors may be efficacious in some tumors in combination with compounds of Formula I or pharmaceutically acceptable salts thereof. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib.

Non-limiting examples of radiotherapy include radioiodide therapy, external-beam radiation, and radium 223 therapy.

Non-limiting examples of surgery include, e.g., open surgery or minimally invasive surgery. Surgery can include, e.g., removing an entire tumor, debulking of a tumor, or removing a tumor that is causing pain or pressure in the subject. Methods for performing open surgery and minimally invasive surgery on a subject having a cancer are known in the art.

Accordingly, also provided herein is a method of treating cancer, comprising administering to a patient in need thereof a pharmaceutical combination for treating cancer which comprises (a) a compound of Formula I or a pharmaceutically acceptable salt thereof, and (b) an additional anti cancer agent, for simultaneous, separate or sequential use for the treatment of cancer, wherein the amounts of the compound of Formula I or a pharmaceutically acceptable salt thereof and the additional anticancer agent are together effective in treating the cancer.

Also provided herein is a method of treating cancer, comprising administering to a patient in need thereof a pharmaceutical combination for treating cancer which comprises (a) a compound of Formula I or a pharmaceutically acceptable salt thereof, and (b) an additional anticancer therapy, wherein the therapy is selected from radiation therapy and surgery. In one embodiment, the additional anticancer therapy is radiation therapy. In one embodiment, the additional anticancer therapy is surgery.

In some embodiments, the additional anticancer agent(s) includes any one of the above listed therapies or therapeutic agents which are standards of care in cancers wherein the cancer is a TAM-associated cancer. In one embodiment, the compound of Formula I the additional anticancer agent is an immunotherapy agent. In one embodiment, the immunotherapy agent is a CTLA-4 inhibitor (e.g., an anti-CTLA-4 antibody), a PD-1 inhibitor (e.g., an anti-PD-1 monoclonal antibody) or a PD-L1 inhibitor (e.g., an anti-PD-L1 monoclonal antibody).

In one embodiment, provided herein is a method for treating cancer, comprising administering a compound of Formula I in combination with an immune checkpoint inhibitor. In some embodiments, the immunotherapy includes one or more immune checkpoint inhibitors (e.g., PDR001 or any of the other exemplary immune checkpoint inhibitors described herein). In some embodiments, the immune checkpoint inhibitor is a CTLA-4 inhibitor (e.g., an anti-CTLA-4 antibody), a PD-1 inhibitor (e.g., an anti-PD-1 monoclonal antibody), a PD-L1 inhibitor (e.g., an anti-PD-L1 monoclonal antibody), a NOX2 inhibitor, an A2A4 inhibitor, a B7-H3 inhibitor (e.g., MGA271), a B7-H4 inhibitor (e.g., an anti-B7-H4 antibody, e.g., those described in Dangaj et al., *Cancer Res.* 73(15):4820-4829, 2013), an EDO inhibitor (e.g., coptisine, 1-methyl-D-tryptophan, NLG-919, indoximod, 1-DL-methyl tryptophan, or the inhibitors described in Brastianos et al., *JACS* 128(50: 16046-16047, 2006), a TIM3 inhibitor, a LAG3 inhibitor (e.g., BMS-986016), TIGIT inhibitor, a BTLA inhibitor, a VISTA inhibitor (e.g., 1141PDCA-170), a ICOS inhibitor, a KIR inhibitor (e.g., lirilumab), a CD39 inhibitor, a SIGLEC7 inhibitor, or a SIGLEC9 inhibitor. In some embodiments, the CTLA-4 inhibitor is ipilimumab (Yervoy®), tremelimumab (CP-675,206), or the aptamers described in Santulli-Marotto et al., *Cancer Res.* 63(21):7483-7489, 2003. In some embodiments, the PD-1 inhibitor is pembrolizumab (Keytruda®), nivolumab (Opdivo®), cemiplimab (Libtayo®), pidilizumab, or 1141PDCA-170. In some embodiments, the anti-PD-1 monoclonal antibody is nivolumab or pembrolizumab. In some embodiments, the anti-PD-1 antibody is pembrolizumab. In some embodiments, the PD-L1 inhibitor is atezolizumab (Tecentriq®), avelumab (Bavencio®), durvalumab (Imfinzi™). In some embodiments, the PD-L1 inhibitor is atezolizumab (Tecentriq®), avelumab (Bavencio®), or durvalumab (Imfinzi™). In one embodiment, the compound of Formula I is selected from the compounds described in Example Nos. 1-201, or pharmaceutically acceptable salts thereof. In some embodiments, a compound of Formula I is selected from i) Example Nos. 1-20; ii) Example Nos. 21-40; iii) Example Nos. 41-60; iv) Example Nos. 61-80; v) Example Nos. 81-100; vi) Example Nos. 101-120; vii) Example Nos. 121-140; viii) Example Nos. 141-160; ix) Example Nos. 161-180; x) Example Nos. 181-201 or pharmaceutically acceptable salts thereof. In some embodiments, provided herein is a method for treating cancer, comprising administering to a patient in need thereof a compound of Formula I in combination with an immune checkpoint inhibitor, wherein the patient is further treated with ionizing radiation. In one embodiment, the cancer overexpresses AXL. In one embodiment, the cancer does not have a B-RAF mutation. In one embodiment, the cancer has a B-RAF mutation. In one embodiment, the cancer has a RAS mutation. In one embodiment, the cancer has a EGFR mutation. In one embodiment, the cancer overexpresses MER. In one embodiment, the cancer is lung cancer. In one embodiment, the cancer is non-small cell lung carcinoma (NSCLC). In one embodiment, the cancer is colon cancer. In one embodiment, the cancer is prostate cancer. In one embodiment, the cancer is melanoma. In one embodiment, the cancer is Acute Lymphoblastic Leukemia (ALL). In one embodiment, the cancer is Acute Myeloid Leukemia (AML).

Combination therapies as described herein may be administered without restriction on the order in which therapies are administered to a patient with a disease or disorder described herein. Thus, in one embodiment, a compound of Formula I or pharmaceutically acceptable salt thereof can be administered prior to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent (e.g., any of the additional anticancer agents described herein) to the subject. In another embodiment, a compound of Formula I or pharmaceutically acceptable salt thereof can be administered prior to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent (e.g., any of the anticancer agents described herein).

In one embodiment, provided herein is a method for treating cancer, comprising sensitizing said cancer to an anti-mitotic drug by administration of a compound of Formula I. In one embodiment, the anti-mitotic drug is a taxane-based chemotherapeutic, such as docetaxel.

In one embodiment, compounds of Formula I may be used in combination with other agents to treat patients who have primary or acquired resistance to at least one additional anti cancer agent.

In one embodiment of methods disclosed herein for treating cancer, compounds of Formula I may be used as monotherapy to treat patients who have developed primary or acquired resistance to at least one additional anticancer agent.

In one embodiment, compounds of Formula I may be used to overcome resistance to at least one additional anticancer agent in a cancer. In one embodiment, a compound of Formula I is used in combination with the at least one additional anticancer agent to which the cancer has developed resistance.

In one embodiment, compounds of Formula I may be used to delay resistance to at least one additional anticancer agent. In one embodiment, a compound of Formula I is used in combination with the at least one additional anticancer agent.

As used herein, the term "resistance" refers to a clinical scenario where a cancer fails to respond to a targeted therapy or immunotherapy. For example, resistance of a cancer can be observed by, e.g., a decrease in the rate of increase of tumor burden in the subject, a lack of a decrease in the tumor burden in the subject, an increase in the dosage of a therapeutic agent over time required to achieve the same therapeutic effect in a patient, and the requirement of co-administration of an additional anticancer agent to achieve the same therapeutic effect as the previous administration of the therapeutic agent as a monotherapy.

As used herein, the term "primary resistance", also known as intrinsic resistance, refers to a clinical scenario where a cancer fails to respond to a targeted therapy or immunotherapy, that is, the cancer is resistant to a therapy without having been previously exposed to the therapy.

As used herein, the term "acquired resistance" refers to a clinical scenario in which a cancer initially responded to a targeted therapy or immunotherapy but after a period of time the cancer stops responding to the treatment (e.g., the cancer relapses and progresses).

In one embodiment of methods disclosed herein for treating cancer, compounds of Formula I may be used as monotherapy to treat patients who have developed primary or acquired resistance to at least one additional anticancer agent.

In one embodiment of methods disclosed herein for treating cancer, compounds of Formula I may be used as in combination with at least one additional anticancer agent to treat patients who have developed primary or acquired resistance to one or more of the at least one additional anticancer agent (e.g., a targeted therapeutic agent).

Targeted therapeutic agents include inhibitors or antibodies against EGFR, HER2, VEGFR, c-Met, Ret, IGFR1, PDGFR, FGFR1, FGFR2, FGFR3, FGFR4, TrkA, TrkB, TrkC, ROS, c-Kit, or Flt-3 and against cancer-associated fusion protein kinases such as Bcr-Abl and EML4-Alk. Inhibitors against EGFR include gefitinib, erlotinib, and nazartinib (see, e.g., U.S. Pat. No. 10,195,208 and *J. Med. Chem.* 59(14):6671-6689, 2016), and inhibitors against EGFR/Her2 include but are not limited to dacomitinib, afatinib, lapatinib and neratinib. Antibodies against the EGFR include but are not limited to cetuximab, panitumumab and necitumumab. Inhibitors of c-Met may be used in combination with compounds of Formula I of pharmaceutically acceptable salts thereof. c-MET inhibitors include onartumzumab, tivantinib, and INC-280. Inhibitors against FGFRs include but not limited to AZD4547, BAY1187982, ARQ087, BGI398, BIBF1120, TKI258, lucitanib, dovitinib, TAS-120, JNJ-42756493, and Debiol347. Inhibitors against Trks include but not limited to larotrectinib (LOXO-101), and entrectinib (RXDX-101). Inhibitors against Abl (or Bcr-Abl) include imatinib, dasatinib, nilotinib, and ponatinib and those against Alk (or EML4-ALK) include crizotinib.

In one embodiment, provided herein are methods of treating a patient having cancer who has been previously treated with a first kinase inhibitor, wherein the first kinase inhibitor is not a compound of Formula I, comprising administering to said patient a therapeutically effective amount of a compound of Formula I or a pharmaceutically acceptable salt thereof. In one embodiment, the patient is treated with a compound of Formula I as a single agent. In one embodiment, the patient is treated with a combination of a compound of Formula I and the previously administered first kinase inhibitor. In one embodiment, the patient is treated with a combination of a compound of Formula I and the previously administered first kinase inhibitor. In one embodiment, the compound of Formula I and the previously administered first kinase inhibitor are administered as separate dosages sequentially in any order. In one embodiment, the kinase inhibitor is an EGFR inhibitor. In one embodiment, the EGFR inhibitor is erlotinib or lapatinib. In one embodiment, the kinase inhibitor is a PI3Kα inhibitor. In one embodiment, the PI3Kα inhibitor is alpelisib. In one embodiment, the kinase inhibitor is a MEK inhibitor. In one embodiment, the MEK inhibitor is binimetinib, U0126, or PD325901. In one embodiment, the kinase inhibitor is an FGFR inhibitor. In one embodiment, the kinase inhibitor is an ALK inhibitor. In one embodiment, the kinase inhibitor is an IGFR1 inhibitor. In one embodiment, the cancer is breast cancer (e.g., triple negative breast cancer), head and neck cancer (e.g., squamous cell head and neck cancer), non-small cell lung cancer, colorectal cancer, esophageal squamous cell carcinoma, or melanoma.

In one embodiment, provided herein are methods of treating a patient having cancer who has been previously treated with an EGFR antibody, comprising administering to said patient a therapeutically effective amount of a compound of Formula I or a pharmaceutically acceptable salt thereof. In one embodiment, the patient is treated with a compound of Formula I as a single agent. In one embodiment, the patient is treated with a combination of a compound of Formula I and the previously administered EGFR antibody. In one embodiment, the compound of Formula I and the previously administered EGFR antibody are administered as separate dosages sequentially in any order. In one embodiment, the EGFR antibody is cetuximab. In one embodiment, the cancer is breast cancer, head and neck cancer, or non-small cell lung cancer In one embodiment, provided herein are methods of treating a patient having cancer who has been previously treated with a first kinase inhibitor, wherein the first kinase inhibitor is not a compound of Formula I, comprising (a) determining that said cancer overexpresses a TAM kinase and/or c-Met kinase (e.g., as compared to a non-cancerous tissue or a cell in the patient or a different subject), and (b) after (a), administering to said patient a therapeutically effective amount of a compound of Formula I or a pharmaceutically acceptable salt thereof. In one embodiment, the step of determining if the cancer overexpresses a TAM kinase and/or a c-Met kinase includes a step of performing an assay on a sample obtained from the patient to determine whether the patient has abnormal (e.g., increased) expression, level, and/or activity of one or more of the TAM kinases and/or c-Met kinase (e.g., as compared to a non-cancerous tissue or cell in the patient or a different subject), e.g., AXL and/or MER and/or TYROS and/or c-Met. In one embodiment, the cancer that was previously treated with the first kinase inhibitor overexpresses AXL. In one embodiment, the cancer that was previously treated with the first kinase inhibitor overexpresses MER. In one embodiment, the cancer that was previously treated with the first kinase inhibitor overexpresses TYRO3. In one embodiment, the cancer that was previously treated with the first kinase inhibitor overexpresses c-Met kinase. In one embodiment, the method further comprises obtaining a sample from the patient. In one embodiment, the sample is a biopsy sample. In one embodiment, the assay is selected from the group consisting of sequencing, immunohistochemistry, enzyme-linked immunosorbent assay, and fluorescence in situ hybridization (FISH). In one embodiment, the first kinase inhibitor is an EGFR inhibitor. In one embodiment, the EGFR inhibitor is erlotinib or lapatinib. In one embodiment, the first kinase inhibitor is a PI3Kα inhibitor. In one embodiment, the PI3Kα inhibitor is alpelisib. In one embodiment, the first kinase inhibitor is a MEK inhibitor. In one embodiment, the MEK inhibitor is binimetinib, U0126, or PD325901. In one embodiment, the first kinase inhibitor is an FGFR inhibitor. In one embodiment, the first kinase inhibitor is an ALK inhibitor. In one embodiment, the first kinase inhibitor is an IGFR1 inhibitor. In one embodiment, the cancer is breast cancer (e.g., triple negative breast cancer), head and neck cancer (e.g., squamous cell head and neck cancer), non-small cell lung cancer, colorectal cancer, esophageal squamous cell carcinoma, or melanoma. In one embodiment, the patient is treated with a compound of Formula I as a single agent. In one embodiment, the patient is treated with a combination of a compound of Formula I and the first kinase inhibitor. In one embodiment, the compound of Formula I and the previously prescribed kinase inhibitor are administered as separate dosages sequentially in any order.

In one embodiment, provided herein is a method of treating a subject having cancer, wherein the method comprises (a) determining that a cancer cell in a sample obtained from a subject having a cancer and previously administered one or more doses of a first kinase inhibitor, wherein the first kinase inhibitor is not a compound of Formula I, overexpresses one or more TAM kinases and/or c-Met kinase (e.g., as compared to a non-cancerous tissue or cell in the subject or a different subject); and (b) administering a compound of Formula I or a pharmaceutically acceptable salt or solvate thereof as a monotherapy or in conjunction with the previously administered first kinase inhibitor to the subject. In one embodiment, the cancer that was previously treated with the first kinase inhibitor overexpresses AXL. In one embodiment, the cancer that was previously treated with the first kinase inhibitor overexpresses MER. In one embodiment, the cancer that was previously treated with the first kinase inhibitor overexpresses TYRO3. In one embodiment, the cancer that was previously treated with the first kinase inhibitor overexpresses c-Met kinase. In one embodiment, the first kinase inhibitor is an EGFR inhibitor. In one embodiment, the EGFR inhibitor is erlotinib or lapatinib. In one embodiment, the first kinase inhibitor is a PI3Kα inhibitor. In one embodiment, the PI3Kα inhibitor is alpelisib. In one embodiment, the first kinase inhibitor is a MEK inhibitor. In one embodiment, the MEK inhibitor is binimetinib, U0126, or PD325901. In one embodiment, the first kinase inhibitor is an FGFR inhibitor. In one embodiment, the first kinase inhibitor is an ALK inhibitor. In one embodiment, the first kinase inhibitor is an IGFR1 inhibitor. In one embodiment, the cancer is breast cancer (e.g., triple negative breast cancer), head and neck cancer (e.g., squamous cell head and neck cancer), non-small cell lung cancer, colorectal cancer, esophageal squamous cell carcinoma, or melanoma. In one embodiment, the patient is treated with a compound of Formula I as a single agent. In one embodiment, the patient is treated with a combination of a compound of Formula I and the first kinase inhibitor. In one embodiment, the compound of Formula I and the previously prescribed kinase inhibitor are administered as separate dosages sequentially in any order.

In one embodiment of methods disclosed herein for treating cancer, compounds of Formula I may be used as monotherapy to treat patients who have developed primary or acquired resistance to chemotherapy.

In one embodiment of methods disclosed herein for treating cancer, compounds of Formula I may be used as in combination with a chemotherapeutic agent to treat patients who have developed primary or acquired resistance to the chemotherapeutic agent.

In one embodiment, provided herein are methods of treating a patient having cancer who has been previously treated with a chemotherapeutic, comprising administering to said patient a therapeutically effective amount of a compound of Formula I or a pharmaceutically acceptable salt thereof. In one embodiment, the patient is treated with a compound of Formula I as a single agent. In one embodiment, the patient is treated with a combination of a compound of Formula I and the previously administered chemotherapeutic. In one embodiment, the chemotherapeutic is selected from taxane-based chemotherapies (e.g., docetaxel), dexamethasone, and cytarabine. In one embodiment, the patient is treated with a compound of Formula I as a single agent. In one embodiment, the patient is treated with a compound of Formula I in combination with the previously administered chemotherapeutic. In one embodiment, the compound of Formula I and the previously administered chemotherapeutic are administered as separate dosages sequentially in any order. In one embodiment, the cancer is selected from leukemias (including acute myeloid leukemia and chronic myeloid leukemia, B-cell acute lymphoblastic leukemia, and T-lineage acute lymphoblastic leukemia), non-small cell lung cancer, pancreatic ductal adenocarcinoma, astrocytoma, lung adenocarcinoma, ovarian cancer, melanoma, and glioblastoma multiforme.

In one embodiment, provided herein are methods of treating a patient having cancer who has been previously treated with a chemotherapeutic, comprising (a) determining that said cancer overexpresses a TAM kinase and/or c-Met kinase (e.g., as compared to a non-cancerous tissue or cell in the patient or a different subject), and (b) after (a), administering to said patient a therapeutically effective amount of a compound of Formula I or a pharmaceutically acceptable salt thereof. In one embodiment, the step of determining if the cancer overexpresses a TAM kinase and/or c-Met kinase includes a step of performing an assay on a sample obtained from the patient to determine whether the patient has abnormal expression, level, and/or activity of one or more of the TAM kinases and/or c-Met kinase, e.g., AXL and/or MER and/or TYRO3 and/or c-Met kinase. In one embodiment, the method further comprises obtaining a sample from the patient. In one embodiment, the sample is a biopsy sample. In one embodiment, the assay is selected from the group consisting of sequencing, immunohistochemistry, enzyme-linked immunosorbent assay, and fluorescence in situ hybridization (FISH). In one embodiment, the patient is treated with a compound of Formula I as a single agent. In one embodiment, the patient is treated with a combination of a compound of Formula I and the previously administered chemotherapeutic. In one embodiment, the chemotherapeutic is selected from taxane-based chemotherapies (e.g., docetaxel), dexamethasone, and cytarabine. In one embodiment, the patient is treated with a compound of Formula I as a single agent. In one embodiment, the patient is treated with a compound of Formula I in combination with the previously administered chemotherapeutic. In one embodiment, the compound of Formula I and the previously administered chemotherapeutic are administered as separate dosages sequentially in any order. In one embodiment, the cancer is selected from leukemias (including acute myeloid leukemia and chronic myeloid leukemia, B-cell acute lymphoblastic leukemia, and T-lineage acute lymphoblastic leukemia), non-small cell lung cancer, pancreatic ductal adenocarcinoma, astrocytoma, lung adenocarcinoma, ovarian cancer, melanoma, and glioblastoma multiforme.

In one embodiment, provided herein is a method of treating a subject having cancer, wherein the method comprises (a) determining that a cancer cell in a sample obtained from a subject having a cancer and previously administered one or more doses of a chemotherapeutic, overexpresses one or more TAM kinases and/or c-Met kinase (e.g., as compared to a non-cancerous tissue or cell in the subject or a different subject); and (b) administering a compound of Formula I or a pharmaceutically acceptable salt or solvate thereof as a monotherapy or in conjunction with the previously administered chemotherapeutic or a different chemotherapeutic. In one embodiment, the cancer that was previously treated with the chemotherapeutic overexpresses AXL. In one embodiment, the cancer that was previously treated with the chemotherapeutic overexpresses MER. In one embodiment, the cancer that was previously treated with the chemotherapeutic overexpresses TYRO3. In one embodiment, the cancer that was previously treated with the chemotherapeutic overexpresses c-Met kinase. In one embodiment, the patient is treated with a compound of Formula I as a single agent. In one embodiment, the patient is treated with a combination of a compound of Formula I and the previously administered chemotherapeutic. In one embodiment, the chemotherapeutic is selected from taxane-based chemotherapies (e.g., docetaxel), dexamethasone, and cytarabine. In one embodiment, the patient is treated with a compound of Formula I as a single agent. In one embodiment, the patient is treated with a compound of Formula I in combination with the previously administered chemotherapeutic. In one embodiment, the compound of Formula I and the previously administered chemotherapeutic are administered as separate dosages sequentially in any order. In one embodiment, the cancer is selected from leukemias (including acute myeloid leukemia and chronic myeloid leukemia, B-cell acute lymphoblastic leukemia, and T-lineage acute lymphoblastic leukemia), non-small cell lung cancer, pancreatic ductal adenocarcinoma, astrocytoma, lung adenocarcinoma, ovarian cancer, melanoma, and glioblastoma multiforme.

Also provided herein is (i) a pharmaceutical combination for treating a cancer in a patient in need thereof, which comprises (a) a compound of Formula I or a pharmaceutically acceptable salt thereof, and (b) at least one additional anti cancer agent (e.g., any of the exemplary additional anticancer agents described herein or known in the art), for simultaneous, separate or sequential use for the treatment of cancer, wherein the amounts of the compound of Formula I or pharmaceutically acceptable salt thereof and of the additional anticancer agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In one embodiment the patient is a human. In some embodiments, the cancer is a TAM-associated cancer.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt thereof and at least one additional anticancer agent (e.g., a chemotherapeutic agent), are both administered to a patient simultaneously in the form of a single composition or dosage. The term "non-fixed combination" means that a compound of Formula I or a pharmaceutically acceptable salt thereof and at least one additional anticancer agent (e.g., chemotherapeutic agent) are formulated as separate compositions or dosages such that they may be administered to a patient in need thereof simultaneously, separately or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) a compound of Formula I or pharmaceutically acceptable salt thereof, and (b) an additional anticancer agent for simultaneous, separate or sequential use for the treatment of cancer, wherein the amounts of the compound of Formula I or pharmaceutically acceptable salt thereof and the additional anti cancer agent are together effective in treating the cancer, in one embodiment, the compound of Formula I or pharmaceutically acceptable salt thereof, and the additional anti cancer agent are administered simultaneously as separate dosages. In one embodiment, the compound of Formula I or pharmaceutically acceptable salt thereof, and the additional anticancer agent are administered as separate dosages sequentially in any order, in jointly therapeutically effective amounts, e.g. in daily or intermittently dosages. In one embodiment, the compound of Formula I or pharmaceutically acceptable salt thereof, and the additional anticancer agent are administered simultaneously as a combined dosage.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of Formula I or a pharmaceutically acceptable salt thereof or a pharmaceutical composition thereof. Such methods can be used in the treatment of one or more of the cancers described herein. In some embodiments, the cancer is a TAM-associated cancer, a c-Met-associated cancer, or both. In some embodiments, the compound of Formula I or a pharmaceutically acceptable salt thereof is used in combination with an additional anticancer agent, including an immunotherapy.

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a TAM-associated cancer, a c-Met-associated cancer, or both, that include: selecting, identifying, or diagnosing a patient as having a TAM-associated cancer, a c-Met-associated cancer, or both, and administering a therapeutically effective amount of a compound of Formula I or a pharmaceutically acceptable salt thereof to the patient selected, identified, or diagnosed as having a TAM-associated cancer, a c-Met-associated cancer, or both. Also provided are methods of decreasing the risk of developing a metastasis or an additional metastasis in a patient having a TAM-associated cancer, a c-Met-associated cancer, or both, that includes administering a therapeutically effective amount of a compound of Formula I or a pharmaceutically acceptable salt or solvent thereof to a patient having a TAM-associated cancer, a c-Met-associated cancer, or both. The decrease in the risk of developing a metastasis or an additional metastasis in a patient having a TAM-associated cancer, a c-Met-associated cancer, or both can be compared to the risk of developing a metastasis or an additional metastasis in the patient prior to treatment, or as compared to a patient or a population of patients having a similar or the same TAM-associated cancer, c-Met-associated cancer, or both, that has received no treatment or a different treatment.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Also provided is a method for inhibiting TAM kinase activity and/or inhibiting c-Met kinase activity in a cell (e.g., a mammalian cell), comprising contacting the cell with a compound of Formula I or a pharmaceutically acceptable salt thereof, or a pharmaceutical composition thereof. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt thereof to a subject having a cell having TAM kinase activity and/or c-Met kinase activity. In some embodiments, the cell is a cancer cell (e.g., a human cancer cell). In one embodiment, the cancer cell is any cancer as described herein. In some embodiments, the cancer cell is a TAM-associated cancer cell. In some embodiments, the cancer cell is a c-Met-associated cancer cell. In some embodiments, the cancer cell is both a TAM-associated cancer cell and a c-Met-associated cancer cell.

In some embodiments, the mammalian cell is in vitro. In some embodiments, the mammalian cell is in vivo. In some embodiments, the mammalian cell is ex vivo.

Also provided herein is a method of inhibiting cell proliferation, in vitro or in vivo, the method comprising contacting a cell with an effective amount of a compound of Formula I or a pharmaceutically acceptable salt thereof, or a pharmaceutical composition thereof as defined herein.

Also provided herein are methods of decreasing immune tolerance in a subject in need thereof that include administering to the subject a therapeutically effective amount of a compound of Formula I or a pharmaceutically acceptable salt thereof, or a pharmaceutical composition thereof as defined herein. As used herein, the term "immune tolerance" refers to a decrease (e.g., a 1% to about 99% decrease, or any of the subranges of this range described herein) in one or more of: the processing of tumor-associated antigens by antigen-presenting cells (e.g., dendritic cells), presentation of antigens to tumor antigen-specific T cells, activation and proliferation of tumor antigen-specific T cells, and maintenance of the T-cell response in a subject (e.g., in a solid tumor in a subject), e.g., as compared to a control (e.g., a corresponding level in a similar subject that does not have a cancer)). In some embodiments of these methods, the subject has been identified or diagnosed as having a cancer (e.g., a TAM-associated cancer (e.g., any of the exemplary TAM-associated cancers described herein), a c-Met-associated cancer (e.g., any of the exemplary c-Met-associated cancers described herein), or both). In some examples, a decrease in immune tolerance in a subject can be detected by observing an about 1% to about 99% (e.g., about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 99%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 10%, about 10% to about 99%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 99%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 99%, about 25% to about 95%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 99%, about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 99%, about 35% to about 95%, about 35% to about 90%, about 35% to about 85%, about 35% to about 80%, about 35% to about 75%, about 35% to about 70%, about 35% to about 65%, about 35% to about 60%, about 35% to about 55%, about 35% to about 50%, about 35% to about 45%, about 35% to about 40%, about 40% to about 99%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 45% to about 99%, about 45% to about 95%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%, about 50% to about 99%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 55% to about 99%, about 55% to about 95%, about 55% to about 90%, about 55% to about 85%, about 55% to about 80%, about 55% to about 75%, about 55% to about 70%, about 55% to about 65%, about 55% to about 60%, about 60% to about 99%, about 60% to about 95%, about 60% to about 90%, about 60% to about 85%, about 60% to about 80%, about 60% to about 75%, about 60% to about 70%, about 60% to about 65%, about 65% to about 99%, about 65% to about 95%, about 65% to about 90%, about 65% to about 85%, about 65% to about 80%, about 65% to about 75%, about 65% to about 70%, about 70% to about 99%, about 70% to about 95%, about 70% to about 90%, about 70% to about 85%, about 70% to about 80%, about 70% to about 75%, about 75% to about 99%, about 75% to about 95%, about 75% to about 90%, about 75% to about 85%, about 75% to about 80%, about 80% to about 99%, about 80% to about 95%, about 80% to about 90%, about 80% to about 85%, about 85% to about 99%, about 85% to about 95%, about 85% to about 90%, about 90% to about 99%, about 90% to about 95%, or about 95% to about 99%) decrease in the level of myeloid-derived suppressor cells (MDSCs) (e.g., cells characterized by expression of CD33, CD14, and low levels of HLA DR) in the subject (e.g., in a sample comprising blood or a biopsy sample obtained from the subject) (e.g., as compared to the level of MDSCs in the subject prior to administration of treatment (e.g., prior to administration of any of the compounds of Formula I or any of the pharmaceutical compositions described herein).

In some examples, a decrease in immune tolerance in a subject can be detected by observing an about 1% to about 99% (or any of the subranges of this range described herein) decrease in the level of Treg cells (e.g., cells characterized by expression of CD4, FOXP3, and CD25) in the subject (e.g., in a sample comprising blood or a biopsy sample obtained from the subject) (e.g., as compared to the level of Tregs in the subject prior to administration of treatment (e.g., prior to administration of any of the compounds of Formula I or any of the pharmaceutical compositions described herein).

In some examples, a decrease in immune tolerance in a subject can be detected by observing an about 1% to about 99% (or any of the subranges of this range described herein) decrease in the level of dendritic cells with reduced expression of CD80/CD86 in the subject (e.g., in a sample comprising blood or a biopsy sample obtained from the subject) (e.g., as compared to the level of dendritic cells with reduced expression of CD80/CD86 in the subject prior to administration of treatment (e.g., prior to administration of any of the compounds of Formula I or any of the pharmaceutical compositions described herein). Exemplary methods for detecting the levels of MDSCs, Tregs, and dendritic cells with reduced expression of CD80/CD86 include, fluorescence-assisted cell sorting and immunofluorescence microscopy.

Also provided herein are methods of inhibiting angiogenesis in a subject in need thereof, the method comprising administering to the subject a therapeutically effective amount of a compound of Formula I or a pharmaceutically acceptable salt thereof, or a pharmaceutical composition thereof as defined herein. In some embodiments, the angiogenesis is tumor angiogenesis and the subject has been identified or diagnosed as having a cancer (e.g., a TAM-associated cancer, a c-Met-associated cancer, or both). In some embodiments, these methods result in a decrease (e.g., a 1% to about 99% decrease, or any of the subranges of this range described herein) in the rate of development of new blood vessels (e.g., as compared to the rate of development of new blood vessels in a similar subject administered a placebo or a different treatment over a similar period of time). Exemplary methods for detecting the formation of new blood vessels include Doppler ultrasound (e.g., Color Dopier Flow Imaging), Ultrasound-Guided Diffus Optical Tomography, MRI, perfusion CT (also called functional multi-detector row CT (f-MDCT)), positron emission tomography (PET), dynamic MRI, dynamic susceptibility contrast enhanced MRI (DSC-MRI), and T1-weighted dynamic MRI (DCE-MRI). Non-limiting methods that can be used to detect the formation of new blood vessels (angiogenesis) are described in Jeswani et al., *Cancer Imaging* 5(1): 131-138, 2005.

Also provided herein are methods of suppressing (e.g., decreasing, e.g., a 1% to about 99% decrease, or any of the subranges of this range described herein) resistance to a therapeutic agent in a subject in need thereof that include administering to the subject a therapeutically effective amount of (i) a compound of Formula I or a pharmaceutically acceptable salt thereof, or any of the pharmaceutical compositions thereof described herein, and (ii) the therapeutic agent, where the therapeutic agent is selected from the group consisting of a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor, a RAF inhibitor, an Akt inhibitor, a FTL-3 inhibitor, and a MAP kinase pathway inhibitor. In some examples of these methods, the c-Met inhibitor is a Type 1 c-Met inhibitor, e.g., crizotinib, capmatinib, NVP-BVU972, AMG 337, bozitinib, glumetinib, savolitinib, or tepotinib. In some examples of these methods, the compound of Formula I or a pharmaceutically acceptable salt thereof, or a pharmaceutical composition thereof, and the therapeutic agent, are administered to the subject at substantially the same time. In some embodiments of these methods, the compound of Formula I or a pharmaceutically acceptable salt thereof, or a pharmaceutical composition thereof, and the therapeutic agent, are formulated in a single dosage form. In some embodiments of these methods, (i) the compound of Formula I or a pharmaceutically salt thereof, or any of the pharmaceutical compositions thereof described herein is administered to the subject prior to administration of (ii) the therapeutic agent to the subject. In some embodiments of these methods, (ii) the therapeutic agent is administered to the subject prior to administration of (i) the compound of Formula I or a pharmaceutically salt thereof, or any of the pharmaceutical compositions thereof described herein.

In some embodiments of these methods, the compound of Formula I or a pharmaceutically acceptable salt thereof, or a pharmaceutical composition thereof, is administered to the subject prior to administration of the therapeutic agent to the subject. In some embodiments of these methods, the therapeutic agent is administered to the subject prior to administration of the compound of Formula I or a pharmaceutically acceptable salt thereof, or a pharmaceutical composition thereof, to the subject.

As used herein, the term "resistance to a therapeutic agent" refers to a reduced or decreased level of sensitivity to treatment with a therapeutic agent (e.g., a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor (e.g., a Type 1 c-Met kinase inhibitor, e.g., crizotinib, capmatinib, and NVP-BVU972), a RAF inhibitor, an Akt inhibitor, a FTL-3 inhibitor, and a MAP kinase pathway inhibitor) in a subject (e.g., as compared to a similar subject or as compared to the level of sensitivity to the therapeutic agent at an earlier time point). For example, resistance to an therapeutic agent in a subject can be observed by a physician, e.g., by observing the requirement of a increasing dosage amounts of a therapeutic agent over time in order to achieve the same therapeutic effect in a subject, observing the requirement for an increased number of doses and/or an increased frequency of doses of a therapeutic agent over time in order to achieve the same therapeutic effect in a subject, a decrease in the observed therapeutic response to treatment with the same dosage of a therapeutic agent over time, or an observed progression of disease or disease relapse in a subject administered a therapeutic agent.

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In one embodiment, a compound of Formula I is formulated as a tablet. In one embodiment, a compound of Formula I is formulated as a capsule. In one embodiment, a compound of Formula I is administered orally. In one embodiment, a compound of Formula I is administered orally once a day. In one embodiment, a compound of Formula I is administered orally twice a day.

Also provided herein are pharmaceutical compositions which contain, as the active ingredient, a compound of Formula I or a pharmaceutically acceptable salt thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In one embodiment, the composition is formulated for oral administration. In one embodiment, the composition is formulated as a tablet or capsule.

The compositions comprising a compound of Formula I or a pharmaceutically acceptable salt thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Examples

The following examples illustrate the invention.

Biological Examples

Example A

AXL Enzyme Assay

Compounds of Formula I were screened for their ability to inhibit AXL kinase using Invitrogen's LanthaScreen™ Eu Kinase Binding technology. His-tagged recombinant human AXL cytoplasmic domain was incubated with 20 nM Alexa-Fluor® Tracer 236 (PR9078A), 2 nM biotinylated anti-His (Cat. No. M4408), and 2 nM europium-labeled Streptavidin (Cat. No. PV5899) along with test compound in a buffer consisting of 25 mM HEPES, pH 7.4, 10 mM $MgCl_2$, 0.01% Triton X-100, and 2% DMSO. Compounds were typically prepared in a threefold serial dilution in DMSO and added to the assay to give the appropriate final concentration. After a 60-minute incubation at 22° C., the reaction was measured using a PerkinElmer EnVision multimode plate reader via TR-FRET dual wavelength detection, and the percent of control (POC) was calculated using a ratiometric emission factor. 100 POC was determined using no test compounds and 0 POC was determined using a concentration of control compound that completely inhibits the enzyme. The POC values are fit to a 4 parameter logistic curve and the $IC_{50}$ value is point where the curve crosses 50 POC.

Example B

MER Enzyme Assay

Compounds of Formula I were screened for their ability to inhibit AXL kinase using Invitrogen's LanthaScreen™ Eu Kinase Binding technology. His-tagged recombinant human MER cytoplasmic domain (5 nM) was incubated with 20 nM Alexa-Fluor® Tracer 236 (PR9078A), 2 nM biotinylated anti-His (Cat. No. M4408), and 2 nM europium-labeled Streptavidin (Cat. No. PV5899) along with test compound in a buffer consisting of 25 mM HEPES, pH 7.4, 10 mM $MgCl_2$, 0.01% Triton X-100, and 2% DMSO. Compounds were typically prepared in a threefold serial dilution in DMSO and added to the assay to give the appropriate final concentration. After a 60-minute incubation at 22° C., the reaction was measured using a PerkinElmer EnVision multimode plate reader via TR-FRET dual wavelength detection, and the percent of control (POC) was calculated using a ratiometric emission factor. 100 POC was determined using no test compounds and 0 POC was determined using a concentration of control compound that completely inhibits the enzyme. The POC values are fit to a 4 parameter logistic curve and the $IC_{50}$ value is point where the curve crosses 50 POC.

Example C

TYRO3 Enzyme Assay

Compounds of Formula I were screened for their ability to inhibit TYRO3 kinase using Invitrogen's LanthaScreen™ Eu Kinase Binding technology. GST-tagged recombinant human TYRO3 kinase domain from Carna (5 nM; Cat. No. PR7480A) was incubated with 20 nM Alexa-Fluor® Tracer 236 (PR9078A) and 2 nM Europium-anti-GST (Cat. No. A15116) along with test compound in a buffer consisting of 25 mM HEPES, pH 7.4, 10 mM $MgCl_2$, 0.01% Triton X-100, and 2% DMSO. Compounds are typically prepared in a threefold serial dilution in DMSO and added to the assay to give the appropriate final concentration. After a 60-minute incubation at 22° C., the reaction was measured using a PerkinElmer EnVision multimode plate reader via TR-FRET dual wavelength detection, and the percent of control (POC) calculated using a ratiometric emission factor. 100 POC was determined using no test compounds and 0 POC was determined using a concentration of control compound that completely inhibits the enzyme. The POC values were fit to a 4 parameter logistic curve and the 1C50 value is point where the curve crosses 50 POC.

The averaged $IC_{50}$'s of compounds tested in the assays of Examples A, B and C are shown in Table 7

TABLE 7

| Ex. | AXL enzyme $IC_{50}$ | MER enzyme $IC_{50}$ | TYRO3 enzyme $IC_{50}$ |
|---|---|---|---|
| 1 | 6.1 | 13.2 | 21.6 |
| 2 | 2.7 | 3.9 | 10.7 |
| 3 | 1.8 | 4.7 | 46.7 |
| 4 | 1.8 | 3.6 | 18.2 |
| 5 | 4.6 | 8.3 | 30.2 |
| 6 | 5.6 | 5.1 | 15.4 |
| 7 | 3.6 | 5.1 | 16.5 |
| 8 | 3.4 | 5.1 | 13.8 |
| 9 | 4.4 | 8.3 | 57.9 |
| 10 | 7.1 | 11.4 | 45.7 |
| 11 | 9.4 | 18.3 | 86 |
| 12 | 18.3 | 36.8 | 295.4 |
| 13 | 4 | 7.2 | 16.9 |
| 14 | 5.4 | 11.6 | 65.7 |
| 15 | 4.4 | 10.4 | 48.1 |
| 16 | 2 | 4.1 | 34.1 |
| 17 | 2.8 | 8.4 | 56.8 |
| 18 | 3.8 | 7.3 | 131.1 |
| 19 | 16.1 | 24.6 | 85.6 |
| 20 | 18.9 | 51.9 | 535.8 |
| 21 | 12.7 | 18.1 | 187.7 |
| 22 | 18.3 | 29.5 | 317.9 |
| 23 | 4 | 6.5 | 29.6 |
| 24 | 7.1 | 13.1 | 119.6 |
| 25 | 1.4 | 2.3 | 7.7 |
| 26 | 3.9 | 4.9 | 41.1 |
| 27 | 3.3 | 11.3 | 64.6 |
| 28 | 19.1 | 37.9 | 374.9 |
| 29 | 5.4 | 11.9 | 51.9 |
| 30 | 6.1 | 12.1 | 79.3 |
| 31 | 4.1 | 7.5 | 76.8 |
| 32 | 2.2 | 5.7 | 37.3 |
| 33 | 0.8 | 2.1 | 14.9 |
| 34 | 1.2 | 2.8 | 19.6 |
| 35 | 3.8 | 8.8 | 26.7 |
| 36 | 2.8 | 4.1 | 13.1 |
| 37 | 2.4 | 3.5 | 8.4 |
| 38 | 1.1 | 3.1 | 29.1 |
| 39 | 3.8 | 11.6 | 96.3 |
| 40 | 2.5 | 7.6 | 98.3 |
| 41 | 0.9 | 3.9 | 13.5 |
| 42 | 1.1 | 7.4 | 53.1 |
| 43 | 2.8 | 2.6 | 18.5 |
| 44 | 7.3 | 19.4 | 109.1 |
| 45 | 1.3 | 2.8 | 12.1 |
| 46 | 2 | 2.7 | 9 |
| 47 | 1.1 | 2.4 | 16.9 |
| 48 | 2 | 2.7 | 9.8 |
| 49 | 2.2 | 5.8 | 23.9 |
| 50 | 4.4 | 9.7 | 40.3 |
| 51 | 1.3 | 4.1 | 18 |
| 52 | 1.8 | 3.9 | 28.4 |
| 53 | 1.8 | 4.6 | 31.7 |
| 54 | 3.5 | 4 | 41.2 |
| 55 | 1.1 | 2 | 7.4 |
| 56 | 1.5 | 3.5 | 20.7 |
| 57 | 1.9 | 4.1 | 20.8 |
| 58 | 2.2 | 4.3 | 9.7 |
| 59 | 1.8 | 3.7 | 25.4 |
| 60 | 5.9 | 6.1 | 28.1 |
| 61 | 2.6 | 4.1 | 22.5 |
| 62 | 3.3 | 7 | 41.6 |
| 63 | 5.6 | 8.2 | 37.7 |
| 64 | 3.8 | 5.1 | 19.2 |
| 65 | 1 | 5.4 | 65.6 |
| 66 | 1.3 | 1.9 | 10.9 |
| 67 | 1.1 | 3.4 | 10.8 |
| 68 | 1.3 | 5.5 | 32.3 |
| 69 | 1.4 | 5.7 | 26.5 |
| 70 | 1 | 5.1 | 25.7 |
| 71 | 5.2 | 8.5 | 192.1 |
| 72 | 0.9 | 2.3 | 6 |
| 73 | 1.1 | 10.8 | 23.8 |
| 74 | 1.6 | 32.5 | 97.5 |
| 75 | 0.6 | 3.8 | 22.2 |
| 76 | 0.5 | 2.5 | 4.2 |
| 77 | 0.7 | 2.8 | 7.2 |
| 78 | 1 | 3.1 | 8.2 |
| 79 | 1.2 | 2.9 | 19.7 |
| 80 | 1.6 | 4.1 | 38 |
| 81 | 1.8 | 4 | 21.8 |
| 82 | 1.6 | 5.3 | 19.3 |
| 83 | 0.5 | 1.6 | 7.2 |
| 84 | 0.6 | 1.9 | 4.3 |
| 85 | 1 | 1.7 | 4.4 |
| 86 | 4.8 | 11 | 104.1 |
| 87 | 12.6 | 33.4 | 432.5 |
| 88 | 6.5 | 30.2 | 363.5 |
| 89 | 0.7 | 19.1 | 74.3 |
| 90 | 0.8 | 13.1 | 76.6 |
| 91 | 1.1 | 4.7 | 4 |
| 92 | 1.5 | 4.4 | 16.3 |
| 93 | 4.7 | 259.6 | 766.6 |
| 94 | 2.9 | 8.7 | 19 |
| 95 | 15.4 | 176.5 | 874.8 |
| 96 | 2.9 | 9.6 | 19.7 |
| 97 | 1.2 | 3.1 | 4.8 |
| 98 | 1.3 | 5.6 | 12.4 |
| 99 | 5.7 | 92.8 | 545.8 |

TABLE 7-continued

| Ex. | AXL enzyme IC$_{50}$ | MER enzyme IC$_{50}$ | TYRO3 enzyme IC$_{50}$ |
|---|---|---|---|
| 100 | 1.6 | 1.6 | 3.9 |
| 101 | 49.7 | 60.4 | 198.2 |
| 102 | 2 | 3.3 | 44.1 |
| 103 | 0.6 | 0.9 | 3.2 |
| 104 | 1.8 | 2.6 | 14.1 |
| 105 | 1.1 | 4 | 9.8 |
| 106 | 1.6 | 6.8 | 16.1 |
| 107 | 2.3 | 3.3 | 9.2 |
| 108 | 0.9 | 2 | 6.1 |
| 109 | 0.9 | 5.2 | 18.7 |
| 110 | 1.3 | 6.6 | 38.5 |
| 111 | 4.4 | 12.5 | 136.9 |
| 112 | 1.6 | 6.4 | 70 |
| 113 | 1.8 | 5.6 | 60.4 |
| 114 | 1.5 | 5.2 | 7.1 |
| 115 | 1.2 | 4.3 | 6.4 |
| 116 | 1.4 | 4.5 | 11.4 |
| 117 | 0.8 | 3.1 | 13.6 |
| 118 | 1.8 | 6.1 | 26.2 |
| 119 | 1.8 | 3.1 | 4.7 |
| 120 | 5 | 6.2 | 27.3 |
| 121 | 1.6 | 2.1 | 4.6 |
| 122 | 3.4 | 9 | 44.7 |
| 123 | 1.3 | 3.8 | 15.3 |
| 124 | 1.8 | 3.5 | 8.3 |
| 125 | 1.3 | 2.7 | 7.1 |
| 126 | 1.5 | 2.4 | 6.7 |
| 127 | 1.1 | 2.3 | 3.7 |
| 128 | 1.2 | 5.3 | 23 |
| 129 | 0.8 | 1.8 | 3.2 |
| 130 | 1.3 | 5.8 | 27.1 |
| 131 | 2.1 | 9.1 | 47.4 |
| 132 | 8.6 | 70 | 347.9 |
| 133 | 5.3 | 37.8 | 129.9 |
| 134 | 4.6 | 32.8 | 169.2 |
| 135 | 3.5 | 17.2 | 64.4 |
| 136 | 3.3 | 26.7 | 88.8 |
| 137 | 5.8 | 27.4 | 74.3 |
| 138 | 6.2 | 36.7 | 159 |
| 139 | 1.7 | 10.8 | 86.2 |
| 140 | 354.6 | 161.2 | 1000 |
| 141 | 484.6 | 178.1 | 1000 |
| 142 | 3.2 | 5.7 | 15.6 |
| 143 | 3.1 | 5.7 | 41.2 |
| 144 | 2.4 | 9.6 | 88.8 |
| 145 | 0.8 | 3.3 | 20.9 |
| 146 | 1.8 | 7 | 46.5 |
| 147 | 5.6 | 45.9 | 91.2 |
| 148 | 1.3 | 3.1 | 12.2 |
| 149 | 2 | 4.1 | 20 |
| 150 | 1.6 | 4.4 | 13.6 |
| 151 | 2 | 2.2 | 2.3 |
| 152 | 1.3 | 4.9 | 8.7 |
| 153 | 2 | 7.9 | 28.2 |
| 154 | 1.6 | 5.9 | 14.4 |
| 155 | 1.6 | 5.6 | 59.5 |
| 156 | 1.2 | 5.2 | 59.5 |
| 157 | 1.4 | 6.2 | 118.3 |
| 158 | 2 | 13.4 | 104 |
| 159 | 2.2 | 18.7 | 420.2 |
| 160 | 1.3 | 2.7 | 15.4 |
| 161 | 1.9 | 4 | 28 |
| 162 | 1.3 | 5.4 | 37.9 |
| 163 | 1.1 | 2.6 | 5.5 |
| 164 | 1.7 | 11.8 | 68.9 |
| 165 | 3.3 | 13.7 | 90 |
| 166 | 22.7 | 72.5 | 475.9 |
| 167 | 3.4 | 19.8 | 224.5 |
| 168 | 4.9 | 11.9 | 248 |
| 169 | 0.7 | 1.5 | 4.4 |
| 170 | 1.9 | 3.9 | 36.2 |
| 171 | 3 | 27.1 | 333.3 |
| 172 | 4.2 | 8.3 | 132.7 |
| 173 | 7.1 | 15.7 | 114.1 |
| 174 | 1.4 | 4.6 | 98.6 |
| 175 | 5.6 | 23.2 | 292.2 |
| 176 | 4.2 | 22 | 728 |
| 177 | 1.6 | 3.5 | 106.1 |
| 178 | 3.6 | 11.5 | 439.2 |
| 179 | 1.3 | 6 | 80.6 |
| 180 | 2 | 11.9 | 140 |
| 181 | 2.5 | 4.1 | 30.8 |
| 182 | 8.6 | 16.7 | 706.8 |
| 183 | 5.4 | 18 | 108.7 |
| 184 | 1.8 | 2.7 | 35.2 |
| 185 | 1.3 | 2.3 | 18.4 |
| 186 | 6.6 | 18.9 | 217.4 |
| 187 | 1.9 | 3.5 | 11.9 |
| 188 | 1.9 | 1.7 | 7.8 |
| 189 | 5.8 | 7.5 | 69.6 |
| 190 | 1.2 | 1.8 | 5 |
| 191 | 4.8 | 8.9 | 73.2 |
| 192 | 3.5 | 10.8 | 61.4 |
| 193 | 2.2 | 6.5 | 12.1 |
| 194 | 4.8 | 11.2 | 97.4 |
| 195 | 1.5 | 3.8 | 13.4 |
| 196 | 1 | 10.5 | 22 |
| 197 | 1.1 | 12.7 | 52.3 |
| 198 | 1.3 | 5.5 | 23.3 |
| 199 | 1.6 | 2.7 | 4.5 |
| 200 | 1.3 | 1.9 | 3.4 |
| 201 | 1.3 | 2.2 | 3.8 |

Example D c-Met Enzyme Assay

EXPERIMENTAL

The affinity of compound binding to wild type and mutant human MET kinases is measured using Invitrogen's LanthaScreen™ Eu Kinase Binding technology. Briefly, GST-tagged recombinant human MET kinase domain from Signal Chem (see Table 8 below for concentration in assay) is incubated with 50 nM Alexa-Fluor® Tracer 236 (Invitrogen Cat No. PR9078A) and 2 nM Europium-anti-GST (Invitrogen Cat. No. A15116) along with test compound in a buffer consisting of 25 mM HEPES, pH 7.4, 10 mM MgCl2, 0.01% Triton X-100, 1 mM DTT, and 2% DMSO. Compounds are typically prepared in a three-fold serial dilution in DMSO and added to the assay to give the appropriate final concentration. After a 60-minute incubation at 22° C., the reaction is measured using a PerkinElmer EnVision multimode plate reader via TR-FRET dual wavelength detection, and the percent of control (POC) calculated using a ratiometric emission factor. 100 POC is determined using no test compounds and 0 POC is determined using a concentration of control compound that completely inhibits the enzyme. The POC values are fit to a 4 parameter logistic curve and the IC50 value is point where the curve crosses 50 POC.

TABLE 8

Concentration of Wild Type and Mutant MET kinases in binding assay

| Met Mutant Enzyme | Source | Catalog Number | MET Amino Acids | Enzyme Concentration in Binding Assay (nM) |
|---|---|---|---|---|
| del Ex14 | SignalChem | M52-12PG | 956-1390 (end) | 5 |
| L1195V | SignalChem | NP-18-156G | 956-1390 (end) | 10 |

TABLE 8-continued

Concentration of Wild Type and Mutant MET kinases in binding assay

| Met Mutant Enzyme | Source | Catalog Number | MET Amino Acids | Enzyme Concentration in Binding Assay (nM) |
|---|---|---|---|---|
| F1200I | SignalChem | M52-12GG | 956-1390 (end) | 2 |
| D1228H | SignalChem | M52-12HG | 956-1390 (end) | 2 |
| D1228N | SignalChem | M52-121G | 956-1390 (end) | 2 |
| Y1230C | SignalChem | M52-12KG | 956-1390 (end) | 2 |
| Y1230H | SignalChem | M52-12MG | 956-1390 (end) | 5 |
| Y1230S | SignalChem | NP18-157G | 956-1390 (end) | 8 |
| MET (wt) | SignalChem | M52-18G | 956-1390 (end) | 10 |

Results

TABLE 9

IC50 of Inhibition of Wild Type and Mutation MET kinases of Exemplary Tested Compounds

| Ex. # | SigChem WT IC50 (nM) | Del14 IC50 (nM) | D1228H IC50 (nM) | D1228N IC50 (nM) | F1200I IC50 (nM) | L1195V IC50 (nM) | Y1230C IC50 (nM) | Y1230H IC50 (nM) | Y1230S IC50 (nM) |
|---|---|---|---|---|---|---|---|---|---|
| 2 | 3.9 | 13.0 | 11.2 | 7.6 | 6.8 | 125.9 | 3.9 | 15.8 | 8.2 |
| 3 | 3.7 | 9.6 | 16.6 | 5.2 | 3.6 | 133.4 | 3.9 | 3.9 | 3.9 |
| 4 | 3.0 | 9.3 | 19.7 | 3.8 | 4.9 | 116.7 | 10.1 | 9.4 | 6.3 |
| 5 | 3.3 | 7.6 | 21.2 | 4.3 | 5.1 | 116.1 | 3.1 | 7.7 | 5.0 |
| 6 | 9.2 | 31.4 | 61.5 | 13.5 | 11.3 | 244.1 | 11.2 | 22.1 | 13.8 |
| 7 | 12.4 | 28.2 | 51.6 | 15.4 | 18.8 | 452.8 | 15.4 | 26.5 | 16.0 |
| 8 | 3.0 | 12.8 | 19.7 | 5.4 | 6.2 | 145.2 | 4.2 | 11.8 | 4.8 |
| 12 | 17.6 | 92.1 | 161.5 | 19.8 | 24.0 | 828.8 | 50.0 | 53.5 | 39.9 |
| 13 | 3.7 | 9.7 | 22.7 | 3.2 | 4.4 | 121.0 | 4.6 | 7.9 | 4.2 |
| 14 | 17.5 | 104.4 | 181.7 | 24.1 | 15.8 | 961.5 | 31.5 | 48.4 | 41.3 |
| 16 | 3.2 | 8.9 | 22.6 | 5.3 | 4.4 | 101.6 | 3.5 | 10.9 | 4.5 |
| 17 | 26.5 | 107.7 | 183.6 | 38.5 | 34.2 | 1383.4 | 44.4 | 59.1 | 30.9 |
| 18 | 49.8 | 116.4 | 435.0 | 87.4 | 75.2 | 3787.7 | 147.6 | 173.9 | 123.0 |
| 19 | 40.1 | 130.3 | 266.9 | 56.5 | 81.0 | 2060.5 | 121.4 | 125.2 | 100.4 |
| 20 | 19.8 | 85.4 | 169.7 | 48.6 | 41.3 | 919.2 | 30.8 | 81.8 | 52.2 |
| 21 | 21.7 | 80.0 | 143.4 | 31.0 | 36.8 | 2122.0 | 68.9 | 92.8 | 59.5 |
| 22 | 22.1 | 78.1 | 141.8 | 63.3 | 48.1 | 2861.3 | 41.3 | 94.8 | 30.8 |
| 23 | 7.7 | 23.3 | 36.9 | 12.2 | 13.1 | 514.7 | 13.7 | 18.3 | 15.7 |
| 24 | 13.9 | 101.7 | 132.1 | 19.2 | 25.0 | 1520.4 | 29.5 | 56.9 | 26.0 |
| 25 | 2.5 | 6.9 | 11.5 | 4.2 | 3.4 | 84.4 | 2.9 | 7.3 | 3.3 |
| 26 | 21.2 | 63.7 | 113.2 | 31.4 | 31.4 | 911.9 | 31.8 | 61.8 | 44.8 |
| 27 | 2.7 | 7.6 | 14.1 | 5.0 | 3.3 | 77.1 | 3.7 | 8.5 | 5.0 |
| 28 | 1.2 | 22.9 | 49.0 | 16.3 | 11.9 | 508.1 | 11.5 | 22.0 | 22.6 |
| 29 | 3.9 | 14.6 | 30.9 | 7.5 | 7.1 | | 6.9 | 16.1 | 8.8 |
| 30 | 4.4 | 19.6 | 28.6 | 6.2 | 4.9 | 166.1 | 6.3 | 12.4 | 6.1 |
| 31 | 10.1 | 31.8 | 52.9 | 15.7 | 15.1 | 415.7 | 16.6 | 22.0 | 15.4 |
| 32 | 3.4 | 7.2 | 9.6 | 5.4 | 4.3 | 101.7 | 3.8 | 5.6 | 3.5 |
| 33 | 23.6 | 62.5 | 132.2 | 35.8 | 28.2 | 1107.5 | 29.6 | 64.3 | 26.4 |
| 34 | 1.5 | 3.9 | 6.8 | 2.3 | 2.6 | 60.7 | 2.9 | 5.0 | 2.4 |
| 35 | 10.6 | 31.0 | 51.7 | 16.5 | 17.2 | 347.7 | 19.3 | 26.6 | 15.6 |
| 36 | 3.4 | 10.2 | 14.2 | 4.4 | 4.1 | 83.3 | 2.4 | 9.2 | 4.8 |
| 37 | 1.1 | 4.6 | 6.1 | 1.9 | 1.3 | 44.6 | 1.3 | 3.9 | 2.2 |
| 38 | 9.4 | 21.5 | 42.7 | 13.0 | 13.2 | 280.4 | 12.8 | 25.0 | 10.7 |
| 39 | 9.5 | 25.4 | 48.7 | 13.8 | 13.2 | 451.2 | 19.5 | 26.5 | 10.5 |
| 40 | 4.9 | 39.5 | 59.1 | 8.7 | 15.6 | 487.8 | 17.2 | 19.8 | 9.4 |
| 41 | 2.6 | 9.3 | 14.3 | 3.3 | 3.6 | 89.5 | 3.6 | 7.6 | 2.7 |
| 42 | 8.5 | 31.6 | 38.5 | 11.1 | 9.5 | 297.8 | 6.6 | 19.4 | 6.0 |
| 43 | 6.3 | 12.0 | 23.8 | 9.1 | 7.4 | 292.6 | 10.5 | 13.9 | 5.4 |
| 44 | 9.7 | 42.1 | 57.3 | 12.0 | 15.0 | 641.0 | 16.3 | 24.0 | 12.0 |
| 45 | 1.9 | 3.8 | 4.9 | 3.1 | 1.4 | 75.3 | 1.4 | 2.6 | 1.8 |
| 46 | 12.2 | 13.9 | 21.5 | 12.5 | 9.7 | 102.2 | 9.5 | 15.9 | 10.2 |
| 47 | 4.7 | 9.0 | 16.3 | 5.8 | 8.0 | 236.8 | 6.3 | 12.0 | 15.0 |
| 50 | 8.0 | 23.3 | 26.7 | 11.9 | 13.5 | 446.4 | 8.2 | 22.2 | 15.6 |
| 51 | 3.8 | 7.0 | 7.8 | 6.7 | 4.9 | 68.8 | 5.4 | 5.2 | 5.4 |
| 52 | 5.9 | 10.7 | 11.7 | 12.0 | 8.1 | 141.3 | 7.2 | 7.8 | 6.3 |
| 53 | 18.1 | 76.0 | 109.6 | 32.0 | 23.6 | 772.6 | 21.3 | 48.8 | 28.1 |
| 54 | 7.3 | 33.5 | 42.8 | 9.5 | 12.9 | 516.5 | 15.4 | 21.6 | 11.3 |
| 55 | 2.6 | 6.0 | 7.7 | 5.4 | 3.2 | 34.4 | 2.6 | 4.3 | 2.8 |
| 56 | 2.9 | 8.4 | 14.8 | 3.4 | 3.6 | 75.8 | 3.0 | 4.9 | 3.2 |
| 57 | 18.2 | 33.0 | 120.0 | 15.9 | 15.4 | 575.7 | 10.7 | 43.9 | 18.3 |
| 58 | 7.2 | 12.7 | 34.8 | 7.6 | 7.5 | 256.8 | 9.1 | 19.9 | 9.7 |
| 59 | 5.7 | 31.0 | 38.1 | 9.6 | 7.8 | 347.0 | 9.3 | 7.9 | 8.4 |
| 60 | 8.2 | 21.3 | 39.2 | 15.3 | 11.5 | 363.1 | 21.2 | 17.4 | 7.9 |
| 61 | 3.0 | 4.6 | 11.7 | 3.4 | 3.8 | 75.9 | 2.9 | 5.8 | 4.7 |
| 62 | 29.4 | 81.0 | 129.4 | 30.9 | 31.9 | 1187.8 | 37.2 | 50.6 | 42.6 |

TABLE 9-continued

IC50 of Inhibition of Wild Type and Mutation MET kinases of Exemplary Tested Compounds

| Ex. # | SigChem WT IC50 (nM) | Del14 IC50 (nM) | D1228H IC50 (nM) | D1228N IC50 (nM) | F1200I IC50 (nM) | L1195V IC50 (nM) | Y1230C IC50 (nM) | Y1230H IC50 (nM) | Y1230S IC50 (nM) |
|---|---|---|---|---|---|---|---|---|---|
| 63 | 6.9 | 15.3 | 36.6 | 5.3 | 8.9 | 321.3 | 9.0 | 13.0 | 6.8 |
| 64 | 15.5 | 28.2 | 46.6 | 23.6 | 20.3 |  | 18.3 | 37.2 | 21.1 |
| 65 | 3.5 | 4.6 | 16.3 | 10.1 | 5.0 | 194.6 | 3.6 | 10.1 | 4.8 |
| 67 | 2.6 | 1.8 | 3.4 | 4.0 | 1.4 | 9.9 | 1.1 | 3.2 | 2.6 |
| 68 | 2.7 | 4.9 | 6.6 | 4.2 | 4.6 | 33.4 | 2.3 | 4.6 | 3.2 |
| 69 | 5.1 | 5.7 | 7.1 | 7.5 | 7.0 | 55.9 | 3.9 | 5.9 | 5.3 |
| 70 | 7.0 | 12.1 | 13.6 | 12.7 | 9.4 | 67.9 | 6.4 | 7.6 | 4.5 |
| 71 | 38.5 | 183.1 | 302.8 | 38.5 | 62.3 | 2169.7 | 79.3 | 88.8 | 89.8 |
| 72 | 2.0 | 1.7 | 2.0 | 2.3 | 2.3 | 8.4 | 1.2 | 2.5 | 1.0 |
| 73 | 4.3 | 4.6 | 4.3 | 5.6 | 4.1 | 27.1 | 2.6 | 4.6 | 2.8 |
| 75 | 3.5 | 7.2 | 7.6 | 4.8 | 12.8 | 40.7 | 3.1 | 4.9 | 2.7 |
| 76 | 2.2 | 6.0 | 4.9 | 3.8 | 3.1 | 29.7 | 1.7 | 4.6 | 1.8 |
| 77 | 2.5 | 4.8 | 4.1 | 4.3 | 2.2 | 36.0 | 1.5 | 5.8 |  |
| 79 | 3.9 | 4.0 | 3.6 | 3.6 | 2.2 | 18.1 | 1.5 | 4.6 | 2.7 |
| 80 | 4.3 | 4.9 | 6.2 | 4.9 | 3.0 | 19.5 | 3.0 | 4.0 | 3.6 |
| 81 | 3.2 | 1.7 | 2.7 | 3.4 | 2.2 | 5.9 | 2.7 | 2.5 | 1.4 |
| 84 | 1.5 | 1.0 | 1.5 | 2.2 | 2.0 | 6.0 | 1.7 | 1.2 | 1.2 |
| 86 | 19.0 | 81.8 | 96.4 | 36.5 | 36.9 | 1558.5 | 23.2 | 86.6 | 41.5 |
| 87 | 37.2 | 105.9 | 73.2 | 67.9 | 42.7 | 838.9 | 44.8 | 118.1 | 84.6 |
| 88 | 7.3 | 63.5 | 39.1 | 21.3 |  | 562.5 | 12.4 | 50.3 | 22.5 |
| 89 | 3.3 | 9.0 | 12.6 | 8.2 | 5.4 | 115.5 | 4.6 | 9.1 | 6.4 |
| 90 | 19.3 | 101.3 | 110.0 | 35.0 | 43.2 | 2453.5 | 58.2 | 93.3 | 49.8 |
| 91 | 1.2 | 0.9 | 1.8 | 2.3 | 1.6 | 3.6 | 1.1 | 1.1 | 1.8 |
| 92 | 1.3 | 3.4 | 4.0 | 3.0 | 3.0 | 45.8 | 1.9 | 2.3 | 1.7 |
| 93 | 23.4 | 66.3 | 107.4 | 35.5 | 19.6 | 2636.3 | 32.9 | 63.3 | 35.7 |
| 94 | 10.2 | 7.2 | 8.9 | 17.5 | 8.4 | 46.0 | 9.3 | 12.1 | 6.3 |
| 95 | 98.8 | 163.4 | 294.2 | 85.8 | 94.6 | 2206.4 | 89.1 | 267.9 | 78.4 |
| 96 | 10.0 | 16.2 | 26.1 | 13.0 |  | 202.2 | 13.8 | 23.4 | 13.8 |
| 97 | 4.1 | 10.1 | 19.2 | 5.9 | 4.7 | 85.8 | 3.8 | 12.4 | 4.0 |
| 98 | 4.0 | 4.8 | 6.8 | 5.0 | 2.9 | 29.6 | 2.3 | 5.7 | 4.1 |
| 99 | 51.0 | 202.3 | 370.1 | 109.0 | 105.9 | 3226.1 | 106.7 | 234.3 | 120.0 |
| 100 | 1.1 | 1.2 | 1.7 | 1.7 | 1.4 | 9.9 | 0.7 | 2.1 | 1.2 |
| 101 | 18.9 | 40.7 | 36.8 | 31.9 | 26.4 | 290.4 | 15.6 | 66.1 | 35.6 |
| 102 | 1.3 | 7.1 | 4.0 | 1.4 | 2.4 | 79.8 | 1.6 | 4.6 | 1.2 |
| 103 | 0.8 | 0.9 | 1.5 | 1.8 | 0.6 | 11.6 | 0.6 | 1.5 | 0.8 |
| 104 | 1.3 | 3.6 | 6.0 | 3.0 | 2.0 | 36.2 | 1.6 | 4.0 | 1.6 |
| 105 | 1.7 | 2.8 | 3.9 | 4.9 | 2.5 | 28.3 | 3.1 | 4.1 | 2.3 |
| 106 | 3.5 | 3.0 | 4.0 | 5.8 | 3.9 | 20.5 | 3.3 | 6.4 | 3.8 |
| 107 | 1.5 | 3.7 | 4.1 | 4.9 | 3.7 | 25.6 | 2.8 | 4.5 | 2.9 |
| 108 | 1.3 | 2.3 | 3.5 | 2.8 | 2.3 | 33.0 | 1.2 | 4.1 | 1.8 |
| 109 | 4.0 | 7.2 | 18.0 | 6.6 | 4.2 | 114.3 | 4.4 | 9.5 | 4.2 |
| 110 | 2.8 | 6.5 | 6.7 | 3.6 | 6.0 | 50.4 | 2.7 | 5.7 | 2.2 |
| 113 | 5.0 | 20.5 | 23.0 | 10.9 | 10.4 | 130.6 | 8.6 | 17.4 | 8.2 |
| 114 | 3.6 | 2.7 | 3.4 | 6.7 | 3.3 | 7.2 | 3.2 | 4.5 | 1.7 |
| 115 | 3.9 | 5.0 | 4.7 | 6.7 | 3.9 | 10.0 | 4.3 | 6.8 | 2.7 |
| 116 | 2.8 | 6.4 | 7.7 | 5.4 | 2.7 | 29.2 | 4.1 | 6.4 | 2.4 |
| 117 | 2.4 | 3.8 | 6.2 | 3.1 | 1.5 | 46.7 | 1.3 | 6.6 | 1.3 |
| 118 | 4.3 | 18.5 | 17.8 | 8.4 | 12.1 | 31.0 | 6.3 | 12.4 | 5.5 |
| 119 | 1.9 | 1.5 | 1.6 | 3.2 | 2.1 | 4.3 | 1.9 | 2.4 | 1.2 |
| 120 | 1.7 | 6.5 | 5.0 | 4.8 | 5.0 | 41.8 | 3.4 | 5.7 | 2.2 |
| 121 | 1.0 | 2.2 | 1.8 | 2.4 | 2.2 | 6.0 | 1.5 | 2.1 | 0.8 |
| 122 | 3.1 | 8.3 | 6.4 | 5.4 | 10.4 | 57.3 | 5.5 | 10.2 | 3.6 |
| 128 | 2.6 | 12.0 | 12.5 | 4.6 | 8.2 | 79.8 | 4.5 | 10.3 | 4.1 |
| 142 | 5.4 | 4.7 | 7.5 | 6.8 | 8.9 | 97.3 | 6.0 | 8.3 | 4.9 |
| 144 | 111.0 | 408.4 | 289.5 | 68.9 | 163.6 | 1819.2 | 117.2 | 483.0 | 289.8 |
| 145 | 4.2 | 9.6 | 14.7 | 8.4 | 6.8 | 184.3 | 4.9 | 12.1 | 9.1 |
| 146 | 2.4 | 5.6 | 7.9 | 5.1 | 5.3 | 31.5 | 2.7 | 6.3 | 3.6 |
| 147 | 73.3 | 277.4 | 256.5 | 154.4 | 133.8 | 2247.3 | 234.9 | 279.0 | 314.3 |
| 148 | 1.2 | 2.6 | 3.5 | 2.1 | 1.7 | 22.0 | 1.7 | 2.3 | 1.4 |
| 150 | 2.8 | 2.6 | 3.3 | 5.7 | 4.5 | 10.8 | 2.6 | 2.7 | 2.5 |
| 151 | 2.5 | 3.4 | 6.4 | 5.4 | 3.3 | 26.5 | 4.1 | 5.0 | 3.2 |
| 152 | 3.2 | 2.4 | 2.9 | 5.1 | 2.7 | 9.0 | 2.9 | 3.6 | 3.0 |
| 153 | 4.5 | 6.6 | 11.0 | 8.9 | 5.3 | 132.2 | 6.6 | 9.4 | 6.6 |
| 154 | 4.2 | 3.0 | 4.3 | 3.9 | 3.2 | 21.5 | 3.8 | 5.6 | 3.2 |
| 155 | 6.8 | 10.7 | 20.9 | 9.5 | 6.7 | 104.0 | 7.0 | 10.3 | 5.9 |
| 156 | 4.3 | 15.0 | 27.5 | 9.1 | 6.7 | 177.2 | 6.1 | 16.7 | 5.9 |
| 157 | 8.9 | 26.6 | 60.0 | 13.7 | 6.8 | 329.6 | 6.1 | 26.7 | 7.1 |
| 158 | 18.0 | 78.6 | 136.6 | 25.0 | 27.1 | 671.5 | 32.1 | 82.0 | 39.8 |
| 159 | 19.2 | 72.7 | 94.6 | 25.3 | 23.4 | 2007.9 | 20.1 | 54.6 | 20.8 |
| 160 | 1.5 | 3.3 | 8.3 | 3.2 | 1.8 | 38.7 | 2.3 | 4.4 | 1.6 |
| 161 | 3.2 | 3.4 | 4.1 | 5.2 | 2.9 | 22.4 | 3.1 | 4.7 | 3.2 |
| 162 | 3.1 | 4.6 | 6.3 | 5.4 | 2.1 | 43.3 | 3.4 | 4.3 | 3.5 |
| 163 | 2.5 | 5.9 | 8.0 | 3.0 | 4.0 | 50.5 | 4.5 | 6.2 | 3.5 |

TABLE 9-continued

IC50 of Inhibition of Wild Type and Mutation MET kinases of Exemplary Tested Compounds

| Ex. # | SigChem WT IC50 (nM) | Del14 IC50 (nM) | D1228H IC50 (nM) | D1228N IC50 (nM) | F1200I IC50 (nM) | L1195V IC50 (nM) | Y1230C IC50 (nM) | Y1230H IC50 (nM) | Y1230S IC50 (nM) |
|---|---|---|---|---|---|---|---|---|---|
| 164 | 4.2 | 6.2 | 7.3 | 6.7 | 4.5 | 35.2 | 6.1 | 6.6 | 4.3 |
| 166 | 29.8 | 50.7 | 78.8 | 38.8 | 28.5 | 329.2 | 33.6 | 44.4 | 18.1 |
| 167 | 33.6 | 156.4 | 134.7 | 55.7 | 74.1 | 598.9 | 86.3 | 128.4 | 71.0 |
| 168 | 9.4 | 52.0 | 39.8 | 12.5 | 20.6 | 285.2 | 10.3 | 32.8 | 10.4 |
| 169 | 2.8 | 3.8 | 3.9 | 4.0 | 1.6 | 27.4 | 2.1 | 4.5 | 1.9 |
| 170 | 8.7 | 37.9 | 14.9 | 10.9 | 4.8 | 143.0 | 5.1 | 16.6 | 5.5 |
| 171 | 9.0 | 40.9 | 16.5 | 9.7 | 17.3 | 114.9 | 10.4 | 18.9 | 8.9 |
| 172 | 3.6 | 16.5 | 16.1 | 5.7 | 4.7 | 42.9 | 3.8 | 7.1 | 2.8 |
| 173 | 27.3 | 106.2 | 153.9 | 44.6 | 51.2 | 913.9 | 70.8 | 63.8 | 41.6 |
| 179 | 2.4 | 3.1 | 4.5 | 5.3 | 4.1 | 17.8 | 3.0 | 4.2 | 3.4 |
| 181 | 6.7 | 12.2 | 14.9 | 8.1 | 8.7 | 110.3 | 6.5 | 12.0 | 10.0 |
| 182 | 65.1 | 393.2 | 624.9 | 60.1 | 97.9 | 4109.7 | 96.8 | 308.2 | 150.6 |
| 183 | 13.1 | 26.4 | 34.1 | 14.3 | 14.8 | 338.8 | 10.5 | 24.2 | 16.6 |
| 184 | 14.1 | 37.0 | 52.8 | 20.0 | 16.2 | 394.0 | 16.1 | 37.4 | 10.9 |
| 185 | 2.0 | 4.7 | 5.0 | 3.2 | 2.3 |  | 2.5 | 4.4 | 2.2 |
| 186 | 24.0 | 41.0 | 139.8 | 33.2 | 27.8 | 1182.7 | 46.8 | 74.1 | 35.1 |
| 187 | 8.5 | 14.8 | 46.9 | 18.4 | 8.9 | 259.5 | 8.6 | 22.3 | 13.6 |
| 189 | 14.0 | 33.4 | 61.3 | 11.9 | 15.5 |  | 22.6 | 27.9 | 16.4 |
| 191 | 10.3 | 29.1 | 63.9 | 12.5 | 14.2 | 505.9 | 14.4 | 32.1 | 17.3 |
| 192 | 5.0 | 19.2 | 39.5 | 10.2 | 5.0 | 263.3 | 9.2 | 17.4 | 9.2 |
| 193 | 1.5 | 2.6 | 4.9 | 3.7 | 2.4 | 45.0 | 1.9 | 3.9 | 1.7 |
| 194 | 3.8 | 23.8 | 44.5 | 6.0 | 6.0 | 191.4 | 9.4 | 21.2 | 9.3 |
| 195 | 1.5 | 2.7 | 3.5 | 3.2 | 2.5 | 31.0 | 1.7 | 4.1 | 1.8 |
| 196 | 2.6 | 10.9 | 7.0 | 4.2 | 5.7 | 44.4 | 4.8 | 7.9 | 4.8 |
| 197 | 2.7 | 10.1 | 7.8 | 6.1 | 5.6 | 54.2 | 3.1 | 10.6 | 4.5 |

Synthetic Examples

Synthesis of Synthetic Intermediates

Preparation 1

3-Fluoro-4-((3-iodo-1-(4-methoxybenzyl)-1H-pyrazolo[3,4-b]pyridin-4-yl)oxy)aniline

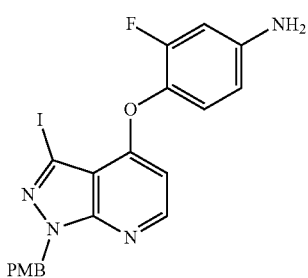

Step A: A mixture of 1-(4-methoxybenzyl)-1H-pyrazolo[3,4-b]pyridin-4-ol (23.5 g, 92.1 mmol), 1,2-difluoro-4-nitrobenzene (14.6 g, 92.1 mmol) and cesium carbonate (30.0 g, 92.1 mmol) in DMF (300 mL) was heated to 100° C. for 1 hour. After cooling to room temperature, the reaction mixture was poured into water (750 mL) and diluted with EtOAc (750 mL). The organic layer was separated. The aqueous phase was re-extracted with EtOAc (1×300 mL, 1×100 mL). The combined organic phases were washed with water (2×300 mL) and brine (300 mL), dried over sodium sulfate, filtered and concentrated to afford 4-(2-fluoro-4-nitrophenoxy)-1-(4-methoxybenzyl)-1H-pyrazolo[3,4-b]pyridine (36.4 g, 100%).

Step B: A stirred mixture of 4-(2-fluoro-4-nitrophenoxy)-1-(4-methoxybenzyl)-1H-pyrazolo[3,4-b]pyridine (36 g, 91.3 mmol) in TFA (250 mL) was heated to 60° C. for 18 h under N₂ with attached reflux condenser. After cooling to room temperature, the reaction mixture was concentrated in vacuo. Toluene (3×75 mL) was utilized to azeotrope residual TFA. The dark mixture was carefully treated with aqueous NaHCO₃ (150 mL total) with stirring. The biphasic mixture was diluted with DCM (50 mL). A tan suspension resulted, which was stirred for 10 min. The suspension was then filtered. The solid (product) was washed with water (50 mL), then DCM (25 mL). The residual water in the solid was removed by toluene azeotrope by rotary evaporation (3×100 mL) at 60° C. to afford 4-(2-fluoro-4-nitrophenoxy)-1H-pyrazolo[3,4-b]pyridine (23 g, 88%).

Step C: To a stirred mixture of 4-(2-fluoro-4-nitrophenoxy)-1H-pyrazolo[3,4-b]pyridine (22 g, 80 mmol) and KOH (14 g, 241 mmol) (crushed by mortar and pestle) in DMF (250 mL) was added I₂ (41 g, 160 mmol). The resulting mixture was heated to 60° C. for 1 h under N₂. The reaction mixture was poured into a saturated aqueous solution of sodium thiosulfate (100 mL). The mixture was extracted with EtOAc (1×250 mL, 2×50 mL). The combined organic phases were washed with 10% LiCl (2×250 mL), dried over sodium sulfate, filtered, and concentrated to obtain crude 4-(2-fluoro-4-nitrophenoxy)-3-iodo-1H-pyrazolo[3,4-b]pyridine (29 g, 70%).

Step D: To a stirred mixture of 4-(2-fluoro-4-nitrophenoxy)-3-iodo-1H-pyrazolo[3,4-b]pyridine (29 g, 72.5 mmol) and 1-(chloromethyl)-4-methoxybenzene (13.6 g, 87.0 mmol) in DMF (250 mL) was added K₂CO₃ (12.0 g, 87.0 mmol). The reaction mixture was stirred for 18 h and then poured into EtOAc (500 mL) and diluted with water (500 mL). The phases were separated, and the aqueous phase was extracted with EtOAc (2×250 mL). The combined organic phases were washed with water (250 mL) and brine (250 mL), dried over sodium sulfate, filtered, and concentrated. The dark brown oil was purified over silica gel (30%

EtOAc in hexanes) to afford 4-(2-fluoro-4-nitrophenoxy)-3-iodo-1-(4-methoxybenzyl)-1H-pyrazolo[3,4-b]pyridine (24.2 g, 61%).

Step E: To a stirred mixture of 4-(2-fluoro-4-nitrophenoxy)-3-iodo-1-(4-methoxybenzyl)-1H-pyrazolo[3,4-b]pyridine (30 g, 57.7 mmol) in EtOH (500 mL) was added $SnCl_2 \cdot 2H_2O$ (59.9 g, 288 mmol). The mixture was heated to 65° C. for 1h under $N_2$. After cooling to room temperature, the mixture was concentrated. The thick mixture was diluted with DCM (500 mL), stirred until solids dissolved, and then basified with 5N aqueous NaOH (100 mL). The resulting suspension was filtered through Celite®, rinsing with DCM (3×50 mL). The filtrate was transferred to a separatory funnel, and the phases were separated. The aqueous phase was re-extracted with DCM (50 mL). The combined organic phases were dried over $Na_2SO_4$, filtered, and concentrated to afford 3-fluoro-4-(3-iodo-1-(4-methoxybenzyl)-1H-pyrazolo[3,4-b]pyridin-4-yloxy)aniline (26.9 g, 90%) as a yellow solid.

Preparation 2

2-(4-fluorophenyl)-3-oxo-2,3-dihydropyridazine-4-carboxylic acid

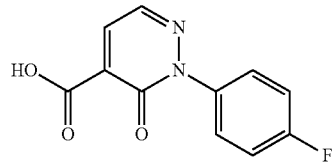 [SMILES: O=C(O)c1ccnn(-c2ccc(F)cc2)c1=O]

Step A: To a 2 L round bottom flask was added a 40% aqueous solution of oxalaldehyde (218 g, 1504 mmol) and while stirring at room temperature, added a mixture of 1-(4-fluorophenyl)hydrazine hydrochloride (48.9 g, 301 mmol), acetic acid (86.1 ml, 1504 mmol), and water (200 mL). The dark reddish brown mixture was stirred at room temperature for 1 h. The solid was removed by filtration and washed with water. The solid was placed in a vacuum oven overnight to afford (E)-2-(2-(4-fluorophenyl)hydrazono)acetaldehyde (48 g, 97.5%) as a brick-red solid.

Step B: Added (E)-2-(2-(4-fluorophenyl)hydrazono)acetaldehyde (48 g, 289 mmol) and 2,2-dimethyl-1,3-dioxane-4,6-dione (43.7 g, 303 mmol) to a 1 L round bottom flask and suspended in toluene (400 mL). Acetic acid (1.65 mL, 28.9 mmol) and piperidine (2.85 mL, 28.9 mmol) were added and mixture was stirred at room temperature overnight. The resulting precipitate was filtered, washed with hexanes and dried in a vacuum oven to afford (E)-5-(2-(2-(4-fluorophenyl)hydrazono)ethylidene)-2,2-dimethyl-1,3-dioxane-4,6-dione (84.8 g, 99%) as a bright red solid.

Step C: To a 3 L 4-neck round bottom equipped with temperature probe, mechanical stirrer and 2 reflux condensers added (E)-5-(2-(2-(4-fluorophenyl)hydrazono)ethylidene)-2,2-dimethyl-1,3-dioxane-4,6-dione (84.8 g, 290.2 mmol) and dissolved in MeOH (1 L). Sodium methoxide (79.62 mL, 348.2 mmol) in MeOH (25% by weight solution) was added and the dark brown solution was stirred and heated to reflux for 1 h. The volume of MeOH was reduced by evaporation and added 500 mL 1N HCl. The precipitate was removed by filtration, washed with water and ether, and dried on full vacuum (oven 60-70° C.) overnight to afford 2-(4-fluorophenyl)-3-oxo-2,3-dihydropyridazine-4-carboxylic acid (56.4 g, 82%) as a yellow solid.

The following compounds were also made using the procedure according to Preparation 2.

| Preparation | Structure | Name |
|---|---|---|
| 3 | 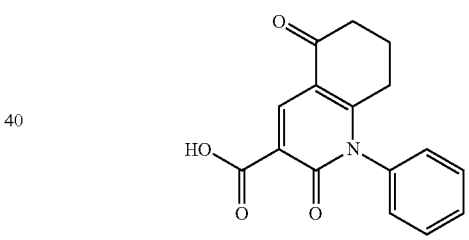 | 2-(4-fluorophenyl)-6-methyl-3-oxo-2,3-dihydropyridazine-4-carboxylic acid |

Preparation 4

2,5-dioxo-1-phenyl-1,2,5,6,7,8-hexahydroquinoline-3-carboxylic acid

Step A: To a stirred solution of cyclohexane-1,3-dione (5.0 g, 45 mmol) in DMF (100 mL) at room temperature under nitrogen was added KOtBu (5.0 g, 45 mmol) followed by ethyl (E)-2-cyano-3-ethoxyacrylate (7.5 g, 45 mmol). The reaction mixture was stirred at room temperature overnight. The mixture was diluted with EtOAc (400 mL) and stirred while 2N aq. HCl (250 mL) was added. The aqueous layer was extracted with EtOAc (2×200 mL) and the combined organic layers were washed with water (4×200 mL) and brine (200 mL), dried over sodium sulfate, filtered and concentrated. The residue was purified over silica gel (0-60% EtOAc/hexanes) to afford ethyl 2,5-dioxo-5,6,7,8-tetrahydro-2H-chromene-3-carboxylate (6.2 g, 59%) as a dark pink oil.

Step B: To a stirred solution of ethyl 2,5-dioxo-5,6,7,8-tetrahydro-2H-chromene-3-carboxylate (543 mg, 2.3 mmol) in EtOH (10 mL) was added aniline (210 μL, 2.3 mmol). The mixture was stirred at room temperature overnight. The resultant solids were filtered, washed with EtOH and dried in vacuo to afford 2,5-dioxo-1-phenyl-1,2,5,6,7,8-hexahydroquinoline-3-carboxylic acid (160 mg, 25%) as a white solid.

The following compounds were also made using the procedure according to Preparation 4.

| Preparation | Structure | Name |
|---|---|---|
| 5 | 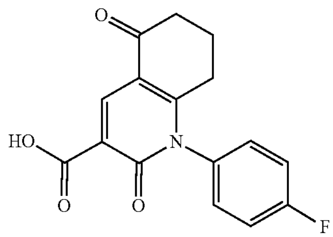 [SMILES: O=C1CCCc2c1cc(C(=O)O)c(=O)n2-c1ccc(F)cc1] | 1-(4-fluorophenyl)-2,5-dioxo-1,2,5,6,7,8-hexahydroquinoline-3-carboxylic acid |
| 6 | 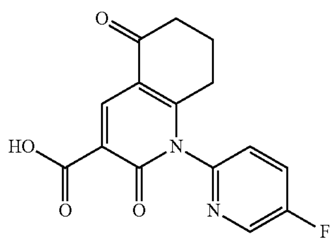 [SMILES: O=C1CCCc2c1cc(C(=O)O)c(=O)n2-c1ccc(F)cn1] | 1-(5-fluoropyridin-2-yl)-2,5-dioxo-1,2,5,6,7,8-hexahydroquinoline-3-carboxylic acid |

Preparation 7

3-(4-fluorophenyl)-1-isopropyl-2,4-dioxo-1,2,3,4-tetrahydropyrimidine-5-carboxylic acid

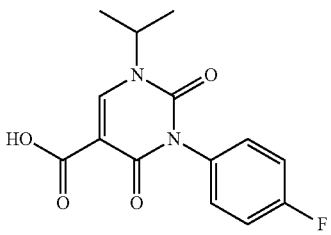 [SMILES: CC(C)n1cc(C(=O)O)c(=O)n(-c2ccc(F)cc2)c1=O]

Step A: To a solution of diethyl 2-(aminomethylene)malonate (2.5 g, 13.4 mmol) in dichloroethane (10 mL) was added 1-fluoro-4-isocyanatobenzene (1.59 mL, 14.0 mmol) followed by DIEA (2.57 mL, 14.7 mmol). The reaction mixture was stirred at 100° C. for 6 h and then cooled to room temperature overnight. The resultant solids were filtered, washed with Et₂O and dried in vacuo to afford diethyl 2-((3-(4-fluorophenyl)ureido)methylene)malonate (3.38 g, 78%) as a white solid.

Step B: To a suspension of diethyl 2-((3-(4-fluorophenyl)ureido)methylene)malonate (3.38 g, 10.4 mmol) in ethanol (15 mL) was added sodium ethoxide (6.23 mL, 21%, 16.7 mmol) dropwise via syringe. The mixture was stirred for 2 h, then concentrated and partitioned between EtOAc (150 mL) and 1M Citric acid (100 mL). The aqueous layer was extracted with EtOAc (2×100 mL) and the combined organic phases were washed with brine (50 mL), dried over Na₂SO₄, filtered and concentrated to afford ethyl 3-(4-fluorophenyl)-2,4-dioxo-1,2,3,4-tetrahydropyrimidine-5-carboxylate (2.83 g, 98%) as a pale yellow solid.

Step C: To a suspension of ethyl 3-(4-fluorophenyl)-2,4-dioxo-1,2,3,4-tetrahydropyrimidine-5-carboxylate (1.0 g, 3.6 mmol) and K₂CO₃ (993 mg, 7.2 mmol) in DMF (5 mL) was added 2-iodopropane (719 µL, 7.2 mmol). The mixture was heated in a sealed tube at 70° C. overnight. The cooled mixture was partitioned between water (50 mL) and EtOAc (50 mL) and the aqueous layer was extracted with EtOAc (2×30 mL). The combined organic phases were washed with water (5×20 mL) and brine (20 mL) then dried over Na₂SO₄, filtered and concentrated to afford ethyl 3-(4-fluorophenyl)-1-isopropyl-2,4-dioxo-1,2,3,4-tetrahydropyrimidine-5-carboxylate (1.14 g, 99%) a pale yellow foam.

Step D: To a solution of ethyl 3-(4-fluorophenyl)-1-isopropyl-2,4-dioxo-1,2,3,4-tetrahydropyrimidine-5-carboxylate (1.14 g, 3.56 mmol) in 4N HCl/dioxanes (10 mL) was added water (2 mL). The mixture was stirred at 70° C. overnight. The cooled mixture was treated with water (20 mL) and the resulting solids filtered, washed with water and dried in vacuo to afford 3-(4-fluorophenyl)-1-isopropyl-2,4-dioxo-1,2,3,4-tetrahydropyrimidine-5-carboxylic acid as a fluffy white solid.

The following compounds were also made using the procedure according to Preparation 7.

| Preparation | Structure | Name |
|---|---|---|
| 8 | 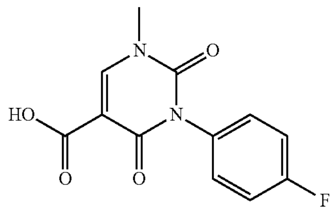 [SMILES: Cn1cc(C(=O)O)c(=O)n(-c2ccc(F)cc2)c1=O] | 3-(4-fluorophenyl)-1-methyl-2,4-dioxo-1,2,3,4-tetrahydropyrimidine-5-carboxylic acid |
| 9 | 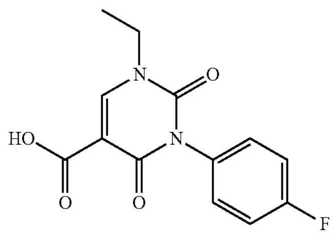 [SMILES: CCn1cc(C(=O)O)c(=O)n(-c2ccc(F)cc2)c1=O] | 1-ethyl-3-(4-fluorophenyl)-2,4-dioxo-1,2,3,4-tetrahydropyrimidine-5-carboxylic acid |
| 10 | 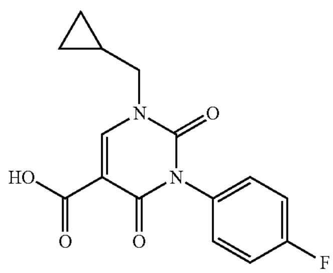 [SMILES: O=C(O)c1cn(CC2CC2)c(=O)n(-c2ccc(F)cc2)c1=O] | 1-(cyclopropylmethyl)-3-(4-fluorophenyl)-2,4-dioxo-1,2,3,4-tetrahydropyrimidine-5-carboxylic acid |
| 11 | 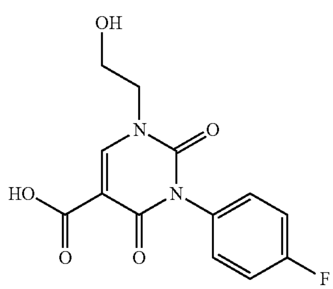 [SMILES: O=C(O)c1cn(CCO)c(=O)n(-c2ccc(F)cc2)c1=O] | 3-(4-fluorophenyl)-1-(2-hydroxyethyl)-2,4-dioxo-1,2,3,4-tetrahydropyrimidine-5-carboxylic acid |
| 12 | 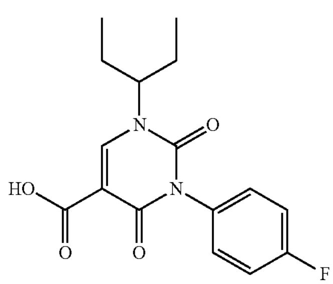 [SMILES: CCC(CC)n1cc(C(=O)O)c(=O)n(-c2ccc(F)cc2)c1=O] | 3-(4-fluorophenyl)-2,4-dioxo-1-(pentan-3-yl)-1,2,3,4-tetrahydropyrimidine-5-carboxylic acid |
| 13 | 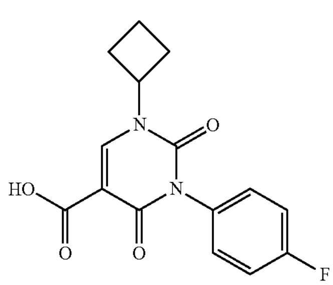 [SMILES: O=C(O)c1cn(C2CCC2)c(=O)n(-c2ccc(F)cc2)c1=O] | 1-cyclobutyl-3-(4-fluorophenyl)-2,4-dioxo-1,2,3,4-tetrahydropyrimidine-5-carboxylic acid |

-continued

| Preparation | Structure | Name |
| --- | --- | --- |
| 14 | 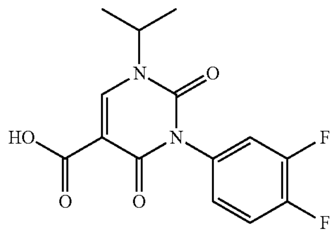 [SMILES: CC(C)n1cc(C(=O)O)c(=O)n(-c2ccc(F)c(F)c2)c1=O] | 3-(3,4-difluorophenyl)-1-isopropyl-2,4-dioxo-1,2,3,4-tetrahydropyrimidine-5-carboxylic acid |
| 15 | 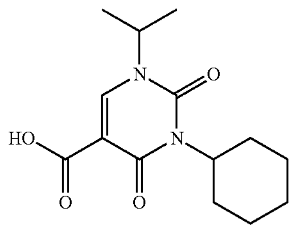 [SMILES: CC(C)n1cc(C(=O)O)c(=O)n(C2CCCCC2)c1=O] | 3-cyclohexyl-1-isopropyl-2,4-dioxo-1,2,3,4-tetrahydropyrimidine-5-carboxylic acid |
| 16 | 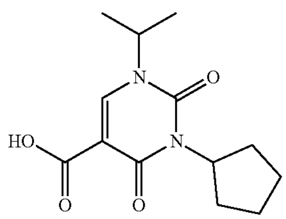 [SMILES: CC(C)n1cc(C(=O)O)c(=O)n(C2CCCC2)c1=O] | 3-cyclopentyl-1-isopropyl-2,4-dioxo-1,2,3,4-tetrahydropyrimidine-5-carboxylic acid |
| 17 | 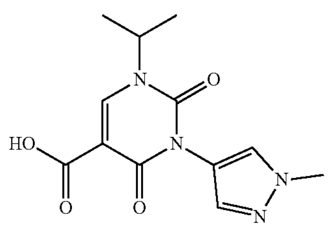 [SMILES: CC(C)n1cc(C(=O)O)c(=O)n(-c2cnn(C)c2)c1=O] | 1-isopropyl-3-(1-methyl-1H-pyrazol-4-yl)-2,4-dioxo-1,2,3,4-tetrahydropyrimidine-5-carboxylic acid |
| 18 | 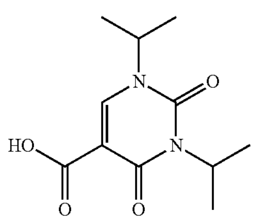 [SMILES: CC(C)n1cc(C(=O)O)c(=O)n(C(C)C)c1=O] | 1,3-diisopropyl-2,4-dioxo-1,2,3,4-tetrahydropyrimidine-5-carboxylic acid |
| 19 | 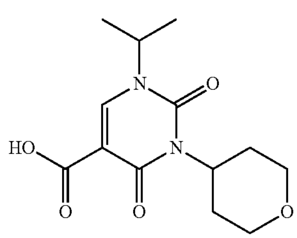 [SMILES: CC(C)n1cc(C(=O)O)c(=O)n(C2CCOCC2)c1=O] | 1-isopropyl-2,4-dioxo-3-(tetrahydro-2H-pyran-4-yl)-1,2,3,4-tetrahydropyrimidine-5-carboxylic acid |

-continued

| Preparation | Structure | Name |
|---|---|---|
| 20 | 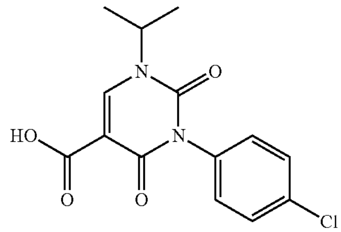 [SMILES: CC(C)n1cc(C(=O)O)c(=O)n(-c2ccc(Cl)cc2)c1=O] | 3-(4-chlorophenyl)-1-isopropyl-2,4-dioxo-1,2,3,4-tetrahydropyrimidine-5-carboxylic acid |
| 21 | 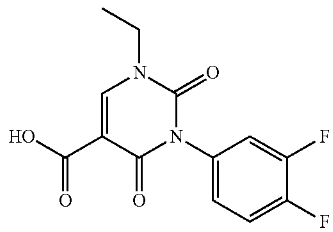 [SMILES: CCn1cc(C(=O)O)c(=O)n(-c2ccc(F)c(F)c2)c1=O] | 3-(3,4-difluorophenyl)-1-ethyl-2,4-dioxo-1,2,3,4-tetrahydropyrimidine-5-carboxylic acid |

Preparation 22

3-(4-fluorophenyl)-1-(1-methylazetidin-3-yl)-2,4-dioxo-1,2,3,4-tetrahydropyrimidine-5-carboxylic acid hydrochloride

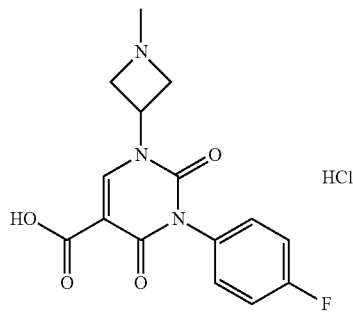 [SMILES: CN1CC(n2cc(C(=O)O)c(=O)n(-c3ccc(F)cc3)c2=O)C1 ; Cl]

Step A: To a suspension of ethyl 3-(4-fluorophenyl)-2,4-dioxo-1,2,3,4-tetrahydropyrimidine-5-carboxylate (1.0 g, 3.6 mmol) and $K_2CO_3$ (993 mg, 7.2 mmol) in DMF (5 mL) was added tert-butyl 3-iodoazetidine-1-carboxylate (2.04 g, 7.2 mmol). The mixture was heated in a sealed tube at 70° C. overnight. The cooled mixture was partitioned between water (50 mL) and EtOAc (50 mL) and the aqueous layer was extracted with EtOAc (2×30 mL). The combined organic phases were washed with water (5×20 mL) and brine (20 mL) then dried over $Na_2SO_4$, filtered and concentrated. The residue was purified over silica gel (0-4% MeOH in DCM) to afford ethyl 1-(1-(tert-butoxycarbonyl)azetidin-3-yl)-3-(4-fluorophenyl)-2,4-dioxo-1,2,3,4-tetrahydropyrimidine-5-carboxylate (0.579 g, 37%).

Step B: To a solution of ethyl 1-(1-(tert-butoxycarbonyl)azetidin-3-yl)-3-(4-fluorophenyl)-2,4-dioxo-1,2,3,4-tetrahydropyrimidine-5-carboxylate (400 mg, 0.92 mmol) in DCM (8 mL) was added TFA (2 mL). The mixture was stirred for 2 h and concentrated to afford crude ethyl 1-(azetidin-3-yl)-3-(4-fluorophenyl)-2,4-dioxo-1,2,3,4-tetrahydropyrimidine-5-carboxylate 2,2,2-trifluoroacetate (413 mg, 100%).

Step C: To a suspension of ethyl 1-(azetidin-3-yl)-3-(4-fluorophenyl)-2,4-dioxo-1,2,3,4-tetrahydropyrimidine-5-carboxylate 2,2,2-trifluoroacetate (200 mg, 0.45 mmol) in dichloroethane (5 mL) was added formaldehyde (37% in water, 181 mg, 2.24 mmol) followed by $NaBH(OAc)_3$ (237 mg, 1.12 mmol). The mixture was stirred vigorously for 4 h. The mixture was treated with 2N $Na_2CO_3$ (10 mL), stirred for 30 min, then extracted with DCM (3×10 mL). The combined organic phases were washed with brine (10 mL), dried over $Na_2SO_4$, filtered and concentrated to afford crude ethyl 3-(4-fluorophenyl)-1-(1-methylazetidin-3-yl)-2,4-dioxo-1,2,3,4-tetrahydropyrimidine-5-carboxylate (127 mg, 82%) as a white solid.

Step D: To a solution of ethyl 3-(4-fluorophenyl)-1-(1-methylazetidin-3-yl)-2,4-dioxo-1,2,3,4-tetrahydropyrimidine-5-carboxylate (174 mg, 0.50 mmol) in 4N HCl/dioxanes (5 mL) was added water (1 mL). The mixture was stirred at 70° C. overnight. The cooled mixture was treated with water (10 mL) and extracted with EtOAc (10 mL). The aqueous layer was concentrated to afford crude 3-(4-fluorophenyl)-1-(1-methylazetidin-3-yl)-2,4-dioxo-1,2,3,4-tetrahydropyrimidine-5-carboxylic acid hydrochloride salt (116 mg, 65%).

Preparation 23

1-cyclopropyl-3-(4-fluorophenyl)-2,4-dioxo-1,2,3,4-tetrahydropyrimidine-5-carboxylic acid

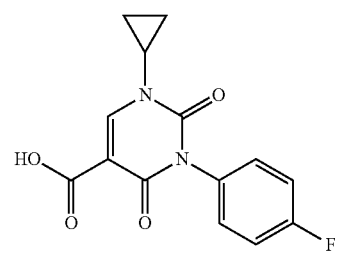 [SMILES: O=C(O)c1cn(C2CC2)c(=O)n(-c2ccc(F)cc2)c1=O]

Step A: To a suspension of ethyl 3-(4-fluorophenyl)-2,4-dioxo-1,2,3,4-tetrahydropyrimidine-5-carboxylate (900 mg, 3.23 mmol), cyclopropylboronic acid (834 mg, 9.70 mmol) and Na$_2$CO$_3$ (1028 mg, 9.70 mmol) in dichloroethane (6 mL) was added a suspension of diacetoxycopper (176 mg, 0.970 mmol) and 2,2'-bipyridine (505 mg, 3.23 mmol) in hot dichloroethane (6 mL). The mixture was heated to 70° C. for 2 h. Additional Na$_2$CO$_3$ (1028 mg, 9.70 mmol), cyclopropylboronic acid (834 mg, 9.70 mmol), diacetoxycopper (176 mg, 0.970 mmol) and 2,2'-bipyridine (505 mg, 3.23 mmol) were added and the reaction mixture was stirred at 70° C. overnight. The reaction mixture was cooled to room temperature and diluted with saturated NH$_4$Cl solution (20 mL). The aqueous layer was extracted with DCM (2×20 mL), dried over sodium sulfate, filtered and concentrated. The residue was purified over silica gel (0-100% EtOAc in hexanes) to afford ethyl 1-cyclopropyl-3-(4-fluorophenyl)-2,4-dioxo-1,2,3,4-tetrahydropyrimidine-5-carboxylate (180 mg, 14%).

Step B; To ethyl 1-cyclopropyl-3-(4-fluorophenyl)-2,4-dioxo-1,2,3,4-tetrahydropyrimidine-5-carboxylate (180 mg, 0.565 mmol) was added hydrogen chloride (1414 μl, 5.65 mmol, 4M in dioxane) and water (0.3 mL). The mixture was heated to 70° C. for 3 h. The reaction mixture was cooled to room temperature and diluted with EtOAc (20 mL) and water (10 mL). The aqueous layer was extracted with EtOAc (2×10 mL). The combined organic was dried over MgSO$_4$, filtered and concentrated afford 1-cyclopropyl-3-(4-fluorophenyl)-2,4-dioxo-1,2,3,4-tetrahydropyrimidine-5-carboxylic acid (180 mg, 110%).

Preparation 24

4-ethoxy-1-(4-fluorophenyl)-2-oxo-1,2-dihydropyridine-3-carboxylic acid

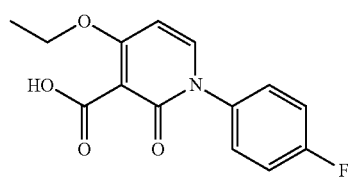 [SMILES: CCOc1ccn(-c2ccc(F)cc2)c(=O)c1C(=O)O]

Step A: Ethyl 4-ethoxy-2-oxo-1,2-dihydropyridine-3-carboxylate (1.0 g, 4.73 mmol), quinolin-8-ol (275 mg, 1.89 mmol) and cesium carbonate (3.09 g, 9.47 mmol) were combined in DMF (10 mL) and purged with Ar for 5 min. Cu(I)iodide (271 mg, 1.42 mmol) and 1-fluoro-4-iodobenzene (819 μL, 7.1 mmol) were added and the mixture stirred in a sealed vessel at 100° C. overnight. The mixture was partitioned between water (100 mL) and EtOAc (100 mL) and the aqueous layer was extracted with EtOAc (2×50 mL). The combined organic phases were washed with water (30 mL), 2N HC-1 (30 mL), water (2×30 mL) and brine (30 mL), dried over Na$_2$SO$_4$, filtered and concentrated to afford ethyl 4-ethoxy-1-(4-fluorophenyl)-2-oxo-1,2-dihydropyridine-3-carboxylate (1.38 g, 95%) as a yellow solid.

Step B: To a solution of ethyl 4-ethoxy-1-(4-fluorophenyl)-2-oxo-1,2-dihydropyridine-3-carboxylate (1.38 g, 4.52 mmol) in EtOH (40 mL) was added 2N HCl (9 mL, 18.1 mmol). The mixture was stirred at 65° C. overnight. After cooling, the solids were filtered, washed with Et$_2$O and dried in vacuo to afford 4-ethoxy-1-(4-fluorophenyl)-2-oxo-1,2-dihydropyridine-3-carboxylic acid (0.418 g, 33%) as a white solid.

The following compound was also made using the procedure according to Preparation 24.

| Preparation | Structure | Name |
|---|---|---|
| 25 | ![structure] | 1-(4-fluorophenyl)-2-oxo-piperidine-3-carboxylic acid |

Preparation 26

2-(4-fluorophenyl)-1-methyl-3-oxo-2,3-dihydro-1H-pyrazole-4-carboxylic acid

Step A: (4-Fluorophenyl)hydrazine hydrochloride (3.13 g, 19.2 mmol) was suspended in EtOH (40 mL) and K$_2$CO$_3$ (5.32 g, 38.5 mmol) was added, followed by the addition of diethyl 2-(ethoxymethylene)malonate (3.85 ml, 19.2 mmol) and the reaction mixture was heated to 80° C. overnight. The cooled reaction was concentrated, diluted with water (100 mL) and acidified with 3N aq. HCl (50 mL) to bring the pH to 3. The aqueous layer was extracted with EtOAc (2×100 mL). The combined organic layers were dried over Na$_2$SO$_4$ and concentrated. The residue was triturated with MeOH (2×10 mL) and the solid was dried to afford ethyl 2-(4-fluorophenyl)-3-oxo-2,3-dihydro-1H-pyrazole-4-carboxylate (2.88 g, 60%).

Step B: To 20 mL vial, ethyl 2-(4-fluorophenyl)-3-oxo-2,3-dihydro-1H-pyrazole-4-carboxylate (1.56 g, 6.23 mmol) and methyl trifluoromethanesulfonate (2.11 ml, 18.7 mmol) was added and heated to 80° C. for 1 h. The reaction mixture was diluted with DCM (50 mL) and washed with saturated NaHCO$_3$ (30 mL). The aqueous layer was extracted with DCM (2×20 mL). The combined organic layers were dried over Na$_2$SO$_4$ and concentrated under vacuum. The residue was purified over silica gel (70-100% EtOAc in hexanes) to afford (4-(ethoxycarbonyl)-2-(4-fluorophenyl)-1-methyl-1,2-dihydro-3H-pyrazol-3-ylidene)(methyl)oxonium trifluoromethanesulfonate (2.143 g, 100%).

Step C: To a 40 mL vial (4-(ethoxycarbonyl)-2-(4-fluorophenyl)-1-methyl-1,2-dihydro-3H-pyrazol-3-ylidene)(methyl)oxonium (1.74 g, 6.23 mmol) added and diluted with THF (6 mL) and MeOH (5 mL). 4N aq. NaOH (9.35 ml, 37.4 mmol) was added and the reaction mixture was heated to 60° C. After 1 h, the reaction mixture was cooled to room temperature. The reaction mixture was concentrated to remove volatile solvents. To the solution was 3N aq. HCl added to bring the pH to 1. The solution was extracted with EtOAc (3×10 mL). The combined organic layers were concentrated under reduced pressure to afford 2-(4-fluorophenyl)-1-methyl-3-oxo-2,3-dihydro-1H-pyrazole-4-carboxylic acid (1.26 g, 85.8%).

The following compound was also made using the procedure according to Preparation 26.

| Preparation | Structure | Name |
|---|---|---|
| 27 | 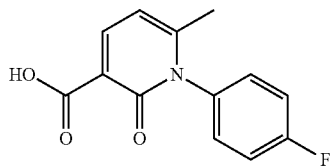 [SMILES: Cc1ccc(C(=O)O)c(=O)n1-c1ccc(F)cc1] | 1-methyl-3-oxo-2-phenyl-2,3-dihydro-1H-pyrazole-4-carboxylic acid |

Preparation 28

1-(4-fluorophenyl)-6-methyl-2-oxo-L2-dihydropyridine-3-carboxylic acid

Step A: A solution of 4-fluoroaniline (1.72 ml, 18.0 mmol) and triethylamine (3.01 ml, 21.6 mmol) in DCM (90 mL) was prepared and purged with an argon balloon. The solution was cooled to 0° C. in an ice bath Ethyl 3-chloro-3-oxopropanoate (2.719 mL, 21.60 mmol) was dissolved in DCM (8 mL) and this solution was added dropwise to the reaction over the course of five minutes. The reaction mixture was allowed to slowly warm to room temperature overnight. The reaction mixture was diluted with water (100 mL) and separated, washed with NaHCO₃ (50 mL×4) and brine (50 mL), dried over sodium sulfate, filtered and concentrated to afford crude ethyl 3-((4-fluorophenyl)amino)-3-oxopropanoate (4.32 g, 106%).

Step B: Ethyl 3-((4-fluorophenyl)amino)-3-oxopropanoate (2 g, 8.88 mmol) was dissolved in ethanol (22 mL). This solution was stirred while (E)-4-methoxybut-3-en-2-one (1.36 mL, 13.3 mmol) was added. After stirring together for 10 min, sodium ethanolate (4.97 mL, 13.3 mmol) was added and heated to reflux for 2 h. The reaction mixture was concentrated and diluted with DCM (200 mL) and washed with 1N HCl (50 mL×2) and brine (50 mL), dried over sodium sulfate, filtered and concentrated. The residue was purified over silica gel (5% MeOH in DCM) to afford 1-(4-fluorophenyl)-6-methyl-2-oxo-1,2-dihydropyridine-3-carboxylic acid (2.2 g, 100%).

Preparation 29

1-(4-fluorophenyl)-4-methyl-2-oxo-1,2-dihydropyridine-3-carboxylic acid

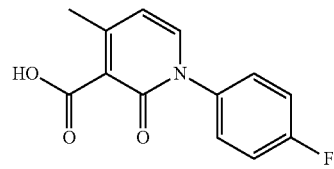 [SMILES: Cc1ccn(-c2ccc(F)cc2)c(=O)c1C(=O)O]

Step A: A solution of 4-fluoroaniline (1.73 mL, 18.0 mmol) and 1H-imidazole (0.249 g, 3.67 mmol) in diethyl 2-(propan-2-ylidene)malonate (9.80 mL, 50 mmol) were combined in a sealed tube and heated to 200° C. under argon for 3 h. The reaction mixture was cooled to room temperature and purified over silica gel (25% EtOAc in hexanes) to afford ethyl 2-((4-fluorophenyl)carbamoyl)-3-methylbut-2-enoate (2.13 g, 31%).

Step B: Ethyl 2-((4-fluorophenyl)carbamoyl)-3-methylbut-2-enoate (2.13 g, 8.03 mmol) was dissolved in 1,1-dimethoxy-N,N-dimethylmethanamine (0.957 g, 8.03 mmol) and heated to 90° C. for 90 minutes in a sealed tube. The reaction mixture was cooled to room temperature and diluted with 30 mL EtOAc and 30 mL saturated NH₄Cl and stirred for 15 minutes. The phases were separated and the organic phase was washed with NH₄Cl (2×30 mL), dried over Na₂SO₄, filtered and concentrated. The residue was purified over silica gel (5% MeOH in DCM) to afford ethyl 1-(4-fluorophenyl)-4-methyl-2-oxo-1,2-dihydropyridine-3-carboxylate (320 mg, 15%).

Step C: Ethyl 1-(4-fluorophenyl)-4-methyl-2-oxo-1,2-dihydropyridine-3-carboxylate (290 mg, 1.05 mmol) was dissolved in MeOH (3 mL) and water (2 mL). LiOH (88 mg, 2.1 mmol) was added and the reaction mixture was heated to 37° C. overnight. The reaction mixture was diluted with water (10 mL) and the methanol removed under reduced pressure. The aqueous layer was extracted with Et₂O (2×50 mL) and the pH was decreased to 1 with 1M HCl. The resultant solids were filtered, washed with water and dried to afford 1-(4-fluorophenyl)-4-methyl-2-oxo-1,2-dihydropyridine-3-carboxylic acid (121 mg, 46%).

Preparation 30

1-(4-fluorophenyl)-5-methyl-2-oxo-1,2-dihydropyridine-3-carboxylic acid

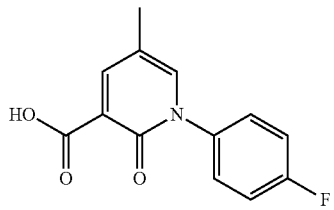 [SMILES: Cc1cc(C(=O)O)c(=O)n(-c2ccc(F)cc2)c1]

Ethyl 3-((4-fluorophenyl)amino)-3-oxopropanoate (18 g, 79.9 mmol) was dissolved in ethanol (200 mL) and (E)-3-ethoxy-2-methylacrylaldehyde (13.7, 119.8 mmol) was added. After 5 min, sodium ethanolate (44.7 ml, 119.8 mmol, 21 wt % in EtOH) was added and the reaction mixture was heated at reflux for 3 h. The reaction mixture was cooled to room temperature and added to a stirred aqueous solution of 2N HCl (2 L) and the mixture was stirred overnight at room temperature. The solids were filtered and washed with 2N HCl (2×500 mL) and water (500 mL). The filter cake and filter paper were transferred to a large Buchi vacuum flask and dried overnight to afford 1-(4-fluorophenyl)-5-methyl-2-oxo-1,2-dihydropyridine-3-carboxylic acid (15.9 g, 80%).

The following compounds were also made using the procedure according to Preparation 30.

Step A: A 250 mL round bottomed flask was charged with methyl 5-bromo-2-oxo-1,2-dihydropyridine-3-carboxylate (2.84 g, 12.2 mmol), (4-fluorophenyl)boronic acid (4.62 g, 33.0 mmol), diacetoxycopper (4.34 g, 23.9 mmol) and DCM (50 mL). Activated molecular sieves (1 g) were added followed by pyridine (3.86 ml, 47.7 mmol). The reaction mixture was stirred for 3 days at room temperature under normal atmosphere. The reaction mixture was diluted to 200 mL with DCM and filtered through Celite®. The filtrate was washed with water (3×250 mL) and brine, dried over sodium sulfate, filtered and concentrated. The residue was purified over silica gel (25% EtOAc in DCM) to afford methyl 5-bromo-1-(4-fluorophenyl)-2-oxo-1,2-dihydropyridine-3-carboxylate (3.53 g, 10.8 mmol, 88.4% yield).

Step B: Methyl 5-bromo-1-(4-fluorophenyl)-2-oxo-1,2-dihydropyridine-3-carboxylate (0.400 g, 1.23 mmol) was dissolved in 10:1 toluene:water (16 mL) and nitrogen was bubbled through this solution for 5 min. Potassium cyclopropyltrifluoroborate (0.726 g, 4.91 mmol), diacetoxypalladium (0.038 g, 0.169 mmol), and $K_3PO_4$ (0.260 g, 1.23 mmol) were added with nitrogen bubbling through the reaction mixture for 1 min. Dicyclohexyl(2',6'-diisopropoxy-[1,1'-biphenyl]-2-yl)phosphane (0.172 g, 0.368 mmol) was added and the reaction mixture was bubbled with nitrogen for 1 min, then sealed and heated to 105° C. overnight. The reaction mixture was partitioned between water and EtOAc, washed with water and brine, dried over sodium sulfate, filtered and concentrated. The residue was

| Preparation | Structure | Name |
|---|---|---|
| 31 | 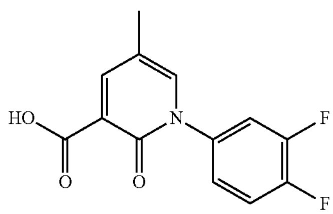 [SMILES: Cc1cc(C(=O)O)c(=O)n(-c2ccc(F)c(F)c2)c1] | 1-(3,4-difluorophenyl)-5-methyl-2-oxo-1,2-dihydropyridine-3-carboxylic acid |
| 32 | 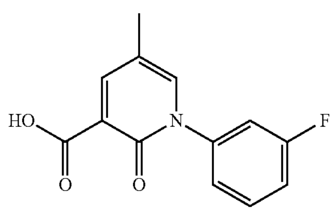 [SMILES: Cc1cc(C(=O)O)c(=O)n(-c2cccc(F)c2)c1] | 1-(3-fluorophenyl)-5-methyl-2-oxo-1,2-dihydropyridine-3-carboxylic acid |

Preparation 33

5-cyclopropyl-1-(4-fluorophenyl)-2-oxo-1,2-dihydropyridine-3-carboxylic acid

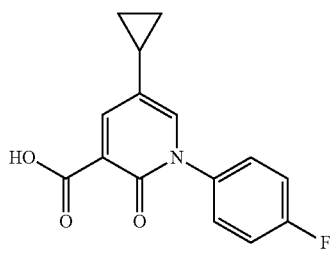 [SMILES: O=C(O)c1cc(C2CC2)cn(-c2ccc(F)cc2)c1=O]

purified over silica gel (80:20 DCM: EtOAc) to afford methyl 5-cyclopropyl-1-(4-fluorophenyl)-2-oxo-1,2-dihydropyridine-3-carboxylate (0.240 g, 0.835 mmol, 68.1% yield).

Step C: Methyl 5-cyclopropyl-1-(4-fluorophenyl)-2-oxo-1,2-dihydropyridine-3-carboxylate (240 mg, 0.835 mmol) was dissolved in THF (20 mL) and MeOH (5 mL). To this was added a solution of lithium hydroxide hydrate (550 mg, 13.1 mmol) in a minimal amount of water (1 mL). After 2.5 h, the reaction mixture was concentrated, diluted with water (5 mL) and pH adjusted to 1 with concentrated HCl. The resulting solid was filtered, washed with 2N HCl and dried to afford 5-cyclopropyl-1-(4-fluorophenyl)-2-oxo-1,2-dihydropyridine-3-carboxylic acid (160 mg, 0.586 mmol, 70.1% yield).

Preparation 34

5-bromo-1-(4-fluorophenyl)-2-oxo-1,2-dihydropyridine-3-carboxylic acid

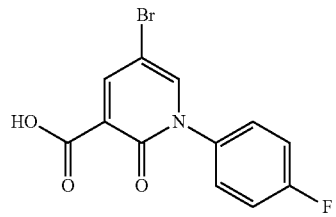 [SMILES: O=C(O)c1cc(Cl)cn(-c2ccc(F)cc2)c1=O]

Step A: A round bottomed flask was charged with methyl 5-bromo-2-oxo-1,2-dihydropyridine-3-carboxylate (1 g, 4.31 mmol), (4-fluorophenyl)boronic acid (1.63 g, 11.6 mmol), diacetoxycopper (1.53 g, 8.40 mmol) and DCM (50 mL). Activated molecular sieves (1 g) were added followed by pyridine (1.36 ml, 16.8 mmol). The reaction mixture was stirred overnight at room temperature under air. The blue slurry was filtered through Celite® and the washed with DCM and concentrated. The concentrate was partitioned between DCM and water, dried over sodium sulfate, filtered and concentrated. The residue was purified over silica gel (25% EtOAc in DCM) to afford methyl 5-bromo-1-(4-fluorophenyl)-2-oxo-1,2-dihydropyridine-3-carboxylate (0.84 g, 60% yield).

Step B: Methyl 5-bromo-1-(4-fluorophenyl)-2-oxo-1,2-dihydropyridine-3-carboxylate (382.3 mg, 1.172 mmol) was dissolved in THF (20 mL) and MeOH (5 mL). To this was added a solution of lithium hydroxide hydrate (491.9 mg, 11.72 mmol) in a minimal amount of water ~1 mL. After 2.5 h, the reaction mixture was concentrated, diluted with water (5 mL) and pH adjusted to 1 with concentrated HCl. The resulting solid was filtered, washed with 2N HCl and dried to afford 5-bromo-1-(4-fluorophenyl)-2-oxo-1,2-dihydropyridine-3-carboxylic acid (287.6 mg, 0.9215 mmol, 78.61% yield).

The following compound was also made using the procedure according to Preparation 34.

| Preparation | Structure | Name |
|---|---|---|
| 35 | 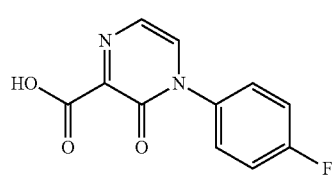 [SMILES: O=C(O)c1nccn(-c2ccc(F)cc2)c1=O] | 5-chloro-1-(4-fluorophenyl)-2-oxo-1,2-dihydropyridine-3-carboxylic acid |

Preparation 36

4-(4-fluorophenyl)-3-oxo-3,4-dihydropyrazine-2-carboxylic acid

Step A: To a stirred mixture of 4-fluorobenzenamine (41 g, 369.0 mmol) in acetic acid (211.2 ml, 3690 mmol) and KCN (31.23 g, 479.7 mmol) in water (50 mL) at 0° C. was added formaldehyde (41.2 ml, 553.5 mmol, 37% in water) dropwise. The dark solution was stirred at 0° C. for 15 minutes and allowed to warm to room temperature overnight. The reaction mixture was diluted with water (500 mL), extracted with EtOAc, washed with 1N NaOH, water, and brine, dried over MgSO$_4$, filtered and concentrated to afford crude 2-(4-fluorophenylamino)acetonitrile (52 g, 93%).

Step B: To a stirred mixture of 2-(4-fluorophenylamino)acetonitrile (52 g, 346 mmol) in 1,2-dichlorobenzene (139 ml, 346 mmol) was added slowly oxalyl dichloride (132 g, 1039 mmol). The reaction mixture was heated to 100° C. and stirred for 5.5 h. The dichlorobenzene was removed by vacuum distillation (10 mm Hg at 75° C.) and the crude material was purified over silica gel (0-1% acetonitrile in DCM) to afford 3,5-dichloro-1-(4-fluorophenyl)pyrazin-2(1H)-one (18 g, 20%).

Step C: 3,5-Dichloro-1-(4-fluorophenyl)pyrazin-2(1H)-one (18 g, 69.5 mmol) was suspended in MeOH (280 mL) and slowly treated with sodium methoxide (23.8 ml, 104 mmol) at 0° C. The reaction mixture was allowed to warm to room temperature and stirred for 5 h. The reaction mixture was neutralized with HCl (17.4 mL, 34.7 mmol, 2N Et$_2$O solution), and concentrated. The residue was taken up in EtOAc (800 mL), washed with aqueous 0.5 N HCl (600 mL), dried over MgSO$_4$, filtered and concentrated to afford 5-chloro-1-(4-fluorophenyl)-3-methoxypyrazin-2(1H)-one (16.1 g, 91%).

Step D: 5-Chloro-1-(4-fluorophenyl)-3-methoxypyrazin-2(1H)-one (43 g, 169 mmol) was suspended in MeOH (2 L) and heated to 50° C. to dissolve all of the solids. The reaction mixture was cooled to room temperature and K$_2$CO$_3$ (23.3 g, 169 mmol) and 10% (dry basis: about 50% water) Pd/C (18.0 g, 8.44 mmol) were added to the mixture at room temperature. The mixture was stirred under a hydrogen atmosphere. After 4 h, the mixture was filtered and concentrated. The residue was taken up in DCM (1500 mL) and washed with water (1000 mL) and brine, dried over MgSO$_4$, filtered and concentrated to afford 1-(4-fluorophenyl)-3-methoxypyrazin-2(1H)-one (22.7 g, 61%).

Step E: 1-(4-Fluorophenyl)-3-methoxypyrazin-2(1H)-one (22.0 g, 100 mmol) was suspended in DMF (200 mL). The mixture was cooled to 0° C. and POCl$_3$ (22.9 ml, 250 mmol) was added dropwise. After addition, the mixture was heated to 90° C. for 2 h and then cooled to 0° C. The reaction mixture was quenched by adding saturated sodium acetate solution (40 mL) and cooling to 0° C. After 20 min, a fine precipitate formed. The solid was removed by filtration and washed with a small portion (50 mL) of saturated sodium acetate solution followed by ice water (100 mL). The solid was dried overnight to afford 3-chloro-1-(4-fluorophenyl) pyrazin-2(1H)-one (14.7 g).

Step F: 3-Chloro-1-(4-fluorophenyl)pyrazin-2(1H)-one (17.9 g, 79.9 mmol), zinc cyanide (5.63 g, 47.9 mmol), dppf (4.43 g, 7.99 mmol), $Pd_2dba_3$ (3.65 g, 3.99 mmol) were suspended in NMP (360 mL). The reaction mixture was stirred under nitrogen at 120° C. overnight. The reaction mixture was cooled, diluted with EtOAc (3000 mL), washed with a 4:1:4 mixture of saturated $NH_4Cl$:conc. $NH_4OH$: water and brine, dried over $MgSO_4$, filtered and concentrated. The residue was purified over silica gel (0-1% MeOH in DCM) to afford 4-(4-fluorophenyl)-3-oxo-3,4-dihydropyrazine-2-carbonitrile (10.76 g, 62%).

Step G: 4-(4-Fluorophenyl)-3-oxo-3,4-dihydropyrazine-2-carbonitrile (10.50 g, 48.80 mmol) was dissolved in concentrated $H_2SO_4$ (104.0 ml, 1952 mmol) and stirred for 2 h. The reaction mixture was slowly poured into methanol (700 mL) at 0° C. After complete addition, the mixture was heated to 70° C. and stirred for 2.5 h. The reaction mixture was cooled to room temperature and poured into 1500 mL of ice. The pH was adjusted to 12 with 5N NaOH. The pH was then adjusted to 2 with 2N HCl, extracted with EtOAc, dried over $MgSO_4$, filtered and concentrated. The residue was triturated with ether and filtered to afford 4-(4-fluorophenyl)-3-oxo-3,4-dihydropyrazine-2-carboxylic acid (9.2 g, 78%).

Preparation 37

6-cyclopropyl-2-(4-fluorophenyl)-3-oxo-2,3-dihydropyridazine-4-carboxylic acid

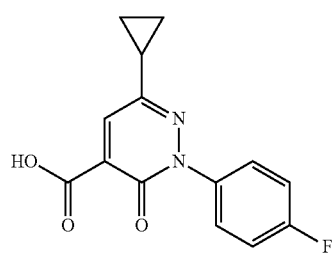 [SMILES: O=C(O)c1cc(C2CC2)nn(-c2ccc(F)cc2)c1=O]

Step A: To 2-cyclopropyl-2-oxoacetaldehyde (0.424 mL, 5.10 mmol) was added a mixture of 4-fluorophenylhydrazine hydrochloride (0.829 g, 5.10 mmol) in AcOH (4.25 mL, 5.10 mmol) and water (4.25 mL, 5.10 mmol) at room temperature while stirring for 20 minutes. The mixture was added to cold water (200 mL) and stirred for 10 minutes. The mixture was filtered and the isolated solids were washed with water (50 mL). The residue was purified over silica gel (1-10% EtOAc in DCM) to obtain (E)-2-cyclopropyl-2-(2-(4-fluorophenyl)hydrazono)acetaldehyde (0.080 g, 0.388 mmol, 7.61% yield) the minor isomer.

Step B: To a solution of (E)-2-cyclopropyl-2-(2-(4-fluorophenyl)hydrazono)acetaldehyde (0.080 g, 0.388 mmol) in toluene (3.88 mL) was added 2,2-dimethyl-1,3-dioxane-4,6-dione (0.0671 g, 0.466 mmol), AcOH (0.00222 mL, 0.0388 mmol) and piperidine (0.00383 ml, 0.0388 mmol). After 1 h, the mixture was added to water (50 mL) and the organics were extracted with EtOAc (25 mL). The organic layer was washed with water (25 mL) and brine (25 mL), dried with $Na_2SO_4$, filtered and concentrated. The residue was purified over silica gel (1-10% EtOAc in DCM) to obtain 6-cyclopropyl-2-(4-fluorophenyl)-3-oxo-2,3-dihydropyridazine-4-carboxylic acid (0.025 g, 0.0912 mmol, 23.5% yield) as a tan solid.

The following compound was also made using the procedure according to Preparation 37

| Preparation | Structure | Name |
|---|---|---|
| 38 | ![structure] | 2-(4-fluorophenyl)-6-isopropyl-3-oxo-2,3-dihydropyridazine-4-carboxylic acid |

Preparation 39

4-(4-fluorophenyl)-2-isopropyl-5-oxo-3-thioxo-2,3,4,5-tetrahydro-1,2,4-triazine-6-carboxylic acid Step A: A mixture of diethyl 2-oxomalonate (4.12 mL, 26.99 mmol) and N-(4-fluorophenyl)hydrazinecarbothioamide (5.0 g, 26.99 mmol) in ethanol (100 mL) was heated at reflux for 2 days. The mixture was cooled to room temperature and filtered. The solids were washed with cold EtOH and dried to afford ethyl 4-(4-fluorophenyl)-5-oxo-3-thioxo-2,3,4,5-tetrahydro-1,2,4-triazine-6-carboxylate (3.85 g, 48%) as a yellow powder.

Step B: To a suspension of ethyl 4-(4-fluorophenyl)-5-oxo-3-thioxo-2,3,4,5-tetrahydro-1,2,4-triazine-6-carboxylate (400 mg, 1.433 mmol) and $K_2CO_3$ (396 mg, 2.865 mmol) in DMF (5 mL) was added 2-iodopropane (287 µL, 2.86 mmol). The mixture was heated in a sealed tube at 65° C. for 1 h. The mixture was cooled to room temperature and partitioned between water (20 mL) and EtOAc (20 mL). The aqueous layer was extracted with EtOAc (2×15 mL). The combined organic phases were washed with water (5×15 mL) and brine (20 mL), dried over $Na_2SO_4$, filtered and concentrated. The residue was purified over silica gel (0-20% EtOAc in hexanes) to afford ethyl 4-(4-fluorophenyl)-2-isopropyl-5-oxo-3-thioxo-2,3,4,5-tetrahydro-1,2,4-triazine-6-carboxylate (211 mg, 46% yield).

Step C: Sulfuric acid (5 mL) was carefully added to a mixture of ethyl 4-(4-fluorophenyl)-2-isopropyl-5-oxo-3-thioxo-2,3,4,5-tetrahydro-1,2,4-triazine-6-carboxylate (211.1 mg, 0.657 mmol) and water (1 mL). The mixture became homogenous after a few minutes. The reaction mixture was stirred at 40° C. overnight, cooled to room temperature, and then carefully added to ice. The mixture was saturated with solid NaCl and was extracted with EtOAc (3×40 mL) The combined EtOAc layers were dried over sodium sulfate, filtered and concentrated to afford 4-(4-fluorophenyl)-2-isopropyl-5-oxo-3-thioxo-2,3,4,5-tetrahydro-1,2,4-triazine-6-carboxylic acid (195 mg, 100%).

Preparation 40

4-(4-fluorophenyl)-2-isopropyl-3,5-dioxo-2,3,4,5-tetrahydro-L2,4-triazine-6-carboxylic acid

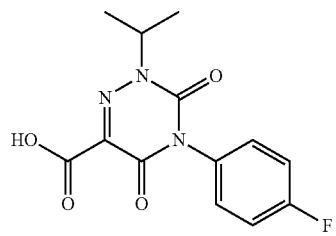 [SMILES: CC(C)n1nc(C(=O)O)c(=O)n(-c2ccc(F)cc2)c1=O]

Step A: To a solution of ethyl 4-(4-fluorophenyl)-5-oxo-3-thioxo-2,3,4,5-tetrahydro-1,2,4-triazine-6-carboxylate (3.85 g, 13.0 mmol) in DMF (35 mL) and acetic acid (14.2 mL, 248.0 mmol) was added 30% aq. $H_2O_2$ (2 mL, 65.2 mmol). The mixture was stirred for 3 days. The reaction mixture was extracted between water (200 mL) and EtOAc (120 mL). The aqueous layer was washed with EtOAc (2×120 mL). The combined organic layers were washed with water (100 mL), sodium bicarbonate (3×100 mL), water (100 mL), and brine (200 mL). The organic layer was then dried with sodium sulfate, filtered and concentrated in vacuo to afford a pale yellow solid. The solid obtained was triturated with ether and filtered. The filtrate was concentrated and purified over silica (0-40% EtOAc in hexanes) to afford ethyl 4-(4-fluorophenyl)-3,5-dioxo-2,3,4,5-tetrahydro-1,2,4-triazine-6-carboxylate (1.6 g, 45%).

Step B: To a suspension of ethyl 4-(4-fluorophenyl)-3,5-dioxo-2,3,4,5-tetrahydro-1,2,4-triazine-6-carboxylate (800 mg, 2.87 mmol) and $K_2CO_3$ (792 mg, 5.73 mmol) in DMF (10 mL) was added 2-iodopropane (573 µL, 5.73 mmol). The mixture was heated in a sealed tube at 65° C. for 1 h. The cooled mixture was partitioned between water (50 mL) and EtOAc (25 mL) and the aqueous layer was extracted with EtOAc (2×25 mL). The combined organic phases were washed with water (5×30 mL) and brine (50 mL), then dried over $Na_2SO_4$, filtered and concentrated. The residue was purified over silica gel (0-20% EtOAc in hexanes) to afford ethyl 4-(4-fluorophenyl)-2-isopropyl-3,5-dioxo-2,3,4,5-tetrahydro-1,2,4-triazine-6-carboxylate (763 mg, 83%).

Step C: Sulfuric acid (10 mL) was carefully added to a mixture of ethyl 4-(4-fluorophenyl)-2-isopropyl-3,5-dioxo-2,3,4,5-tetrahydro-1,2,4-triazine-6-carboxylate (763.7 mg, 2.377 mmol) and water (2 mL). The mixture became homogenous after a few minutes. The reaction mixture was stirred at 40° C. overnight, cooled to room temperature, and carefully added to ice. The mixture was saturated with solid NaCl and was extracted from EtOAc (3×40 mL) The combined organic layers were dried over sodium sulfate, filtered and concentrated to afford 4-(4-fluorophenyl)-2-isopropyl-3,5-dioxo-2,3,4,5-tetrahydro-1,2,4-triazine-6-carboxylic acid (713 mg, 102%).

The following compounds were also made using the procedure according to Preparation 40.

| Preparation | Structure | Name |
|---|---|---|
| 41 | 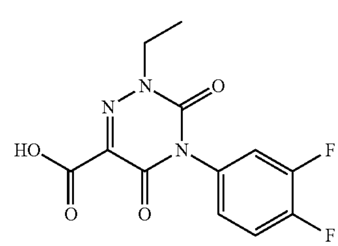 [SMILES: CCn1nc(C(=O)O)c(=O)n(-c2ccc(F)c(F)c2)c1=O] | 4-(3,4-difluorophenyl)-2-ethyl-3,5-dioxo-2,3,4,5-tetrahydro-1,2,4-triazine-6-carboxylic acid |
| 42 | 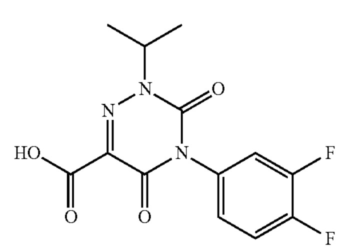 [SMILES: CC(C)n1nc(C(=O)O)c(=O)n(-c2ccc(F)c(F)c2)c1=O] | 4-(3,4-difluorophenyl)-2-isopropyl-3,5-dioxo-2,3,4,5-tetrahydro-1,2,4-triazine-6-carboxylic acid |

| Preparation | Structure | Name |
|---|---|---|
| 43 | 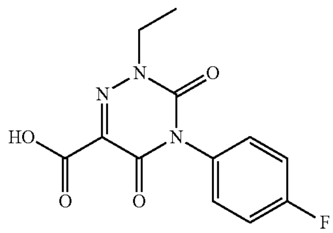 [SMILES: CCn1nc(C(=O)O)c(=O)n(-c2ccc(F)cc2)c1=O] | 2-ethyl-4-(4-fluorophenyl)-3,5-dioxo-2,3,4,5-tetrahydro-1,2,4-triazine-6-carboxylic acid |

Preparation 41

5-(4-fluorophenyl)-1-methyl-4-oxo-1,4-dihydropyridine-3-carboxylic acid

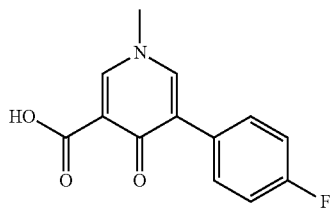 [SMILES: Cn1cc(C(=O)O)c(=O)c(-c2ccc(F)cc2)c1]

Step A: A mixture of methyl 5-bromo-4-hydroxynicotinate (100 mg, 0.431 mmol) and Cs₂CO₃ (211 mg, 0.646 mmol) was diluted with DMF (2 mL), placed under a nitrogen atmosphere and heated to 75° C. for 10 min. The reaction mixture was allowed to cool to room temperature. MeI (40.4 μl, 0.646 mmol) was added and the reaction mixture was stirred for 3 h. The reaction mixture was diluted with water and extracted with DCM/IPA (3:1). The combined organic layers were dried over MgSO₄, filtered and concentrated. The residue was purified over silica gel (1-10% methanol in DCM with 1% NH₄OH) to afford methyl 5-bromo-1-methyl-4-oxo-1,4-dihydropyridine-3-carboxylate (92 mg, 0.374 mmol, 86.8% yield).

Step B: A mixture of methyl 5-bromo-1-methyl-4-oxo-1,4-dihydropyridine-3-carboxylate (92 mg, 0.37 mmol), (4-fluorophenyl)boronic acid (105 mg, 0.75 mmol) and Pd(PPh₃)₄ (22 mg, 0.019 mmol) was diluted with dioxane (1 mL) followed by the addition of Na₂CO₃ (561 μl, 1.1 mmol, 2.0 M). The reaction mixture was purged with argon, sealed and heated to 90° C. overnight. The reaction mixture was allowed to cool, and the cooled mixture was diluted with water and adjusted to pH 2 with 1N HCl. The mixture was extracted with three times with DCM/IPA (3/1). The combined organic layers were dried over MgSO₄, filtered and concentrated. The product was triturated with diethyl ether to afford 5-(4-fluorophenyl)-1-methyl-4-oxo-1,4-dihydropyridine-3-carboxylic acid.

The following compounds were also made using the procedure according to Preparation 41.

| Preparation | Structure | Name |
|---|---|---|
| 42 | 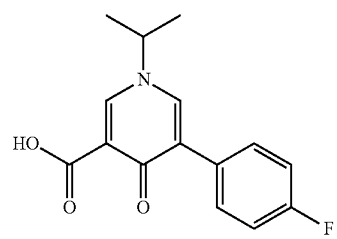 [SMILES: CC(C)n1cc(C(=O)O)c(=O)c(-c2ccc(F)cc2)c1] | 5-(4-fluorophenyl)-1-isopropyl-4-oxo-1,4-dihydropyridine-3-carboxylic acid |
| 43 | 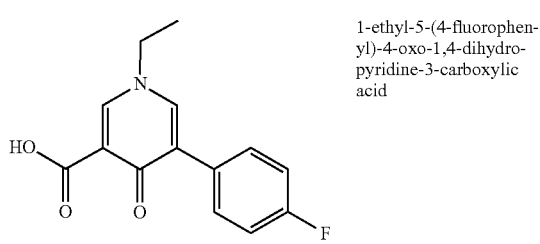 | 1-ethyl-5-(4-fluorophenyl)-4-oxo-1,4-dihydropyridine-3-carboxylic acid |

| Preparation | Structure | Name |
|---|---|---|
| 44 | 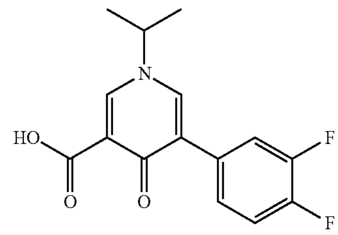 [SMILES: CC(C)n1cc(C(=O)O)c(=O)c(-c2ccc(F)c(F)c2)c1] | 5-(3,4-difluorophenyl)-1-isopropyl-4-oxo-1,4-dihydropyridine-3-carboxylic acid |
| 45 | 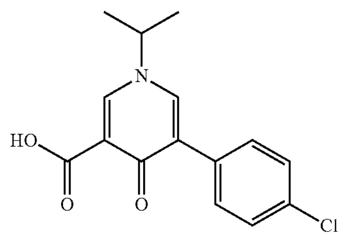 [SMILES: CC(C)n1cc(C(=O)O)c(=O)c(-c2ccc(Cl)cc2)c1] | 5-(4-chlorophenyl)-1-isopropyl-4-oxo-1,4-dihydropyridine-3-carboxylic acid |
| 46 | 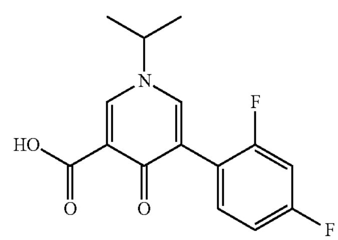 [SMILES: CC(C)n1cc(C(=O)O)c(=O)c(-c2ccc(F)cc2F)c1] | 5-(2,4-difluorophenyl)-1-isopropyl-4-oxo-1,4-dihydropyridine-3-carboxylic acid |

Preparation 47

1-(4-fluorophenyl)-2-oxo-5-vinyl-1,2-dihydropyridine-3-carboxylic acid

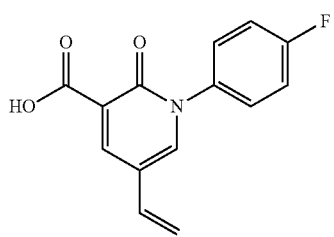 [SMILES: C=Cc1cc(C(=O)O)c(=O)n(-c2ccc(F)cc2)c1]

Step A: In a 125 mL screw-top pressure vial, methyl 5-bromo-1-(4-fluorophenyl)-2-oxo-1,2-dihydropyridine-3-carboxylate (0.400 g, 1.227 mmol) was dissolved in 10:1 toluene:water (16 mL) and nitrogen was bubbled through this solution for 5 minutes. Potassium trifluoro(vinyl)borate (0.6572 g, 4.906 mmol), diacetoxypalladium (0.04131 g, 0.1840 mmol), and $K_3PO_4$ (0.7811 g, 3.680 mmol) were added with nitrogen bubbling through the reaction for 1 minute. Dicyclohexyl(2',6'-diisopropoxy-[1,1'-biphenyl]-2-yl)phosphane (0.1717 g, 0.3680 mmol) was added and the reaction mixture was bubbled with nitrogen for 1 minute, then sealed and heated to 110° C. overnight. The reaction mixture was cooled and partitioned between water and ethyl acetate. The organic layer was washed with water and brine, dried over sodium sulfate, filtered and concentrated. The residue was purified over silica gel (20% EtOAc in DCM) to afford methyl 1-(4-fluorophenyl)-2-oxo-5-vinyl-1,2-dihydropyridine-3-carboxylate.

Step B: Methyl 1-(4-fluorophenyl)-2-oxo-5-vinyl-1,2-dihydropyridine-3-carboxylate was dissolved in MeOH (50 mL) and water (5 mL). LiOH (500 mg) was added and the reaction mixture was heated to 40° C. for 1.5 h. The MeOH was removed by rotary evaporation and diluted with water (50 mL). Concentrated HCl was added until pH 1. The resultant precipitate was filtered and dried to afford 1-(4-fluorophenyl)-2-oxo-5-vinyl-1,2-dihydropyridine-3-carboxylic acid (209.6 mg, 66% yield).

The following compounds were also made using the procedure according to Preparation 47.

| Preparation | Structure | Name |
|---|---|---|
| 48 | 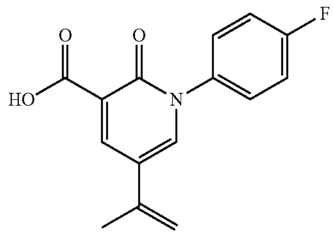 [SMILES: C=C(C)c1cc(C(=O)O)c(=O)n(-c2ccc(F)cc2)c1] | 1-(4-fluorophenyl)-2-oxo-5-(prop-1-en-2-yl)-1,2-dihydropyridine-3-carboxylic acid |
| 49 | 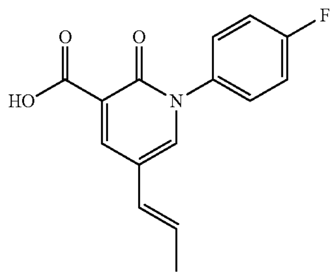 [SMILES: C/C=C/c1cc(C(=O)O)c(=O)n(-c2ccc(F)cc2)c1] | (E)-1-(4-fluorophenyl)-2-oxo-5-(prop-1-en-1-yl)-1,2-dihydropyridine-3-carboxylic acid |

Preparation 50

5-(4-fluorophenyl)-6-oxo-5-azaspiro[2.5]octane-7-carboxylic acid

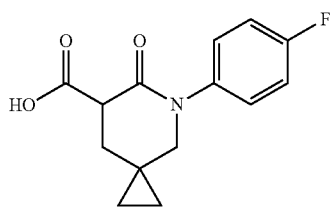 [SMILES: O=C(O)C1CC2(CC2)CN(c2ccc(F)cc2)C1=O]

Step A: A solution of 1-(hydroxymethyl)cyclopropane-1-carbonitrile (541 mg, 5.57 mmol) in DCM (10 mL) was cooled to 0° C. in an ice bath and methanesulfonyl chloride (684 µL, 8.36 mmol) was added, followed by triethylamine (1708 µl, 12.3 mmol), and the reaction mixture was stirred at 0° C. for 1 h and warmed to room temperature. The reaction mixture was diluted with DCM (10 mL), washed with brine, dried over sodium sulfate and concentrated to afford crude (1-cyanocyclopropyl)methyl methanesulfonate (976 mg, 100% yield).

Step B: Diethyl malonate (765 µl, 5.01 mmol) was added to a solution of sodium hydride (243 mg, 6.08 mmol) in THF (25 mL) followed by the addition of (1-cyanocyclopropyl)methyl methanesulfonate (976 mg, 5.57 mmol) and the reaction mixture was refluxed for 4 days. The reaction mixture was cooled and partitioned between MTBE (50 mL) and 2N HCl (50 mL), washed of MTBE with 2N HCl (25 mL) and brine (25 mL), dried over sodium sulfate, filtered and concentrated. The crude material was purified over silica gel (5-95% EtOAc in hexanes) to afford diethyl 2-((1-cyanocyclopropyl)methyl)malonate (430 mg, 1.80 mmol, 32.3% yield).

Step C: Diethyl 2-((1-cyanocyclopropyl)methyl)malonate (275 mg, 1.15 mmol) was dissolved in EtOH (50 mL) in a 250 mL Parr shaker bottle. $PtO_2$ (14 mg, 0.06 mmol) was added and the mixture was maintained under 50 psi $H_2$ for 48 hours. Additional $PtO_2$ (14 mg, 0.06 mmol) was added to the Parr shaker and the reaction was maintained under at 50 psi $H_2$ overnight. The reaction mixture was filtered, the solids were washed with ethanol and the filtrate was concentrated. The residue was purified over silica gel (0-20% MeOH in EtOAc) to afford ethyl 6-oxo-5-azaspiro[2.5]octane-7-carboxylate (98 mg, 43.2% yield).

Step D: Ethyl 6-oxo-5-azaspiro[2.5]octane-7-carboxylate (0.098 g, 0.4969 mmol), cesium carbonate (0.4857 g, 1.491 mmol) and quinolin-8-ol (0.02885 g, 0.1987 mmol) were suspended in DMF (2 mL) and purged under argon for 5 minutes. Copper (I) iodide (0.03785 g, 0.1987 mmol) and 1-fluoro-4-iodobenzene (0.08595 mL, 0.7453 mmol) were added and the reaction mixture was heated to 100° C. overnight in a sealed tube under argon. The reaction mixture was cooled and partitioned between water and EtOAc (3×25), dried over sodium sulfate, filtered and concentrated. The residue was purified over silica gel (0-100% EtOAc in DCM) to afford ethyl 5-(4-fluorophenyl)-6-oxo-5-azaspiro[2.5]octane-7-carboxylate (40 mg, 0.1373 mmol, 27.63% yield).

Step E: Ethyl 5-(4-fluorophenyl)-6-oxo-5-azaspiro[2.5]octane-7-carboxylate (32.7 mg, 0.112 mmol) was dissolved in EtOH (25 mL) and lithium hydroxide hydrate (9.42 mg, 0.224 mmol) was added as a solid. Water (2 mL) was added and the reaction mixture was heated to 35° C. After 1 h, additional lithium hydroxide hydrate (9.42 mg, 0.224 mmol) was added. After an additional hour, EtOH was removed under reduced pressure. Water (25 mL) was added to the residue and the pH was lowered to <2 with the addition of concentrated HCl. The cloudy suspension was extracted with EtOAc (3×15 mL), dried over sodium sulfate, filtered and concentrated to afford 5-(4-fluorophenyl)-6-oxo-5-azaspiro[2.5]octane-7-carboxylic acid (23 mg, 0.0874 mmol, 77.8% yield) as a white solid.

Preparation 51

1-(4-fluorophenyl)-3-methyl-2-oxopiperidine-3-carboxylic acid

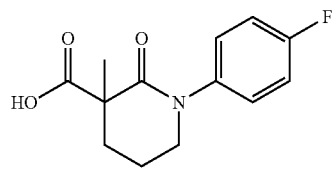 [SMILES: CC1(C(=O)O)CCCN(c2ccc(F)cc2)C1=O]

Step A: Ethyl 2-oxopiperidine-3-carboxylate (500 mg, 2.921 mmol), cesium carbonate (2855 mg, 8.762 mmol) and quinolin-8-ol (169.6 mg, 1.168 mmol) were suspended in DMF (6 mL) and purged under argon for 5 minutes. To this solution were added copper(I) iodide (222.5 mg, 1.168 mmol) and 1-fluoro-4-iodobenzene (505.2 µL, 4.381 mmol) and the reaction mixture was heated to 100° C. overnight in a sealed tube. The reaction mixture was cooled and partitioned between EtOAc and water, extracted with EtOAc, washed with brine, dried over sodium sulfate, filtered and concentrated. The residue was purified over silica gel (0-100% EtOAc in DCM) to afford ethyl 1-(4-fluorophenyl)-2-oxopiperidine-3-carboxylate (468 mg, 1.76 mmol, 60.4% yield).

Step B: Ethyl 1-(4-fluorophenyl)-2-oxopiperidine-3-carboxylate (468 mg, 1.76 mmol) was dissolved in DCM (10 mL). Cesium carbonate (2299 mg, 7.06 mmol) was added and the reaction mixture was stirred for 5 min. Iodomethane (659 µl, 10.6 mmol) was added and the reaction mixture was stirred overnight at room temperature. Additional iodomethane (659 µl, 10.6 mmol) was added and the reaction mixture was heated to 35° C. for 5 h and then at room temperature over the weekend. The reaction mixture was diluted with DCM (50 mL), filtered through Celite® and concentrated. The residue was purified over silica gel (0-40% EtOAc in hexanes) to afford ethyl 1-(4-fluorophenyl)-3-methyl-2-oxopiperidine-3-carboxylate (420 mg, 1.50 mmol, 85.2% yield) as a clear oil that was used directly in the next step without purification.

Step C: Ethyl 1-(4-fluorophenyl)-3-methyl-2-oxopiperidine-3-carboxylate (420 mg, 1.50 mmol) was dissolved in EtOH (3 mL), and lithium hydroxide hydrate (63.1 mg, 1.50 mmol) was added, followed by water (3 mL) and the reaction mixture was heated to 35° C. After 2 h, additional lithium hydroxide hydrate (63.1 mg, 1.50 mmol) was added and the reaction mixture was allowed to stir at room temperature overnight. The reaction mixture was concentrated, diluted with water (25 mL) and the pH was lowered to <2 by the addition of concentrated HCl. The cloudy mixture was extracted with EtOAc, washed with brine, dried over sodium sulfate, filtered and concentrated to afford 1-(4-fluorophenyl)-3-methyl-2-oxopiperidine-3-carboxylic acid (390 mg, 1.55 mmol, 103% yield).

Preparation 52

4-((6-aminopyridin-3-yl)oxy)-N-(1-methoxy-2-methylpropan-2-yl)-1-(4-methoxybenzyl)-1H-pyrazolo[3,4-b]pyridin-3-amine

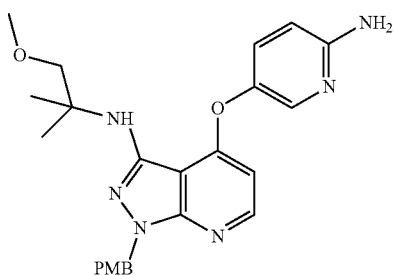

Step A: 4-Chloro-1H-pyrazolo[3,4-b]pyridine (11.6 g, 75.5 mmol) was dissolved in DMF (100 mL) and ground potassium hydroxide (12.7 g, 227 mmol) was added, followed by $I_2$ (34.5 g, 136 mmol). The resulting dark solution was stirred under nitrogen at 50° C. for 2 h. The reaction mixture was quenched by addition of aqueous 10% $NaHSO_3$ (75 mL). The suspension was further diluted by addition of water (100 mL) and filtered. The resulting precipitate was washed with water (3×30 mL), dried by toluene azeotrope (3×50 mL) by rotary evaporation to afford 4-chloro-3-iodo-1H-pyrazolo[3,4-b]pyridine (21.0 g, 88%).

Step B: 4-Chloro-3-iodo-1H-pyrazolo[3,4-b]pyridine (21.0 g, 75.1 mmol) was dissolved in DMF (100 mL). $K_2CO_3$ (20.8 g, 150 mmol) and 1-(chloromethyl)-4-methoxybenzene (12.3 ml, 90.2 mmol) were added and the reaction mixture was stirred under nitrogen overnight. The reaction mixture was diluted with water (100 mL) and filtered. The isolated solids were washed with water (3×30 mL) and purified over silica gel (25% EtOAc in hexanes) to afford 4-chloro-3-iodo-1-(4-methoxybenzyl)-1H-pyrazolo [3,4-b]pyridine.

Step C: To a mixture of 2-chloro-5-hydroxypyridine (1.69 g, 13.1 mmol) and 4-chloro-3-iodo-1-(4-methoxybenzyl)-1H-pyrazolo[3,4-b]pyridine (2.61 g, 6.53 mmol) in DMA (32 mL) was added $Cs_2CO_3$ (6.38 g, 19.6 mmol) and the reaction mixture was heated to 120° C. for 1 h. The reaction mixture was cooled to room temperature and poured into water (500 mL). The resulting solid was filtered and purified over silica gel (25-100% EtOAc in hexanes) to afford 4-((6-chloropyridin-3-yl)oxy)-3-iodo-1-(4-methoxybenzyl)-1H-pyrazolo[3,4-b]pyridine (1.87 g, 3.80 mmol, 58.1% yield) as a white solid.

Step D: (2-Methoxy-1,1-dimethylethyl)amine (0.185 mL, 1.52 mmol), 4-((6-chloropyridin-3-yl)oxy)-3-iodo-1-(4-methoxybenzyl)-1H-pyrazolo[3,4-b]pyridine (0.250 g, 0.507 mmol), K₂CO₃ (0.561 g, 4.06 mmol) and pyrrole-2-carboxylic acid (0.0282 g, 0.254 mmol) were suspended in DMSO (2.5 mL) and the reaction mixture was degassed for 5 min with Ar. Copper(I) iodide (0.0483 g, 0.254 mmol) was added and the reaction mixture was heated to 70° C. under argon for 66 h. The cooled reaction mixture was added to 50 mL water and extracted with DCM, washed with saturated NaHCO₃ (15 mL) and brine (15 mL), dried over sodium sulfate, filtered and concentrated. The residue was purified over silica gel (10-100% EtOAc in hexanes) to afford 4-((6-chloropyridin-3-yl)oxy)-N-(1-methoxy-2-methyl propan-2-yl)-1-(4-m ethoxybenzyl)-1H-pyrazolo[3,4-b]pyridin-3-amine (0.147 g, 0.276 mmol, 54.5% yield).

Step E: To a solution of 4-((6-chloropyridin-3-yl)oxy)-N-(1-methoxy-2-methylpropan-2-yl)-1-(4-methoxybenzyl)-1H-pyrazolo[3,4-b]pyridin-3-amine (0.050 g, 0.11 mmol) in toluene (0.5 mL) was added 2-dicyclohexylphosphino-2',6'-dimethoxy-1,1'-biphenyl (0.0066 g, 0.016 mmol) followed by tris(dibenzylideneacetone)dipalladium (0) (0.0049 g, 0.0053 mmol) and lithium bis(trimethylsilyl)amide (0.040 mL, 0.21 mmol). The solution was degassed with Ar for 10 min and heated to 80° C. over the weekend. The cooled reaction mixture was poured into water (25 mL) and extracted with DCM. The combined organic layers were washed with saturated NaHCO₃ (15 mL) and brine (15 mL), dried over sodium sulfate, filtered and concentrated. The residue was purified over silica gel (10-50% EtOAc in hexanes) to obtain 4-((6-aminopyridin-3-yl)oxy)-N-(1-methoxy-2-methylpropan-2-yl)-1-(4-methoxybenzyl)-1H-pyrazolo[3,4-b]pyridin-3-amine (0.033 g, 0.037 mmol, 34% yield).

Preparation 53

(R)-2-((4-(4-amino-2-fluorophenoxy)-1-(4-methoxybenzyl)-1H-pyrazolo[3,4-b]pyridin-3-yl)amino)propan-1-ol

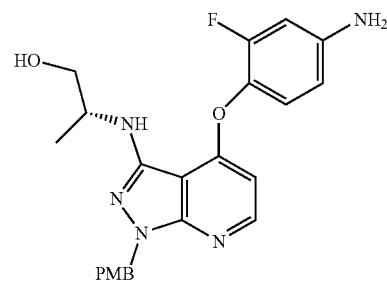

3-Fluoro-4-((3-iodo-1-(4-methoxybenzyl)-1H-pyrazolo[3,4-b]pyridin-4-yl)oxy)aniline (Preparation 1; 1.0 g, 2.04 mmol), K₂CO₃ (2.26 g, 16.3 mmol) and pyrrole-2-carboxylic acid (113 mg, 1.02 mmol) were suspended in DMSO (20 mL) and the mixture was degassed for 5 min with Ar. Cu(I)iodide (194 mg, 1.02 mmol) and D-alaninol (476 µL, 6.12 mmol) were added and the mixture heated to 60° C. in a sealed tube overnight. The mixture was cooled and partitioned between water (100 mL) and EtOAc (100 mL) and the aqueous layer was extracted with EtOAc (2×50 mL). The combined organic phases were washed with water (5×30 mL) and brine (30 mL), dried over Na₂SO₄, filtered and concentrated. The residue was purified over silica gel (0-3% MeOH in DCM) to afford (R)-2-((4-(4-amino-2-fluorophenoxy)-1-(4-methoxybenzyl)-1H-pyrazolo[3,4-b]pyridin-3-yl)amino)propan-1-ol (0.716 g, 80%) as a light brown foam.

The following compounds were also made using the procedure according to Preparation 53.

| Preparation | Structure | Name |
|---|---|---|
| 54 | ![structure] | (S)-2-((4-(4-amino-2-fluorophenoxy)-1-(4-methoxybenzyl)-1H-pyrazolo[3,4-b]pyridin-3-yl)amino)propan-1-ol |
| 55 | ![structure] | (S)-4-(4-amino-2-fluorophenoxy)-1-(4-methoxybenzyl)-N-(1-methoxypropan-2-yl)-1H-pyrazolo[3,4-b]-pyridin-3-amine |

| Preparation | Structure | Name |
|---|---|---|
| 56 | 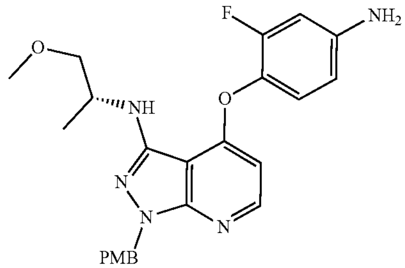 | (R)-4-(4-amino-2-fluorophenoxy)-1-(4-methoxybenzyl)-N-(1-methoxypropan-2-yl)-1H-pyrazolo[3,4-b]pyridin-3-amine |
| 57 | 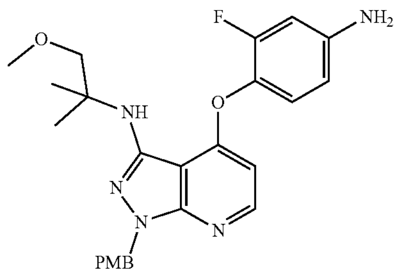 | 4-(4-amino-2-fluorophenoxy)-N-(1-methoxy-2-methylpropan-2-yl)-1-(4-methoxybenzyl)-1H-pyrazolo[3,4-b]pyridin-3-amine |
| 58 | 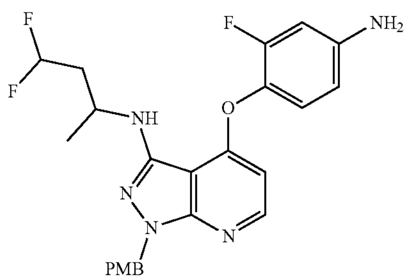 | 4-(4-amino-2-fluorophenoxy)-N-(4,4-difluorobutan-2-yl)-1-(4-methoxybenzyl)-1H-pyrazolo[3,4-b]pyridin-3-amine |
| 59 | 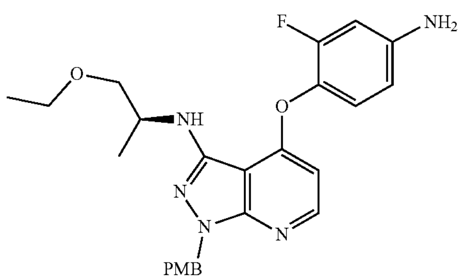 | (S)-4-(4-amino-2-fluorophenoxy)-N-(1-ethoxypropan-2-yl)-1-(4-methoxybenzyl)-1H-pyrazolo[3,4-b]pyridin-3-amine |

Preparation 60

(R)-2-((4-((6-aminopyridin-3-yl)oxy)-1-(4-methoxybenzyl)-1H-pyrazolo[3,4-b]pyridin-3-yl)amino)propan-1-ol

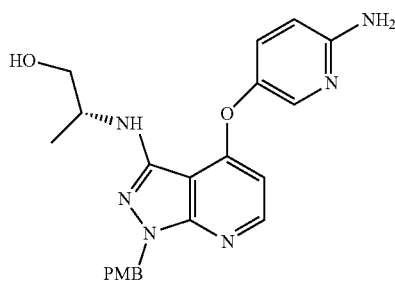

Step A: D-Alaninol (0.142 ml, 1.83 mmol), 4-((6-chloropyridin-3-yl)oxy)-3-iodo-1-(4-methoxybenzyl)-1H-pyrazolo[3,4-b]pyridine (0.300 g, 0.609 mmol), $K_2CO_3$ (0.673 g, 4.87 mmol) and pyrrole-2-carboxylic acid (0.0338 g, 0.304 mmol) were suspended in DMSO (6.09 ml, 0.609 mmol) and then this mixture was degassed for 5 min with Ar. Copper(I) iodide (0.0483 g, 0.254 mmol) was added and heated to 60° C. under argon overnight. The cooled reaction mixture was added to 25 mL cold water while stirring, the resultant solids were filtered and washed with 10 mL hexanes. The solids were purified over silica gel (10-100% EtOAc in hexanes) to afford (R)-2-((4-((6-chloropyridin-3-yl)oxy)-1-(4-methoxybenzyl)-1H-pyrazolo[3,4-b]pyridin-3-yl)amino)propan-1-ol (0.155 g, 0.352 mmol, 57.9% yield) as a clear oil.

Step B: (R)-2-((4-((6-chloropyridin-3-yl)oxy)-1-(4-methoxybenzyl)-1H-pyrazolo[3,4-b]pyridin-3-yl)amino)propan-1-ol (0.155 g, 0.352 mmol) was dissolved in DMF (3.52 ml, 0.352 mmol), cooled to 0° C. and then treated with imidazole (0.0360 g, 0.529 mmol) followed by tert-butyldimethylsilyl chloride (0.0797 g, 0.529 mmol). The mixture was allowed to warm to room temperature over 1 h. The reaction mixture was partitioned between water and EtOAc, washed with water and brine, dried over sodium sulfate, filtered and concentrated to afford (R)—N-(1-((tert-butyldimethylsilyl)oxy)propan-2-yl)-4-((6-chloropyridin-3-yl)oxy)-1-(4-methoxybenzyl)-1H-pyrazolo[3,4-b]pyridin-3-amine (0.218 g, 0.393 mmol, 112% yield) as a clear oil.

Step C: To a mixture of tert-butyl carbamate (0.277 g, 2.36 mmol), Cs$_2$CO$_3$ (0.256 g, 0.787 mmol), tris(dibenzylideneacetone)dipalladium (0) (0.0360 g, 0.0393 mmol), and 2-(dicyclohexylphosphino)-2',4',6'-tri-1-propyl-1,1'-biphenyl (0.0375 g, 0.0787 mmol) was added a solution of (R)—N-(1-((tert-butyldimethylsilyl)oxy)propan-2-yl)-4-((6-chloropyridin-3-yl)oxy)-1-(4-methoxybenzyl)-1H-pyrazolo[3,4-b]pyridin-3-amine (0.218 g, 0.393 mmol) in 1,4-dioxane (3.9 ml). This mixture was degassed for 2 min with Ar and heated to 100° C. for 16 h in a sealed tube. The reaction mixture was cooled and partitioned between EtOAc (2×25 mL) and water (25 mL), washed with brine (25 mL), dried over sodium sulfate, filtered and concentrated. The residue was purified over silica gel (10-50% EtOAc in hexanes) to afford tert-butyl (R)-(5-((3-((1-((tert-butyldimethylsilyl)oxy)propan-2-yl)amino)-1-(4-methoxybenzyl)-1H-pyrazolo[3,4-b]pyridin-4-yl)oxy)pyridin-2-yl)carbamate (0.147 g, 0.232 mmol, 58.9% yield) as a white solid.

Step D: To tert-butyl (R)-(5-((3-((1-((tert-butyldimethylsilyl)oxy)propan-2-yl)amino)-1-(4-methoxybenzyl)-1H-pyrazolo[3,4-b]pyridin-4-yl)oxy)pyridin-2-yl)carbamate (0.147 g, 0.232 mmol) was added 4N HCl in 1,4-dioxane (9.26 ml, 0.232 mmol) and the reaction mixture was stirred overnight. The reaction mixture was concentrated and partitioned between DCM and 1N NaOH, washed with water and brine, dried over sodium sulfate, filtered and concentrated to afford (R)-2-((4-((6-aminopyridin-3-yl)oxy)-1-(4-methoxybenzyl)-1H-pyrazolo[3,4-b]pyridin-3-yl)amino)propan-1-ol (0.091 g, 0.216 mmol, 93.5% yield).

The following compound was also made using the procedure according to Preparation 60.

Preparation 63

N-(3-fluoro-4-((3-iodo-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide

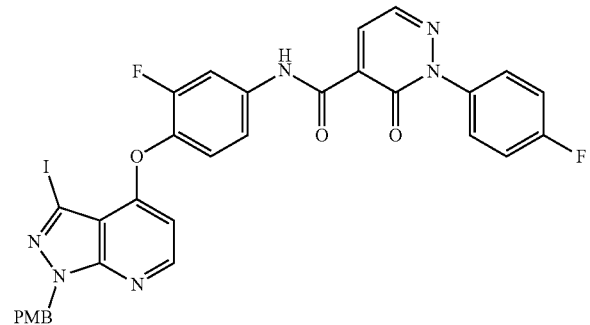

To a 200 mL flask was added 3-fluoro-4-((3-iodo-1-(4-methoxybenzyl)-1H-pyrazolo[3,4-b]pyridin-4-yl)oxy)aniline (5 g, 10.2 mmol), 2-(4-fluorophenyl)-3-oxo-2,3-dihydropyridazine-4-carboxylic acid (2.87 g, 12.2 mmol), 3-(((ethylimino)methylene)amino)-N,N-dimethylpropan-1-amine hydrochloride (2.93 g, 15.3 mmol), and 1H-benzo[d][1,2,3]triazol-1-ol (2.07 g, 15.3 mmol). DMF (50 mL) was stirred at room temperature for 1 h. The reaction mixture was poured into ice water (200 mL) and allowed to stir for 30 min. The precipitate was filtered and washed with water (100 mL) and hexanes (100 mL). The product was triturated with MeOH and dried to afford N-(3-fluoro-4-((3-iodo-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (6.68 g, 92%) as a yellow brown solid.

The following compound was also made using the procedure according to Preparation 63.

| Preparation | Structure | Name |
|---|---|---|
| 61 | ![structure] | 4-((6-aminopyridin-3-yl)oxy)-N-(4,4-difluorobutan-2-yl)-1-(4-methoxybenzyl)-1H-pyrazolo[3,4-b]pyridin-3-amine |
| 62 | ![structure] | (R)-4-((6-aminopyridin-3-yl)oxy)-1-(4-methoxybenzyl)-N-(1-methoxypropan-2-yl)-1H-pyrazolo[3,4-b]pyridin-3-amine |

| Preparation | Structure | Name |
|---|---|---|
| 64 | 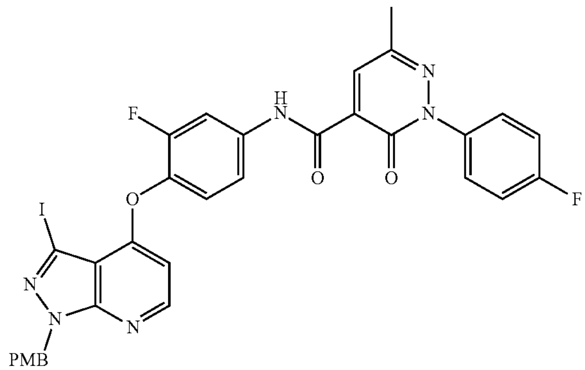 | N-(3-fluoro-4-((3-iodo-1-(4-methoxybenzyl)-1H-pyrazolo[3,4-b]-pyridin-4-yl)oxy)phenyl)-2-(4-fluorophenyl)-6-methyl-3-oxo-2,3-dihydropyridazine-4-carboxamide |

Preparation 65

N-(3-fluoro-4-((3-iodo-1-(4-methoxybenzyl)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide

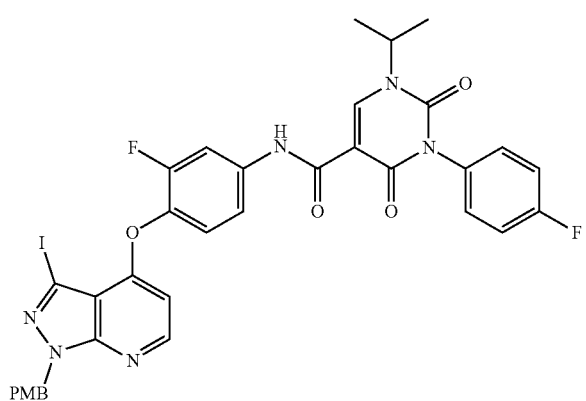

To a stirred solution of 3-(4-fluorophenyl)-1-isopropyl-2,4-dioxo-1,2,3,4-tetrahydropyrimidine-5-carboxylic acid (500 mg, 1.71 mmol) and HATU (0.887 g, 2.33 mmol) in DMF (10 mL) at room temperature was added DIEA (813 μL, 4.67 mmol) followed by 3-fluoro-4-((3-iodo-1-(4-methoxybenzyl)-1H-pyrazolo[3,4-b]pyridin-4-yl)oxy)aniline (762 mg, 1.56 mmol). The reaction mixture was stirred at room temperature overnight and partitioned between water (30 mL) and EtOAc (30 mL) and the aqueous layer was extracted with EtOAc (2×20 mL). The combined organic phases were washed with water (5×10 mL) and brine (10 mL), dried over $Na_2SO_4$, filtered and concentrated. The residue was purified over silica gel (30-100% EtOAc in hexanes) to afford N-(3-fluoro-4-((3-iodo-1-(4-methoxybenzyl)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (1.13 g, 95%).

The following compounds were also made using the procedure according to Preparation 65.

| Preparation | Structure | Name |
|---|---|---|
| 66 | 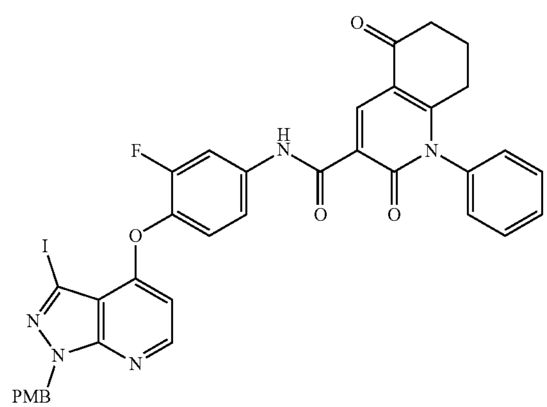 | N-(3-fluoro-4-((3-iodo-1-(4-methoxybenzyl)-1H-pyrazolo[3,4-b]pyridin-4-yl)oxy)phenyl)-2,5-dioxo-1-phenyl-1,2,5,6,7,8-hexahydroquinoline-3-carboxamide |

| Preparation | Structure | Name |
|---|---|---|
| 67 | 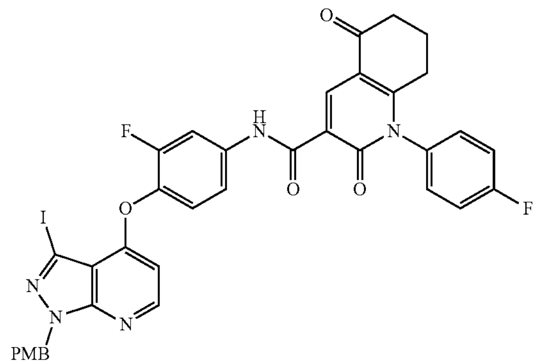 | N-(3-fluoro-4-((3-iodo-1-(4-methoxybenzyl)-1H-pyrazolo[3,4-b]pyridin-4-yl)oxy)phenyl)-1-(4-fluorophenyl)-2,5-dioxo-1,2,5,6,7,8-hexahydro-quinoline-3-carboxamide |

Example 1

N-(3-fluoro-4-((3-((2-hydroxyethyl)amino)-1H-pyrazolo[3,4-b]pyridin-4-yl)oxy)phenyl)-2-(4-fluorophenyl)-3-oxo-2,3-dihydropyridazine-4-carboxamide

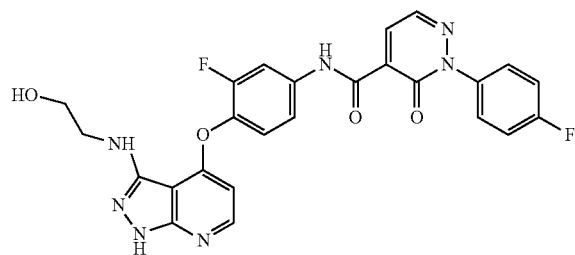 [SMILES: O=C(Nc1ccc(Oc2ccnc3[nH]nc(NCCO)c23)c(F)c1)c1ccnn(-c2ccc(F)cc2)c1=O]

Step A: Ethanolamine (0.0213 mL, 0.354 mmol), N-(3-fluoro-4-((3-iodo-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (Preparation 63; 0.050 g, 0.0708 mmol), $K_2CO_3$ (0.0489 g, 0.354 mmol) and L-proline (0.00407 g, 0.0354 mmol) were suspended in DMSO (0.708 mL) and degassed for 5 min with Ar. Copper(I) iodide (0.00674 g, 0.0354 mmol) was added and the reaction mixture was heated to 80° C. under argon overnight. The reaction mixture was partitioned between water (15 mL) and EtOAc (15 mL) and the combined the organic layers were washed with brine, dried over $Na_2SO_4$, filtered and concentrated to afford crude N-(3-fluoro-4-((3-((2-hydroxyethyl)amino)-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide, which was taken in the next step without further purification.

Step B: To a solution of crude N-(3-fluoro-4-((3-((2-hydroxyethyl)amino)-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (0.0453 g, 0.0708 mmol) in 2 mL DCM was added 4 mL TFA and the reaction mixture was stirred for 2 hr at 50° C. The reaction mixture was concentrated in vacuo and resuspended in 2 mL of a solution of 60:40 ACN: water with 2% TFA. The product was purified by C18 HPLC (5-95% ACN in water with 0.2% TFA). The fractions containing the product were free-based with saturated $NaHCO_3$ (15 mL) and the water layer was extracted with DCM (2×15 mL). The pooled organic layer was washed with brine (15 mL), dried over $Na_2SO_4$, filtered and concentrated in vacuo to afford N-(3-fluoro-4-((3-((2-hydroxyethyl)amino)-1H-pyrazolo[3,4-b]pyridin-4-yl)oxy)phenyl)-2-(4-fluorophenyl)-3-oxo-2,3-dihydropyridazine-4-carboxamide (0.0022 g, 0.00424 mmol, 5.98% yield) as an off-white solid. Mass spectrum: m/z=520.1 (M+H). $^1$H NMR ($d_6$-DMSO) δ 12.20 (s, 1H), 11.70 (s, 1H), 8.39 (d, 1H), 8.27 (d, 1H), 8.16 (s, 1H), 8.04 (d, 1H), 7.69 (m, 1H), 7.61 (m, 1H), 7.51 (t, 1H), 7.42 (m, 2H), 6.04 (d, 1H), 3.64 (t, 2H), 3.36 (t, 2H).

The following compounds were also synthesized using the procedure according to Example 1.

| Ex. No. | Structure | Name | Mass spectrum (apci) m/z |
|---|---|---|---|
| 2 | 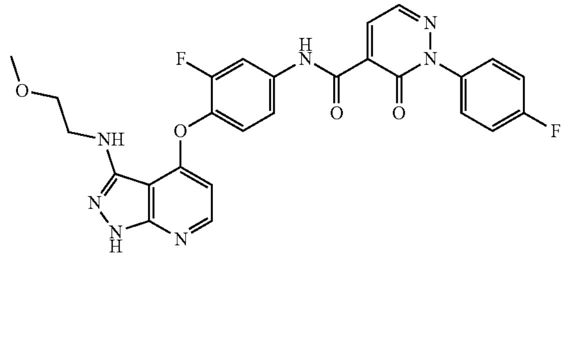 [SMILES: COCCNc1n[nH]c2nccc(Oc3ccc(NC(=O)c4ccnn(-c5ccc(F)cc5)c4=O)cc3F)c12] | N-(3-fluoro-4-((3-((2-methoxyethyl)amino)-1H-pyrazolo[3,4-b]pyridin-4-yl)oxy)phenyl)-2-(4-fluorophenyl)-3-oxo-2,3-dihydropyridazine-4-carboxamide | 534.1 (M + H) |

-continued

| Ex. No. | Structure | Name | Mass spectrum (apci) m/z |
|---|---|---|---|
| 3 | 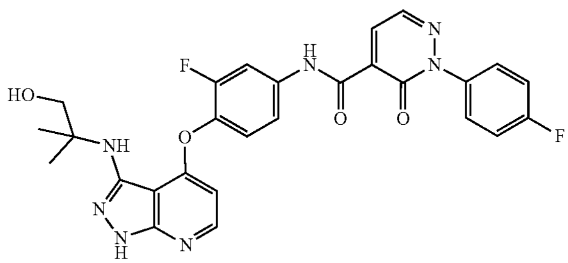 [SMILES: CC(C)(CO)Nc1n[nH]c2nccc(Oc3ccc(NC(=O)c4ccnn(-c5ccc(F)cc5)c4=O)cc3F)c12] | N-(3-fluoro-4-((3-((1-hydroxy-2-methyl-propan-2-yl)amino)-1H-pyrazolo[3,4-b]-pyridin-4-yl)oxy)-phenyl)-2-(4-fluoro-phenyl)-3-oxo-2,3-dihydropyridazine-4-carboxamide | 548.1 (M + H) |
| 4 | 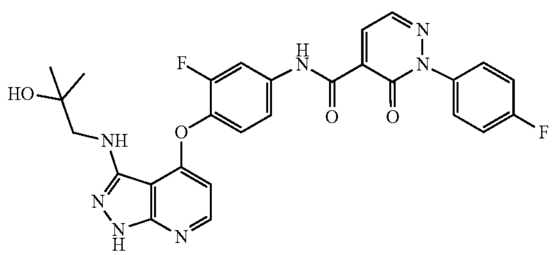 [SMILES: CC(C)(O)CNc1n[nH]c2nccc(Oc3ccc(NC(=O)c4ccnn(-c5ccc(F)cc5)c4=O)cc3F)c12] | N-(3-fluoro-4-((3-((2-hydroxy-2-methyl-propyl)amino)-1H-pyrazolo[3,4-b]-pyridin-4-yl)oxy)-phenyl)-2-(4-fluoro-phenyl)-3-oxo-2,3-dihydropyridazine-4-carboxamide | 548.2 (M + H) |
| 5 | 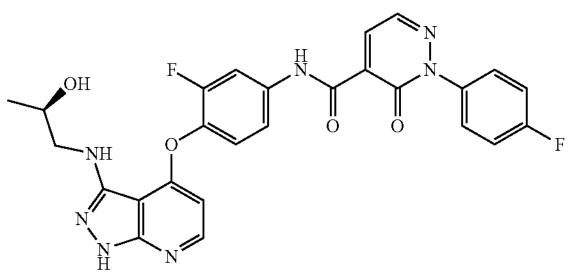 [SMILES: C[C@@H](O)CNc1n[nH]c2nccc(Oc3ccc(NC(=O)c4ccnn(-c5ccc(F)cc5)c4=O)cc3F)c12] | (R)-N-(3-fluoro-4-((3-((2-hydroxypropyl)-amino)-1H-pyrazolo-[3,4-b]pyridin-4-yl)-oxy)phenyl)-2-(4-fluorophenyl)-3-oxo-2,3-dihydropyrida-zine-4-carboxamide | 534.1 (M + H) |
| 6 | 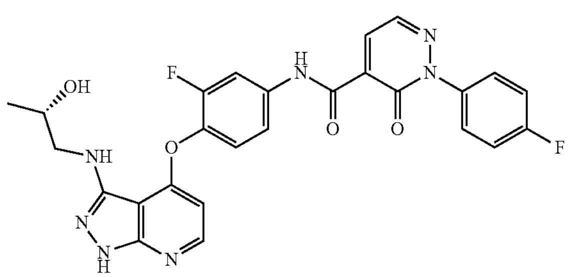 [SMILES: C[C@H](O)CNc1n[nH]c2nccc(Oc3ccc(NC(=O)c4ccnn(-c5ccc(F)cc5)c4=O)cc3F)c12] | (S)-N-(3-fluoro-4-((3-((2-hydroxypropyl)-amino)-1H-pyrazolo-[3,4-b]pyridin-4-yl)-oxy)phenyl)-2-(4-fluorophenyl)-3-oxo-2,3-dihydropyrida-zine-4-carboxamide | 534.1 (M + H) |
| 7 | 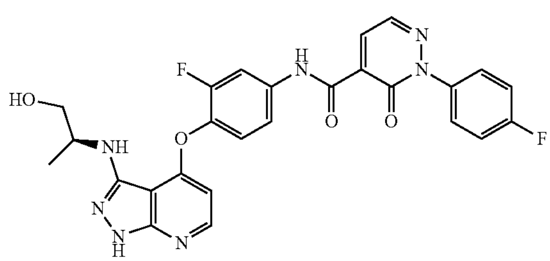 [SMILES: C[C@@H](CO)Nc1n[nH]c2nccc(Oc3ccc(NC(=O)c4ccnn(-c5ccc(F)cc5)c4=O)cc3F)c12] | (S)-N-(3-fluoro-4-((3-((1-hydroxypropan-2-yl)amino)-1H-pyrazolo[3,4-b]pyridin-4-yl)oxy)phenyl)-2-(4-fluorophenyl)-3-oxo-2,3-dihydropyridazine-4-carboxamide | 534.1 (M + H) |

| Ex. No. | Structure | Name | Mass spectrum (apci) m/z |
|---|---|---|---|
| 8 | 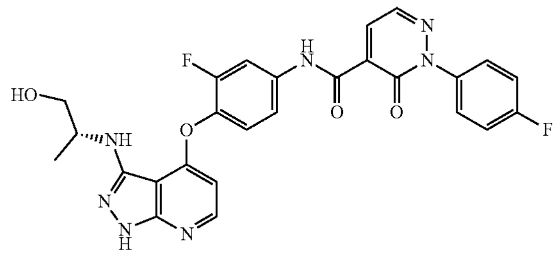 | (R)-N-(3-fluoro-4-((3-((1-hydroxypropan-2-yl)amino)-1H-pyrazolo[3,4-b]pyridin-4-yl)oxy)phenyl)-2-(4-fluorophenyl)-3-oxo-2,3-dihydropyridazine-4-carboxamide | 534.1 (M + H) |
| 9 | 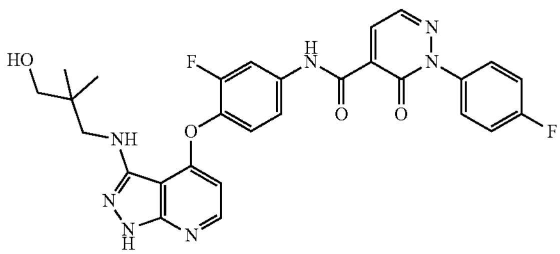 | N-(3-fluoro-4-((3-((3-hydroxy-2,2-dimethylpropyl)amino)-1H-pyrazolo[3,4-b]pyridin-4-yl)oxy)phenyl)-2-(4-fluorophenyl)-3-oxo-2,3-dihydropyridazine-4-carboxamide | 562.2 (M + H) |
| 10 | 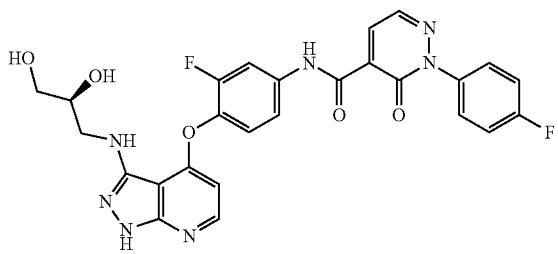 [SMILES: O=C(Nc1ccc(Oc2ccnc3[nH]nc(NC[C@H](O)CO)c23)c(F)c1)c1ccnn(-c2ccc(F)cc2)c1=O] | (S)-N-(4-((3-((2,3-dihydroxypropyl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 550.1 (M + H) |
| 11 | 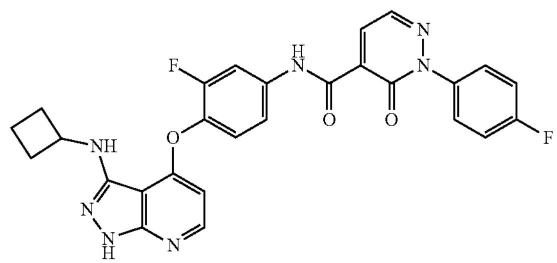 [SMILES: O=C(Nc1ccc(Oc2ccnc3[nH]nc(NC4CCC4)c23)c(F)c1)c1ccnn(-c2ccc(F)cc2)c1=O] | N-(4-((3-(cyclobutylamino)-1H-pyrazolo[3,4-b]pyridin-4-yl)oxy)-3-fluorophenyl)-2-(4-fluorophenyl)-3-oxo-2,3-dihydropyridazine-4-carboxamide | 530.2 (M + H) |
| 12 | 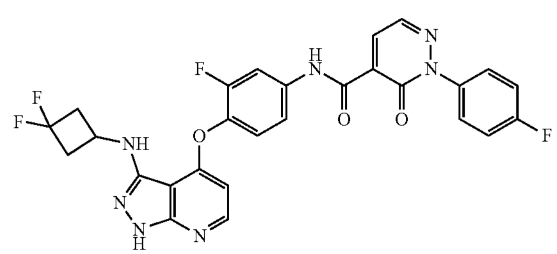 [SMILES: O=C(Nc1ccc(Oc2ccnc3[nH]nc(NC4CC(F)(F)C4)c23)c(F)c1)c1ccnn(-c2ccc(F)cc2)c1=O] | N-(4-((3-((3,3-difluorocyclobutyl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 566.2 (M + H) |
| 13 | 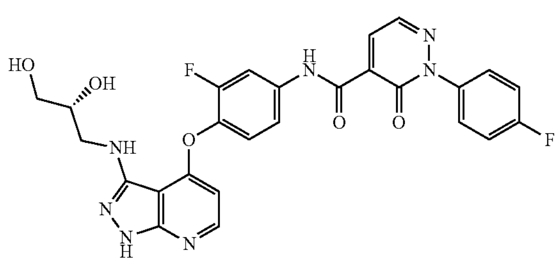 [SMILES: O=C(Nc1ccc(Oc2ccnc3[nH]nc(NC[C@@H](O)CO)c23)c(F)c1)c1ccnn(-c2ccc(F)cc2)c1=O] | (R)-N-(4-((3-((2,3-dihydroxypropyl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 550.2 (M + H) |

-continued

| Ex. No. | Structure | Name | Mass spectrum (apci) m/z |
|---|---|---|---|
| 14 | 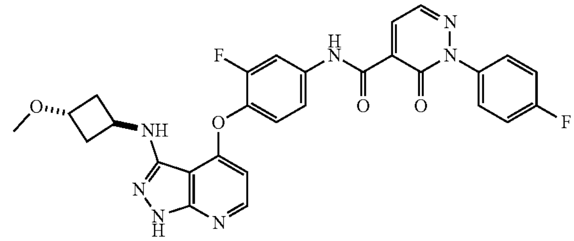 [SMILES: CO[C@H]1C[C@H](Nc2n[nH]c3nccc(Oc4ccc(NC(=O)c5ccnn(-c6ccc(F)cc6)c5=O)cc4F)c23)C1] | N-(3-fluoro-4-((3-(((1r,3r)-3-methoxy-cyclobutyl)amino)-1H-pyrazolo[3,4-b]-pyridin-4-yl)oxy)-phenyl)-2-(4-fluoro-phenyl)-3-oxo-2,3-dihydropyridazine-4-carboxamide | 560.2 (M + H) |
| 15 | 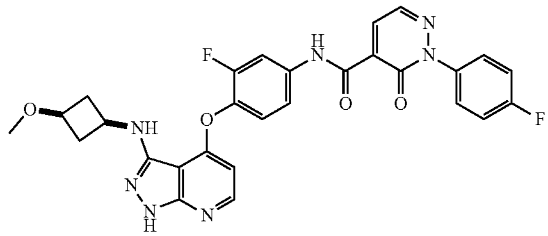 | N-(3-fluoro-4-((3-(((1s,3s)-3-methoxy-cyclobutyl)amino)-1H-pyrazolo[3,4-b]-pyridin-4-yl)oxy)-phenyl)-2-(4-fluoro-phenyl)-3-oxo-2,3-dihydropyridazine-4-carboxamide | 560.2 (M + H) |
| 16 | 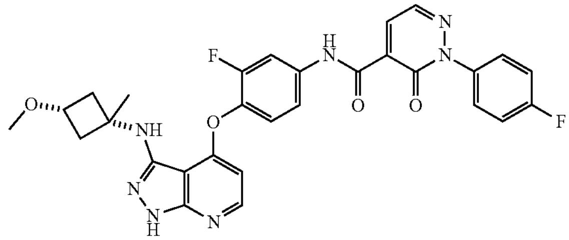 | N-(3-fluoro-4-((3-(((1s,3s)-3-hydroxy-1-methylcyclobutyl)-amino)-1H-pyrazolo-[3,4-b]pyridin-4-yl)-oxy)phenyl)-2-(4-fluorophenyl)-3-oxo-2,3-dihydropyridazine-4-carboxamide | 560.2 (M + H) |

Example 17

N-(3-fluoro-4-((3-((1-(methoxymethyl)cyclopropyl)amino)-1H-pyrazolo[3,4-b]pyridin-4-yl)oxy)phenyl)-2-(4-fluorophenyl)-3-oxo-2,3-dihydropyridazine-4-carboxamide

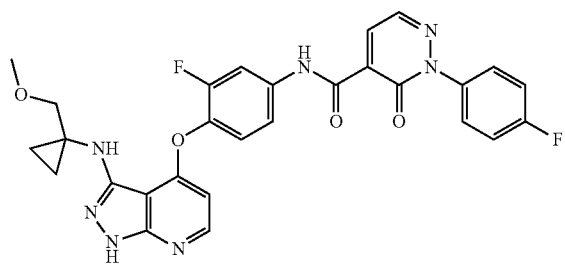 [SMILES: COCC1(Nc2n[nH]c3nccc(Oc4ccc(NC(=O)c5ccnn(-c6ccc(F)cc6)c5=O)cc4F)c23)CC1]

1-(Methoxymethyl)cyclopropan-1-amine hydrochloride (0.087 g, 0.637 mmol), N-(3-fluoro-4-((3-iodo-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (Preparation 63; 0.150 g, 0.212 mmol), $K_2CO_3$ (0.235 g, 1.70 mmol) and pyrrole-2-carboxylic acid (0.0118 g, 0.106 mmol) were suspended in DMSO (2.12 ml, 0.212 mmol) and the reaction mixture was degassed for 5 min with Ar. Copper(I) iodide (0.0202 g, 0.106 mmol) was added and the reaction mixture was heated to 60° C. under argon for 22 h. The mixture was partitioned between water and EtOAc, the aqueous phase was extracted with EtOAc and the combined organic layers were washed with brine (2×15 mL), dried over sodium sulfate, filtered and concentrated. The resulting oil was purified over silica gel (0-10% MeOH in DCM). The isolated product was suspended in 5 mL DCM and 10 mL TFA and stirred for 16 h at 50° C. The mixture was concentrated in vacuo and the residue was suspended in 2 mL of a solution of 60:40 ACN:water with 2% TFA. The product was purified by C18 HPLC (5-95% ACN in water with 0.2% TFA). The fractions containing the product were free-based with saturated $NaHCO_3$ (15 mL) and the aqueous phase was extracted with DCM (2×15 mL). The combined organic layers were washed with brine (15 mL), dried over sodium sulfate, filtered and concentrated to afford N-(3-fluoro-4-((3-((1-(methoxymethyl)cyclopropyl)amino)-1H-pyrazolo[3,4-b]pyridin-4-yl)oxy)phenyl)-2-(4-fluorophenyl)-3-oxo-2,3-dihydropyridazine-4-carboxamide (0.0221 g, 0.0395 mmol, 18.6% yield) as a yellow solid. Mass spectrum: m/z=560.2 (M+H). $^1$H NMR ($d_6$-DMSO) δ 12.23 (s, 1H), 11.69 (s, 1H), 8.38 (d, 1H), 8.26 (d, 1H), 8.14 (d, 1H), 8.02 (dd, 1H), 7.68 (m, 2H), 7.59 (m, 1H), 7.48 (t, 1H), 7.41 (m, 2H), 6.03 (m, 1H), 5.72 (s, 1H), 3.55 (s, 2H), 3.25 (s, 3H), 0.82 (m, 2H), 0.72 (m, 2H).

The following compounds were also synthesized using the procedure according to Example 17.

| Ex. No. | Structure | Name | Mass spectrum (apci) m/z |
|---|---|---|---|
| 18 | 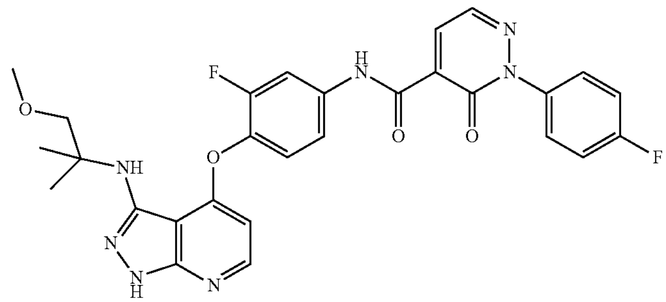 [SMILES: COCC(C)(C)Nc1n[nH]c2nccc(Oc3ccc(NC(=O)c4ccnn(-c5ccc(F)cc5)c4=O)cc3F)c12] | N-(3-fluoro-4-((3-((1-methoxy-2-methylpropan-2-yl)amino)-1H-pyrazolo[3,4-b]pyridin-4-yl)oxy)phenyl)-2-(4-fluorophenyl)-3-oxo-2,3-dihydropyridazine-4-carboxamide | 562.2 (M + H) |
| 19 | 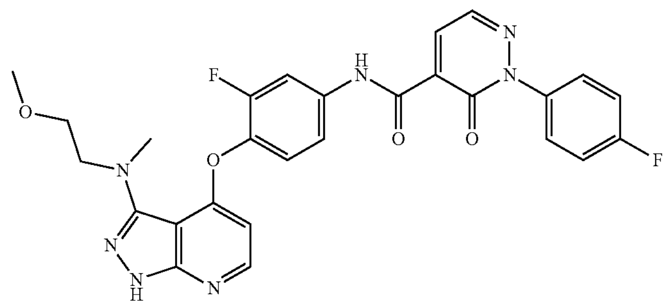 [SMILES: COCCN(C)c1n[nH]c2nccc(Oc3ccc(NC(=O)c4ccnn(-c5ccc(F)cc5)c4=O)cc3F)c12] | N-(3-fluoro-4-((3-((2-methoxyethyl)(methyl)amino)-1H-pyrazolo[3,4-b]pyridin-4-yl)oxy)phenyl)-2-(4-fluorophenyl)-3-oxo-2,3-dihydropyridazine-4-carboxamide | 548.1 (M + H) |
| 20 | 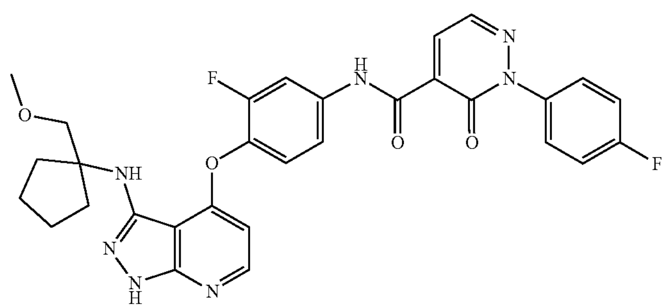 [SMILES: COCC1(Nc2n[nH]c3nccc(Oc4ccc(NC(=O)c5ccnn(-c6ccc(F)cc6)c5=O)cc4F)c23)CCCC1] | N-(3-fluoro-4-((3-((1-(methoxymethyl)cyclopentyl)amino)-1H-pyrazolo[3,4-b]pyridin-4-yl)oxy)phenyl)-2-(4-fluorophenyl)-3-oxo-2,3-dihydropyridazine-4-carboxamide | 588.2 (M + H) |
| 21 | 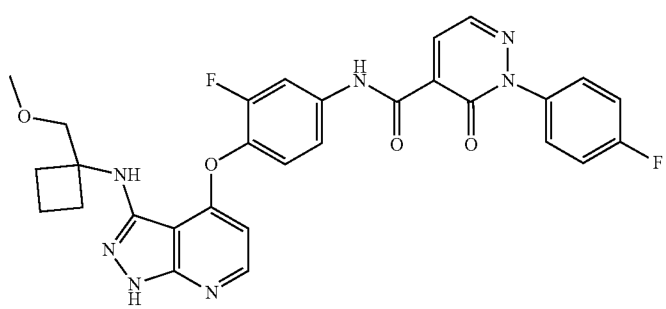 [SMILES: COCC1(Nc2n[nH]c3nccc(Oc4ccc(NC(=O)c5ccnn(-c6ccc(F)cc6)c5=O)cc4F)c23)CCC1] | N-(3-fluoro-4-((3-((1-(methoxymethyl)cyclobutyl)amino)-1H-pyrazolo[3,4-b]pyridin-4-yl)oxy)phenyl)-2-(4-fluorophenyl)-3-oxo-2,3-dihydropyridazine-4-carboxamide | 574.2 (M + H) |
| 22 | 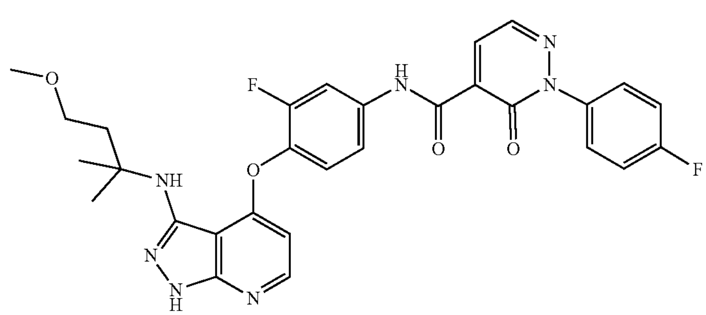 [SMILES: COCCC(C)(C)Nc1n[nH]c2nccc(Oc3ccc(NC(=O)c4ccnn(-c5ccc(F)cc5)c4=O)cc3F)c12] | N-(3-fluoro-4-((3-((4-methoxy-2-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 576.2 (M + H) |

-continued

| Ex. No. | Structure | Name | Mass spectrum (apci) m/z |
|---|---|---|---|
| 23 | 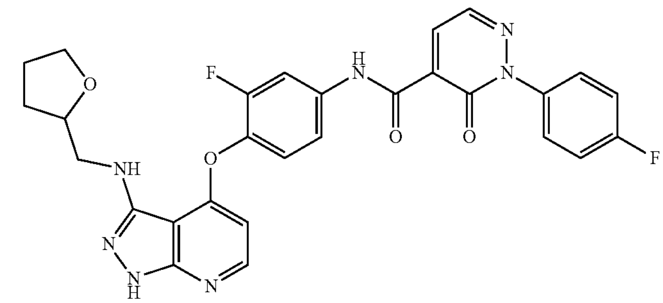 [SMILES: O=C(Nc1ccc(Oc2ccnc3[nH]nc(NCC4CCCO4)c23)c(F)c1)c1ccnn(-c2ccc(F)cc2)c1=O] | N-(3-fluoro-4-((3-(((tetrahydrofuran-2-yl)methyl)amino)-1H-pyrazolo[3,4-b]pyridin-4-yl)oxy)phenyl)-2-(4-fluorophenyl)-3-oxo-2,3-dihydropyridazine-4-carboxamide | 560.2 (M + H) |
| 24 | 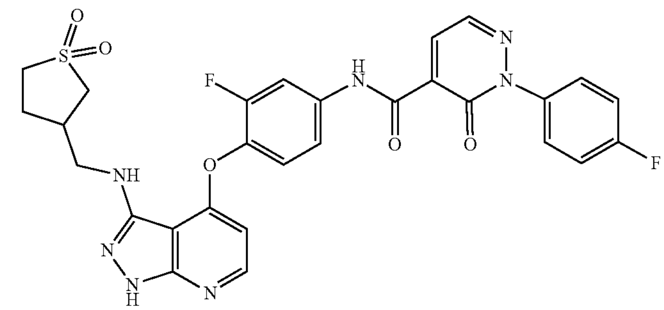 [SMILES: O=C(Nc1ccc(Oc2ccnc3[nH]nc(NCC4CCS(=O)(=O)C4)c23)c(F)c1)c1ccnn(-c2ccc(F)cc2)c1=O] | N-(4-((3-(((1,1-dioxidotetra-hydrothiophen-3-yl)methyl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 608.1 (M + H) |
| 25 | 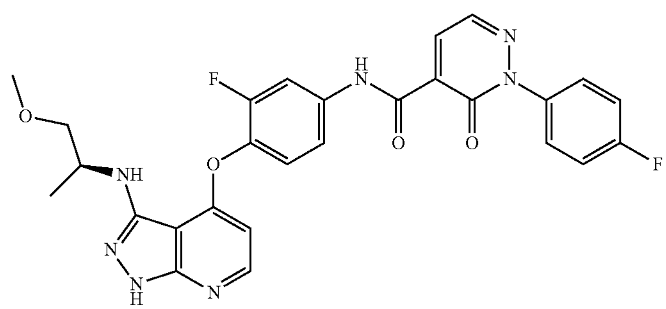 [SMILES: COC[C@H](C)Nc1n[nH]c2nccc(Oc3ccc(NC(=O)c4ccnn(-c5ccc(F)cc5)c4=O)cc3F)c12] | (S)-N-(3-fluoro-4-((3-((1-methoxypropan-2-yl)amino)-1H-pyrazolo[3,4-b]pyridin-4-yl)oxy)phenyl)-2-(4-fluorophenyl)-3-oxo-2,3-dihydropyridazine-4-carboxamide | 548.2 (M + H) |
| 26 | 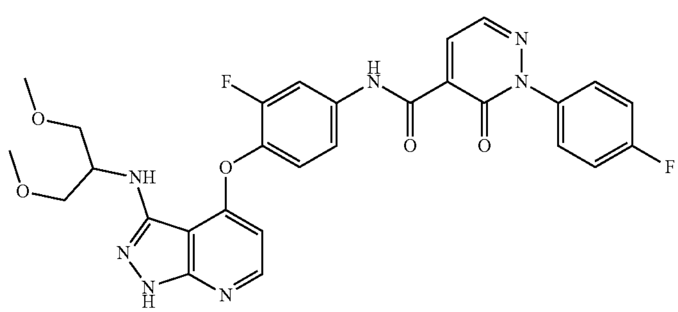 [SMILES: COCC(COC)Nc1n[nH]c2nccc(Oc3ccc(NC(=O)c4ccnn(-c5ccc(F)cc5)c4=O)cc3F)c12] | N-(4-((3-((1,3-dimethoxypropan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 578.2 (M + H) |
| 27 | 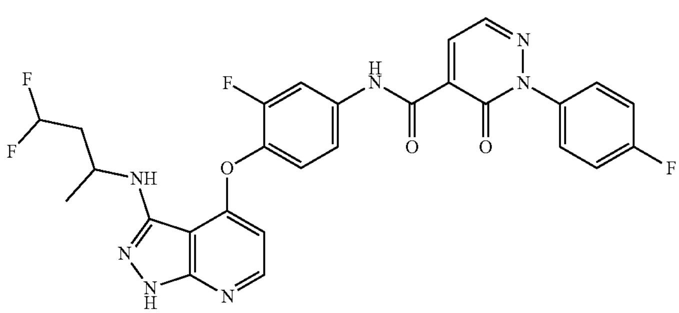 [SMILES: CC(CC(F)F)Nc1n[nH]c2nccc(Oc3ccc(NC(=O)c4ccnn(-c5ccc(F)cc5)c4=O)cc3F)c12] | N-(4-((3-((4,4-difluorobutan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 568.2 (M + H) |

| Ex. No. | Structure | Name | Mass spectrum (apci) m/z |
|---|---|---|---|
| 28 | 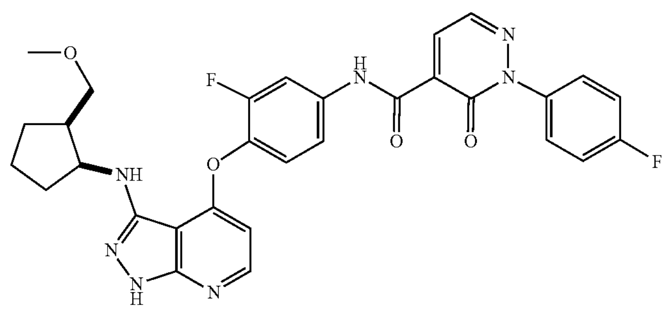 [SMILES: COC[C@@H]1CCC[C@@H]1Nc1n[nH]c2nccc(Oc3ccc(NC(=O)c4ccnn(-c5ccc(F)cc5)c4=O)cc3F)c12] | N-(3-fluoro-4-((3-((cis-2-(methoxymethyl)cyclopentyl)amino)-1H-pyrazolo[3,4-b]pyridin-4-yl)oxy)phenyl)-2-(4-fluorophenyl)-3-oxo-2,3-dihydropyridazine-4-carboxamide | 588.2 (M + H) |
| 29 | 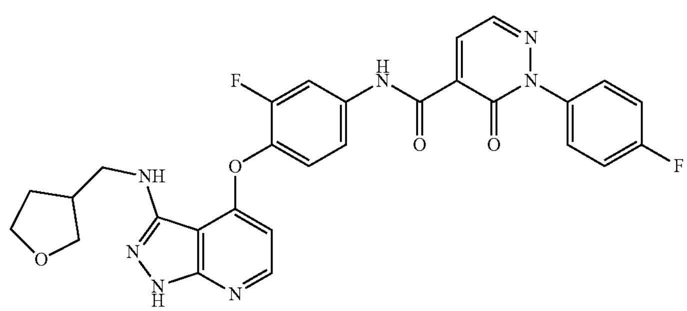 [SMILES: O=C(Nc1ccc(Oc2ccnc3[nH]nc(NCC4CCOC4)c23)c(F)c1)c1ccnn(-c2ccc(F)cc2)c1=O] | N-(3-fluoro-4-((3-(((tetrahydrofuran-3-yl)methyl)amino)-1H-pyrazolo[3,4-b]pyridin-4-yl)oxy)phenyl)-2-(4-fluorophenyl)-3-oxo-2,3-dihydropyridazine-4-carboxamide | 560.2 (M + H) |
| 30 | 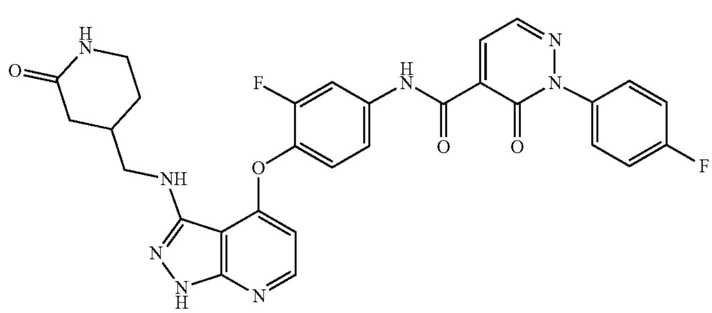 [SMILES: O=C1CC(CNc2n[nH]c3nccc(Oc4ccc(NC(=O)c5ccnn(-c6ccc(F)cc6)c5=O)cc4F)c23)CCN1] | N-(3-fluoro-4-((3-(((2-oxopiperidin-4-yl)methyl)amino)-1H-pyrazolo[3,4-b]pyridin-4-yl)oxy)phenyl)-2-(4-fluorophenyl)-3-oxo-2,3-dihydropyridazine-4-carboxamide | 587.2 (M + H) |
| 31 | 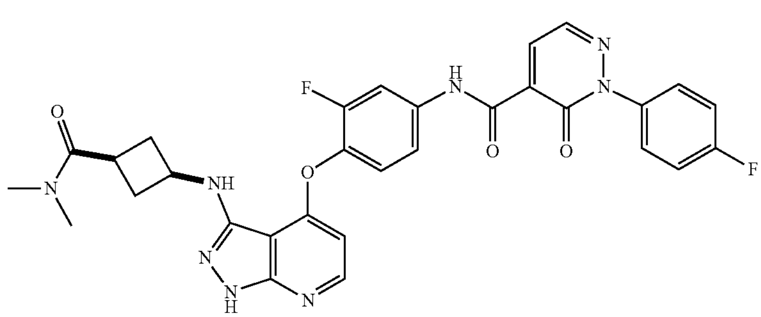 [SMILES: CN(C)C(=O)[C@H]1C[C@@H](Nc2n[nH]c3nccc(Oc4ccc(NC(=O)c5ccnn(-c6ccc(F)cc6)c5=O)cc4F)c23)C1] | N-(4-((3-(((1s,3s)-3-(dimethylcarbamoyl)cyclobutyl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 601.2 (M + H) |

Example 32

N-(4-((3-((1,3-dihydroxy-2-methylpropan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide

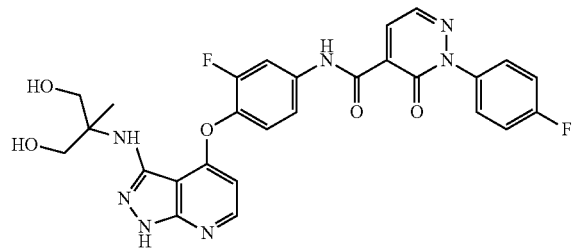 [SMILES: CC(CO)(CO)Nc1n[nH]c2nccc(Oc3ccc(NC(=O)c4ccnn(-c5ccc(F)cc5)c4=O)cc3F)c12]

2-Amino-2-methyl-1,3-propanediol (0.0670 g, 0.637 mmol), N-(3-fluoro-4-((3-iodo-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (Preparation 63; 0.150 g, 0.212 mmol), $K_2CO_3$ (0.235 g, 1.70 mmol) and pyrrole-2-carboxylic acid (0.0118 g, 0.106 mmol) were suspended in DMSO (2.12 ml, 0.212 mmol) and degassed for 5 min with Ar. Copper(I) iodide (0.0202 g, 0.106 mmol) was added and the reaction mixture was heated to 60° C. under argon for 22 h. To this mixture were added CuI 0.5 eq., pyrrole-2-carboxylic acid (0.5 eq.) and 1 eq. of 2-amino-2-methyl-1,3-propanediol and the reaction mixture was stirred at 70° C. for 16 h. The reaction mixture was cooled, then partitioned between water and EtOAc. The aqueous phase was extracted with EtOAc and the combined organic layers were washed with brine, dried over sodium sulfate, filtered and concentrated in vacuo. The resulting oil was purified over silica gel (30-100% EtOAc in hexanes). The isolated product was suspended in 2 mL DCM and 4 mL TFA and stirred for 16 h at 50° C. The mixture was concentrated in vacuo and the residue was suspended in 5 mL DCM and 5 mL 1M LiOH and stirred at room temperature for 30 min. The mixture was partitioned between saturated $NaHCO_3$ (15 mL) and DCM (15 mL). The aqueous phase was extracted with EtOAc (2×15 mL). The combined organic layers were washed with brine, dried over sodium sulfate, filtered and concentrated. The residue was suspended in 3 mL of a solution of 60:40 ACN:water with 2% TFA. The product was purified via C18 chromatography (5-95% ACN in water with 0.2% TFA). The fractions containing the product were free-based with saturated $NaHCO_3$ (15 mL) and the aqueous phase was extracted with DCM. The combined organic layers were washed with brine, dried over sodium sulfate, filtered and concentrated to afford N-(4-((3-((1,3-dihydroxy-2-methylpropan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide (0.0127 g, 0.0225 mmol, 10.6% yield) as a yellow solid. Mass spectrum: m/z=564.2 (M+H). $^1$H NMR ($d_6$-DMSO) δ 12.21 (s, 1H), 11.70 (s, 1H), 8.38 (d, 1H), 8.26 (d, 1H), 8.15 (d, 1H), 8.03 (dd, 1H), 7.68 (m, 2H), 7.59 (m, 1H), 7.50 (t, 1H), 7.41 (m, 2H), 6.04 (dd, 1H), 5.24 (s, 1H), 4.87 (t, 2H), 3.65 (dd, 2H), 3.50 (dd, 2H), 1.32 (s, 3H).

The following compounds were also synthesized using the procedure according to Example 32.

| Ex. No. | Structure | Name | Mass spectrum (apci) m/z |
|---|---|---|---|
| 33 | 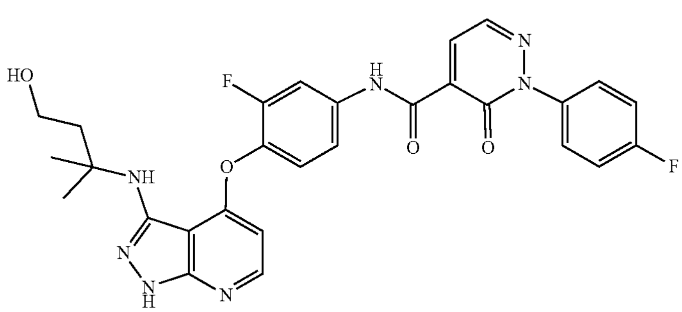 [SMILES: CC(C)(CCO)Nc1n[nH]c2nccc(Oc3ccc(NC(=O)c4ccnn(-c5ccc(F)cc5)c4=O)cc3F)c12] | N-(3-fluoro-4-((3-((4-hydroxy-2-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 562.2 (M + H) |
| 34 | 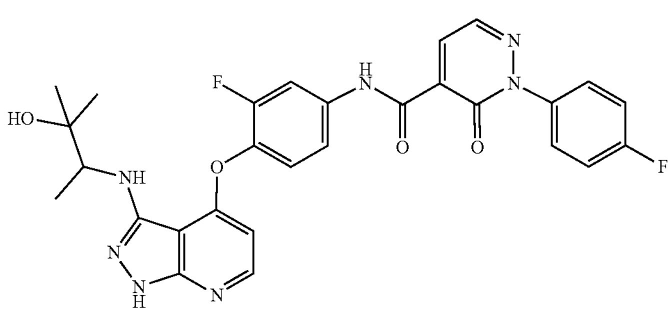 [SMILES: CC(Nc1n[nH]c2nccc(Oc3ccc(NC(=O)c4ccnn(-c5ccc(F)cc5)c4=O)cc3F)c12)C(C)(C)O] | N-(3-fluoro-4-((3-((3-hydroxy-3-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 562.1 (M + H) |

| Ex. No. | Structure | Name | Mass spectrum (apci) m/z |
|---|---|---|---|
| 35 | 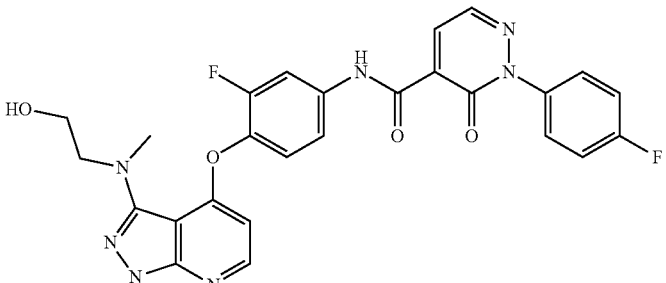 | N-(3-fluoro-4-((3-((2-hydroxyethyl)(methyl)amino)-1H-pyrazolo[3,4-b]pyridin-4-yl)oxy)phenyl)-2-(4-fluorophenyl)-3-oxo-2,3-dihydropyridazine-4-carboxamide | 534.1 (M + H) |
| 36 | 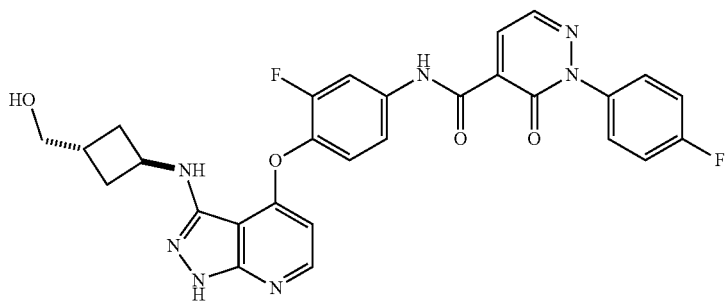 [SMILES: O=C(Nc1ccc(Oc2ccnc3[nH]nc(N[C@H]4C[C@H](CO)C4)c23)c(F)c1)c1ccnn(-c2ccc(F)cc2)c1=O] | N-(3-fluoro-4-((3-(((1r,3r)-3-(hydroxymethyl)cyclobutyl)amino)-1H-pyrazolo[3,4-b]pyridin-4-yl)oxy)phenyl)-2-(4-fluorophenyl)-3-oxo-2,3-dihydropyridazine-4-carboxamide | 560.1 (M + H) |
| 37 | 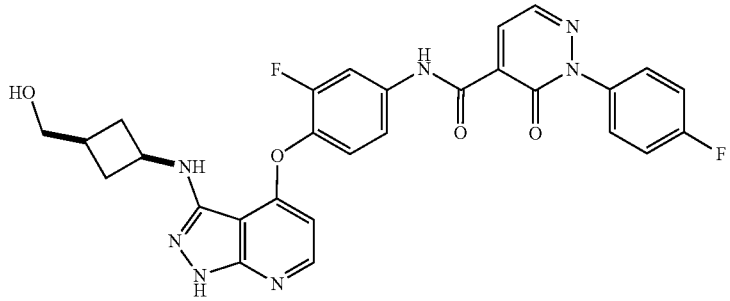 [SMILES: O=C(Nc1ccc(Oc2ccnc3[nH]nc(N[C@H]4C[C@@H](CO)C4)c23)c(F)c1)c1ccnn(-c2ccc(F)cc2)c1=O] | N-(3-fluoro-4-((3-(((1s,3s)-3-(hydroxymethyl)cyclobutyl)amino)-1H-pyrazolo[3,4-b]pyridin-4-yl)oxy)phenyl)-2-(4-fluorophenyl)-3-oxo-2,3-dihydropyridazine-4-carboxamide | 560.1 (M + H) |
| 38 | 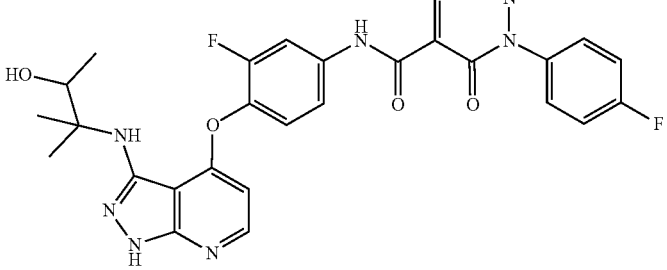 | N-(3-fluoro-4-((3-((3-hydroxy-2-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 562.2 (M + H) |
| 39 | 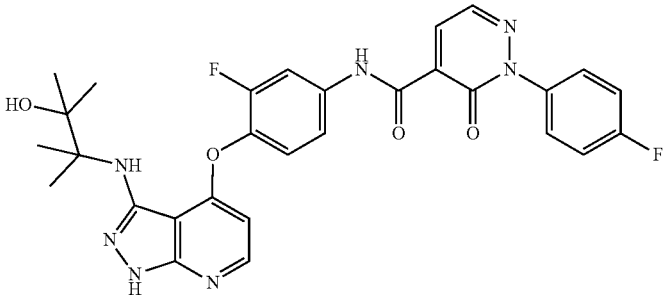 [SMILES: CC(C)(O)C(C)(C)Nc1n[nH]c2nccc(Oc3ccc(NC(=O)c4ccnn(-c5ccc(F)cc5)c4=O)cc3F)c12] | N-(3-fluoro-4-((3-((3-hydroxy-2,3-dimethylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 576.2 (M + H) |

-continued

| Ex. No. | Structure | Name | Mass spectrum (apci) m/z |
|---|---|---|---|
| 40 | 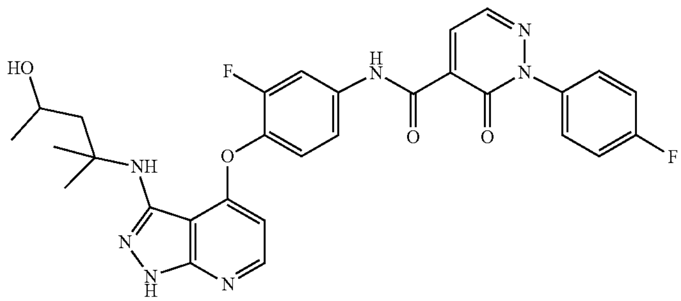 [SMILES: CC(O)CC(C)(C)Nc1n[nH]c2nccc(Oc3ccc(NC(=O)c4ccnn(-c5ccc(F)cc5)c4=O)cc3F)c12] | N-(3-fluoro-4-((3-((4-hydroxy-2-methylpentan-2-yl)amino)-1H-pyrazolo[3,4-b]pyridin-4-yl)oxy)phenyl)-2-(4-fluorophenyl)-3-oxo-2,3-dihydropyridazine-4-carboxamide | 576.2 (M + H) |
| 41 | 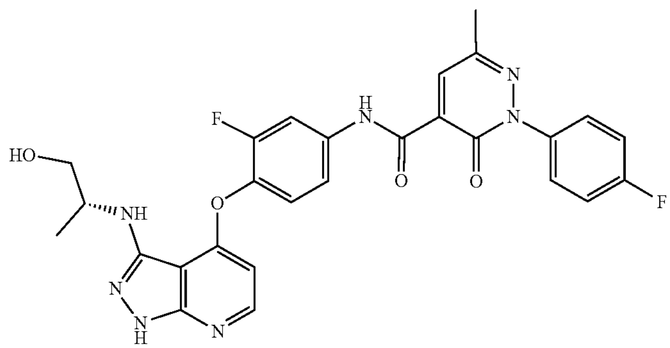 [SMILES: Cc1cc(C(=O)Nc2ccc(Oc3ccnc4[nH]nc(N[C@H](C)CO)c34)c(F)c2)c(=O)n(-c2ccc(F)cc2)n1] | (R)-N-(3-fluoro-4-((3-((1-hydroxypropan-2-yl)amino)-1H-pyrazolo[3,4-b]pyridin-4-yl)oxy)phenyl)-2-(4-fluorophenyl)-6-methyl-3-oxo-2,3-dihydropyridazine-4-carboxamide | 548.2 (M + H) |
| 42 | 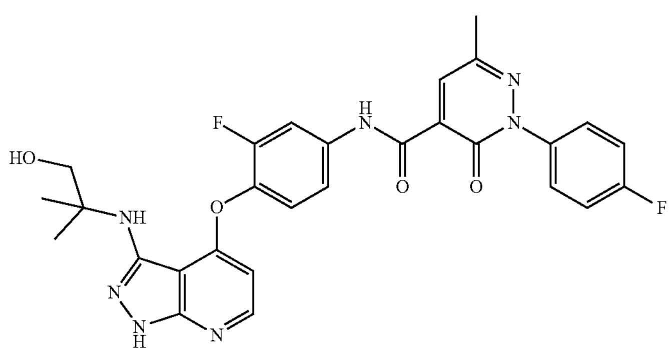 [SMILES: Cc1cc(C(=O)Nc2ccc(Oc3ccnc4[nH]nc(NC(C)(C)CO)c34)c(F)c2)c(=O)n(-c2ccc(F)cc2)n1] | N-(3-fluoro-4-((3-((1-hydroxy-2-methylpropan-2-yl)amino)-1H-pyrazolo[3,4-b]pyridin-4-yl)oxy)phenyl)-2-(4-fluorophenyl)-6-methyl-3-oxo-2,3-dihydropyridazine-4-carboxamide | 562.2 (M + H) |
| 43 | 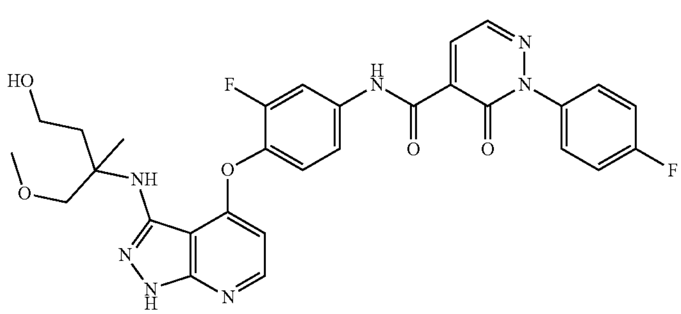 [SMILES: COCC(C)(CCO)Nc1n[nH]c2nccc(Oc3ccc(NC(=O)c4ccnn(-c5ccc(F)cc5)c4=O)cc3F)c12] | N-(3-fluoro-4-((3-((4-hydroxy-1-methoxy-2-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 592.2 (M + H) |

| Ex. No. | Structure | Name | Mass spectrum (apci) m/z |
|---|---|---|---|
| 44 | 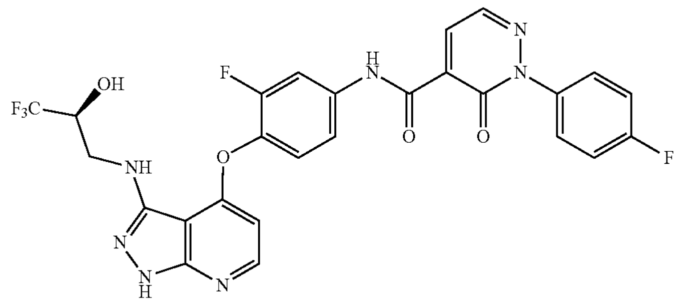 [SMILES: O=C(Nc1ccc(Oc2ccnc3[nH]nc(NC[C@H](O)C(F)(F)F)c23)c(F)c1)c1ccnn(-c2ccc(F)cc2)c1=O] | (S)-N-(3-fluoro-4-((3-((3,3,3-trifluoro-2-hydroxypropyl)amino)-1H-pyrazolo[3,4-b]pyridin-4-yl)oxy)phenyl)-2-(4-fluorophenyl)-3-oxo-2,3-dihydropyridazine-4-carboxamide | 588.1 (M + H) |
| 45 | 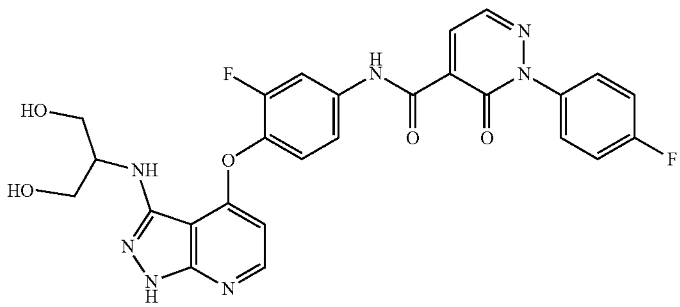 | N-(4-((3-((1,3-dihydroxypropan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 550.2 (M + H) |
| 46 | 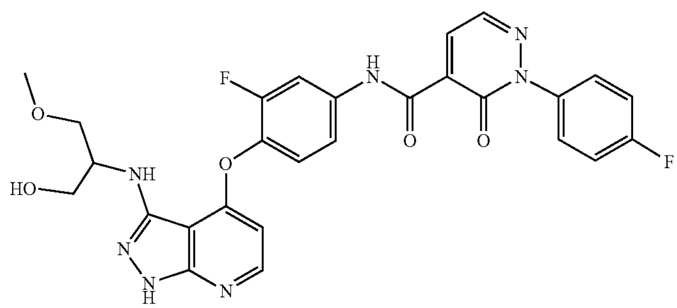 | N-(3-fluoro-4-((3-((1-hydroxy-3-methoxypropan-2-yl)amino)-1H-pyrazolo[3,4-b]pyridin-4-yl)oxy)phenyl)-2-(4-fluorophenyl)-3-oxo-2,3-dihydropyridazine-4-carboxamide | 554.1 (M + H) |
| 47 | 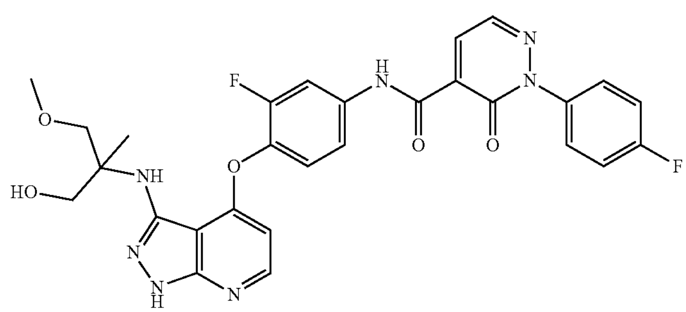 | N-(3-fluoro-4-((3-((1-hydroxy-3-methoxy-2-methylpropan-2-yl)amino)-1H-pyrazolo[3,4-b]pyridin-4-yl)oxy)phenyl)-2-(4-fluorophenyl)-3-oxo-2,3-dihydropyridazine-4-carboxamide | 578.2 (M + H) |
| 48 | 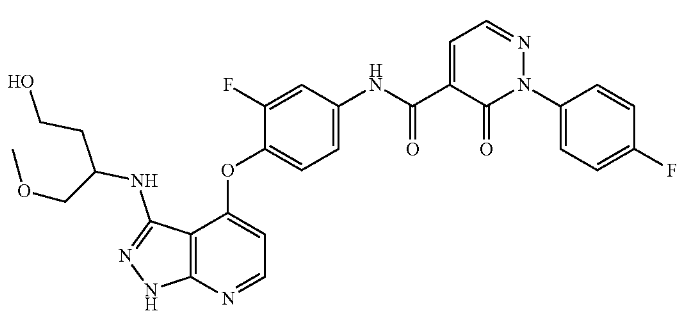 [SMILES: COCC(CCO)Nc1n[nH]c2nccc(Oc3ccc(NC(=O)c4ccnn(-c5ccc(F)cc5)c4=O)cc3F)c12] | N-(3-fluoro-4-((3-((4-hydroxy-1-methoxybutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 578.2 (M + H) |

| Ex. No. | Structure | Name | Mass spectrum (apci) m/z |
|---|---|---|---|
| 49 | 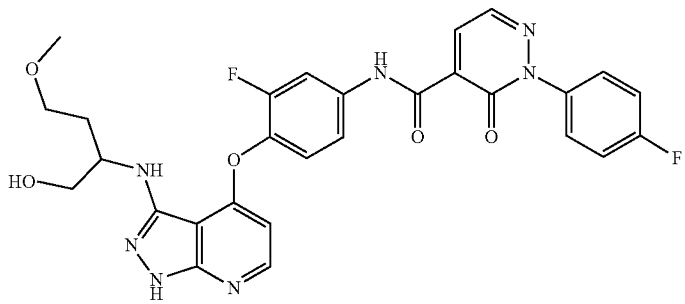 [SMILES: COCCC(CO)Nc1n[nH]c2nccc(Oc3ccc(NC(=O)c4ccnn(-c5ccc(F)cc5)c4=O)cc3F)c12] | N-(3-fluoro-4-((3-((1-hydroxy-4-methoxybutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 578.2 (M + H) |
| 50 | 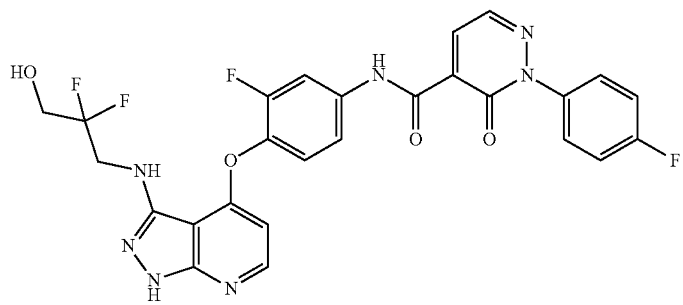 [SMILES: O=C(Nc1ccc(Oc2ccnc3[nH]nc(NCC(F)(F)CO)c23)c(F)c1)c1ccnn(-c2ccc(F)cc2)c1=O] | N-(4-((3-((2,2-difluoro-3-hydroxypropyl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 570.2 (M + H) |
| 51 | 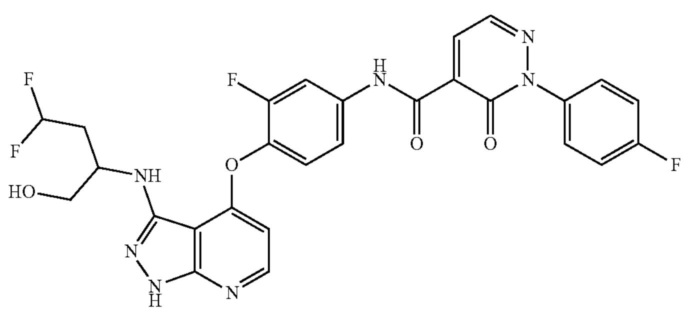 | N-(4-((3-((4,4-difluoro-1-hydroxybutan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 584.2 (M + H) |
| 52 | 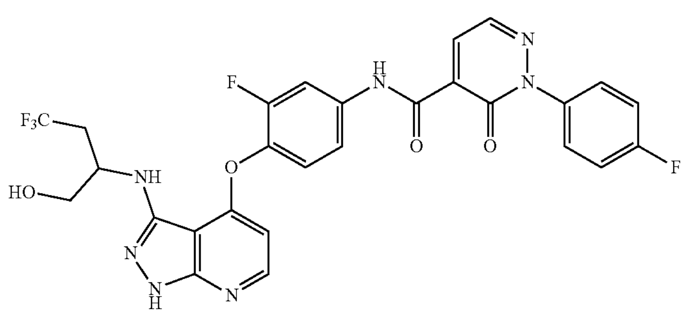 | N-(3-fluoro-4-((3-((4,4,4-trifluoro-1-hydroxybutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 602.2 (M + H) |

-continued

| Ex. No. | Structure | Name | Mass spectrum (apci) m/z |
|---|---|---|---|
| 53 | 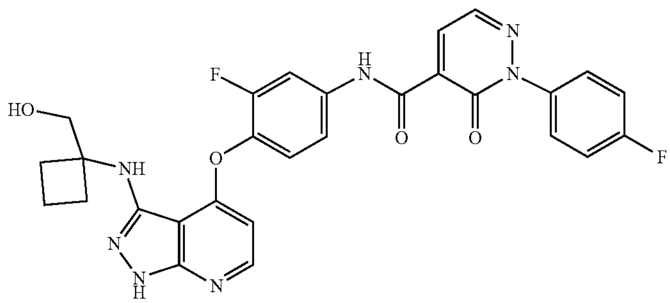 [SMILES: O=C(Nc1ccc(Oc2ccnc3[nH]nc(NC4(CO)CCC4)c23)c(F)c1)c1ccnn(-c2ccc(F)cc2)c1=O] | N-(3-fluoro-4-((3-((1-(hydroxymethyl)cyclobutyl)amino)-1H-pyrazolo[3,4-b]pyridin-4-yl)oxy)phenyl)-2-(4-fluorophenyl)-3-oxo-2,3-dihydropyridazine-4-carboxamide | 560.2 (M + H) |
| 54 | 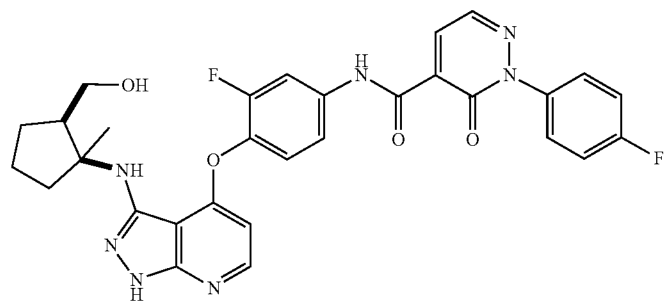 [SMILES: C[C@]1(Nc2n[nH]c3nccc(Oc4ccc(NC(=O)c5ccnn(-c6ccc(F)cc6)c5=O)cc4F)c23)CCC[C@H]1CO] | N-(3-fluoro-4-((3-(((1S,2R)-2-(hydroxymethyl)-1-methylcyclopentyl)amino)-1H-pyrazolo[3,4-b]pyridin-4-yl)oxy)phenyl)-2-(4-fluorophenyl)-3-oxo-2,3-dihydropyridazine-4-carboxamide | 588.2 (M + H) |
| 55 | 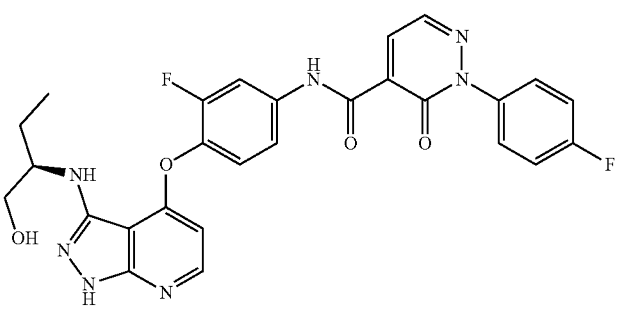 [SMILES: CC[C@H](CO)Nc1n[nH]c2nccc(Oc3ccc(NC(=O)c4ccnn(-c5ccc(F)cc5)c4=O)cc3F)c12] | (R)-N-(3-fluoro-4-((3-((1-hydroxybutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 548.2 (M + H) |
| 56 | 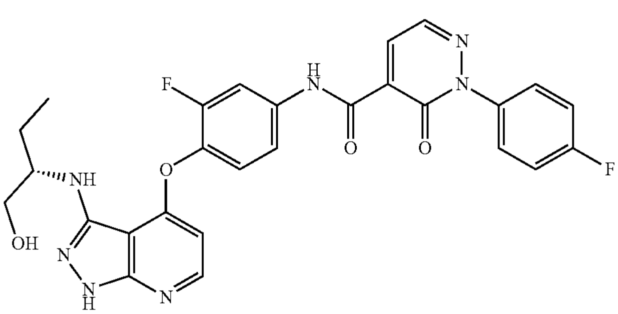 [SMILES: CC[C@@H](CO)Nc1n[nH]c2nccc(Oc3ccc(NC(=O)c4ccnn(-c5ccc(F)cc5)c4=O)cc3F)c12] | (S)-N-(3-fluoro-4-((3-((1-hydroxybutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 548.1 (M + H) |

Example 57

N-(3-fluoro-4-((3-((1-(hydroxymethyl)cyclopropyl)amino)-1H-pyrazolo[3,4-b]pyridin-4-yl)oxy)phenyl)-2-(4-fluorophenyl)-3-oxo-2,3-dihydropyridazine-4-carboxamide

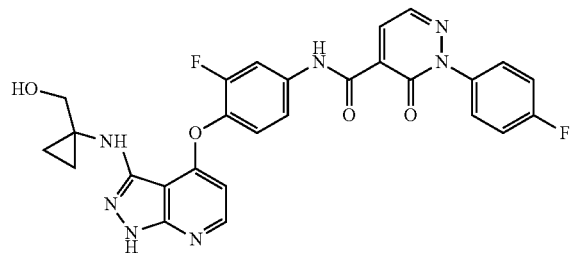 [SMILES: O=C(Nc1ccc(Oc2ccnc3[nH]nc(NC4(CO)CC4)c23)c(F)c1)c1ccnn(-c2ccc(F)cc2)c1=O]

Step A: N-(3-fluoro-4-((3-iodo-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (Preparation 63; 150 mg, 0.212 mmol), (1-aminocyclopropyl)methanol hydrochloride (26.2 mg, 0.212 mmol), 1H-pyrrole-2-carboxylic acid (11.8 mg, 0.106 mmol), and K$_2$CO$_3$ (235 mg, 1.70 mmol) were suspended in DMSO (2 mL) and nitrogen bubbled through the mixture for 5 min. Copper(I) iodide (20.2 mg, 0.106 mmol) was added and the reaction mixture was heated to 60° C. overnight. The reaction mixture was cooled to room temperature, diluted with water (10 mL), stirred for 10 min, and then filtered. The isolated solids were suspended in DCM/MeOH, dried with sodium sulfate, filtered through Celite® and the filtrate was concentrated. The residue was purified over silica gel (10-100% EtOAc in hex) to afford N-(3-fluoro-4-((3-((1-(hydroxymethyl)cyclopropyl)amino)-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (75 mg, 0.113 mmol, 53.1% yield) as a yellow solid.

Step B: N-(3-fluoro-4-((3-((1-(hydroxymethyl)cyclopropyl)amino)-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (75 mg, 0.11 mmol) was dissolved in DCM (0.5 mL) and TFA (0.5 mL). The reaction mixture was heated to 50° C. overnight and then concentrated. The residue was dissolved in MeOH and excess was K$_2$CO$_3$ added. The mixture was stirred for 10 min, then partitioned between water and DCM. The organic layer was dried over sodium sulfate, filtered and concentrated. The residue was purified over silica gel (0 to 10% MeOH in DCM) to afford N-(3-fluoro-4-((3-((1-(hydroxymethyl)cyclopropyl)amino)-1H-pyrazolo[3,4-b]pyridin-4-yl)oxy)phenyl)-2-(4-fluorophenyl)-3-oxo-2,3-dihydropyridazine-4-carboxamide (33 mg, 0.060 mmol, 54% yield) as an orange solid. Mass spectrum: m/z=546.2 (M+H). $^1$H NMR (d$_6$-DMSO) δ 12.22 (s, 1H), 11.70 (s, 1H), 8.38 (d, 1H), 8.26 (d, 1H), 8.14 (d, 1H), 8.03 (dd, 1H), 7.68 (m, 2H), 7.59 (m, 1H), 7.48 (t, 1H), 7.41 (m, 2H), 6.03 (m, 1H), 5.76 (s, 1H), 3.59 (s, 2H), 0.75 (m, 4H).

The following compounds were also synthesized using the procedure according to Example 57.

| Ex. No. | Structure | Name | Mass spectrum (apci) m/z |
|---|---|---|---|
| 58 | 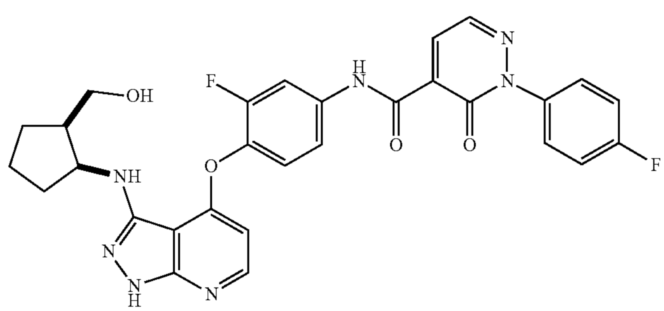 [SMILES: O=C(Nc1ccc(Oc2ccnc3[nH]nc(N[C@H]4CCC[C@H]4CO)c23)c(F)c1)c1ccnn(-c2ccc(F)cc2)c1=O] | N-(3-fluoro-4-((3-((cis-2-(hydroxymethyl)cyclopentyl)amino)-1H-pyrazolo[3,4-b]pyridin-4-yl)oxy)phenyl)-2-(4-fluorophenyl)-3-oxo-2,3-dihydropyridazine-4-carboxamide | 574.2 (M + H) |
| 59 | 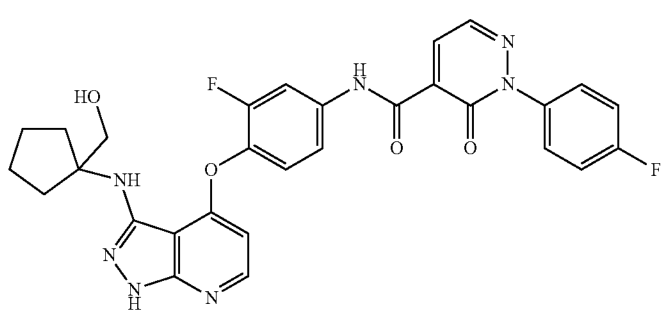 [SMILES: O=C(Nc1ccc(Oc2ccnc3[nH]nc(NC4(CO)CCCC4)c23)c(F)c1)c1ccnn(-c2ccc(F)cc2)c1=O] | N-(3-fluoro-4-((3-((1-(hydroxymethyl)cyclopentyl)amino)-1H-pyrazolo[3,4-b]pyridin-4-yl)oxy)phenyl)-2-(4-fluorophenyl)-3-oxo-2,3-dihydropyridazine-4-carboxamide | 574.2 (M + H) |

| Ex. No. | Structure | Name | Mass spectrum (apci) m/z |
|---|---|---|---|
| 60 | 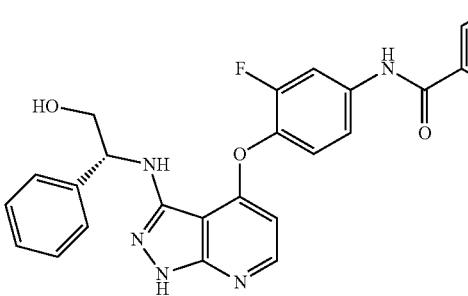 | (R)-N-(3-fluoro-4-((3-((2-hydroxy-1-phenylethyl)amino)-1H-pyrazolo[3,4-b]pyridin-4-yl)oxy)phenyl)-2-(4-fluorophenyl)-3-oxo-2,3-dihydropyridazine-4-carboxamide | 596.2 (M + H) |
| 61 | 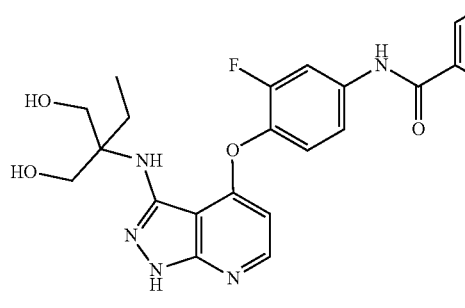 | N-(3-fluoro-4-((3-((1-hydroxy-2-(hydroxymethyl)butan-2-yl)amino)-1H-pyrazolo[3,4-b]pyridin-4-yl)oxy)phenyl)-2-(4-fluorophenyl)-3-oxo-2,3-dihydropyridazine-4-carboxamide | 578.2 (M + H) |
| 62 | 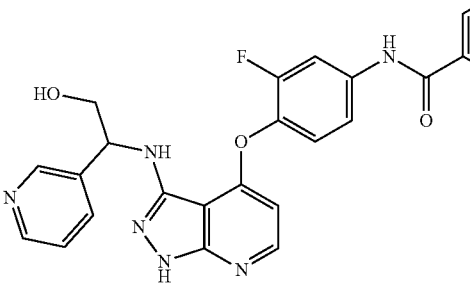 | N-(3-fluoro-4-((3-((2-hydroxy-1-(pyridin-3-yl)ethyl)amino)-1H-pyrazolo[3,4-b]pyridin-4-yl)oxy)phenyl)-2-(4-fluorophenyl)-3-oxo-2,3-dihydropyridazine-4-carboxamide | 597.2 (M + H) |
| 63 | 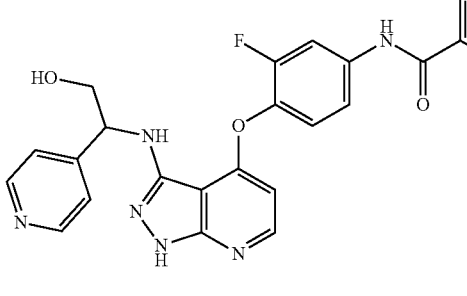 | N-(3-fluoro-4-((3-((2-hydroxy-1-(pyridin-4-yl)ethyl)amino)-1H-pyrazolo[3,4-b]pyridin-4-yl)oxy)phenyl)-2-(4-fluorophenyl)-3-oxo-2,3-dihydropyridazine-4-carboxamide | 597.2 (M + H) |
| 64 | 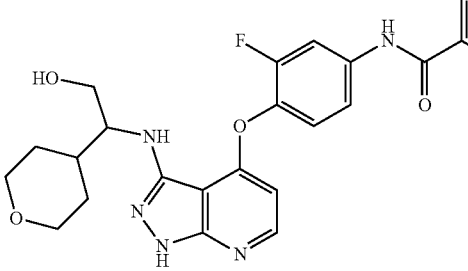 | N-(3-fluoro-4-((3-((2-hydroxy-1-(tetrahydro-2H-pyran-4-yl)ethyl)amino)-1H-pyrazolo[3,4-b]pyridin-4-yl)oxy)phenyl)-2-(4-fluorophenyl)-3-oxo-2,3-dihydropyridazine-4-carboxamide | 604.2 (M + H) |

-continued

| Ex. No. | Structure | Name | Mass spectrum (apci) m/z |
|---|---|---|---|
| 65 | 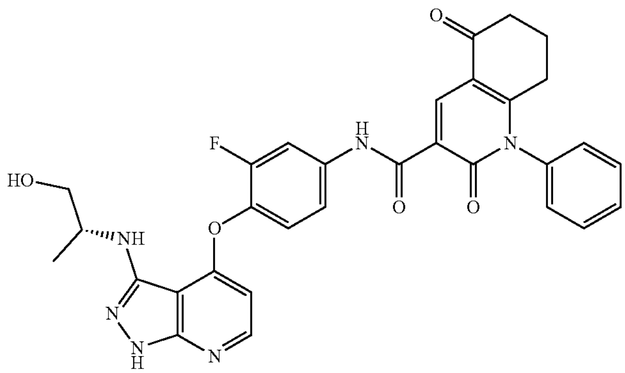 [SMILES: C[C@H](CO)Nc1n[nH]c2nccc(Oc3ccc(NC(=O)c4cc5c(n(-c6ccccc6)c4=O)CCCC5=O)cc3F)c12] | (R)-N-(3-fluoro-4-((3-((1-hydroxypropan-2-yl)amino)-1H-pyrazolo[3,4-b]pyridin-4-yl)oxy)phenyl)-2,5-dioxo-1-phenyl-1,2,5,6,7,8-hexahydroquinoline-3-carboxamide | 583.2 (M + H) |
| 66 | 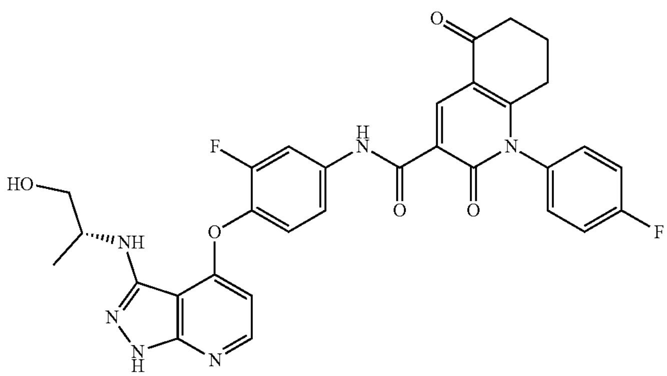 [SMILES: C[C@H](CO)Nc1n[nH]c2nccc(Oc3ccc(NC(=O)c4cc5c(n(-c6ccc(F)cc6)c4=O)CCCC5=O)cc3F)c12] | N-(3-fluoro-4-((3-iodo-1-(4-methoxybenzyl)-1H-pyrazolo[3,4-b]pyridin-4-yl)oxy)phenyl)-1-(4-fluorophenyl)-2,5-dioxo-1,2,5,6,7,8-hexahydroquinoline-3-carboxamide | 601.2 (M + H) |
| 67 | 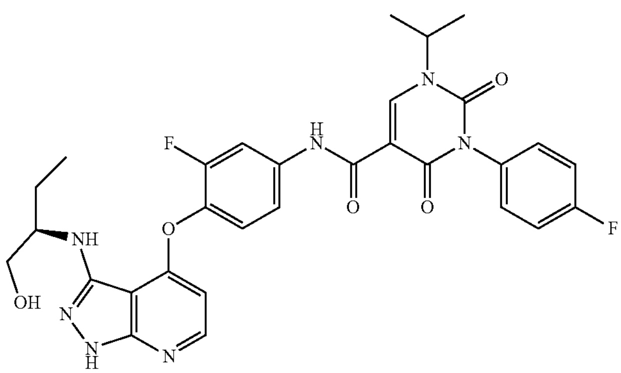 [SMILES: CC[C@H](CO)Nc1n[nH]c2nccc(Oc3ccc(NC(=O)c4cn(C(C)C)c(=O)n(-c5ccc(F)cc5)c4=O)cc3F)c12] | (R)-N-(3-fluoro-4-((3-((1-hydroxybutan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |
| 68 | 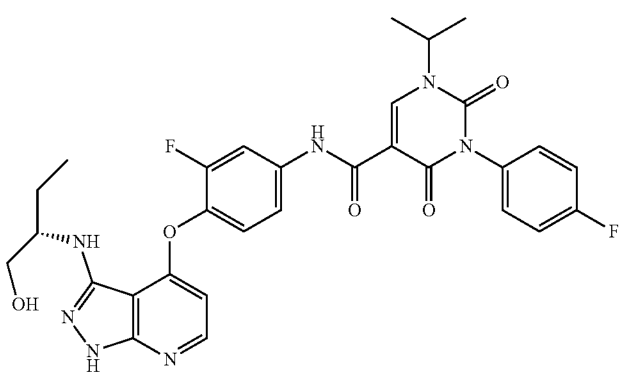 [SMILES: CC[C@@H](CO)Nc1n[nH]c2nccc(Oc3ccc(NC(=O)c4cn(C(C)C)c(=O)n(-c5ccc(F)cc5)c4=O)cc3F)c12] | (S)-N-(3-fluoro-4-((3-((1-hydroxybutan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |

| Ex. No. | Structure | Name | Mass spectrum (apci) m/z |
|---|---|---|---|
| 69 | 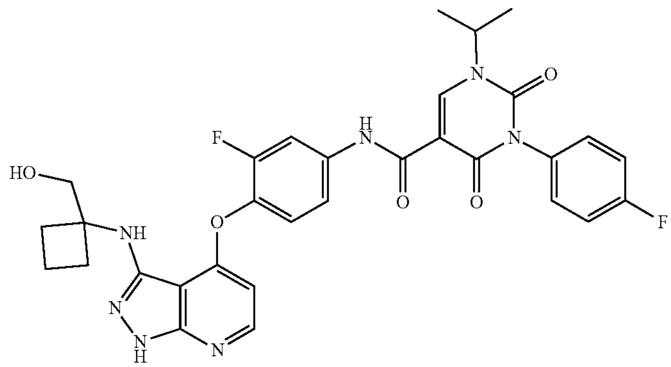 [SMILES: CC(C)n1cc(C(=O)Nc2ccc(Oc3ccnc4[nH]nc(NC5(CO)CCC5)c34)c(F)c2)c(=O)n(-c2ccc(F)cc2)c1=O] | N-(3-fluoro-4-((3-((1-(hydroxymethyl)cyclobutyl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 618.2 (M + H) |
| 70 | 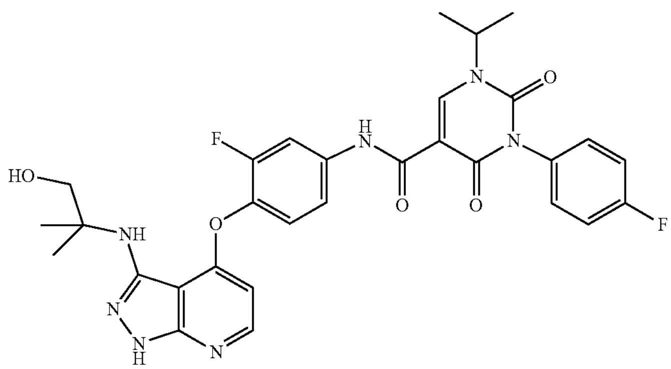 [SMILES: CC(C)n1cc(C(=O)Nc2ccc(Oc3ccnc4[nH]nc(NC(C)(C)CO)c34)c(F)c2)c(=O)n(-c2ccc(F)cc2)c1=O] | N-(3-fluoro-4-((3-((1-hydroxy-2-methylpropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |

Example 71

2-(4-fluorophenyl)-N-(5-((3-((1-methoxy-2-methylpropan-2-yl)amino)-1H-pyrazolo[3,4-b]pyridin-4-yl)oxy)pyridin-2-yl)-3-oxo-2,3-dihydropyridazine-4-carboxamide

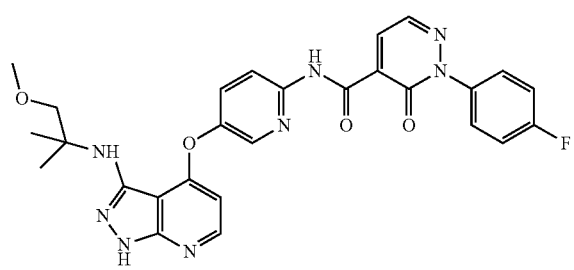 [SMILES: COCC(C)(C)Nc1n[nH]c2nccc(Oc3ccc(NC(=O)c4ccnn(-c5ccc(F)cc5)c4=O)nc3)c12]

To a mixture of 4-((6-aminopyridin-3-yl)oxy)-N-(1-methoxy-2-methylpropan-2-yl)-1-(4-methoxybenzyl)-1H-pyrazolo[3,4-b]pyridin-3-amine (Preparation 52; 0.033 g, 0.074 mmol), 2-(4-fluorophenyl)-3-oxo-2,3-dihydropyridazine-4-carboxylic acid (0.034 g, 0.15 mmol), EDCI (0.085 g, 0.44 mmol) and HOBt (0.060 g, 0.44 mmol) was added DMF (0.7 mL), and the reaction mixture was stirred for 2 h. The reaction mixture was diluted with water, stirred for 30 min and then filtered. The isolated solids were washed with water and hexanes. The solids were dissolved in TFA (2 mL) and heated to 50° C. overnight. The reaction mixture was concentrated and purified by C18 chromatography (5-95% ACN in water with 0.2% TFA). The fractions containing the product were free-based with saturated NaHCO$_3$ (30 mL) and the aqueous phase was extracted with DCM (2×15 mL). The combined organic layers were washed with saturated NaHCO$_3$ (15 mL) and brine (15 mL), dried over sodium sulfate, filtered and concentrated to afford 2-(4-fluorophenyl)-N-(5-((3-((1-methoxy-2-methylpropan-2-yl)amino)-1H-pyrazolo[3,4-b]pyridin-4-yl)oxy)pyridin-2-yl)-3-oxo-2,3-dihydropyridazine-4-carboxamide (0.0020 g, 0.0037 mmol, 5.0% yield). Mass spectrum: m/z=545.2 (M+H). $^1$H NMR (CDCl$_3$) δ 12.20 (s, 1H), 8.47 (d, 1H), 8.40 (d, 1H), 8.33 (d, 1H), 8.22 (d, 1H), 8.17 (m, 1H), 7.67-7.60 (m, 3H), 7.22 (m, 2H), 6.10 (d, 1H), 5.02 (br s, 1H), 3.52 (s, 2H), 3.36 (s, 3H), 1.47 (s, 6H).

Example 72

(R)—N-(3-fluoro-4-((3-((1-hydroxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide

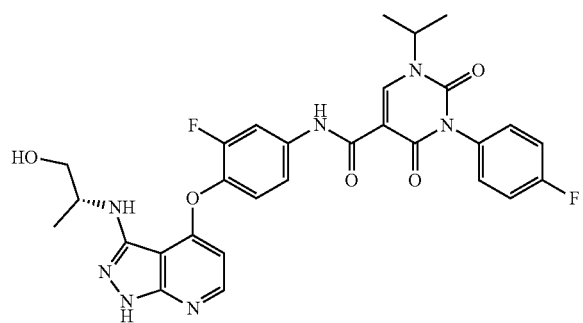

Step A: N-(3-fluoro-4-((3-iodo-1-(4-methoxybenzyl)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (Preparation 65; 200 mg, 0.26 mmol), D-Alaninol (61 µL, 0.785 mmol), K$_2$CO$_3$ (289 mg, 2.09 mmol) and pyrrole-2-carboxylic acid (0.0145 g, 0.131 mmol) were suspended in DMSO (5 mL) and the mixture was degassed for 5 min with Ar. Cu(I)iodide was added and the mixture was heated to 60° C. in a sealed tube overnight and then cooled to room temperature. The cooled mixture was partitioned between water (10 mL) and EtOAc (10 mL) and the aqueous layer was extracted with EtOAc (2×10 mL). The combined organic phases were washed with water (5×10 mL) and brine (10 mL), then dried over Na$_2$SO$_4$, filtered and concentrated. The residue was purified over silica gel (0-5% MeOH in DCM) to afford (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (98 mg, 53%) as a white solid.

Step B: To a solution of (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (98 mg, 0.14 mmol) in DCM (2 mL) was added TFA (4 mL). The mixture was stirred at 35° C. overnight. The mixture was concentrated and dried in vacuo. The residue was dissolved in MeOH/DCM, treated with K$_2$CO$_3$ (57 mg, 0.41 mmol) and stirred at RT for 4 h. The mixture was filtered and concentrated. The residue was purified over silica gel (0-7.5% MeOH in DCM) to afford (R)—N-(3-fluoro-4-((3-((1-hydroxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (68 mg, 83%) as a yellow solid. Mass spectrum: m/z=592.2 (M+H). $^1$H NMR (CDCl$_3$) δ 11.00 (s, 1H), 8.69 (s, 1H), 8.16 (d, 1H), 7.90 (dd, 1H), 7.30 (m, 1H), 7.27 (s, 2H), 7.25 (s, 2H), 7.22 (d, 1H), 6.12 (d, 1H), 4.98 (m, 1H), 4.02 (m, 1H), 3.83 (dd, 1H), 3.71 (dd, 1H), 1.51 (d, 6H), 1.34 (d, 3H).

The following compounds were also synthesized using the procedure according to Example 72.

| Ex. No. | Structure | Name | Mass Spectrum |
|---|---|---|---|
| 73 | 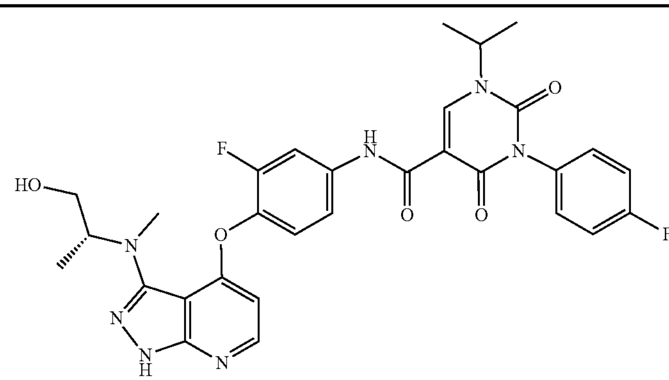 | (R)-N-(3-fluoro-4-((3-((1-hydroxypropan-2-yl)(methyl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |
| 74 | 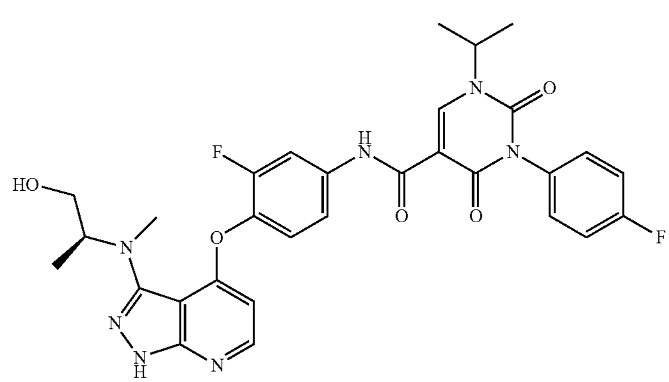 [SMILES: CC(C)n1cc(C(=O)Nc2ccc(Oc3ccnc4[nH]nc(N(C)[C@@H](C)CO)c34)c(F)c2)c(=O)n(-c2ccc(F)cc2)c1=O] | (S)-N-(3-fluoro-4-((3-((1-hydroxypropan-2-yl)(methyl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |

-continued

| Ex. No. | Structure | Name | Mass Spectrum |
|---|---|---|---|
| 75 | 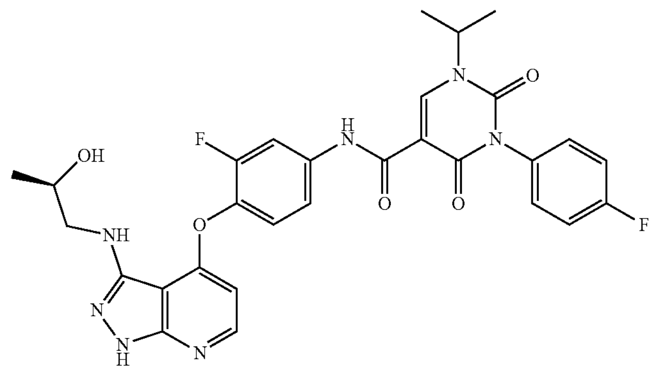 [SMILES: CC(C)n1cc(C(=O)Nc2ccc(Oc3ccnc4[nH]nc(NC[C@@H](C)O)c34)c(F)c2)c(=O)n(-c2ccc(F)cc2)c1=O] | (R)-N-(3-fluoro-4-((3-((2-hydroxypropyl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 592.2 (M + H) |
| 76 | 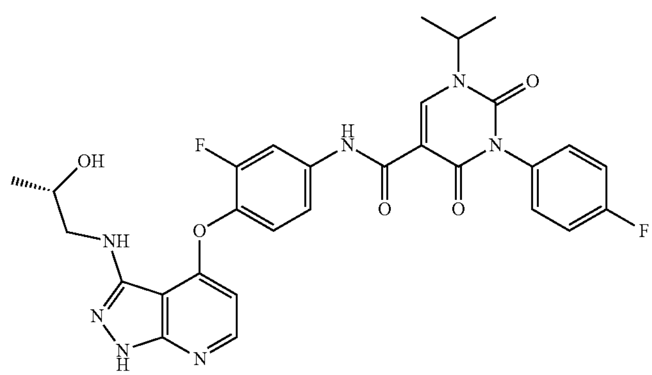 [SMILES: CC(C)n1cc(C(=O)Nc2ccc(Oc3ccnc4[nH]nc(NC[C@H](C)O)c34)c(F)c2)c(=O)n(-c2ccc(F)cc2)c1=O] | (S)-N-(3-fluoro-4-((3-((2-hydroxypropyl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 592.2 (M + H) |
| 77 | 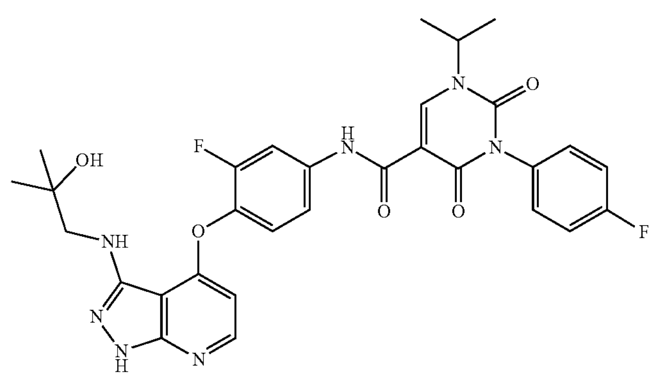 [SMILES: CC(C)n1cc(C(=O)Nc2ccc(Oc3ccnc4[nH]nc(NCC(C)(C)O)c34)c(F)c2)c(=O)n(-c2ccc(F)cc2)c1=O] | N-(3-fluoro-4-((3-((2-hydroxy-2-methylpropyl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |
| 78 | 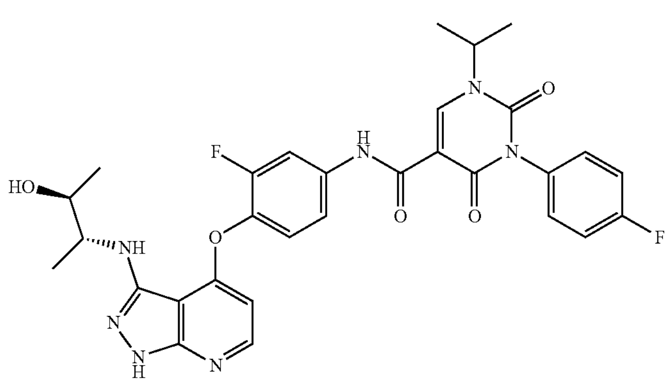 [SMILES: CC(C)n1cc(C(=O)Nc2ccc(Oc3ccnc4[nH]nc(N[C@H](C)[C@H](C)O)c34)c(F)c2)c(=O)n(-c2ccc(F)cc2)c1=O] | N-(3-fluoro-4-((3-(((2R,3S)-3-hydroxybutan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |

| Ex. No. | Structure | Name | Mass Spectrum |
|---|---|---|---|
| 79 | 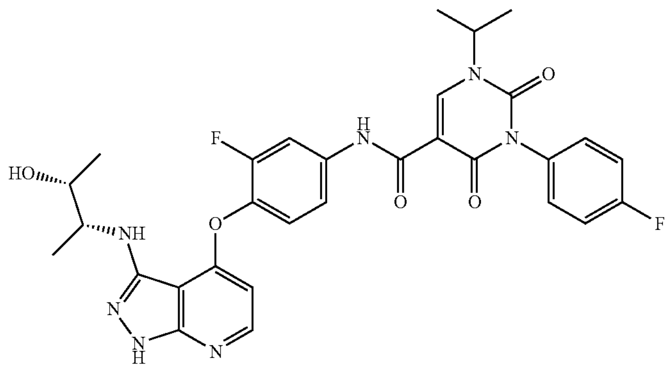 [SMILES: CC(C)n1cc(C(=O)Nc2ccc(Oc3ccnc4[nH]nc(N[C@H](C)[C@@H](C)O)c34)c(F)c2)c(=O)n(-c2ccc(F)cc2)c1=O] | N-(3-fluoro-4-((3-(((2R,3R)-3-hydroxybutan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |
| 80 | 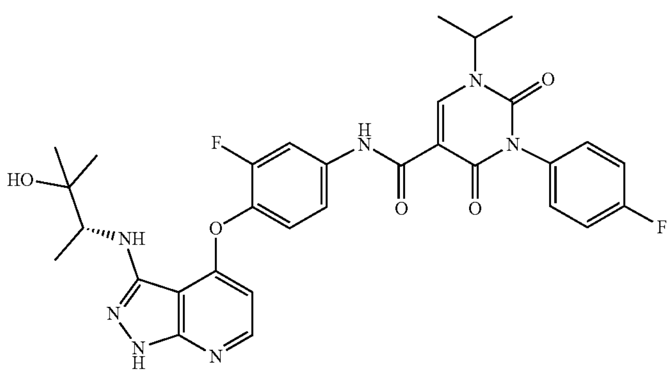 [SMILES: CC(C)n1cc(C(=O)Nc2ccc(Oc3ccnc4[nH]nc(N[C@H](C)C(C)(C)O)c34)c(F)c2)c(=O)n(-c2ccc(F)cc2)c1=O] | (R)-N-(3-fluoro-4-((3-((3-hydroxy-3-methylbutan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 620.2 (M + H) |
| 81 | 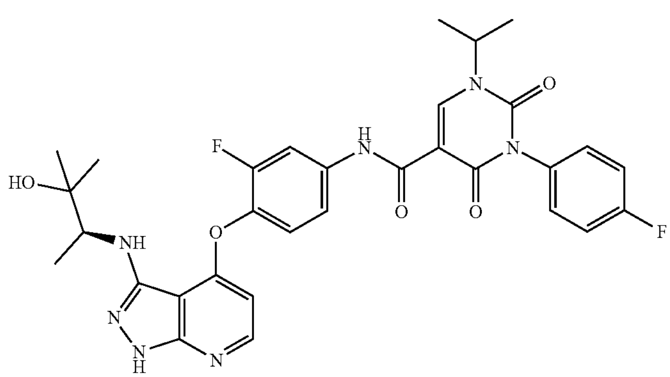 [SMILES: CC(C)n1cc(C(=O)Nc2ccc(Oc3ccnc4[nH]nc(N[C@@H](C)C(C)(C)O)c34)c(F)c2)c(=O)n(-c2ccc(F)cc2)c1=O] | (S)-N-(3-fluoro-4-((3-((3-hydroxy-3-methylbutan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 620.2 (M + H) |

Example 82

(R)—N-(3-fluoro-4-((3-((1-hydroxypropan-2-yl)amino)-1H-pyrazolo[3,4-b]pyridin-4-yl)oxy)phenyl)-3-(4-fluorophenyl)-1-methyl-2,4-dioxo-1,2,3,4-tetrahydropyrimidine-5-carboxamide hydrochloride

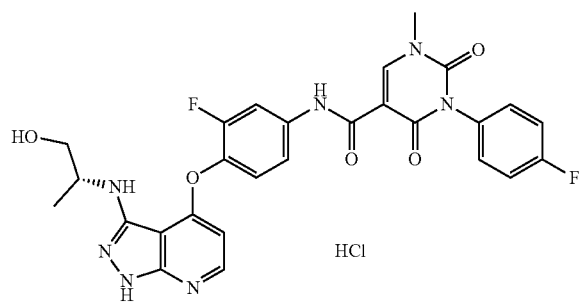

Step A: To a stirred solution of 3-(4-fluorophenyl)-1-methyl-2,4-dioxo-1,2,3,4-tetrahydropyrimidine-5-carboxylic acid (66.4 mg, 0.251 mmol) and HATU (0.1304 g, 0.3429 mmol) in DMF (3 mL) at room temperature was added DIEA (119 μL, 0.686 mmol) followed by (R)-2-((4-(4-amino-2-fluorophenoxy)-1-(4-methoxybenzyl)-1H-pyrazolo[3,4-b]pyridin-3-yl)amino)propan-1-ol (Preparation 53; 100 mg, 0.229 mmol) and stirred overnight. The reaction mixture was partitioned between water (20 mL) and EtOAc (20 mL) and the aqueous layer was extracted with EtOAc (2×10 mL). The combined organic phases were washed with water (5×10 mL) and brine (10 mL), dried over $Na_2SO_4$, filtered and concentrated. The residue was purified over silica gel (0-5% MeOH in DCM) to afford (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-3-(4-fluorophenyl)-1-methyl-2,4-dioxo-1,2,3,4-tetrahydropyrimidine-5-carboxamide (123 mg, 79%).

Step B: To a solution of (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-3-(4-fluorophenyl)-1-methyl-2,4-dioxo-1,2,3,4-tetrahydropyrimidine-5-carboxamide (123.0 mg, 0.180 mmol) in DCM (1 mL) was added TFA (2 mL). The mixture was stirred at 35° C. for 7 h and then cooled to room temperature overnight. The mixture was concentrated and the residue dissolved in MeOH/DCM, treated with $K_2CO_3$ (74.6 mg, 0.540 mmol) and stirred for 5.5 h. The mixture was filtered and concentrated, and the residue was and purified over silica gel (0-5% MeOH in DCM). The purified compound was dissolved in DCM (5 mL), treated with 4N HCl/dioxanes (0.5 mL), concentrated and dried in vacuo to afford (R)—N-(3-fluoro-4-((3-((1-hydroxypropan-2-yl)amino)-1H-pyrazolo[3,4-b]pyridin-4-yl)oxy)phenyl)-3-(4-fluorophenyl)-1-methyl-2,4-dioxo-1,2,3,4-tetrahydropyrimidine-5-carboxamide hydrochloride (20.3 mg, 18%) as a yellow solid. Mass spectrum: m/z=564.2 (M+H-HCl). $^1$H NMR (CDCl$_3$) δ 11.05 (s, 1H), 8.67 (s, 1H), 8.26 (d, 1H), 7.95 (dd, 1H), 7.36-7.22 (m, 6H), 6.22 (d, 1H), 4.02 (m, 1H), 3.76 (m, 1H), 3.71 (s, 3H), 3.65 (m, 1H), 1.35 (d, 3H).

The following compounds were also synthesized using the procedure according to Example 82.

| Ex. No. | Structure | Name | Mass Spectrum |
|---|---|---|---|
| 83 | 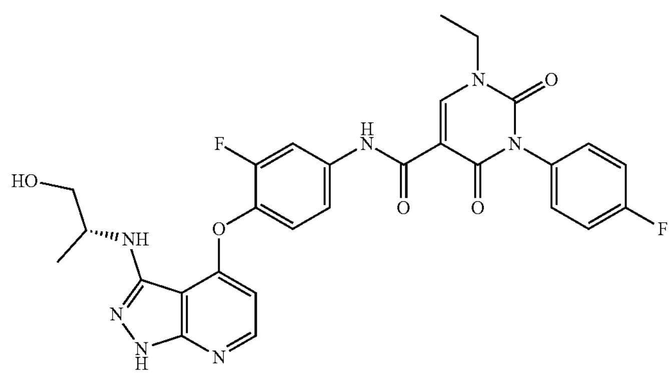 [SMILES: CCn1cc(C(=O)Nc2ccc(Oc3ccnc4[nH]nc(N[C@H](C)CO)c34)c(F)c2)c(=O)n(-c2ccc(F)cc2)c1=O] | (R)-1-ethyl-N-(3-fluoro-4-((3-((1-hydroxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 578.2 (M + H) |
| 84 | 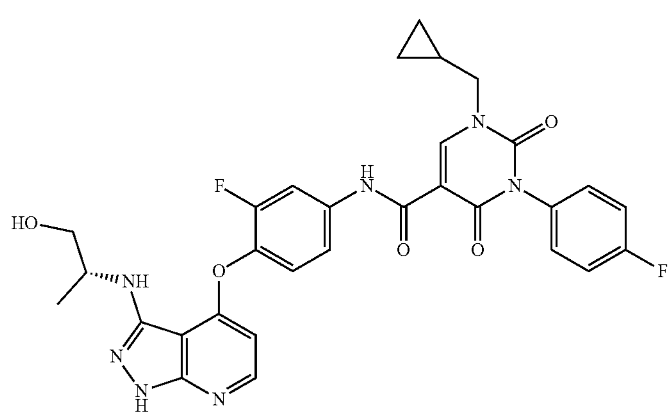 [SMILES: C[C@H](CO)Nc1n[nH]c2nccc(Oc3ccc(NC(=O)c4cn(CC5CC5)c(=O)n(-c5ccc(F)cc5)c4=O)cc3F)c12] | (R)-1-(cyclopropylmethyl)-N-(3-fluoro-4-((3-((1-hydroxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 604.2 (M + H) |

| Ex. No. | Structure | Name | Mass Spectrum |
|---|---|---|---|
| 85 | 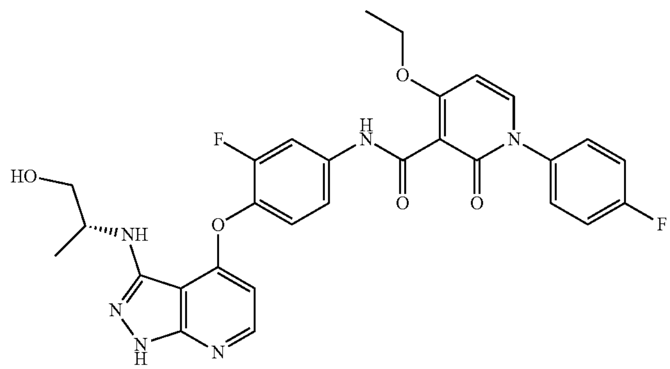 [SMILES: CCOc1ccn(-c2ccc(F)cc2)c(=O)c1C(=O)Nc1ccc(Oc2ccnc3[nH]nc(N[C@H](C)CO)c23)c(F)c1] | (R)-4-ethoxy-N-(3-fluoro-4-((3-((1-hydroxypropan-2-yl)amino)-1H-pyrazolo[3,4-b]pyridin-4-yl)oxy)phenyl)-1-(4-fluorophenyl)-2-oxo-1,2-dihydropyridine-3-carboxamide | 577.2 (M + H) |
| 86 | 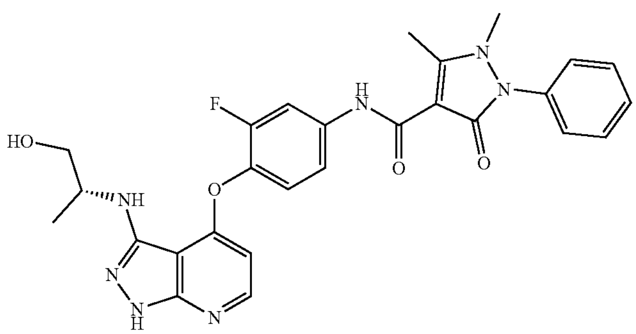 [SMILES: Cc1c(C(=O)Nc2ccc(Oc3ccnc4[nH]nc(N[C@H](C)CO)c34)c(F)c2)c(=O)n(-c2ccccc2)n1C] | (R)-N-(3-fluoro-4-((3-((1-hydroxypropan-2-yl)amino)-1H-pyrazolo[3,4-b]pyridin-4-yl)oxy)phenyl)-1,5-dimethyl-3-oxo-2-phenyl-2,3-dihydro-1H-pyrazole-4-carboxamide | 532.2 (M + H) |
| 87 | 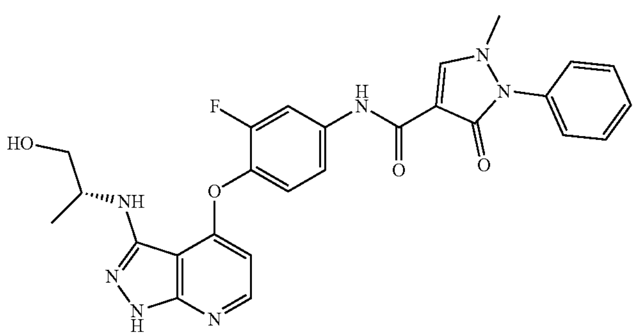 [SMILES: C[C@H](CO)Nc1n[nH]c2nccc(Oc3ccc(NC(=O)c4cn(C)n(-c5ccccc5)c4=O)cc3F)c12] | (R)-N-(3-fluoro-4-((3-((1-hydroxypropan-2-yl)amino)-1H-pyrazolo[3,4-b]pyridin-4-yl)oxy)phenyl)-1-methyl-3-oxo-2-phenyl-2,3-dihydro-1H-pyrazole-4-carboxamide | 518.2 (M + H) |
| 88 | 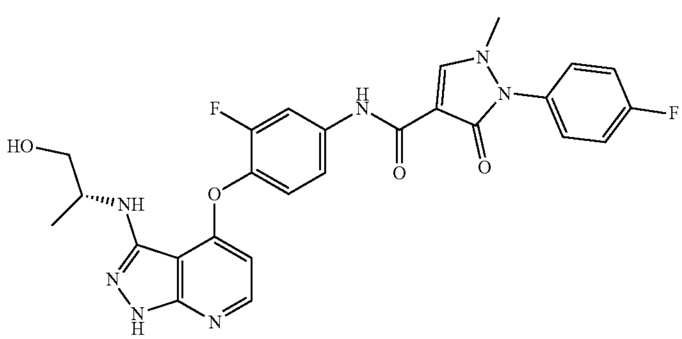 [SMILES: C[C@H](CO)Nc1n[nH]c2nccc(Oc3ccc(NC(=O)c4cn(C)n(-c5ccc(F)cc5)c4=O)cc3F)c12] | (R)-N-(3-fluoro-4-((3-((1-hydroxypropan-2-yl)amino)-1H-pyrazolo[3,4-b]pyridin-4-yl)oxy)phenyl)-2-(4-fluorophenyl)-1-methyl-3-oxo-2,3-dihydro-1H-pyrazole-4-carboxamide | 536.2 (M + H) |

| Ex. No. | Structure | Name | Mass Spectrum |
|---|---|---|---|
| 89 | 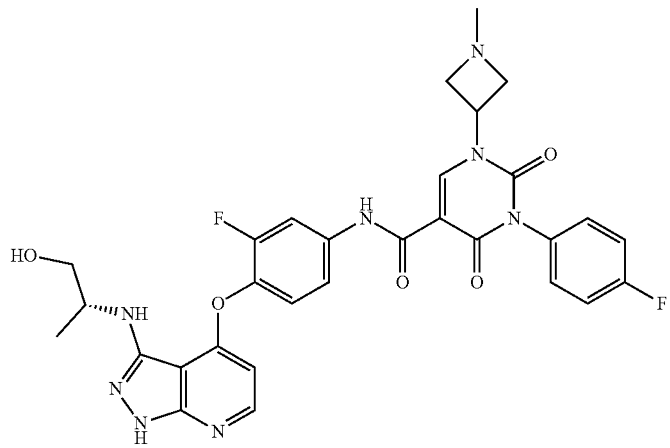 [SMILES: C[C@H](CO)Nc1n[nH]c2nccc(Oc3ccc(NC(=O)c4cn(C5CN(C)C5)c(=O)n(-c5ccc(F)cc5)c4=O)cc3F)c12] | (R)-N-(3-fluoro-4-((3-((1-hydroxypropan-2-yl)amino)-1H-pyrazolo[3,4-b]pyridin-4-yl)oxy)phenyl)-3-(4-fluorophenyl)-1-(1-methylazetidin-3-yl)-2,4-dioxo-1,2,3,4-tetrahydropyrimidine-5-carboxamide | 619.2 (M + H) |
| 90 | 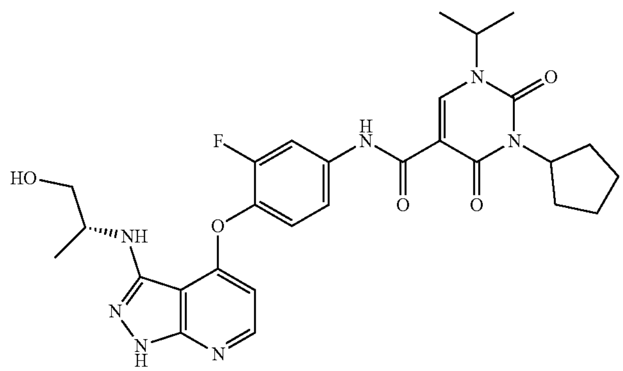 [SMILES: CC(C)n1cc(C(=O)Nc2ccc(Oc3ccnc4[nH]nc(N[C@H](C)CO)c34)c(F)c2)c(=O)n(C2CCCC2)c1=O] | (R)-3-cyclopentyl-N-(3-fluoro-4-((3-((1-hydroxypropan-2-yl)amino)-1H-pyrazolo[3,4-b]pyridin-4-yl)oxy)phenyl)-1-isopropyl-2,4-dioxo-1,2,3,4-tetrahydropyrimidine-5-carboxamide | 566.2 (M + H) |
| 91 | 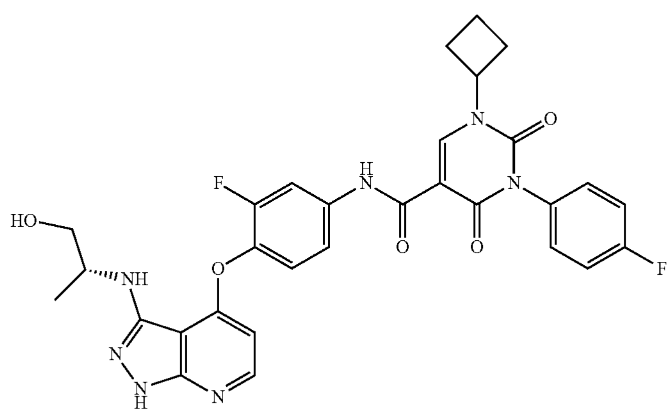 [SMILES: C[C@H](CO)Nc1n[nH]c2nccc(Oc3ccc(NC(=O)c4cn(C5CCC5)c(=O)n(-c5ccc(F)cc5)c4=O)cc3F)c12] | (R)-1-cyclobutyl-N-(3-fluoro-4-((3-((1-hydroxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 604.2 (M + H) |
| 92 | 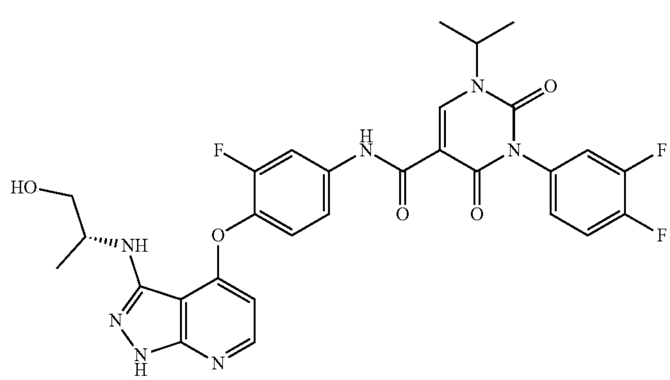 [SMILES: CC(C)n1cc(C(=O)Nc2ccc(Oc3ccnc4[nH]nc(N[C@H](C)CO)c34)c(F)c2)c(=O)n(-c2ccc(F)c(F)c2)c1=O] | (R)-3-(3,4-difluorophenyl)-N-(3-fluoro-4-((3-((1-hydroxypropan-2-yl)amino)-1H-pyrazolo[3,4-b]pyridin-4-yl)oxy)phenyl)-1-isopropyl-2,4-dioxo-1,2,3,4-tetrahydropyrimidine-5-carboxamide | 610.2 (M + H) |

-continued

| Ex. No. | Structure | Name | Mass Spectrum |
|---|---|---|---|
| 93 | 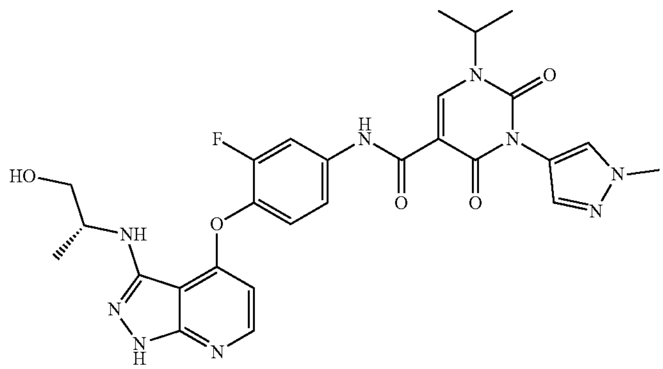 [SMILES: CC(C)n1cc(C(=O)Nc2ccc(Oc3ccnc4[nH]nc(N[C@H](C)CO)c34)c(F)c2)c(=O)n(-c2cnn(C)c2)c1=O] | (R)-N-(3-fluoro-4-((3-((1-hydroxypropan-2-yl)amino)-1H-pyrazolo[3,4-b]pyridin-4-yl)oxy)phenyl)-1-isopropyl-3-(1-methyl-1H-pyrazol-4-yl)-2,4-dioxo-1,2,3,4-tetrahydropyrimidine-5-carboxamide | 578.2 (M + H) |
| 94 | 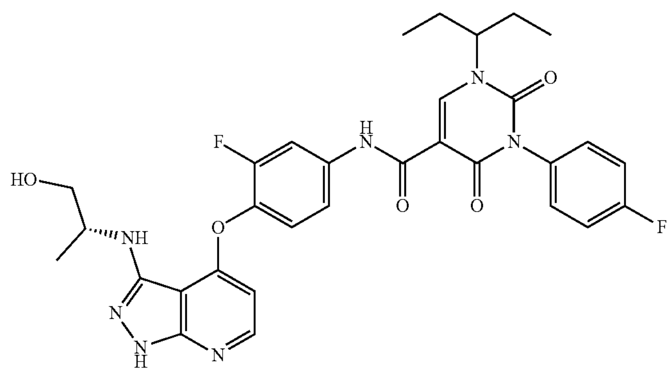 [SMILES: CCC(CC)n1cc(C(=O)Nc2ccc(Oc3ccnc4[nH]nc(N[C@H](C)CO)c34)c(F)c2)c(=O)n(-c2ccc(F)cc2)c1=O] | (R)-N-(3-fluoro-4-((3-((1-hydroxypropan-2-yl)amino)-1H-pyrazolo[3,4-b]pyridin-4-yl)oxy)phenyl)-3-(4-fluorophenyl)-2,4-dioxo-1-(pentan-3-yl)-1,2,3,4-tetrahydropyrimidine-5-carboxamide | 620.2 (M + H) |
| 95 | 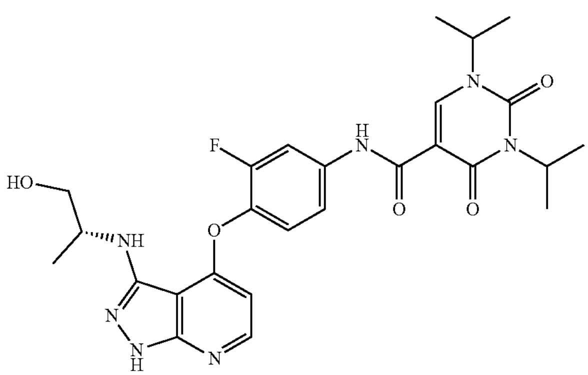 [SMILES: CC(C)n1cc(C(=O)Nc2ccc(Oc3ccnc4[nH]nc(N[C@H](C)CO)c34)c(F)c2)c(=O)n(C(C)C)c1=O] | (R)-N-(3-fluoro-4-((3-((1-hydroxypropan-2-yl)amino)-1H-pyrazolo[3,4-b]pyridin-4-yl)oxy)phenyl)-1,3-diisopropyl-2,4-dioxo-1,2,3,4-tetrahydropyrimidine-5-carboxamide | 540.2 (M + H) |
| 96 | 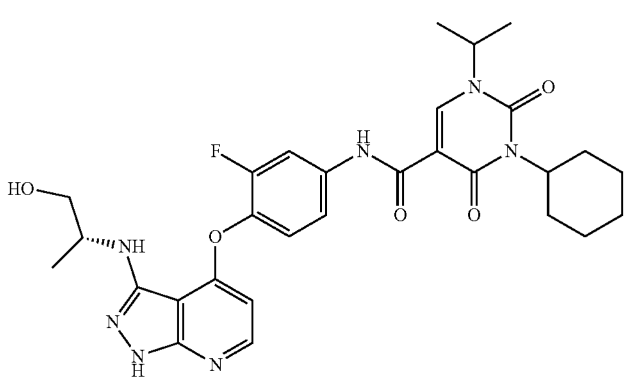 [SMILES: CC(C)n1cc(C(=O)Nc2ccc(Oc3ccnc4[nH]nc(N[C@H](C)CO)c34)c(F)c2)c(=O)n(C2CCCCC2)c1=O] | (R)-3-cyclohexyl-N-(3-fluoro-4-((3-((1-hydroxypropan-2-yl)amino)-1H-pyrazolo[3,4-b]pyridin-4-yl)oxy)phenyl)-1-isopropyl-2,4-dioxo-1,2,3,4-tetrahydropyrimidine-5-carboxamide | 580.3 (M + H) |

| Ex. No. | Structure | Name | Mass Spectrum |
|---|---|---|---|
| 97 | 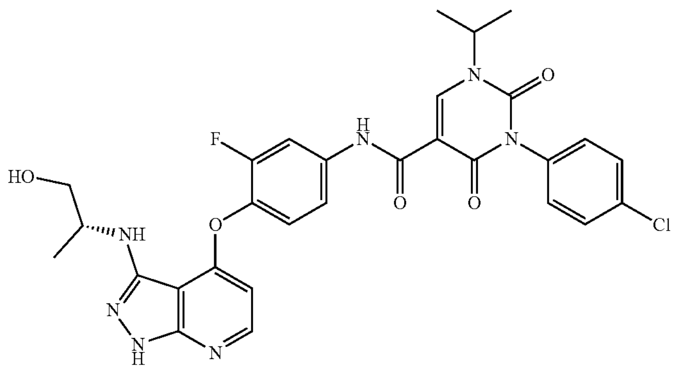 [SMILES: CC(C)n1cc(C(=O)Nc2ccc(Oc3ccnc4[nH]nc(N[C@H](C)CO)c34)c(F)c2)c(=O)n(-c2ccc(Cl)cc2)c1=O] | (R)-3-(4-chlorophenyl)-N-(3-fluoro-4-((3-((1-hydroxypropan-2-yl)amino)-1H-pyrazolo[3,4-b]pyridin-4-yl)oxy)phenyl)-1-isopropyl-2,4-dioxo-1,2,3,4-tetrahydropyrimidine-5-carboxamide | 608.2 (M + H) |
| 98 | 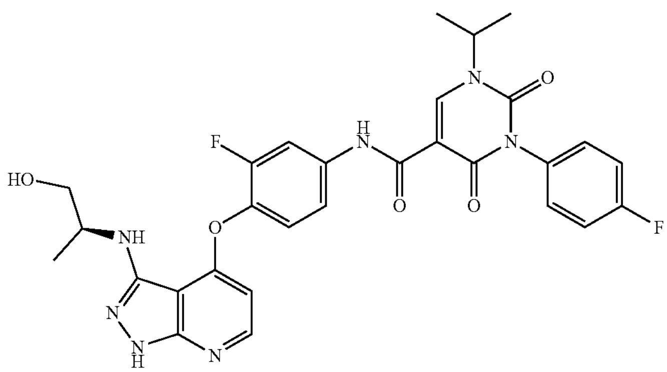 [SMILES: CC(C)n1cc(C(=O)Nc2ccc(Oc3ccnc4[nH]nc(N[C@@H](C)CO)c34)c(F)c2)c(=O)n(-c2ccc(F)cc2)c1=O] | (S)-N-(3-fluoro-4-((3-((1-hydroxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 592.2 (M + H) |
| 99 | 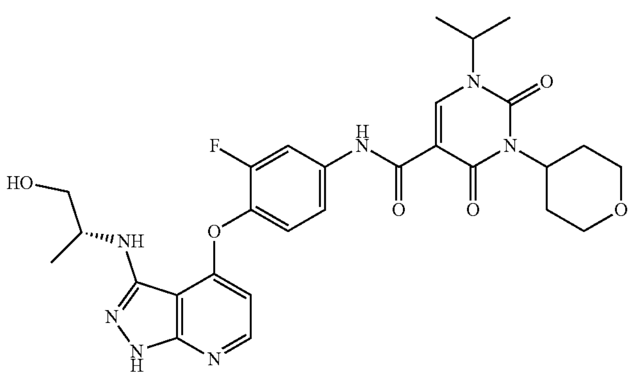 [SMILES: CC(C)n1cc(C(=O)Nc2ccc(Oc3ccnc4[nH]nc(N[C@H](C)CO)c34)c(F)c2)c(=O)n(C2CCOCC2)c1=O] | (R)-N-(3-fluoro-4-((3-((1-hydroxypropan-2-yl)amino)-1H-pyrazolo[3,4-b]pyridin-4-yl)oxy)phenyl)-1-isopropyl-2,4-dioxo-3-(tetrahydro-2H-pyran-4-yl)-1,2,3,4-tetrahydropyrimidine-5-carboxamide | 582.2 (M + H) |
| 100 | 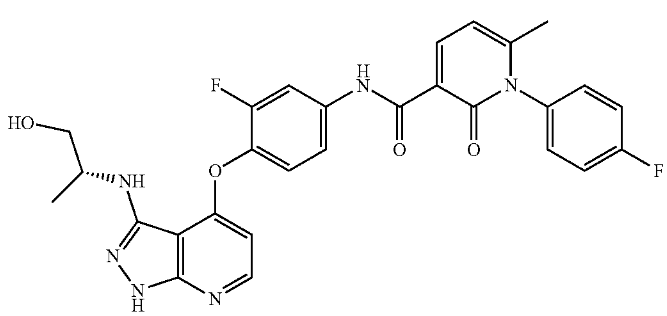 [SMILES: Cc1ccc(C(=O)Nc2ccc(Oc3ccnc4[nH]nc(N[C@H](C)CO)c34)c(F)c2)c(=O)n1-c1ccc(F)cc1] | (R)-N-(3-fluoro-4-((3-((1-hydroxypropan-2-yl)amino)-1H-pyrazolo[3,4-b]pyridin-4-yl)oxy)phenyl)-1-(4-fluorophenyl)-6-methyl-2-oxo-1,2-dihydropyridine-3-carboxamide | 547.2 (M + H) |

-continued

| Ex. No. | Structure | Name | Mass Spectrum |
|---|---|---|---|
| 101 | 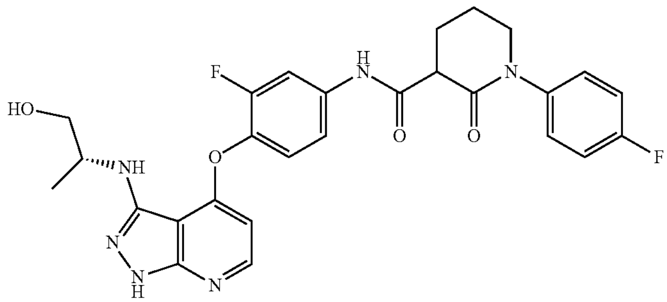 [SMILES: C[C@H](CO)Nc1n[nH]c2nccc(Oc3ccc(NC(=O)C4CCCN(c5ccc(F)cc5)C4=O)cc3F)c12] | N-(3-fluoro-4-((3-(((R)-1-hydroxypropan-2-yl)amino)-1H-pyrazolo[3,4-b]pyridin-4-yl)oxy)phenyl)-1-(4-fluorophenyl)-2-oxopiperidine-3-carboxamide | 537.3 (M + H) |
| 102 | 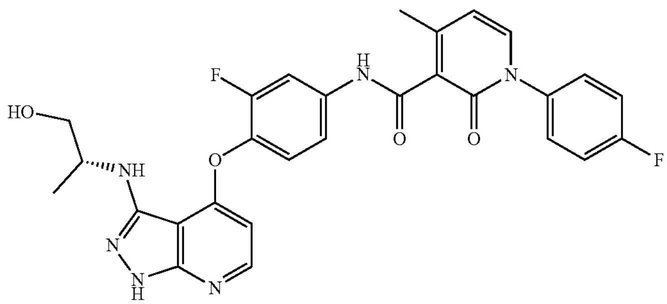 [SMILES: Cc1ccn(-c2ccc(F)cc2)c(=O)c1C(=O)Nc1ccc(Oc2ccnc3[nH]nc(N[C@H](C)CO)c23)c(F)c1] | (R)-N-(3-fluoro-4-((3-((1-hydroxypropan-2-yl)amino)-1H-pyrazolo[3,4-b]pyridin-4-yl)oxy)phenyl)-1-(4-fluorophenyl)-4-methyl-2-oxo-1,2-dihydropyridine-3-carboxamide | 547.2 (M + H) |
| 103 | 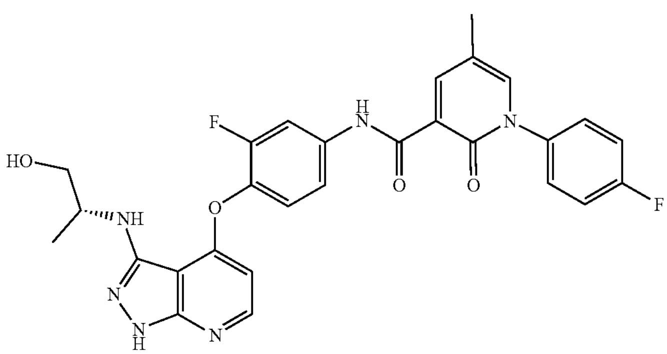 | (R)-N-(3-fluoro-4-((3-((1-hydroxypropan-2-yl)amino)-1H-pyrazolo[3,4-b]pyridin-4-yl)oxy)phenyl)-1-(4-fluorophenyl)-5-methyl-2-oxo-1,2-dihydropyridine-3-carboxamide | 547.2 (M + H) |
| 104 | 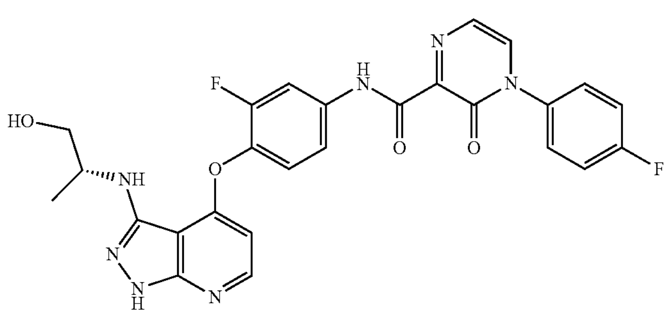 [SMILES: C[C@H](CO)Nc1n[nH]c2nccc(Oc3ccc(NC(=O)c4nccn(-c5ccc(F)cc5)c4=O)cc3F)c12] | (R)-N-(3-fluoro-4-((3-((1-hydroxypropan-2-yl)amino)-1H-pyrazolo[3,4-b]pyridin-4-yl)oxy)phenyl)-4-(4-fluorophenyl)-3-oxo-3,4-dihydropyrazine-2-carboxamide | 534.2 (M + H) |

-continued

| Ex. No. | Structure | Name | Mass Spectrum |
|---|---|---|---|
| 105 | 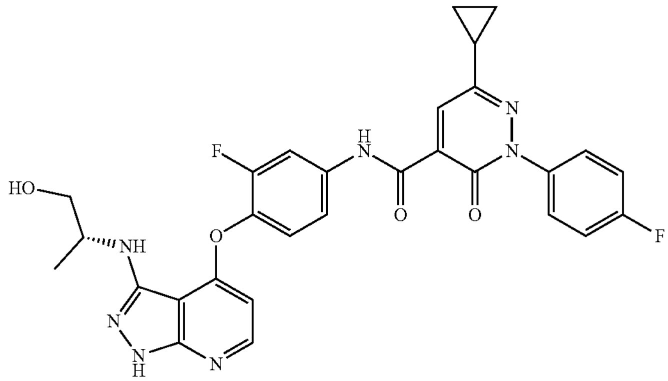 [SMILES: C[C@H](CO)Nc1n[nH]c2nccc(Oc3ccc(NC(=O)c4cc(C5CC5)nn(-c5ccc(F)cc5)c4=O)cc3F)c12] | (R)-6-cyclopropyl-N-(3-fluoro-4-((3-((1-hydroxypropan-2-yl)amino)-1H-pyrazolo[3,4-b]pyridin-4-yl)oxy)phenyl)-2-(4-fluorophenyl)-3-oxo-2,3-dihydropyridazine-4-carboxamide | 574.2 (M + H) |
| 106 | 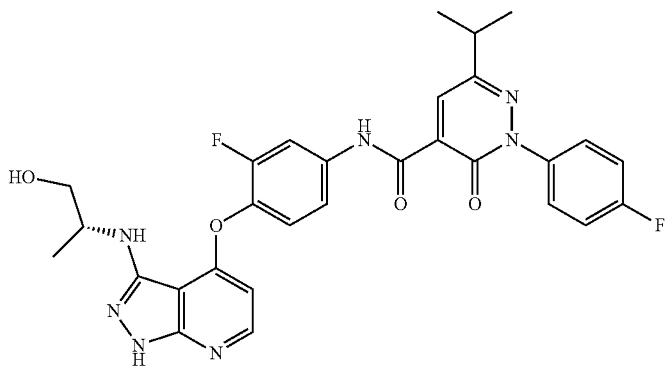 [SMILES: CC(C)c1cc(C(=O)Nc2ccc(Oc3ccnc4[nH]nc(N[C@H](C)CO)c34)c(F)c2)c(=O)n(-c2ccc(F)cc2)n1] | (R)-N-(3-fluoro-4-((3-((1-hydroxypropan-2-yl)amino)-1H-pyrazolo[3,4-b]pyridin-4-yl)oxy)phenyl)-2-(4-fluorophenyl)-6-isopropyl-3-oxo-2,3-dihydropyridazine-4-carboxamide | 576.2 (M + H) |
| 107 | 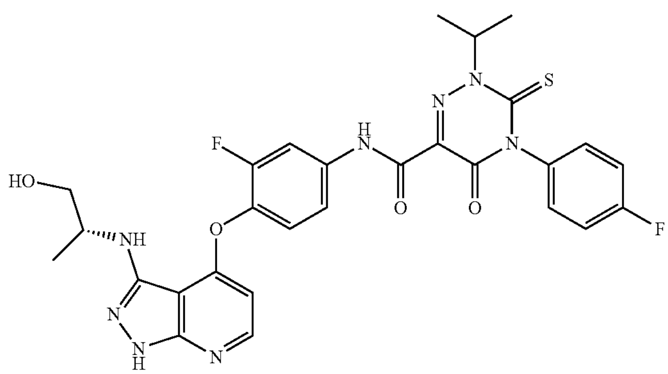 | (R)-N-(3-fluoro-4-((3-((1-hydroxypropan-2-yl)amino)-1H-pyrazolo[3,4-b]pyridin-4-yl)oxy)phenyl)-4-(4-fluorophenyl)-2-isopropyl-5-oxo-3-thioxo-2,3,4,5-tetrahydro-1,2,4-triazine-6-carboxamide | 609.2 (M + H) |
| 108 | 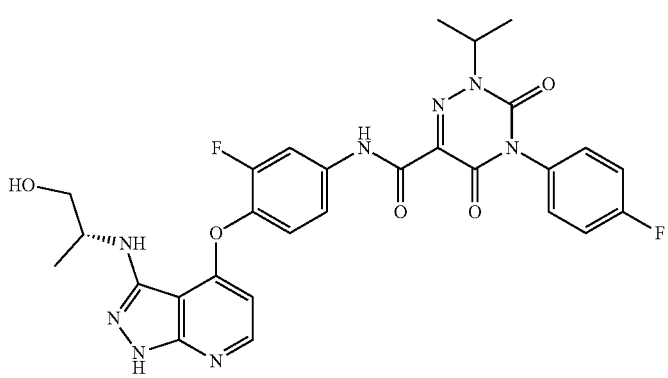 | (R)-N-(3-fluoro-4-((3-((1-hydroxypropan-2-yl)amino)-1H-pyrazolo[3,4-b]pyridin-4-yl)oxy)phenyl)-4-(4-fluorophenyl)-2-isopropyl-3,5-dioxo-2,3,4,5-tetrahydro-1,2,4-triazine-6-carboxamide | 593.2 (M + H) |

-continued

| Ex. No. | Structure | Name | Mass Spectrum |
|---|---|---|---|
| 109 | 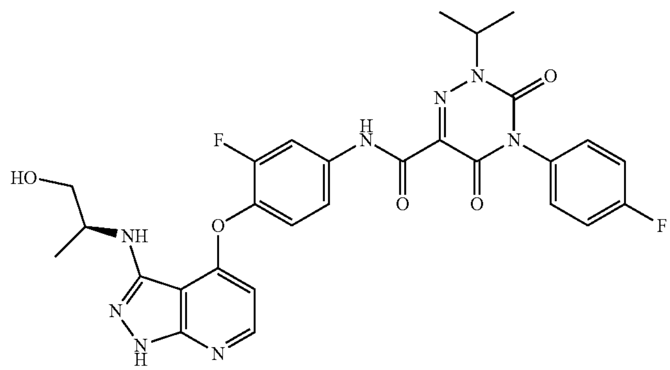 [SMILES: CC(C)n1nc(C(=O)Nc2ccc(Oc3ccnc4[nH]nc(N[C@@H](C)CO)c34)c(F)c2)c(=O)n(-c2ccc(F)cc2)c1=O] | (S)-N-(3-fluoro-4-((3-((1-hydroxypropan-2-yl)amino)-1H-pyrazolo[3,4-b]pyridin-4-yl)oxy)phenyl)-4-(4-fluorophenyl)-2-isopropyl-3,5-dioxo-2,3,4,5-tetrahydro-1,2,4-triazine-6-carboxamide | 593.2 (M + H) |
| 110 | 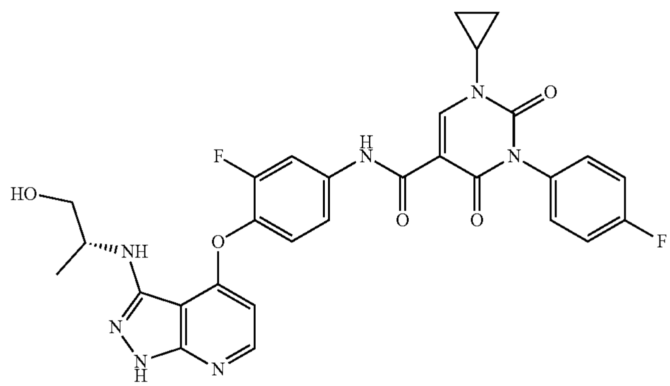 [SMILES: C[C@H](CO)Nc1n[nH]c2nccc(Oc3ccc(NC(=O)c4cn(C5CC5)c(=O)n(-c5ccc(F)cc5)c4=O)cc3F)c12] | (R)-1-cyclopropyl-N-(3-fluoro-4-((3-((1-hydroxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 590.2 (M + H) |
| 111 | 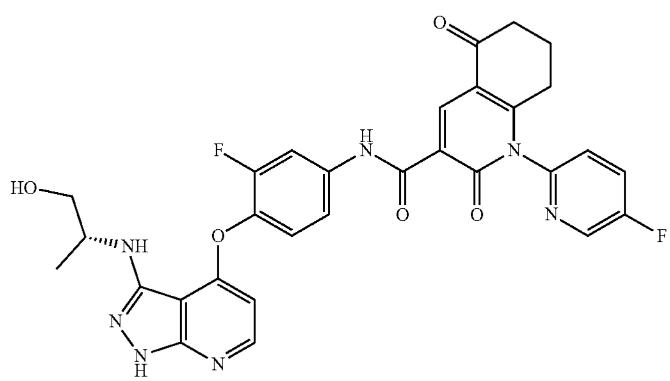 [SMILES: C[C@H](CO)Nc1n[nH]c2nccc(Oc3ccc(NC(=O)c4cc5c(n(-c6ccc(F)cn6)c4=O)CCCC5=O)cc3F)c12] | (R)-N-(3-fluoro-4-((3-((1-hydroxypropan-2-yl)amino-1H-pyrazolo[3,4-b]pyridin-4-yl)oxy)phenyl)-1-(5-fluoropyridin-2-yl)-2,5-dioxo-1,2,5,6,7,8-hexahydroquinoline-3-carboxamide | 602.2 (M + H) |
| 112 | 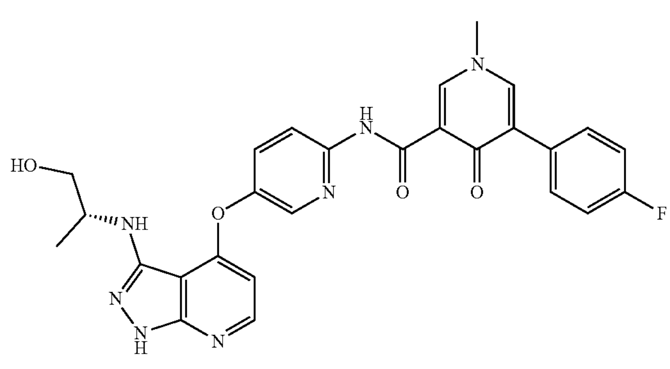 [SMILES: C[C@H](CO)Nc1n[nH]c2nccc(Oc3ccc(NC(=O)c4cn(C)cc(-c5ccc(F)cc5)c4=O)nc3)c12] | (R)-5-(4-fluorophenyl)-N-(5-((3-((1-hydroxypropan-2-yl)amino)-1H-pyrazolo[3,4-b]pyridin-4-yl)oxy)pyridin-2-yl)-1-methyl-4-oxo-1,4-dihydropyridine-3-carboxamide | 530.2 (M + H) |

| Ex. No. | Structure | Name | Mass Spectrum |
|---|---|---|---|
| 113 | 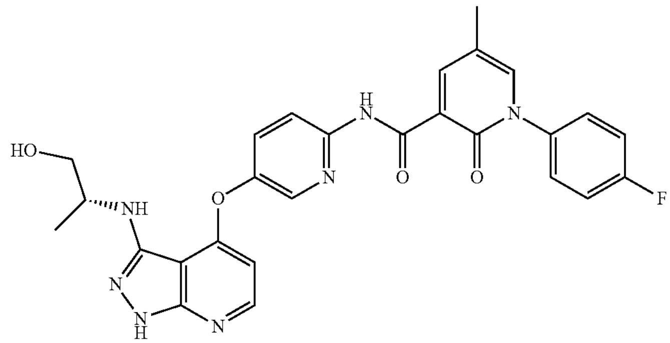 [SMILES: Cc1cc(C(=O)Nc2ccc(Oc3ccnc4[nH]nc(N[C@H](C)CO)c34)cn2)c(=O)n(-c2ccc(F)cc2)c1] | (R)-1-(4-fluorophenyl)-N-(5-((3-((1-hydroxypropan-2-yl)amino)-1H-pyrazolo[3,4-b]pyridin-4-yl)oxy)pyridin-2-yl)-5-methyl-2-oxo-1,2-dihydropyridine-3-carboxamide | 530.2 (M + H) |
| 114 | 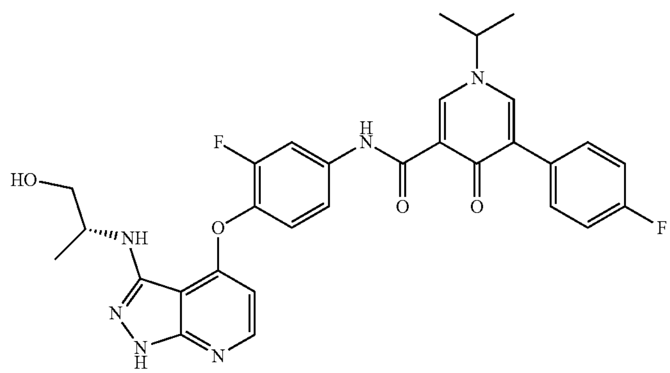 [SMILES: CC(C)n1cc(C(=O)Nc2ccc(Oc3ccnc4[nH]nc(N[C@H](C)CO)c34)c(F)c2)c(=O)c(-c2ccc(F)cc2)c1] | (R)-N-(3-fluoro-4-((3-((1-hydroxypropan-2-yl)amino)-1H-pyrazolo[3,4-b]pyridin-4-yl)oxy)phenyl)-5-(4-fluorophenyl)-1-isopropyl-4-oxo-1,4-dihydropyridine-3-carboxamide | 575.2 (M + H) |
| 115 | 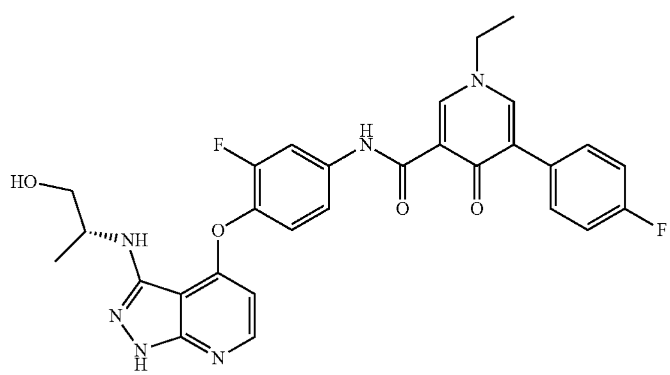 [SMILES: CCn1cc(C(=O)Nc2ccc(Oc3ccnc4[nH]nc(N[C@H](C)CO)c34)c(F)c2)c(=O)c(-c2ccc(F)cc2)c1] | (R)-1-ethyl-N-(3-fluoro-4-((3-((1-hydroxypropan-2-yl)amino)-1H-pyrazolo[3,4-b]pyridin-4-yl)oxy)phenyl)-5-(4-fluorophenyl)-4-oxo-1,4-dihydropyridine-3-carboxamide | 561.2 (M + H) |
| 116 | 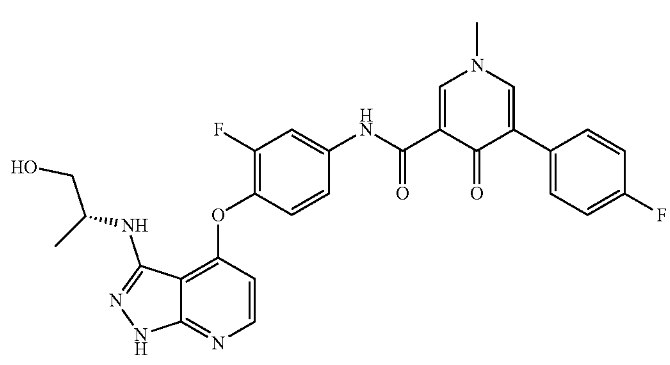 [SMILES: C[C@H](CO)Nc1n[nH]c2nccc(Oc3ccc(NC(=O)c4cn(C)cc(-c5ccc(F)cc5)c4=O)cc3F)c12] | (R)-N-(3-fluoro-4-((3-((1-hydroxypropan-2-yl)amino)-1H-pyrazolo[3,4-b]pyridin-4-yl)oxy)phenyl)-5-(4-fluorophenyl)-1-methyl-4-oxo-1,4-dihydropyridine-3-carboxamide | 547.2 (M + H) |

| Ex. No. | Structure | Name | Mass Spectrum |
|---|---|---|---|
| 117 | 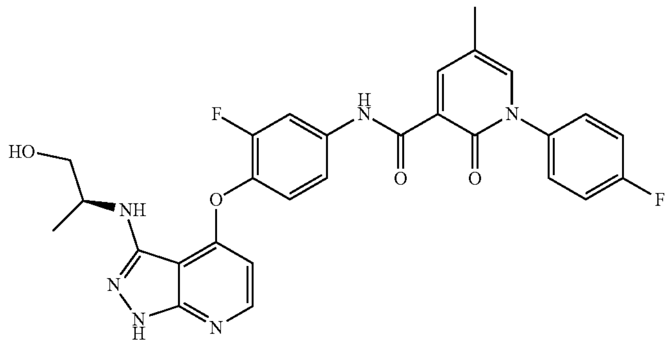 [SMILES: Cc1cc(C(=O)Nc2ccc(Oc3ccnc4[nH]nc(N[C@@H](C)CO)c34)c(F)c2)c(=O)n(-c2ccc(F)cc2)c1] | (S)-N-(3-fluoro-4-((3-((1-hydroxypropan-2-yl)amino)-1H-pyrazolo[3,4-b]pyridin-4-yl)oxy)phenyl)-1-(4-fluorophenyl)-5-methyl-2-oxo-1,2-dihydropyridine-3-carboxamide | 547.2 (M + H) |
| 118 | 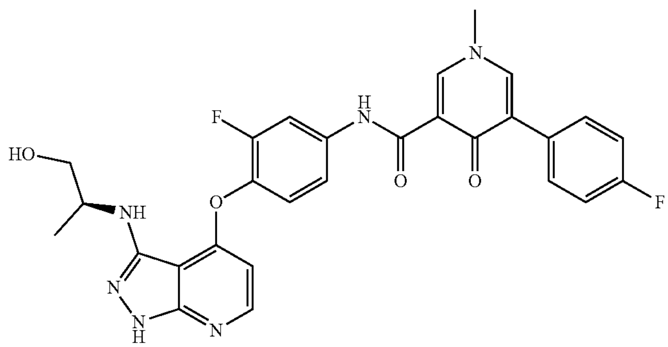 [SMILES: C[C@@H](CO)Nc1n[nH]c2nccc(Oc3ccc(NC(=O)c4cn(C)cc(-c5ccc(F)cc5)c4=O)cc3F)c12] | (S)-N-(3-fluoro-4-((3-((1-hydroxypropan-2-yl)amino)-1H-pyrazolo[3,4-b]pyridin-4-yl)oxy)phenyl)-5-(4-fluorophenyl)-1-methyl-4-oxo-1,4-dihydropyridine-3-carboxamide | 547.2 (M + H) |
| 119 | 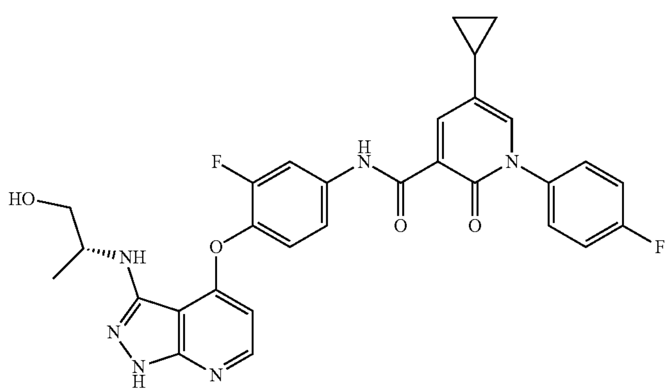 [SMILES: C[C@H](CO)Nc1n[nH]c2nccc(Oc3ccc(NC(=O)c4cc(C5CC5)cn(-c5ccc(F)cc5)c4=O)cc3F)c12] | (R)-5-cyclopropyl-N-(3-fluoro-4-((3-((1-hydroxypropan-2-yl)amino)-1H-pyrazolo[3,4-b]pyridin-4-yl)oxy)phenyl)-1-(4-fluorophenyl)-2-oxo-1,2-dihydropyridine-3-carboxamide | 573.2 (M + H) |
| 120 | 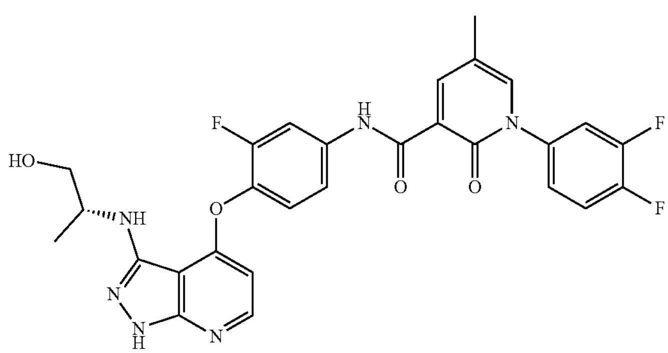 [SMILES: Cc1cc(C(=O)Nc2ccc(Oc3ccnc4[nH]nc(N[C@H](C)CO)c34)c(F)c2)c(=O)n(-c2ccc(F)c(F)c2)c1] | (R)-1-(3,4-difluorophenyl)-N-(3-fluoro-4-((3-((1-hydroxypropan-2-yl)amino)-1H-pyrazolo[3,4-b]pyridin-4-yl)oxy)phenyl)-5-methyl-2-oxo-1,2-dihydropyridine-3-carboxamide | 565.1 (M + H) |

-continued

| Ex. No. | Structure | Name | Mass Spectrum |
|---|---|---|---|
| 121 | 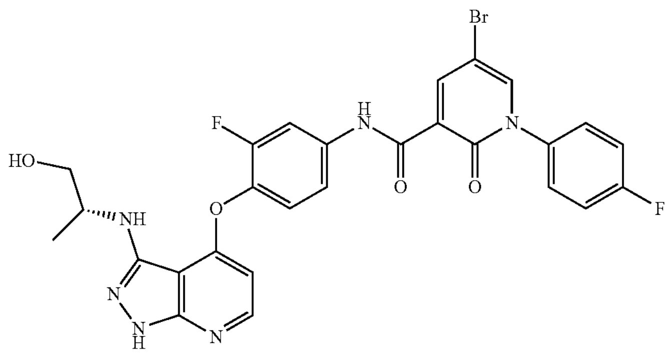 [SMILES: C[C@H](CO)Nc1n[nH]c2nccc(Oc3ccc(NC(=O)c4cc(Br)cn(-c5ccc(F)cc5)c4=O)cc3F)c12] | (R)-5-bromo-N-(3-fluoro-4-((3-((1-hydroxypropan-2-yl)amino)-1H-pyrazolo[3,4-b]pyridin-4-yl)oxy)phenyl)-1-(4-fluorophenyl)-2-oxo-1,2-dihydropyridine-3-carboxamide | 611.1, 613.1 (M + H) |
| 122 | 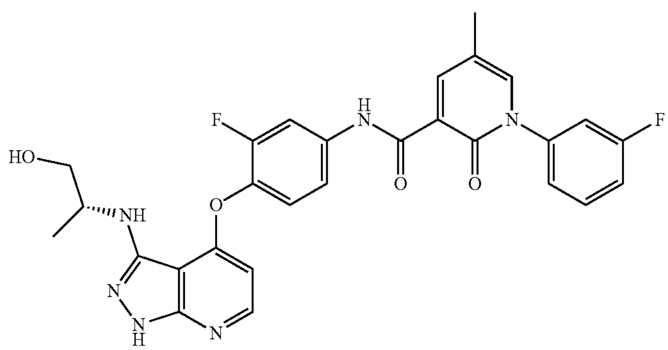 [SMILES: Cc1cc(C(=O)Nc2ccc(Oc3ccnc4[nH]nc(N[C@H](C)CO)c34)c(F)c2)c(=O)n(-c2cccc(F)c2)c1] | (R)-N-(3-fluoro-4-((3-((1-hydroxypropan-2-yl)amino)-1H-pyrazolo[3,4-b]pyridin-4-yl)oxy)phenyl)-1-(3-fluorophenyl)-5-methyl-2-oxo-1,2-dihydropyridine-3-carboxamide | 547.2 (M + H) |
| 123 | 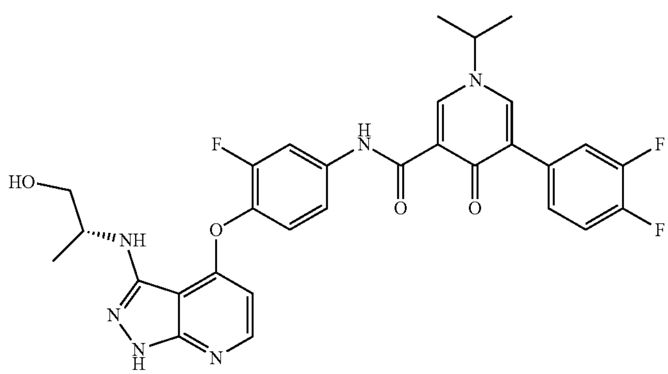 [SMILES: CC(C)n1cc(C(=O)Nc2ccc(Oc3ccnc4[nH]nc(N[C@H](C)CO)c34)c(F)c2)c(=O)c(-c2ccc(F)c(F)c2)c1] | (R)-5-(3,4-difluorophenyl)-N-(3-fluoro-4-((3-((1-hydroxypropan-2-yl)amino)-1H-pyrazolo[3,4-b]pyridin-4-yl)oxy)phenyl)-1-isopropyl-4-oxo-1,4-dihydropyridine-3-carboxamide | 593.2 (M + H) |
| 124 | 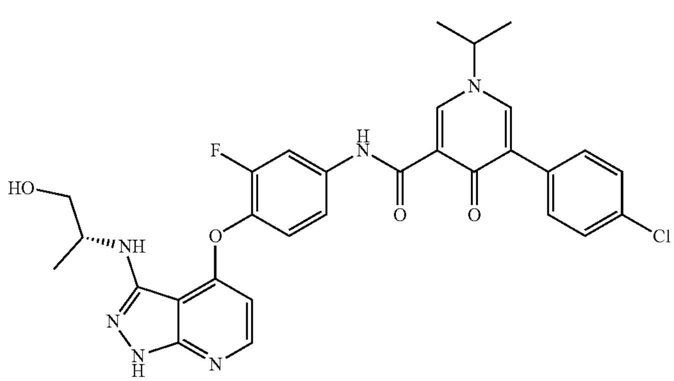 [SMILES: CC(C)n1cc(C(=O)Nc2ccc(Oc3ccnc4[nH]nc(N[C@H](C)CO)c34)c(F)c2)c(=O)c(-c2ccc(Cl)cc2)c1] | (R)-5-(4-chlorophenyl)-N-(3-fluoro-4-((3-((1-hydroxypropan-2-yl)amino)-1H-pyrazolo[3,4-b]pyridin-4-yl)oxy)phenyl)-1-isopropyl-4-oxo-1,4-dihydropyridine-3-carboxamide | 591.2 (M + H) |

| Ex. No. | Structure | Name | Mass Spectrum |
|---|---|---|---|
| 125 | 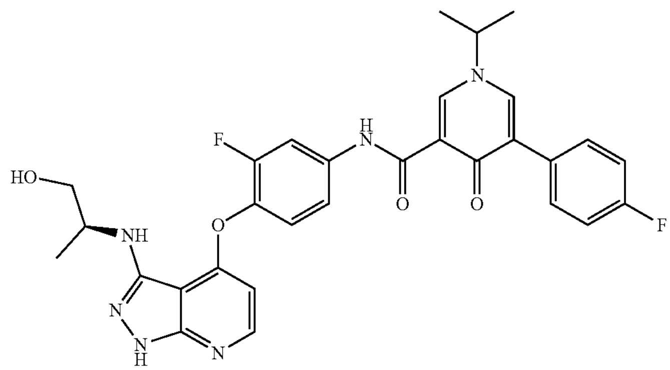 [SMILES: CC(C)n1cc(C(=O)Nc2ccc(Oc3ccnc4[nH]nc(N[C@@H](C)CO)c34)c(F)c2)c(=O)c(-c2ccc(F)cc2)c1] | (S)-N-(3-fluoro-4-((3-((1-hydroxypropan-2-yl)amino)-1H-pyrazolo[3,4-b]pyridin-4-yl)oxy)phenyl)-5-(4-fluorophenyl)-1-isopropyl-4-oxo-1,4-dihydropyridine-3-carboxamide | 575.2 (M + H) |
| 126 | 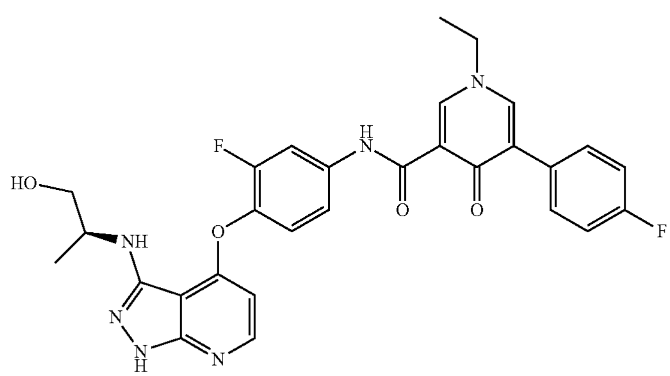 [SMILES: CCn1cc(C(=O)Nc2ccc(Oc3ccnc4[nH]nc(N[C@@H](C)CO)c34)c(F)c2)c(=O)c(-c2ccc(F)cc2)c1] | (S)-1-ethyl-N-(3-fluoro-4-((3-((1-hydroxypropan-2-yl)amino)-1H-pyrazolo[3,4-b]pyridin-4-yl)oxy)phenyl)-5-(4-fluorophenyl)-4-oxo-1,4-dihydropyridine-3-carboxamide | 561.2 (M + H) |
| 127 | 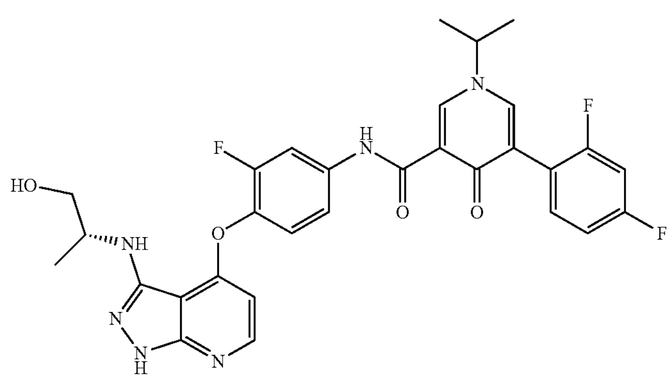 [SMILES: CC(C)n1cc(C(=O)Nc2ccc(Oc3ccnc4[nH]nc(N[C@H](C)CO)c34)c(F)c2)c(=O)c(-c2ccc(F)cc2F)c1] | (R)-5-(2,4-difluorophenyl)-N-(3-fluoro-4-((3-((1-hydroxypropan-2-yl)amino)-1H-pyrazolo[3,4-b]pyridin-4-yl)oxy)phenyl)-1-isopropyl-4-oxo-1,4-dihydropyridine-3-carboxamide | 593.2 (M + H) |
| 128 | 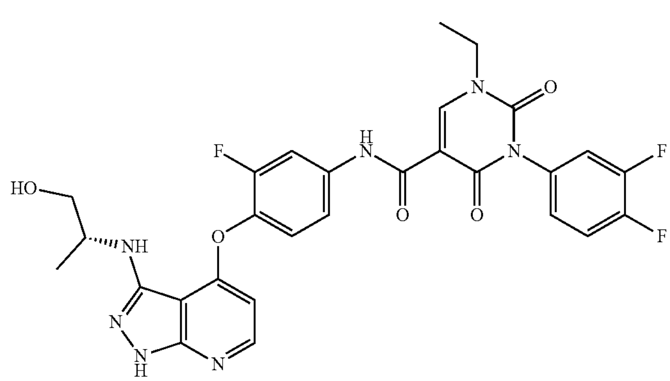 [SMILES: CCn1cc(C(=O)Nc2ccc(Oc3ccnc4[nH]nc(N[C@H](C)CO)c34)c(F)c2)c(=O)n(-c2ccc(F)c(F)c2)c1=O] | (R)-3-(3,4-difluorophenyl)-1-ethyl-N-(3-fluoro-4-((3-((1-hydroxypropan-2-yl)amino)-1H-pyrazolo[3,4-b]pyridin-4-yl)oxy)phenyl)-2,4-dioxo-1,2,3,4-tetrahydropyrimidine-5-carboxamide | 596.2 (M + H) |

-continued

| Ex. No. | Structure | Name | Mass Spectrum |
|---|---|---|---|
| 129 | 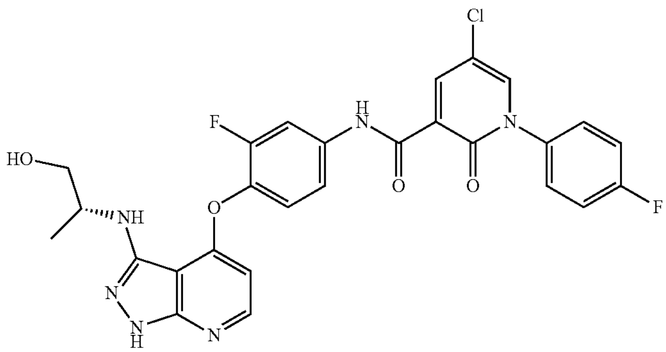 | (R)-5-chloro-N-(3-fluoro-4-((3-((1-hydroxypropan-2-yl)amino)-1H-pyrazolo[3,4-b]pyridin-4-yl)oxy)phenyl)-1-(4-fluorophenyl)-2-oxo-1,2-dihydropyridine-3-carboxamide | 567.2 (M + H) |
| 130 | 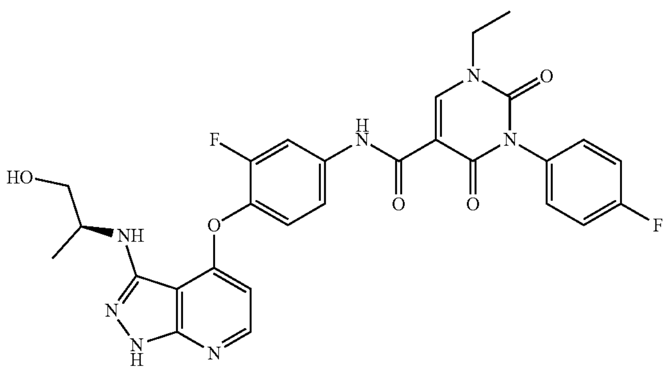 [SMILES: CCn1cc(C(=O)Nc2ccc(Oc3ccnc4[nH]nc(N[C@@H](C)CO)c34)c(F)c2)c(=O)n(-c2ccc(F)cc2)c1=O] | (S)-1-ethyl-N-(3-fluoro-4-((3-((1-hydroxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 578.2 (M + H) |
| 131 | 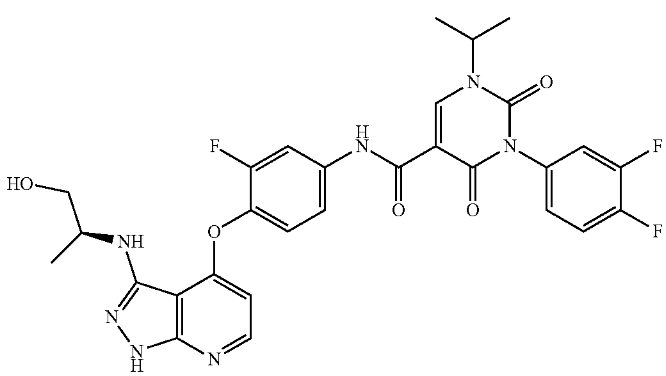 [SMILES: CC(C)n1cc(C(=O)Nc2ccc(Oc3ccnc4[nH]nc(N[C@@H](C)CO)c34)c(F)c2)c(=O)n(-c2ccc(F)c(F)c2)c1=O] | (S)-3-(3,4-difluorophenyl)-N-(3-fluoro-4-((3-((1-hydroxypropan-2-yl)amino)-1H-pyrazolo[3,4-b]pyridin-4-yl)oxy)phenyl)-1-isopropyl-2,4-dioxo-1,2,3,4-tetrahydropyrimidine-5-carboxamide | 610.2 (M + H) |
| 132 | 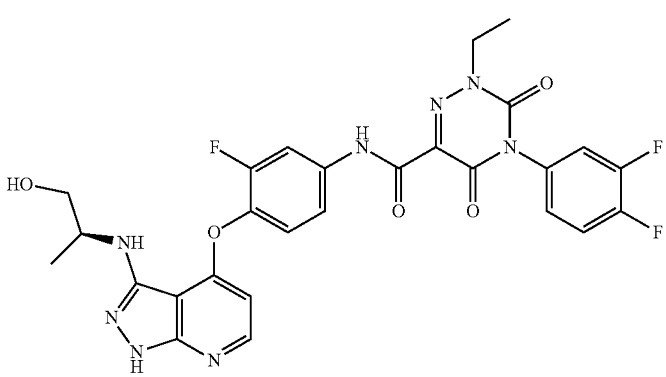 [SMILES: CCn1nc(C(=O)Nc2ccc(Oc3ccnc4[nH]nc(N[C@@H](C)CO)c34)c(F)c2)c(=O)n(-c2ccc(F)c(F)c2)c1=O] | (S)-4-(3,4-difluorophenyl)-2-ethyl-N-(3-fluoro-4-((3-((1-hydroxypropan-2-yl)amino)-1H-pyrazolo[3,4-b]pyridin-4-yl)oxy)phenyl)-3,5-dioxo-2,3,4,5-tetrahydro-1,2,4-triazine-6-carboxamide | 597.2 (M + H) |

-continued

| Ex. No. | Structure | Name | Mass Spectrum |
|---|---|---|---|
| 133 | 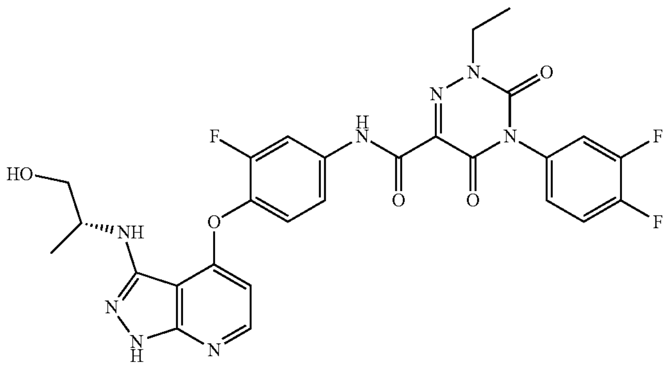 [SMILES: CCn1nc(C(=O)Nc2ccc(Oc3ccnc4[nH]nc(N[C@H](C)CO)c34)c(F)c2)c(=O)n(-c2ccc(F)c(F)c2)c1=O] | (R)-4-(3,4-difluorophenyl)-2-ethyl-N-(3-fluoro-4-((3-((1-hydroxypropan-2-yl)amino)-1H-pyrazolo[3,4-b]pyridin-4-yl)oxy)phenyl)-3,5-dioxo-2,3,4,5-tetrahydro-1,2,4-triazine-6-carboxamide | 597.2 (M + H) |
| 134 | 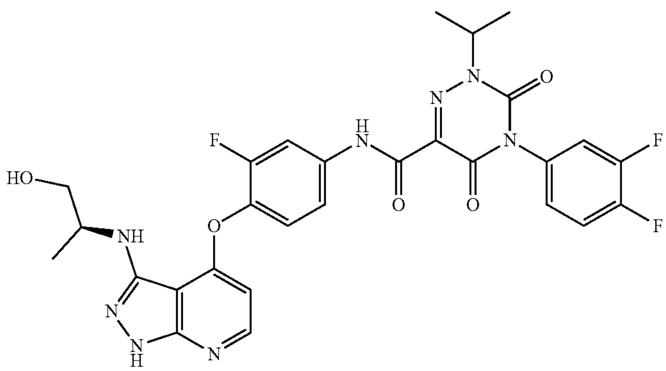 | (S)-4-(3,4-difluorophenyl)-N-(3-fluoro-4-((3-((1-hydroxypropan-2-yl)amino)-1H-pyrazolo[3,4-b]pyridin-4-yl)oxy)phenyl)-2-isopropyl-3,5-dioxo-2,3,4,5-tetrahydro-1,2,4-triazine-6-carboxamide | 611.2 (M + H) |
| 135 | 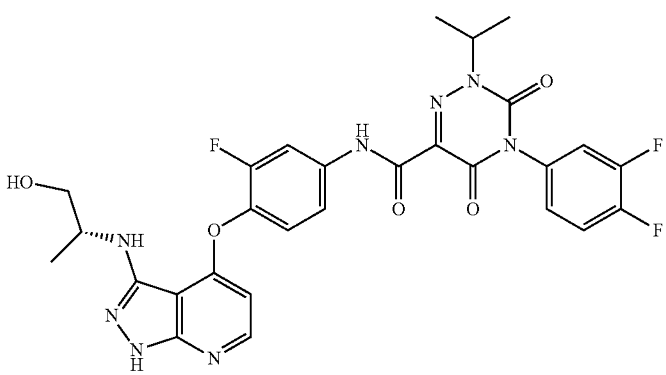 [SMILES: CC(C)n1nc(C(=O)Nc2ccc(Oc3ccnc4[nH]nc(N[C@H](C)CO)c34)c(F)c2)c(=O)n(-c2ccc(F)c(F)c2)c1=O] | (R)-4-(3,4-difluorophenyl)-N-(3-fluoro-4-((3-((1-hydroxypropan-2-yl)amino)-1H-pyrazolo[3,4-b]pyridin-4-yl)oxy)phenyl)-2-isopropyl-3,5-dioxo-2,3,4,5-tetrahydro-1,2,4-triazine-6-carboxamide | 611.2 (M + H) |
| 136 | 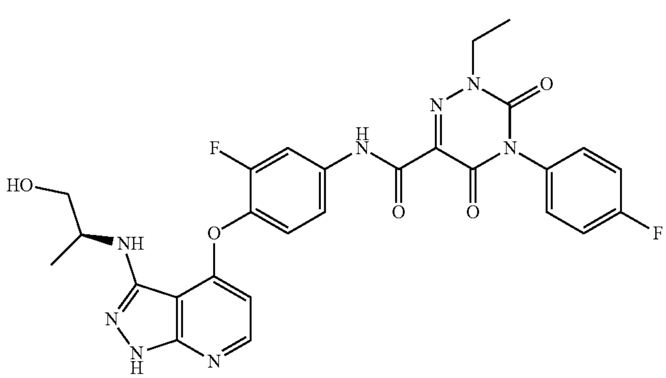 [SMILES: CCn1nc(C(=O)Nc2ccc(Oc3ccnc4[nH]nc(N[C@@H](C)CO)c34)c(F)c2)c(=O)n(-c2ccc(F)cc2)c1=O] | (S)-2-ethyl-N-(3-fluoro-4-((3-((1-hydroxypropan-2-yl)amino)-1H-pyrazolo[3,4-b]pyridin-4-yl)oxy)phenyl)-4-(4-fluorophenyl)-3,5-dioxo-2,3,4,5-tetrahydro-1,2,4-triazine-6-carboxamide | 579.2 (M + H) |

| Ex. No. | Structure | Name | Mass Spectrum |
|---|---|---|---|
| 137 | 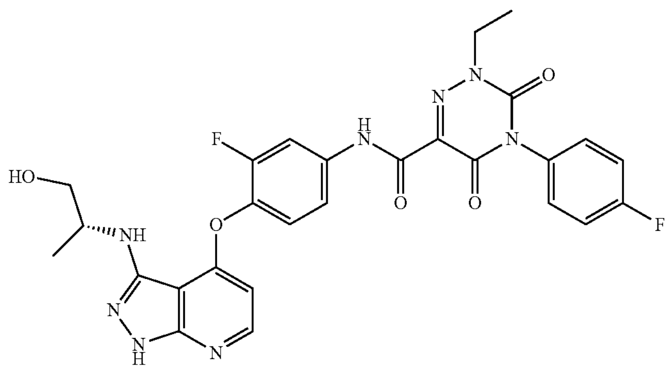 [SMILES: CCn1nc(C(=O)Nc2ccc(Oc3ccnc4[nH]nc(N[C@H](C)CO)c34)c(F)c2)c(=O)n(-c2ccc(F)cc2)c1=O] | (R)-2-ethyl-N-(3-fluoro-4-((3-((1-hydroxypropan-2-yl)amino)-1H-pyrazolo[3,4-b]pyridin-4-yl)oxy)phenyl)-4-(4-fluorophenyl)-3,5-dioxo-2,3,4,5-tetrahydro-1,2,4-triazine-6-carboxamide | 579.2 (M + H) |
| 138 | 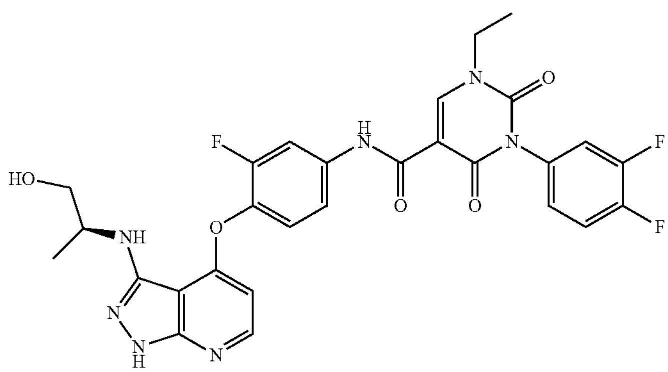 [SMILES: CCn1cc(C(=O)Nc2ccc(Oc3ccnc4[nH]nc(N[C@@H](C)CO)c34)c(F)c2)c(=O)n(-c2ccc(F)c(F)c2)c1=O] | (S)-3-(3,4-difluorophenyl)-1-ethyl-N-(3-fluoro-4-((3-((1-hydroxypropan-2-yl)amino)-1H-pyrazolo[3,4-b]pyridin-4-yl)oxy)phenyl)-2,4-dioxo-1,2,3,4-tetrahydropyrimidine-5-carboxamide | 596.2 (M + H) |
| 139 | 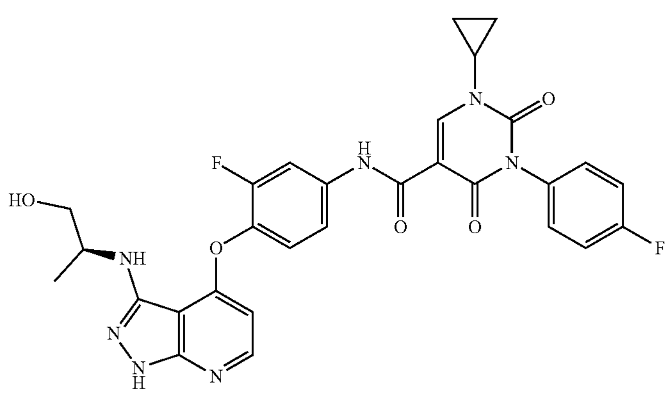 [SMILES: C[C@@H](CO)Nc1n[nH]c2nccc(Oc3ccc(NC(=O)c4cn(C5CC5)c(=O)n(-c5ccc(F)cc5)c4=O)cc3F)c12] | (S)-1-cyclopropyl-N-(3-fluoro-4-((3-((1-hydroxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 590.2 (M + H) |
| 140 | 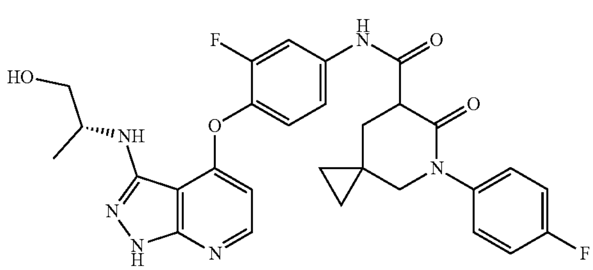 [SMILES: C[C@H](CO)Nc1n[nH]c2nccc(Oc3ccc(NC(=O)C4CC5(CC5)CN(c5ccc(F)cc5)C4=O)cc3F)c12] | N-(3-fluoro-4-((3-(((R)-1-hydroxypropan-2-yl)amino)-1H-pyrazolo[3,4-b]pyridin-4-yl)oxy)phenyl)-5-(4-fluorophenyl)-6-oxo-5-azaspiro[2.5]octane-7-carboxamide | 563.2 (M + H) |

| Ex. No. | Structure | Name | Mass Spectrum |
|---|---|---|---|
| 141 | 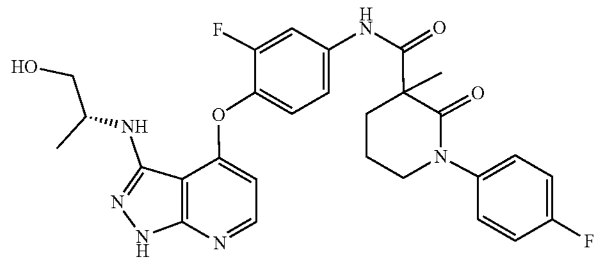 | N-(3-fluoro-4-((3-(((R)-1-hydroxypropan-2-yl)amino)-1H-pyrazolo[3,4-b]pyridin-4-yl)oxy)phenyl)-1-(4-fluorophenyl)-3-methyl-2-oxopiperidine-3-carboxamide | 551.2 (M + H) |

Example 142

(R)—N-(3-fluoro-4-((3-((1-hydroxypropan-2-yl)amino)-1H-pyrazolo[3,4-b]pyridin-4-yl)oxy)phenyl)-5-hydroxy-2-oxo-1-phenyl-1,2-dihydroquinoline-3-carboxamide

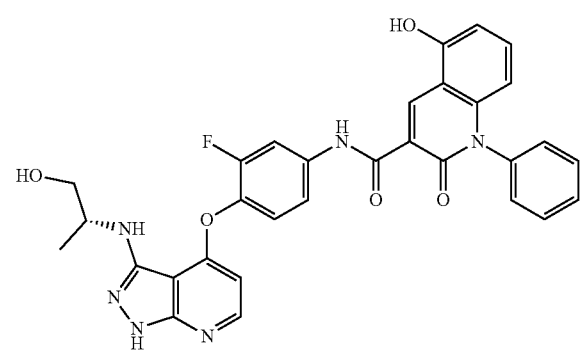

Step A: N-(3-fluoro-4-((3-iodo-1-(4-methoxybenzyl)-1H-pyrazolo[3,4-b]pyridin-4-yl)oxy)phenyl)-2,5-dioxo-1-phenyl-1,2,5,6,7,8-hexahydroquinoline-3-carboxamide (Preparation 66; 400 mg, 0.53 mmol), D-alaninol (124 µL, 1.59 mmol), $K_2CO_3$ (585 mg, 4.24 mmol) and pyrrole-2-carboxylic acid (0.0294 g, 0.265 mmol) were suspended in DMSO (5 mL) and the mixture was degassed for 5 min with Ar. Cu(I)iodide was added and the mixture heated to 60° C. in a sealed tube overnight. The cooled mixture was partitioned between water (30 mL) and EtOAc (30 mL) and the aqueous layer was extracted with EtOAc (2×20 mL). The combined organic phases were washed with water (5×20 mL) and brine (20 mL), dried over $Na_2SO_4$, filtered and concentrated. The residue was purified over silica gel to afford 2 products. The lower Rf material was isolated to afford (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-5-hydroxy-2-oxo-1-phenyl-1,2-dihydroquinoline-3-carboxamide (41 mg, 11%).

Step B: (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-5-hydroxy-2-oxo-1-phenyl-1,2-dihydroquinoline-3-carboxamide (41 mg, 0.06 mmol) was dissolved in DCM (0.5 mL) and TFA (1 mL) was added and the reaction was warmed to 35° C. for 4 h. The cooled mixture was concentrated, diluted with DCM and concentrated again. The residue was dissolved in MeOH with a small amount of DCM to aid solubility and $K_2CO_3$ (20 mg) was added. After stirring for 2 h, the reaction mixture was filtered and concentrated. The residue was purified over silica gel (0-12% MeOH in DCM) to afford (R)—N-(3-fluoro-4-((3-((1-hydroxypropan-2-yl)amino)-1H-pyrazolo[3,4-b]pyridin-4-yl)oxy)phenyl)-5-hydroxy-2-oxo-1-phenyl-1,2-dihydroquinoline-3-carboxamide (11.2 mg, 33%). Mass spectrum: m/z=581.2 (M+H). $^1$H NMR ($CD_3OD$) δ 12.23 (s, 1H), 9.58 (d, 1H), 8.13 (d, 1H), 8.00 (dd, 1H), 7.71-7.57 (m, 3H), 7.40 (ddd, 1H), 7.35-7.29 (m, 6H), 7.23 (t, 1H), 6.73 (d, 1H), 6.14 (d, 1H), 6.09 (dd, 1H), 3.93 (m, 1H), 3.70 (d, 2H), 1.34 (d, 3H).

Example 143

(R)-2-(4-fluorophenyl)-N-(5-((3-((1-hydroxypropan-2-yl)amino)-1H-pyrazolo[3,4-b]pyridin-4-yl)oxy)pyridin-2-yl)-3-oxo-2,3-dihydropyridazine-4-carboxamide hydrochloride

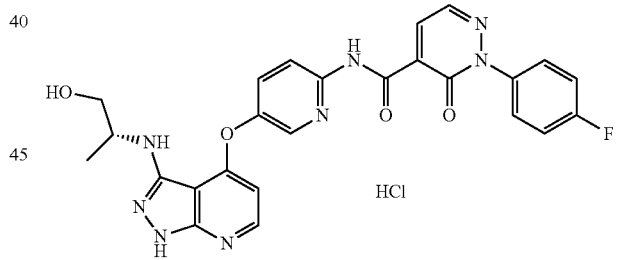

To a mixture of (R)-2-((4-((6-aminopyridin-3-yl)oxy)-1-(4-methoxybenzyl)-1H-pyrazolo[3,4-b]pyridin-3-yl)amino)propan-1-ol (Preparation 60; 0.030 g, 0.071 mmol), 2-(4-fluorophenyl)-3-oxo-2,3-dihydropyridazine-4-carboxylic acid (0.033 g, 0.14 mmol), EDCI (0.082 g, 0.43 mmol) and HOBt (0.058 g, 0.43 mmol) was added DMF (0.7 ml). The reaction mixture was allowed to stir for 4 h and was then added to 50 mL of water while stirring. The resultant solids were filtered and washed with water (15 mL) and hexanes (15 mL) and purified via C18 chromatography (5-95% ACN in water with 0.2% TFA). The purified material was dissolved in TFA (2 mL) and heated to 50° C. for 4 h. The reaction mixture was concentrated and partitioned between DCM and 1M LiOH. The combined organic layers were dried over sodium sulfate, filtered and concentrated. The residue was purified by C18 chromatography (5-95% ACN in water with 0.2% TFA). The fractions containing the product were concentrated in vacuo and then treated with 4N F1C1 in dioxanes. A small amount of methanol (5 mL) was added to make sure everything was in solution. The mixture was concentrated in vacuo. The isolated solids were dried overnight to provide (R)-2-(4-fluorophenyl)-N-(5-((3-((1-hydroxypropan-2-yl)amino)-1H-pyrazolo[3,4-b]pyridin-4-yl)oxy)pyridin-2-yl)-3-oxo-2,3-dihydropyridazine-4-carboxamide hydrochloride (0.0054 g, 0.0092 mmol, 13% yield) as a yellow solid. Mass spectrum: m/z=517.2 (M+H-HCl). $^1$H NMR (d$_6$-DMSO) δ 12.13 (s, 1H), 8.45 (d, 1H), 8.42 (d, 1H), 8.40 (d, 1H), 8.34 (d, 1H), 8.22 (s, 1H), 7.96 (m, 1H), 7.69 (m, 2H), 7.41 (m, 2H), 6.13 (d, 1H), 3.80 (m, 1H), 3.73-3.65 (m, 2H), 3.55-3.45 (m, 3H), 1.22 (d, 3H).

The following compounds were also made using the procedure according to Example 143.

11.3 g, 38.5 mmol) was dissolved in DMF (150 mL) and 2-(3H-[1,2,3]triazolo[4,5-b]pyridin-3-yl)-1,1,3,3-tetramethylisouronium hexafluorophosphate(V) (14.7 g, 38.5 mmol) was added. The reaction mixture was stirred for 10 min, and then triethylamine (13.4 ml, 96.3 mmol) was added to the mixture. (R)-4-(4-amino-2-fluorophenoxy)-1-(4-methoxybenzyl)-N-(1-methoxypropan-2-yl)-1H-pyrazolo[3,4-b]pyridin-3-amine (14.5 g, 32.1 mmol), dissolved in DMF (50 mL) was added to the reaction and the reaction mixture was stirred overnight. The reaction mixture was partitioned between 80% brine and MTBE. The combined organic layers were dried over Na$_2$SO$_4$, filtered and concentrated, during which solids formed. The concentrated solution was filtered to afford pure product. The filtrate was purified over silica gel (40-80% EtOAc in hexanes) to afford additional

| Ex No | Structure | Name | Mass Spectrum |
|---|---|---|---|
| 144 | 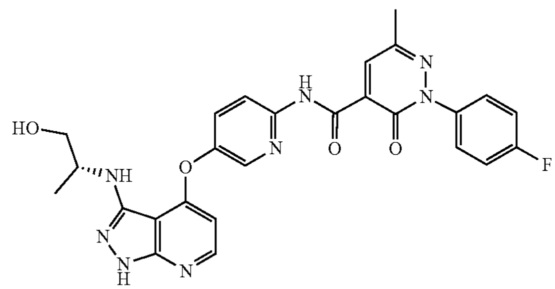 [SMILES: Cc1cc(C(=O)Nc2ccc(Oc3ccnc4[nH]nc(N[C@H](C)CO)c34)cn2)c(=O)n(-c2ccc(F)cc2)n1] | (R)-2-(4-fluorophenyl)-N-(5-((3-((1-hydroxypropan-2-yl)amino)-1H-pyrazolo[3,4-b]pyridin-4-yl)oxy)pyridin-2-yl)-6-methyl-3-oxo-2,3-dihydropyridazine-4-carboxamide | 531.2 (M + H) |
| 145 | 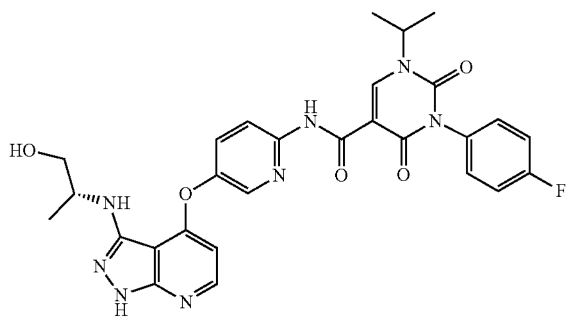 [SMILES: CC(C)n1cc(C(=O)Nc2ccc(Oc3ccnc4[nH]nc(N[C@H](C)CO)c34)cn2)c(=O)n(-c2ccc(F)cc2)c1=O] | (R)-3-(4-fluorophenyl)-N-(5-((3-((1-hydroxypropan-2-yl)amino)-1H-pyrazolo[3,4-b]pyridin-4-yl)oxy)pyridin-2-yl)-1-isopropyl-2,4-dioxo-1,2,3,4-tetrahydropyrimidine-5-carboxamide | 575.2 (M + H) |

Example 146

(R)—N-(3-fluoro-4-((3-((1-methoxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide hydrochloride

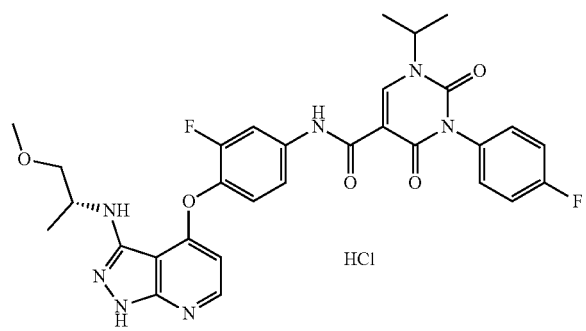 [SMILES: COC[C@@H](C)Nc1n[nH]c2nccc(Oc3ccc(NC(=O)c4cn(C(C)C)c(=O)n(-c5ccc(F)cc5)c4=O)cc3F)c12 ; Cl]

Step A: 3-(4-Fluorophenyl)-1-isopropyl-2,4-dioxo-1,2,3,4-tetrahydropyrimidine-5-carboxylic acid (Preparation 7;

product. The combined lots afforded (R)—N-(3-fluoro-4-((1-(4-methoxybenzyl)-3-((1-methoxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (22.3 g, 30.7 mmol, 95.7% yield).

Step B: (R)—N-(3-fluoro-4-((1-(4-methoxybenzyl)-3-((1-methoxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (22.3 g, 30.7 mmol) was dissolved in TFA (40 mL) and heated to 50° C. After 4 h, additional TFA (10 mL) added. After 8 h, the reaction mixture was cooled and carefully poured into MTBE (150 mL) with vigorous stirring. The solids were dissolved in EtOAc and washed with saturated NaHCO$_3$, dried over sodium sulfate, filtered and concentrated. The residue was purified over silica gel (70-100% EtOAc in hexanes) to afford a solid. The solid was dissolved in DCM (100 mL), and 5M HCl in IPA added (1.5 eq). The solution was added slowly to 700 mL Et$_2$O with stirring. The mixture was stirred for 10 min, then filtered and the solids were washed with Et$_2$O. The isolated solids were dried in vacuum oven to afford (R)—N-(3-fluoro-4-((3-((1-methoxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide hydrochloride (13.9 g, 21.6 mmol, 70.5% yield) as a bright yellow solid. Mass spectrum: m/z=606.2 (M+H-HCl). ¹H NMR (d₆-DMSO) δ 11.07 (s, 1H), 8.68 (s, 1H), 8.24 (d, 1H), 8.03 (dd, 1H), 7.57 (dd, 1H), 7.50 (t, 1H), 7.43 (m, 2H), 7.36 (m, 2H), 6.11 (dd, 1H), 4.78 (m, 1H), 3.98 (m, 1H), 3.51 (dd, 1H), 3.39 (dd, 1H), 1.43 (d, 6H), 1.23 (d, 3H).

The following compounds were also made using the procedure according to Example 146.

| Ex. No. | Structure | Name | Mass Spectrum |
|---|---|---|---|
| 147 | 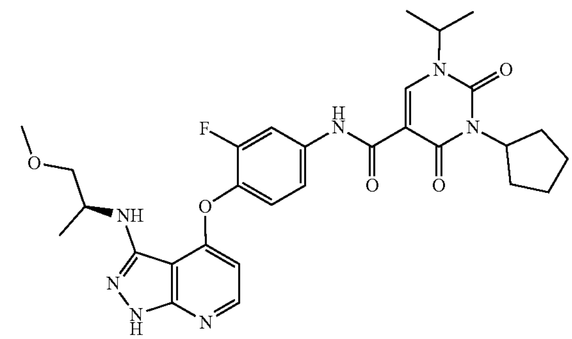 [SMILES: COC[C@H](C)Nc1n[nH]c2nccc(Oc3ccc(NC(=O)c4cn(C(C)C)c(=O)n(C5CCCC5)c4=O)cc3F)c12] | (S)-3-cyclopentyl-N-(3-fluoro-4-((3-((1-methoxypropan-2-yl)amino)-1H-pyrazolo[3,4-b]-pyridin-4-yl)oxy)phenyl)-1-isopropyl-2,4-dioxo-1,2,3,4-tetrahydropyrimidine-5-carboxamide | 580.3 (M + H) |
| 148 | 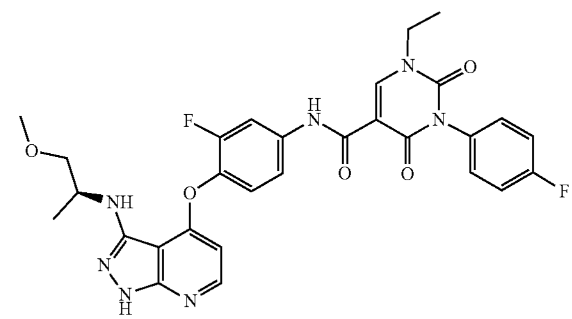 [SMILES: CCn1cc(C(=O)Nc2ccc(Oc3ccnc4[nH]nc(N[C@@H](C)COC)c34)c(F)c2)c(=O)n(-c2ccc(F)cc2)c1=O] | (S)-1-ethyl-N-(3-fluoro-4-((3-((1-methoxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 592.2 (M + H) |
| 149 | 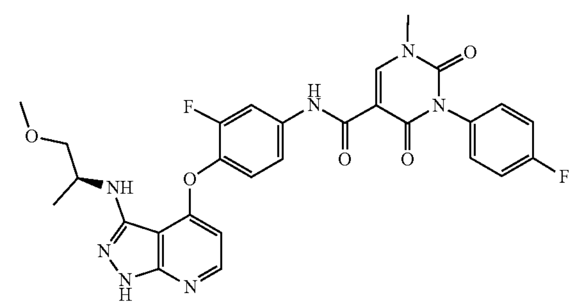 [SMILES: COC[C@H](C)Nc1n[nH]c2nccc(Oc3ccc(NC(=O)c4cn(C)c(=O)n(-c5ccc(F)cc5)c4=O)cc3F)c12] | (S)-N-(3-fluoro-4-((3-((1-methoxypropan-2-yl)amino)-1H-pyrazolo[3,4-b]pyridin-4-yl)oxy)phenyl)-3-(4-fluorophenyl)-1-methyl-2,4-dioxo-1,2,3,4-tetrahydropyrimidine-5-carboxamide | 578.2 (M + H) |
| 150 | 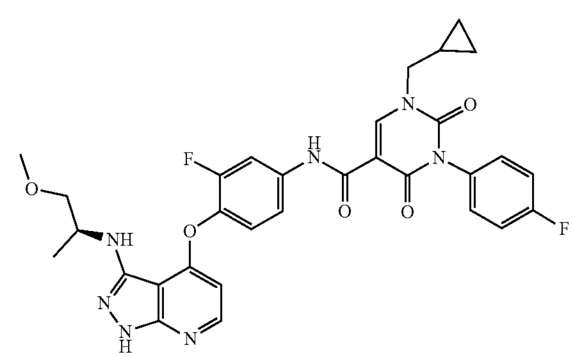 [SMILES: COC[C@H](C)Nc1n[nH]c2nccc(Oc3ccc(NC(=O)c4cn(CC5CC5)c(=O)n(-c5ccc(F)cc5)c4=O)cc3F)c12] | (S)-1-(cyclopropylmethyl)-N-(3-fluoro-4-((3-((1-methoxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 618.2 (M + H) |

-continued

| Ex. No. | Structure | Name | Mass Spectrum |
|---|---|---|---|
| 151 | 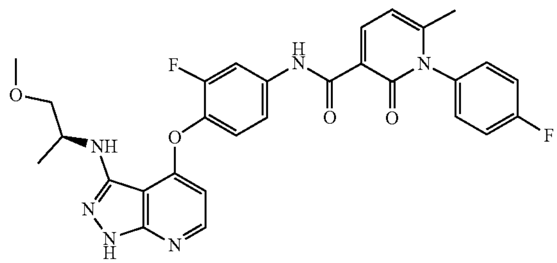 [SMILES: COC[C@H](C)Nc1n[nH]c2nccc(Oc3ccc(NC(=O)c4ccc(C)n(-c5ccc(F)cc5)c4=O)cc3F)c12] | (S)-N-(3-fluoro-4-((3-((1-methoxypropan-2-yl)amino)-1H-pyrazolo[3,4-b]pyridin-4-yl)oxy)phenyl)-1-(4-fluorophenyl)-6-methyl-2-oxo-1,2-dihydropyridine-3-carboxamide | 561.2 (M + H) |
| 152 | 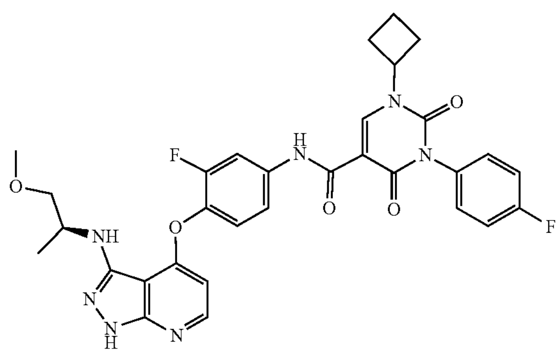 [SMILES: COC[C@H](C)Nc1n[nH]c2nccc(Oc3ccc(NC(=O)c4cn(C5CCC5)c(=O)n(-c5ccc(F)cc5)c4=O)cc3F)c12] | (S)-1-cyclobutyl-N-(3-fluoro-4-((3-((1-methoxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 618.2 (M + H) |
| 153 | 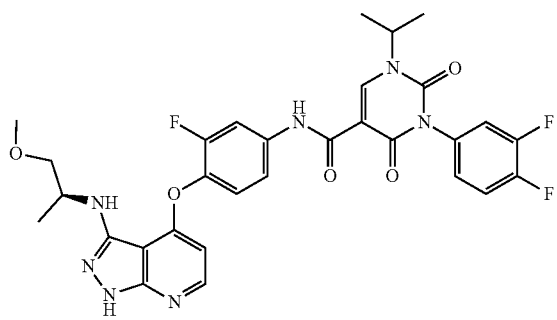 [SMILES: COC[C@H](C)Nc1n[nH]c2nccc(Oc3ccc(NC(=O)c4cn(C(C)C)c(=O)n(-c5ccc(F)c(F)c5)c4=O)cc3F)c12] | (S)-3-(3,4-difluorophenyl)-N-(3-fluoro-4-((3-((1-methoxypropan-2-yl)amino)-1H-pyrazolo[3,4-b]pyridin-4-yl)oxy)phenyl)-1-isopropyl-2,4-dioxo-1,2,3,4-tetrahydropyrimidine-5-carboxamide | 624.2 (M + H) |
| 154 | 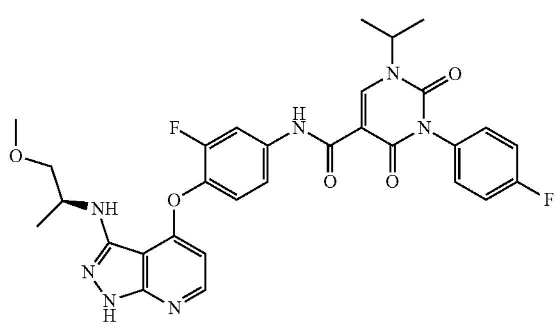 | (S)-N-(3-fluoro-4-((3-((1-methoxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 606.2 (M + H) |
| 155 | 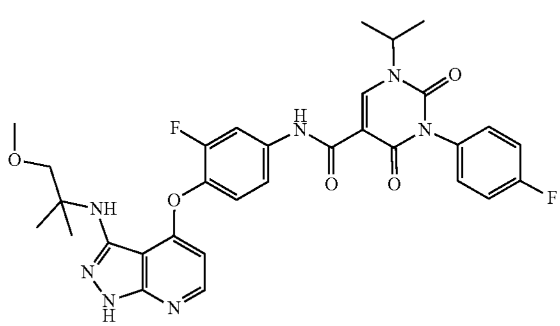 [SMILES: COCC(C)(C)Nc1n[nH]c2nccc(Oc3ccc(NC(=O)c4cn(C(C)C)c(=O)n(-c5ccc(F)cc5)c4=O)cc3F)c12] | N-(3-fluoro-4-((3-((1-methoxy-2-methylpropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 620.2 (M + H) |

-continued

| Ex. No. | Structure | Name | Mass Spectrum |
|---|---|---|---|
| 156 | 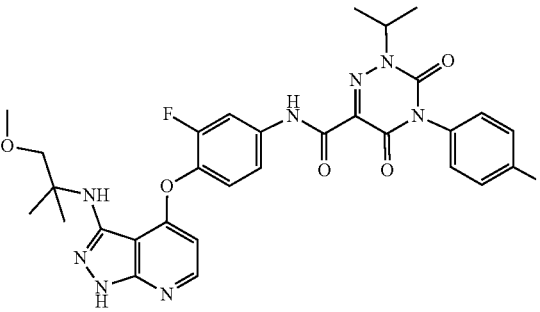 | N-(3-fluoro-4-((3-((1-methoxy-2-methyl-propan-2-yl)amino)-1H-pyrazolo[3,4-b]-pyridin-4-yl)oxy)phen-yl)-4-(4-fluorophenyl)-2-isopropyl-3,5-dioxo-2,3,4,5-tetrahydro-1,2,4-triazine-6-carboxamide | 621.2 (M + H) |
| 157 | 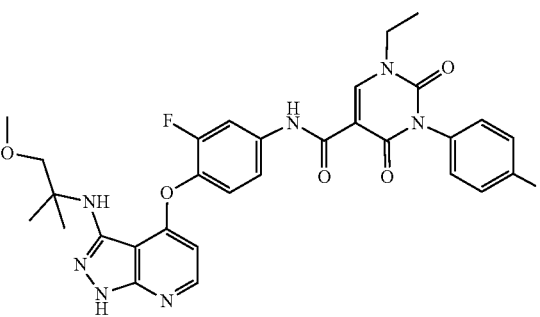 | 1-ethyl-N-(3-fluoro-4-((3-((1-methoxy-2-methylpropan-2-yl)-amino)-1H-pyrazolo-[3,4-b]pyridin-4-yl)-oxy)phenyl)-3-(4-fluorophenyl)-2,4-dioxo-1,2,3,4-tetra-hydropyrimidine-5-carboxamide | 606.2 (M + H) |
| 158 | 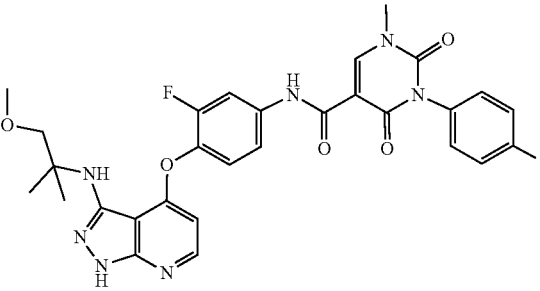 | N-(3-fluoro-4-((3-((1-methoxy-2-methyl-propan-2-yl)amino)-1H-pyrazolo[3,4-b]pyridin-4-yl)oxy)phenyl)-3-(4-fluorophenyl)-1-methyl-2,4-dioxo-1,2,3,4-tetrahydropyrimidine-5-carboxamide | 592.2 (M + H) |
| 159 | 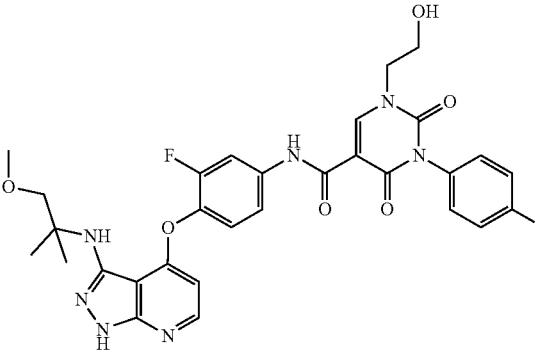 | N-(3-fluoro-4-((3-((1-methoxy-2-methyl-propan-2-yl)amino)-1H-pyrazolo[3,4-b]-pyridin-4-yl)oxy)-phenyl)-3-(4-fluoro-phenyl)-1-(2-hydroxy-ethyl)-2,4-dioxo-1,2,3,4-tetrahydropyrimidine-5-carboxamide | 622.2 (M + H) |
| 160 | 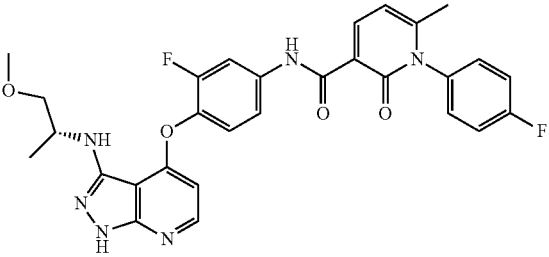 [SMILES: COC[C@@H](C)Nc1n[nH]c2nccc(Oc3ccc(NC(=O)c4ccc(C)n(-c5ccc(F)cc5)c4=O)cc3F)c12] | (R)-N-(3-fluoro-4-((3-((1-methoxypropan-2-yl)amino)-1H-pyrazolo-[3,4-b]pyridin-4-yl)-oxy)phenyl)-1-(4-fluorophenyl)-6-meth-yl-2-oxo-1,2-dihydro-pyridine-3-carboxamide | 561.2 (M + H) |

-continued

| Ex. No. | Structure | Name | Mass Spectrum |
|---|---|---|---|
| 161 | 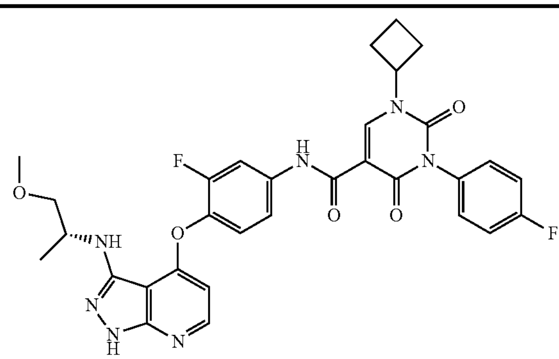 | (R)-1-cyclobutyl-N-(3-fluoro-4-((3-((1-methoxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide | 618.3 (M + H) |
| 162 | 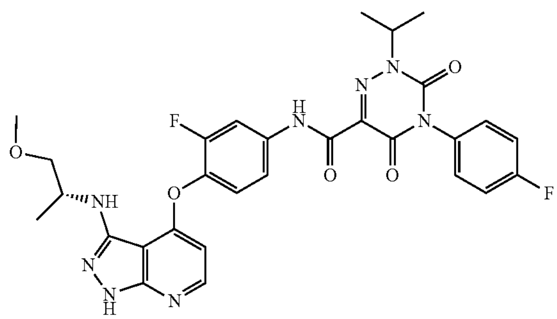 [SMILES: COC[C@@H](C)Nc1n[nH]c2nccc(Oc3ccc(NC(=O)c4nn(C(C)C)c(=O)n(-c5ccc(F)cc5)c4=O)cc3F)c12] | (R)-N-(3-fluoro-4-((3-((1-methoxypropan-2-yl)amino)-1H-pyrazolo[3,4-b]pyridin-4-yl)oxy)phenyl)-4-(4-fluorophenyl)-2-isopropyl-3,5-dioxo-2,3,4,5-tetrahydro-1,2,4-triazine-6-carboxamide | 607.2 (M + H) |
| 163 | 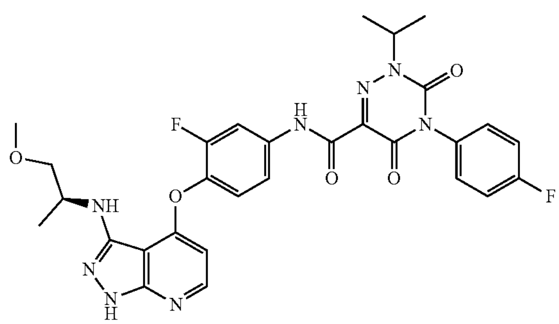 | (S)-N-(3-fluoro-4-((3-((1-methoxypropan-2-yl)amino)-1H-pyrazolo[3,4-b]pyridin-4-yl)oxy)phenyl)-4-(4-fluorophenyl)-2-isopropyl-3,5-dioxo-2,3,4,5-tetrahydro-1,2,4-triazine-6-carboxamide | 607.2 (M + H) |
| 164 | 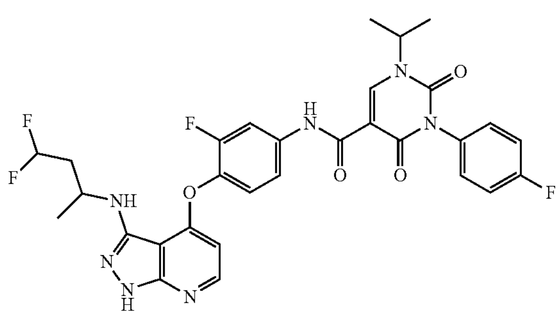 [SMILES: CC(CC(F)F)Nc1n[nH]c2nccc(Oc3ccc(NC(=O)c4cn(C(C)C)c(=O)n(-c5ccc(F)cc5)c4=O)cc3F)c12] | N-(4-((3-((4,4-difluorobutan-2-yl)amino)-1H-pyrazolo[3,4-b]pyridin-4-yl)oxy)-3-fluorophenyl)-3-(4-fluorophenyl)-1-isopropyl-2,4-dioxo-1,2,3,4-tetrahydropyrimidine-5-carboxamide | 626.2 (M + H) |
| 165 | 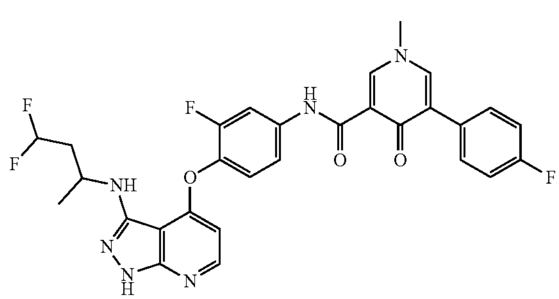 [SMILES: CC(CC(F)F)Nc1n[nH]c2nccc(Oc3ccc(NC(=O)c4cn(C)cc(-c5ccc(F)cc5)c4=O)cc3F)c12] | N-(4-((3-((4,4-difluorobutan-2-yl)amino)-1H-pyrazolo[3,4-b]pyridin-4-yl)oxy)-3-fluorophenyl)-5-(4-fluorophenyl)-1-methyl-4-oxo-1,4-dihydropyridine-3-carboxamide | 581.2 (M + H) |

-continued

| Ex. No. | Structure | Name | Mass Spectrum |
|---|---|---|---|
| 166 | 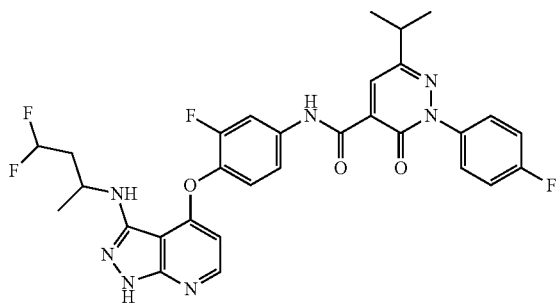 [SMILES: CC(CC(F)F)Nc1n[nH]c2nccc(Oc3ccc(NC(=O)c4cc(C(C)C)nn(-c5ccc(F)cc5)c4=O)cc3F)c12] | N-(4-((3-((4,4-difluoro-butan-2-yl)amino)-1H-pyrazolo[3,4-b]pyridin-4-yl)oxy)-3-fluoro-phenyl)-2-(4-fluoro-phenyl)-6-isopropyl-3-oxo-2,3-dihydropyrida-zine-4-carboxamide | 610.2 (M + H) |
| 167 | 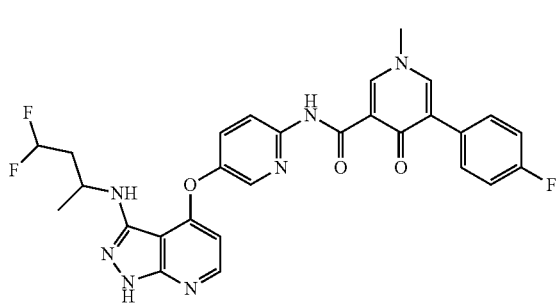 [SMILES: CC(CC(F)F)Nc1n[nH]c2nccc(Oc3ccc(NC(=O)c4cn(C)cc(-c5ccc(F)cc5)c4=O)nc3)c12] | N-(5-((3-((4,4-difluoro-butan-2-yl)amino)-1H-pyrazolo[3,4-b]pyridin-4-yl)oxy)pyridin-2-yl)-5-(4-fluorophenyl)-1-methyl-4-oxo-1,4-dihydropyridine-3-carboxamide | 564.2 (M + H) |
| 168 | 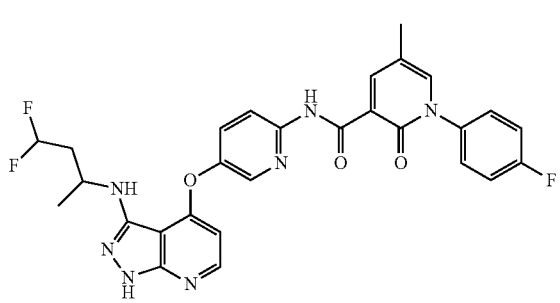 [SMILES: Cc1cc(C(=O)Nc2ccc(Oc3ccnc4[nH]nc(NC(C)CC(F)F)c34)cn2)c(=O)n(-c2ccc(F)cc2)c1] | N-(5-((3-((4,4-difluoro-butan-2-yl)amino)-1H-pyrazolo[3,4-b]pyridin-4-yl)oxy)pyridin-2-yl)-1-(4-fluorophenyl)-5-methyl-2-oxo-1,2-dihydropyridine-3-carboxamide | 564.2 (M + H) |
| 169 | 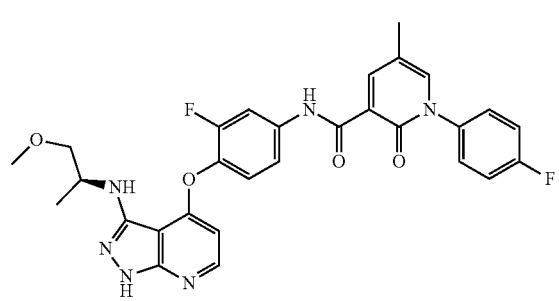 [SMILES: COC[C@H](C)Nc1n[nH]c2nccc(Oc3ccc(NC(=O)c4cc(C)cn(-c5ccc(F)cc5)c4=O)cc3F)c12] | (S)-N-(3-fluoro-4-((3-((1-methoxypropan-2-yl)amino)-1H-pyrazolo-[3,4-b]pyridin-4-yl)-oxy)phenyl)-1-(4-fluorophenyl)-5-methyl-2-oxo-1,2-dihydro-pyridine-3-carboxamide | 561.2 (M + H) |
| 170 | 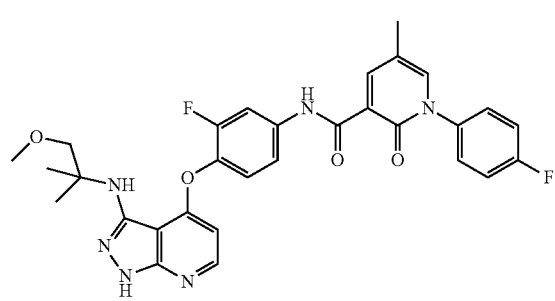 [SMILES: COCC(C)(C)Nc1n[nH]c2nccc(Oc3ccc(NC(=O)c4cc(C)cn(-c5ccc(F)cc5)c4=O)cc3F)c12] | N-(3-fluoro-4-((3-((1-methoxy-2-methyl-propan-2-yl)amino)-1H-pyrazolo[3,4-b]-pyridin-4-yl)oxy)-phenyl)-1-(4-fluoro-phenyl)-5-methyl-2-oxo-1,2-dihydropyri-dine-3-carboxamide | 575.2 (M + H) |

-continued

| Ex. No. | Structure | Name | Mass Spectrum |
|---|---|---|---|
| 171 | 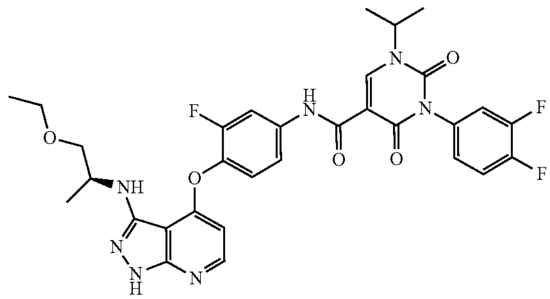 [SMILES: CCOC[C@H](C)Nc1n[nH]c2nccc(Oc3ccc(NC(=O)c4cn(C(C)C)c(=O)n(-c5ccc(F)c(F)c5)c4=O)cc3F)c12] | (S)-3-(3,4-difluorophenyl)-N-(4-((3-((1-ethoxypropan-2-yl)amino)-1H-pyrazolo[3,4-b]pyridin-4-yl)oxy)-3-fluorophenyl)-1-isopropyl-2,4-dioxo-1,2,3,4-tetrahydropyrimidine-5-carboxamide | 638.3 (M + H) |
| 172 | 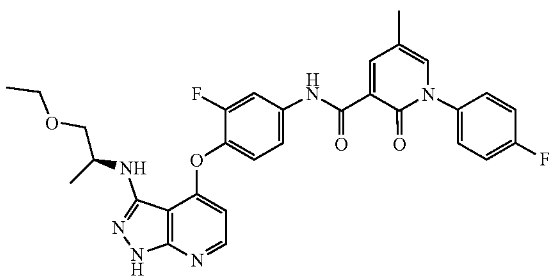 | (S)-N-(4-((3-((1-ethoxypropan-2-yl)amino)-1H-pyrazolo[3,4-b]pyridin-4-yl)oxy)-3-fluorophenyl)-1-(4-fluorophenyl)-5-methyl-2-oxo-1,2-dihydropyridine-3-carboxamide | 575.2 (M + H) |
| 173 | 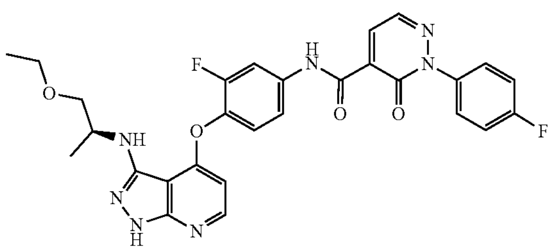 [SMILES: CCOC[C@H](C)Nc1n[nH]c2nccc(Oc3ccc(NC(=O)c4ccnn(-c5ccc(F)cc5)c4=O)cc3F)c12] | (S)-N-(4-((3-((1-ethoxypropan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 562.2 (M + H) |
| 174 | 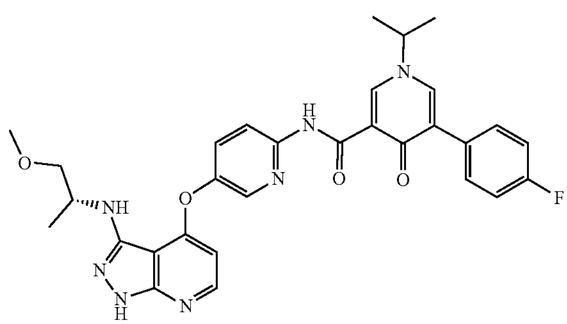 [SMILES: COC[C@@H](C)Nc1n[nH]c2nccc(Oc3ccc(NC(=O)c4cn(C(C)C)cc(-c5ccc(F)cc5)c4=O)nc3)c12] | (R)-5-(4-fluorophenyl)-1-isopropyl-N-(5-((3-((1-methoxypropan-2-yl)amino)-1H-pyrazolo[3,4-b]pyridin-4-yl)oxy)pyridin-2-yl)-4-oxo-1,4-dihydropyridine-3-carboxamide | 572.2 (M + H) |
| 175 | 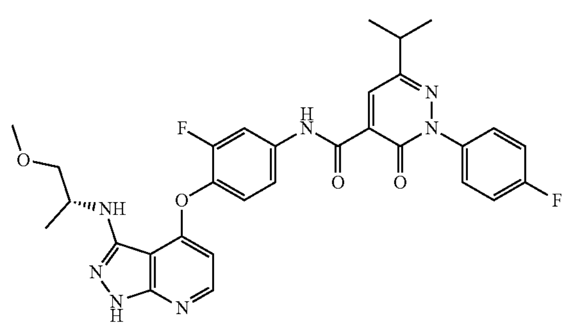 [SMILES: COC[C@@H](C)Nc1n[nH]c2nccc(Oc3ccc(NC(=O)c4cc(C(C)C)nn(-c5ccc(F)cc5)c4=O)cc3F)c12] | (R)-N-(3-fluoro-4-((3-((1-methoxypropan-2-yl)amino)-1H-pyrazolo[3,4-b]pyridin-4-yl)oxy)phenyl)-2-(4-fluorophenyl)-6-isopropyl-3-oxo-2,3-dihydropyridazine-4-carboxamide | 590.2 (M + H) |

| Ex. No. | Structure | Name | Mass Spectrum |
|---|---|---|---|
| 176 | 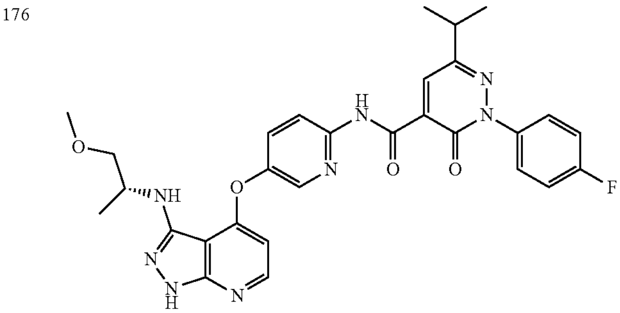 | (R)-2-(4-fluorophenyl)-6-isopropyl-N-(5-((3-((1-methoxypropan-2-yl)amino)-1H-pyrazolo[3,4-b]pyridin-4-yl)oxy)pyridin-2-yl)-3-oxo-2,3-dihydropyridazine-4-carboxamide | 573.2 (M + H) |
| 177 | 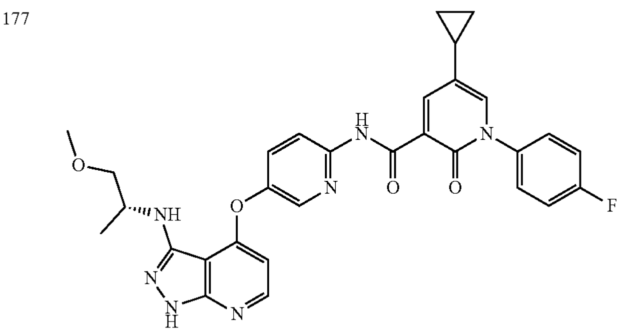 | (R)-5-cyclopropyl-1-(4-fluorophenyl)-N-(5-((3-((1-methoxypropan-2-yl)amino)-1H-pyrazolo[3,4-b]pyridin-4-yl)oxy)pyridin-2-yl)-2-oxo-1,2-dihydropyridine-3-carboxamide | 570.3 (M + H) |
| 178 | 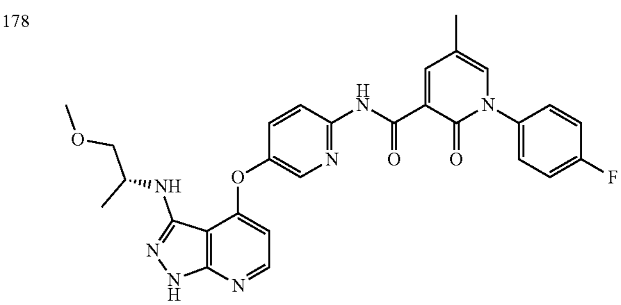 | (R)-1-(4-fluorophenyl)-N-(5-((3-((1-methoxypropan-2-yl)amino)-1H-pyrazolo[3,4-b]pyridin-4-yl)oxy)pyridin-2-yl)-5-methyl-2-oxo-1,2-dihydropyridine-3-carboxamide | 544.2 (M + H) |

Example 179

(R)-(cyclopropylmethyl)-N-(3-fluoro-4-((3-((1-methoxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide

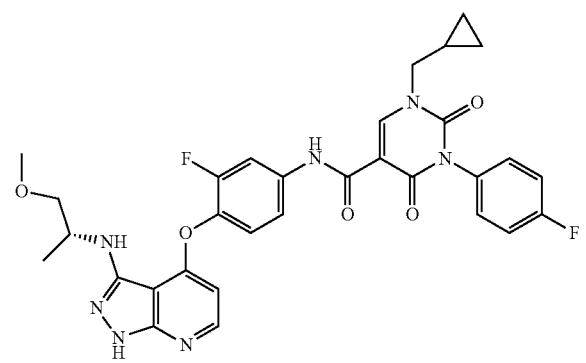 [SMILES: COC[C@@H](C)Nc1n[nH]c2nccc(Oc3ccc(NC(=O)c4cn(CC5CC5)c(=O)n(-c5ccc(F)cc5)c4=O)cc3F)c12]

To a mixture of 1-(cyclopropylmethyl)-3-(4-fluorophenyl)-2,4-dioxo-1,2,3,4-tetrahydropyrimidine-5-carboxylic acid (Preparation 10; 0.0438 g, 0.144 mmol), (R)-4-(4-amino-2-fluorophenoxy)-1-(4-methoxybenzyl)-N-(1-methoxypropan-2-yl)-1H-pyrazolo[3,4-b]pyridin-3-amine (0.050 g, 0.111 mmol), EDCI (0.0637 g, 0.332 mmol) and HOBt (0.0449 g, 0.332 mmol) was added DMF (1.1 ml) and stirred overnight. The reaction mixture was added to 30 mL of cold water while stirring. The resulting solids were filtered and washed with water (15 mL) and hexanes (5 mL). The isolated solids were suspended in 5 mL DCM, treated with 5 mL TFA and left to stir for 2 hr at 50° C. The reaction mixture was concentrated and partitioned between saturated NaHCO$_3$ and DCM. The organic layer was washed with water and then brine, dried over Na$_2$SO$_4$, filtered and concentrated. The residue was purified over silica gel (5-50% EtOAc in DCM) to afford (R)-1-(cyclopropylmethyl)-N-(3-fluoro-4-((3-((1-methoxypropan-2-yl)amino)-1H-pyrazolo[3,4-b]pyridin-4-yl)oxy)phenyl)-3-(4-fluorophenyl)-2,4-dioxo-1,2,3,4-tetrahydropyrimidine-5-carboxamide (54 mg, 71%). Mass spectrum: m/z=618.2 (M+H). $^1$H NMR (d$_6$-DMSO) δ 12.19 (s, 1H), 11.03 (s, 1H), 8.92 (s, 1H), 8.13 (d, 1H), 8.00 (dd, 1H), 7.53 (ddd, 1H), 7.45 (m, 3H), 7.36 (m, 2H), 6.02 (dd, 1H), 5.09 (d, 1H), 3.96 (m, 1H), 3.86 (d, 2H), 3.50 (dd, 1H), 3.37 (dd, 1H), 3.27 (s, 3H), 1.22 (d, 3H), 0.57 (m, 2H), 0.44 (m, 2H).

The following compounds were also made using the procedure according to Example 179.

The filtrate was washed with water and brine, dried over Na$_2$SO$_4$, filtered through Celite® and concentrated. The residue was purified over silica gel (0-10% MeOH in DCM) to afford methyl 1-((4-(2-fluoro-4-(2-(4-fluorophenyl)-3-oxo-2,3-dihydropyridazine-4-carboxamido)phenoxy)-1-(4-

| Ex. No. | Structure | Name | Mass Spectrum |
|---|---|---|---|
| 180 | 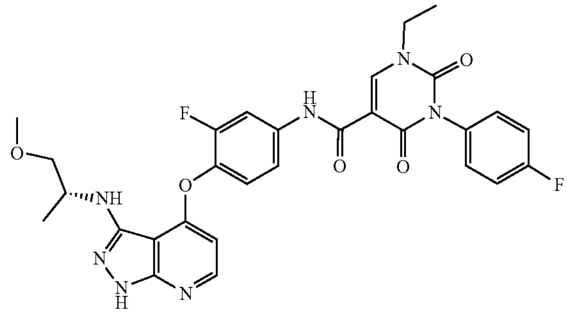 [SMILES: CCn1cc(C(=O)Nc2ccc(Oc3ccnc4[nH]nc(N[C@H](C)COC)c34)c(F)c2)c(=O)n(-c2ccc(F)cc2)c1=O] | (R)-1-ethyl-N-(3-fluoro-4-((3-((1-methoxypropan-2-yl)-amino)-1H-pyrazolo-[3,4-b]pyridin-4-yl)-oxy)phenyl)-3-(4-fluorophenyl)-2,4-dioxo-1,2,3,4-tetra-hydropyrimidine-5-carboxamide | 592.2 (M + H) |
| 181 | 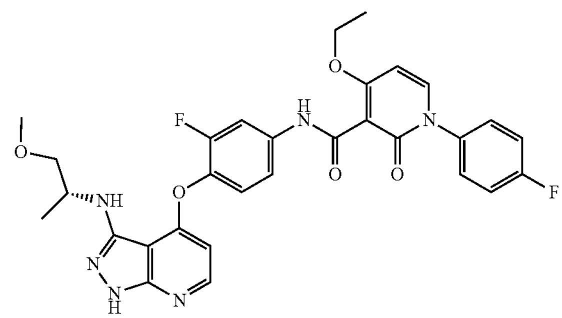 [SMILES: CCOc1ccn(-c2ccc(F)cc2)c(=O)c1C(=O)Nc1ccc(Oc2ccnc3[nH]nc(N[C@H](C)COC)c23)c(F)c1] | (R)-4-ethoxy-N-(3-fluoro-4-((3-((1-methoxypropan-2-yl)-amino)-1H-pyrazolo-[3,4-b]pyridin-4-yl)-oxy)phenyl)-1-(4-fluorophenyl)-2-oxo-1,2-dihydropyridine-3-carboxamide | 591.2 (M + H) |

Example 182

N-(3-fluoro-4-((3-((1-(2-hydroxypropan-2-yl)cyclopentyl)amino)-1H-pyrazolo[3,4-b]pyridin-4-yl)oxy)phenyl)-2-(4-fluorophenyl)-3-oxo-2,3-dihydropyridazine-4-carboxamide

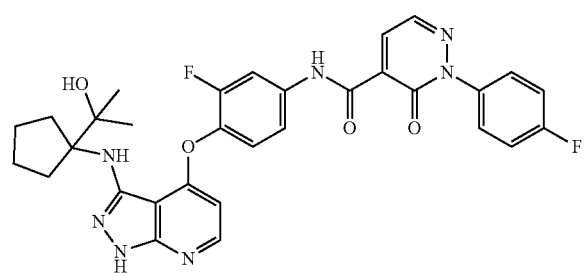 [SMILES: CC(C)(O)C1(Nc2n[nH]c3nccc(Oc4ccc(NC(=O)c5ccnn(-c6ccc(F)cc6)c5=O)cc4F)c23)CCCC1]

Step A: N-(3-fluoro-4-((3-iodo-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (Preparation 63; 75 mg, 0.11 mmol), methyl 1-aminocyclopentane-1-carboxylate hydrochloride (57 mg, 0.32 mmol), 1H-pyrrole-2-carboxylic acid (5.9 mg, 0.053 mmol) and K$_2$CO$_3$ (117 mg, 0.85 mmol) were suspended in DMSO (1 mL) and nitrogen bubbled through for 5 min. Copper(I) iodide (10 mg, 0.053 mmol) was added and the reaction was heated to 70° C. overnight. The reaction mixture was cooled, diluted with EtOAc (10 mL), stirred for 10 min and filtered. methoxybenzyl)-1H-pyrazolo[3,4-b]pyridin-3-yl)amino)cyclopentane-1-carboxylate (25 mg, 0.035 mmol, 33% yield).

Step B: Methyl 1-((4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)amino)cyclopentane-1-carboxylate (25 mg, 0.035 mmol) was dissolved in THF (1 mL) and methylmagnesium bromide (99 µl, 0.14 mmol) was added. The reaction mixture was stirred for 10 min. The reaction mixture was partitioned between saturated NH$_4$Cl and EtOAc, and the organic layer was washed with brine, dried over sodium sulfate, filtered and concentrated to afford N-(3-fluoro-4-((3-((1-(2-hydroxypropan-2-yl)cyclopentyl)amino)-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (17 mg, 0.024 mmol, 68% yield).

Step C: N-(3-fluoro-4-((3-((1-(2-hydroxypropan-2-yl)cyclopentyl)amino)-1-(4-methoxybenzyl)-1H-pyrazolo[3,4-b]pyridin-4-yl)oxy)phenyl)-2-(4-fluorophenyl)-3-oxo-2,3-dihydropyridazine-4-carboxamide (17 mg, 0.024 mmol) was dissolved in DCM (1 mL) and TFA (2 mL) was added. The reaction mixture was stirred at 37° C. overnight. The reaction mixture was concentrated and partitioned between DCM and 1N NaOH. The organic layer was dried over sodium sulfate, filtered and concentrated. The residue was purified over silica gel (1-15% MeOH in DCM) to afford N-(3-fluoro-4-((3-((1-(2-hydroxypropan-2-yl)cyclopentyl)amino)-1H-pyrazolo[3,4-b]pyridin-4-yl)oxy)phenyl)-2-(4-fluorophenyl)-3-oxo-2,3-dihydropyridazine-4-carboxamide (9.4 mg, 0.016 mmol, 66% yield) as a yellow solid. Mass spectrum: m/z=602.2 (M+H). $^1$H NMR (CDCl$_3$) δ 11.85 (s, 1H), 9.26 (s, 1H), 8.42 (d, 1H), 8.18 (d, 1H), 7.97 (dd, 1H), 7.60 (m, 2H), 7.42 (ddd, 1H), 7.32-7.22 (m, 3H), 6.10 (dd, 1H), 5.02 (s, 1H), 2.36 (m, 2H), 2.16 (m, 2H), 1.85 (m, 4H), 1.55 (s, 6H).

Example 183

2-((4-(2-fluoro-4-(2-(4-fluorophenyl)-3-oxo-2,3-dihydropyridazine-4-carboxamido)phenoxy)-1H-pyrazolo[3,4-b]pyridin-3-yl)amino)-2-methylpropyl hydrogen sulfate

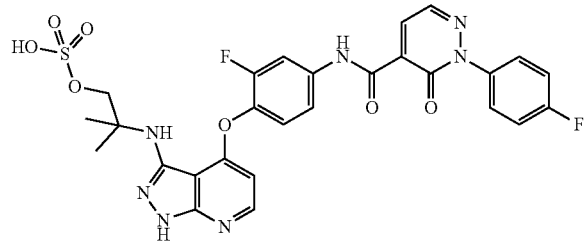 [SMILES: CC(C)(COS(=O)(=O)O)Nc1n[nH]c2nccc(Oc3ccc(NC(=O)c4ccnn(-c5ccc(F)cc5)c4=O)cc3F)c12]

N-(3-fluoro-4-((3-((1-hydroxy-2-methylpropan-2-yl)amino)-1H-pyrazolo[3,4-b]pyridin-4-yl)oxy)phenyl)-2-(4-fluorophenyl)-3-oxo-2,3-dihydropyridazine-4-carboxamide (Example 3; 50 mg, 0.0913 mmol) was suspended in DMF (1 mL) and warmed to 50° C. Sulfurochloridic acid (9 µl, 0.14 mmol) was added and the reaction mixture was stirred for 10 min. The reaction mixture was cooled to RT, MTBE (2 mL) was added, and the reaction mixture was stirred vigorously for 10 min. The reaction mixture was decanted and the remaining oil was treated with water (2 mL) with vigorous stirring. The resulting solids were filtered and dried to afford 2-((4-(2-fluoro-4-(2-(4-fluorophenyl)-3-oxo-2,3-dihydropyridazine-4-carboxamido)phenoxy)-1H-pyrazolo[3,4-b]pyridin-3-yl)amino)-2-methylpropyl hydrogen sulfate (44 mg, 0.0701 mmol, 76.8% yield) as a yellow solid. Mass spectrum: m/z=548.2 (M+H-SO3). $^1$H NMR (CDCl$_3$) δ 12.38 (br s, 1H), 11.70 (s, 1H), 8.37 (d, 1H), 8.27 (d, 1H), 8.18 (m, 1H), 8.03 (dd, 1h), 7.69 (m, 2H), 7.61-7.49 (m, 2H), 7.41 (m, 2H), 6.08 (d, 1H), 3.86 (s, 2H), 1.40 (s, 6H).

Examples 184 and 185

(S)—N-(3-fluoro-4-((3-((3-hydroxy-3-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide (Example 184) and (R)—N-(3-fluoro-4-((3-((3-hydroxy-3-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide (Example 185)

Example 184

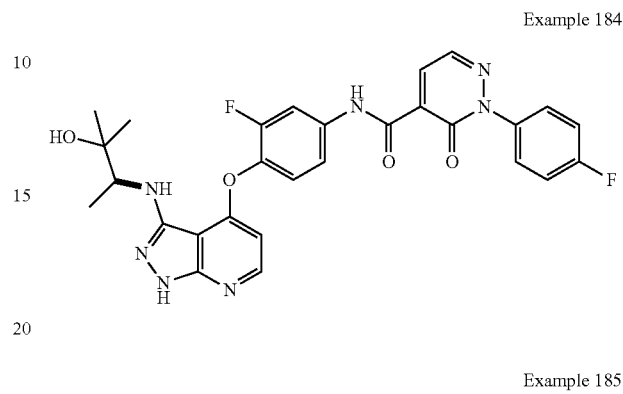

Example 185

N-(3-fluoro-4-((3-((3-hydroxy-3-methylbutan-2-yl)amino)-1H-pyrazolo[3,4-b]pyridin-4-yl)oxy)phenyl)-2-(4-fluorophenyl)-3-oxo-2,3-dihydropyridazine-4-carboxamide was purified via SFC on a Chiral Tech IA column (5-70% MeOH:IPA:DIEA 80:20:0.1) to afford each purified enantiomer. Absolute configuration is not known. Peak 1: Mass spectrum: m/z=562.1 (M+H). Peak 2: Mass spectrum: m/z=562.1 (M+H).

Following the procedure in Example 184, the following single enantiomers, prepared as racemates as described above, were isolated from their racemic mixtures.

| Ex. No. | Structure | Name | Mass Spectrum |
|---|---|---|---|
| 186 | 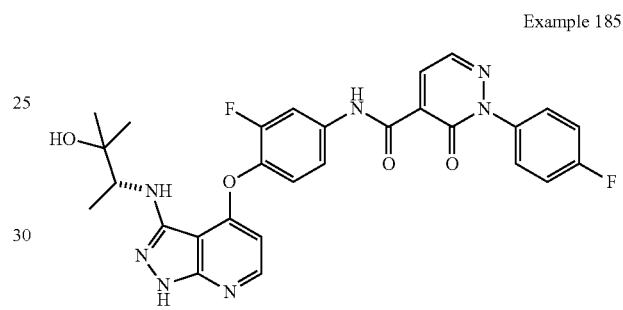 | N-(3-fluoro-4-((3-(((1S,2R)-2-(hydroxymethyl)cyclopentyl)amino)-1H-pyrazolo-[3,4-b]pyridin-4-yl)-oxy)phenyl)-2-(4-fluorophenyl)-3-oxo-2,3-dihydropyridazine-4-carboxamide | 574.2 (M + H) |

| Ex. No. | Structure | Name | Mass Spectrum |
|---|---|---|---|
| 187 | 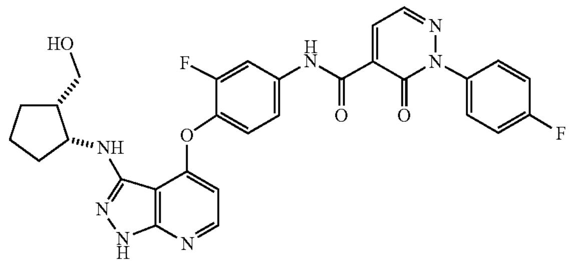 | N-(3-fluoro-4-((3-(((1R,2S)-2-(hydroxymethyl)cyclopentyl)-amino)-1H-pyrazolo[3,4-b]pyridin-4-yl)oxy)phenyl)-2-(4-fluorophenyl)-3-oxo-2,3-dihydropyridazine-4-carboxamide | 574.2 (M + H) |
| 188 | 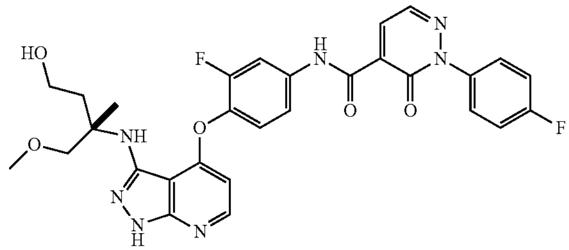 [SMILES: COC[C@](C)(CCO)Nc1n[nH]c2nccc(Oc3ccc(NC(=O)c4ccnn(-c5ccc(F)cc5)c4=O)cc3F)c12] | (S)-N-(3-fluoro-4-((3-((4-hydroxy-1-methoxy-2-methyl-butan-2-yl)amino)-1H-pyrazolo[3,4-b]-pyridin-4-yl)oxy)-phenyl)-2-(4-fluoro-phenyl)-3-oxo-2,3-dihydropyridazine-4-carboxamide | 592.2 (M + H) |
| 189 | 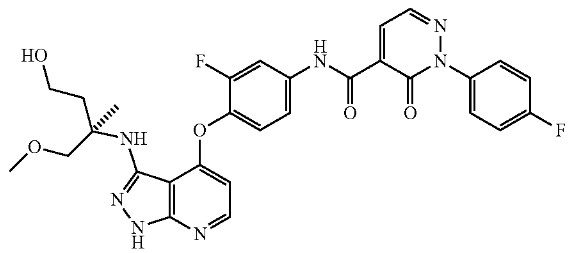 [SMILES: COC[C@@](C)(CCO)Nc1n[nH]c2nccc(Oc3ccc(NC(=O)c4ccnn(-c5ccc(F)cc5)c4=O)cc3F)c12] | (R)-N-(3-fluoro-4-((3-((4-hydroxy-1-methoxy-2-methyl-butan-2-yl)amino)-1H-pyrazolo[3,4-b]-pyridin-4-yl)oxy)-phenyl)-2-(4-fluoro-phenyl)-3-oxo-2,3-dihydropyridazine-4-carboxamide | 592.2 (M + H) |
| 190 | 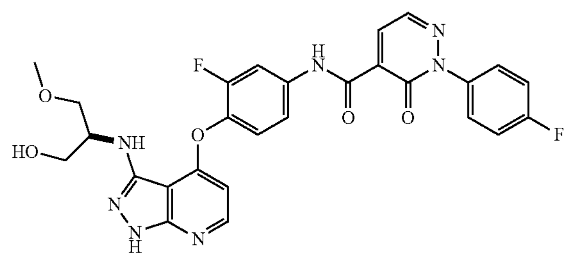 [SMILES: COC[C@H](CO)Nc1n[nH]c2nccc(Oc3ccc(NC(=O)c4ccnn(-c5ccc(F)cc5)c4=O)cc3F)c12] | (S)-N-(3-fluoro-4-((3-((1-hydroxy-3-methoxypropan-2-yl)-amino)-1H-pyrazolo-[3,4-b]pyridin-4-yl)-oxy)phenyl)-2-(4-fluorophenyl)-3-oxo-2,3-dihydropyridazine-4-carboxamide | 564.2 (M + H) |
| 191 | 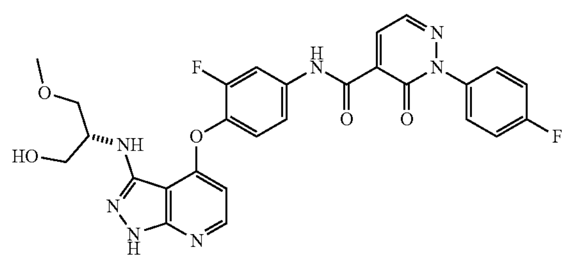 | (R)-N-(3-fluoro-4-((3-((1-hydroxy-3-methoxypropan-2-yl)-amino)-1H-pyrazolo-[3,4-b]pyridin-4-yl)-oxy)phenyl)-2-(4-(fluorophenyl)-3-oxo-2,3-dihydropyridazine-4-carboxamide | 564.1 (M + H) |
| 192 | 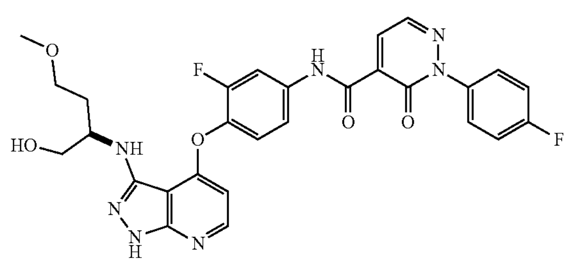 [SMILES: COCC[C@H](CO)Nc1n[nH]c2nccc(Oc3ccc(NC(=O)c4ccnn(-c5ccc(F)cc5)c4=O)cc3F)c12] | (R)-N-(3-fluoro-4-((3-((1-hydroxy-4-methoxybutan-2-yl)amino)-1H-pyrazolo[3,4-b]-pyridin-4-yl)oxy)-phenyl)-2-(4-fluoro-phenyl)-3-oxo-2,3-dihydropyridazine-4-carboxamide | 578.2 (M + H) |

-continued

| Ex. No. | Structure | Name | Mass Spectrum |
|---|---|---|---|
| 193 | 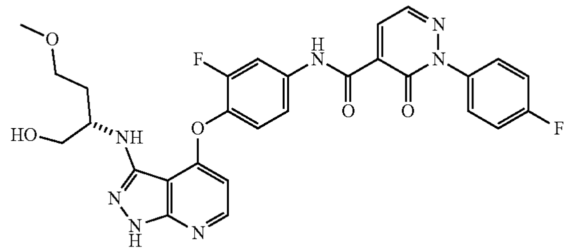 [SMILES: COCC[C@@H](CO)Nc1n[nH]c2nccc(Oc3ccc(NC(=O)c4ccnn(-c5ccc(F)cc5)c4=O)cc3F)c12] | (S)-N-(3-fluoro-4-((3-((1-hydroxy-4-methoxybutan-2-yl)amino)-1H-pyrazolo[3,4-b]pyridin-4-yl)oxy)phenyl)-2-(4-fluorophenyl)-3-oxo-2,3-dihydropyridazine-4-carboxamide | 578.2 (M + H) |
| 194 | 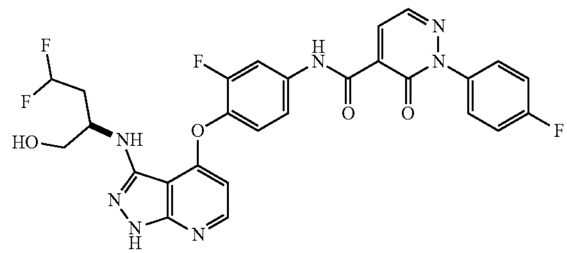 [SMILES: O=C(Nc1ccc(Oc2ccnc3[nH]nc(N[C@@H](CO)CC(F)F)c23)c(F)c1)c1ccnn(-c2ccc(F)cc2)c1=O] | (R)-N-(4-((3-((4,4-difluoro-1-hydroxybutan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 584.2 (M + H) |
| 195 | 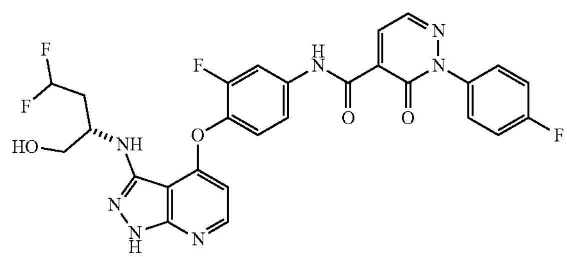 [SMILES: O=C(Nc1ccc(Oc2ccnc3[nH]nc(N[C@H](CO)CC(F)F)c23)c(F)c1)c1ccnn(-c2ccc(F)cc2)c1=O] | (S)-N-(4-((3-((4,4-difluoro-1-hydroxybutan-2-yl)amino)-1H-pyrazolo[3,4-b]pyridin-4-yl)oxy)-3-fluorophenyl)-2-(4-fluorophenyl)-3-oxo-2,3-dihydropyridazine-4-carboxamide | 584.2 (M + H) |

Example 196

N-(4-((3-amino-1H-pyrazolo[3,4-b]pyridin-4-yl)oxy)-3-fluorophenyl)-3-(4-fluorophenyl)-1-isopropyl-2,4-dioxo-1,2,3,4-tetrahydropyrimidine-5-carboxamide

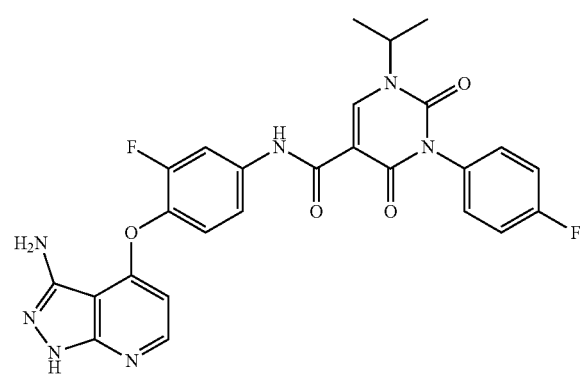 [SMILES: CC(C)n1cc(C(=O)Nc2ccc(Oc3ccnc4[nH]nc(N)c34)c(F)c2)c(=O)n(-c2ccc(F)cc2)c1=O]

Step A: A suspension of N-(3-fluoro-4-((3-iodo-1-(4-methoxybenzyl)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide (Preparation 65; 100 mg, 0.13 mmol), tert-butyl carbamate (0.153 g, 1.3 mmol), N1,N2-dimethylethane-1,2-diamine (0.032 ml, 0.26 mmol), $K_3PO_4$ (0.16 g, 0.78 mmol) and copper(I) iodide (0.024 g, 0.13 mmol) in dioxane (2 mL) was stirred at 60° C. for 12 h. The reaction mixture was diluted with water (30 mL) and extracted with DCM (3×20 mL). The organic layer was washed with brine (15 mL), dried over sodium sulfate, filtered and concentrated. The residue was purified over silica gel (20-60% EtOAc in hexanes) to afford tert-butyl (4-(2-fluoro-4-(3-(4-fluorophenyl)-1-isopropyl-2,4-dioxo-1,2,3,4-tetrahydropyrimidine-5-carboxamido)phenoxy)-1-(4-methoxybenzyl)-1H-pyrazolo[3,4-b]pyridin-3-yl)carbamate (45.8 mg, 46%).

Step B: To a solution of tert-butyl (4-(2-fluoro-4-(3-(4-fluorophenyl)-1-isopropyl-2,4-dioxo-1,2,3,4-tetrahydropyrimidine-5-carboxamido)phenoxy)-1-(4-methoxybenzyl)-1H-pyrazolo[3,4-b]pyridin-3-yl)carbamate (45.8 mg, 0.061 mmol) in DCM (1 mL) was added TFA (2 mL). The mixture was stirred at 35° C. for 6 h, then at room temperature overnight. The mixture was concentrated and the residue was dissolved in MeOH/DCM, treated with $K_2CO_3$ (25.2 mg, 0.182 mmol) and stirred for 3 h. The mixture was filtered and concentrated. The residue was purified over silica gel (0-5% MeOH in DCM) to afford N-(4-((3-amino-1H-pyrazolo[3,4-b]pyridin-4-yl)oxy)-3-fluorophenyl)-3-(4-fluorophenyl)-1-isopropyl-2,4-dioxo-1,2,3,4-tetrahydropyrimidine-5-carboxamide (20.3 mg, 60%). Mass spectrum: m/z=534.2 (M+H). $^1$H NMR (CDCl$_3$) δ 10.97 (s, 1H), 9.65 (s, 1H), 8.69 (s, 1H), 8.21 (d, 1H), 7.89 (dd, 1H), 7.29 (ddd, 1H), 7.27-7.20 (m, 4H), 6.11 (dd, 1H), 4.98 (m, 1H), 4.50 (s, 2H), 1.51 (d, 6H).

The following compounds were also synthesized using the procedure according to Example 196.

| Ex. No. | Structure | Name | Mass Spectrum |
|---|---|---|---|
| 197 | 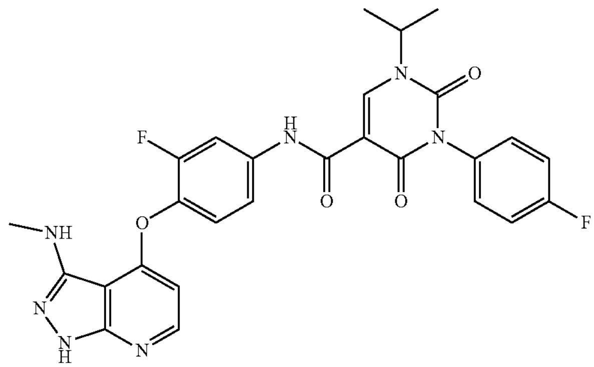 [SMILES: CNc1n[nH]c2nccc(Oc3ccc(NC(=O)c4cn(C(C)C)c(=O)n(-c5ccc(F)cc5)c4=O)cc3F)c12] | N-(3-fluoro-4-((3-(methylamino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide | 548.2 (M + H) |
| 198 | 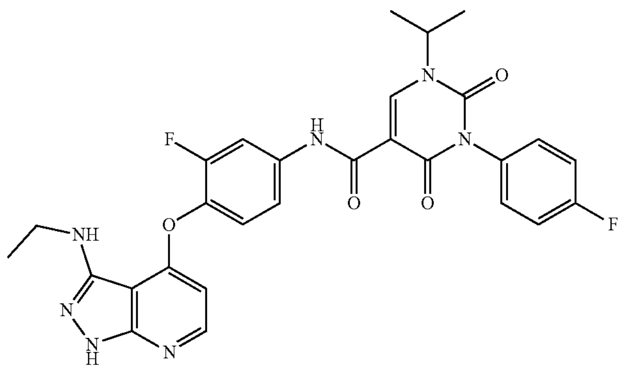 [SMILES: CCNc1n[nH]c2nccc(Oc3ccc(NC(=O)c4cn(C(C)C)c(=O)n(-c5ccc(F)cc5)c4=O)cc3F)c12] | N-(4-((3-(ethylamino)-1H-pyrazolo[3,4-b]-pyridin-4-yl)oxy)-3-fluorophenyl)-3-(4-fluorophenyl)-1-isopropyl-2,4-dioxo-1,2,3,4-tetrahydropyrimidine-5-carboxamide | 562.2 (M + H) |

Example 199

(R)—N-(3-fluoro-4-((3-((1-hydroxypropan-2-yl)amino)-1H-pyrazolo[3,4-b]pyridin-4-yl)oxy)phenyl)-1-(4-fluorophenyl)-5-isopropyl-2-oxo-1,2-dihydropyridine-3-carboxamide hydrochloride

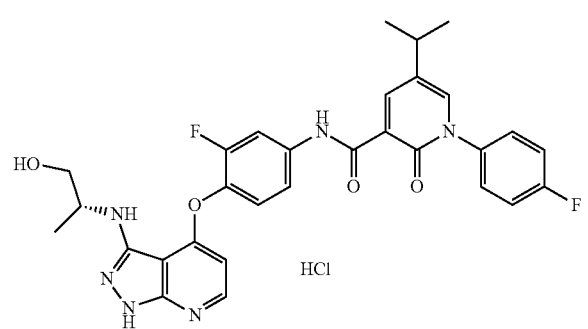

Step A: 1-(4-Fluorophenyl)-2-oxo-5-(prop-1-en-2-yl)-1,2-dihydropyridine-3-carboxylic acid (Preparation 48; 93.7 mg, 0.343 mmol) was dissolved in DMF (3 mL). 2-(3H-[1,2,3]triazolo[4,5-b]pyridin-3-yl)-1,1,3,3-tetramethylisouronium hexafluorophosphate(V) (130 mg, 0.343 mmol) was added and the solution was stirred for 5 minutes followed by the addition of N-ethyl-N-isopropylpropan-2-amine (119 μl, 0.686 mmol) and (R)-2-((4-(4-amino-2-fluorophenoxy)-1-(4-methoxybenzyl)-1H-pyrazolo[3,4-b]pyridin-3-yl)amino)propan-1-ol (Preparation 53; 100 mg, 0.229 mmol). After stirring overnight, the reaction mixture was partitioned between water and EtOAc, washed with water and brine, dried over sodium sulfate, filtered and concentrated. The residue was purified over silica gel to afford (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-1-(4-fluorophenyl)-2-oxo-5-(prop-1-en-2-yl)-1,2-dihydropyridine-3-carboxamide (194 mg, 0.280 mmol, 123% yield).

Step B: (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-1-(4-fluorophenyl)-2-oxo-5-(prop-1-en-2-yl)-1,2-dihydropyridine-3-carboxamide (190 mg, 0.274 mmol) was dissolved in 25 mL of methanol and 5 mL of EtOAc. 10% Pd/C (30 mg, 0.253 mmol) was added and the solution was purged with hydrogen balloon and stirred under balloon pressure of hydrogen for 1 h. The reaction mixture was filtered and concentrated. The residue was purified over silica gel (20% DCM in EtOAc) to afford (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-1-(4-fluorophenyl)-5-isopropyl-2-oxo-1,2-dihydropyridine-3-carboxamide (138 mg, 0.199 mmol, 72.4% yield).

Step C: (R)—N-(3-fluoro-4-((3-((1-hydroxypropan-2-yl)amino)-1-(4-methoxybenzyl)-1H-pyrazolo[3,4-b]pyridin-4-yl)oxy)phenyl)-1-(4-fluorophenyl)-5-isopropyl-2-oxo-1,2-dihydropyridine-3-carboxamide (138 mg, 0.199 mmol) was slurried in DCM (1 mL) and TFA (20 mL) added and heated to 50 C for 4 h. The reaction mixture was concentrated, partitioned between EtOAc and 1M NaOH, dried over sodium sulfate, filtered and concentrated. The residue was purified over silica gel and the isolated product was converted to the HCl salt to afford (R)—N-(3-fluoro-4-((3-((1-hydroxypropan-2-yl)amino)-1H-pyrazolo[3,4-b]pyridin-4- yl)oxy)phenyl)-1-(4-fluorophenyl)-5-isopropyl-2-oxo-1,2-dihydropyridine-3-carboxamide hydrochloride as a yellow solid. Mass spectrum: m/z=575.2 (M+H-HCl). $^1$H NMR (CDCl$_3$) δ 12.30 (s, 1H), 8.72 (d, 1H), 8.68 (d, 1H), 8.06 (dd, 1H), 7.46-7.39 (m, 4H), 7.31-7.24 (m, 3H), 6.12 (d, 1H), 5.32 (br s, 1H), 4.17 (m, 1H), 3.92 (dd, 1H), 3.72 (dd, 1H), 2.87 (m, 1H), 1.38 (d, 3H), 1.30 (d, 6H).

The following compounds were also synthesized using the procedure according to Example 199.

| Pd(PPh$_3$)$_4$ | Tetrakis(triphenylphosphine)palladium (0) |
|---|---|
| Pd$_2$(dba)$_3$ | tris(dibenzylideneacetone)dipalladium (0) |
| TFA | Trifluoroacetic acid |
| TEEF | tetrahydrofuran |
| X-PHOS | dicyclohexyl(2',4',6'-triisopropyl-[1,1'-biphenyl]-2-yl)phosphine |

| Ex. No. | Structure | Name | Mass Spectrum |
|---|---|---|---|
| 200 | 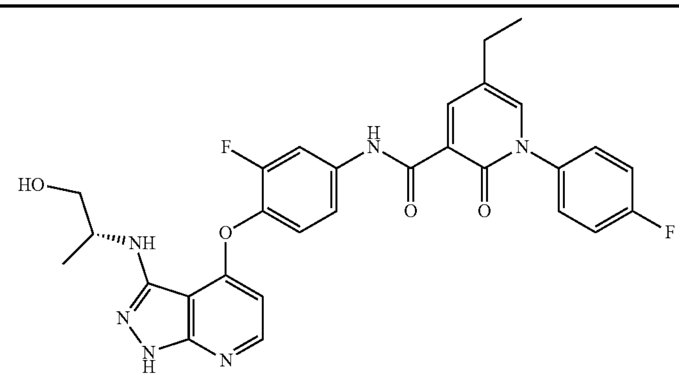 | (R)-5-ethyl-N-(3-fluoro-4-((3-((1-hydroxypropan-2-yl)amino)-1H-pyrazolo[3,4-b]pyridin-4-yl)oxy)-phenyl)-1-(4-fluorophenyl)-2-oxo-1,2-dihydropyridine-3-carboxamide | 561.2 (M + H) |
| 201 | 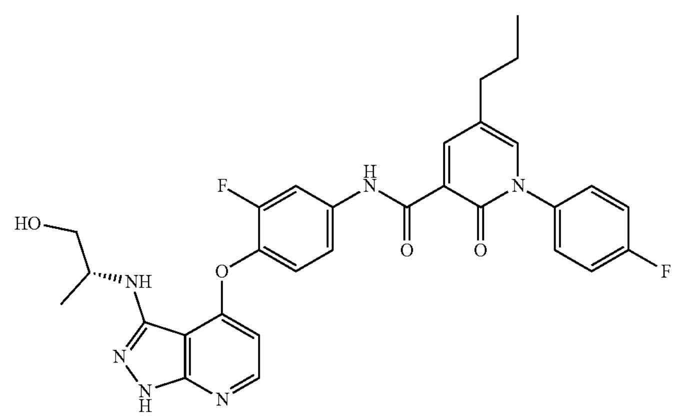 [SMILES: CCCc1cc(C(=O)Nc2ccc(Oc3ccnc4[nH]nc(N[C@H](C)CO)c34)c(F)c2)c(=O)n(-c2ccc(F)cc2)c1] | (R)-N-(3-fluoro-4-((3-((1-hydroxypropan-2-yl)amino)-1H-pyrazolo[3,4-b]pyridin-4-yloxy)phenyl)-1-(4-fluorophenyl)-2-oxo-5-propyl-1,2-dihydropyridine-3-carboxamide | 575.2 (M + H) |

Abbreviations

| ACN | acetonitrile |
|---|---|
| AcOH | acetic acid |
| Boc, BOC | tert-butyl carboxylate group |
| DCM | Dichloromethane |
| DIEA | N,N-Diisopropylethylamine |
| DMA | N,N-Dimethylacetamide |
| DMF | N,N-Dimethylformamide |
| DMSO | Dimethylsulfoxide |
| Et$_2$O | Diethyl Ether |
| EtOAc | Ethyl Acetate |
| EtOH | Ethanol |
| eq | equivalent |
| h | hour, hours |
| HATU | 1-[Bis(dimethylamino)methylene]-1H-1,2,3-triazolo[4,5-b]pyridinium 3-oxide hexafluorophosphate or 2-(7-Aza-1H-benzotriazole-1-yl)-1,1,3,3-tetramethyluronium hexafluorophosphate |
| HOAc | Acetic Acid |
| IPA | Isopropyl alcohol |
| min | minute, minutes |
| MTBE | Methyl tert-Butyl Ether |
| 10% Pd/C | Palladium 10 wt % (dry basis), active carbon, wet, Degussa |

EXEMPLARY EMBODIMENTS

Embodiment 1. A compound of formula I, wherein the compound is a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt or solvate thereof.

Embodiment 2. A pharmaceutical combination which comprises (a) a compound of Formula I or a pharmaceutically acceptable salt thereof, and (b) an additional therapeutic agent.

Embodiment 3. A pharmaceutical combination which comprises (a) a compound of Formula T or a pharmaceutically acceptable salt thereof, and (b) an additional therapeutic agent, for use in therapy.

Embodiment 4. The pharmaceutical combination of Embodiment 2, or for use of Embodiment 3, wherein the compound of Formula I or the pharmaceutically acceptable salt thereof and the additional therapeutic agent are formulated as separate compositions or dosages for simultaneous, separate or sequential use for use in therapy, wherein the amounts of the compound of Formula I or a pharmaceutically acceptable salt thereof and of the additional therapeutic agent are together therapeutically effective.

Embodiment 5. A pharmaceutical composition, comprising (a) a compound of Formula I or a pharmaceutically acceptable salt thereof, (b) an additional therapeutic agent, and (c) a pharmaceutically acceptable diluent or carrier.

Embodiment 6. The pharmaceutical combination of Embodiment 2, or for use of Embodiment 3, or the pharmaceutical composition of Embodiment 5, wherein the additional therapeutic agent is an anti cancer agent.

Embodiment 7. The pharmaceutical combination of Embodiment 2, or for use of Embodiment 3, or the pharmaceutical composition of Embodiment 5, wherein the additional therapeutic agent is binimetinib and encorafenib.

Embodiment 8. The pharmaceutical combination of Embodiment 2, or for use of Embodiment 3, or the pharmaceutical composition of Embodiment 5, wherein the additional therapeutic agent is binimetinib.

Embodiment 9. The pharmaceutical combination of Embodiment 2, or for use of Embodiment 3, or the pharmaceutical composition of Embodiment 5, wherein the additional therapeutic agent is encorafenib.

Embodiment 10. The pharmaceutical combination of Embodiment 2, or for use of Embodiment 3, or the pharmaceutical composition of Embodiment 5, wherein the additional therapeutic agent is selumetinib.

Embodiment 11. The pharmaceutical combination of Embodiment 2, or for use of Embodiment 3, or the pharmaceutical composition of Embodiment 5, wherein the additional therapeutic agent is sorafenib.

Embodiment 12. The pharmaceutical combination of Embodiment 2, or for use of Embodiment 3, or the pharmaceutical composition of Embodiment 5, wherein the additional therapeutic agent is trametinib.

Embodiment 13. The pharmaceutical combination of Embodiment 2, or for use of Embodiment 3, or the pharmaceutical composition of Embodiment 5, wherein the additional therapeutic agent is vemurafenib.

Embodiment 14. The pharmaceutical combination of Embodiment 2, or for use of Embodiment 3, or the pharmaceutical composition of Embodiment 5, wherein the additional therapeutic agent is an EGFR inhibitor.

Embodiment 15. The pharmaceutical combination of Embodiment 2, or for use of Embodiment 3, or the pharmaceutical composition of Embodiment 5, wherein the additional therapeutic agent is cetuximab or a biosimilar thereof.

Embodiment 16. The pharmaceutical combination of Embodiment 2, or for use of Embodiment 3, or the pharmaceutical composition of Embodiment 5, wherein the additional therapeutic agent is panitumumab or a biosimilar thereof.

Embodiment 17. The pharmaceutical combination of Embodiment 2, or for use of Embodiment 3, or the pharmaceutical composition of Embodiment 5, wherein the additional therapeutic agent is erlotinib.

Embodiment 18. The pharmaceutical combination of Embodiment 2, or for use of Embodiment 3, or the pharmaceutical composition of Embodiment 5, wherein the additional therapeutic agent is lapatinib.

Embodiment 19. The pharmaceutical combination of Embodiment 2, or for use of Embodiment 3, or the pharmaceutical composition of Embodiment 5, wherein the additional therapeutic agent is gefitinib.

Embodiment 20. The pharmaceutical combination of Embodiment 2, or for use of Embodiment 3, or the pharmaceutical composition of Embodiment 5, wherein the additional therapeutic agent is a checkpoint inhibitor.

Embodiment 21. The pharmaceutical combination of Embodiment 2, or for use of Embodiment 3, or the pharmaceutical composition of Embodiment 5, wherein the additional therapeutic agent is nivolumab or a biosimilar thereof.

Embodiment 22. The pharmaceutical combination of Embodiment 2, or for use of Embodiment 3, or the pharmaceutical composition of Embodiment 5, wherein the additional therapeutic agent is pembrolizumab or a biosimilar thereof.

Embodiment 23. The pharmaceutical combination of Embodiment 2, or for use of Embodiment 3, or the pharmaceutical composition of Embodiment 5, wherein the additional therapeutic agent is cemiplimab or a biosimilar thereof.

Embodiment 24. The pharmaceutical combination of Embodiment 2, or for use of Embodiment 3, or the pharmaceutical composition of Embodiment 5, wherein the additional therapeutic agent is pidilizumab or a biosimilar thereof.

Embodiment 25. The pharmaceutical combination of Embodiment 2, or for use of Embodiment 3, or the pharmaceutical composition of Embodiment 5, wherein the additional therapeutic agent is atezolizumab or a biosimilar thereof.

Embodiment 26. The pharmaceutical combination of Embodiment 2, or for use of Embodiment 3, or the pharmaceutical composition of Embodiment 5, wherein the additional therapeutic agent is avelumab or a biosimilar thereof.

Embodiment 27. The pharmaceutical combination of Embodiment 2, or for use of Embodiment 3, or the pharmaceutical composition of Embodiment 5, wherein the additional therapeutic agent is durvalumab or a biosimilar thereof.

Embodiment 28. A pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt thereof, and (b) an additional therapeutic agent.

Embodiment 29. A pharmaceutical combination which comprises (a) a compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt thereof, and (b) an additional therapeutic agent, for use in therapy.

Embodiment 30. The pharmaceutical combination of Embodiment 28, or for use of Embodiment 29, wherein the compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or the pharmaceutically acceptable salt thereof and the additional therapeutic agent are formulated as separate compositions or dosages for simultaneous, separate or sequential use for use in therapy, wherein the amounts of the compound of Example No. 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt thereof and of the additional therapeutic agent are together therapeutically effective.

Embodiment 31. A pharmaceutical composition, comprising (a) a compound of Example No 25, 37, 46, 48, 55, 58, 72, 76, 77, 78, 83, 84, 85, 91, 97, 100, 103, 105, 107, 108, 114, 115, 119, 121, 124, 125, 126, 127, 129, 151, 152, 163, 169, 188, 190, 199, 200, or 201, or a pharmaceutically acceptable salt thereof, (b) an additional therapeutic agent, and (c) a pharmaceutically acceptable diluent or carrier.

Embodiment 32. The pharmaceutical combination of Embodiment 28, or for use of Embodiment 29, or the pharmaceutical composition of Embodiment 31, wherein the additional therapeutic agent is an anticancer agent.

Embodiment 33. The pharmaceutical combination of Embodiment 28, or for use of Embodiment 29, or the pharmaceutical composition of Embodiment 31, wherein the additional therapeutic agent is binimetinib and encorafenib.

Embodiment 34. The pharmaceutical combination of Embodiment 28, or for use of Embodiment 29, or the pharmaceutical composition of Embodiment 31, wherein the additional therapeutic agent is binimetinib.

Embodiment 35. The pharmaceutical combination of Embodiment 28, or for use of Embodiment 29, or the pharmaceutical composition of Embodiment 31, wherein the additional therapeutic agent is encorafenib.

Embodiment 36. The pharmaceutical combination of Embodiment 28, or for use of Embodiment 29, or the pharmaceutical composition of Embodiment 31, wherein the additional therapeutic agent is selumetinib.

Embodiment 37. The pharmaceutical combination of Embodiment 28, or for use of Embodiment 29, or the pharmaceutical composition of Embodiment 31, wherein the additional therapeutic agent is sorafenib.

Embodiment 38. The pharmaceutical combination of Embodiment 28, or for use of Embodiment 29, or the pharmaceutical composition of Embodiment 31, wherein the additional therapeutic agent is trametinib.

Embodiment 39. The pharmaceutical combination of Embodiment 28, or for use of Embodiment 29, or the pharmaceutical composition of Embodiment 31, wherein the additional therapeutic agent is vemurafenib.

Embodiment 40. The pharmaceutical combination of Embodiment 28, or for use of Embodiment 29, or the pharmaceutical composition of Embodiment 31, wherein the additional therapeutic agent is an EGFR inhibitor.

Embodiment 41. The pharmaceutical combination of Embodiment 28, or for use of Embodiment 29, or the pharmaceutical composition of Embodiment 31, wherein the additional therapeutic agent is cetuximab or a biosimilar thereof.

Embodiment 42. The pharmaceutical combination of Embodiment 28, or for use of Embodiment 29, or the pharmaceutical composition of Embodiment 31, wherein the additional therapeutic agent is panitumumab or a biosimilar thereof.

Embodiment 43. The pharmaceutical combination of Embodiment 28, or for use of Embodiment 29, or the pharmaceutical composition of Embodiment 31, wherein the additional therapeutic agent is erlotinib.

Embodiment 44. The pharmaceutical combination of Embodiment 28, or for use of Embodiment 29, or the pharmaceutical composition of Embodiment 31, wherein the additional therapeutic agent is lapatinib.

Embodiment 45. The pharmaceutical combination of Embodiment 28, or for use of Embodiment 29, or the pharmaceutical composition of Embodiment 31, wherein the additional therapeutic agent is gefitinib.

Embodiment 46. The pharmaceutical combination of Embodiment 28, or for use of Embodiment 29, or the pharmaceutical composition of Embodiment 31, wherein the additional therapeutic agent is a checkpoint inhibitor.

Embodiment 47. The pharmaceutical combination of Embodiment 28, or for use of Embodiment 29, or the pharmaceutical composition of Embodiment 31, wherein the additional therapeutic agent is nivolumab or a biosimilar thereof.

Embodiment 48. The pharmaceutical combination of Embodiment 28, or for use of Embodiment 29, or the pharmaceutical composition of Embodiment 31, wherein the additional therapeutic agent is pembrolizumab or a biosimilar thereof.

Embodiment 49. The pharmaceutical combination of Embodiment 28, or for use of Embodiment 29, or the pharmaceutical composition of Embodiment 31, wherein the additional therapeutic agent is cemiplimab or a biosimilar thereof.

Embodiment 50. The pharmaceutical combination of Embodiment 28, or for use of Embodiment 29, or the pharmaceutical composition of Embodiment 31, wherein the additional therapeutic agent is pidilizumab or a biosimilar thereof.

Embodiment 51. The pharmaceutical combination of Embodiment 28, or for use of Embodiment 29, or the pharmaceutical composition of Embodiment 31, wherein the additional therapeutic agent is atezolizumab or a biosimilar thereof.

Embodiment 52. The pharmaceutical combination of Embodiment 28, or for use of Embodiment 29, or the pharmaceutical composition of Embodiment 31, wherein the additional therapeutic agent is avelumab or a biosimilar thereof.

Embodiment 53. The pharmaceutical combination of Embodiment 28, or for use of Embodiment 29, or the pharmaceutical composition of Embodiment 31, wherein the additional therapeutic agent is durvalumab or a biosimilar thereof.

Embodiment 54. A pharmaceutical combination which comprises (a) a compound of Example No. 25, or a pharmaceutically acceptable salt thereof, and (b) an additional therapeutic agent.

Embodiment 55. A pharmaceutical combination which comprises (a) a compound of Example No. 25, or a pharmaceutically acceptable salt thereof, and (b) an additional therapeutic agent, for use in therapy.

Embodiment 56. The pharmaceutical combination of Embodiment 54, or for use of Embodiment 55, wherein the compound of Example No. 25, or the pharmaceutically acceptable salt thereof and the additional therapeutic agent are formulated as separate compositions or dosages for simultaneous, separate or sequential use for use in therapy, wherein the amounts of the compound of Example No. 25 or a pharmaceutically acceptable salt thereof and of the additional therapeutic agent are together therapeutically effective.

Embodiment 57. A pharmaceutical composition, comprising (a) a compound of Example No. 25, or a pharmaceutically acceptable salt thereof, (b) an additional therapeutic agent, and (c) a pharmaceutically acceptable diluent or carrier.

Embodiment 58. The pharmaceutical combination of Embodiment 54, or for use of Embodiment 55, or the pharmaceutical composition of Embodiment 57, wherein the additional therapeutic agent is an anticancer agent.

Embodiment 59. The pharmaceutical combination of Embodiment 54, or for use of Embodiment 55, or the pharmaceutical composition of Embodiment 57, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 60. A pharmaceutical combination which comprises (a) a compound of Example No. 37, or a pharmaceutically acceptable salt thereof, and (b) an additional therapeutic agent.

Embodiment 61. A pharmaceutical combination which comprises (a) a compound of Example No. 37, or a pharmaceutically acceptable salt thereof, and (b) an additional therapeutic agent, for use in therapy.

Embodiment 62. The pharmaceutical combination of Embodiment 60, or for use of Embodiment 61, wherein the compound of Example No. 37, or the pharmaceutically acceptable salt thereof and the additional therapeutic agent are formulated as separate compositions or dosages for simultaneous, separate or sequential use for use in therapy, wherein the amounts of the compound of Example No. 37, or a pharmaceutically acceptable salt thereof and of the additional therapeutic agent are together therapeutically effective.

Embodiment 63. A pharmaceutical composition, comprising (a) a compound of Example No. 37, or a pharmaceutically acceptable salt thereof, (b) an additional therapeutic agent, and (c) a pharmaceutically acceptable diluent or carrier.

Embodiment 64. The pharmaceutical combination of Embodiment 60, or for use of Embodiment 61, or the pharmaceutical composition of Embodiment 63, wherein the additional therapeutic agent is an anticancer agent.

Embodiment 65. The pharmaceutical combination of Embodiment 60, or for use of Embodiment 61, or the pharmaceutical composition of Embodiment 63, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 66. A pharmaceutical combination which comprises (a) a compound of Example No. 46, or a pharmaceutically acceptable salt thereof, and (b) an additional therapeutic agent.

Embodiment 67. A pharmaceutical combination which comprises (a) a compound of Example No. 46, or a pharmaceutically acceptable salt thereof, and (b) an additional therapeutic agent, for use in therapy.

Embodiment 68. The pharmaceutical combination of Embodiment 66, or for use of Embodiment 67, wherein the compound of Example No. 46, or the pharmaceutically acceptable salt thereof and the additional therapeutic agent are formulated as separate compositions or dosages for simultaneous, separate or sequential use for use in therapy, wherein the amounts of the compound of Example No. 46, or a pharmaceutically acceptable salt thereof and of the additional therapeutic agent are together therapeutically effective.

Embodiment 69. A pharmaceutical composition, comprising (a) a compound of Example No. 46, or a pharmaceutically acceptable salt thereof, (b) an additional therapeutic agent, and (c) a pharmaceutically acceptable diluent or carrier.

Embodiment 70. The pharmaceutical combination of Embodiment 66, or for use of Embodiment 67, or the pharmaceutical composition of Embodiment 69, wherein the additional therapeutic agent is an anticancer agent.

Embodiment 71. The pharmaceutical combination of Embodiment 66, or for use of Embodiment 67, or the pharmaceutical composition of Embodiment 70, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 72. A pharmaceutical combination which comprises (a) a compound of Example No. 48, or a pharmaceutically acceptable salt thereof, and (b) an additional therapeutic agent.

Embodiment 73. A pharmaceutical combination which comprises (a) a compound of Example No. 48, or a pharmaceutically acceptable salt thereof, and (b) an additional therapeutic agent, for use in therapy.

Embodiment 74. The pharmaceutical combination of Embodiment 72, or for use of Embodiment 73, wherein the compound of Example No. 48, or the pharmaceutically acceptable salt thereof and the additional therapeutic agent are formulated as separate compositions or dosages for simultaneous, separate or sequential use for use in therapy, wherein the amounts of the compound of Example No. 48, or a pharmaceutically acceptable salt thereof and of the additional therapeutic agent are together therapeutically effective.

Embodiment 75. A pharmaceutical composition, comprising (a) a compound of Example No. 48, or a pharmaceutically acceptable salt thereof, (b) an additional therapeutic agent, and (c) a pharmaceutically acceptable diluent or carrier.

Embodiment 76. The pharmaceutical combination of Embodiment 72, or for use of Embodiment 73, or the pharmaceutical composition of Embodiment 75, wherein the additional therapeutic agent is an anticancer agent.

Embodiment 77. The pharmaceutical combination of Embodiment 72, or for use of Embodiment 73, or the pharmaceutical composition of Embodiment 75, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 78. A pharmaceutical combination which comprises (a) a compound of Example No. 55, or a pharmaceutically acceptable salt thereof, and (b) an additional therapeutic agent.

Embodiment 79. A pharmaceutical combination which comprises (a) a compound of Example No. 55, or a pharmaceutically acceptable salt thereof, and (b) an additional therapeutic agent, for use in therapy.

Embodiment 80. The pharmaceutical combination of Embodiment 78, or for use of Embodiment 79, wherein the compound of Example No. 55, or the pharmaceutically acceptable salt thereof and the additional therapeutic agent are formulated as separate compositions or dosages for simultaneous, separate or sequential use for use in therapy, wherein the amounts of the compound of Example No. 55, or a pharmaceutically acceptable salt thereof and of the additional therapeutic agent are together therapeutically effective.

Embodiment 81. A pharmaceutical composition, comprising (a) a compound of Example No. 55, or a pharmaceutically acceptable salt thereof, (b) an additional therapeutic agent, and (c) a pharmaceutically acceptable diluent or carrier.

Embodiment 82. The pharmaceutical combination of Embodiment 78, or for use of Embodiment 79, or the pharmaceutical composition of Embodiment 81, wherein the additional therapeutic agent is an anticancer agent.

Embodiment 83. The pharmaceutical combination of Embodiment 78, or for use of Embodiment 79, or the pharmaceutical composition of Embodiment 81, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 84. A pharmaceutical combination which comprises (a) a compound of Example No. 58, or a pharmaceutically acceptable salt thereof, and (b) an additional therapeutic agent.

Embodiment 85. A pharmaceutical combination which comprises (a) a compound of Example No. 58, or a pharmaceutically acceptable salt thereof, and (b) an additional therapeutic agent, for use in therapy.

Embodiment 86. The pharmaceutical combination of Embodiment 84, or for use of Embodiment 85, wherein the compound of Example No. 58, or the pharmaceutically acceptable salt thereof and the additional therapeutic agent are formulated as separate compositions or dosages for simultaneous, separate or sequential use for use in therapy, wherein the amounts of the compound of Example No. 58, or a pharmaceutically acceptable salt thereof and of the additional therapeutic agent are together therapeutically effective.

Embodiment 87. A pharmaceutical composition, comprising (a) a compound of Example No. 58, or a pharmaceutically acceptable salt thereof, (b) an additional therapeutic agent, and (c) a pharmaceutically acceptable diluent or carrier.

Embodiment 88. The pharmaceutical combination of Embodiment 84, or for use of Embodiment 85, or the pharmaceutical composition of Embodiment 87, wherein the additional therapeutic agent is an anticancer agent.

Embodiment 89. The pharmaceutical combination of Embodiment 84, or for use of Embodiment 85, or the pharmaceutical composition of Embodiment 87, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 90. A pharmaceutical combination which comprises (a) a compound of Example No. 72, or a pharmaceutically acceptable salt thereof, and (b) an additional therapeutic agent.

Embodiment 91. A pharmaceutical combination which comprises (a) a compound of Example No. 72, or a pharmaceutically acceptable salt thereof, and (b) an additional therapeutic agent, for use in therapy.

Embodiment 92. The pharmaceutical combination of Embodiment 90, or for use of Embodiment 91, wherein the compound of Example No. 72, or the pharmaceutically acceptable salt thereof and the additional therapeutic agent are formulated as separate compositions or dosages for simultaneous, separate or sequential use for use in therapy, wherein the amounts of the compound of Example No. 72, or a pharmaceutically acceptable salt thereof and of the additional therapeutic agent are together therapeutically effective.

Embodiment 93. A pharmaceutical composition, comprising (a) a compound of Example No. 72, or a pharmaceutically acceptable salt thereof, (b) an additional therapeutic agent, and (c) a pharmaceutically acceptable diluent or carrier.

Embodiment 94. The pharmaceutical combination of Embodiment 90, or for use of Embodiment 91, or the pharmaceutical composition of Embodiment 93, wherein the additional therapeutic agent is an anticancer agent.

Embodiment 95. The pharmaceutical combination of Embodiment 90, or for use of Embodiment 91, or the pharmaceutical composition of Embodiment 93, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 96. A pharmaceutical combination which comprises (a) a compound of Example No. 76, or a pharmaceutically acceptable salt thereof, and (b) an additional therapeutic agent.

Embodiment 97. A pharmaceutical combination which comprises (a) a compound of Example No. 76, or a pharmaceutically acceptable salt thereof, and (b) an additional therapeutic agent, for use in therapy.

Embodiment 98. The pharmaceutical combination of Embodiment 96, or for use of Embodiment 97, wherein the compound of Example No. 76, or the pharmaceutically acceptable salt thereof and the additional therapeutic agent are formulated as separate compositions or dosages for simultaneous, separate or sequential use for use in therapy, wherein the amounts of the compound of Example No. 76, or a pharmaceutically acceptable salt thereof and of the additional therapeutic agent are together therapeutically effective.

Embodiment 99. A pharmaceutical composition, comprising (a) a compound of Example No. 76, or a pharmaceutically acceptable salt thereof, (b) an additional therapeutic agent, and (c) a pharmaceutically acceptable diluent or carrier.

Embodiment 100. The pharmaceutical combination of Embodiment 96, or for use of Embodiment 97, or the pharmaceutical composition of Embodiment 99, wherein the additional therapeutic agent is an anticancer agent.

Embodiment 101. The pharmaceutical combination of Embodiment 96, or for use of Embodiment 97, or the pharmaceutical composition of Embodiment 99, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 102. A pharmaceutical combination which comprises (a) a compound of Example No. 77, or a pharmaceutically acceptable salt thereof, and (b) an additional therapeutic agent.

Embodiment 103. A pharmaceutical combination which comprises (a) a compound of Example No. 77, or a pharmaceutically acceptable salt thereof, and (b) an additional therapeutic agent, for use in therapy.

Embodiment 104. The pharmaceutical combination of Embodiment 102, or for use of Embodiment 103, wherein the compound of Example No. 77, or the pharmaceutically acceptable salt thereof and the additional therapeutic agent are formulated as separate compositions or dosages for simultaneous, separate or sequential use for use in therapy, wherein the amounts of the compound of Example No. 77, or a pharmaceutically acceptable salt thereof and of the additional therapeutic agent are together therapeutically effective.

Embodiment 105. A pharmaceutical composition, comprising (a) a compound of Example No. 77, or a pharmaceutically acceptable salt thereof, (b) an additional therapeutic agent, and (c) a pharmaceutically acceptable diluent or carrier.

Embodiment 106. The pharmaceutical combination of Embodiment 102, or for use of Embodiment 103, or the pharmaceutical composition of Embodiment 105, wherein the additional therapeutic agent is an anticancer agent.

Embodiment 107. The pharmaceutical combination of Embodiment 102, or for use of Embodiment 103, or the pharmaceutical composition of Embodiment 105, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 108. A pharmaceutical combination which comprises (a) a compound of Example No. 78, or a pharmaceutically acceptable salt thereof, and (b) an additional therapeutic agent.

Embodiment 109. A pharmaceutical combination which comprises (a) a compound of Example No. 78, or a pharmaceutically acceptable salt thereof, and (b) an additional therapeutic agent, for use in therapy.

Embodiment 110. The pharmaceutical combination of Embodiment 108, or for use of Embodiment 109, wherein the compound of Example No. 78, or the pharmaceutically acceptable salt thereof and the additional therapeutic agent are formulated as separate compositions or dosages for simultaneous, separate or sequential use for use in therapy, wherein the amounts of the compound of Example No. 78, or a pharmaceutically acceptable salt thereof and of the additional therapeutic agent are together therapeutically effective.

Embodiment 111. A pharmaceutical composition, comprising (a) a compound of Example No. 78, or a pharmaceutically acceptable salt thereof, (b) an additional therapeutic agent, and (c) a pharmaceutically acceptable diluent or carrier.

Embodiment 112. The pharmaceutical combination of Embodiment 108, or for use of Embodiment 109, or the pharmaceutical composition of Embodiment 111, wherein the additional therapeutic agent is an anticancer agent.

Embodiment 113. The pharmaceutical combination of Embodiment 108, or for use of Embodiment 109, or the pharmaceutical composition of Embodiment 111, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 114. A pharmaceutical combination which comprises (a) a compound of Example No. 83, or a pharmaceutically acceptable salt thereof, and (b) an additional therapeutic agent.

Embodiment 115. A pharmaceutical combination which comprises (a) a compound of Example No. 83, or a pharmaceutically acceptable salt thereof, and (b) an additional therapeutic agent, for use in therapy.

Embodiment 116. The pharmaceutical combination of Embodiment 114, or for use of Embodiment 115, wherein the compound of Example No. 83, or the pharmaceutically acceptable salt thereof and the additional therapeutic agent are formulated as separate compositions or dosages for simultaneous, separate or sequential use for use in therapy, wherein the amounts of the compound of Example No. 83, or a pharmaceutically acceptable salt thereof and of the additional therapeutic agent are together therapeutically effective.

Embodiment 117. A pharmaceutical composition, comprising (a) a compound of Example No. 83, or a pharmaceutically acceptable salt thereof, (b) an additional therapeutic agent, and (c) a pharmaceutically acceptable diluent or carrier.

Embodiment 118. The pharmaceutical combination of Embodiment 114, or for use of Embodiment 115, or the pharmaceutical composition of Embodiment 117, wherein the additional therapeutic agent is an anticancer agent.

Embodiment 119. The pharmaceutical combination of Embodiment 114, or for use of Embodiment 115, or the pharmaceutical composition of Embodiment 117, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 120. A pharmaceutical combination which comprises (a) a compound of Example No. 84, or a pharmaceutically acceptable salt thereof, and (b) an additional therapeutic agent.

Embodiment 121. A pharmaceutical combination which comprises (a) a compound of Example No. 84, or a pharmaceutically acceptable salt thereof, and (b) an additional therapeutic agent, for use in therapy.

Embodiment 122. The pharmaceutical combination of Embodiment 120, or for use of Embodiment 121, wherein the compound of Example No. 84, or the pharmaceutically acceptable salt thereof and the additional therapeutic agent are formulated as separate compositions or dosages for simultaneous, separate or sequential use for use in therapy, wherein the amounts of the compound of Example No. 84, or a pharmaceutically acceptable salt thereof and of the additional therapeutic agent are together therapeutically effective.

Embodiment 123. A pharmaceutical composition, comprising (a) a compound of Example No. 84, or a pharmaceutically acceptable salt thereof, (b) an additional therapeutic agent, and (c) a pharmaceutically acceptable diluent or carrier.

Embodiment 124. The pharmaceutical combination of Embodiment 120, or for use of Embodiment 121, or the pharmaceutical composition of Embodiment 123, wherein the additional therapeutic agent is an anticancer agent.

Embodiment 125. The pharmaceutical combination of Embodiment 120, or for use of Embodiment 121, or the pharmaceutical composition of Embodiment 123, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 126. A pharmaceutical combination which comprises (a) a compound of Example No. 85, or a pharmaceutically acceptable salt thereof, and (b) an additional therapeutic agent.

Embodiment 127. A pharmaceutical combination which comprises (a) a compound of Example No. 85, or a pharmaceutically acceptable salt thereof, and (b) an additional therapeutic agent, for use in therapy.

Embodiment 128. The pharmaceutical combination of Embodiment 126, or for use of Embodiment 127, wherein the compound of Example No. 85, or the pharmaceutically acceptable salt thereof and the additional therapeutic agent are formulated as separate compositions or dosages for simultaneous, separate or sequential use for use in therapy, wherein the amounts of the compound of Example No. 85, or a pharmaceutically acceptable salt thereof and of the additional therapeutic agent are together therapeutically effective.

Embodiment 129. A pharmaceutical composition, comprising (a) a compound of Example No. 85, or a pharmaceutically acceptable salt thereof, (b) an additional therapeutic agent, and (c) a pharmaceutically acceptable diluent or carrier.

Embodiment 130. The pharmaceutical combination of Embodiment 126, or for use of Embodiment 127, or the pharmaceutical composition of Embodiment 129, wherein the additional therapeutic agent is an anticancer agent.

Embodiment 131. The pharmaceutical combination of Embodiment 126, or for use of Embodiment 127, or the pharmaceutical composition of Embodiment 129, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 132. A pharmaceutical combination which comprises (a) a compound of Example No. 91, or a pharmaceutically acceptable salt thereof, and (b) an additional therapeutic agent.

Embodiment 133. A pharmaceutical combination which comprises (a) a compound of Example No. 91, or a pharmaceutically acceptable salt thereof, and (b) an additional therapeutic agent, for use in therapy.

Embodiment 134. The pharmaceutical combination of Embodiment 132, or for use of Embodiment 133, wherein the compound of Example No. 91, or the pharmaceutically acceptable salt thereof and the additional therapeutic agent are formulated as separate compositions or dosages for simultaneous, separate or sequential use for use in therapy, wherein the amounts of the compound of Example No. 91, or a pharmaceutically acceptable salt thereof and of the additional therapeutic agent are together therapeutically effective.

Embodiment 135. A pharmaceutical composition, comprising (a) a compound of Example No. 91, or a pharmaceutically acceptable salt thereof, (b) an additional therapeutic agent, and (c) a pharmaceutically acceptable diluent or carrier.

Embodiment 136. The pharmaceutical combination of Embodiment 132, or for use of Embodiment 133, or the pharmaceutical composition of Embodiment 135, wherein the additional therapeutic agent is an anticancer agent.

Embodiment 137. The pharmaceutical combination of Embodiment 132, or for use of Embodiment 133, or the pharmaceutical composition of Embodiment 135, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 138. A pharmaceutical combination which comprises (a) a compound of Example No. 97, or a pharmaceutically acceptable salt thereof, and (b) an additional therapeutic agent.

Embodiment 139. A pharmaceutical combination which comprises (a) a compound of Example No. 97, or a pharmaceutically acceptable salt thereof, and (b) an additional therapeutic agent, for use in therapy.

Embodiment 140. The pharmaceutical combination of Embodiment 138, or for use of Embodiment 139, wherein the compound of Example No. 97, or the pharmaceutically acceptable salt thereof and the additional therapeutic agent are formulated as separate compositions or dosages for simultaneous, separate or sequential use for use in therapy, wherein the amounts of the compound of Example No. 97, or a pharmaceutically acceptable salt thereof and of the additional therapeutic agent are together therapeutically effective.

Embodiment 141. A pharmaceutical composition, comprising (a) a compound of Example No. 97, or a pharmaceutically acceptable salt thereof, (b) an additional therapeutic agent, and (c) a pharmaceutically acceptable diluent or carrier.

Embodiment 142. The pharmaceutical combination of Embodiment 138, or for use of Embodiment 139, or the pharmaceutical composition of Embodiment 141, wherein the additional therapeutic agent is an anticancer agent.

Embodiment 143. The pharmaceutical combination of Embodiment 138, or for use of Embodiment 139, or the pharmaceutical composition of Embodiment 141, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 144. A pharmaceutical combination which comprises (a) a compound of Example No. 100, or a pharmaceutically acceptable salt thereof, and (b) an additional therapeutic agent.

Embodiment 145. A pharmaceutical combination which comprises (a) a compound of Example No. 100, or a pharmaceutically acceptable salt thereof, and (b) an additional therapeutic agent, for use in therapy.

Embodiment 146. The pharmaceutical combination of Embodiment 144, or for use of Embodiment 145, wherein the compound of Example No. 100, or the pharmaceutically acceptable salt thereof and the additional therapeutic agent are formulated as separate compositions or dosages for simultaneous, separate or sequential use for use in therapy, wherein the amounts of the compound of Example No. 100, or a pharmaceutically acceptable salt thereof and of the additional therapeutic agent are together therapeutically effective.

Embodiment 147. A pharmaceutical composition, comprising (a) a compound of Example No. 100, or a pharmaceutically acceptable salt thereof, (b) an additional therapeutic agent, and (c) a pharmaceutically acceptable diluent or carrier.

Embodiment 148. The pharmaceutical combination of Embodiment 144, or for use of Embodiment 145, or the pharmaceutical composition of Embodiment 147, wherein the additional therapeutic agent is an anticancer agent.

Embodiment 149. The pharmaceutical combination of Embodiment 144, or for use of Embodiment 145, or the pharmaceutical composition of Embodiment 147, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 150. A pharmaceutical combination which comprises (a) a compound of Example No. 103, or a pharmaceutically acceptable salt thereof, and (b) an additional therapeutic agent.

Embodiment 151. A pharmaceutical combination which comprises (a) a compound of Example No. 103, or a pharmaceutically acceptable salt thereof, and (b) an additional therapeutic agent, for use in therapy.

Embodiment 152. The pharmaceutical combination of Embodiment 150, or for use of Embodiment 151, wherein the compound of Example No. 103, or the pharmaceutically acceptable salt thereof and the additional therapeutic agent are formulated as separate compositions or dosages for simultaneous, separate or sequential use for use in therapy, wherein the amounts of the compound of Example No. 103, or a pharmaceutically acceptable salt thereof and of the additional therapeutic agent are together therapeutically effective.

Embodiment 153. A pharmaceutical composition, comprising (a) a compound of Example No. 103, or a pharmaceutically acceptable salt thereof, (b) an additional therapeutic agent, and (c) a pharmaceutically acceptable diluent or carrier.

Embodiment 154. The pharmaceutical combination of Embodiment 150, or for use of Embodiment 151, or the pharmaceutical composition of Embodiment 153, wherein the additional therapeutic agent is an anticancer agent.

Embodiment 155. The pharmaceutical combination of Embodiment 150, or for use of Embodiment 151, or the pharmaceutical composition of Embodiment 153, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 156. A pharmaceutical combination which comprises (a) a compound of Example No. 105, or a pharmaceutically acceptable salt thereof, and (b) an additional therapeutic agent.

Embodiment 157. A pharmaceutical combination which comprises (a) a compound of Example No. 105, or a pharmaceutically acceptable salt thereof, and (b) an additional therapeutic agent, for use in therapy.

Embodiment 158. The pharmaceutical combination of Embodiment 156, or for use of Embodiment 157, wherein the compound of Example No. 105, or the pharmaceutically acceptable salt thereof and the additional therapeutic agent are formulated as separate compositions or dosages for simultaneous, separate or sequential use for use in therapy, wherein the amounts of the compound of Example No. 105, or a pharmaceutically acceptable salt thereof and of the additional therapeutic agent are together therapeutically effective.

Embodiment 159. A pharmaceutical composition, comprising (a) a compound of Example No. 105, or a pharmaceutically acceptable salt thereof, (b) an additional therapeutic agent, and (c) a pharmaceutically acceptable diluent or carrier.

Embodiment 160. The pharmaceutical combination of Embodiment 156, or for use of Embodiment 157, or the pharmaceutical composition of Embodiment 159, wherein the additional therapeutic agent is an anticancer agent.

Embodiment 161. The pharmaceutical combination of Embodiment 156, or for use of Embodiment 157, or the pharmaceutical composition of Embodiment 159, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 162. A pharmaceutical combination which comprises (a) a compound of Example No. 107, or a pharmaceutically acceptable salt thereof, and (b) an additional therapeutic agent.

Embodiment 163. A pharmaceutical combination which comprises (a) a compound of Example No. 107, or a pharmaceutically acceptable salt thereof, and (b) an additional therapeutic agent, for use in therapy.

Embodiment 164. The pharmaceutical combination of Embodiment 162, or for use of Embodiment 163, wherein the compound of Example No. 107, or the pharmaceutically acceptable salt thereof and the additional therapeutic agent are formulated as separate compositions or dosages for simultaneous, separate or sequential use for use in therapy, wherein the amounts of the compound of Example No. 107, or a pharmaceutically acceptable salt thereof and of the additional therapeutic agent are together therapeutically effective.

Embodiment 165. A pharmaceutical composition, comprising (a) a compound of Example No. 107, or a pharmaceutically acceptable salt thereof, (b) an additional therapeutic agent, and (c) a pharmaceutically acceptable diluent or carrier.

Embodiment 166. The pharmaceutical combination of Embodiment 162, or for use of Embodiment 163, or the pharmaceutical composition of Embodiment 165, wherein the additional therapeutic agent is an anticancer agent.

Embodiment 167. The pharmaceutical combination of Embodiment 162, or for use of Embodiment 163, or the pharmaceutical composition of Embodiment 165, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 168. A pharmaceutical combination which comprises (a) a compound of Example No. 108, or a pharmaceutically acceptable salt thereof, and (b) an additional therapeutic agent.

Embodiment 169. A pharmaceutical combination which comprises (a) a compound of Example No. 108, or a pharmaceutically acceptable salt thereof, and (b) an additional therapeutic agent, for use in therapy.

Embodiment 170. The pharmaceutical combination of Embodiment 168, or for use of Embodiment 169, wherein the compound of Example No. 108, or the pharmaceutically acceptable salt thereof and the additional therapeutic agent are formulated as separate compositions or dosages for simultaneous, separate or sequential use for use in therapy, wherein the amounts of the compound of Example No. 108, or a pharmaceutically acceptable salt thereof and of the additional therapeutic agent are together therapeutically effective.

Embodiment 171. A pharmaceutical composition, comprising (a) a compound of Example No. 108, or a pharmaceutically acceptable salt thereof, (b) an additional therapeutic agent, and (c) a pharmaceutically acceptable diluent or carrier.

Embodiment 172. The pharmaceutical combination of Embodiment 168, or for use of Embodiment 169, or the pharmaceutical composition of Embodiment 171, wherein the additional therapeutic agent is an anticancer agent.

Embodiment 173. The pharmaceutical combination of Embodiment 168, or for use of Embodiment 169, or the pharmaceutical composition of Embodiment 171, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 174. A pharmaceutical combination which comprises (a) a compound of Example No. 114, or a pharmaceutically acceptable salt thereof, and (b) an additional therapeutic agent.

Embodiment 175. A pharmaceutical combination which comprises (a) a compound of Example No. 114, or a pharmaceutically acceptable salt thereof, and (b) an additional therapeutic agent, for use in therapy.

Embodiment 176. The pharmaceutical combination of Embodiment 174, or for use of Embodiment 175, wherein the compound of Example No. 114, or the pharmaceutically acceptable salt thereof and the additional therapeutic agent are formulated as separate compositions or dosages for simultaneous, separate or sequential use for use in therapy, wherein the amounts of the compound of Example No. 114, or a pharmaceutically acceptable salt thereof and of the additional therapeutic agent are together therapeutically effective.

Embodiment 177. A pharmaceutical composition, comprising (a) a compound of Example No. 114, or a pharmaceutically acceptable salt thereof, (b) an additional therapeutic agent, and (c) a pharmaceutically acceptable diluent or carrier.

Embodiment 178. The pharmaceutical combination of Embodiment 174, or for use of Embodiment 175, or the pharmaceutical composition of Embodiment 177, wherein the additional therapeutic agent is an anticancer agent.

Embodiment 179. The pharmaceutical combination of Embodiment 174, or for use of Embodiment 175, or the pharmaceutical composition of Embodiment 177, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 180. A pharmaceutical combination which comprises (a) a compound of Example No. 115, or a pharmaceutically acceptable salt thereof, and (b) an additional therapeutic agent.

Embodiment 181. A pharmaceutical combination which comprises (a) a compound of Example No. 115, or a pharmaceutically acceptable salt thereof, and (b) an additional therapeutic agent, for use in therapy.

Embodiment 182. The pharmaceutical combination of Embodiment 180, or for use of Embodiment 181, wherein the compound of Example No. 115, or the pharmaceutically acceptable salt thereof and the additional therapeutic agent are formulated as separate compositions or dosages for simultaneous, separate or sequential use for use in therapy, wherein the amounts of the compound of Example No. 115, or a pharmaceutically acceptable salt thereof and of the additional therapeutic agent are together therapeutically effective.

Embodiment 183. A pharmaceutical composition, comprising (a) a compound of Example No. 115, or a pharmaceutically acceptable salt thereof, (b) an additional therapeutic agent, and (c) a pharmaceutically acceptable diluent or carrier.

Embodiment 184. The pharmaceutical combination of Embodiment 180, or for use of Embodiment 181, or the pharmaceutical composition of Embodiment 183, wherein the additional therapeutic agent is an anticancer agent.

Embodiment 185. The pharmaceutical combination of Embodiment 180, or for use of Embodiment 181, or the pharmaceutical composition of Embodiment 183, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 186. A pharmaceutical combination which comprises (a) a compound of Example No. 119, or a pharmaceutically acceptable salt thereof, and (b) an additional therapeutic agent.

Embodiment 187. A pharmaceutical combination which comprises (a) a compound of Example No. 119, or a pharmaceutically acceptable salt thereof, and (b) an additional therapeutic agent, for use in therapy.

Embodiment 188. The pharmaceutical combination of Embodiment 186, or for use of Embodiment 187, wherein the compound of Example No. 119, or the pharmaceutically acceptable salt thereof and the additional therapeutic agent are formulated as separate compositions or dosages for simultaneous, separate or sequential use for use in therapy, wherein the amounts of the compound of Example No. 119, or a pharmaceutically acceptable salt thereof and of the additional therapeutic agent are together therapeutically effective.

Embodiment 189. A pharmaceutical composition, comprising (a) a compound of Example No. 119, or a pharmaceutically acceptable salt thereof, (b) an additional therapeutic agent, and (c) a pharmaceutically acceptable diluent or carrier.

Embodiment 190. The pharmaceutical combination of Embodiment 186, or for use of Embodiment 187, or the pharmaceutical composition of Embodiment 189, wherein the additional therapeutic agent is an anticancer agent.

Embodiment 191. The pharmaceutical combination of Embodiment 186, or for use of Embodiment 187, or the pharmaceutical composition of Embodiment 189, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 192. A pharmaceutical combination which comprises (a) a compound of Example No. 121, or a pharmaceutically acceptable salt thereof, and (b) an additional therapeutic agent.

Embodiment 193. A pharmaceutical combination which comprises (a) a compound of Example No. 121, or a pharmaceutically acceptable salt thereof, and (b) an additional therapeutic agent, for use in therapy.

Embodiment 194. The pharmaceutical combination of Embodiment 192, or for use of Embodiment 193, wherein the compound of Example No. 121, or the pharmaceutically acceptable salt thereof and the additional therapeutic agent are formulated as separate compositions or dosages for simultaneous, separate or sequential use for use in therapy, wherein the amounts of the compound of Example No. 121, or a pharmaceutically acceptable salt thereof and of the additional therapeutic agent are together therapeutically effective.

Embodiment 195. A pharmaceutical composition, comprising (a) a compound of Example No. 121, or a pharmaceutically acceptable salt thereof, (b) an additional therapeutic agent, and (c) a pharmaceutically acceptable diluent or carrier.

Embodiment 196. The pharmaceutical combination of Embodiment 192, or for use of Embodiment 193, or the pharmaceutical composition of Embodiment 195, wherein the additional therapeutic agent is an anticancer agent.

Embodiment 197. The pharmaceutical combination of Embodiment 192, or for use of Embodiment 193, or the pharmaceutical composition of Embodiment 195, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 198. A pharmaceutical combination which comprises (a) a compound of Example No. 124, or a pharmaceutically acceptable salt thereof, and (b) an additional therapeutic agent.

Embodiment 199. A pharmaceutical combination which comprises (a) a compound of Example No. 124, or a pharmaceutically acceptable salt thereof, and (b) an additional therapeutic agent, for use in therapy.

Embodiment 200. The pharmaceutical combination of Embodiment 198, or for use of Embodiment 199, wherein the compound of Example No. 124, or the pharmaceutically acceptable salt thereof and the additional therapeutic agent are formulated as separate compositions or dosages for simultaneous, separate or sequential use for use in therapy, wherein the amounts of the compound of Example No. 124, or a pharmaceutically acceptable salt thereof and of the additional therapeutic agent are together therapeutically effective.

Embodiment 201. A pharmaceutical composition, comprising (a) a compound of Example No. 124, or a pharmaceutically acceptable salt thereof, (b) an additional therapeutic agent, and (c) a pharmaceutically acceptable diluent or carrier.

Embodiment 202. The pharmaceutical combination of Embodiment 198, or for use of Embodiment 199, or the pharmaceutical composition of Embodiment 201, wherein the additional therapeutic agent is an anticancer agent.

Embodiment 203. The pharmaceutical combination of Embodiment 198, or for use of Embodiment 199, or the pharmaceutical composition of Embodiment 201, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 204. A pharmaceutical combination which comprises (a) a compound of Example No. 125, or a pharmaceutically acceptable salt thereof, and (b) an additional therapeutic agent.

Embodiment 205. A pharmaceutical combination which comprises (a) a compound of Example No. 125, or a pharmaceutically acceptable salt thereof, and (b) an additional therapeutic agent, for use in therapy.

Embodiment 206. The pharmaceutical combination of Embodiment 204, or for use of Embodiment 205, wherein the compound of Example No. 125, or the pharmaceutically acceptable salt thereof and the additional therapeutic agent are formulated as separate compositions or dosages for simultaneous, separate or sequential use for use in therapy, wherein the amounts of the compound of Example No. 125, or a pharmaceutically acceptable salt thereof and of the additional therapeutic agent are together therapeutically effective.

Embodiment 207. A pharmaceutical composition, comprising (a) a compound of Example No. 125, or a pharmaceutically acceptable salt thereof, (b) an additional therapeutic agent, and (c) a pharmaceutically acceptable diluent or carrier.

Embodiment 208. The pharmaceutical combination of Embodiment 204, or for use of Embodiment 205, or the pharmaceutical composition of Embodiment 207, wherein the additional therapeutic agent is an anticancer agent.

Embodiment 209. The pharmaceutical combination of Embodiment 204, or for use of Embodiment 205, or the pharmaceutical composition of Embodiment 207, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 210. A pharmaceutical combination which comprises (a) a compound of Example No. 126, or a pharmaceutically acceptable salt thereof, and (b) an additional therapeutic agent.

Embodiment 211. A pharmaceutical combination which comprises (a) a compound of Example No. 126, or a pharmaceutically acceptable salt thereof, and (b) an additional therapeutic agent, for use in therapy.

Embodiment 212. The pharmaceutical combination of Embodiment 210, or for use of Embodiment 211, wherein the compound of Example No. 126, or the pharmaceutically acceptable salt thereof and the additional therapeutic agent are formulated as separate compositions or dosages for simultaneous, separate or sequential use for use in therapy, wherein the amounts of the compound of Example No. 126, or a pharmaceutically acceptable salt thereof and of the additional therapeutic agent are together therapeutically effective.

Embodiment 213. A pharmaceutical composition, comprising (a) a compound of Example No. 126, or a pharmaceutically acceptable salt thereof, (b) an additional therapeutic agent, and (c) a pharmaceutically acceptable diluent or carrier.

Embodiment 214. The pharmaceutical combination of Embodiment 210, or for use of Embodiment 211, or the pharmaceutical composition of Embodiment 213, wherein the additional therapeutic agent is an anticancer agent.

Embodiment 215. The pharmaceutical combination of Embodiment 210, or for use of Embodiment 211, or the pharmaceutical composition of Embodiment 213, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 216. A pharmaceutical combination which comprises (a) a compound of Example No. 127, or a pharmaceutically acceptable salt thereof, and (b) an additional therapeutic agent.

Embodiment 217. A pharmaceutical combination which comprises (a) a compound of Example No. 127, or a pharmaceutically acceptable salt thereof, and (b) an additional therapeutic agent, for use in therapy.

Embodiment 218. The pharmaceutical combination of Embodiment 216, or for use of Embodiment 217, wherein the compound of Example No. 127, or the pharmaceutically acceptable salt thereof and the additional therapeutic agent are formulated as separate compositions or dosages for simultaneous, separate or sequential use for use in therapy, wherein the amounts of the compound of Example No. 127, or a pharmaceutically acceptable salt thereof and of the additional therapeutic agent are together therapeutically effective.

Embodiment 219. A pharmaceutical composition, comprising (a) a compound of Example No. 127, or a pharmaceutically acceptable salt thereof, (b) an additional therapeutic agent, and (c) a pharmaceutically acceptable diluent or carrier.

Embodiment 220. The pharmaceutical combination of Embodiment 216, or for use of Embodiment 217, or the pharmaceutical composition of Embodiment 219, wherein the additional therapeutic agent is an anticancer agent.

Embodiment 221. The pharmaceutical combination of Embodiment 216, or for use of Embodiment 217, or the pharmaceutical composition of Embodiment 219, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 222. A pharmaceutical combination which comprises (a) a compound of Example No. 129, or a pharmaceutically acceptable salt thereof, and (b) an additional therapeutic agent.

Embodiment 223. A pharmaceutical combination which comprises (a) a compound of Example No. 129, or a pharmaceutically acceptable salt thereof, and (b) an additional therapeutic agent, for use in therapy.

Embodiment 224. The pharmaceutical combination of Embodiment 222, or for use of Embodiment 223, wherein the compound of Example No. 129, or the pharmaceutically acceptable salt thereof and the additional therapeutic agent are formulated as separate compositions or dosages for simultaneous, separate or sequential use for use in therapy, wherein the amounts of the compound of Example No. 129, or a pharmaceutically acceptable salt thereof and of the additional therapeutic agent are together therapeutically effective.

Embodiment 225. A pharmaceutical composition, comprising (a) a compound of Example No. 129, or a pharmaceutically acceptable salt thereof, (b) an additional therapeutic agent, and (c) a pharmaceutically acceptable diluent or carrier.

Embodiment 226. The pharmaceutical combination of Embodiment 222, or for use of Embodiment 223, or the pharmaceutical composition of Embodiment 225, wherein the additional therapeutic agent is an anticancer agent.

Embodiment 227. The pharmaceutical combination of Embodiment 222, or for use of Embodiment 223, or the pharmaceutical composition of Embodiment 225, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 228. A pharmaceutical combination which comprises (a) a compound of Example No. 151, or a pharmaceutically acceptable salt thereof, and (b) an additional therapeutic agent.

Embodiment 229. A pharmaceutical combination which comprises (a) a compound of Example No. 151, or a pharmaceutically acceptable salt thereof, and (b) an additional therapeutic agent, for use in therapy.

Embodiment 230. The pharmaceutical combination of Embodiment 228, or for use of Embodiment 229, wherein the compound of Example No. 151, or the pharmaceutically acceptable salt thereof and the additional therapeutic agent are formulated as separate compositions or dosages for simultaneous, separate or sequential use for use in therapy, wherein the amounts of the compound of Example No. 151, or a pharmaceutically acceptable salt thereof and of the additional therapeutic agent are together therapeutically effective.

Embodiment 231. A pharmaceutical composition, comprising (a) a compound of Example No. 151, or a pharmaceutically acceptable salt thereof, (b) an additional therapeutic agent, and (c) a pharmaceutically acceptable diluent or carrier.

Embodiment 232. The pharmaceutical combination of Embodiment 228, or for use of Embodiment 229, or the pharmaceutical composition of Embodiment 231, wherein the additional therapeutic agent is an anticancer agent.

Embodiment 233. The pharmaceutical combination of Embodiment 228, or for use of Embodiment 229, or the pharmaceutical composition of Embodiment 231, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 234. A pharmaceutical combination which comprises (a) a compound of Example No. 152, or a pharmaceutically acceptable salt thereof, and (b) an additional therapeutic agent.

Embodiment 235. A pharmaceutical combination which comprises (a) a compound of Example No. 152, or a pharmaceutically acceptable salt thereof, and (b) an additional therapeutic agent, for use in therapy.

Embodiment 236. The pharmaceutical combination of Embodiment 234, or for use of Embodiment 235, wherein the compound of Example No. 152, or the pharmaceutically acceptable salt thereof and the additional therapeutic agent are formulated as separate compositions or dosages for simultaneous, separate or sequential use for use in therapy, wherein the amounts of the compound of Example No. 152, or a pharmaceutically acceptable salt thereof and of the additional therapeutic agent are together therapeutically effective.

Embodiment 237. A pharmaceutical composition, comprising (a) a compound of Example No. 152, or a pharmaceutically acceptable salt thereof, (b) an additional therapeutic agent, and (c) a pharmaceutically acceptable diluent or carrier.

Embodiment 238. The pharmaceutical combination of Embodiment 234, or for use of Embodiment 235, or the pharmaceutical composition of Embodiment 237, wherein the additional therapeutic agent is an anticancer agent.

Embodiment 239. The pharmaceutical combination of Embodiment 234, or for use of Embodiment 235, or the pharmaceutical composition of Embodiment 237, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 240. A pharmaceutical combination which comprises (a) a compound of Example No. 163, or a pharmaceutically acceptable salt thereof, and (b) an additional therapeutic agent.

Embodiment 241. A pharmaceutical combination which comprises (a) a compound of Example No. 163, or a pharmaceutically acceptable salt thereof, and (b) an additional therapeutic agent, for use in therapy.

Embodiment 242. The pharmaceutical combination of Embodiment 240, or for use of Embodiment 241, wherein the compound of Example No. 163, or the pharmaceutically acceptable salt thereof and the additional therapeutic agent are formulated as separate compositions or dosages for simultaneous, separate or sequential use for use in therapy, wherein the amounts of the compound of Example No. 163, or a pharmaceutically acceptable salt thereof and of the additional therapeutic agent are together therapeutically effective.

Embodiment 243. A pharmaceutical composition, comprising (a) a compound of Example No. 163, or a pharmaceutically acceptable salt thereof, (b) an additional therapeutic agent, and (c) a pharmaceutically acceptable diluent or carrier.

Embodiment 244. The pharmaceutical combination of Embodiment 240, or for use of Embodiment 241, or the pharmaceutical composition of Embodiment 243, wherein the additional therapeutic agent is an anticancer agent.

Embodiment 245. The pharmaceutical combination of Embodiment 240, or for use of Embodiment 241, or the pharmaceutical composition of Embodiment 243, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 246. A pharmaceutical combination which comprises (a) a compound of Example No. 169, or a pharmaceutically acceptable salt thereof, and (b) an additional therapeutic agent.

Embodiment 247. A pharmaceutical combination which comprises (a) a compound of Example No. 169, or a pharmaceutically acceptable salt thereof, and (b) an additional therapeutic agent, for use in therapy.

Embodiment 248. The pharmaceutical combination of Embodiment 246, or for use of Embodiment 247, wherein the compound of Example No. 169, or the pharmaceutically acceptable salt thereof and the additional therapeutic agent are formulated as separate compositions or dosages for simultaneous, separate or sequential use for use in therapy, wherein the amounts of the compound of Example No. 169, or a pharmaceutically acceptable salt thereof and of the additional therapeutic agent are together therapeutically effective.

Embodiment 249. A pharmaceutical composition, comprising (a) a compound of Example No. 169, or a pharmaceutically acceptable salt thereof, (b) an additional therapeutic agent, and (c) a pharmaceutically acceptable diluent or carrier.

Embodiment 250. The pharmaceutical combination of Embodiment 246, or for use of Embodiment 247, or the pharmaceutical composition of Embodiment 249, wherein the additional therapeutic agent is an anticancer agent.

Embodiment 251. The pharmaceutical combination of Embodiment 246, or for use of Embodiment 247, or the pharmaceutical composition of Embodiment 249, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 252. A pharmaceutical combination which comprises (a) a compound of Example No. 188, or a pharmaceutically acceptable salt thereof, and (b) an additional therapeutic agent.

Embodiment 253. A pharmaceutical combination which comprises (a) a compound of Example No. 188, or a pharmaceutically acceptable salt thereof, and (b) an additional therapeutic agent, for use in therapy.

Embodiment 254. The pharmaceutical combination of Embodiment 252, or for use of Embodiment 253, wherein the compound of Example No. 188, or the pharmaceutically acceptable salt thereof and the additional therapeutic agent are formulated as separate compositions or dosages for simultaneous, separate or sequential use for use in therapy, wherein the amounts of the compound of Example No. 188, or a pharmaceutically acceptable salt thereof and of the additional therapeutic agent are together therapeutically effective.

Embodiment 255. A pharmaceutical composition, comprising (a) a compound of Example No. 188, or a pharmaceutically acceptable salt thereof, (b) an additional therapeutic agent, and (c) a pharmaceutically acceptable diluent or carrier.

Embodiment 256. The pharmaceutical combination of Embodiment 252, or for use of Embodiment 253, or the pharmaceutical composition of Embodiment 255, wherein the additional therapeutic agent is an anticancer agent.

Embodiment 257. The pharmaceutical combination of Embodiment 252, or for use of Embodiment 253, or the pharmaceutical composition of Embodiment 255, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 258. A pharmaceutical combination which comprises (a) a compound of Example No. 190, or a pharmaceutically acceptable salt thereof, and (b) an additional therapeutic agent.

Embodiment 259. A pharmaceutical combination which comprises (a) a compound of Example No. 190, or a pharmaceutically acceptable salt thereof, and (b) an additional therapeutic agent, for use in therapy.

Embodiment 260. The pharmaceutical combination of Embodiment 258, or for use of Embodiment 259, wherein the compound of Example No. 190, or the pharmaceutically acceptable salt thereof and the additional therapeutic agent are formulated as separate compositions or dosages for simultaneous, separate or sequential use for use in therapy, wherein the amounts of the compound of Example No. 190, or a pharmaceutically acceptable salt thereof and of the additional therapeutic agent are together therapeutically effective.

Embodiment 261. A pharmaceutical composition, comprising (a) a compound of Example No. 190, or a pharmaceutically acceptable salt thereof, (b) an additional therapeutic agent, and (c) a pharmaceutically acceptable diluent or carrier.

Embodiment 262. The pharmaceutical combination of Embodiment 258, or for use of Embodiment 259, or the pharmaceutical composition of Embodiment 261, wherein the additional therapeutic agent is an anticancer agent.

Embodiment 263. The pharmaceutical combination of Embodiment 258, or for use of Embodiment 259, or the pharmaceutical composition of Embodiment 261, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 264. A pharmaceutical combination which comprises (a) a compound of Example No. 199, or a pharmaceutically acceptable salt thereof, and (b) an additional therapeutic agent.

Embodiment 265. A pharmaceutical combination which comprises (a) a compound of Example No. 199, or a pharmaceutically acceptable salt thereof, and (b) an additional therapeutic agent, for use in therapy.

Embodiment 266. The pharmaceutical combination of Embodiment 264, or for use of Embodiment 265, wherein the compound of Example No. 199, or the pharmaceutically acceptable salt thereof and the additional therapeutic agent are formulated as separate compositions or dosages for simultaneous, separate or sequential use for use in therapy, wherein the amounts of the compound of Example No. 199, or a pharmaceutically acceptable salt thereof and of the additional therapeutic agent are together therapeutically effective.

Embodiment 267. A pharmaceutical composition, comprising (a) a compound of Example No. 199, or a pharmaceutically acceptable salt thereof, (b) an additional therapeutic agent, and (c) a pharmaceutically acceptable diluent or carrier.

Embodiment 268. The pharmaceutical combination of Embodiment 264, or for use of Embodiment 265, or the pharmaceutical composition of Embodiment 267, wherein the additional therapeutic agent is an anticancer agent.

Embodiment 269. The pharmaceutical combination of Embodiment 264, or for use of Embodiment 265, or the pharmaceutical composition of Embodiment 267, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 270. A pharmaceutical combination which comprises (a) a compound of Example No. 200, or a pharmaceutically acceptable salt thereof, and (b) an additional therapeutic agent.

Embodiment 271. A pharmaceutical combination which comprises (a) a compound of Example No. 200, or a pharmaceutically acceptable salt thereof, and (b) an additional therapeutic agent, for use in therapy.

Embodiment 272. The pharmaceutical combination of Embodiment 270, or for use of Embodiment 271, wherein the compound of Example No. 200, or the pharmaceutically acceptable salt thereof and the additional therapeutic agent are formulated as separate compositions or dosages for simultaneous, separate or sequential use for use in therapy, wherein the amounts of the compound of Example No. 200, or a pharmaceutically acceptable salt thereof and of the additional therapeutic agent are together therapeutically effective.

Embodiment 273. A pharmaceutical composition, comprising (a) a compound of Example No. 200, or a pharmaceutically acceptable salt thereof, (b) an additional therapeutic agent, and (c) a pharmaceutically acceptable diluent or carrier.

Embodiment 274. The pharmaceutical combination of Embodiment 270, or for use of Embodiment 271, or the pharmaceutical composition of Embodiment 273, wherein the additional therapeutic agent is an anticancer agent.

Embodiment 275. The pharmaceutical combination of Embodiment 270, or for use of Embodiment 271, or the pharmaceutical composition of Embodiment 273, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

Embodiment 276. A pharmaceutical combination which comprises (a) a compound of Example No. 201, or a pharmaceutically acceptable salt thereof, and (b) an additional therapeutic agent.

Embodiment 277. A pharmaceutical combination which comprises (a) a compound of Example No. 201, or a pharmaceutically acceptable salt thereof, and (b) an additional therapeutic agent, for use in therapy.

Embodiment 278. The pharmaceutical combination of Embodiment 276, or for use of Embodiment 277, wherein the compound of Example No. 201, or the pharmaceutically acceptable salt thereof and the additional therapeutic agent are formulated as separate compositions or dosages for simultaneous, separate or sequential use for use in therapy, wherein the amounts of the compound of Example No. 201, or a pharmaceutically acceptable salt thereof and of the additional therapeutic agent are together therapeutically effective.

Embodiment 279. A pharmaceutical composition, comprising (a) a compound of Example No. 201, or a pharmaceutically acceptable salt thereof, (b) an additional therapeutic agent, and (c) a pharmaceutically acceptable diluent or carrier.

Embodiment 280. The pharmaceutical combination of Embodiment 276, or for use of Embodiment 277, or the pharmaceutical composition of Embodiment 279, wherein the additional therapeutic agent is an anticancer agent.

Embodiment 281. The pharmaceutical combination of Embodiment 276, or for use of Embodiment 277, or the pharmaceutical composition of Embodiment 279, wherein the additional therapeutic agent is selected from the group consisting of binimetinib, encorafenib, selumetinib, sorafenib, trametinib, vemurafenib, cetuximab or a biosimilar thereof, panitumumab or a biosimilar thereof, erlotinib, lapatinib, gefitinib, nivolumab or a biosimilar thereof, pembrolizumab or a biosimilar thereof, cemiplimab or a biosimilar thereof, pidilizumab or a biosimilar thereof, atezolizumab or a biosimilar thereof, avelumab or a biosimilar thereof, and durvalumab or a biosimilar thereof.

What is claimed is:

1. A method for treating cancer in a patient in need thereof, the method comprising administering to the patient a therapeutically effective amount of (R)—N-(3-fluoro-4-((3-((1-hydroxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide having the structure

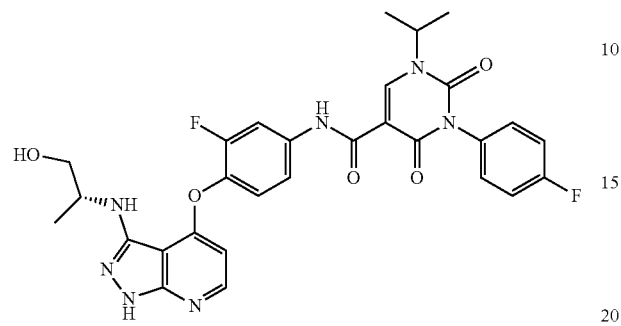

or a pharmaceutically acceptable salt thereof.

2. A method for treating cancer in a patient in need thereof, the method comprising administering to the patient a therapeutically effective amount of (R)—N-(3-fluoro-4-(3-((1-hydroxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide having the structure

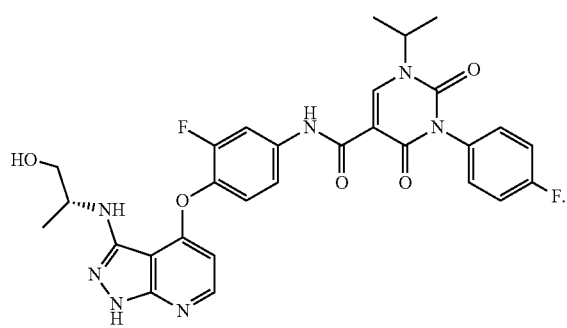

3. The method of claim 1, wherein said cancer is selected from cervical cancer, gastrointestinal cancer, esophageal cancer, endometrial cancer, liver cancer, melanoma, Merkel cell carcinoma, lung cancer, head and neck cancer, renal cell carcinoma, and bladder cancer.

4. A method for treating cancer in a patient in need thereof, the method comprising administering to the patient a therapeutically effective amount of (R)—N-(3-fluoro-4-((3-((1-hydroxypropan-2-yl)amino)-1H-pyrazolo[3,4-b]pyridin-4-yl)oxy)phenyl)-3-(4-fluorophenyl)-1-isopropyl-2,4-dioxo-1,2,3,4-tetrahydropyrimidine-5-carboxamide having the structure

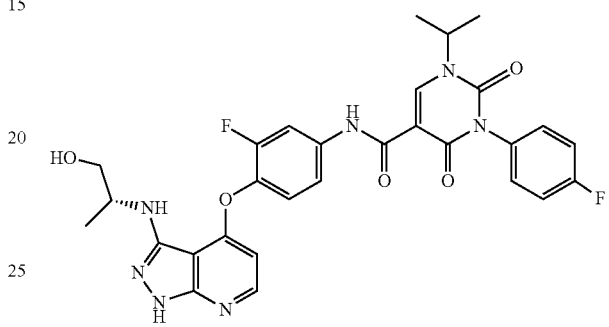

or a pharmaceutically acceptable salt thereof and a therapeutically effective amount of an anti-PD-1 antibody.

5. The method of claim 4, wherein the anti-PD-1 antibody is pembrolizumab.

6. The method of claim 4, further comprising administering a therapeutically effective amount of a VEGFR inhibitor.

7. The method of claim 6, wherein the VEGFR inhibitor is axitinib.

8. The method of claim 5, further comprising administering a therapeutically effective amount of a VEGFR inhibitor.

9. The method of claim 8, wherein the VEGFR inhibitor is axitinib.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial

```
<220> FEATURE:
<223> OTHER INFORMATION: synthetic oligonucleotide

<400> SEQUENCE: 1
aagctctttc tttctctctg tt                                              22

<210> SEQ ID NO 2
<211> LENGTH: 28
<212> TYPE: DNA
<213> ORGANISM: Artificial
<220> FEATURE:
<223> OTHER INFORMATION: synthetic oligonucleotide

<400> SEQUENCE: 2
accgagctac ttttccagaa ggtatatt                                        28

<210> SEQ ID NO 3
<211> LENGTH: 20
<212> TYPE: DNA
<213> ORGANISM: Artificial
<220> FEATURE:
<223> OTHER INFORMATION: synthetic oligonucleotide

<400> SEQUENCE: 3
cccatgatag ccgtctttaa                                                 20

<210> SEQ ID NO 4
<211> LENGTH: 11
<212> TYPE: DNA
<213> ORGANISM: Artificial
<220> FEATURE:
<223> OTHER INFORMATION: synthetic oligonucleotide

<400> SEQUENCE: 4
ctttctctct g                                                          11

<210> SEQ ID NO 5
<211> LENGTH: 19
<212> TYPE: DNA
<213> ORGANISM: Artificial
<220> FEATURE:
<223> OTHER INFORMATION: synthetic oligonucleotide

<400> SEQUENCE: 5
ttctctctgt tttaagatc                                                  19

<210> SEQ ID NO 6
<211> LENGTH: 12
<212> TYPE: DNA
<213> ORGANISM: Artificial
<220> FEATURE:
<223> OTHER INFORMATION: synthetic oligonucleotide

<400> SEQUENCE: 6
ctttctctct gt                                                         12
```